US009220723B2

(12) United States Patent
Ren et al.

(10) Patent No.: US 9,220,723 B2
(45) Date of Patent: Dec. 29, 2015

(54) CANCER THERAPY

(75) Inventors: Ruibao Ren, Newton, MA (US); Benjamin Cuiffo, Somerville, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 20 days.

(21) Appl. No.: 13/805,621

(22) PCT Filed: Jun. 23, 2011

(86) PCT No.: PCT/US2011/041682

§ 371 (c)(1), (2), (4) Date: Apr. 23, 2013

(87) PCT Pub. No.: WO2011/163512

PCT Pub. Date: Dec. 29, 2011

(65) Prior Publication Data

US 2013/0210890 A1 Aug. 15, 2013

Related U.S. Application Data

(60) Provisional application No. 61/357,845, filed on Jun. 23, 2010.

(51) Int. Cl.

| | |
|---|---|
| ***C12N 15/113*** | (2010.01) |
| ***A61K 31/713*** | (2006.01) |
| ***A61K 31/336*** | (2006.01) |

(52) U.S. Cl.

CPC ............ *A61K 31/713* (2013.01); *A61K 31/336* (2013.01); *C12N 15/1137* (2013.01); *C12Y 203/01085* (2013.01); *C12N 2310/14* (2013.01)

(58) Field of Classification Search

None

See application file for complete search history.

(56) References Cited

U.S. PATENT DOCUMENTS

| | | | | |
|---|---|---|---|---|
| 2004/0077570 | A1 | 4/2004 | Freier et al. | |
| 2009/0202569 | A1* | 8/2009 | Mashima et al. .......... | 424/174.1 |
| 2009/0208990 | A1 | 8/2009 | Deschenes et al. | |
| 2010/0166747 | A1* | 7/2010 | Beltran et al. ............ | 424/133.1 |

OTHER PUBLICATIONS

Ducker et al. Oncogene 2004, vol. 23, pp. 9230-9237.*

Cuiffo, B, et al., Palmitoylation of oncogenic NRAS is essential for leukemogenesis, Blood, 115(17): 3598-3605 (2010).

Janes, P.W. et al., Activation of the Ras signalling pathway in human breast cancer cells overexpressing erbB-2, Oncogene, 9(12): 3601-3608 (1994).

International Search Report for PCT/US11/41682, 4 pages (Dec. 6, 2011).

Lawrence, D.S. et al., Structure-Activity Studies of Cerulenin Analogues as Protein Palmitoylation Inhibitors, J. Med. Chem, 42: 4932-4941 (1999).

Swarthout, J.T. et al., DHHC9 and GCP16 Constitute a Human Protein Fatty Acyltransferase with Specificity for H- and N-Ras, The Journal of Biological Chemistry, 280(35): 31141-31148 (2005).

Written Opinion for PCT/US11/41682, 9 pages (Dec. 6, 2011).

Blum, R., et al., Inhibitors of Chronically Active Ras: Potential for Treatment of Human Malignancies, Recent Patents on Anti-Cancer Drug Discovery, 2:1:31-47 (2008).

Ducker, C. E., et al., Discovery and characterization of inhibitors of human palmitoyl acyltransferases, Mol. Cancer Ther. 5:7:1647-1659 (2006).

European Extended Search Report for European Application No. 11798947.5, Nov. 13, 2014, 13 pages .

Flavin R., et al., Fatty acid synthase as a potential therapeutic target in cancer, Future Medicine Ltd., Future Oncol. 6:4:551-562 (2010).

Jennings, G. C., et al., 2-Bromopalmitate and 2-(2-hydroxy-5-nitro-benzylidene)-benzo[b]thiophen-2-one ihibit DHHC-mediated palmitoylation in vitro, Journal of Lipid Research, 50:233-242 (2009).

Mansilla, F., et al., Differential expression of DHHC9 in microsatellite stable and instable human colorectal cancer subgroups, British Journal of Cancer, 96:12:1896-1903 (2007).

Shiraishi, T., et al., Tynicamycin Enhances Tumor Necrosis Factor-Related Apoptosis-Inducing Ligand-Induced Apoptosis in Human Prostate Cancer Cells, Cancer Res., 65:63646370 (2005).

* cited by examiner

*Primary Examiner* — Tracy Vivlemore

(74) *Attorney, Agent, or Firm* — Choate, Hall & Stewart LLP; Brenda Herschbach Jarrell, JD

(57) ABSTRACT

The present invention provides agents useful in the treatment of cancer, as well as systems for identifying and/or characterizing such agents, and systems for identifying and/or characterizing patient populations responsive to particular agents.

9 Claims, 253 Drawing Sheets

2-Bromopalmitic acid

Tunicamycin

Cerulenin

Compound 7e

FIG. 11B
| Type 1 (farnesyl peptide) palmitoylation inhibitors | Type 2 (myristoyl peptide) palmitoylation inhibitor |
| --- | --- |
| 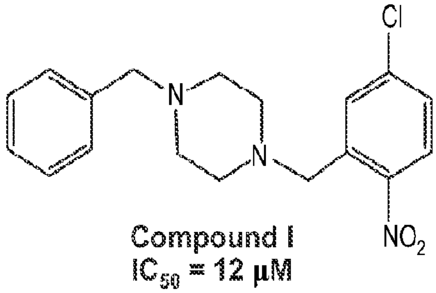 Compound I $IC_{50}$ = 12 μM | 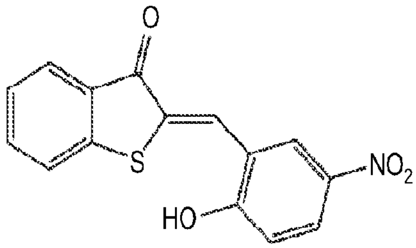 Compound V $IC_{50}$ = 0.5 μM |
| 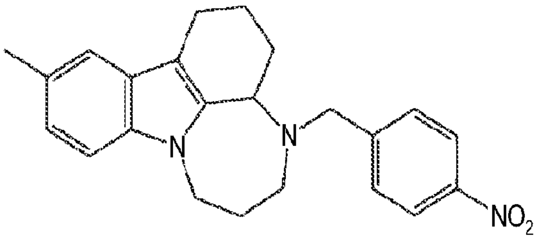 Compound II $IC_{50}$ = 4 μM | |
| 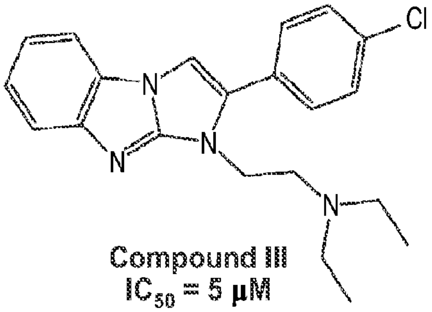 Compound III $IC_{50}$ = 5 μM | |
| 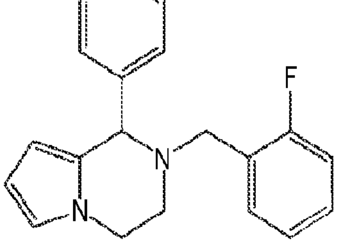 Compound IV $IC_{50}$ = 1 μM | |
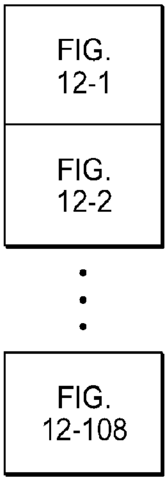
FIG. 12
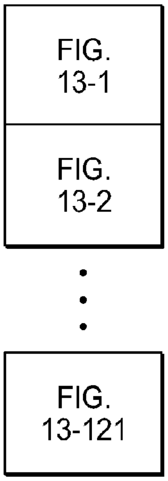
FIG. 13

ZDHHC1:

```
FEATURES             Location/Qualifiers
     source          1..2026
                     /organism="Homo sapiens"
                     /mol_type="mRNA"
                     /db_xref="taxon:9606"
                     /chromosome="16"
                     /map="16q22.1"
     gene            1..2026
                     /gene="ZDHHC1"
                     /gene_synonym="C16orf1; HSU90653; ZNF377"
                     /note="zinc finger, DHHC-type containing 1"
                     /db_xref="GeneID:29800"
                     /db_xref="HGNC:17916"
                     /db_xref="HPRD:15707"
     exon            1..266
                     /gene="ZDHHC1"
                     /gene_synonym="C16orf1; HSU90653; ZNF377"
                     /inference="alignment:Splign"
                     /number=1
     exon            267..313
                     /gene="ZDHHC1"
                     /gene_synonym="C16orf1; HSU90653; ZNF377"
                     /inference="alignment:Splign"
                     /number=2
     CDS             305..1762
                     /gene="ZDHHC1"
                     /gene_synonym="C16orf1; HSU90653; ZNF377"
                     /note="DHHC-domain-containing cysteine-rich protein;
zinc
                     finger, DHHC domain containing 1; DHHC-1; zinc finger
                     protein 377; zinc finger DHHC domain-containing protein
1;
```

FIG. 12-1

DHHC domain-containing cysteine-rich protein 1"
/codon_start=1
/product="probable palmitoyltransferase ZDHHC1"
/protein_id="NP_037436.1"
/db_xref="GI:24307963"
/db_xref="CCDS:CCDS10836.1"
/db_xref="GeneID:29800"
/db_xref="HGNC:17916"
/db_xref="HPRD:15707"

/translation="MYKMNICNKPSNKTAPEKSVWTAPAQPSGPSPELQGQRSRRNGW

SWPPHPLQIVAWLLYLFFAVIGFGILVPLLPHHWVPAGYACMGAIFAGHLVVHLTAVS

IDPADANVRDKSYAGPLPIFNRSQHAHVIEDLHCNLCNVDVSARSKHCSACNKCVCGF

DHHCKWLNNCVGERNYRLFLHSVASALLGVLLLVLVATYVFVEFFVNPMRLRTNRHFE

VLKNHTDVWFVFLPAAPVETQAPAILALAALLILLGLLSTALLGHLLCFHIYLMWHKL

TTYEYIVQHRPPQEAKGVHRELESCPPKMRPIQEMEFYMRTFRHMRPEPPGQAGPAAV

NAKHSRPASPDPTPGRRDCAGPPVQVEWDRKKPLPWRSPLLLLAMWGPQAPPCLCRKR

GRGACIKCERLRPRIRRRGLGPPAAAPARRRIPRTPALCTPLALPAPTTRRRQSPWTR
FQWRRRAWAAPLWPPRGAGADSPRWRGRRVRPPFS"

exon 314..556
/gene="ZDHHC1"
/gene_synonym="C16orf1; HSU90653; ZNF377"
/inference="alignment:Splign"
/number=3 exon 557..732
/gene="ZDHHC1"
/gene_synonym="C16orf1; HSU90653; ZNF377"
/inference="alignment:Splign"
/number=4 exon 733..834

FIG. 12-2

```
                    /gene="ZDHHC1"
                    /gene_synonym="C16orf1; HSU90653; ZNF377"
                    /inference="alignment:Splign"
                    /number=5
     exon           835..959
                    /gene="ZDHHC1"
                    /gene_synonym="C16orf1; HSU90653; ZNF377"
                    /inference="alignment:Splign"
                    /number=6
     exon           960..1118
                    /gene="ZDHHC1"
                    /gene_synonym="C16orf1; HSU90653; ZNF377"
                    /inference="alignment:Splign"
                    /number=7
     exon           1119..1231
                    /gene="ZDHHC1"
                    /gene_synonym="C16orf1; HSU90653; ZNF377"
                    /inference="alignment:Splign"
                    /number=8
     exon           1232..1314
                    /gene="ZDHHC1"
                    /gene_synonym="C16orf1; HSU90653; ZNF377"
                    /inference="alignment:Splign"
                    /number=9
     exon           1315..1534
                    /gene="ZDHHC1"
                    /gene_synonym="C16orf1; HSU90653; ZNF377"
                    /inference="alignment:Splign"
                    /number=10
     exon           1535..2009
                    /gene="ZDHHC1"
                    /gene_synonym="C16orf1; HSU90653; ZNF377"
                    /inference="alignment:Splign"
                    /number=11
```

FIG. 12-3

```
ORIGIN
        1 gcccctccag cctgctggag ccggagccgg agccggagcc ggagccggag ccggagccag
       61 agccagagct cgaggactca ccggcccagt ctccgtccgg gatggggccc cgctcccggg
      121 cgcgttgccg cccagtcccg gggaccgtcc ctaccgcgag ggtctgaggc gcggctgccc
      181 cggggagggt ggaaggccag gcgtggggcc cgaacctctg gctgactttg gcagggccca
      241 tctggcacgg cctccgcggc gcgcagctgt tttcaagtca gcaaacattt actgaggatc
      301 tactatgtac aagatgaaca tctgcaacaa gccctccaac aagacggccc ctgagaagag
      361 tgtgtggacg gcaccggcac agcccagcgg accctcccct gagctgcagg gccagcgatc
      421 ccgccggaat gggtggagct ggccccctca cccgctccag attgtggcct ggctgctgta
      481 cctcttcttt gctgtgatcg gctttgggat ccttgttccc ctcctgcctc accactgggt
      541 gcccgctggc tacgcttgca tgggcgccat ctttgctggc caccttgtgg tgcacctgac
      601 cgccgtctcc atcgatccag cagatgccaa cgtgcgggac aagagctatg cggggcccct
      661 gcccatcttc aaccgaagcc agcacgcaca tgtcattgaa gacctgcact gcaacttgtg
      721 caacgtggat gtgagcgctc gctccaagca ctgcagcgcc tgcaacaagt gcgtgtgcgg
      781 tttcgaccac cactgcaagt ggctcaacaa ctgtgtgggc gagcggaact accggctctt
      841 tctacacagt gttgcatccg ctttactggg cgtcctgctc ctggtgctgg tggccacata
      901 tgtcttcgtg gagttctttg tcaaccccat gcgtctgcgc accaaccgac actttgaagt
      961 cctgaagaat cacacggatg tgtggttcgt gttcctgcct gccgcccccg tggagaccca
     1021 ggcccctgcc atcctggccc tggccgccct gctcatcctt ctgggcctcc tgtccacagc
     1081 cctcctgggg cacctgctct gcttccacat ttatctcatg tggcacaagc tcaccaccta
     1141 tgagtacatc gtgcagcacc gcccaccaca ggaggccaag gggttcaca gggagctcga
     1201 gtcatgtcct cccaagatgc ggcccattca ggagatggag ttctacatgc ggaccttcag
     1261 acatatgcgc ccagagcccc ctggccaggc cgggccagca gcagtgaatg ccaaacactc
     1321 tcgccctgcc tccccggatc cgaccccagg taggagggac tgtgctgggc ctccggtcca
     1381 ggtggagtgg gatagaaaga agcctctacc ctggcgctcg cctctgcttc ttttggcgat
     1441 gtggggccct caggctcccc cgtgtctctg cagaaaaaga ggaagaggcg cgtgtataaa
     1501 gtgcgaacgt ctgagacctc ggatccggcg tcggggccta gggcccccag ccgccgctcc
     1561 agctcgtcga cggattccgc ggacgccagc cctgtgcacg ccgctggccc tgccggcgcc
     1621 taccactcgg cgtcggcaga gtccgtggac gagattccag tggcgcagac gcgcctgggc
     1681 agcgccgctc tggccgcccc gcggggccgg ggccgacagc ccacgctggc gcggcaggcg
     1741 cgtgcgcccg ccgttttcgt gagcccgagc agcggcgagc ccagggcgcc gggcggccgg
     1801 gaggctggtc tggcttagct gggccgagag gccggagggc cgagttagag cggccggcct
     1861 gactctctat gcaacacccc atccttgccg caccgagtgc actttagggg cccctacggc
     1921 cggcgggatc ggcctccctc ccccacgact cagcaatacc cgccccaccg gctgtgatgc
     1981 tccaataaac tttttatgc ttttgcggaa aaaaaaaaaa aaaaaa
//
```

FIG. 12-4

ZDHHC2:

```
FEATURES             Location/Qualifiers
     source          1..4012
                     /organism="Homo sapiens"
                     /mol_type="mRNA"
                     /db_xref="taxon:9606"
                     /chromosome="8"
                     /map="8p21.3-p22"
     gene            1..4012
                     /gene="ZDHHC2"
                     /gene_synonym="DHHC2; ZNF372"
                     /note="zinc finger, DHHC-type containing 2"
                     /db_xref="GeneID:51201"
                     /db_xref="HGNC:18469"
                     /db_xref="HPRD:15715"
     exon            1..527
                     /gene="ZDHHC2"
                     /gene_synonym="DHHC2; ZNF372"
                     /inference="alignment:Splign"
                     /number=1
     CDS             398..1501
                     /gene="ZDHHC2"
                     /gene_synonym="DHHC2; ZNF372"
                     /note="rec; zinc finger, DHHC domain containing 2; ream;
                     DHHC-2; zinc finger protein 372; reduced expression in
                     cancer protein; zinc finger DHHC domain-containing
protein
                     2; reduced expression associated with metastasis
protein"
                     /codon_start=1
                     /product="palmitoyltransferase ZDHHC2"
                     /protein_id="NP_057437.1"
                     /db_xref="GI:7705949"
                     /db_xref="CCDS:CCDS47810.1"
                     /db_xref="GeneID:51201"
```

FIG. 12-5

```
                     /db_xref="HGNC:18469"
                     /db_xref="HPRD:15715"
/translation="MAPSGPGSSARRRCRRVLYWIPVVFITLLLGWSYYAYAIQLCIV
SMENTGEQVVCLMAYHLLFAMFVWSYWKTIFTLPMNPSKEFHLSYAEKDLLEREPRGE
AHQEVLRRAAKDLPIYTRTMSGAIRYCDRCQLIKPDRCHHCSVCDKCILKMDHHCPWV
NNCVGFSNYKFFLLFLAYSLLYCLFIAATDLQYFIKFWTNGLPDTQAKFHIMFLFFAA
AMFSVSLSSLFGYHCWLVSKNKSTLEAFRSPVFRHGTDKNGFSLGFSKNMRQVFGDEK
KYWLLPIFSSLGDGCSFPTCLVNQDPEQASTPAGLNSTAKNLENHQFPAKPLRESQSH
                     LLTDSQSWTESSINPGKCKAGMSNPALTMENET"
     exon            528..554
                     /gene="ZDHHC2"
                     /gene_synonym="DHHC2; ZNF372"
                     /inference="alignment:Splign"
                     /number=2
     exon            555..649
                     /gene="ZDHHC2"
                     /gene_synonym="DHHC2; ZNF372"
                     /inference="alignment:Splign"
                     /number=3
     exon            650..770
                     /gene="ZDHHC2"
                     /gene_synonym="DHHC2; ZNF372"
                     /inference="alignment:Splign"
                     /number=4
     exon            771..840
                     /gene="ZDHHC2"
                     /gene_synonym="DHHC2; ZNF372"
                     /inference="alignment:Splign"
                     /number=5
```

FIG. 12-6

```
exon            841..873
                /gene="ZDHHC2"
                /gene_synonym="DHHC2; ZNF372"
                /inference="alignment:Splign"
                /number=6
exon            874..994
                /gene="ZDHHC2"
                /gene_synonym="DHHC2; ZNF372"
                /inference="alignment:Splign"
                /number=7
exon            995..1127
                /gene="ZDHHC2"
                /gene_synonym="DHHC2; ZNF372"
                /inference="alignment:Splign"
                /number=8
exon            1128..1254
                /gene="ZDHHC2"
                /gene_synonym="DHHC2; ZNF372"
                /inference="alignment:Splign"
                /number=9
exon            1255..1347
                /gene="ZDHHC2"
                /gene_synonym="DHHC2; ZNF372"
                /inference="alignment:Splign"
                /number=10
exon            1348..1460
                /gene="ZDHHC2"
                /gene_synonym="DHHC2; ZNF372"
                /inference="alignment:Splign"
                /number=11
exon            1461..1535
                /gene="ZDHHC2"
                /gene_synonym="DHHC2; ZNF372"
                /inference="alignment:Splign"
                /number=12
```

```
     exon            1536..4012
                     /gene="ZDHHC2"
                     /gene_synonym="DHHC2; ZNF372"
                     /inference="alignment:Splign"
                     /number=13
     STS             1541..1660
                     /gene="ZDHHC2"
                     /gene_synonym="DHHC2; ZNF372"
                     /standard_name="RH36493"
                     /db_xref="UniSTS:4085"
ORIGIN
        1 gtgggagccc gcgaggtggc ccgagcgagg gccccgcatc cccgcagagc ccgcccgagg
       61 gcgcagcctg ccacgccagg ggaggcggcc gggcggcggg gaacggcggg ggcggagcgc
      121 agcctcccga cgccgccgcc tcaccgcccc cctccgcctc ctcggcctcc gctcgcagcc
      181 gccgcctccg cctccgccgg gctgaggagc cgggagtccg ccgcgccggc tcggggctgc
      241 gggatgggga gttagcgcca cggcggcggc agtggccgca gcgcaccccg ccgccgccca
      301 ggagcccgtc cagccagggg tgccgggccc gcccagcccg ccccggagcc aggcccgcgg
      361 gcggcggcgg agctgggcag gtggatgcgg ctggaagatg gcgccctcgg gcccgggcag
      421 cagcgccagg cggcggtgcc ggcgggtgct gtactggatc ccggtggtgt tcatcaccct
      481 cctgctcggc tggtcctact acgcctacgc catccagctg tgcatagtgt ccatggaaaa
      541 cactggcgaa caagttgtgt gcctgatggc ctatcatcta ctttttgcaa tgtttgtctg
      601 gtcatactgg aaaactatct ttacattacc aatgaatcct tcaaaagaat tccatctctc
      661 ttatgcagag aaagatttgt tggagagaga gccaagagga gaagcccatc aggaagttct
      721 taggcgagca gccaaggatc ttcccatcta taccaggacc atgtctggag ccatccgata
      781 ctgtgacaga tgccaactta taaaaccaga tcgctgccat cactgctccg tctgtgataa
      841 atgtattttg aagatggatc atcattgtcc atgggtgaac aattgtgttg gattttcaaa
      901 ttataagttc tttctccttt tcttggctta ttctctgctc tactgccttt ttattgcggc
      961 aacagattta cagtatttta tcaaattttg gacaaatggc ctacctgata ctcaagccaa
     1021 gttccatatt atgtttttat tctttgctgc agctatgttt tctgtcagct tgtcttctct
     1081 gtttggctat cattgttggc tagtcagcaa aaataaatct acattagagg cattcagaag
     1141 tccagtattt cgacatggaa cagataagaa tggattcagc ttgggtttca gtaaaaacat
     1201 gcgacaagtt tttggtgatg agaagaagta ctggttgcta cccatttttt caagtctagg
     1261 tgatggctgc tcctttccaa cttgccttgt taaccaggat cctgaacaag catctactcc
     1321 tgcagggctg aattccacag ctaaaaatct cgaaaaccat cagtttcctg caaagccatt
     1381 gagagagtcc cagagccacc ttcttactga ttctcagtct tggacggaga gcagcataaa
     1441 cccaggaaaa tgcaaagctg gtatgagcaa tcctgcatta accatggaaa atgagactta
     1501 actcttcaag caagataaat tcatacttta taaaagtatc aatgctgtag atggatggaa
```

FIG. 12-9

```
1561 gaggcttccc acaggaaggt gccaccagtc agttgtgcct atgtcccttt ggctggaaat
1621 gcagaatatg aattgattag ttctctccaa gccattgctt aaaatataac atgttttgga
1681 tccaatacac acattgttac aactaacaca aattcctatt aaatattaaa agtagttctg
1741 gtttattaat caacggggaa aacatcttct ccaaaaaact tggaataaat ccaaggacca
1801 gtttttaccc aaatatatgg gtagcacagt ttatcacata gaaactccat taatcatctg
1861 attttccgaa tctgaaaatt gagactatta agatattagg atttcagaga tttcaagtca
1921 cattataatg ataagcatta ttcataaaac ttgttacctt taagaaggtg gaagtggcaa
1981 accatacttc tttttttcc tctgatgtga atccagcctc agactgagtg aactgtaata
2041 attatgaatt cattacagag tccaggtggc ctgcagttga agatcatcaa ccatttttgc
2101 ctcacttaat tccagccttt tgttttctgc tggaaaataa gtgtggacat tgaagcttga
2161 gctctcaaag cagttggctg gaatactttt gtcagaatac ggtacatttc tattacatca
2221 gaaatatatt ttcatctctt cttgttaaat tgggaggaaa tttatgatag caattatgaa
2281 gattgtttta tgacattctt ttgtcagttt ggctttctaa aaatctcttt ttagattatt
2341 tctcctgttg aacatagtaa aactattgaa tttctcttaa gaattcctaa taggtcaata
2401 gatttaccct ccagtgatat ctatattatt tctttctcgt ctcatcaaaa tgatgacagg
2461 taaactatat ttttccttaa acacctatta cagttaaatt atgcaaatca ttaaataaaa
2521 atcatacaac ttttggaaag ttagttcaac atgaactaaa atggcatgct atttggaaat
2581 ttagtttgag ataaactaaa gtgtgttgat gccagaatgt tcagcttcag taaatataat
2641 aagctcttgt gccttgtatg cactatttaa aaaaagtttt ttttatttga gtccagtata
2701 attcatgtaa atgttaacaa ttagaataat actctgtatg ctttttgat actgattttg
2761 agaatttaaa gcagattacc ttttaaaact ggaccaacta agtaattggt atttaatcaa
2821 agagaaaatg gtaataaact tttcaaaatc tttgttaaac caaacattca acacaaaata
2881 aactagaagg ccagaggata atggaataaa agatcattgc aattacttat ccttcctaaa
2941 aatatagttt tatattaatt gtgcttatgg aagaaacaat gtcagccaag tccattttat
3001 agtttgagtg caattctttg aacaatagaa atatctgcag tctttcacag atttgtatta
3061 tgctgaagag tttcatctga caatctgctt caagaaatct cagaaaatat gataacattt
3121 taactttcat tttagagcac gttttggtca tttttaaaaa tacctaaagt gccagaccgg
3181 aacctatagc tactgctaga agtcttaaaa aaaccaacag cagcacagga tgtattaaga
3241 attatatgaa gtcaggtttg tttttttttt tttttttttt tcaaagcaca gtactgttag
3301 ctgtttttgt ggacaggatt cgattaagta ttccctcttg tcaaactgga agctagggga
3361 aaaagaggga ttttatcctt ttactcttct agagtactgt taatgcccct ttcccacagt
3421 cttttatata attaaatata tgtcaataca cattagaatc agatttgaaa aagttaaaac
3481 aatttcattg ttgtaattgt tccctttctg ttttcatata gtgaataacc tttaaagggt
3541 tgtttgtttt tgttttgaat tataggagtt ataatctttg gagatgattg catatctcat
3601 tagatatgca atataaattt atctgagtga acaaagtgct aaataaatag atctacattt
3661 tgtacatatt tatataaaat ttacctttaa gtatttactt taaaaaattt aatggcttaa
```

```
3721 ctcgaacttg aagacacata cttcaactgt ccttattgtc cattaaactg ataattttga
3781 ttttcttgc ttttatagat tttactatat aggaatcaag atttaagaaa ttttgcatta
3841 aaaatagtgt accaatgctt catatacgtt agttatttgc tattatgtag ggaagaggat
3901 tgttatttca aagatatatt aaagaacagt tgcatctgaa tataatcatg atgcattcaa
3961 tgaagttcat atccatgaat tcactcctaa tataccctaa taaagtggtt ga
//
```

ZDHHC3 (isoform 1 of 3):

```
FEATURES             Location/Qualifiers
     source          1..12630
                     /organism="Homo sapiens"
                     /mol_type="mRNA"
                     /db_xref="taxon:9606"
                     /chromosome="3"
                     /map="3p21.31"
     gene            1..12630
                     /gene="ZDHHC3"
                     /gene_synonym="DKFZp313D2314; FLJ20209; FLJ45940; GODZ;
                     ZNF373"
                     /note="zinc finger, DHHC-type containing 3"
                     /db_xref="GeneID:51304"
                     /db_xref="HGNC:18470"
     exon            1..250
                     /gene="ZDHHC3"
                     /gene_synonym="DKFZp313D2314; FLJ20209; FLJ45940; GODZ;
                     ZNF373"
                     /inference="alignment:Splign"
                     /number=1
     exon            251..580
                     /gene="ZDHHC3"
                     /gene_synonym="DKFZp313D2314; FLJ20209; FLJ45940; GODZ;
                     ZNF373"
                     /inference="alignment:Splign"
                     /number=2
```

FIG. 12-10

CDS 275..1174
/gene="ZDHHC3"
/gene_synonym="DKFZp313D2314; FLJ20209; FLJ45940; GODZ; ZNF373"
/note="isoform 1 is encoded by transcript variant 1; Golgi apparatus-specific protein with DHHC zinc finger domain; DHHC1 protein; zinc finger, DHHC domain containing 3; golgi-specific DHHC Zinc Finger Protein; DHHC-3; zinc finger protein 373; zinc finger DHHC domain-containing protein 3; palmitoyltransferase ZDHHC3"
/codon_start=1
/product="palmitoyltransferase ZDHHC3 isoform 1"
/protein_id="NP_001128651.1"
/db_xref="GI:206597477"
/db_xref="CCDS:CCDS46811.1"
/db_xref="GeneID:51304"
/db_xref="HGNC:18470"

/translation="MMLIPTHHFRNIERKPEYLQPEKCVPPPYPGPVGTMWFIRDGCG

IACAIVTWFLVLYAEFVVLFVMLIPSRDYVYSIINGIVFNLLAFLALASHCRAMLTDP

GAVPKGNATKEFIESLQLKPGQVVYKCPKCCSIKPDRAHHCSVCKRCIRKMDHHCPWV

NNCVGENNQKYFVLFTMYIALISLHALIMVGFHFLHCFEEDWTKCSSFSPPTTVILLI

LLCFEGLLFLIFTSVMFGTQVHSICTDETGIEQLKKEERRWAKKTKWMNMKAVFGHPF
SLGWASPFATPDQGKADPYQYVV"

exon 581..705
/gene="ZDHHC3"
/gene_synonym="DKFZp313D2314; FLJ20209; FLJ45940; GODZ; ZNF373"
/inference="alignment:Splign"
/number=3

FIG. 12-11

```
exon            706..802
                /gene="ZDHHC3"
                /gene_synonym="DKFZp313D2314; FLJ20209; FLJ45940; GODZ;
                ZNF373"
                /inference="alignment:Splign"
                /number=4
exon            803..884
                /gene="ZDHHC3"
                /gene_synonym="DKFZp313D2314; FLJ20209; FLJ45940; GODZ;
                ZNF373"
                /inference="alignment:Splign"
                /number=5
exon            885..1015
                /gene="ZDHHC3"
                /gene_synonym="DKFZp313D2314; FLJ20209; FLJ45940; GODZ;
                ZNF373"
                /inference="alignment:Splign"
                /number=7
exon            1016..12602
                /gene="ZDHHC3"
                /gene_synonym="DKFZp313D2314; FLJ20209; FLJ45940; GODZ;
                ZNF373"
                /inference="alignment:Splign"
                /number=8a
STS             1906..2764
                /gene="ZDHHC3"
                /gene_synonym="DKFZp313D2314; FLJ20209; FLJ45940; GODZ;
                ZNF373"
                /standard_name="ZDHHC3__4936"
                /db_xref="UniSTS:462956"
STS             2442..2560
                /gene="ZDHHC3"
                /gene_synonym="DKFZp313D2314; FLJ20209; FLJ45940; GODZ;
                ZNF373"
                /standard_name="A005U27"
                /db_xref="UniSTS:21034"
```

FIG. 12-12

```
     STS             2442..2560
                     /gene="ZDHHC3"
                     /gene_synonym="DKFZp313D2314; FLJ20209; FLJ45940; GODZ;
                     ZNF373"
                     /standard_name="G20511"
                     /db_xref="UniSTS:21033"
     STS             2556..2694
                     /gene="ZDHHC3"
                     /gene_synonym="DKFZp313D2314; FLJ20209; FLJ45940; GODZ;
                     ZNF373"
                     /standard_name="D3S4221"
                     /db_xref="UniSTS:26874"
polyA_signal    2673..2678
                /gene="ZDHHC3"
                /gene_synonym="DKFZp313D2314; FLJ20209; FLJ45940; GODZ;
                ZNF373"
polyA_site      2700
                /gene="ZDHHC3"
                /gene_synonym="DKFZp313D2314; FLJ20209; FLJ45940; GODZ;
                ZNF373"
polyA_signal    3807..3812
                /gene="ZDHHC3"
                /gene_synonym="DKFZp313D2314; FLJ20209; FLJ45940; GODZ;
                ZNF373"
polyA_site      3834
                /gene="ZDHHC3"
                /gene_synonym="DKFZp313D2314; FLJ20209; FLJ45940; GODZ;
                ZNF373"
STS             7507..7670
                /gene="ZDHHC3"
                /gene_synonym="DKFZp313D2314; FLJ20209; FLJ45940; GODZ;
                ZNF373"
                /standard_name="RH103204"
                /db_xref="UniSTS:97537"
```

FIG. 12-13

```
STS             7527..7768
                /gene="ZDHHC3"
                /gene_synonym="DKFZp313D2314; FLJ20209; FLJ45940; GODZ;
                ZNF373"
                /standard_name="STS-AA027089"
                /db_xref="UniSTS:5753"
polyA_signal    7787..7792
                /gene="ZDHHC3"
                /gene_synonym="DKFZp313D2314; FLJ20209; FLJ45940; GODZ;
                ZNF373"
polyA_site      7813
                /gene="ZDHHC3"
                /gene_synonym="DKFZp313D2314; FLJ20209; FLJ45940; GODZ;
                ZNF373"
polyA_signal    7864..7869
                /gene="ZDHHC3"
                /gene_synonym="DKFZp313D2314; FLJ20209; FLJ45940; GODZ;
                ZNF373"
polyA_site      7884
                /gene="ZDHHC3"
                /gene_synonym="DKFZp313D2314; FLJ20209; FLJ45940; GODZ;
                ZNF373"
STS             9016..10454
                /gene="ZDHHC3"
                /gene_synonym="DKFZp313D2314; FLJ20209; FLJ45940; GODZ;
                ZNF373"
                /db_xref="UniSTS:484717"
STS             12340..12477
                /gene="ZDHHC3"
                /gene_synonym="DKFZp313D2314; FLJ20209; FLJ45940; GODZ;
                ZNF373"
                /standard_name="RH98231"
                /db_xref="UniSTS:92255"
polyA_signal    12577..12582
                /gene="ZDHHC3"
```

```
                     /gene_synonym="DKFZp313D2314; FLJ20209; FLJ45940; GODZ;
                     ZNF373"
     polyA_site      12602
                     /gene="ZDHHC3"
                     /gene_synonym="DKFZp313D2314; FLJ20209; FLJ45940; GODZ;
                     ZNF373"
ORIGIN
        1 gcgtcatcaa cctgcgcggc ggccgctcct gcagccgcgg ccgccgccac tgccgggaga
       61 gctcgatggg cttctcctgc gcgccgcccg gtgtctggcc gagtccagag agccgcggcg
      121 cctcgttccg aggagccatc gccgaagccc gaggccgggt cccgggttgg ggactgcagg
      181 ggaaggcagc ggcggcggcg gcgggagccc caccggggtc tgggactggg gaactgcctc
      241 cggcttcacg atgccagtat ggacagaata gcttatgatg cttatcccca cccaccactt
      301 ccgaaacatt gagcggaaac cagaatacct ccagccagag aagtgtgtcc caccccccta
      361 ccctggtcct gtgggaacca tgtggtttat ccgtgacggc tgtggcatcg cctgtgccat
      421 cgttacctgg tttctggtcc tctatgcgga gttcgtggtc ctctttgtca tgctgattcc
      481 atctcgagac tacgtgtata gcatcatcaa cggaattgtg ttcaacctgc tggccttctt
      541 ggccctggcc tcccactgcc gggccatgct gacggacccc ggggcagtgc ccaaaggaaa
      601 tgccactaaa gaattcatcg agagtttaca gttgaagcct gggcaggtgg tgtacaagtg
      661 ccccaaatgc tgcagcatca agcccgaccg agcccaccac tgcagtgttt gtaagcggtg
      721 cattcggaag atggaccacc actgtccctg ggtcaacaac tgtgtaggcg agaacaacca
      781 gaagtacttc gtcctgttta caatgtacat agctctcatt tccttgcacg ccctcatcat
      841 ggtgggattc cacttcctgc attgctttga agaagattgg acaaagtgca gctccttctc
      901 tccacccacc acagtgattc tccttatcct gctgtgcttt gagggcctgc tcttcctcat
      961 tttcacatca gtgatgtttg ggacccaggt gcactccatc tgcacagatg agacgggaat
     1021 agaacaattg aaaaaggaag agagaagatg ggctaaaaaa acaaaatgga tgaacatgaa
     1081 agccgttttt ggccacccct tctctctagg ctgggccagc cccttttgcca cgccagacca
     1141 agggaaggca gacccgtacc agtatgtggt ctgaaggacc ccgaccggca tggccactca
     1201 gacacaagtc cacaccacag cactaccgtc ccatccgttc tcatgaatgt ttaaatcgaa
     1261 aaagcaaaac aactactctt aaaacttttt ttatgtctca agtaaaatgg ctgagcattg
     1321 cagagaaaaa aaaaagtccc cacattttat tttttaaaaa ccatcctttc gatttctttt
     1381 ggtgaccgaa gctgctctct tttcctttta aaatcacttc tctggcctct ggtttctctc
     1441 tgctgtctgt ctggcatgac taatgtagag ggcgctgtct cgcgctgtgc ccattctact
     1501 aactgagtga gacatgacgc tgtgcgtgga tggaatagtc tggacacctg gtgggggatg
     1561 catgggaaag ccaggagggc cctgacctcc cactgcccag gaggcagtgg cgggctcccc
     1621 gatgggacat aaaacctcac cgaagatgga tgcttacccc ttgaggcctg agaagggcag
     1681 gatcagaagg gaccttggca cagcgacctc atcccccaag tggacacggt ttgcctgcta
```

FIG. 12-16

1741 actcgcaaag caattgcctg ccttgtactt tatgggcttg gggtgtgtag aatgattttg
1801 cgggggagtg gggagaaaga tgaaagaggt cttatttgta ttctgaatca gcaattatat
1861 tccctgtgat tatttggaag agtgtgtagg aaagacgttt ttccagttca aaatgcctta
1921 tacaatcaag aggaaaaaaa attacacaat ttcaggcaag ctacgttttc ctttgtttca
1981 tctgcttcct ctctcaccac cccatctccc tctcttcccc agcaagatgt caattaagca
2041 gtgtgaattc tgactgcaat aggcaccagt gcccaacaca tacagcccca ccatcatccc
2101 cttctcattt tataaacctc aaagtggatt cactttctga tagttaaccc ccataaatgt
2161 gcacgtacct gtgtcttatc tatattttaa cctgggagac tgttgtcctg gcatggagat
2221 gaccatgatg ctggggttac ctcacagtcc ccaccctttc aaagttgaca tatggccatc
2281 ccattggcca gaatccacag acacacctaa gcctgtggca ctgggacaga atagattttc
2341 catttgagag gcacttcctg tgtcagtctt gtttgaagga ggtggtgatg gtggatagag
2401 gtgaaggagg tagggagtgc cctccaagtg caaaaataac aaatatgatt attgaccatc
2461 ggggaattct cacacattga tttgtttttt aagcaattgc cagaaacccc ctttttttagc
2521 ttttgcttgg ggtgggggta ggagttaagg tttattcaat cctgtcctgg gtagggcgaa
2581 agttaatcta gccatgtgat ttttcagaaa agtaagtgga acatgctgcc acttttcaat
2641 tctgtcagtg cttccacatg gaaacaaaat gcaataaaat ttttccaaaa cctgttctga
2701 tttagctctc tcttgaggtg ttacccttag tgggaggccg actatccaca atctacttga
2761 gttttctctg gttgggtgtt tgtttcattg ctctgtctct tgaatgagga tactttattt
2821 tttttgtttt aaaatgcatt tatggtccct ctcttgaacc agcttgcccc accaggcctc
2881 tttcctttgc tttctgcagc ctgaatcaat tcctttgtgc tgatgggctc tcctaagagc
2941 tttcctgagt cagttaactt tacctcgtgt ctacggtgct attcatgcga tacgggcgag
3001 gctgagatgc taagattaaa aagaaaagaa tgctgtttta gatcaagttg atagcatttg
3061 ttttccatat gcttttttaa aatttttttca taacatacag ctcagttagg tgtatgaaag
3121 aagtcttatt gtattaaata actagagcag ggctacagct ctggccctcc cctaggggga
3181 agagattggt aatactccat cttccagggc atttttttaaa gtgagccagg ttagctcttt
3241 tcccctggca tttctcagga atgcagtaga tagtgctgaa gatgcactga ctttttttta
3301 gtcctaaaaa tagaaactcc tcctttaaag ctgtgcatac tatgcttatc tttccaatag
3361 agtgcggttc cttcagatat cctataggat tctgcctctg gttttgtata ggccttggct
3421 agaaagagtc aatgtttctg agctctcaaa ccagttgctc tcagaagata ggaatacccc
3481 aaggttcctg gcatttttcc tatttcattt ttgttcagac tgatattttg ccaagagcac
3541 aatgactgag gaatgtagcc atcatttgca gggtagtgat tggttcccag cctggcttcc
3601 acacaggaca ggaagggaaa gcatccctga gctctcctca gtatttccgg atgtaatgaa
3661 agagcacatc tttctacaca aagtcagccc caacttttgg cttggtcaca ggagttctga
3721 tagtactgtt tggtgcactc atgggaaatt gaaccagtcg tagccacagt ctttcagagc
3781 ctggcctctg gggagtggaa gtgaaaaata aagatgtggc ttgttggatt gtgatcccca
3841 gcttcctttc cttctgtcaa ctctgtcagg tttgtgttca tagcaactag actgaatatg

FIG. 12-17

3901 caaaaggctt agatccaagc aaatctataa tctatgcata tttgcatggg cttggtaata
3961 tcatgtacac aaaacacatt tgggtagaag tgcatgtgct aaatctcctt ttagtcccac
4021 cattttgtct tcttcatact gtacttcctc tttttgttt gagacaaggt cttgctctgt
4081 cacccaggct ggaatgcagt ggcacaatta gagctcactg cagccttgaa ctcctgggct
4141 caagtgattc ttgtgccttg gcctcctgaa tatccagggc tacaggcacg tactaccatg
4201 cctggctaat ttttttgttt tttaatagag tcagggtctc actgtgttgc cctagctagt
4261 ctcaaatgcc cggcctccag caatttcct gccttagcct cccaaagtcc tgggattaca
4321 ggcgtgagcc actgggccca gccctgtact tcttgaaaaa gccccaagta ttagcttttg
4381 ctcatctggc taggccactt aaatagttag aatccaccgt cccctaatgc agaaaccgtt
4441 taggtgaggt aaattaacaa acattttaag ccgggcgcgg acacttctca ctgtggacat
4501 ccctcacgcc tgtaatccca gcactttggg aggccgaggc gggcagatca cgaggtcaag
4561 agatcgagat catcctggct aacacggtga aaccctgtct ctactaaaaa tataaaaaaa
4621 ttagctgggc gtggtggcag gcgtctgtag tcccagctac ttgggaggct gaggcaggag
4681 aatggcgtga acccgggaag tggagcttgc agtgagccaa gatcgcacca ctgcactcca
4741 gcctgggcga cagagtgaga ctccgtctca aaaaaaaaaa acaaacattt taaacatgta
4801 tgtgaggttg gcattacaca gaaactcctc tccgggtggg ctgggatggg ctttctcagc
4861 caggctaatg ggttttaaat ttctctcttt tcaagacttg cagtgcatca gcttaaaggg
4921 tgagccagcc agtagagggg aaggcgcccc acctagaagg tgcccttaga tatcaaagaa
4981 atgtgaaaag agaaagattt tgctagaatc ctcctcaaag gtgttcttga ggttgccaga
5041 ccagcaacgt caacatcagc atcacctgag aacttgttag aaatgcacat tctcggtccc
5101 caccccaggc taccgaacca gaaaccgagc ggggcccagc agcccgtgtc ttaacagccc
5161 tccaggtgat tctgactatc aagtttgaga atccagttgg ggctagcagg agtccccccct
5221 caggtggtcc ctgatgcctg ctggtgatat gggtcttgtg tgctgctggg ctcagcatag
5281 tgcagttggg gtgtgctgat tgtgagacag gcacgtgttc cctccgcgga gaagccactg
5341 agactgcctt ccctcataag ctgcggcctc cccaacaaac aactgccaag acatcaaaga
5401 aagtctgtat gaagcagatc caaattatta gcctgcccac cactccttgt gcatctcatc
5461 agtggaaccc atctctagac caagggccct ttgggtgaag aagcagcccg gaagggaaag
5521 agaaaagagt agaaccaagg gacctccaga tgggagcggc ggccggtgag tagtctagag
5581 ccaggggcat tgtagcagcc tggatacatg acctgaacac gtcttgacct ttgctttcta
5641 cgtgtgggtt tcaacaccca tgtggctttt tcttgtattc tttaaatatg tatctggctt
5701 aggatcacct catagaagag aaagaattca cagtgaagca gaaacaagcc actgaccagc
5761 gtactcccaa cctgaacctt ctttttctca ccctctccct caagtaaaca tcttgctgac
5821 ttgagcagtg tgattgccgt agcaaagcag agtggccccc agggatcccg ctctgttggg
5881 cccacaggag gagccgatga agctgatcca aggagtgagg acaagcgctg cagagggacg
5941 ttcgctaaaa gccttctagg ggccgcacat gctctaacac ggacataagg atgccctgaa
6001 tttctgcagc tgaggccata tagtctggtg accaagtatt tgggtcctgg cttcagtctt 6061 tggttgaaat gtctgcttgg ctacttatta ccgcacctac taccaaaata tgaccttgag
6121 cagtaacttc tttaagcctc agtttttca tctgaaaacg ggaatgataa tctaaatcac
6181 aaagttaatg gaaggattaa atgagggtga tgaataggaa tgtatagcgt ctggccctgg
6241 tatggcttta taaatgttag ctgtgttgga gctgtgcttt tcaaaccatt ggtcacagcc
6301 attcatggtt tgcaaccagc atgtttttca agaaaaatgt ttaatgcatt acatattgca
6361 ggataagtat tgttttatga agcttaggga gttgtgtgta tatgtgttct ggaatgcaac
6421 agaaaaatgt ttcctcttgt gggttacaat atagaggtat gaaatctctg atgaggagag
6481 acagtgttat ctggcccgct atgaagagac acatttgcat aggctgctcc ctgaggctct
6541 ggctttctac atctgatgat acagggagca gggaacagcc tgttctcgtt ctgtggggct
6601 cagctgagtc tgttctgcac agactcttcc ttcctcggga gccttagtcc taatacattc
6661 attttggagt gttggtgagt ttgttcacag atcacagctc atgtgtcacc cagactgacc
6721 tgggccaaaa ggcccatcac acaccctgca agagcttctg gtgtcgacta tgaccccctt
6781 accaggcatc aaccattttt gttcgttctc ttgagcctga agctactatt actgctcctc
6841 tgcaaacctc aagcttaaga actttgcctg caggatccct ttaaatccac acaaaactca
6901 aaattgagtc ctaccaggaa aaagcagccc tcagcccatt tttatacatc ggatttgttt
6961 gcaatatttt ctttctagac tcaaaagtca acactccctg aaagtttgtc gactttactg
7021 ctgaagacct ctggtagaca ggccaggctc tgtctggaat actttatgag gttggtgagg
7081 aggttgagta taatccaaga gtgcctatct gggagcatgc cacatgaatg gcaaataatc
7141 atcctgtggg ctcttggctt cattcccctt ctctctgact gagctcagcc tgggcacagt
7201 ggtgatttgc agtagaactg gaaacctgtt gggcagaaaa aaagacacta gttctggttc
7261 cagttctgat acataacaag ctagatgagc cttggccacc gtcatggcct cttggaactt
7321 ctgtttcttc cccatctgcc aatcatcaat actcataccc acctcctcac aaggaggcca
7381 taaaaaccta tggtcatggc tttgagtcca agtcagtgtg gatgcagcca gtctgtcatt
7441 tttgggtgtt tcctctgtag ccgggtctgc catatggtga tgtcccagct ctcgtgctat
7501 gaagttaaag cctctttctc aacaggctgc agatgatcac ccaggaagag aatgcagaat
7561 gcccaaagca aaccatctca gctggtcact gcttctgtgc caagaaggga ggcctggcga
7621 ggggccagtc aggaagcagc atggcatcac atgctcatga cccacatgaa ggtcccttta
7681 gacttgtgtc aacaagatcc attttctgaa acaactattt ttgttctgat tataaaagta
7741 acattggctc attggtaaaa cttggattgt gtgagaagtc tacagaaata aatacaaatc
7801 ctctagaatt ccatccccaa aagtaaccac tcagacaaat gttctaatgt catgtaaaac
7861 catattaaac catcttttct agctgcatag tgttatagaa tcatttgctt aaccatcatt
7921 attgggcatt tctcatttcc agctttgcat tattataatt cagtgttcaa gtttgtattg
7981 cataaatctt tgtctcagat tattgattat ttttaaactt tttgtgaaat cagacttaca
8041 aaaatgtgac aaaaacagta caaagagttc ccatgtacct ttcagtcagt ctcaccaaag
8101 gtaaacattt tatacaacca taatacaaat ataaaaccct ggacattggc aacaccatac
8161 ccttaactaa tgtatgtacc ttattcacat ttctccagtt gtcccattaa cacccttttc

8221 tgttccagga tcccacactg catcatttgc gatgtctcct tagtctcctc cagtttgtga
8281 cagttcctca gtcttccttt gtctttcatg accttgaccc tttttaaaaa tcgaggtgaa
8341 attcctgtaa cacaaaatta gccattttaa agtgtacatt taatgcattc acaatgtttt
8401 gtaaccacca ggtctgtctg gttccaaaat cttttcatca atctttgacc cttttgaaga
8461 ttgtagggca ggtattctgt aggctgtcct tcagattgtg tttttgatgt ttttctcatg
8521 attagattga ggttaggcat ttggggcagg agcactgctg aagcaatgtg tcctcgttgc
8581 accgtatcag gaggcatatg gtgttgatac gtttcattat tgtgatgtta actttgatca
8641 ttgggtgaag gtggtacgtg caatgtttct tccctgctat taaggtactg tttttccctt
8701 tgtaattgat aagtatctta tgaggatata cttttgagat ccaatttttt taacttagaa
8761 tttattcaaa agtcaagaat cttaaatctc tgaaatggcg tgggaagaaa aagtgctaga
8821 tacacagaga tctttcttga gtcatgtgaa ggagcagtgc ccaagcccag caaacccaca
8881 gcaaattccc ttggcttcca gaagagatgg agaaagcagt gcccccagtg gagggtcaaa
8941 ggcctctgtg cagggtgttg tgggcctgga gagctggcct ggccatgtct ttacctcctc
9001 tgggcatctc cccaccccaa caccctttct gtggcctggt ggctgagttg cagccgacac
9061 ccagaggcag gtgagttgac agcttggaag aggctgcagg gtggatctgc tgcatgagca
9121 ggcctgagcc cagccttacc tccccacagt ggtcctgtgt gccctccggc tgcctaatgc
9181 atgttggcac ttgctgtacg agcacccgct tcttcacctc gcatgctgtt tgtgtcctgc
9241 actccttcct taaccccatc gtccttctgc tgtgtttgca gcccctatct accctggtgg
9301 gagtggccaa aaatatttag gaggggatca ccagtttgta gtggcctcag aggatgtgtg
9361 gtccccctta tgcctcagcc actcatcagc ctagcccctg cccatcatct ggcattgcac
9421 ttgtggaagg aaagaagggg agggctgggt ggtgggtgga gaacacgtca gtccaccagg
9481 cgggccctgc ttgctgtgtt cctccacgct gctgtccacc cacaccccag cagtcctctg
9541 agggacctcc cgggggtgac ctgggccaca acagactgcc cactcagacc ccatcttacc
9601 catgccgtgg acaccccgcc cccccccccg ccactgctat gctatagctg ggggtgtcta
9661 tgtgagctgt acagcccagc accacgctga cgatgttctt catccccttc tccctgcagg
9721 gcatcgagcg cctcaaacga aagaaccagc ccagggagca catggggagc tggcagtcag
9781 taaaggagac ctttggtggg gacttctccc tgaactggtt caaccccttc tccagaccgt
9841 gtcagccaga gatccccagt gacaaagaca tggtgcggca ggtgacatcg ctgtcagaca
9901 ccgaaacaat ggaggatcca tcagaggaga caaaggacga ggactctgtg gaggtgacag
9961 atgaatagat gctgctgtgg ggagagaagc aaacactaaa aagtgctgtc aaccttcatc
10021 ctggggtttt ggctaaaggg gcttatgggc atggtgcgct cccagcaccc ccagtgcttc
10081 ccttagccac tcgcttggcc ttgccatttc ccctccttct tctctccatg ttgggccagg
10141 tctgggggtc gggagtaggc tggggacatc agaggaggat gggggctttc tcagagttca
10201 tctaagaaga gtctgcactg agacggctca tcaagaaccg ttctccaaga ctgggtggct
10261 ttcacattct ccgcccagca aagggagctt ttgaacaggg catcccaggg gcagaaaaga
10321 gcttgccttt ggctttcccc aggatttctg tcttctcttg ggaaggctgg gcccctggct

FIG. 12-20

10381 cctggctttg agaagtaagg ttgtgacaga aggaccgggc agggcttgcc ttggggacct
10441 gggttgggac actgacatca ggggagacta gcctggaaag actgcagagc tgccagctac
10501 tcccctggaaa gggcttcccc atgctgcctg ccgaaattag gaggtagacg tggctgccac
10561 atctacctgc aagggccagg catggttcaa agaggaccct gcattaagct ctacacacac
10621 atgtgcagga catgtccagc atggacagag ccagagttaa gacagtagca ccgaaaatca
10681 gccccccattc cacagacact ggagtcttca ctgagcgaga cagctgggag ctgtcctgcc
10741 tgtggctaca tatctagcca ttcacagatg tggatatggg aaggacctct ttggagctac
10801 tggggactcc ctaaccactc gcatgagaac ttaattgaat gttacctctt ggagggagtc
10861 taataacaca tgtaggtaga actgaccata aaccctgcct gtgtgtttga aaaggccact
10921 tctcccaaat tggtgcccat cttgtctctg aaaagatggg tgatggccag ggtctgctca
10981 ttgatgaatc agatgaatca ggaagataga caaacacaca cacacacaca cacacccccac
11041 caggatgagt ctgccctcta ttcaccccat ttgaagcctg tggtgtctgt gaccactgct
11101 gaaggtctga gcagcgttct ggtgctccta aaccccattc cagtggttgc tgaagcagca
11161 tcttctgcac aaagcccaac agaagggttc ttatccccgt ttggtataag aagtggattc
11221 accacccact ccctccacgt gcctttgttc ctctctttgg cccatttccc cagcgtctac
11281 tggcgtcagg attggcagga gcacaggcac tcagcagagc atgcccctgc aagacctcag
11341 tgttagggcc cccttccag ctccaggcaa aagggcatga gtcctggccc caaggggcct
11401 gtggctgcag ttcagaggag aagaaggtca gtgtttggag gtgcagcctc aggatgctca
11461 gaaaggaaac tggcgaccgt gagaaagaaa agagccaagc agcatcctgg ttcttggaca
11521 gcatctttgg acactctgtg aagggcaacg atcctgccag agaccgtctc tctacaactg
11581 atgacccact agggcctggg gttaattgct caaaggcccc agtgttcaca aagccacctc
11641 tgccctaacc cttgccagag ctctccaact atgacccacg agaggggtga tggtgggatt
11701 ctaacatcaa cagagcaacc agaaagacat tgggcctccc acactcaggc tgcaggccca
11761 ctttcttggt ccttatcagc tttaatattt attaatgacg acataggagc ccgagtcacc
11821 tgtaaaggcc attaacttgc aatctggaca ggaagttgac gctcaccact ttgggtaaca
11881 gctgctctga ctgtagggcc ccctatttgt tgtcctaacc cagaagcagc tctgggctgc
11941 caggatggtg gatggaatac cagagagttc acactaggga ggaagcaatg cctgcccccct
12001 ggagtctcct agggggcagc agttagaata agggaagagg atttgctggt cactgtttcc
12061 tgacatgggt ttccatggtg agttcaggcc tgaggacagc agtgtctgca aaaccacatg
12121 gcccctgaga aatgtccttg cacattgggc ttcaaactcc tcttctagcg aatccatctt
12181 ggcctgaaag cagaggtaca acaccagccc caaaggcaat tctgttttca gattggttcc
12241 tctggaaagg aaggctgggg tgagggggca ttttacttgc acagaggctg accctgcctc
12301 ccctcttcac tgaccccatc tccaaggtag acctcagcca tgtcagtccc tgttctggca
12361 ggtgctgggc tgggccacag ccagggttat gtaggtaatt aacctgtcca accctgagcc
12421 tcgcctcccc acaccagcaa cacagtggtc tctctgtggt gaccattcac agcataacat

```
    12481 tctgcttagc ctcagactga aagcattgca actgatgtca aaaccagatg agatcttaca
    12541 gggagagaga ttgggtgcaa tttgcctctt tctttgaata aaaagctctt tgctcaccct
    12601 caaaaaaaaa aaaaaaaaaa aaaaaaaaaa
//
```

ZDHHC4:

```
FEATURES             Location/Qualifiers
     source          1..1570
                     /organism="Homo sapiens"
                     /mol_type="mRNA"
                     /db_xref="taxon:9606"
                     /chromosome="7"
                     /map="7p22.1"
     gene            1..1570
                     /gene="ZDHHC4"
                     /gene_synonym="FLJ10479; ZNF374"
                     /note="zinc finger, DHHC-type containing 4"
                     /db_xref="GeneID:55146"
                     /db_xref="HGNC:18471"
     exon            1..287
                     /gene="ZDHHC4"
                     /gene_synonym="FLJ10479; ZNF374"
                     /inference="alignment:Splign"
                     /number=1b
     exon            288..442
                     /gene="ZDHHC4"
                     /gene_synonym="FLJ10479; ZNF374"
                     /inference="alignment:Splign"
                     /number=2b
     exon            443..566
                     /gene="ZDHHC4"
                     /gene_synonym="FLJ10479; ZNF374"
                     /inference="alignment:Splign"
                     /number=3
```

FIG. 12-21

CDS 450..1484
/gene="ZDHHC4"
/gene_synonym="FLJ10479; ZNF374"
/note="zinc finger, DHHC domain containing 4; DHHC-4;
zinc
finger protein 374; zinc finger DHHC domain-containing
protein 4"
/codon_start=1
/product="probable palmitoyltransferase ZDHHC4"
/protein_id="NP_001127859.1"
/db_xref="GI:197304686"
/db_xref="CCDS:CCDS5352.1"
/db_xref="GeneID:55146"
/db_xref="HGNC:18471"

/translation="MDFLVLFLFYLASVLMGLVLICVCSKTHSLKGLARGGAQIFSCI

IPECLQRAVHGLLHYLFHTRNHTFIVLHLVLQGMVYTEYTWEVFGYCQELELSLHYLL

LPYLLLGVNLFFFTLTCGTNPGIITKANELLFLHVYEFDEVMFPKNVRCSTCDLRKPA

RSKHCSVCNWCVHRFDHHCVWVNNCIGAWNIRYFLIYVLTLTASAATVAIVSTTFLVH

LVVMSDLYQETYIDDLGHLHVMDTVFLIQYLFLTFPRIVFMLGFVVVLSFLLGGYLLF

VLYLAATNQTTNEWYRGDWAWCQRCPLVAWPPSAEPQVHRNIHSHGLRSNLQEIFLPA
FPCHERKKQE"

exon 567..640
/gene="ZDHHC4"
/gene_synonym="FLJ10479; ZNF374"
/inference="alignment:Splign"
/number=4 exon 641..819
/gene="ZDHHC4"
/gene_synonym="FLJ10479; ZNF374"
/inference="alignment:Splign"
/number=5

FIG. 12-22

```
exon            820..945
                /gene="ZDHHC4"
                /gene_synonym="FLJ10479; ZNF374"
                /inference="alignment:Splign"
                /number=6
exon            946..1190
                /gene="ZDHHC4"
                /gene_synonym="FLJ10479; ZNF374"
                /inference="alignment:Splign"
                /number=7
STS             1079..1215
                /gene="ZDHHC4"
                /gene_synonym="FLJ10479; ZNF374"
                /standard_name="RH93371"
                /db_xref="UniSTS:90991"
exon            1191..1553
                /gene="ZDHHC4"
                /gene_synonym="FLJ10479; ZNF374"
                /inference="alignment:Splign"
                /number=8
STS             1300..1494
                /gene="ZDHHC4"
                /gene_synonym="FLJ10479; ZNF374"
                /standard_name="A008D23"
                /db_xref="UniSTS:27450"
STS             1434..1490
                /gene="ZDHHC4"
                /gene_synonym="FLJ10479; ZNF374"
                /standard_name="STS-Z41394"
                /db_xref="UniSTS:25243"
STS             1439..1542
                /gene="ZDHHC4"
                /gene_synonym="FLJ10479; ZNF374"
                /standard_name="D7S2646"
                /db_xref="UniSTS:34431"
```

FIG. 12-23

ORIGIN

```
        1 gatgtcacga gcccgcagga agtctcgtat cgcgcccggg aggcgccgga gcccagcggc
       61 tggcggtaag gccgcctccg cggggctgtg ggaagcttgg gctgtcccag gaccgtcagt
      121 ctcctcctct gaccctccct ttccccttgt gtgtagggcc gccgtcccac ccccacctcg
      181 cccgagtccg gggcggcccc ggtgtcccct ccgagcctgc tgcactccac gtccccctac
      241 cagggctcca gcccccaggg aaatctccga ccaggcccgc ccaggagcca gatccaggct
      301 cctggaagaa ccatgtccgg cagctactgg tcatgccagg cacacactgc tgcccaagag
      361 gagctgctgt ttgaattatc tgtgaatgtt gggaagagga atgccagagc tgccggctga
      421 aaattaccca accaagagaa atctgcagga tggactttct ggtcctcttc ttgttctacc
      481 tggcttcggt gctgatgggt cttgttctta tctgcgtctg ctcgaaaacc catagcttga
      541 aaggcctggc caggggagga gcacagatat tttcctgtat aattccagaa tgtcttcaga
      601 gagccgtgca tggattgctt cattaccttt tccatacgag aaaccacacc ttcattgtcc
      661 tgcacctggt cttgcaaggg atggtttata ctgagtacac ctgggaagta tttggctact
      721 gtcaggagct ggagttgtcc ttgcattacc ttcttctgcc ctatctgctg ctaggtgtaa
      781 acctgttttt tttcaccctg acttgtggaa ccaatcctgg cattataaca aaagcaaatg
      841 aattattatt tcttcatgtt tatgaatttg atgaagtgat gtttccaaag aacgtgaggt
      901 gctctacttg tgatttaagg aaaccagctc gatccaagca ctgcagtgtg tgtaactggt
      961 gtgtgcaccg tttcgaccat cactgtgttt gggtgaacaa ctgcatcggg gcctggaaca
     1021 tcaggtactt cctcatctac gtcttgacct tgacggcctc ggctgccacc gtcgccattg
     1081 tgagcaccac ttttctggtc cacttggtgg tgatgtcaga tttataccag gagacttaca
     1141 tcgatgacct tggacacctc catgttatgg acacggtctt tcttattcag tacctgttcc
     1201 tgacttttcc acggattgtc ttcatgctgg gctttgtcgt ggttctgagc ttcctcctgg
     1261 gtggctacct gttgtttgtc ctgtatctgg cggccaccaa ccagactact aacgagtggt
     1321 acagaggtga ctgggcctgg tgccagcgtt gtccccttgt ggcctggcct ccgtcagcag
     1381 agccccaagt ccaccggaac attcactccc atgggcttcg gagcaacctt caagagatct
     1441 ttctacctgc ctttccatgt catgagagga agaaacaaga atgacaagtg tatgactgcc
     1501 tttgagctgt agttcccgtt tatttacaca tgtggatcct cgttttccaa gcaaaaaaaa
     1561 aaaaaaaaaa
//
```

FIG. 12-24

ZDHHC5:

FIG. 12-25

```
FEATURES             Location/Qualifiers
     source          1..4582
                     /organism="Homo sapiens"
                     /mol_type="mRNA"
                     /db_xref="taxon:9606"
                     /chromosome="11"
                     /map="11q12.1"
     gene            1..4582
                     /gene="ZDHHC5"
                     /gene_synonym="DKFZp586K0524; KIAA1748; ZNF375"
                     /note="zinc finger, DHHC-type containing 5"
                     /db_xref="GeneID:25921"
                     /db_xref="HGNC:18472"
                     /db_xref="HPRD:15720"
     exon            1..186
                     /gene="ZDHHC5"
                     /gene_synonym="DKFZp586K0524; KIAA1748; ZNF375"
                     /inference="alignment:Splign"
                     /number=1
     exon            187..1360
                     /gene="ZDHHC5"
                     /gene_synonym="DKFZp586K0524; KIAA1748; ZNF375"
                     /inference="alignment:Splign"
                     /number=2
     CDS             1257..3404
                     /gene="ZDHHC5"
                     /gene_synonym="DKFZp586K0524; KIAA1748; ZNF375"
                     /note="zinc finger, DHHC domain containing 5;
                     membrane-associated DHHC5 zinc finger protein; DHHC-5;
                     zinc finger protein 375; zinc finger DHHC
                     domain-containing protein 5"
                     /codon_start=1
                     /product="probable palmitoyltransferase ZDHHC5"
```

/protein_id="NP_056272.2"
/db_xref="GI:41152072"
/db_xref="CCDS:CCDS7965.1"
/db_xref="GeneID:25921"
/db_xref="HGNC:18472"
/db_xref="HPRD:15720"

/translation="MPAESGKRFKPSKYVPVSAAAIFLVGATTLFFAFTCPGLSLYVS

PAVPIYNAIMFLFVLANFSMATFMDPGIFPRAEEDEDKEDDFRAPLYKTVEIKGIQVR

MKWCATCRFYRPPRCSHCSVCDNCVEEFDHHCPWVNNCIGRRNYRYFFLFLLSLTAHI

MGVFGFGLLYVLYHIEELSGVRTAVTMAVMCVAGLFFIPVAGLTGFHVVLVARGRTTN

EQVTGKFRGGVNPFTNGCCNNVSRVLCSSPAPRYLGRPKKEKTIVIRPPFLRPEVSDG

QITVKIMDNGIQGELRRTKSKGSLEITESQSADAEPPPPPKPDLSRYTGLRTHLGLAT

NEDSSLLAKDSPPTPTMYKYRPGYSSSSTSAAMPHSSSAKLSRGDSLKEPTSIAESSR

HPSYRSEPSLEPESFRSPTFGKSFHFDPLSSGSRSSSLKSAQGTGFELGQLQSIRSEG

TTSTSYKSLANQTRNGSLSYDSLLTPSDSPDFESVQAGPEPDPPLGYTSPFLSARLAQ

QREAERHPRLVPTGPTHREPSPVRYDNLSRHIVASLQEREKLLRQSPPLPGREEEPGL

GDSGIQSTPGSGHAPRTSSSSDDSKRSPLGKTPLGRPAVPRFGKPDGLRGRGVGSPEP

GPTAPYLGRSMSYSSQKAQPGVSETEEVALQPLLTPKDEVQLKTTYSKSNGQPKSLGS
ASPGPGQPPLSSPTRGGVKKVSGVGGTTYEISV"

exon 1361..1482
/gene="ZDHHC5"
/gene_synonym="DKFZp586K0524; KIAA1748; ZNF375"
/inference="alignment:Splign"
/number=3

FIG. 12-26

```
exon            1483..1640
                /gene="ZDHHC5"
                /gene_synonym="DKFZp586K0524; KIAA1748; ZNF375"
                /inference="alignment:Splign"
                /number=4
exon            1641..1813
                /gene="ZDHHC5"
                /gene_synonym="DKFZp586K0524; KIAA1748; ZNF375"
                /inference="alignment:Splign"
                /number=5
exon            1814..1916
                /gene="ZDHHC5"
                /gene_synonym="DKFZp586K0524; KIAA1748; ZNF375"
                /inference="alignment:Splign"
                /number=6
exon            1917..2008
                /gene="ZDHHC5"
                /gene_synonym="DKFZp586K0524; KIAA1748; ZNF375"
                /inference="alignment:Splign"
                /number=7
exon            2009..2141
                /gene="ZDHHC5"
                /gene_synonym="DKFZp586K0524; KIAA1748; ZNF375"
                /inference="alignment:Splign"
                /number=8
exon            2142..2265
                /gene="ZDHHC5"
                /gene_synonym="DKFZp586K0524; KIAA1748; ZNF375"
                /inference="alignment:Splign"
                /number=9
exon            2266..2378
                /gene="ZDHHC5"
                /gene_synonym="DKFZp586K0524; KIAA1748; ZNF375"
                /inference="alignment:Splign"
                /number=10
exon            2379..3238
```

FIG. 12-27

```
                     /gene="ZDHHC5"
                     /gene_synonym="DKFZp586K0524; KIAA1748; ZNF375"
                     /inference="alignment:Splign"
                     /number=11
     exon            3239..4560
                     /gene="ZDHHC5"
                     /gene_synonym="DKFZp586K0524; KIAA1748; ZNF375"
                     /inference="alignment:Splign"
                     /number=12
     STS             4251..4532
                     /gene="ZDHHC5"
                     /gene_synonym="DKFZp586K0524; KIAA1748; ZNF375"
                     /standard_name="D11S4384"
                     /db_xref="UniSTS:33107"
     STS             4254..4463
                     /gene="ZDHHC5"
                     /gene_synonym="DKFZp586K0524; KIAA1748; ZNF375"
                     /standard_name="A003A41"
                     /db_xref="UniSTS:32856"
     STS             4294..4458
                     /gene="ZDHHC5"
                     /gene_synonym="DKFZp586K0524; KIAA1748; ZNF375"
                     /standard_name="D11S2272E"
                     /db_xref="UniSTS:76902"
     polyA_site      4557
                     /gene="ZDHHC5"
                     /gene_synonym="DKFZp586K0524; KIAA1748; ZNF375"
ORIGIN
        1 gagacccggc actgagggca acggccgcgc gccggctccg agacgagcga cgcctggcgg
       61 gagcgcgcgg cagcggggcg ggcgtggagc gtgcgggggc cgcgcgctgc ttctctgagg
      121 caggacggca ctgccgggag gcggcggtga caacgacggc ggtggtgacg ggcaccgggc
      181 tcgcgggtga gacacagtaa cctggttgaa ctctgcatct ggaaagctga agactgaaga
      241 aagataagag acattgacta gtctggaaac agggacatct ttggaacttc gttttcatcc
      301 acagtaaact tttgaagtgt catcaattgg aattgatttc ttcatcttat tctgcctatt
      361 gggaagaaca tggcttcaag gattttaagt ttccctttag ttttacatga actttgtagg
      421 aaacagagcc cttaaagggc ttgggaataa caagaagaga ttgaagacag agaagcttgc
```

481 cctgttttcc ttgccccttc aaagaaaagg atttacagct caaacttaga acagctgttg
541 tccagcttta gccatcaaga gagaaataaa ttaaaccacc attgccagac tacaagccct
601 ggtgaagtca gggtgtggga gtggtggcat tgagaagact acctaaaaga gacaaagact
661 gcagtaaaca aagctcctct ttaaagttgg aaggggcctc aggttccttc ttggattgaa
721 atagaaatag aaacacaggg cacacctctt ttaggtgcag ctcacatttt atggaactgt
781 agtcgtggag gtactatagt atctcagaag aatttttctt tgcccaaagt tttttgcca
841 taccctgata ttctctcctt cttttgaaga cctgcctcca tccatgagct gtatcttgat
901 ctgtctgact gtccatgttt tccacctgca accatttgca tgtgtacagc ctactgtttg
961 tctccagttt ttaaactgta caagttgtgt ttcttaatct tcccttctgc cttgttctgg
1021 ggaggtggtt attcatcatt tggaatcacc tttcccctc ccatgtgctt tccttcattt
1081 gagatctttt gacctttggc tttatttggg aggggaagg gtgataaagt tttctgtttc
1141 cctggttttc ttttgtactc ctctctgttg cttccctcct cccattttct tgtctgttct
1201 gccgctgtgt gggcctgggc tatgcggcag ggcagatttc ccatcagagc tccaacatgc
1261 ccgcagagtc tggaaagaga ttcaaaccca gcaagtatgt cccggtctct gcagccgcca
1321 tcttcctagt gggagctacg acactcttct ttgcctttac gtgtccagga ctaagcctgt
1381 atgtgtcacc tgcagtgccc atctacaatg caattatgtt tctctttgtg ttggccaact
1441 tcagcatggc caccttcatg gacccaggga ttttccctcg agctgaggag gatgaggaca
1501 aggaagatga tttccgagct cccctttaca aaacagtgga gataaagggc atccaggtgc
1561 gcatgaaatg gtgtgccacc tgccgctttt accgtccccc tcgatgttcc cactgcagtg
1621 tctgtgacaa ctgtgtggag gaatttgatc atcactgccc ctgggtgaat aactgtattg
1681 gtcgccggaa ctaccgttat tttttccttt tcctcctttc cctgacagcc cacattatgg
1741 gtgtgtttgg ctttggcctc ctttatgtcc tctaccacat agaggaactc tcaggggtcc
1801 gcacggctgt cacaatggca gtaatgtgtg tggctggctt attcttcatc cctgtagctg
1861 gcctcacggg atttcacgtg gttctggtgg ccaggggacg cacaaccaat gaacaggtta
1921 cgggtaaatt ccggggaggt gtgaacccct tcaccaatgg ctgctgtaac aatgtcagcc
1981 gtgttctctg cagttctcca gcacccaggt atttggggag accaaagaaa gagaagacaa
2041 ttgtaatcag acctcccttc cttcgaccag aagtttcaga tgggcagata actgtgaaga
2101 tcatggataa tggcatccag ggagagctga ggagaacaaa gtctaaggga agcctggaga
2161 taacagagag ccagtctgca gatgctgaac ctccacctcc tcctaagcca gacctgagcc
2221 gttacacagg gttgcgaaca cacctcggct tggctactaa tgaggatagt agcttattgc
2281 ccaaggacag ccccccgaca cctaccatgt acaagtatcg gccgggttac agtagcagca
2341 gtacgtcagc tgccatgccg cattcctcca gcgccaagtt gagtcgtggg gacagcttga
2401 aggagccaac ctcaattgca gagagcagcc gtcaccccag ctaccgctca gagcccagct
2461 tggaaccaga gagcttccgt tctcctacct ttggcaaaag ttttcacttc gatccactat
2521 ccagtggctc acgctcctcc agcctcaagt cagcccaggg cacaggcttt gagctgggcc
2581 agttgcaatc cattcgttca gagggcacca cctccacctc ctataagagc ctggccaacc

FIG. 12-30

2641 agacacgcaa tggaagccta tcttatgaca gcttgctcac accttcagac agccctgatt
2701 ttgagtcagt gcaggcaggg cctgagccag acccaccttt aggctatacc tctcccttcc
2761 tgtcagccag gctggcccag caacgggaag ctgagaggca cccacgtttg gtgccaactg
2821 gcccaacaca ccgagagccc tcaccagtcc gttacgacaa tctgtcgcgc cacattgtgg
2881 cctctctcca ggaacgagag aagttgctgc gccagtcacc cccactcccg ggccgtgagg
2941 aagaaccagg cttgggggac tcaggcattc agtcaacacc aggctcgggc catgcccctc
3001 gtactagttc ctcctcagat gattcaaaga gatcaccttt gggcaagact ccactgggac
3061 gcccagctgt cccccgtttt ggcaagccag atgggctaag gggccgggga gtagggtccc
3121 ctgaaccagg cccaacagcc ccatacctgg gccgatcgat gtcttacagc agccaaaaag
3181 cccaacctgc tgtctctgag acagaagaag tggccttgca gccattactg acacccaaag
3241 atgaagtaca gctgaagacc acctacagca aatccaacgg gcagcccaag agcttaggct
3301 cagcctcccc tggcccaggc cagccacctc tcagtagccc cacgagggga ggagtcaaga
3361 aggtgtcagc ggttggtggt accacctatg agatttcggt gtgagccttc ggcacctccc
3421 ctcccccaacc cctctgcgcc tacaccaaag ggcccccaggt ggccaccttc cttccctcaa
3481 ggggctcccc tcccgtgcat ggacattttt taaaccaccg attccaagag gatgaggagt
3541 gttttctaaa atgcagtagg cttggggagt cggagagttg gggccctgag actggggtag
3601 caaccccccc ttttatcttt taagaccttc ccttccttga tccctggacc agactcagtg
3661 gacatttgtg caattgctcg ccctggaggg aaccagatca tttttaaacc agaaataatt
3721 ttttttatta ttgttacgga ttctattttt ttcctcttct gcgttaccag gtgtgtgtgt
3781 acatataata tatatatata tatattataa atatcaaaga aattatatat ctatcctggg
3841 atgggaaaat gagggaggga tacatatacg gagggggatc ttactcttcc cattcctcag
3901 accagcagga aaagagggga gacgtcagtc tttttcctgt ggttccctct catttgtccc
3961 agttactaac tacggaaata gcatcctctg ctggtgctaa gtgtgattag gaagaagcct
4021 ggggagaggt gagtctggaa ttttggtcac aagagggaag gacttggaga ggagaattag
4081 ttttctaggc tcattggcat ttagtttccc taggaaaggg gtcaaaactt caagacactg
4141 gtggtggtgg gagatcagga aaataacttg gcctagctca aacaatattg gataatcccc
4201 tccttggggc agagggatta gagtgtgctc ctactggccc cttggagcct cccctagctt
4261 acacagttaa cttgatttta aaatccaagg ccaggagaga agaatccaaa aagcaatatt
4321 tttcatcaca tgccaaaaac gggggataga gagaaggagt ggcaggccta ggcccctccg
4381 attgtccctt gggggttacc cctcagccca cctcactatg gtgctgggta gaggggatac
4441 ctgggttcta acctctaaat aggggagatc ccagcctcca caaagaggcc cttttatttt
4501 ttattctgat tagccatttt aaaccaacga ggaataaaaa gaaatcctga tctaaccagc
4561 aaaaaaaaaa aaaaaaaaaa aa

ZDHHC6:

```
FEATURES             Location/Qualifiers
     source          1..2187
                     /organism="Homo sapiens"
                     /mol_type="mRNA"
                     /db_xref="taxon:9606"
                     /chromosome="10"
                     /map="10q25.2"
     gene            1..2187
                     /gene="ZDHHC6"
                     /gene_synonym="FLJ21952; ZNF376"
                     /note="zinc finger, DHHC-type containing 6"
                     /db_xref="GeneID:64429"
                     /db_xref="HGNC:19160"
                     /db_xref="HPRD:15721"
     exon            1..210
                     /gene="ZDHHC6"
                     /gene_synonym="FLJ21952; ZNF376"
                     /inference="alignment:Splign"
                     /number=1
     exon            211..691
                     /gene="ZDHHC6"
                     /gene_synonym="FLJ21952; ZNF376"
                     /inference="alignment:Splign"
                     /number=2
     CDS             425..1666
                     /gene="ZDHHC6"
                     /gene_synonym="FLJ21952; ZNF376"
                     /note="zinc finger, DHHC domain containing 6; DHHC-6;
zinc
                     finger protein 376; transmembrane protein H4; zinc
finger
                     DHHC domain-containing protein 6"
                     /codon_start=1
```

FIG. 12-31

/product="probable palmitoyltransferase ZDHHC6"
/protein_id="NP_071939.1"
/db_xref="GI:11968053"
/db_xref="CCDS:CCDS7574.1"
/db_xref="GeneID:64429"
/db_xref="HGNC:19160"
/db_xref="HPRD:15721"

/translation="MGTFCSVIKFENLQELKRLCHWGPIIALGVIAICSTMAMIDSVL

WYWPLHTTGGSVNFIMLINWTVMILYNYFNAMFVGPGFVPLGWKPEISQDTMYLQYCK

VCQAYKAPRSHHCRKCNRCVMKMDHHCPWINNCCGYQNHASFTLFLLLAPLGCIHAAF

IFVMTMYTQLYHRLSFGWNIVKIDMSAARRDPLPIVPFGLAAFATTLFALGLALGTTI

AVGMLFFIQMKIILRNKTSIESWIEEKAKDRIQYYQLDEVFVFPYDMGSRWRNFKQVF

TWSGVPEGDGLEWPVREGCHQYSLTIEQLKQKADKRVRSVRYKVIEDYSGACCPLNKG

IKTFFTSPCTEEPRIQLQKGEFILATRGLRYWLYGDKILDDSFIEGVSRIRGWFPRKC
VEKCPCDAETDQAPEGEKKNR"

exon 692..783
/gene="ZDHHC6"
/gene_synonym="FLJ21952; ZNF376"
/inference="alignment:Splign"
/number=3

STS 783..942
/gene="ZDHHC6"
/gene_synonym="FLJ21952; ZNF376"
/standard_name="D10S1390E"
/db_xref="UniSTS:151387"

exon 784..943
/gene="ZDHHC6"
/gene_synonym="FLJ21952; ZNF376"
/inference="alignment:Splign"

FIG. 12-32

```
                    /number=4
exon                944..1105
                    /gene="ZDHHC6"
                    /gene_synonym="FLJ21952; ZNF376"
                    /inference="alignment:Splign"
                    /number=5
exon                1106..1159
                    /gene="ZDHHC6"
                    /gene_synonym="FLJ21952; ZNF376"
                    /inference="alignment:Splign"
                    /number=6
exon                1160..1327
                    /gene="ZDHHC6"
                    /gene_synonym="FLJ21952; ZNF376"
                    /inference="alignment:Splign"
                    /number=7
exon                1328..1369
                    /gene="ZDHHC6"
                    /gene_synonym="FLJ21952; ZNF376"
                    /inference="alignment:Splign"
                    /number=8
exon                1370..1515
                    /gene="ZDHHC6"
                    /gene_synonym="FLJ21952; ZNF376"
                    /inference="alignment:Splign"
                    /number=9
exon                1516..1562
                    /gene="ZDHHC6"
                    /gene_synonym="FLJ21952; ZNF376"
                    /inference="alignment:Splign"
                    /number=10
exon                1563..2170
                    /gene="ZDHHC6"
                    /gene_synonym="FLJ21952; ZNF376"
                    /inference="alignment:Splign"
                    /number=11
```

FIG. 12-33

```
     STS             1903..2103
                     /gene="ZDHHC6"
                     /gene_synonym="FLJ21952; ZNF376"
                     /standard_name="A005C33"
                     /db_xref="UniSTS:2005"
     STS             1903..2103
                     /gene="ZDHHC6"
                     /gene_synonym="FLJ21952; ZNF376"
                     /standard_name="G20705"
                     /db_xref="UniSTS:2004"
ORIGIN
        1 agagtcctgg cgagggcgct ggccgagagg tgctcggctt gtagcaggtc ccgcactcca
       61 gcctctcgct gccagggttt gctctctgct tgtcctgggc tgaggtgtcc atgacggagt
      121 catccaagga ggaaaaaatc tgttccgggt gagcccaggc cgcccccggat atgcgatggc
      181 tgaggagcag acaccaggga ccacactgag gttgggtttc agaccaagac actggattct
      241 cctacttaag ataaagagct ttgggtgcct gacagtgaaa atggtgtaat ctgcgttaac
      301 agttcacagc ttgaaggcat gacaattaaa gaacacacat ggacttgtgg cacatggaaa
      361 tgtgcgcaca gaaaaaggaa atctataatt cttttaaagt aggaaggcat tcttccttgc
      421 caaaatgggt acgttctgtt cggttatcaa gtttgaaaat ctacaagaat taaagagact
      481 gtgtcactgg ggtcccatca tagcccttgc tgttatagca atatgttcta ccatggccat
      541 gattgactct gtgttgtggt attggccctt acatacaact ggaggaagtg tgaatttcat
      601 catgttgata aattggactg tcatgattct ttataattac ttcaatgcca tgtttgtcgg
      661 tccgggcttt gtccctctgg ggtggaaacc ggaaatttct caggatacca tgtatctcca
      721 gtattgtaaa gtctgccaag catacaaggc accacgttca catcactgca gaaagtgtaa
      781 cagatgtgtg atgaagatgg accatcactg tccttggatc aacaactgtt gtggttacca
      841 aaatcatgct tcgttcacac tgtttctcct tttagcacca ctgggttgta tccatgctgc
      901 tttcattttt gtgatgacta tgtacacaca gctttatcat cggctctcct ttgggtggaa
      961 cacagtgaag atcgacatga gtgcagcccg gagagatcct cttccaattg ttccatttgg
     1021 attagctgca tttgctacca ccttgtttgc cttgggatta gctttaggaa caaccatagc
     1081 tgttgggatg ttgtttttta tccagatgaa aataattctc agaaacaaaa cttctattga
     1141 gtcatggatt gaagagaagg ctaaagatcg aattcagtat tatcaactag atgaagtctt
     1201 tgtttttcca tatgatatgg gaagtagatg gaggaacttt aaacaggtat ttacgtggtc
     1261 agggctccct gaaggagatg gacttgagtg gccagtaaga gaaggctgtc accaatacag
     1321 cttaacaata gaacagttga aacaaaaagc agataagaga gtcagaagtg ttcgctataa
     1381 agtaatagaa gattatagtg gtgcctgctg ccctctgaat aaaggaatca aaaccttctt
     1441 cacaagtccc tgcaccgaag agcctcgaat acagctgcaa aaaggggaat tcattttagc
```

FIG. 12-34

```
1501 cacaagaggt ttacgatact ggttatatgg agacaaaatt cttgatgatt cctttataga
1561 aggtctttca agaataaggg gttggttccc tagaaaatgt gtggaaaagt gtccctgtga
1621 tgctcaaaca gatcaagccc cagaggggga gaagaaaaat agatagctgc tgttaaaaca
1681 aaattatcct ttaagtctgc ttaattactt gaaaattgta catattacta aagaattatg
1741 caatcagcct actctggtta agatgttctt ttcctcaaag gtgccctagt gccatgattt
1801 aaatattttt attaccattt tgaaatggag aagccattct gcatatgcct ttgaattcct
1861 gcccttcttt accacctctt cctccccctc aaaggaaaaa catttcatcc aagtaagtta
1921 acggcatttt ctgtaggatt ttcttatgca ctgcacactc tggacctcac ctgcagatac
1981 agttcccccc ttgccaggag catctgcatg tggtacttct cttttccctc agttgatatt
2041 tcttatatga tattctagat actatagaac tcaatttgtc agattcagta taacctcaga
2101 ttttcttacc tgtcttttaa aaatgcagat tttgtcaaat caaataaaga tcaatggatg
2161 ttggctataa aaaaaaaaaa aaaaaaa
//
```

ZDHHC7:

```
FEATURES             Location/Qualifiers
     source          1..3279
                     /organism="Homo sapiens"
                     /mol_type="mRNA"
                     /db_xref="taxon:9606"
                     /chromosome="16"
                     /map="16q24.1"
     gene            1..3279
                     /gene="ZDHHC7"
                     /gene_synonym="FLJ10792; FLJ20279; SERZ-B; SERZ1;
ZNF370"
                     /note="zinc finger, DHHC-type containing 7"
                     /db_xref="GeneID:55625"
                     /db_xref="HGNC:18459"
     exon            1..250
                     /gene="ZDHHC7"
                     /gene_synonym="FLJ10792; FLJ20279; SERZ-B; SERZ1;
ZNF370"
```

FIG. 12-35

```
                     /inference="alignment:Splign"
                     /number=1
     exon            251..336
                     /gene="ZDHHC7"
                     /gene_synonym="FLJ10792; FLJ20279; SERZ-B; SERZ1;
ZNF370"
                     /inference="alignment:Splign"
                     /number=2
     exon            337..668
                     /gene="ZDHHC7"
                     /gene_synonym="FLJ10792; FLJ20279; SERZ-B; SERZ1;
ZNF370"
                     /inference="alignment:Splign"
                     /number=3
     CDS             354..1391
                     /gene="ZDHHC7"
                     /gene_synonym="FLJ10792; FLJ20279; SERZ-B; SERZ1;
ZNF370"
                     /note="isoform 1 is encoded by transcript variant 1;
zinc
                     finger, DHHC domain containing 7; Sertoli cell gene with
                     zinc finger domain-β DHHC-7; zinc finger protein 370;
                     zinc finger DHHC domain-containing protein 7;
                     palmitoyltransferase ZDHHC7"
                     /codon_start=1
                     /product="palmitoyltransferase ZDHHC7 isoform 1"
                     /protein_id="NP_001139020.1"
                     /db_xref="GI:224493964"
                     /db_xref="CCDS:CCDS45538.1"
                     /db_xref="GeneID:55625"
                     /db_xref="HGNC:18459"

/translation="MQPSGHRLRDVEHHPLLAENDNYDSSSSSSSEADVADRVWFIRD

GCGMICAVMTWLLVAYADFVVTFVMLLPSKDFWYSVVNGVIFNCLAVLALSSHLRTML
```

FIG. 12-36

```
            TDPEKSSDCRPSACTVKTGLDPTLVGICGEGIESVQSLLLGAVPKGNATKEYMESLQL

            KPGEVIYKCPKCCCIKPERAHHCSICKRCIRKMDHHCPWVNNCVGEKNQRFFVLFTMY

            IALSSVHALILCGFQFISCVRGQWTECSDFSPPITVILLIFLCLEGLLFFTFTAVMFG

            TQIHSICNDETEIERLKSEKPTWERRLRWEGMKSVFGGPPSLLWMNPFVGFRFRRLPT
                                 RPRKGGPEFSV"
     exon            669..779
                     /gene="ZDHHC7"
                     /gene_synonym="FLJ10792; FLJ20279; SERZ-B; SERZ1;
ZNF370"
                     /inference="alignment:Splign"
                     /number=4
     exon            780..904
                     /gene="ZDHHC7"
                     /gene_synonym="FLJ10792; FLJ20279; SERZ-B; SERZ1;
ZNF370"
                     /inference="alignment:Splign"
                     /number=5
     exon            905..1001
                     /gene="ZDHHC7"
                     /gene_synonym="FLJ10792; FLJ20279; SERZ-B; SERZ1;
ZNF370"
                     /inference="alignment:Splign"
                     /number=6
     exon            1002..1083
                     /gene="ZDHHC7"
                     /gene_synonym="FLJ10792; FLJ20279; SERZ-B; SERZ1;
ZNF370"
                     /inference="alignment:Splign"
                     /number=7
     exon            1084..1214
                     /gene="ZDHHC7"
                     /gene_synonym="FLJ10792; FLJ20279; SERZ-B; SERZ1;
```

FIG. 12-37

```
ZNF370"
                    /inference="alignment:Splign"
                    /number=8
     exon           1215..3274
                    /gene="ZDHHC7"
                    /gene_synonym="FLJ10792; FLJ20279; SERZ-B; SERZ1;
ZNF370"
                    /inference="alignment:Splign"
                    /number=9
     STS            3031..3161
                    /gene="ZDHHC7"
                    /gene_synonym="FLJ10792; FLJ20279; SERZ-B; SERZ1;
ZNF370"
                    /standard_name="D16S3320"
                    /db_xref="UniSTS:8792"
ORIGIN
        1 acttccggcg ctcgcaccgc cccgctctcc agccaaggct ccgggctgag gcatttgctt
       61 ggctgcagcc tccttccgac ctgccccggcg ggacccaggg gaccaagccg agccgagccg
      121 cggggcccgc tccagcccgg ccatgagcgc ggccgcatga tgcgtccctg cctcggccgc
      181 tgcagtcgcc gccgccgccg ccgcaggccg ggaggagccg cagcgccggg cgacccccgcc
      241 cgggcctcgg atccgatcac ataggacagt atgcacctta agatcctgaa gaaacggcac
      301 aaaatgttca agtgatgttt agaaataact tgtgagggtg cgtcagggaa atcatgcagc
      361 catcaggaca caggctccgg gacgtcgagc atcatcctct cctggctgaa aatgacaact
      421 atgactcttc atcgtcctcc tcctccgagg ctgacgtggc tgaccgggtc tggttcatcc
      481 gtgacggctg cggcatgatc tgtgctgtca tgacgtggct tctggtcgcc tatgcagact
      541 tcgtggtgac tttcgtcatg ctgctgcctt ccaaagactt ctggtactct gtggtcaacg
      601 gggtcatctt taactgcttg gccgtgcttg ccctgtcatc ccacctgaga accatgctca
      661 ccgaccctga aaaatccagt gactgccgac catctgcctg cacagtgaaa actgggctgg
      721 acccaaccct tgtgggcatt tgtggtgagg gaaccgagtc tgtgcaaagc ctcctgcttg
      781 gggcagtacc caaaggaaac gctacgaaag aatacatgga gagcttgcag ctgaagcccg
      841 gggaagtcat ctacaagtgc cccaagtgct gctgtattaa acccgagcgc gcccaccact
      901 gcagtatttg caaaagatgt attcggaaaa tggatcatca ctgcccgtgg gtgaacaatt
      961 gtgtaggaga aaagaatcaa agatttttttg tgctcttcac tatgtatata gctctgtctt
     1021 cagtccatgc tctgatcctt tgtggatttc agttcatctc ctgtgtccga gggcagtgga
     1081 ctgaatgcag tgatttttca cctccgataa ctgtaatcct gttgatcttc ctgtgccttg
     1141 agggtcttct gtttttcact ttcactgcag ttatgtttgg cacccaaatc cactccatat
```

FIG. 12-38

1201 gcaacgacga gacggagatc gagcgattga aaagtgagaa gcccacatgg gagcggaggc
1261 tgcgatggga agggatgaag tccgtctttg gggggccccc ctcactcctc tggatgaatc
1321 cctttgtggg cttccgattt aggcgactgc ccacgagacc cagaaaaggt ggccccggagt
1381 tctcagtgtg aggcgtggct catcagactg aaacttgctc acagacttcc agttatttat
1441 ttggggtctg aaggatatca acagctcatc tgtgaccaac agggcaactg gaacctacac
1501 aaaccaattg cttgcagcaa gcagagtttt atatatttat agtcacagat ggcagaggaa
1561 gaggctctca gtccccacct gtacaacaac ggaaaggtgt gtggccacac gaagaagcca
1621 aacgccgtgg cctcctgcag agctggggct tctgtggaga atacttcggg ttattacatg
1681 ggttattcaa atcctgggtc ctgagctgct gtttccaatc atgaagaaaa acagtgaatc
1741 cagtgaacag ggattctcca agcagtcatt tcagggggct cctgctgacc ccgccactca
1801 gcagtgcact ccccggatca cagcagggcg tttacataga aagacgtttt ggtctcgatt
1861 agctccgatg ctttgcactg aagttgcaaa agatctgtgc actgaacagt gaaggtggct
1921 tccggcacac tcccccgctgc cccggaagag acatcctttg accctctcag caagtctgtg
1981 tgtgtgcgtg tctgtgcgtg tgcgcgcgtg tgtgcatgtg tgtcaaaatt gccagtgttg
2041 tttaggcaat gtaacattta ccggctgtgt acagcaaaca agctattttt tagaaaccga
2101 cgtttcaggg aagaggggag agagccgcgg ggtcctgccc gtggttacta tgaatgtatt
2161 gctgttggag gacatctcga tccaaagaac agccgttcct gtgcggcccc tcgttgccct
2221 cctgctttca tttttaaag aaatcttgag tgcttgaggg ccttggaact gattttttt
2281 ttttgttcca gccaaattag cagtgtataa atggcaccta ggtaagagca gagctgcggc
2341 tcggtgactt gatacttggg gcagcccgat gctgtgtgtg gggcagggga ggcatcctta
2401 ctggagaggc agggcccagc cattgggcac ctctgggaag gggaggggac catgaggcag
2461 ccagcccctg gcaggggcga ctgtgccacc gcaggcagcg ctccagtcgg gaatggccag
2521 gatggcgccc tcttgttgga gtttttggtt agcttttacg ttttcttctc cacccacggc
2581 acaggtgata aaataggatc cttggtgcgg agcttaaaat tatgccagaa agccaacagc
2641 tcccctcgtg gggccttgcc ttaaacttgc ctggtttgta catttttttgc cggacgcatc
2701 aagaagcaat ctgtgacaaa gtctgagggt cttcctttat gcttgccctc cacactaaga
2761 gaagttggcg tctccctcct gggaattgtt ttgcctttct gttcatctgt gaactgtttt
2821 ttgtttttaa ttactctgta ccccatccga atcagggctt ctaccactgc tgatgcaaaa
2881 ccacaaaggg acctacctga gccaccgtcc tagccaagcg agcaaacctg caggggggttt
2941 ggaagtggac ttggtcaccg cagaagcgtg tgcgccgttg ggggaagagc tgcgtcacag
3001 ccagagggac aaagtgtggg tgatcctgga gacgccagtt tccgagattg ttctgcatat
3061 tcatttgcac attgttgtct gggttggaca tgcgtgtggg cttcagtgtg aggcttttaa
3121 tatgtatatc ctgttatcaa taaaacaatt atccaagtgg ttgaatcctg tgagacttgg
3181 caagtgtgtg caaatcaagt atacttgact tttcaacctc ttctttcaat gtaactttta
3241 tatgaaataa agtaatcaat taacagttct caaaaaaaa

ZDHHC8:

```
FEATURES             Location/Qualifiers
     source          1..3520
                     /organism="Homo sapiens"
                     /mol_type="mRNA"
                     /db_xref="taxon:9606"
                     /chromosome="22"
                     /map="22q11.21"
     gene            1..3520
                     /gene="ZDHHC8"
                     /gene_synonym="ZDHHCL1; ZNF378"
                     /note="zinc finger, DHHC-type containing 8"
                     /db_xref="GeneID:29801"
                     /db_xref="HGNC:18474"
                     /db_xref="HPRD:12298"
                     /db_xref="MIM:608784"
     exon            1..210
                     /gene="ZDHHC8"
                     /gene_synonym="ZDHHCL1; ZNF378"
                     /inference="alignment:Splign"
                     /number=1
     CDS             107..2404
                     /gene="ZDHHC8"
                     /gene_synonym="ZDHHCL1; ZNF378"
                     /note="zinc finger, DHHC domain containing 8; DHHC-8;
zinc
                     finger protein 378; zinc finger DHHC domain-containing
                     protein 8; zinc finger, DHHC domain like containing 1;
                     membrane-associated DHHC8 zinc finger protein"
                     /codon_start=1
                     /product="probable palmitoyltransferase ZDHHC8"
                     /protein_id="NP_037505.1"
                     /db_xref="GI:32698692"
                     /db_xref="CCDS:CCDS13776.1"
```

FIG. 12-40

/db_xref="GeneID:29801"
/db_xref="HGNC:18474"
/db_xref="HPRD:12298"
/db_xref="MIM:608784"

/translation="MPRSPGTRLKPAKYIPVATAAALLVGSSTLFFVFTCPWLTRAVS

PAVPVYNGIIFLFVLANFSMATFMDPGVFPRADEDEDKEDDFRAPLYKNVDVRGIQVR

MKWCATCHFYRPPRCSHCSVCDNCVEDFDHHCPWVNNCIGRRNYRYFFLFLLSLSAHM

VGVVAFGLVYVLNHAEGLGAAHTTITMAVMCVAGLFFIPVIGLTGFHVVLVTRGRTTN

EQVTGKFRGGVNPFTRGCCGNVEHVLCSPLAPRYVVEPPRLPLAVSLKPPFLRPELLD

RAAPLKVKLSDNGLKAGLGRSKSKGSLDRLDEKPLDLGPPLPPKIEAGTFSSDLQTPR

PGSAESALSVQRTSPPTPAMYKFRPAFPTGPKVPFCGPGEQVPGPDSLTLGDDSIRSL

DFVSEPSLDLPDYGPGGLHAAYPPSPPLSASDAFSGALRSLSLKASSRRGGDHVALQP

LRSEGGPPTPHRSIFAPHALPNRNGSLSYDSLLNPGSPGGHACPAHPAVGVAGYHSPY

LHPGATGDPPRPLPRSFSPVLGPRPREPSPVRYDNLSRTIMASIQERKDREERERLLR

SQADSLFGDSGVYDAPSSYSLQQASVLSEGPRGPALRYGSRDDLVAGPGFGGARNPAL

QTSLSSLSSSVSRAPRTSSSSLQADQASSNAPGPRPSSGSHRSPARQGLPSPPGTPHS

PSYAGPKAVAFIHTDLPEPPPSLTVQRDHPQLKTPPSKLNGQSPGLARLGPATGPPGP
SASPTRHTLVKKVSGVGGTTYEISV"

exon 211..332
/gene="ZDHHC8"
/gene_synonym="ZDHHCL1; ZNF378"
/inference="alignment:Splign"
/number=2

FIG. 12-41

```
exon            333..490
                /gene="ZDHHC8"
                /gene_synonym="ZDHHCL1; ZNF378"
                /inference="alignment:Splign"
                /number=3
exon            491..663
                /gene="ZDHHC8"
                /gene_synonym="ZDHHCL1; ZNF378"
                /inference="alignment:Splign"
                /number=4
exon            664..766
                /gene="ZDHHC8"
                /gene_synonym="ZDHHCL1; ZNF378"
                /inference="alignment:Splign"
                /number=5
exon            767..858
                /gene="ZDHHC8"
                /gene_synonym="ZDHHCL1; ZNF378"
                /inference="alignment:Splign"
                /number=6
exon            859..1000
                /gene="ZDHHC8"
                /gene_synonym="ZDHHCL1; ZNF378"
                /inference="alignment:Splign"
                /number=7
exon            1001..1121
                /gene="ZDHHC8"
                /gene_synonym="ZDHHCL1; ZNF378"
                /inference="alignment:Splign"
                /number=8
exon            1122..1231
                /gene="ZDHHC8"
                /gene_synonym="ZDHHCL1; ZNF378"
                /inference="alignment:Splign"
                /number=9
```

FIG. 12-42

```
     exon            1232..2232
                     /gene="ZDHHC8"
                     /gene_synonym="ZDHHCL1; ZNF378"
                     /inference="alignment:Splign"
                     /number=10
     exon            2233..3455
                     /gene="ZDHHC8"
                     /gene_synonym="ZDHHCL1; ZNF378"
                     /inference="alignment:Splign"
                     /number=11
     STS             3191..3322
                     /gene="ZDHHC8"
                     /gene_synonym="ZDHHCL1; ZNF378"
                     /standard_name="RH91790"
                     /db_xref="UniSTS:87197"
     polyA_signal    3437..3442
                     /gene="ZDHHC8"
                     /gene_synonym="ZDHHCL1; ZNF378"
     polyA_site      3455
                     /gene="ZDHHC8"
                     /gene_synonym="ZDHHCL1; ZNF378"
ORIGIN
        1 ccgcgggtcc tgcgccgcgt ccagcccgcc cgcccgaccc cggcccgacc ccggccggcc
       61 ctgcccgccc ggcccggggg agggatgccg cggcgcggcg cccaggatgc cccgcagccc
      121 ccggacgcgc ctcaaacccg ccaagtacat cccggtggcc acggccgccg cgctgctggt
      181 cggctccagc accctcttct tcgtgttcac gtgcccgtgg ttgacacgag ctgtgtcccc
      241 agctgttccc gtctacaatg gcatcatctt cctctttgtc ctggccaact tcagcatggc
      301 cactttcatg gaccctggtg ttttcccccg agcggatgag gatgaggaca aggaggacga
      361 cttccgggct ccgctgtaca agaacgtgga tgtgcgaggt atccaggtcc gcatgaagtg
      421 gtgtgccacg tgccacttct accgcccgcc gcgctgctcc cactgcagcg tctgtgacaa
      481 ctgtgtagag gactttgacc accactgccc ctgggtcaac aactgcatcg ggcgtcgaaa
      541 ctatcgctac ttcttcctgt tcctgctgtc actcagtgca cacatggtgg gcgtcgtggc
      601 cttcggcctg gtctacgtgc tgaaccacgc tgaggggctg ggagccgcgc acaccaccat
      661 caccatggct gtcatgtgtg tggccggcct cttcttcatc cctgtcattg gcctcactgg
      721 cttccatgtg gtgctggtca ctcgggggcg caccaccaac gagcaggtga ctgggaagtt
      781 ccgcgggggt gtgaaccctt tcacccgacg ctgctgtggg aatgtggagc acgtgctgtg
```

841 tagcccccctg gcgccccggt acgtggtgga gccaccccgg ctgccgctcg cggtgagttt
901 gaagccgcct ttccttaggc ctgaactcct ggaccgagct gcaccgctca aggtcaagct
961 tagtgacaac gggctgaagg ctggcctggg ccgtagcaag tccaagggca gcctggaccg
1021 gctggatgag aagccactgg acttggggcc accactgccc cccaagatag aggctggcac
1081 gttcagcagt gacctgcaga ccccgcgccc aggcagtgct gagagtgccc tgtcggtgca
1141 gaggaccagc cccccgacac ctgccatgta caagtttagg ccggctttcc ccacgggtcc
1201 caaggtgccc ttctgtggac caggcgagca ggttccaggc cctgattccc tgaccctggg
1261 ggacgacagc atccgtagcc tggactttgt gtccgagccg agcctggacc tccctgacta
1321 tgggccaggg ggcctgcatg cagcctaccc gccatcccca ccgctcagcg cctctgatgc
1381 cttctcgggc gctttgcgct ccctgagcct caaggcctcg agccggcggg gcggggatca
1441 tgtggccctg cagcccctgc gctctgaggg ggggcccccc acgccccacc gtagcatttt
1501 tgccccccat gcactgccca accgcaacgg cagcctgtcc tatgacagcc tgctcaatcc
1561 tggctcgcct ggtggccacg cctgccctgc ccacccagca gttggcgtgg ccggatacca
1621 ctcaccctac ctgcatcctg gggcaacggg cgacccgcca cggcccctac cccgcagctt
1681 cagccccgtg ctgggccccc gccccggga gccctcgcct gtgcgctacg acaacctgtc
1741 caggaccatc atggcatcca tccaggagcg caaggacagg gaggagcgtg agcgcctgct
1801 gcgctcccag gccgactcac tcttcggcga ctcaggcgtc tatgacgctc ccagctccta
1861 cagcctgcag caggccagtg tgctgtccga gggcccccga ggtcccgcgc tgcgctatgg
1921 ctccagagac gaccttgtgg ctgggcccgg cttcggtggc gcccgcaacc ctgccctgca
1981 gacgtcactg tcctcgctgt ccagctccgt gagccgtgca ccgcggacgt cgtcctcctc
2041 cctgcaggct gatcaggcca gcagcaacgc cccggggccc cggcccagca gtggctcaca
2101 caggtcacct gcacgccagg gcctgccctc cccgcccggc actccccact caccatccta
2161 cgcgggcccc aaagctgtcg ccttcatcca cacggacctc ccagagccac cgccctcgct
2221 gaccgtgcag agggaccacc ctcagctgaa gactccccca agtaagctta atgggcagtc
2281 cccgggcctg gcccggctgg gacctgccac cggcccccca gggccctctg ccagccctac
2341 acggcacacg ctggttaaga aggtgtccgg cgtgggtggg accacctacg agatctcggt
2401 gtgaggactg actgccacac atccgccatg gtgccacggg gaccaggacc ccacagcgca
2461 ccccccctcc ccaccaactt ctctgcccca gggacccgag gccaccccag cctggtgtgg
2521 acccatcggc gggagagagt gccacgcctc cacagcttgc cccaagcgct ctgcctgccc
2581 gtccactcat ctgcccatgg ggaagtcggc tcactgggac aagggccact gggctggtct
2641 gtgtctgggc ctgtcccatg gctggggcag tgaggggggcc cagtcagcct ctttggggca
2701 ccctctctca gccaggcttg gcccactgcc atcacccagc accccagatc accgccaggc
2761 cagcccccaa tggtcccctt acggacaggt cccagagatg gacagaggca cccagggccc
2821 ccaccgtcct tctgacacag cctgtgggct cccggaccga gtgtcccccg ccaggctact
2881 cctaactaac gcgttgcctt tcacggaccc cgctggaagc ttgtagcttg gcaaggctga
2941 tgcttctgcc ctggcctgct ctgggtggtg gtggataggt ggacagacgg ccagccagcc

```
3001 agctgtggcc gggggcccgg ctccatgtgt cccgtgtctg tgtgctgtgc tgccgcgccg
3061 tgtctgatgt gtcagtgctc cggccgccgc tgtccctttc atcaaagcct taacctttgc
3121 tttatgctct tgtgggaggc gacgggggggg caggcggcag caggcacggg ggtgatgctg
3181 ccacaggggg ctggtgacac ccagagcccc ctccccagcc ctcaggccct ccctgccaaa
3241 ctggagaacc ccaccccaag gcatgccacg tccgcagccc cggcctggct gcggtgctcg
3301 cgccgtggga aagcacactg gggaggggtc agtgcttccc ttggtgtcag ggacctgaga
3361 gtaagcacat gacagcgtct gcttgcgttg tgtctgtttt atgtttttat atctacatct
3421 atatatctat aattttatta aaaaaaagaa aaagaaaaaa aaaaaaaaaa aaaaaaaaaa
3481 aaaaaaaaaa aaaaaaaaaa aaaaaaaaaa aaaaaaaaaa
//
```

ZDHHC9:

```
FEATURES             Location/Qualifiers
     source          1..2949
                     /organism="Homo sapiens"
                     /mol_type="mRNA"
                     /db_xref="taxon:9606"
                     /chromosome="X"
                     /map="Xq26.1"
     gene            1..2949
                     /gene="ZDHHC9"
                     /gene_synonym="CGI-89; CXorf11; DHHC9; MMSA-1; MRXSZ;
                     ZDHHC10; ZNF379; ZNF380"
                     /note="zinc finger, DHHC-type containing 9"
                     /db_xref="GeneID:51114"
                     /db_xref="HGNC:18475"
                     /db_xref="HPRD:06759"
                     /db_xref="MIM:300646"
     exon            1..202
                     /gene="ZDHHC9"
                     /gene_synonym="CGI-89; CXorf11; DHHC9; MMSA-1; MRXSZ;
                     ZDHHC10; ZNF379; ZNF380"
                     /inference="alignment:Splign"
                     /number=1
```

FIG. 12-45

```
exon            203..270
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=2b
exon            271..572
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=3
STS             282..431
                /gene="ZDHHC9"
                /gene_synonym="CGI-89; CXorf11; DHHC9; MMSA-1; MRXSZ;
                ZDHHC10; ZNF379; ZNF380"
                /standard_name="ZDHHC9"
                /db_xref="UniSTS:506676"
CDS             406..1500
                /gene="ZDHHC9"
                /gene_synonym="CGI-89; CXorf11; DHHC9; MMSA-1; MRXSZ;
                ZDHHC10; ZNF379; ZNF380"
                /note="Asp-His-His-Cys domain containing protein 9; zinc
                finger, DHHC domain containing 9; zinc finger, DHHC-type
                containing 10; zinc finger, DHHC domain containing 10;
                antigen MMSA-1; DHHC-9; zinc finger protein 379; zinc
                finger DHHC domain-containing protein 9"
                /codon_start=1
                /product="palmitoyltransferase ZDHHC9"
                /protein_id="NP_057116.2"
                /db_xref="GI:56682972"
                /db_xref="CCDS:CCDS35395.1"
                /db_xref="GeneID:51114"
                /db_xref="HGNC:18475"
                /db_xref="HPRD:06759"
                /db_xref="MIM:300646"
```

FIG. 12-46

/translation="MSVMVVRKKVTRKWEKLPGRNTFCCDGRVMMARQKGIFYLTLFL

ILGTCTLFFAFECRYLAVQLSPAIPVFAAMLFLFSMATLLRTSFSDPGVIPRALPDEA

AFIEMEIEATNGAVPQGQRPPPRIKNFQINNQIVKLKYCYTCKIFRPPRASHCSICDN

CVERFDHHCPWVGNCVGKRNYRYFYLFILSLSLLTIYVFAFNIVYVALKSLKIGFLET

LKETPGTVLEVLICFFTLWSVVGLTGFHTFLVALNQTTNEDIKGSWTGKNRVQNPYSH

GNIVKNCCEVLCGPLPPSVLDRRGILPLEESGSRPPSTQETSSSLLPQSPAPTEHLNS

NEMPEDSSTPEEMPPPEPPEPPQEAAEAEK"

exon 573..733
/gene="ZDHHC9"
/gene_synonym="CGI-89; CXorf11; DHHC9; MMSA-1; MRXSZ;
ZDHHC10; ZNF379; ZNF380"
/inference="alignment:Splign"
/number=4 exon 734..892
/gene="ZDHHC9"
/gene_synonym="CGI-89; CXorf11; DHHC9; MMSA-1; MRXSZ;
ZDHHC10; ZNF379; ZNF380"
/inference="alignment:Splign"
/number=5 exon 893..1030
/gene="ZDHHC9"
/gene_synonym="CGI-89; CXorf11; DHHC9; MMSA-1; MRXSZ;
ZDHHC10; ZNF379; ZNF380"
/inference="alignment:Splign"
/number=6 exon 1031..1079
/gene="ZDHHC9"
/gene_synonym="CGI-89; CXorf11; DHHC9; MMSA-1; MRXSZ;
ZDHHC10; ZNF379; ZNF380"
/inference="alignment:Splign"
/number=7

FIG. 12-47

```
exon            1080..1182
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=8
exon            1183..1286
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=9
exon            1287..1383
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=10
exon            1384..2934
                /gene="ZDHHC9"
                /gene_synonym="CGI-89; CXorf11; DHHC9; MMSA-1; MRXSZ;
                ZDHHC10; ZNF379; ZNF380"
                /inference="alignment:Splign"
                /number=11
STS             2744..2895
                /gene="ZDHHC9"
                /gene_synonym="CGI-89; CXorf11; DHHC9; MMSA-1; MRXSZ;
                ZDHHC10; ZNF379; ZNF380"
                /standard_name="STS-R49987"
                /db_xref="UniSTS:1743"
polyA_signal    2913..2918
                /gene="ZDHHC9"
                /gene_synonym="CGI-89; CXorf11; DHHC9; MMSA-1; MRXSZ;
                ZDHHC10; ZNF379; ZNF380"
```

FIG. 12-48 polyA_site 2934
/gene="ZDHHC9"
/gene_synonym="CGI-89; CXorf11; DHHC9; MMSA-1; MRXSZ; ZDHHC10; ZNF379; ZNF380"

ORIGIN

```
   1 tgaggagcgt tccatttggc cagtggtggg cggttgccac agctggttta gggccccgac
  61 cactggggcc ccttgtcagg aggagacagc ctcccggccc ggggaggaca agtcgctgcc
 121 acctttggct gccgacgtga ttccctggga cggtccgttt cctgccgtca gctgccggcc
 181 gagttgggtc tccgtggttc aggccggctc cccctteetg gtctcccttc tcccgctggg
 241 ccggtttatc gggaggagat tgtcttccag ggctagcaat tggacttttg atgatgtttg
 301 acccagcggc aggaatagca ggcaacgtga tttcaaagct gggctcagcc tctgtttctt
 361 ctctcgtgta atcgcaaaac ccattttgga gcaggaattc caatcatgtc tgtgatggtg
 421 gtgagaaaga aggtgacacg gaaatgggag aaactcccag gcaggaacac cttttgctgt
 481 gatggccgcg tcatgatggc ccggcaaaag ggcatttttct acctgacccct tttcctcatc
 541 ctggggacat gtacactctt cttcgccttt gagtgccgct acctggctgt tcagctgtct
 601 cctgccatcc ctgtatttgc tgccatgctc ttcctttttct ccatggctac actgttgagg
 661 accagcttca gtgaccctgg agtgattcct cgggcgctac cagatgaagc agctttcata
 721 gaaatggaga tagaagctac caatggtgcg gtgccccagg gccagcgacc accgcctcgt
 781 atcaagaatt tccagataaa caaccagatt gtgaaactga aatactgtta cacatgcaag
 841 atcttccggc ctccccgggc ctcccattgc agcatctgtg acaactgtgt ggagcgcttc
 901 gaccatcact gcccctgggt ggggaattgt gttggaaaga ggaactaccg ctacttctac
 961 ctcttcatcc tttctctctc cctcctcaca atctatgtct tcgccttcaa catcgtctat
1021 gtggccctca aatctttgaa aattggcttc ttggagacat tgaaagaaac tcctggaact
1081 gttctagaag tcctcatttg cttctttaca ctctggtccg tcgtgggact gactggattt
1141 catactttcc tcgtggctct caaccagaca accaatgaag acatcaaagg atcatggaca
1201 gggaagaatc gcgtccagaa tccctacagc catggcaata ttgtgaagaa ctgctgtgaa
1261 gtgctgtgtg gcccccttgcc ccccagtgtg ctggatcgaa ggggtatttt gccactggag
1321 gaaagtggaa gtcgacctcc cagtactcaa gagaccagta gcagcctctt gccacagagc
1381 ccagccccca cagaacacct gaactcaaat gagatgccgg aggacagcag cactcccgaa
1441 gagatgccac ctccagagcc cccagagcca ccacaggagg cagctgaagc tgagaagtag
1501 cctatctatg gaagagactt ttgtttgtgt ttaattaggg ctatgagaga tttcaggtga
1561 gaagttaaac ctgagacaga gagcaagtaa gctgtccctt ttaactgttt ttctttggtc
1621 tttagtcacc cagttgcaca ctggcatttt cttgctgcaa gctttttttaa atttctgaac
1681 tcaaggcagt ggcagaagat gtcagtcacc tctgataact ggaaaaatgg gtctcttggg
1741 ccctggcact ggttctccat ggcctcagcc acagggtccc cttggacccc ctctcttccc
1801 tccagatccc agccctcctg cttggggtca ctggtctcat tctggggcta aaagtttttg
```

```
1861 agactggctc aaatcctccc aagctgctgc acgtgctgag tccagaggca gtcacagaga
1921 cctctggcca ggggatccta actgggttct tggggtcttc aggactgaag aggagggaga
1981 gtggggtcag aagattctcc tggccaccaa gtgccagcat tgcccacaaa tccttttagg
2041 aatgggacag gtaccttcca cttgttgtat ttattagtgt agcttctcct ttgtctccca
2101 tccactctga cacctaagcc ccactctttt cccattagat atatgtaagt agttgtagta
2161 gagataataa ttgacatttc tcgtagacta cccagaaact tttttaatac ctgtgccatt
2221 ctcaataaga atttatgaga tgccagcggc atagcccttc acactctctg tctcatctct
2281 cctcctttct cattagcccc ttttaatttg tttttccttt tgactcctgc tcccattagg
2341 agcaggaatg gcagtaataa aagtctgcac tttggtcatt tcttttcctc agaggaagcc
2401 tgagtgctca cttaaacact atcccctcag actccctgtg tgaggcctgc agaggccctg
2461 aatgcacaaa tgggaaacca aggcacagag aggctctcct ctcctctcct ctcccccgat
2521 gtaccctcaa aaaaaaaaaa atgctaacca gttcttccat taagcctcgg ctgagtgagg
2581 gaaagcccag cactgctgcc ctctcgggta actcacccta aggcctcggc ccacctctgg
2641 ctatggtaac cacactgggg gcttcctcca agccccgctc ttccagcact tccaccggca
2701 gagtcccaga gccacttcac cctgggggtg ggctgtggcc cccagtcagc tctgctcagg
2761 acctgctcta tttcagggaa gaagatttat gtattatatg tggctatatt tcctagagca
2821 cctgtgtttt cctctttcta agccagggtc ctgtctggat gacttatgcg gtgggggagt
2881 gtaaaccaga acttttcatc tatttgaagg cgattaaact gtgtctaatg caaaaaaaaa
2941 aaaaaaaaa
//
```

ZDHHC11:

```
FEATURES             Location/Qualifiers
     source          1..2618
                     /organism="Homo sapiens"
                     /mol_type="mRNA"
                     /db_xref="taxon:9606"
                     /chromosome="5"
                     /map="5p15.33"
     gene            1..2618
                     /gene="ZDHHC11"
                     /gene_synonym="FLJ13153; ZNF399"
                     /note="zinc finger, DHHC-type containing 11"
                     /db_xref="GeneID:79844"
```

```
                    /db_xref="HGNC:19158"
                    /db_xref="HPRD:15708"
     exon           1..606
                    /gene="ZDHHC11"
                    /gene_synonym="FLJ13153; ZNF399"
                    /inference="alignment:Splign"
                    /number=1
     CDS            385..1623
                    /gene="ZDHHC11"
                    /gene_synonym="FLJ13153; ZNF399"
                    /note="zinc finger, DHHC domain containing 11; DHHC-11;
                    zinc finger protein 399; zinc finger DHHC
                    domain-containing protein 11"
                    /codon_start=1
                    /product="probable palmitoyltransferase ZDHHC11"
                    /protein_id="NP_079062.1"
                    /db_xref="GI:13376150"
                    /db_xref="CCDS:CCDS3857.1"
                    /db_xref="GeneID:79844"
                    /db_xref="HGNC:19158"
                    /db_xref="HPRD:15708"

/translation="MDTRSGSQCSVTPEAILNNEKLVLPPRISRVNGWSLPLHYFQVV

TWAVFVGLSSATFGIFIPFLPHAWKYIAYVVTGGIFSFHLVVHLIASCIDPADSNVRL

MKNYSQPMPLFDRSKHAHVIQNQFCHLCKVTVNKKTKHCISCNKCVSGFDHHCKWINN

CVGSRNYWFFFSTVASATAGMLCLIAILLYVLVQYLVNPGVLRTDPRYEDVKNMNTWL

LFLPLFPVQVQTLIVVIIGMLVLLLDFLGLVHLGQLLIFHIYLKAKKMTTFEYLINNR

KEESSKHQAVRKDPYVQMDKGVLQQGAGALGSSAQGVKAKSSLLIHKHLCHFCTSVNQ

DGDSTAREGDEDPCPSALGAKARNSRLICRRLCQFSTRVHPDGGSMAQEADDAPSIST
                    LGLQQETTEPMKTDSAESED"
```

FIG. 12-51 exon 607..785
/gene="ZDHHC11"
/gene_synonym="FLJ13153; ZNF399"
/inference="alignment:Splign"
/number=2 exon 786..887
/gene="ZDHHC11"
/gene_synonym="FLJ13153; ZNF399"
/inference="alignment:Splign"
/number=3 exon 888..1012
/gene="ZDHHC11"
/gene_synonym="FLJ13153; ZNF399"
/inference="alignment:Splign"
/number=4 exon 1013..1168
/gene="ZDHHC11"
/gene_synonym="FLJ13153; ZNF399"
/inference="alignment:Splign"
/number=5 exon 1169..1284
/gene="ZDHHC11"
/gene_synonym="FLJ13153; ZNF399"
/inference="alignment:Splign"
/number=6 exon 1285..1319
/gene="ZDHHC11"
/gene_synonym="FLJ13153; ZNF399"
/inference="alignment:Splign"
/number=7 exon 1320..1407
/gene="ZDHHC11"
/gene_synonym="FLJ13153; ZNF399"
/inference="alignment:Splign"
/number=8

FIG. 12-52

```
     exon            1408..1442
                     /gene="ZDHHC11"
                     /gene_synonym="FLJ13153; ZNF399"
                     /inference="alignment:Splign"
                     /number=9
     exon            1443..1530
                     /gene="ZDHHC11"
                     /gene_synonym="FLJ13153; ZNF399"
                     /inference="alignment:Splign"
                     /number=10
     exon            1531..1565
                     /gene="ZDHHC11"
                     /gene_synonym="FLJ13153; ZNF399"
                     /inference="alignment:Splign"
                     /number=11
     exon            1566..1630
                     /gene="ZDHHC11"
                     /gene_synonym="FLJ13153; ZNF399"
                     /inference="alignment:Splign"
                     /number=12
     exon            1631..2606
                     /gene="ZDHHC11"
                     /gene_synonym="FLJ13153; ZNF399"
                     /inference="alignment:Splign"
                     /number=13
     STS             1688..1887
                     /gene="ZDHHC11"
                     /gene_synonym="FLJ13153; ZNF399"
                     /standard_name="A008P27"
                     /db_xref="UniSTS:55169"
ORIGIN
        1 gtgaacgggt tgtgggacct gtcgctgtgt gggggctgtc gagcactccc cagaacgtaa
       61 caaatcctca ggggaactga tcggcggtcg cgcgggcact gggtcctcca caccctggag
      121 agccgttttc cgttgccact ccgctctggc cggggtcaca ttctgcagca tgtctgttca
      181 ttcccctggg cggggccctg caccgactcc agcccagccc ctgctccctc tgcggggaac
      241 gtggccccag gcagtgctgg gccattggct gtcagtgctg gtcctggccg ctgcattccc
```

301 agtccccttg gtctctgtga cagtgggcgg ggccggccct cccaggatct gacggcgcag
361 gtcctcccct tctgtgtcct gcagatggac acccgctccg ggagccagtg ttccgtcacc
421 ccagaagcca tactcaataa tgaaaagctg gtcttgccgc cccgcatctc cagagtgaac
481 ggctggtcgt taccccctgca ctacttccag gtggtgacct gggctgtctt cgtgggcctt
541 tcctcggcca ccttcgggat cttcattccc ttcctgcctc acgcgtggaa atacattgcc
601 tacgtggtga ccggggggat cttctcgttc cacctcgtcg tccacctgat cgcgtcctgc
661 atcgacccgg ccgactccaa tgtcagactc atgaagaact attctcagcc catgcccctc
721 ttcgacagat caaaacatgc acacgtgatc cagaatcagt tctgccacct gtgcaaggtc
781 accgtgaaca agaaaaccaa acactgcatt tcctgcaata agtgtgtgtc cggcttcgac
841 caccactgca aatggatcaa caactgcgtg ggaagccgga attattggtt cttcttcagc
901 actgtggcct cggccacagc tggcatgctc tgcctgatcg ccatcctgct gtatgtcctc
961 gtccagtacc tcgtgaaccc cggggtgctc cgcacggacc ccaggtatga agatgtcaag
1021 aatatgaaca cgtggctgct gttcctcccc ctgttcccgg tgcaggtgca gaccctgata
1081 gtcgtgatca tcgggatgct cgtgctcctg ctggactttc ttggcttggt gcacctgggc
1141 cagctgctca tcttccacat ctacctgaag gccaagaaga tgaccacctt tgagtatctc
1201 attaataacc gcaaagaaga gagttcaaaa catcaagcag tgaggaaaga tccatacgtg
1261 caaatggaca aaggagttct ccagcaagga gctggcgccc tgggctcatc tgcacaggga
1321 gtcaaagcca agagctccct gctgattcac aagcacttat gtcacttctg cacttcagta
1381 aaccaggatg gggattcgac ggcacgggaa ggggatgaag acccgtgtcc atctgcactt
1441 ggagccaagg ccaggaactc ccggctgatt tgcaggcgcc tgtgtcagtt ctccactcgt
1501 gtacacccag acggggggctc gatggcacag gaagcagatg atgccccgag tatatctaca
1561 cttgggctgc aacaagaaac aacagagccc atgaaaactg acagtgctga aagtgaagac
1621 tgagattcag gagctcaggt gcccctgtga tccaggtctt ctaccctgaa accccaccct
1681 ccatcaaggt cctgcctgta gagtctacct tgcaaagcct cctgctccta cccatgctac
1741 aggccaggaa ccagagccca tcatctcaga ggcccctgga tgtccttcga aggaaccagg
1801 accctcagag cccagcatcc atctctgtca tcatcttcat cacacccaaa gaagagccag
1861 ccttgcagga gggtttacat ctccaggaag atgggctgcc agcaactgca gaggatgcag
1921 ccacctgctt aactgtgctg tccagccagc cagccagctg cagggcctct tgctgcttaa
1981 gagctgatgg gccgggcatg ttggctcaca cctgtgagca cagtactggg aaatgggagc
2041 acagtactag gaaatgggag cacagtactg ggaaatggga gcacagtact gggaaatggg
2101 ggctcacagc actgcaaaat gggagcacag tattgggaaa tgggagcaca gtactgggaa
2161 gtgggagcac agtactgaga agtgggagca cagtactgag aaatgggagt acactactga
2221 gaaatgggag cacagtactg ggaaatgggc atacagtact gagaaatggg agcacacagt
2281 actgggaaat gggagcacag tactgggaaa tgggagccca cagtactggg aaaggggagt
2341 tcacagtact cggaaatggg agcatagtac tgggaaatgg gagcacagta ctgggaaatg

FIG. 12-55

```
     2401 ggagcatagt actgggaaac cccagacctg gattctgagt ttttcagcct agcccagact
     2461 tcttatctta gtagacaaaa agagtcaata ccagagaacc agaggcatcc tctgtatttt
     2521 aatgaactct gcattttaat ctgtttagta gtcatttttt aaaagataat cagttttcca
     2581 aatatatcta taagttacta cgtgcaaaaa aaaaaaaa
//
```

ZDHHC11B:

```
FEATURES             Location/Qualifiers
     source          1..1621
                     /organism="Homo sapiens"
                     /mol_type="mRNA"
                     /db_xref="taxon:9606"
                     /chromosome="5"
     gene            1..1621
                     /gene="ZDHHC11B"
                     /note="Derived by automated computational analysis using
                     gene prediction method: GNOMON. Supporting evidence
                     includes similarity to: 4 ESTs, 2 Proteins"
                     /db_xref="GeneID:653082"
                     /db_xref="HGNC:32962"
     CDS             1..1083
                     /gene="ZDHHC11B"
                     /codon_start=1
                     /product="zinc finger, DHHC-type containing 11B isoform
1"
                     /protein_id="XP_931146.2"
                     /db_xref="GI:239742476"
                     /db_xref="GeneID:653082"
                     /db_xref="HGNC:32962"

/translation="MDTRSGSQCSVTPEAIRNNEELVLPPRISRVNGWSLPLHYFRVV

TWAVFVGLSLATFRIFIPLLPHSWKYIAYVVTGGIFSFHLVVHLIASCIDPADSNVRL

MKNYSQPMPLFDRSKHAHVIQNQFCHLCKVTVNKKTKHCISCNKCVSGFDHHCKWINN
```

CVGSRNYWFFFSTVASAIAGMLCLIAILLYVLVQYLVNPRVLRTDPRYEDVKNMNTWL

LFLPLFPVQVQTLIVVIIRMLVLLLDLLGLVQLGQLLIFHIYLKAKKMTTFEYLINTR

KEESSKHQAVRKDPYVQMDKGFLQQGAGALGSSAQGVKAKSSLLIYKCPCHFCTSVNQ
DGDSKAQGRLTALPQDFREQAPVTWK"

ORIGIN

```
        1 atggacaccc gctccgggag ccagtgttcc gtcaccccag aagccatacg caacaatgaa
       61 gagctggtct tgccgccccg catctccaga gtgaacggct ggtcgttacc cctgcactac
      121 ttccgggtgg tgacttgggc tgtcttcgtt ggcctttcct tggccacctt caggatcttc
      181 attcccctcc tgcctcactc gtggaaatac atcgcctatg tggtgaccgg ggggatcttc
      241 tcgttccacc tcgtcgtcca cctgatcgcg tcctgcatcg acccggccga ctccaatgtc
      301 agactcatga agaactattc tcagcccatg cccctcttcg acagatcaaa acatgcacac
      361 gtgatccaga atcagttctg ccacctgtgc aaggtcaccg tgaacaagaa aaccaaacac
      421 tgcatttcct gcaataagtg tgtgtccggc ttcgaccacc actgcaaatg gatcaacaac
      481 tgcgtggcaa gccggaatta ttggttcttc ttcagcactg tggcctcggc cacagctggc
      541 atgctctgcc tgatcgccat cctgctgtat gtcctcgtcc agtacctcgt gaaccccagg
      601 gtgctccgca cggaccccag gtatgaagat gtcaagaata tgaacacgtg gctgctgttc
      661 ctccccctgt tcccggtgca ggtgcagact ctgatagtcg tgatcatcag gatgctcgtg
      721 ctcctgctgg accttcttgg cttggtgcag ctgggccagc tgctcatctt ccacatctac
      781 ctgaaggcca agaagatgac cacctttgag tatctcatta atacccgcaa agaagagagt
      841 tcaaaacatc aagcagtgag gaaagatcca tacgtgcaaa tggacaaagg atttctccag
      901 caaggagctg gcgccctggg ctcatctgca cagggagtca aggccaagag ctccctgctg
      961 atttacaaat gcccatgtca cttctgcact tcagtaaacc aggacgggga ttcgaaggca
     1021 cagggccgcc tcaccgcact tccccaggat ttcagggaac aggctcctgt gacttggaaa
     1081 tgaaaatgga tcacccaacc tggaggaaca gtgaggctgg tgtccaagac ttgccccttg
     1141 cctgcacttc cagcaaagat ttggagacac tcagtggaaa ccaatcgagc cccccagccca
     1201 cccccgccca gactcagcca ccaaagttcc ctcactgcat gtggcacacg ggctcatggg
     1261 agtttctctg cctgcgattg tccacgttga caccttctgc acaggtgcat ttgtgagtcc
     1321 cctcggtgtc tctgcagcat ctatgtgtgg atgaatagtg aagccacatg aggcctggtc
     1381 tgaagcagag aagatccgct cagcatcacg ttgaatccca agcccgcatc tccgtgggct
     1441 ccaggacaat cctatgaaaa tgacaccgtc ggttcattgt tcacatcggg gaggagaatt
     1501 ccgtctgaaa atgagcgtga cttcactgac acccaagtcc gtggcacagc cctgtgctga
     1561 gctccacaga cctacagtcc atcgcctccc cttcgagtgg gcccagggct gcagacagca
     1621 t
//
```

FIG. 12-56

ZDHHC12:

```
FEATURES             Location/Qualifiers
     source          1..1184
                     /organism="Homo sapiens"
                     /mol_type="mRNA"
                     /db_xref="taxon:9606"
                     /chromosome="9"
                     /map="9q34.11"
     gene            1..1184
                     /gene="ZDHHC12"
                     /gene_synonym="FLJ14524; MGC13153; MGC54050; ZNF400"
                     /note="zinc finger, DHHC-type containing 12"
                     /db_xref="GeneID:84885"
                     /db_xref="HGNC:19159"
                     /db_xref="HPRD:15709"
     exon            1..136
                     /gene="ZDHHC12"
                     /gene_synonym="FLJ14524; MGC13153; MGC54050; ZNF400"
                     /inference="alignment:Splign"
                     /number=1
     CDS             37..840
                     /gene="ZDHHC12"
                     /gene_synonym="FLJ14524; MGC13153; MGC54050; ZNF400"
                     /note="zinc finger, DHHC domain containing 12; DHHC-12;
                     zinc finger protein 400; zinc finger DHHC
                     domain-containing protein 12"
                     /codon_start=1
                     /product="probable palmitoyltransferase ZDHHC12"
                     /protein_id="NP_116188.2"
                     /db_xref="GI:21361910"
                     /db_xref="CCDS:CCDS6909.1"
                     /db_xref="GeneID:84885"
                     /db_xref="HGNC:19159"
                     /db_xref="HPRD:15709"
```

FIG. 12-57

/translation="MAPWALLSPGVLVRTGHTVLTWGITLVLFLHDTELRQWEEQGEL

LLPLTFLLLVLGSLLLYLAVSLMDPGYVNVQPQPQEELKEEQTAMVPPAIPLRRCRYC

LVLQPLRARHCRECRRCVRRYDHHCPWMENCVGERNHPLFVVYLALQLVVLLWGLYLA

WSGLRFFQPWGLWLRSSGLLFATFLLLSLFSLVASLLLVSHLYLVASNTTTWEFISSH
RIAYLRQRPSNPFDRGLTRNLAHFFCGWPSGSWETLWAEEEEEGSSPAV"

exon 137..273
/gene="ZDHHC12"
/gene_synonym="FLJ14524; MGC13153; MGC54050; ZNF400"
/inference="alignment:Splign"
/number=2 exon 274..351
/gene="ZDHHC12"
/gene_synonym="FLJ14524; MGC13153; MGC54050; ZNF400"
/inference="alignment:Splign"
/number=3 exon 352..518
/gene="ZDHHC12"
/gene_synonym="FLJ14524; MGC13153; MGC54050; ZNF400"
/inference="alignment:Splign"
/number=4 exon 519..1152
/gene="ZDHHC12"
/gene_synonym="FLJ14524; MGC13153; MGC54050; ZNF400"
/inference="alignment:Splign"
/number=5

ORIGIN 1 gggcgcttct tccgggtggg gccccgggcc gaggcgatgg cgccctgggc gctcctcagc
61 cctgcgggtcc tggtgcggac cgggcacacc gtgctgacct ggggaatcac gctggtgctc
121 ttcctgcacg ataccgagct gcggcaatgg gaggagcagg gggagctgct cctgcccctc
181 accttcctgc tcctggtgct gggctccctg ctgctctacc tcgctgtgtc actcatggac
241 cctggctacg tgaatgtgca gccccagcct caggaggagc tcaaagagga gcagacagcc
301 atggttcctc cagccatccc tcttcggcgc tgcagatact gcctggtgct gcagcccctg
361 agggctcggc actgccgtga gtgccgccgt tgcgtccgcc gctacgacca ccactgcccc

FIG. 12-58

```
 421 tggatggaga actgtgtggg agagcgcaac cacccactct ttgtggtcta cctggcgctg
 481 cagctggtgg tgcttctgtg gggcctgtac ctggcatggt caggcctccg gttcttccag
 541 ccctggggtc tgtggttgcg gtccagcggg ctcctgttcg ccaccttcct gctgctgtcc
 601 ctcttctcgt tggtggccag cctgctcctc gtctcgcacc tctacctggt ggccagcaac
 661 accaccacct gggaattcat ctcctcacac cgcatcgcct atctccgcca gcgccccagc
 721 aaccccttcg accgaggcct gacccgcaac ctggcccact tcttctgtgg atggccctca
 781 gggtcctggg agaccctctg ggctgaggag gaggaagagg gcagcagccc agctgtttag
 841 ggttgctgga ggccgggcta ccgtcttgtg cctgaaaacc acggggcctg tccccagctg
 901 gggtgagcgc tcagagggcc tggggccctc actcctgccc acgcctccca gaccccagaa
 961 cggagcttca agtcagacag atccctgcct tggtgggcag ttctgccttc caaggaagaa
1021 ggggaagaaa aggacctgtg ggtggctcag gcccaagcag accccgggct ccaccccagc
1081 cccgcccagg ctgctgccag tgcacacttt tacaaattta atataaagca agtccagtct
1141 taaaaagaca aaaaaaaaaa aaaaaaaaaa aaaaaaaaaa aaaa
//
```

ZDHHC13:

```
FEATURES             Location/Qualifiers
     source          1..2448
                     /organism="Homo sapiens"
                     /mol_type="mRNA"
                     /db_xref="taxon:9606"
                     /chromosome="11"
                     /map="11p15.1"
     gene            1..2448
                     /gene="ZDHHC13"
                     /gene_synonym="FLJ10852; FLJ10941; HIP14L; HIP3RP;
                     MGC64994"
                     /note="zinc finger, DHHC-type containing 13"
                     /db_xref="GeneID:54503"
                     /db_xref="HGNC:18413"
                     /db_xref="HPRD:15710"
                     /db_xref="MIM:612815"
     CDS             106..1974
                     /gene="ZDHHC13"
```

FIG. 12-59

/gene_synonym="FLJ10852; FLJ10941; HIP14L; HIP3RP;
MGC64994"
/note="isoform 1 is encoded by transcript variant 1;
huntingtin interacting protein HIP3RP; HIP14-like;
HIP14-related protein; zinc finger, DHHC domain
containing
13; DHHC-13; huntingtin-interacting protein HIP3RP;
putative MAPK-activating protein PM03; putative
NF-kappa-B-activating protein 209; zinc finger DHHC
domain-containing protein 13; huntingtin-interacting
protein 14-related protein; probable
palmitoyltransferase
ZDHHC13"
/codon_start=1
/product="probable palmitoyltransferase ZDHHC13 isoform
1"
/protein_id="NP_061901.2"
/db_xref="GI:47933346"
/db_xref="CCDS:CCDS44550.1"
/db_xref="GeneID:54503"
/db_xref="HGNC:18413"
/db_xref="HPRD:15710"
/db_xref="MIM:612815"

/translation="MEGPGLGSQCRNHSHGPHPPGFGRYGICAHENKELANAREALPL

IEDSSNCDIVKATQYGIFERCKELVEAGYDVRQPDKENVSLLHWAAINNRLDLVKFYI

SKGAVVDQLGGDLNSTPLHWAIRQGHLPMVILLLQHGADPTLIDGEGFSSIHLAVLFQ

HMPIIAYLISKGQSVNMTDVNGQTPLMLSAHKVIGPEPTGFLLKFNPSLNVVDKIHQN

TPLHWAVAAGNVNAVDKLLEAGSSLDIQNVKGETPLDMALQNKNQLIIHMLKTEAKMR

ANQKFRLWRWLQKCELFLLLMLSVITMWAIGYILDFNSDSWLLKGCLLVTLFFLTSLF

FIG. 12-60

PRFLVGYKNLVYLPTAFLLSSVFWIFMTWFILFFPDLAGAPFYFSFIFSIVAFLYFFY

KTWATDPGFTKASEEEKKVNIITLAETGSLDFRTFCISCLIRKPLRSLHCHVCNCCVA

RYDQHCLWTGRCIGFGNHHYYIFFLFFLSMVCGWIIYGSFIYLSSHCATTFKEDGLWT

YLNQIVACSPWVLYILMLATFHFSWSTFLLLNQLFQIAFLGLTSHERISLQKQSKHMK

QTLSLRKTPYNLGFMQNLADFFQCGCFGLVKPCVVDWTSQYTMVFHPAREKVLRSV"

polyA_site 2428
/gene="ZDHHC13"
/gene_synonym="FLJ10852; FLJ10941; HIP14L; HIP3RP; MGC64994"

ORIGIN 1 gggcgccagc aggaagtggg agaagaggcg acccaaggcg ggctggcggg ctggcggcag
61 tcgctacttg cctagtagcc tcagccgctg tgggctcctg gggagatgga ggggccgggg
121 ctgggctcgc agtgcaggaa tcacagccat ggcccccacc ctccaggatt tggtcgatat
181 ggcatctgtg cacatgaaaa caaagaactt gccaatgcaa gagaagctct tcctcttata
241 gaggactcta gtaactgtga cattgtcaaa gctactcaat acggaatttt tgaacgatgt
301 aaagagttgg tagaagcagg atatgatgtc aggcaaccag ataaagaaaa tgtgtcgctt
361 cttcattggg ctgctattaa caacagactg gatcttgtaa agttttatat ttcaaaaggt
421 gctgttgtag atcagttggg tggagattta aattcaactc ctcttcactg ggccatccga
481 caaggacatt tacctatggt catattatta ctccagcatg gtgcagaccc cactcttatt
541 gatggagagg gattcagcag catccacctg gcagtattgt ttcaacacat gcctattata
601 gcatatctca tctcaaaggg acagagtgtg aatatgacag atgtaaatgg gcagacacct
661 ctcatgttat cagctcacaa agtaattggg ccagaaccaa ctggatttct tttaaagttt
721 aatccttctc tcaatgtggt tgataaaata caccaaaaca ctccacttca ctgggcagtt
781 gcagcaggaa atgttaatgc agttgataag ctttggaag ctggttctag cctggatatc
841 cagaatgtta agggagaaac acctcttgat atggctctac aaaacaaaaa tcagctcatt
901 attcatatgc taaaaacaga agccaaaatg agagccaacc aaaagttcag actttggagg
961 tggctgcaga aatgcgagct cttcctgctg ctgatgcttt ctgtgattac catgtgggct
1021 attggataca tattggactt caattcagat tcttggcttt taaaaggatg tcttctagta
1081 acactgtttt ttctgacatc tttgtttcca aggttcctgg ttgggtataa gaaccttgta
1141 tacttaccaa cagcctttct gctaagttct gtttttttgga tatttatgac ttggttcatc
1201 ttatttttttc ctgatttagc aggagccccct ttctatttca gtttcatttt cagcatagta
1261 gcctttctat actttttcta taagacttgg gcaactgatc caggcttcac taaggcttct

FIG. 12-61

```
1321 gaagaagaaa agaaagtgaa tatcatcacc cttgcagaaa ctggctctct ggacttcaga
1381 acattttgta catcatgtct tataaggaag ccattaaggt cactccactg ccatgtatgc
1441 aactgctgtg tggctcgata tgatcaacac tgcctgtgga ctggacggtg cataggtttt
1501 ggcaaccatc actattacat attcttcttg tttttccttt ccatggtatg tggctggatt
1561 atatatggat ctttcatcta tttgtccagt cattgtgcca caacattcaa agaagatgga
1621 ttatggactt acctcaatca gattgtggcc tgttcccctt gggttttata tatcttgatg
1681 ctagcaactt tccatttctc atggtcaaca tttttattat taaatcaact ctttcagatt
1741 gcctttctgg gcctgacctc ccatgagaga atcagcctgc agaagcagag caagcatatg
1801 aaacagacgt tgtccctcag gaagacacca tacaatcttg gattcatgca gaacctggca
1861 gatttctttc agtgtggctg ctttggcttg gtgaagccct gtgtggtaga ttggacatca
1921 cagtacacca tggtctttca cccagccagg gagaaggttc ttcgctcagt atgaagaaaa
1981 gcaacccaaa actctcaatc tgatttgttt ttgtttatgt cgatgcccctg tagtttgaaa
2041 gtgaagtaaa gatttagaat tcacctaagt ccaaaggaaa acacgtggtt tttaaagcca
2101 ttaggtaaaa aaagttctca ataaaggcat tacaattttt taggtttaga aagatggact
2161 tttctgataa atcttggcag acatctaaaa aaaaaaccat atttttcaca agaaaatgca
2221 agttactttt tttgcaaata atactcactg attatggata aaatggaata ttttcagata
2281 ctatattggc tgtttcaaaa tagtactatt ctttaaactt gtaatttttg ctaagttatt
2341 tgtctttgtt gtatctataa atatgtaaaa aatatttaaa tagatgtacc tgttttgctt
2401 tcacacttaa taaaaaattt ttttttgtag ttgaaaaaaa aaaaaaaa
//
```

ZDHHC14:

```
FEATURES             Location/Qualifiers
     source          1..2821
                     /organism="Homo sapiens"
                     /mol_type="mRNA"
                     /db_xref="taxon:9606"
                     /chromosome="6"
                     /map="6q25.3"
     gene            1..2821
                     /gene="ZDHHC14"
                     /gene_synonym="FLJ20984; NEW1CP"
                     /note="zinc finger, DHHC-type containing 14"
                     /db_xref="GeneID:79683"
```

FIG. 12-62

/db_xref="HGNC:20341"
/db_xref="HPRD:15711"
exon 1..742
/gene="ZDHHC14"
/gene_synonym="FLJ20984; NEW1CP"
/inference="alignment:Splign"
/number=1
CDS 498..1964
/gene="ZDHHC14"
/gene_synonym="FLJ20984; NEW1CP"
/note="isoform 1 is encoded by transcript variant 1;
NEW1
domain containing protein; zinc finger, DHHC domain
containing 14; DHHC-14; NEW1 domain-containing protein;
zinc finger DHHC domain-containing protein 14; probable
palmitoyltransferase ZDHHC14"
/codon_start=1
/product="probable palmitoyltransferase ZDHHC14 isoform
1"
/protein_id="NP_078906.2"
/db_xref="GI:24371241"
/db_xref="CCDS:CCDS5252.1"
/db_xref="GeneID:79683"
/db_xref="HGNC:20341"
/db_xref="HPRD:15711"

/translation="MPPGGGGPMKDCEYSQISTHSSSPMESPHKKKKIAARRKWEVFP

GRNKFFCNGRIMMARQTGVFYLTLVLILVTSGLFFAFDCPYLAVKITPAIPAVAGILF

FFVMGTLLRTSFSDPGVLPRATPDEAADLERQIDIANGTSSGGYRPPPRTKEVIINGQ

TVKLKYCFTCKIFRPPRASHCSLCDNCVERFDHHCPWVGNCVGKRNYRFFYMFILSLS

FLTVFIFAFVITHVILRSQQTGFLNALKDSPASVLEAVVCFFSVWSIVGLSGFHTYLI

FIG. 12-63

SSNQTTNEDIKGSWSNKRGKENYNPYSYGNIFTNCCVALCGPISPSLIDRRGYIQPDT

PQPAAPSNGITMYGATQSQSDMCDQDQCIQSTKFVLQAAATPLLQSEPSLTSDELHLP

GKPGLGTPCASLTLGPPTPPASMPNLAEATLADVMPRKDEHMGHQFLTPDEAPSPPRL
LAAGSPLAHSRTMHVLGLASQDSLHEDSVRGLVKLSSV"

exon 743..903
/gene="ZDHHC14"
/gene_synonym="FLJ20984; NEW1CP"
/inference="alignment:Splign"
/number=2 exon 904..1062
/gene="ZDHHC14"
/gene_synonym="FLJ20984; NEW1CP"
/inference="alignment:Splign"
/number=3 exon 1063..1200
/gene="ZDHHC14"
/gene_synonym="FLJ20984; NEW1CP"
/inference="alignment:Splign"
/number=4 exon 1201..1249
/gene="ZDHHC14"
/gene_synonym="FLJ20984; NEW1CP"
/inference="alignment:Splign"
/number=5 exon 1250..1352
/gene="ZDHHC14"
/gene_synonym="FLJ20984; NEW1CP"
/inference="alignment:Splign"
/number=6 exon 1353..1462
/gene="ZDHHC14"
/gene_synonym="FLJ20984; NEW1CP"
/inference="alignment:Splign"
/number=7

```
     exon            1463..1565
                     /gene="ZDHHC14"
                     /gene_synonym="FLJ20984; NEW1CP"
                     /inference="alignment:Splign"
                     /number=8
     exon            1566..2787
                     /gene="ZDHHC14"
                     /gene_synonym="FLJ20984; NEW1CP"
                     /inference="alignment:Splign"
                     /number=9a
     STS             2210..2333
                     /gene="ZDHHC14"
                     /gene_synonym="FLJ20984; NEW1CP"
                     /standard_name="SHGC-34875"
                     /db_xref="UniSTS:56404"
     STS             2524..2660
                     /gene="ZDHHC14"
                     /gene_synonym="FLJ20984; NEW1CP"
                     /standard_name="RH46611"
                     /db_xref="UniSTS:4850"
     STS             2654..2780
                     /gene="ZDHHC14"
                     /gene_synonym="FLJ20984; NEW1CP"
                     /standard_name="WI-14340"
                     /db_xref="UniSTS:60432"
ORIGIN
        1 gaaggagtgg acccaacctg gccgcgccgc agaagtggct cccgaggaag ccggcgccgg
       61 ggccgccgcc tcgtgtcccc tcggggcgca gtgctcgggg gtcggcgggc cagagccgag
      121 gcgcggccgg ggagccgggg gctgcggggc cgagcgggca gccgcgcgag ggggcgggcg
      181 ctcggcgacc cgggggccgg ccgggctgag ccccgcgccc cgggacgcgg gctggaagcg
      241 acggaggagt gctgccgcgg gctgcggacc agcgccgtcc cctcacggag cggggattct
      301 gctatgacag ttgggctccc cggagggtta acctgggtgt cctcggcaaa gttgtcgccg
      361 agccgggagc ccgtgtaggg gccgcggcgc cgcggctcgg ggggcggccg ggcggccggc
      421 ggcggtcgtg gctcggcggg gcccgcgcgg ccggggggct cctgggggtg tgcgcccccca
      481 gccggctgcc ctcgtggatg cctccccggcg gcggcgggcc catgaaagac tgcgagtaca
      541 gccagatcag cacccacagc tcctccccca tggagtcgcc ccacaagaag aagaaaatcg
```

FIG. 12-66

```
 601 cggccccggag gaaatgggag gtgttcccgg gaagaaacaa gttcttctgt aacgggagga
 661 tcatgatggc ccggcagacg ggcgtcttct acctgacgct cgtcctcatc ctggtcacta
 721 gcggactctt cttcgccttc gactgtccgt acctggcggt gaaaatcacc cctgccatcc
 781 ctgcagtcgc tggcatcctg ttcttctttg tgatggggac cctgctccgc accagcttca
 841 gcgaccccgg agtcctccca cgagccacgc ctgatgaagc cgccgatctg gaaaggcaaa
 901 tagatatcgc aaacggcacc agttcacggg ggtaccgccc gcctcccaga accaaagaag
 961 tcatcatcaa tggccagacc gtgaaactta aatactgttt cacctgcaag attttccggc
1021 cccctcgcgc ctcccattgc agcctttgtg ataactgcgt agaacggttt gatcaccact
1081 gtccctgggt aggcaactgt gtggggaaaa gaaactacag atttttttat atgtttattt
1141 tatctctgtc ttttctgaca gtctttatat ttgcattcgt tatcacccac gtcattcttc
1201 gttcacagca aacaggattc ctaaatgccc ttaaggacag tcctgcaagc gtcctggagg
1261 ctgtggtgtg cttcttctct gtctggtcca tcgttggcct ctcaggattc cacacctact
1321 tgatcagctc caaccagaca acaaatcagg acattaaagg atcctggtca aataaaagag
1381 gtaaagaaaa ttacaatccc tacagctacg gaaatatctt taccaactgc tgtgttgccc
1441 tgtgtgggcc catctcacca agcctgatcg acagaagagg gtacatccag cccgacacgc
1501 cgcagccagc agcaccctcc aatggcatca ccatgtacgg ggccacgcag tcacagagtg
1561 acatgtgcga ccaagaccag tgcattcaga gcaccaaatt cgttttgcag gctgcagcca
1621 cgcccctgct gcagagcgag cccagcctca ccagcgacga gctgcacctg cccgggaagc
1681 ctggcctggg cacgccctgc gccagcctca cactgggccc gcccacaccg cccgcctcca
1741 tgcccaacct cgccgaggcc acgctcgcgg acgtgatgcc ccggaaagat gagcacatgg
1801 gccaccagtt cctgacgccc gatgagcgcc cctcgccccc caggctactg gcggcgggca
1861 gccccctggc gcacagccgc accatgcacg tgctgggcct ggccagccag gactccctgc
1921 atgaggactc tgtgcgcggc ctggtgaagc tcagctccgt gtgaccccaca tggccccagg
1981 ccgggggaca ccagaggctc ctccatcggc agcaggagtg agcggagggg tgtgtcccac
2041 agcgactttc ccagccaatg ccacggtgga gatgacagcc ccaggtctgg ggtacagaga
2101 ccacttagga tggcacaggg tggctgcccc cggatgctga gagcttggtt tcatttgaat
2161 tttcttcccc aacctgagtg ctttgacaac aatggaaata gagaagtggc tgctttcttt
2221 tggtgaccct ccaggggtgg aatcggagtg tgtctgcccg cccttgtgac agacacacgg
2281 aaggcttctg acgcttgtgg ccagactgca attgcactta tgtgttatgc tactaatatt
2341 tgaaacagac ctgccattcc atttgttaat taaaaaaaaa aaaaatccta aagggaaaaa
2401 accgaccagg tgtggatctg catgcccacgc tgccgtctgt gttacagtgg tgttgctatt
2461 tccaaggaag tgctgctttc tttttctttt tttaattttg tgaattttca agtgctgttt
2521 tgttggaaga cagtgcaacg aactgacact aatggacagt gtcatcactc agcttactgg
2581 gctgaggcgt ctgtggagag gtggcaccgg ggctgcagag ggcggctggg gttccgtcgt
2641 gtcgggtgtc acttcacctt ctgtttcggc gctcgatgag gtctcgtgtt gagatattgt
```

```
    2701 gtgccacaac ccccacagtc ttcacctccg tgtgtgatga aacttcccgt ggacagccaa
    2761 taaaatgacg tcctctgtta ttttggaaaa aaaaaaaaaa aaaaaaaaaa aaaaaaaaaa
    2821 a
//
```

ZDHHC15:

```
FEATURES             Location/Qualifiers
     source          1..1782
                     /organism="Homo sapiens"
                     /mol_type="mRNA"
                     /db_xref="taxon:9606"
                     /chromosome="X"
                     /map="Xq13.3"
     gene            1..1782
                     /gene="ZDHHC15"
                     /gene_synonym="FLJ31812; MGC119974; MGC119975;
MGC119976;
                     MRX91"
                     /note="zinc finger, DHHC-type containing 15"
                     /db_xref="GeneID:158866"
                     /db_xref="HGNC:20342"
                     /db_xref="HPRD:06758"
                     /db_xref="MIM:300576"
     STS             1..1106
                     /gene="ZDHHC15"
                     /gene_synonym="FLJ31812; MGC119974; MGC119975;
MGC119976;
                     MRX91"
                     /db_xref="UniSTS:482995"
     exon            1..152
                     /gene="ZDHHC15"
                     /gene_synonym="FLJ31812; MGC119974; MGC119975;
MGC119976;
```

FIG. 12-67

MRX91"
/inference="alignment:Splign"
/number=1
CDS 17..1030
/gene="ZDHHC15"
/gene_synonym="FLJ31812; MGC119974; MGC119975;
MGC119976;
MRX91"
/note="zinc finger, DHHC domain containing 15"
/codon_start=1
/product="zinc finger, DHHC-type containing 15"
/protein_id="NP_659406.1"
/db_xref="GI:21450653"
/db_xref="CCDS:CCDS14430.1"
/db_xref="GeneID:158866"
/db_xref="HGNC:20342"
/db_xref="HPRD:06758"
/db_xref="MIM:300576"

/translation="MRRGWKMALSGGLRCCRRVLSWVPVLVIVLVVLWSYYAYVFELC

LVTVLSPAEKVIYLILYHAIFVFFTWTYWKSIFTLPQQPNQKFHLSYTDKERYENEER

PEVQKQMLVDMAKKLPVYTRTGSGAVRFCDRCHLIKPDRCHHCSVCAMCVLKMDHHCP

WVNNCIGFSNYKFFLQFLAYSVLYCLYIATTVFSYFIKYWRGELPSVRSKFHVLFLLF

VACMFFVSLVILFGYHCWLVSRNKTTLEAFCTPVFTSGPEKNGFNLGFIKNIQQVFGD

KKKFWLIPIGSSPGDGHSFPMRSMNESQNPLLANEETWEDNEDDNQDYPEGSSSLAVE
TET"
exon 153..179
/gene="ZDHHC15"
/gene_synonym="FLJ31812; MGC119974; MGC119975;
MGC119976;
MRX91"

FIG. 12-68

```
                    /inference="alignment:Splign"
                    /number=2
     exon           180..274
                    /gene="ZDHHC15"
                    /gene_synonym="FLJ31812; MGC119974; MGC119975;
MGC119976;
                    MRX91"
                    /inference="alignment:Splign"
                    /number=3
     exon           275..395
                    /gene="ZDHHC15"
                    /gene_synonym="FLJ31812; MGC119974; MGC119975;
MGC119976;
                    MRX91"
                    /inference="alignment:Splign"
                    /number=4
     exon           396..465
                    /gene="ZDHHC15"
                    /gene_synonym="FLJ31812; MGC119974; MGC119975;
MGC119976;
                    MRX91"
                    /inference="alignment:Splign"
                    /number=5
     exon           466..498
                    /gene="ZDHHC15"
                    /gene_synonym="FLJ31812; MGC119974; MGC119975;
MGC119976;
                    MRX91"
                    /inference="alignment:Splign"
                    /number=6
     exon           499..619
                    /gene="ZDHHC15"
                    /gene_synonym="FLJ31812; MGC119974; MGC119975;
MGC119976;
                    MRX91"
```

FIG. 12-69

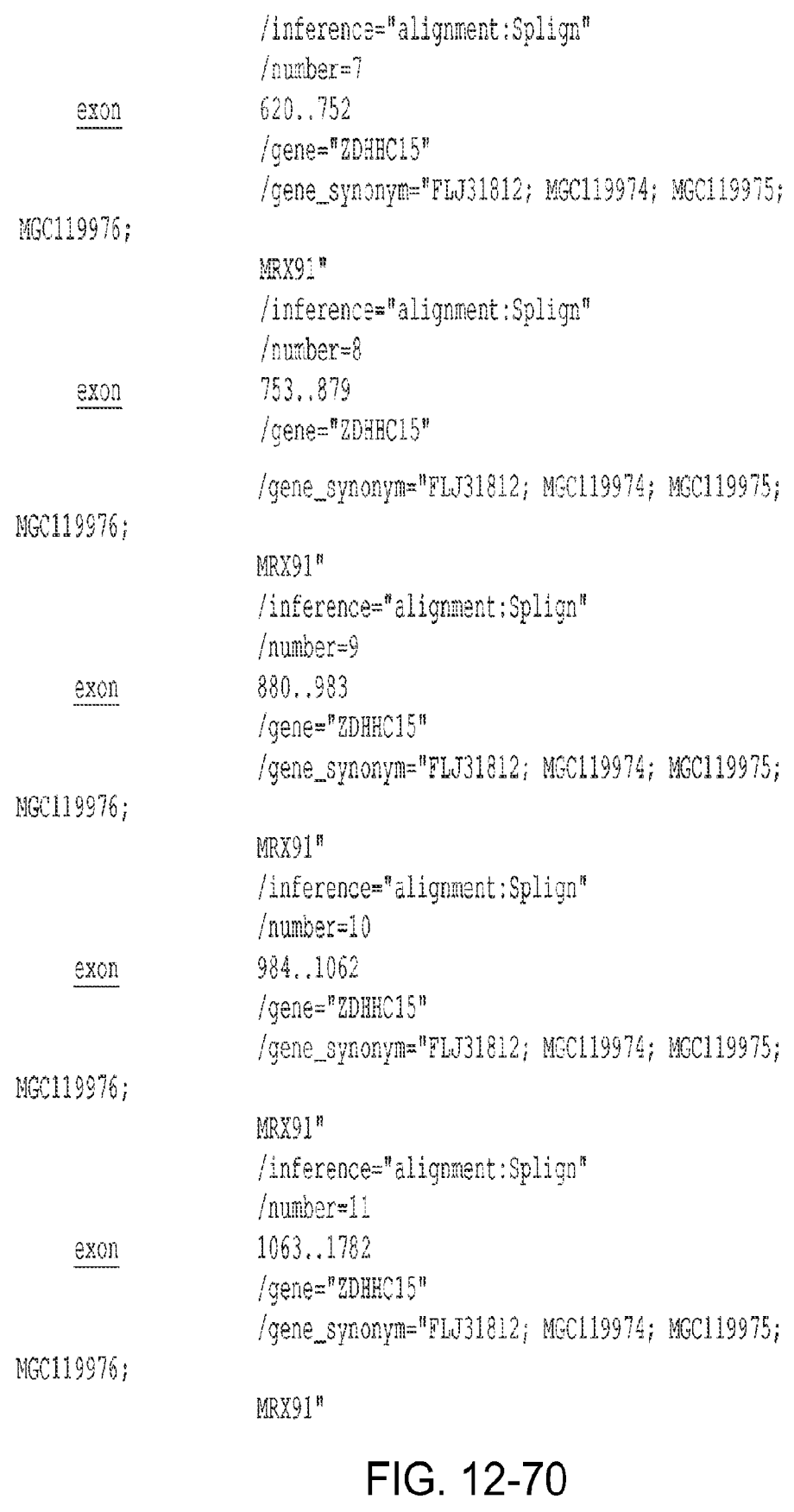

/inference="alignment:Splign"
/number=7
exon 620..752
/gene="ZDHHC15"
/gene_synonym="FLJ31812; MGC119974; MGC119975;
MGC119976;
MRX91"
/inference="alignment:Splign"
/number=8
exon 753..879
/gene="ZDHHC15"
/gene_synonym="FLJ31812; MGC119974; MGC119975;
MGC119976;
MRX91"
/inference="alignment:Splign"
/number=9
exon 880..983
/gene="ZDHHC15"
/gene_synonym="FLJ31812; MGC119974; MGC119975;
MGC119976;
MRX91"
/inference="alignment:Splign"
/number=10
exon 984..1062
/gene="ZDHHC15"
/gene_synonym="FLJ31812; MGC119974; MGC119975;
MGC119976;
MRX91"
/inference="alignment:Splign"
/number=11
exon 1063..1782
/gene="ZDHHC15"
/gene_synonym="FLJ31812; MGC119974; MGC119975;
MGC119976;
MRX91"

FIG. 12-70

/inference="alignment:Splign"
/number=12

ORIGIN 1 gatcttcgag ccaaagatgc ggcgaggctg gaagatggct ctgtctgggg ggctgcggtg
61 ctgccgccgg gtactgtcct gggtgccagt gctcgttatt gtcctcgtcg tgctctggtc
121 ctactatgcc tacgtctttg aactctgcct ggtgactgtt ttgagcccag cagaaaaagt
181 tatttacctc atactctacc atgccatctt tgtgttcttt acctggacct actggaagtc
241 tatctttaca ctcccacagc agccaaacca gaagttccac ttgtcctaca cagacaagga
301 gcgctatgaa aatgaagaaa gacctgaggt ccagaagcag atgcttgttg atatggccaa
361 aaagctaccg gtttacacaa gaactggaag tggagctgta cgattctgtg accggtgtca
421 tctgatcaag ccagaccgct gccaccactg ctctgtctgt gctatgtgtg tgttaaaaat
481 ggatcatcac tgcccttggg ttaataactg cattggattt tccaactaca aattcttcct
541 tcaattctta gcttactctg ttctctactg cctgtacatt gctacgacag tcttcagcta
601 tttcatcaaa tactggagag gggaattacc cagtgttcgc tctaagttcc atgtcctttt
661 tcttctcttt gtggcctgca tgtttttgt cagccttgtg attctctttg gttaccattg
721 ttggcttgtc agcagaaaca aaaccacctt agaggccttc tgcactccag tgtttacaag
781 tggcccagag aaaaatgggt tcaaccttgg cttcatcaag aatatccagc aggtgtttgg
841 agataagaag aagttctggt taatacctat tggttccagc cctggtgatg gacactcctt
901 ccctatgagg tctatgaatg agtcacagaa cccactgcta gcaaatgaag aaacctggga
961 agacaacgag gatgacaacc aagattatcc agaaggctca tcatctcttg ctgtggaaac
1021 ggaaacatag cagttttcac atttcctgca tctctcagac aggactcacc atctctgcct
1081 cccatgaggc ttacagagtt caatgttgga aatcattgta atcttcaaaa taagtcaccg
1141 tgttggattg aaagcttcaa aatttgaaag aattccatca aatacttgct gtgtaaatgt
1201 ttctggactt tatgttattt aatttactga ctgaaatcca atttggaatt tggtagcagt
1261 taattcaagc caattttttt tgtttcttca tttcccctcc cccaatccat gaaagcctaa
1321 atgtaaaata tatcttttca ttcatcttat caggtaaaag gaaattcaga aaatttcctt
1381 agagtcttta attcccccac aaagattatt aatcacatat atagggcctt tttggtgttg
1441 aagggaatca aactacattt gctgcttgtg tgcgtgtgca tttgtgaaca cgtacagcat
1501 atctatacaa aattctgcta tagtgtgaaa atcagggcta aaaacctgaa gcctttgttt
1561 aattatgctt ttcctctaaa tagcaactta aatatttgct agactttgaa tcatcgctat
1621 atcaagtatc taaaatttgg gagggtgaat cagtacactg tgaccaaggt cctcaaattg
1681 gaatttgaac aacaatgtaa aacctgttct gtcacaaatg ttcctgaaag caccacagct
1741 actcaagaag atcaaattca ggacataaac tttattgaac at

FIG. 12-71

ZDHHC16:

| FEATURES | Location/Qualifiers |
|---|---|
| source | 1..1816<br>/organism="Homo sapiens"<br>/mol_type="mRNA"<br>/db_xref="taxon:9606"<br>/chromosome="10"<br>/map="10q24.1" |
| gene | 1..1816<br>/gene="ZDHHC16"<br>/gene_synonym="APH2; MGC2993"<br>/note="zinc finger, DHHC-type containing 16"<br>/db_xref="GeneID:84287"<br>/db_xref="HGNC:20714"<br>/db_xref="HPRD:15712" |
| exon | 1..181<br>/gene="ZDHHC16"<br>/gene_synonym="APH2; MGC2993"<br>/inference="alignment:Splign"<br>/number=1a |
| exon | 182..429<br>/gene="ZDHHC16"<br>/gene_synonym="APH2; MGC2993"<br>/inference="alignment:Splign"<br>/number=3 |
| CDS | 187..1320<br>/gene="ZDHHC16"<br>/gene_synonym="APH2; MGC2993"<br>/note="isoform 1 is encoded by transcript variant 1; Abl-philin 2; zinc finger, DHHC domain containing 16; DHHC-16; zinc finger DHHC domain-containing protein 16; probable palmitoyltransferase ZDHHC16"<br>/codon_start=1<br>/product="probable palmitoyltransferase ZDHHC16 isoform |

/protein_id="NP_115703.2"
/db_xref="GI:37594455"
/db_xref="CCDS:CCDS7460.1"
/db_xref="GeneID:84287"
/db_xref="HGNC:20714"
/db_xref="HPRD:15712"

/translation="MRGQRSLLLGPARLCLRLLLLLGYRRRCPPLLRGLVQRWRYGKV

CLRSLLYNSFGGSDTAVDAAFEPVYWLVDNVIRWFGVVFVVLVIVLTGSIVAIAYLCV

LPLILRTYSVPRLCWHFFYSHWNLILIVFHYYQAITTPPGYPPQGRNDIATVSICKKC

IYPKPARTHHCSICNRCVLKMDHHCPWLNNCVGHYNHRYFFSFCFFMTLGCVYCSYGS

WDLFREAYAAIEKMKQLDKNKLQAVANQTYHQTPPPTFSFRERMTHKSLVYLWFLCSS

VALALGALTVWHAVLISRGETSIERHINKKERRRLQAKGRVFRNPYNYGCLDNWKVFL
GVDTGRHWLTRVLLPSSHLPHGNGMSWEPPPWVTAHSASVMAV"

exon 430..624
/gene="ZDHHC16"
/gene_synonym="APH2; MGC2993"
/inference="alignment:Splign"
/number=4 exon 625..713
/gene="ZDHHC16"
/gene_synonym="APH2; MGC2993"
/inference="alignment:Splign"
/number=5 exon 714..742
/gene="ZDHHC16"
/gene_synonym="APH2; MGC2993"
/inference="alignment:Splign"
/number=6 exon 743..876

FIG. 12-73

```
                /gene="ZDHHC16"
                /gene_synonym="APH2; MGC2993"
                /inference="alignment:Splign"
                /number=7a
exon            877..924
                /gene="ZDHHC16"
                /gene_synonym="APH2; MGC2993"
                /inference="alignment:Splign"
                /number=8
exon            925..1010
                /gene="ZDHHC16"
                /gene_synonym="APH2; MGC2993"
                /inference="alignment:Splign"
                /number=9
exon            1011..1134
                /gene="ZDHHC16"
                /gene_synonym="APH2; MGC2993"
                /inference="alignment:Splign"
                /number=10
exon            1135..1205
                /gene="ZDHHC16"
                /gene_synonym="APH2; MGC2993"
                /inference="alignment:Splign"
                /number=11
exon            1206..1799
                /gene="ZDHHC16"
                /gene_synonym="APH2; MGC2993"
                /inference="alignment:Splign"
                /number=12
STS             1504..1682
                /gene="ZDHHC16"
                /gene_synonym="APH2; MGC2993"
                /standard_name="A002I07"
                /db_xref="UniSTS:56306"
STS             1633..1782
                /gene="ZDHHC16"
```

FIG. 12-74

```
                     /gene_synonym="APH2; MGC2993"
                     /standard_name="SHGC-31924"
                     /db_xref="UniSTS:61660"
     STS             1633..1753
                     /gene="ZDHHC16"
                     /gene_synonym="APH2; MGC2993"
                     /standard_name="RH11297"
                     /db_xref="UniSTS:75220"
ORIGIN
        1 gtgtggttga ggatgggctg gcggcgggtc cgggtccgct gcctggcgct gcgggcggcg
       61 ggccatggtg gtttggattg agccgggccc ggccggggcg ccgagtcgga gggggtggca
      121 gtgagcggcg gcagaggcta cggggctcgg tttggctgac tggggagtcg gcaggcggca
      181 ggaaccatgc gaggccagcg gagcctgctg ctgggcccgg cccgcctctg cctccgcctc
      241 cttctgctgc tgggttacag gcgccgctgt ccacctctac tccggggtct agtacagcgc
      301 tggcgctacg gcaaggtctg cctgcgctcc ctgctctaca actcctttgg gggcagtgac
      361 accgctgttg atgctgcctt tgagcctgtc tactggctgg tagacaacgt gatccgctgg
      421 tttggagtgg tgttcgtggt cctggtgatc gtgctgacag gctccattgt agctatcgcc
      481 tacctgtgtg tcctgcctct catcctccga acctactcag tgccacgact ctgctggcat
      541 ttcttctata gccactggaa tctgatcctg attgtcttcc actactacca ggccatcacc
      601 actccgcctg ggtacccacc ccagggcagg aatgatatcg ccaccgtctc catctgtaag
      661 aagtgcattt accccaagcc agcccgaaca caccactgca gcatctgcaa caggtgtgtg
      721 ctgaagatgg atcaccactg cccctggcta aacaattgtg tgggccacta taaccatcgg
      781 tacttcttct ctttctgctt tttcatgact ctgggctgtg tctactgcag ctatggaagt
      841 tgggaccttt tccgggaggc ttatgctgcc attgagaaaa tgaaacagct cgacaagaac
      901 aaactacagg cggttgccaa ccagacttat caccagaccc caccacccac cttctccttt
      961 cgagaaagga tgactcacaa gagtcttgtc tacctctggt tcctgtgcag ttctgtggca
     1021 cttgccctgg gtgccctaac tgtatggcat gctgttctca tcagtcgagg tgagactagc
     1081 atcgaaaggc acatcaacaa gaaggagaga cgtcggctac aggccaaggg cagagtattt
     1141 aggaatcctt acaactacgg ctgcttggac aactggaagg tattcctggg tgtggataca
     1201 ggaaggcact ggcttactcg ggtgctctta ccttctagtc acttgcccca tgggaatgga
     1261 atgagctggg agccccctcc ctgggtgact gctcactcag cctctgtgat ggcagtgtga
     1321 gctggactgt gtcagccacg actcgagcac tcattctgct ccctatgtta tttcaagggc
     1381 ctccaagggc agcttttctc agaatccttg atcaaaaaga gccagtgggc ctgccttagg
     1441 gtaccatgca ggacaattca aggaccagcc tttttaccac tgcagaagaa agacacaatg
     1501 tggagaaatc ttaggactga catcccttta ctcaggcaaa cagaagttcc aaccccagac
```

FIG. 12-75

```
1561 taggggtcag gcagctagct acctaccttg cccagtgctg acccggacct cctccaggat
1621 acagcactgg agttggccac cacctcttct acttgctgtc tgaaaaaaca cctgactagt
1681 acagctgaga tcttggcttc tcaacagggc aaagatacca ggcctgctgc tgaggtcact
1741 gccacttctc acatgctgct taagggagca caaataaagg tattcgattt ttaaagataa
1801 aaaaaaaaaa aaaaaa
//
```

ZDHHC17:

```
FEATURES             Location/Qualifiers
     source          1..4771
                     /organism="Homo sapiens"
                     /mol_type="mRNA"
                     /db_xref="taxon:9606"
                     /chromosome="12"
                     /map="12q21.2"
     gene            1..4771
                     /gene="ZDHHC17"
                     /gene_synonym="HIP14; HIP3; HSPC294; HYPH; KIAA0946"
                     /note="zinc finger, DHHC-type containing 17"
                     /db_xref="GeneID:23390"
                     /db_xref="HGNC:18412"
                     /db_xref="HPRD:09697"
                     /db_xref="MIM:607799"
     exon            1..256
                     /gene="ZDHHC17"
                     /gene_synonym="HIP14; HIP3; HSPC294; HYPH; KIAA0946"
                     /inference="alignment:Splign"
                     /number=1
     CDS             164..2062
                     /gene="ZDHHC17"
                     /gene_synonym="HIP14; HIP3; HSPC294; HYPH; KIAA0946"
                     /note="Huntingtin interacting protein H; huntingtin
                     interacting protein 3; huntingtin interacting protein
14;
```

FIG. 12-76 zinc finger, DHHC domain containing 17; HIP-3; HIP-14;
DHHC-17; huntingtin yeast partner H;
huntingtin-interacting protein 3; huntingtin-interacting
protein H; huntingtin-interacting protein 14; putative
MAPK-activating protein PM11; putative
NF-kappa-B-activating protein 205; zinc finger DHHC
domain-containing protein 17"
/codon_start=1
/product="palmitoyltransferase ZDHHC17"
/protein_id="NP_056151.2"
/db_xref="GI:103471993"
/db_xref="CCDS:CCDS44946.1"
/db_xref="GeneID:23390"
/db_xref="HGNC:18412"
/db_xref="HPRD:09697"
/db_xref="MIM:607799"

/translation="MQREEGFNTKMADGPDEYDTEAGCVPLLHPEEIKPQSHYNHGYG

EPLGRKTHIDDYSTWDIVKATQYGIYERCRELVEAGYDVRQPDKENVTLLHWAAINNR

IDLVKYYISKGAIVDQLGGDLNSTPLHWATRQGHLSMVVQLMKYGADPSLIDGEGCSC

IHLAAQFGHTSIVAYLIAKGQDVDMMDQNGMTPLMWAAYRTHSVDPTRLLLTFNVSVN

LGDKYHKNTALHWAVLAGNTTVISLLLEAGANVDAQNIKGESALDLAKQRKNVWMINH

LQEARQAKGYDNPSFLRKLKADKEFRQKVMLGTPFLVIWLVGFIADLNIDSWLIKGLM

YGGVWATVQFLSKSFFDHSMHSALPLGIYLATKFWMYVTWFFWFWNDLNFLFIHLPFL

ANSVALFYNFGKSWKSDPGIIKATEEQKKKTIVELAETGSLDLSIFCSTCLIRKPVRS

KHCGVCNRCIAKFDHHCPWVGNCVGAGNHRYFMGYLFFLLFMICWMIYGCISYWGLHC

ETTYTKDGFWTYITQIATCSPWMFWMFLNSVFHFMWVAVLLMCQMYQISCLGITTNER

```
MNARRYKHFKVTTTSIESPFNHGCVRNIIDFFEFRCCGLFRPVIVDWTRQYTIEYDQI
                    SGSGYQLV"
     exon           257..360
                    /gene="ZDHHC17"
                    /gene_synonym="HIP14; HIP3; HSPC294; HYPH; KIAA0946"
                    /inference="alignment:Splign"
                    /number=2
     exon           361..483
                    /gene="ZDHHC17"
                    /gene_synonym="HIP14; HIP3; HSPC294; HYPH; KIAA0946"
                    /inference="alignment:Splign"
                    /number=3
     exon           484..561
                    /gene="ZDHHC17"
                    /gene_synonym="HIP14; HIP3; HSPC294; HYPH; KIAA0946"
                    /inference="alignment:Splign"
                    /number=4
     exon           562..706
                    /gene="ZDHHC17"
                    /gene_synonym="HIP14; HIP3; HSPC294; HYPH; KIAA0946"
                    /inference="alignment:Splign"
                    /number=5
     exon           707..771
                    /gene="ZDHHC17"
                    /gene_synonym="HIP14; HIP3; HSPC294; HYPH; KIAA0946"
                    /inference="alignment:Splign"
                    /number=6
     exon           772..934
                    /gene="ZDHHC17"
                    /gene_synonym="HIP14; HIP3; HSPC294; HYPH; KIAA0946"
                    /inference="alignment:Splign"
                    /number=7
     exon           935..1060
                    /gene="ZDHHC17"
                    /gene_synonym="HIP14; HIP3; HSPC294; HYPH; KIAA0946"
                    /inference="alignment:Splign"
```

/number=8
exon 1061..1203
/gene="ZDHHC17"
/gene_synonym="HIP14; HIP3; HSPC294; HYPH; KIAA0946"
/inference="alignment:Splign"
/number=9
exon 1204..1304
/gene="ZDHHC17"
/gene_synonym="HIP14; HIP3; HSPC294; HYPH; KIAA0946"
/inference="alignment:Splign"
/number=10
exon 1305..1429
/gene="ZDHHC17"
/gene_synonym="HIP14; HIP3; HSPC294; HYPH; KIAA0946"
/inference="alignment:Splign"
/number=11
exon 1430..1492
/gene="ZDHHC17"
/gene_synonym="HIP14; HIP3; HSPC294; HYPH; KIAA0946"
/inference="alignment:Splign"
/number=12
exon 1493..1586
/gene="ZDHHC17"
/gene_synonym="HIP14; HIP3; HSPC294; HYPH; KIAA0946"
/inference="alignment:Splign"
/number=13
exon 1587..1670
/gene="ZDHHC17"
/gene_synonym="HIP14; HIP3; HSPC294; HYPH; KIAA0946"
/inference="alignment:Splign"
/number=14
exon 1671..1828
/gene="ZDHHC17"
/gene_synonym="HIP14; HIP3; HSPC294; HYPH; KIAA0946"
/inference="alignment:Splign"
/number=15

FIG. 12-79

```
     STS             1698..1798
                     /gene="ZDHHC17"
                     /gene_synonym="HIP14; HIP3; HSPC294; HYPH; KIAA0946"
                     /standard_name="SHGC-44319"
                     /db_xref="UniSTS:24567"
     exon            1829..1923
                     /gene="ZDHHC17"
                     /gene_synonym="HIP14; HIP3; HSPC294; HYPH; KIAA0946"
                     /inference="alignment:Splign"
                     /number=16
     exon            1924..4771
                     /gene="ZDHHC17"
                     /gene_synonym="HIP14; HIP3; HSPC294; HYPH; KIAA0946"
                     /inference="alignment:Splign"
                     /number=17
     STS             4414..4679
                     /gene="ZDHHC17"
                     /gene_synonym="HIP14; HIP3; HSPC294; HYPH; KIAA0946"
                     /standard_name="WI-19323"
                     /db_xref="UniSTS:79247"
     STS             4557..4679
                     /gene="ZDHHC17"
                     /gene_synonym="HIP14; HIP3; HSPC294; HYPH; KIAA0946"
                     /standard_name="RH11174"
                     /db_xref="UniSTS:79246"
RIGIN
        1 agaaacccgc gccctccgag gggggagggg acagaggggg cgtcacgggg gcaggagaag
       61 aaggaggagg acgcccgcgt cgcctccggc ggggctcgcg ctcgcccccgc gctcgccctc
      121 cgcctcgccc gagccccggg agggtgaaac gctttctccc agcatgcagc gggaggaggg
      181 atttaacacc aagatggcgg acggcccgga tgagtacgat accgaagcgg gctgtgtgcc
      241 ccttctccac ccagaggaaa tcaaacccca aagccattat aaccatggat atggtgaacc
      301 tcttggacgg aaaactcata ttgatgatta cagcacatgg gacatagtca aggctacaca
      361 atatggaata tatgaacgct gtcgagaatt ggtggaagca ggttatgatg tacggcaacc
      421 ggacaaagaa aatgttaccc tcctccattg ggctgccatc aataacagaa tagatttagt
      481 caaatactat atttcgaaag gtgctattgt ggatcaactt ggaggggacc tgaattcaac
      541 tccattgcac tgggccacaa gacaaggcca tctatccatg gttgtgcaac taatgaaata
```

601 tggtgcagat ccttcattaa ttgatggaga aggatgtagc tgtattcatc tggctgctca
661 gttcggacat acctcaattg ttgcttatct catagcaaaa ggacaggatg tagatatcat
721 ggatcagaat ggaatgacgc ctttaatgtg ggcagcatat agaacacata gtgtggatcc
781 aactagattg cttttaacat tcaatgtttc agttaacctt ggtgacaagt atcacaaaaa
841 cactgctctg cattgggcag tgctagcagg gaataccaca gtcattagcc ttcttctgga
901 agctggagct aatgttgatg cccagaatat caagggcgaa tcagcgcttg atttggcaaa
961 acagagaaaa aatgtgtgga tgatcaacca cttacaagag gcaaggcaag caaaaggata
1021 tgacaatccg tccttcctta gaaagctgaa agctgataag gaatttcggc agaaagtaat
1081 gttaggaact cctttcctag ttatttggct ggttgggttt atagcagacc taaatattga
1141 ttcttggctc attaaagggc taatgtatgg tggtgtttgg gctacagtac agtttctttc
1201 aaaatccttt ttcgatcatt caatgcatag tgcattgccc cttgggatat atttggcaac
1261 caaattctgg atgtatgtga cgtggttctt ctggttttgg aatgatctca actttttatt
1321 tatccatctt ccattccttg ccaatagtgt tgcacttttc tacaattttg gaaaatcttg
1381 gaaatcacat ccagggatta ttaaagcaac agaagagcaa aagaaaaaga caatagttga
1441 acttgcacag acaggaagtc tggacctcag tatattctgc agtacctgtt tgatacgaaa
1501 accggtgagg tccaaacatt gtggtgtgtg caaccgctgt atagcaaaat ttgatcatca
1561 ttgcccatgg gtgggtaact gtgtaggtgc aggcaaccat agatatttta tgggctacct
1621 attcttcttg ctttttatga tctgctggat gatttatggt tgtatatctt actggggact
1681 ccactgtgag accacttaca ccaaggatgg attttggaca tacattactc agattgccac
1741 gtgttcacct tggatgtttt ggatgttcct gaacagtgtt ttccacttca tgtgggtggc
1801 tgtattactc atgtgtcaga tgtaccagat atcatgttta ggtattacta caaatgaaag
1861 aatgaatgcc aggagataca agcactttaa agtcacaaca acgtctattg aaagcccatt
1921 caaccatgga tgtgtaagaa atattataga cttctttgaa tttcgatgct gtggcctctt
1981 tcgtcctgtt atcgtggact ggaccaggca gtatacaata gaatatgacc aaatatcagg
2041 atctgggtac cagctggtgt agcgacatct tatcctatga agcatattgc tgagtggtgc
2101 ctgaaaattg tgtctgtccg tgtctttctc acactcgaat ccacatcctt tgaacaacag
2161 catgctatgt gtagggctaa tgctgaattt tacagtcttt ttttcaacac ttttattaac
2221 aaaagtaaac atggacagaa cacactgcca tttctgggaa gagtaaagat gataaaaaat
2281 aattttaatg gttcttaatg tggaaattca caacatactc aacttttggg ttttgttctc
2341 acagtatttt tcacaaaaaa agcgtaaact tattctattg acagacatgg tgtactgatc
2401 agaaatgttc agttttaact aaaactaaat ttatgttatt tggctaaatg ttatgatcca
2461 gtctagtacg agtattgcat ctaattccag gagcattgtt ttaagttgat tgactagtta
2521 ttatgtacat ttcagaatgt acacataaat actgtgatga aaatcatgtg attgggatct
2581 actgtgatgt tgtcttcaaa ggcaggagaa aataatgttc acaataaaat gtgctaacaa
2641 tgttttgttt ctatcagctg ttgcaatgct gatatatttc tagttcagtg aaataatttg
2701 tagtaacctt actctgaggt tttacggtct gataatgaag cacttgcatg agtatagtaa 2761 gtcatgtttt tttgttcaaa tttaaaagcc ctgctaattg catgacacac cacatagaat
2821 gtatactagc agatactatc cagtgaagca taaattagaa tttaatttga tgttcaaaaa
2881 cagttccatt tttaagggtt aaggtggtat tttcaagaaa aggcagaaca aataatgcaa
2941 aattctcagt aatagtgata catggatata cttcctttta aattctcagc tgcaaaataa
3001 ttgtagacaa aataatggca tttaactaaa gatggagcat gatctaagta catagcacat
3061 gtgaataaaa gaaaagctga cagtatattc tggtttcaat aaaatgacct atcagaaagt
3121 agaatttcat ccccaagagt atttcagttt atccaatatt gagtaagttc tgaaacagtt
3181 ttagaaaaaa ttttcttttt gttaaatgtg atgcactgat caatttttgt cacagcattt
3241 tcataccttc atggtggact actagtcact gcttccataa atattgttta cagggtgaga
3301 tttggtttat tcatcttaag tgctgtagca aactgtggtt cgagcaacct gtgggaaatc
3361 tgtgagaggg aatggggtgg gagatgtggg ggaatggtgg tcagactgat gacagatcct
3421 agaccaatgt aaagaatgtg tatctgtata taaataattt atcaaatagt tttctctttg
3481 tgtctgtgtt agtgttttta aagctgctca tttcattttg tccaaccaaa aagaaaaggg
3541 agataactaa tgagcttcta gtgatgttca aaattgctgt taataggcat tataccctgc
3601 aagttcactg catgtctgat gcttggtaaa actagtcttc cctgtaaaat gcagattaca
3661 ggtattaaag caatctagtg gtatacccgc cccttgcctt agtaagagga gcagtgaaat
3721 gtatatagtt gatgttcagt atttccaagt accattttta tatagtagct tatttgacca
3781 taagtcacac atcaaaaaaa gattaccctt agtgtatgtg ttttaatatt agaaaattgg
3841 catatgtact ttatttttga aaagggaaga gatgggtgtg gggtggcaat agcattgtgc
3901 cattttgtca tagaatgtaa aaattggtta actttacaaa tgtcagctag ttttgactac
3961 taattggggg aaattttaga taatttttaa attcaaagtt atttataaaa tgctagaatt
4021 tgttttaatt ttttgtattt tgagccactt cacatgaaga ctcagttgca tttttatcga
4081 atacattttt atcaacagtt aaagactatg gtggtttttt cagagtttgg ctaagaatgt
4141 tgttaccatc ttctttgttt gtggtacaat attttcagtg caaaagagat gtcattcagt
4201 taaaaagaca aacctctaga tgtgtaatta catggaaaat actagcaatg tgaatgcttt
4261 tgtagtaacc atcttgtagt acctgtgaaa tctataactc agaaatggtc agatggtcag
4321 gagccagcta tgcagcagta taccatctgt ttaattattt tgtaggtcct gtgtgtggaa
4381 ccaactataa acccagttct aaagttgtgt atgatggtga acctttggga atagttctta
4441 tcaacttaat tggatacttt tagcaaatag gaacttaatt ctcagcactg aacatgaatt
4501 acttccttgg agttttttt cattcatatt tttgttgttt ccaggaattt atttgatatt
4561 aatgggcgta aaacagcatc attgtactta agctatggat gtttttattt tatattttct
4621 ttatttataa ctgtgccaag tattattttg ctacttaccg tgttattctg tggaaagaaa
4681 aacctgtaaa gtgtttaata aattagccct ccttacataa attaaatgtc aaaattttgt
4741 aaaatattaa tcagaataaa tactgactct t

FIG. 12-82

ZDHHC18:

```
FEATURES             Location/Qualifiers
     source          1..3163
                     /organism="Homo sapiens"
                     /mol_type="mRNA"
                     /db_xref="taxon:9606"
                     /chromosome="1"
                     /map="1p36.11"
     gene            1..3163
                     /gene="ZDHHC18"
                     /gene_synonym="DKFZp66702416"
                     /note="zinc finger, DHHC-type containing 18"
                     /db_xref="GeneID:84243"
                     /db_xref="HGNC:20712"
                     /db_xref="HPRD:15713"
     exon            1..430
                     /gene="ZDHHC18"
                     /gene_synonym="DKFZp66702416"
                     /inference="alignment:Splign"
                     /number=1
     CDS             96..1262
                     /gene="ZDHHC18"
                     /gene_synonym="DKFZp66702416"
                     /note="zinc finger, DHHC domain containing 18; DHHC-18;
                     zinc finger DHHC domain-containing protein 18"
                     /codon_start=1
                     /product="palmitoyltransferase ZDHHC18"
                     /protein_id="NP_115659.1"
                     /db_xref="GI:45433499"
                     /db_xref="CCDS:CCDS30650.1"
                     /db_xref="GeneID:84243"
                     /db_xref="HGNC:20712"
                     /db_xref="HPRD:15713"
```

FIG. 12-83

/translation="MKDCEYQQISPGAAPLPASPGARRPGPAASPTPGPGPAPPAAPA

PPRWSSSGSGSGSGSGSLGRRPRRKWEVFPGRNRFYCGGRLMLAGHGGVFALTLLLIL

TTTGLFFVFDCPYLARKLTLAIPIIAAILFFFVMSCLLQTSFTDPGILPRATVCEAAA

LEKQIDNTGSSTYRPPPRTREVLINGQMVKLKYCFTCKMFRPPRTSHCSVCDNCVERF

DHHCPWVGNCVGRRNYRFFYAFILSLSFLTAFIFACVVTHLTLRAQGSNFLSTLKETP

ASVLELVICFFSIWSILGLSGFHTYLVASNLTTNEDIKGSWSSKRGGEASVNPYSHKS

IITNCCAVLCGPLPPSLIDRRGFVQSDTVLPSPIRSDEPACRAKPDASMVGGHP"

exon 431..591
/gene="ZDHHC18"
/gene_synonym="DKFZp667O2416"
/inference="alignment:Splign"
/number=2 exon 592..741
/gene="ZDHHC18"
/gene_synonym="DKFZp667O2416"
/inference="alignment:Splign"
/number=3 exon 742..879
/gene="ZDHHC18"
/gene_synonym="DKFZp667O2416"
/inference="alignment:Splign"
/number=4 exon 880..928
/gene="ZDHHC18"
/gene_synonym="DKFZp667O2416"
/inference="alignment:Splign"
/number=5 exon 929..1031
/gene="ZDHHC18"
/gene_synonym="DKFZp667O2416"
/inference="alignment:Splign"

FIG. 12-84

```
                     /number=6
     exon            1032..1144
                     /gene="ZDHHC18"
                     /gene_synonym="DKFZp66702416"
                     /inference="alignment:Splign"
                     /number=7
     exon            1145..3136
                     /gene="ZDHHC18"
                     /gene_synonym="DKFZp66702416"
                     /inference="alignment:Splign"
                     /number=8
     STS             1976..2118
                     /gene="ZDHHC18"
                     /gene_synonym="DKFZp66702416"
                     /standard_name="SHGC-74485"
                     /db_xref="UniSTS:44073"
     STS             2828..3097
                     /gene="ZDHHC18"
                     /gene_synonym="DKFZp66702416"
                     /standard_name="A002B28"
                     /db_xref="UniSTS:17559"
     STS             2828..3097
                     /gene="ZDHHC18"
                     /gene_synonym="DKFZp66702416"
                     /standard_name="G19894"
                     /db_xref="UniSTS:17558"
     STS             2911..3065
                     /gene="ZDHHC18"
                     /gene_synonym="DKFZp66702416"
                     /standard_name="RH12522"
                     /db_xref="UniSTS:32019"
ORIGIN
        1 gcgcgcgccg ccgctgccac ctccgctgct cggcccggtc ccggagtggc ccggccggcc
       61 cgcggggcgc ggagccgagg cccgcggctg gctgcatgaa ggactgcgag taccagcaga
      121 tcagccccgg ggccgccccg ctgcccgcct ccccgggggc gcgccgtccc ggccccgccg
      181 cgtccccgac tccgggcccc gggcccgcgc cgcccgccgc ccccgccccg ccgcgctgga
```

241 gcagcagcgg cagcggcagc ggcagcggga gcgggagcct cggccgccgc ccacggcgca
301 agtgggaggt gttcccgggt cgcaatcgct tctactgcgg cggccgcctc atgctggccg
361 gccacggcgg cgtcttcgcg ctcacgctgc tgctcatcct caccaccacc ggcctcttct
421 tcgtctttga ctgtccctac ctggctcgca agctgaccct tgccatcccc atcatcgctg
481 ccatcctctt cttcttcgtc atgagctgcc tgctgcagac aagcttcacc gaccctggga
541 tcctgccccg ggccactgtc tgtgaagcag ccgccctgga gaaacagatc gacaacacag
601 gcagttctac ataccggcca ccccctcgga cccgggaggt gctgatcaac gggcagatgg
661 tgaagctgaa gtactgcttc acctgcaaga tgttccggcc accccgaacc tcacactgca
721 gtgtctgcga caactgtgtg gaacgatttg accatcactg cccctgggtg ggcaactgtg
781 tggggagacg gaactatcgc ttcttctacg cgtttattct ctccctctca ttcctgacgg
841 ccttcatctt cgcctgtgtg gtcacccacc tgacgttgcg cgctcaggga agcaacttcc
901 tctccactct gaaggagaca ccagcaagcg tgctggagtt ggtgatctgc ttcttctcca
961 tctggtccat tctgggcctc tcagggtttc acacgtacct cgtcgcctcc aacctgacta
1021 ctaatgaaga catcaaaggc tcgtggtcca gcaagagggg cggtgaggcc tctgtcaacc
1081 cctacagcca taaaagtatt atcaccaact gctgtgctgt gctctgtggc cccctacctc
1141 ccagcctaat tgaccggagg ggatttgtgc agtccgacac cgtgttgccc tcacccatca
1201 gaagcgatga gccagcctgc agagccaagc ctgatgccag catggtagga ggccacccct
1261 gaccacggct cagtacttgc cacctgctgg cctgtctgac cctccgcact cacctgccgg
1321 gaccctccct attccatcca agggaagcag aactgccaaa gactcaagtc ttttcatatt
1381 tatttcccat cctgcgtggc tttccctgaa ctgttccgtg gctgtgccct ctgctcccca
1441 aacccaggtt cccacagcct tgggccctag gtaccccagc tgatcagtgc caggagagac
1501 cagagcctct ggaggctacc caggggacca caccaagtcc ttgcctgtgc cgggcgagcc
1561 ctgtgtgagt gaggctgtga actgagcgtg aggcctccca ggtgggggaa ctgcttgggc
1621 cttgctgagc cagggtcctc agggtgaagc aggactgagg agtggccagc tctggatagc
1681 tggctgtgga gaggaagcct ccatgggctg ctttggtctg tgggctcctt cattcccttg
1741 gtgataattt ccctttcttc tgtgggattt ttggtggggt tttccccct tttttatgga
1801 gttggccaat aggattgagt tggggctcca gtagagaagg cagggttggt ggtgggtggg
1861 ggcagcctgt atcagacaaa ggtaaatcag ccagccaggc acccacagcc tcagctcctg
1921 tgcagttcct gggcagcaca gtggaagtgg gagcctggtc cttcccctgc ccatggagag
1981 ctctttaagg gatcccagcc tgcccctcca cttctctccc aagccaggtc ccggcatggg
2041 tgggttatgc tcatgctggc aatacttgaa acgggtttat taatgctggg tattttgcac
2101 aattttatag acctcttttc tacatagtct tttttaaatg gaaggagaaa atgtcagcca
2161 cattactgtc tgtgtagtgc caggtgaagg gttatcagaa ggctggttgg ttttaataag
2221 tttattccaa gagaccttct ggctggaatg agtgagagtg tgtgtgcatg tgtgtgtgtg
2281 ttcatgtgtg ccctgtatga atgtggctgg ctcccatatc ccctgggctg ccccctgccc
2341 catccccttt gagtatcaga agcactctga gccaagggga caggggggcac gtgcactggt

```
2401 cacgagaaaa ccctgggctc ccactggggc tcagcccagc ctcctatctt tccttcttct
2461 atggacttca gacagccagt gtctggggac tctgccactc tacccccagc cctacccacc
2521 agcccccagg tgaggcttcc agctgggacc tgcccagaca ggctgagcct gggcgtggtg
2581 ggtggggtga tggctctggg gagcggctgc catcctacaa gccacacccc ctcctctgag
2641 ctctgaatat gggacccagt gccaggagct ggaagacaag gtgtttctgc caaacgggga
2701 cctccatcca gagaaaagga agaaggtgca gggtgggcca agaggcaagt gaaggttggc
2761 ctgagtctgg gccggaaact cagaggatgt ttctcctctg ctgggagctg tagtttctta
2821 tcaaaataga tattgttcca ccatccccct ccttggccct tcaagtgggc tgaagccctt
2881 ggaaagtgac ataggaagtc cccagatctt gcccttctca ctccagaggc tagtggtcac
2941 agacagctgg gaatggcagc cacagagggt cccctctggg agaaacagct tcaccccagc
3001 ctcagggccc tgggccatca ctgcagtggc cctgggaggt gaggaagaag ctggctagag
3061 gagggggctc ccacctacct tttatttaag ccagtattct ttgttcctgc ttgtaataaa
3121 acttcagttt ataagaaaaa aaaaaagaaa aaaaaaaaaa aaa
//
```

ZDHHC19:

```
FEATURES             Location/Qualifiers
     source          1..1370
                     /organism="Homo sapiens"
                     /mol_type="mRNA"
                     /db_xref="taxon:9606"
                     /chromosome="3"
                     /map="3q29"
     gene            1..1370
                     /gene="ZDHHC19"
                     /gene_synonym="DHHC19; MGC33345"
                     /note="zinc finger, DHHC-type containing 19"
                     /db_xref="GeneID:131540"
                     /db_xref="HGNC:20713"
     exon            1..260
                     /gene="ZDHHC19"
                     /gene_synonym="DHHC19; MGC33345"
                     /inference="alignment:Splign"
                     /number=1
```

FIG. 12-87

CDS 115..1044
/gene="ZDHHC19"
/gene_synonym="DHHC19; MGC33345"
/note="zinc finger, DHHC domain containing 19; DHHC-19;
zinc finger DHHC domain-containing protein 19"
/codon_start=1
/product="probable palmitoyltransferase ZDHHC19"
/protein_id="NP_001034706.1"
/db_xref="GI:88900493"
/db_xref="CCDS:CCDS43190.1"
/db_xref="GeneID:131540"
/db_xref="HGNC:20713"

/translation="MTLLTDATPLVKEPHPLPLVPRPWFLPSLFAAFNVVLLVFFSGL

FFAFPCRWLAQNGEWAFPVITGSLFVLTFFSLVSLNFSDPGILHQGSAEQGPLTVHVV

WVNHGAFRLQWCPKCCFHRPPRTYHCPWCNICVEDFDHHCKWVNNCIGHRNFRFFMLL

VLSLCLYSGAMLVTCLIFLVRTTHLPFSTDKAIAIVVAVSAAGLLVPLSLLLLIQALS

VSSADRTYKGKCRHLQGYNPFDQGCASNWYLTICAPLGPKYMAEAVQLQRVVGPDWTS
MPNLHPPMSPSALNPPAPTSGSLQSREGTPGAW"

exon 261..382
/gene="ZDHHC19"
/gene_synonym="DHHC19; MGC33345"
/inference="alignment:Splign"
/number=2 exon 383..522
/gene="ZDHHC19"
/gene_synonym="DHHC19; MGC33345"
/inference="alignment:Splign"
/number=3 exon 523..695
/gene="ZDHHC19"

FIG. 12-88

```
                     /gene_synonym="DHHC19; MGC33345"
                     /inference="alignment:Splign"
                     /number=4
     exon            696..801
                     /gene="ZDHHC19"
                     /gene_synonym="DHHC19; MGC33345"
                     /inference="alignment:Splign"
                     /number=5
     exon            802..887
                     /gene="ZDHHC19"
                     /gene_synonym="DHHC19; MGC33345"
                     /inference="alignment:Splign"
                     /number=6
     exon            888..1063
                     /gene="ZDHHC19"
                     /gene_synonym="DHHC19; MGC33345"
                     /inference="alignment:Splign"
                     /number=7
     exon            1064..1337
                     /gene="ZDHHC19"
                     /gene_synonym="DHHC19; MGC33345"
                     /inference="alignment:Splign"
                     /number=8
     STS             1214..1332
                     /gene="ZDHHC19"
                     /gene_synonym="DHHC19; MGC33345"
                     /standard_name="RH92567"
                     /db_xref="UniSTS:89484"
ORIGIN
        1 ctttcaccct gggctgcggc tctgaggctg ccgtggccat ggagctctgg aagctgggct
       61 gggggaggaa gcctggtggc tctgacctcc cctggaggcg aaggaggccc agccatgaca
      121 ctcttaacgg atgccacgcc gctggtgaag gagcccccatc ccctgcctct ggtcccacgt
      181 ccctggttcc tccctagcct ctttgctgcc ttcaatgtgg tgctgctggt ctttttcagt
      241 ggcctcttct tcgcattccc ttgcaggtgg ctggctcaga acggggagtg ggcctttcct
      301 gttatcacag gctccctctt tgtccttacc ttcttcagtc ttgtttcact caacttctca
      361 gaccctggca tcttacatca aggctccgct gagcagggcc ccttgacggt gcacgtggtg
```

FIG. 12-89

```
 421 tgggtgaacc acggggcctt ccgcctgcaa tggtgtccaa agtgctgctt ccaccgcccg
 481 ccccggactt accactgccc ctggtgcaac atctgtgtgg aggactttga ccaccactgc
 541 aagtgggtca ataactgcat cggtcaccgc aacttccgct tcttcatgct gcttgtcctg
 601 tccctgtgcc tctactcggg cgccatgctg gtcacctgtc tcatcttcct ggtgcgcaca
 661 acccacctgc ccttctccac cgacaaggcc atcgccatcg tggtggccgt gtccgccgcg
 721 ggcctcctgg tgccgctgtc cctcctgctg ctgatccagg cactgtccgt gagctcggcc
 781 gaccgcacct acaagggcaa gtgcagacac cttcagggat acaacccctt cgaccagggc
 841 tgtgccagca actggtattt aacaatttgt gcaccactgg gacccaagta catggctgaa
 901 gctgtccagc tgcagagagt ggtggggcct gactggacat ccatgccgaa tctgcacccct
 961 ccaatgtccc cctctgctct caaccccca gccccaacct ctgggtccct acaaagcagg
1021 gaagggaccc ccgggggcgtg gtgaggctgc agctctccag gagttccaca cgggcccagt
1081 gctgcccctg ctgctgcagg agcccccagg cgaggttcgg ccttcctctc gcccctgtgc
1141 acccggagat gcccacagca ccagcacctg agctcacctc cgaacccgcc tcctgaaccc
1201 gcctcctgaa cctgcctcct tacctcccac ttcctgagcc ctgagtggaa gcctttctgt
1261 gccttgccct ttgcccactc ccctggtggg actgccaaga ccctcaatgc ccattaaata
1321 ctcttgcctg cctcttaaaa aaaaaaaaaa aaaaaaaaaa aaaaaaaaaa
```
//

ZDHHC20:

```
FEATURES             Location/Qualifiers
     source          1..1514
                     /organism="Homo sapiens"
                     /mol_type="mRNA"
                     /db_xref="taxon:9606"
                     /chromosome="13"
                     /map="13q12.11"
     gene            1..1514
                     /gene="ZDHHC20"
                     /gene_synonym="FLJ25952; MGC126005"
                     /note="zinc finger, DHHC-type containing 20"
                     /db_xref="GeneID:253832"
                     /db_xref="HGNC:20749"
                     /db_xref="HPRD:08078"
```

FIG. 12-90 exon 1..231
/gene="ZDHHC20"
/gene_synonym="FLJ25952; MGC126005"
/inference="alignment:Splign"
/number=1
STS 34..1337
/gene="ZDHHC20"
/gene_synonym="FLJ25952; MGC126005"
/db_xref="UniSTS:490024"
CDS 114..1178
/gene="ZDHHC20"
/gene_synonym="FLJ25952; MGC126005"
/note="DHHC-containing protein 20; 4933421L13Rik; zinc finger, DHHC domain containing 20; DHHC-20; zinc finger DHHC domain-containing protein 20"
/codon_start=1
/product="probable palmitoyltransferase ZDHHC20"
/protein_id="NP_694983.2"
/db_xref="GI:49457851"
/db_xref="CCDS:CCDS45017.1"
/db_xref="GeneID:253832"
/db_xref="HGNC:20749"
/db_xref="HPRD:08078"

/translation="MAPWTLWRCCQRVVGWVPVLFITFVVVWSYYAYVVELCVFTIFG
NEENGKTVVYLVAFHLFFVMFVWSYWMTIFTSPASPSKEFYLSNSEKERYEKEFSQER
QQEILRRAARALPIYTTSASKTIRYCEKCQLIKPDRAHHCSACDSCILKMDHHCPWVN
NCVGFSNYKFFLLFLLYSLLYCLFVAATVLEYFIKFWTNELTDTRAKFHVLFLFFVSA
MFFISVLSLFSYHCWLVGKNRTTIESFRAPTFSYGPDGNGFSLGCSKNWRQVFGDEKK

FIG. 12-91

```
YWLLPIFSSLGDGCSFPTRLVGMDPEQASVTNQNEYARSGSNQPFPIKPLSESKNRLL
                    DSESQWLENGAEEGIVKSGV"
     exon           232..258
                    /gene="ZDHHC20"
                    /gene_synonym="FLJ25952; MGC126005"
                    /inference="alignment:Splign"
                    /number=2
     STS            257..383
                    /gene="ZDHHC20"
                    /gene_synonym="FLJ25952; MGC126005"
                    /standard_name="RH69325"
                    /db_xref="UniSTS:72733"
     exon           259..362
                    /gene="ZDHHC20"
                    /gene_synonym="FLJ25952; MGC126005"
                    /inference="alignment:Splign"
                    /number=3
     exon           363..483
                    /gene="ZDHHC20"
                    /gene_synonym="FLJ25952; MGC126005"
                    /inference="alignment:Splign"
                    /number=4
     exon           484..553
                    /gene="ZDHHC20"
                    /gene_synonym="FLJ25952; MGC126005"
                    /inference="alignment:Splign"
                    /number=5
     exon           554..586
                    /gene="ZDHHC20"
                    /gene_synonym="FLJ25952; MGC126005"
                    /inference="alignment:Splign"
                    /number=6
     exon           587..707
                    /gene="ZDHHC20"
                    /gene_synonym="FLJ25952; MGC126005"
                    /inference="alignment:Splign"
```

FIG. 12-92

```
                     /number=7
     exon            708..840
                     /gene="ZDHHC20"
                     /gene_synonym="FLJ25952; MGC126005"
                     /inference="alignment:Splign"
                     /number=8
     exon            841..967
                     /gene="ZDHHC20"
                     /gene_synonym="FLJ25952; MGC126005"
                     /inference="alignment:Splign"
                     /number=9
     exon            968..1057
                     /gene="ZDHHC20"
                     /gene_synonym="FLJ25952; MGC126005"
                     /inference="alignment:Splign"
                     /number=10
     exon            1058..1170
                     /gene="ZDHHC20"
                     /gene_synonym="FLJ25952; MGC126005"
                     /inference="alignment:Splign"
                     /number=11
     exon            1171..1457
                     /gene="ZDHHC20"
                     /gene_synonym="FLJ25952; MGC126005"
                     /inference="alignment:Splign"
                     /number=12
ORIGIN
        1 ccgaggcggg ggagctggac cagcagccgc ctggagcgtc cgagtcaccg tcgccggggc
       61 tcccgcgctc cccagaacgg tgggacgcgg ggctcggcag ccgccagcgg aacatggcgc
      121 cctggacgct gtggcgctgc tgccagcgcg tcgtgggctg ggtgccggtg ctcttcatca
      181 ccttcgtggt cgtctggtcc tactacgcgt acgtggtgga gctctgcgtg tttactattt
      241 ttggaaatga agaaaatgga aagaccgttg tttaccttgt ggctttccat ctgttctttg
      301 ttatgtttgt atggtcctat tggatgacaa ttttcacatc tcccgcttcc ccctccaaag
      361 acttctactt gtccaattct gaaaaggaac gttatgaaaa agaattcagc caagaaagac
      421 aacaagaaat tttgagaaga gcagcaagag ctttacctat ctataccaca tcagcttcaa
      481 aaactatcag atattgtgaa aaatgtcagc tgattaaacc tgatcgggcg catcactgct
```

FIG. 12-93

```
 541 cagcctgtga ctcatgtatt cttaagatgg atcatcactg tccttgggtg aataactgtg
 601 tcggattttc taattacaaa ttcttcctgc tgtttttatt gtattcccta ttatattgcc
 661 ttttcgtggc tgcaacagtt ttagagtact ttataaaatt ttggacgaat gaactgacag
 721 atacacgtgc aaaattccac gtactttttc ttttctttgt gtctgcaatg ttcttcatca
 781 gcgtcctctc acttttcagc taccactgct ggctagttgg aaaaaataga acaacaatag
 841 aatcattccg cgcacccacg ttttcatacg gacctgatgg aaatggtttc tctcttggat
 901 gcagtaaaaa ttggagacaa gtctttggtg atgaaaagaa atattggcta cttccaatat
 961 tttcaagctt gggtgatggt tgcagttttc caactcgcct tgtggggatg gatccagaac
1021 aagcttctgt tacaaaccag aatgagtatg ccagaagtgg ctcaaatcaa ccttttccta
1081 tcaaaccact tagtgaatca aaaaaccgct tgttggacag tgaatctcag tggctggaga
1141 atggagctga agaaggcatc gtcaaatcag gtgtatgaaa acattataga ctggtatttt
1201 caattttcat ttgcaagaaa atgatcagtg gaatgaaata actgaagtat aacagaagat
1261 atatttttta aaacggaaag cctttgtaca gttcctggga ttcacagaag cactactcca
1321 gagcagaatg atgccttaat cttaagtgtc catttgtgca gcattgactt agagctacaa
1381 aagtgactta atgttattct ggaaataata cttacctgtt atgagttgct ataatatgag
1441 ctgtcatcac attttaaaaa aaaaaaaaaa aaaaaaaaaa aaaaaaaaaa aaaaaaaaaa
1501 aaaaaaaaaa aaaa
```

//

DHHC21:

```
FEATURES             Location/Qualifiers
     source          1..3265
                     /organism="Homo sapiens"
                     /mol_type="mRNA"
                     /db_xref="taxon:9606"
                     /chromosome="9"
                     /map="9p22.3"
     gene            1..3265
                     /gene="ZDHHC21"
                     /gene_synonym="DHHC-21; DNZ1"
                     /note="zinc finger, DHHC-type containing 21"
                     /db_xref="GeneID:340481"
                     /db_xref="HGNC:20750"
                     /db_xref="HPRD:15716"
```

FIG. 12-94

```
     exon            1..246
                     /gene="ZDHHC21"
                     /gene_synonym="DHHC-21; DNZ1"
                     /inference="alignment:Splign"
                     /number=1
     exon            247..295
                     /gene="ZDHHC21"
                     /gene_synonym="DHHC-21; DNZ1"
                     /inference="alignment:Splign"
                     /number=2
     exon            296..425
                     /gene="ZDHHC21"
                     /gene_synonym="DHHC-21; DNZ1"
                     /inference="alignment:Splign"
                     /number=3
     exon            426..624
                     /gene="ZDHHC21"
                     /gene_synonym="DHHC-21; DNZ1"
                     /inference="alignment:Splign"
                     /number=4
     CDS             471..1268
                     /gene="ZDHHC21"
                     /gene_synonym="DHHC-21; DNZ1"
                     /EC_number="2.3.1.-"
                     /note="9130404H11Rik; HSPC097; zinc finger, DHHC domain
                     containing 21; zinc finger DHHC domain-containing
otein
                     21"
                     /codon_start=1
                     /product="probable palmitoyltransferase ZDHHC21"
                     /protein_id="NP_848661.1"
                     /db_xref="GI:30425538"
                     /db_xref="CCDS:CCDS6475.1"
                     /db_xref="GeneID:340481"
                     /db_xref="HGNC:20750"
                     /db_xref="HPRD:15716"
```

FIG. 12-95

/translation="MGLRIHFVVDPHGWCCMGLIVFVWLYNIVLIPKIVLFPHYEEGH

IPGILIIIFYGISIFCLVALVRASITDPGRLPENPKIPHGEREFWELCNKCNLMRPKR

SHHCSRCGHCVRRMDHHCPWINNCVGEDNHWLFLQLCFYTELLTCYALMFSFCHYYYF

LPLKKRNLDLFVFRHELAIMRLAAFMGITMLVGITGLFYTQLIGIITDTTSIEKMSNC
CEDISRPRKPWQQTFSEVFGTRWKILWFIPFRQRQPLRVPYHFANHV"

exon 625..723
/gene="ZDHHC21"
/gene_synonym="DHHC-21; DNZ1"
/inference="alignment:Splign"
/number=5 exon 724..835
/gene="ZDHHC21"
/gene_synonym="DHHC-21; DNZ1"
/inference="alignment:Splign"
/number=6 exon 836..974
/gene="ZDHHC21"
/gene_synonym="DHHC-21; DNZ1"
/inference="alignment:Splign"
/number=7 exon 975..1091
/gene="ZDHHC21"
/gene_synonym="DHHC-21; DNZ1"
/inference="alignment:Splign"
/number=8 exon 1092..1135
/gene="ZDHHC21"
/gene_synonym="DHHC-21; DNZ1"
/inference="alignment:Splign"
/number=9 exon 1136..3204
/gene="ZDHHC21"
/gene_synonym="DHHC-21; DNZ1"

FIG. 12-96

/inference="alignment:Splign"
/number=10

ORIGIN

```
   1 ccgtcgcggc tcccgggagc taagcgagac ggcgacggcg gcagtcgtcc ctccccacgc
  61 gggcgcgcgg gcatgcggac acccactcgg ccggtccagg ccctcaggct cccggaagcg
 121 gaaggggaga gcggcccggc ctgggcggcg gcgccggagg aggcggaggt ggcgcggcag
 181 gaggagggga aagagctgct ggtggtcggg agagcggcgg cagcgagagg cgagccagcg
 241 gcgacgaatg aagaactttt tcacttactg caggattttc agcttcagca agcaggttct
 301 catggagaac tgttattgaa gagagatcca tttggtggga tataattaaa aaaaatgaat
 361 caaaagaaaa tctctaaatg cagattccag aaaaattaca gcacatctca gtgaatttgc
 421 aagtggatca tccttccttg tgggttagca ggcagttata agattgcaaa atgggtctcc
 481 ggattcactt tgttgttgac ccacatggtt ggtgctgcat gggtttgatt gtctttgttt
 541 ggttatacaa tattgtttta attcccaaaa ttgtcctctt tcctcactat gaagaaggac
 601 atattccagg catattaata ataatattct atggcatttc catattctgt ctggttgcct
 661 tagtgagggc ctccataact gatccaggaa gactccctga gaaccccaag atcccacatg
 721 gagaaaggga gttctgggaa ttatgtaaca agtgtaattt gatgagacca aagcgttccc
 781 atcactgcag ccgctgcggc cactgtgtga ggagaatgga tcatcactgt ccatggatta
 841 acaattgtgt tggtgaagat aatcattggc tctttctgca gttgtgtttc tacactgaac
 901 ttcttacttg ctacgcactg atgtttttctt tctgccacta ttactatttt cttccactaa
 961 aaaagcgtaa tttggacctc tttgttttta gacatgaatt ggccataatg agactagcag
1021 cctttatggg cattactatg ttagttggaa taactggact cttttacact caactaattg
1081 gcatcatcac agatacaaca tctattgaaa agatgtcaaa ctgttgtgaa gatatatcga
1141 ggccccgaaa gccatggcag cagaccttct cagaagtttt tggcactcgt tggaagatcc
1201 tgtggttcat tcctttcagg cagaggcaac cactgcgagt tccctaccac tttgccaatc
1261 atgtctaaac agatggatgg tgggcacaga tgggtcctcc atgctggcaa tgcgttacag
1321 gttttatgat aatagaacta tgacagtctt caagtcaatt aaaatccacc caccaatctt
1381 aggcatcata atgtgcccca ggctttattt taatagtgat cttgatcctg ttgtgggact
1441 aatacaagat ctatatttaa gttttaaagc atgtttactt tcaaattagc tttccacagg
1501 gatttcttga aatgcttttg ttattaaact caaaaggcag tgattaggat gaaataattg
1561 tacataattt attttagtac tgacagtgtt acagattcta atttatggta aatttcagat
1621 gtttatttaa aattttcact tttaaacagt aaccaaatct aaatttaatt attcaggttt
1681 tacaaaagtt gatacacctt cttatagtat aggtaaattt tctttttcaa atccaattta
1741 aaataacctt tccttttaaa tgtgctgcaa cgtttttaaa aatgcagcag cataggagtg
1801 aacaacagca acacaaaacg ggcattggtt tcttaggagt ggcttgctta cgttttcttc
1861 tttttcttc accaaaacca acatgaaagt accactgaag taaaacacca actacctacc
1921 ttactataaa ggaaatgtta aaattttttt cacaataatt ttttcaattt tcactattac
```

FIG. 12-97

```
1981 tgttgtaatt attgattgtg attaaaatat ttgctcccag gagaactcct gaccagtggg
2041 catgtattcc tattttatcc taagatttta atgagcaaaa aggggagaga atttgcaata
2101 acttcacaat taccttttct agtgcagtta tattagaatg catatgtttt taaaatgcta
2161 gtataactag atagtatata atgtacagta taaagaggaa tattgtgctt ttgaaaagag
2221 tatacttttt acttttattt atgtactagt agatgtaaaa tttcgcattg aaggtttata
2281 tatattggcc aactcatata gaaattttat ttataggaag ctactactaa aaaaagtcac
2341 taactttgtg tacctataat ccctaaatta aaattaaatt ttaattggct ggctgtaatt
2401 tgcattgaga gaccttttac tagtagctag tgttaggaag tgaacctaaa ataagaaaat
2461 ataatgatct gtgtttatca ttagccttgt acaaatgtaa attactaata gtgatgttct
2521 tttgcaaggc atagaacatt tgtatgaaaa gacatttagt atgctttgaa aaaaactcag
2581 cttttagttt ttttccatta gaatactgca aaacccatat atctttttaa aaaatttatg
2641 tactcacagt ctttcccttg aagagaagat tgaaaaagtc tactgttcat aaaccatgct
2701 aacattttcc ttttagctag ttttgaaagt aaggaacaat acctgggaaa taataaaaca
2761 gaaggttacc attgtcagcc agttggctat actgtggtta gttctttcag aaattgtaaa
2821 tatcttgtag catattctga aataatagag taagttcttc tcagagatgt taatatcatg
2881 tttttcatgt tctaattaga atactttatt acttacaaac tcagaaatac gaacagaaat
2941 acagcagacg aacatattta ttggtactga aaagagatgt agtaaattaa atagaagaaa
3001 tatatttata aagcttagtg aaacacaaaa ttagaatgtt catgtcaggc acaagggttt
3061 ggattttgtg caagctaatt tggccacatt tggcctggtg acagaactgt tcataaggaa
3121 gtaatatata gataaggtag gtagatatca gttgaatgcc ttatattgta tacattcctt
3181 tcaaataaag accttgagaa aacaaaaaaa aaaaaaaaaa aaaaaaaaaa aaaaaaaaaa
3241 aaaaaaaaac aaaaaaaaaa aaaaa
//
```

DHHC22:

```
FEATURES             Location/Qualifiers
     source          1..3408
                     /organism="Homo sapiens"
                     /mol_type="mRNA"
                     /db_xref="taxon:9606"
                     /chromosome="14"
                     /map="14q24.3"
     gene            1..3408
                     /gene="ZDHHC22"
                     /gene_synonym="C14orf59"
```

/note="zinc finger, DHHC-type containing 22"
/db_xref="GeneID:283576"
/db_xref="HGNC:20106"
/db_xref="HPRD:12655"

exon 1..189
/gene="ZDHHC22"
/gene_synonym="C14orf59"
/inference="alignment:Splign"
/number=1 exon 190..729
/gene="ZDHHC22"
/gene_synonym="C14orf59"
/inference="alignment:Splign"
/number=2

CDS 204..995
/gene="ZDHHC22"
/gene_synonym="C14orf59"
/note="zinc finger, DHHC domain containing 22; DHHC-22;
zinc finger DHHC domain-containing protein 22"
/codon_start=1
/product="putative palmitoyltransferase ZDHHC22"
/protein_id="NP_777636.2"
/db_xref="GI:145046234"
/db_xref="CCDS:CCDS45140.1"
/db_xref="GeneID:283576"
/db_xref="HGNC:20106"
/db_xref="HPRD:12655"

/translation="MLALRLLNVVAPAYFLCISLVTFVLQLFLFLPSMREDPAAARLF

SPALLHGALFLFLSANALGNYVLVIQNSPDDLGACQGASARKTPCPSPSTHFCRVCAR

VTLRHDHHCFFTGNCIGSRNMRNFVLFCLYTSLACLYSMVAGVAYISAVLSISFAHPL

AFLTLLPTSISQFFSGAVLGSEMFVILMLYLWFAIGLACAGFCCHQLLLILRGQTRHQ

VRKGVAVRARPWRKNLQEVFGKRWLLGLLVPMFNVGSESSKQQDK"

```
     exon            730..3408
                     /gene="ZDHHC22"
                     /gene_synonym="C14orf59"
                     /inference="alignment:Splign"
                     /number=3
ORIGIN
        1 ccttactcgc tggcgcccaa gtgggaagcc agcagctgcc cgctccctcc tccccacatc
       61 cccgctactt gcccagttcc cgaagcgaag cgcaggctgc gagccagccg ggccgagtcc
      121 acaactttgc agcctcgggc agggcgagag ccggcgtccg gggctcctct tgtcggcgac
      181 cagagctcgg aatgtaatcg aggatgctgg ccctgcggct gctcaacgtg gtggcccccg
      241 cctacttctt gtgcatctcc ctggtgacct tcgtgctgca gctcttcctc ttcctgccca
      301 gcatgcgcga ggaccccgcg gccgcccggc tcttctcgcc cgccctgctc cacggggcgc
      361 tcttcctatt cctctcggcc aacgccctgg gcaattacgt ccttgtcatc cagaactccc
      421 cagacgacct gggggcctgc caggggccct cggccaggaa gactccatgc ccctcaccta
      481 gcacccactt ctgccgagtg tgcgccagag tcaccctgag gcacgaccat cactgtttct
      541 tcaccggcaa ctgcatcggc agcaggaaca tgcgcaactt cgtcctgttc tgcctctaca
      601 cctccctggc ctgcctctac tccatggtgg ccggcgtggc ctacatctcc gctgtccttt
      661 ccatctcctt cgcccacccc ttggccttcc tcacgctcct gcccacctcc atcagccagt
      721 tcttctccgg agctgtcctg ggttctgaaa tgttcgtcat cctcatgctc tacctctggt
      781 tcgccatcgg cctggcctgc gccggcttct gctgccacca gctgctgttg atcctccgcg
      841 ggcagacccg ccaccaggtg cggaaggggg tggcagtgag ggcccggccc tggcgcaaga
      901 acttacaaga ggtcttcgga aagaggtggc tgctgggcct gctggtcccc atgttcaatg
      961 tcggaagtga gagctccaag cagcaggata agtagtagac actcccgtca tttatctctc
     1021 tgtctctgtc ttgactcctc ctgagcataa aaccatggca gccttgtctc cacccatgac
     1081 tcactacaac cttgtgctgg taaggtccta gcatcttccc ctcaccttcc acccatgaga
     1141 acagcgtgag ctggtggatc atgacaagga ggaaaaatgt ccccccaggc atttctaggc
     1201 tcctcacgag ccagccaggt ggctgctagc tgttaggctg cctctgcttt ctttccgtcc
     1261 ccttgggatc cctgctttcc ccctcttcct ggctcatcca ttctccaccg tgtctcattc
     1321 atcactgctg tctgctagag cccttcctct cagcccccat gttgggagag gggagtggat
     1381 tcttgctgct ggtatgagac tccctgggac ctagaggctg gcaaatgttt aaaatcacca
     1441 cgtgtaagag gcagccaagt cagctctgcc aactgctagg ggagttggga aagagtgggt
     1501 gtgtgtccgc atcccctctg taggaaaaag aacttagtag cttgctgctc cctcaccacc
     1561 ccccaccagg ttcaagaccc tttttctggg agacagcaat caatggcctg ctttttccaa
     1621 atgttattcc ctgtccaccc tgccccatct ggccggccca gcccagtcca ggacctggct
     1681 ggatgcttcc tgtccctgga actcttccag cctttctact tgatctccag cccccaggtc
     1741 tttgccagat gatgggaagg caaggaagaa gggacaggga aagataatta ctgataaatg
```

FIG. 12-100

```
1801 aaggggatat tcgactgtat aaccatatgg aagtgtgtgt gtgtgtgtgt gtgtgtgtgt
1861 gagagagaga gagagagaga tgggtggtgg tgagaagtgt tgttagaaac atataggaat
1921 aatgcctagg ggaaagggag aagtgagagg gacaattggg ttcatttatg ccctatacaa
1981 agggcattcc agcagctgaa actcttcaat gtttgaatgg ctgcctgtga aggtagtgag
2041 tgccccatca ctggaggtat tccagcagag tctaggcagt cgtctgccag gcatgctgtg
2101 gaagggattt ctgtacaggg tcattctagg tgagcttaca cattccttcc aaccccaagg
2161 ttctgatgtc ctggttgtga ttgctggacc cagaggcaag atctgcagag atgcctgtga
2221 gatatttgct ttcctagagg ggagtgtggg catgggaggg gtctgaaaat caggacccaa
2281 cccagccact gaagagagag tctctgcaga gacagggcta cctgggtggt tgaggggact
2341 gacatttgag gacagggaga tggagcagtg tcattgtcag tggcagggca tggggggcag
2401 tggtgagcta aggctgagga gtggagatga ccagaatata agggtgcaat tcccagacca
2461 tccctgcgca tctgactgac tccggtggag gcactgctgt gtgttttctg aaacctagag
2521 gaccagacct ctggggcata taagggagta gggacaacac aagtgccccc tcctgactgg
2581 gtcccaaagc caatatgaca tccatgcagg cagcagtgct gaatccatgc cctgcaatgt
2641 ccaaccgcca actgcagtga cccgctgata gctgcgcaac agcctgggtt cttgagcaga
2701 gattgggagg actttactgt ggttctgcct tcacaccccc tagagagcta atgtagtatt
2761 ggctccacct gctcacattt ctccctccca tactcattcc ttcactcatc catcctacgt
2821 atatttattg agtgccaact acgttcccag cctcttccag gcactggcaa tgcagtgatg
2881 aacaggatga caagattcat gccatcaggg gcaccttgtc actgccgtct gtgcactgat
2941 tcacactccc tgcaaaatgg tcactctgcc atcttggtgg ttggtggggc aggtcatttg
3001 gaaataaaga atgtgataga gatggctgaa gaggggaagc ctaggctgcc tcaatggagg
3061 agtcgctggg ggcatttca cccacaattc tggccatact taagcaatgg gagggagagg
3121 gaggagggga agatctgggc aattttggcc ttgactcttt cctggctcca gagctcaagc
3181 ttagaagcca gccctgctat ttccagcctc ctgaaggctc agcacggtga ggcctgacat
3241 cctggggaag ggcaacaggg agacctacag gatgttggct gcttgcagac tggtcaatgg
3301 gggatgacgg tggggaggtt gccagatgtg agacttgagt agcatttgta cacatggccc
3361 tgtattgtcc ttgaagaaca tcaataaaat atatggtttt aaattgga
//
```

ZDHHC23:

```
FEATURES             Location/Qualifiers
     source          1..3778
                     /organism="Homo sapiens"
                     /mol_type="mRNA"
                     /db_xref="taxon:9606"
```

FIG. 12-101

```
                     /chromosome="3"
                     /map="3q13.31"
     gene            1..3778
                     /gene="ZDHHC23"
                     /gene_synonym="MGC42530; NIDD"
                     /note="zinc finger, DHHC-type containing 23"
                     /db_xref="GeneID:254887"
                     /db_xref="HGNC:28654"
                     /db_xref="HPRD:15717"
     exon            1..290
                     /gene="ZDHHC23"
                     /gene_synonym="MGC42530; NIDD"
                     /inference="alignment:Splign"
                     /number=1
     exon            291..460
                     /gene="ZDHHC23"
                     /gene_synonym="MGC42530; NIDD"
                     /inference="alignment:Splign"
                     /number=2
     CDS             300..1529
                     /gene="ZDHHC23"
                     /gene_synonym="MGC42530; NIDD"
                     /note="zinc finger, DHHC domain containing 23; DHHC-23;
                     zinc finger DHHC domain-containing protein 23"
                     /codon_start=1
                     /product="probable palmitoyltransferase ZDHHC23"
                     /protein_id="NP_775841.2"
                     /db_xref="GI:50234886"
                     /db_xref="CCDS:CCDS33827.1"
                     /db_xref="GeneID:254887"
                     /db_xref="HGNC:28654"
                     /db_xref="HPRD:15717"

/translation="MTQKGSMKPVKKKKTEEPELEPLCCCEYIDRNGEKNHVATCLCD

CQDLDEGCDRWITCKSLQPETCERIMDTISDRLRIPWLRGAKKVNISIIPPLVLLPVF
```

FIG. 12-102

LHVASWHFLLGVVVLTSLPVLALWYYYLTHRRKEQTLFFLSLGLFSLGYMYYVFLQEV

VPKGRVGPVQLAVLTCGLFLILLALHRAKKNPGYLSNPASGDRSLSSSQLECLSRKGQ

EKTKGFPGADMSGSLNNRTTKDDPKGSSKMPAGSPTKAKEDWCAKCQLVRPARAWHCR

ICGICVRRMDHHCVWINSCVGESNHQAFILALLIFLLTSVYGITLTLDTICRDRSVFT

ALFYCPGVYANYSSALSFTCVWYSVIITAGMAYIFLIQLINISYNVTEREVQQALRQK

TGRRLLCGLIVDTGLLG"

exon 461..1171
/gene="ZDHHC23"
/gene_synonym="MGC42530; NIDD"
/inference="alignment:Splign"
/number=3 exon 1172..1339
/gene="ZDHHC23"
/gene_synonym="MGC42530; NIDD"
/inference="alignment:Splign"
/number=4 exon 1340..1515
/gene="ZDHHC23"
/gene_synonym="MGC42530; NIDD"
/inference="alignment:Splign"
/number=5 exon 1516..3778
/gene="ZDHHC23"
/gene_synonym="MGC42530; NIDD"
/inference="alignment:Splign"
/number=6

STS 2422..2578
/gene="ZDHHC23"
/gene_synonym="MGC42530; NIDD"
/standard_name="RH12338"
/db_xref="UniSTS:74454"

STS 3544..3659

FIG. 12-103

```
                     /gene="ZDHHC23"
                     /gene_synonym="MGC42530; NIDD"
                     /standard_name="A005A39"
                     /db_xref="UniSTS:55346"
     STS             3544..3659
                     /gene="ZDHHC23"
                     /gene_synonym="MGC42530; NIDD"
                     /standard_name="G20226"
                     /db_xref="UniSTS:55345"
     STS             3551..3750
                     /gene="ZDHHC23"
                     /gene_synonym="MGC42530; NIDD"
                     /standard_name="D3S3313"
                     /db_xref="UniSTS:28853"
     STS             3645..3744
                     /gene="ZDHHC23"
                     /gene_synonym="MGC42530; NIDD"
                     /standard_name="D3S2836E"
                     /db_xref="UniSTS:150866"
ORIGIN
        1 ggggcacccg gaagcgcgcg tggacctggc gcaccgagcc gggcgggcgg aggggcggtt
       61 gggacggcgc ggggaggcgg gcgcgccgcc cgggccgcgg cgggctgtgg tcacaggtgg
      121 gcggctgcgg cgagggagcg gccgagcgga gcccgggtcc cggagactcc tgccgtcacg
      181 cccggggctc cgcgtagcag agatcgggag acgcgtctgt gcctccgggg aagccgaccc
      241 atctcccctc cgcctctttg gctgcagttg cacctccggc cagagggcag gtgcaaatca
      301 tgacacagaa gggcagtatg aagcctgtga agaaaaagaa aaccgaagaa cctgaattgg
      361 agcccctgtg ctgctgcgag tacatagatc ggaatgggga aaagaaccac gtggctactt
      421 gtttgtgtga ttgtcaagat ctggatgaag ggtgtgatcg atggattaca tgtaaatctt
      481 tacagccaga gacttgtgaa agaatcatgg atacaatttc tgatcgcctc cgaattcctt
      541 ggcttagggg agccaaaaaa gtgaacatca gcatcatccc tccgcttgtc ctgctgcctg
      601 tcttccttca tgtggcttcc tggcatttcc tcctgggggt ggtggttttg acctcccttc
      661 ctgtgctggc actgtggtac tactacctca ctcacagaag gaaagaacag accctgtttt
      721 tcctgagcct tggactgttc tctctgggct acatgtacta tgtgttcctg caggaagtgg
      781 tccccaaagg gcgtgtgggt cccgttcagc tggcggttct tacctgcggg ttatttctga
      841 tactcttagc cttgcacaga gccaagaaga atccaggcta cctcagcaat ccagcaagcg
      901 gtgacagatc tctaagcagc agccagctgg agtgcctgag cagaaagggg caggagaaga
```

961 ccaaagggtt ccctggggca gacatgtcgg gcagtctcaa caatcgcaca acaaaggatg
1021 accccaaggg ctcttccaag atgccagctg gaagccccac caaagcgaag gaggactggt
1081 gtgccaagtg ccagctggtg cgaccagccc gggcatggca ctgccggata tgtggcatct
1141 gtgtgaggag aatggatcat cattgtgtct ggataaatag ctgcgttgga gaatcaaatc
1201 atcaagcatt tatacttgcc cttttgatct tcttgctcac ctcggtgtat gggatcacac
1261 tgaccttgga caccatttgt agagacagaa gtgtcttcac agctcttttc tattgtcctg
1321 gagtttatgc aaattacagc tcggctctgt ccttcacctg cgtgtggtac tctgtgatca
1381 tcacagcagg catggcctac atcttcctga tccagctgat caacatcagc tacaatgtga
1441 ctgagcggga agtccagcag gccctccgac agaagactgg gcgccggctc ctctgcgggc
1501 tcatcgtgga cacagggtta cttggatgag ccaactccgc ttccttccca tggataggaa
1561 gggactctgt gtattattca ggtttattgg cacgaagata cttgttttaa gttccttgag
1621 aacccatgat ggacagttga cacaatgctt aaacctgtca aaagatgagt gatcttgtgt
1681 gggaaaagcc ttcccaggcg tctgtaccga aaggagcagc aaacaagggg ctaatccatg
1741 agcagtgttc tgtaggctct gtgacatctt tggtttatag gattttggag ccttttatga
1801 tctggaacta tttgaggggt ttcattatag gccttggttc tctccagggg ccagatgagt
1861 ttattgtgga atctttgaaa ggacaaggcc tctgtgaatg aatcagtccc agggaagcat
1921 ttggtggtgg cggcagtgga ggattgcccg gtgaacctat aaatcagcag tctcttgggc
1981 agaggagcaa gcccctcgaa catgatttca aacaagcagg tcctcttctc tcatctcacg
2041 tccttagtct ctgttaatga acatactgga tgtggagttt aataaattac ctactatcat
2101 ctggccactt agattattat cacaccactg tggactgttc ctggggggag aagaacagac
2161 cgatttgaaa gattcaaggg agaaagatta aggatcagga ttgcatgaaa gaagaaaatc
2221 cttcaatatt taaaatgttt cttacaatac ccacggagca cttttatggt tccagccgag
2281 cgttcctgaa atgaactgac cattaacagc gcctctttga taggttaccc tgatgctgct
2341 aaagtaaagc cttaagtgtg tttttgggac aacgtgctgc ttattccacc tcagccacat
2401 atgtgtttgt gtttaggata ttgtaaatct ttgctaagta gtgttttcct tggtgaatga
2461 agtcattgtt gtcttcaagt gtaccatctg cctagcaaaa aattgctaca aactttctct
2521 tatgcaatag tccttggtac ttctaatatt tttagcaaga gacaattttc tgtactagaa
2581 tcttccactg ccagaaaaca cagtgccagt aaggttctac ataccactga ccatctgctt
2641 aatagacatg tatttccttt gactaggaca ttagcttttg attataaagc tcaactagta
2701 taagcaaaaa tataacatct agaagcacag ttttagccag gatgtttaaa aattacagtt
2761 ttgtgagact taagggtctt tttaacctag gtaagtttat atgacctaac ttaattgtag
2821 ccatattctg gtaccttcca ttttgaaaag tagaggttgc ttaagcaagc aatggataat
2881 aagagacttt tcctgaggca cctgtttgga atctggtttt ctcagcggca gcttgacatg
2941 tgcacccttt tgtattaaac actgcaaggg tgatgcaggg gagcaggaaa gccatcctaa
3001 actcactact gagtacgatt cactatgttc ctgtggatgt ctgctgtgac taatataaat
3061 ttcttgcaga atcagctaca cttaattatg ttgctgatag acaagcatcc acgcttcagc

```
3121 tggcactaag tgttttcatt gtaggatcag cagcaggtta aagactgaac ggttagtgaa
3181 gacaaatgtc ttaagaggct gcgatgtcta ggttgggctt gtgacttctt agtggcctag
3241 ccttcttgat ggcaccttga aagtgaactt ctagaaatct acatttaaaa ggcaaagctt
3301 taaaagcaga gctagtctat tctagttact gatgcaacta aaattctgta tttcttaaga
3361 tggagccact gacgagatgt cacagtatag agcctgcagt ctcaactcat tgtgatccta
3421 atggtctggg tgattggatg gtttgagttg ttagggattt tgagtttttc attttattgc
3481 atatctgggt tggatgttag actaaaggaa acccaggaat atttacctgg tgttacattt
3541 aatatttaat gtaactggtc tagcaacatt aagggggatt tctgaagcca actccggagg
3601 ctgtgggctg cacattttgc actgttttta tatacttgta ttcatatcct cttatcacct
3661 cagactcaga cacaaggcct tttacatgga aattttacaa attacttcca tttatgtaaa
3721 ataacgtcct gtgaccaagt tgtttaaatg gaaaataaag tgctttcttt aaggcaaaa
//
```

ZDHHC24:

```
FEATURES             Location/Qualifiers
     source          1..1319
                     /organism="Homo sapiens"
                     /mol_type="mRNA"
                     /db_xref="taxon:9606"
                     /chromosome="11"
                     /map="11q13.2"
     gene            1..1319
                     /gene="ZDHHC24"
                     /note="zinc finger, DHHC-type containing 24"
                     /db_xref="GeneID:254359"
                     /db_xref="HGNC:27387"
                     /db_xref="HPRD:17325"
     exon            1..478
                     /gene="ZDHHC24"
                     /inference="alignment:Splign"
                     /number=1
     CDS             198..1052
                     /gene="ZDHHC24"
                     /note="zinc finger, DHHC domain containing 24; DHHC-24;
```

FIG. 12-106

```
                     zinc finger DHHC domain-containing protein 24"
                     /codon_start=1
                     /product="probable palmitoyltransferase ZDHHC24"
                     /protein_id="NP_997223.1"
                     /db_xref="GI:46409316"
                     /db_xref="CCDS:CCDS8143.1"
                     /db_xref="GeneID:254359"
                     /db_xref="HGNC:27387"
                     /db_xref="HPRD:17325"

/translation="MGQPWAAGSTDGAPAQLPLVLTALWAAAVGLELAYVLVLGPGPP

PLGPLARALQLALAAFQLLNLLGNVGLFLRSDPSIRGVMLAGRGLGQGWAYCYQCQSQ

VPPRSGHCSACRVCILRRDHHCRLLGRCVGFGNYRPFLCLLLHAAGVLLHVSVLLGPA

LSALLRAHTPLHMAALLLLPWLMLLTGRVSLAQFALAFVTDTCVAGALLCGAGLLFHG

MLLLRGQTTWEWARGQHSYDLGPCHNLQAALGPRWALVWLWPFLASPLPGDGITFQTT
                     ADVGHTAS"
     exon            479..756
                     /gene="ZDHHC24"
                     /inference="alignment:Splign"
                     /number=2
     exon            757..1317
                     /gene="ZDHHC24"
                     /inference="alignment:Splign"
                     /number=3
ORIGIN
        1 gattccgagc gcctccactg ctggtccgtt ggccagatca actcgccgcg tgggccggcc
       61 gttccctgag agtctgagcg ctcgccgcac cccttccga gcttctattg gccgtagcag
      121 acgtccgtct gccgctatct ccgccccaat acggaagcgg cctagtcctc cggctccgac
      181 agctgggtgt ccaggccatg ggcagccct gggcggctgg gagcacggac ggggcgcccg
```

FIG. 12-107

241 cgcagctgcc tctcgtgctc accgcgctgt gggccgcggc cgtgggcctg gagctggctt
301 acgtgctggt gctcggtccc gggccgccgc cgctgggacc cctggcccgg gccttgcagc
361 tggcgctggc cgccttccag ctgctcaacc tgctgggcaa cgtggggctc ttcctgcgct
421 cggatcccag catccgtggc gtgatgctgg ccggccgcgg tctgggccag ggctgggctt
481 actgctacca atgccaaagc caggtgccgc cacgcagcgg acactgctct gcctgccgcg
541 tctgcatcct gcgtcgggac caccactgcc gcctgctggg ccgctgcgtg ggcttcggca
601 actaccggcc cttcctgtgc ctgctgcttc atgccgccgg cgtcctgctc cacgtctctg
661 tgctgctggg ccctgcactg tcggccctgc tgcgagccca cacgcccctc cacatggctg
721 ccctcctcct gcttccctgg ctcatgttgc tcacaggcag agtgtctctg gcacagtttg
781 ccttggcctt cgtgacggac acgtgcgtgg cgggtgcgct gctgtgcggg gctgggctgc
841 tcttccatgg gatgctgctg ctgcggggcc agaccacatg ggagtgggct cggggccagc
901 actcctatga cctgggtccc tgccacaacc tgcaggcagc cctggggccc cgctgggccc
961 tcgtctggct ctggcccttc ctggcctccc cattgcctgg ggatgggatc accttccaga
1021 ccacagcaga tgtgggacac acagcctcct gactccagga agagccagag ctgtgcaggg
1081 aggaaggggt gagagggggg cccccacacc tagactcagt aaggaagtcg ggttggacct
1141 taacatctgc attggacaac tccacccctt ccttggcctt gcccctgccc gcctacactc
1201 ctacgtgtcc agggcttggg ccgtgactta ggcagaggag tgcagaggag ggtctggcag
1261 gggctgctca ggccgcctag ctgccccttt gccaggttaa taaagcactg acttgttaa

FASN:

FIG. 13-1

```
FEATURES             Location/Qualifiers
     source          1..8481
                     /organism="Homo sapiens"
                     /mol_type="mRNA"
                     /db_xref="taxon:9606"
                     /chromosome="17"
                     /map="17q25"
     gene            1..8481
                     /gene="FASN"
                     /gene_synonym="FAS; MGC14367; MGC15706; OA-519; SDR27X1"
                     /note="fatty acid synthase"
                     /db_xref="GeneID:2194"
                     /db_xref="HGNC:3594"
                     /db_xref="HPRD:02567"
                     /db_xref="MIM:600212"
     exon            1..110
                     /gene="FASN"
                     /gene_synonym="FAS; MGC14367; MGC15706; OA-519; SDR27X1"
                     /inference="alignment:Splign"
                     /number=1
     exon            111..244
                     /gene="FASN"
                     /gene_synonym="FAS; MGC14367; MGC15706; OA-519; SDR27X1"
                     /inference="alignment:Splign"
                     /number=2
     CDS             118..7653
                     /gene="FASN"
                     /gene_synonym="FAS; MGC14367; MGC15706; OA-519; SDR27X1"
                     /EC_number="2.3.1.85"
                     /EC_number="2.3.1.38"
                     /EC_number="2.3.1.39"
                     /EC_number="2.3.1.41"
                     /EC_number="3.1.2.14"
```

FIG. 13-2

/EC_number="1.3.1.10"
/EC_number="4.2.1.61"
/EC_number="1.1.1.100"
/note="short chain dehydrogenase/reductase family 27X, member 1"
/codon_start=1
/product="fatty acid synthase"
/protein_id="NP_004095.4"
/db_xref="GI:41872631"
/db_xref="CCDS:CCDS11801.1"
/db_xref="GeneID:2194"
/db_xref="HGNC:3594"
/db_xref="HPRD:02567"
/db_xref="MIM:600212"

/translation="MEEVVIAGMSGKLPESENLQEFWDNLIGGVDMVTDDDRRWKAGL

YGLPRRSGKLKDLSRFDASFFGVHPKQAHTMDPQLRLLLEVTYEAIVDGGINPDSLRG

THTGVWVGVSGSETSEALSRDPETLVGYSMVGCQRAMMANRLSFFFDFRGPSIALDTA

CSSSLMALQNAYQAIHSGQCPAAIVGGINVLLKPNTSVQFLRLGMLSPEGTCKAFDTA

GNGYCRSEGVVAVLLTKKSLARRVYATILNAGTNTDGFKEQGVTFPSGDIQEQLIRSL

YQSAGVAPESFEYIEAHGTGTKVGDPQELNGITRALCATRQEPLLIGSTKSNMGHPEP

ASGLAALAKVLLSLEHGLWAPNLHFHSPNPEIPALLDGRLQVVDQPLPVRGGNVGINS

FGFGGSNVHIILRPNTQPPPAPAPHATLPRLLRASGRTPEAVQKLLEQGLRHSQDLAF

LSMLNDIAAVPATAMPFRGYAVLGGERGGPEVQQVPAGERPLWFICSGMGTQWRGMGL

SLMRLDRFRDSILRSDEAVKPFGLKVSQLLLSTDESTFDDIVHSFVSLTAIQIGLIDL

LSCMGLRPDGIVGHSLGEVACGYADGCLSQEEAVLAAYWRGQCIKEAHLPPGAMAAVG

LSWEECKQRCPPGVVPACHNSKDTVTISGPQAPVFEFVEQLRKEGVFAKEVRTGGMAF

HSYFMEAIAPPLLQELKKVIREPKPRSARWLSTSIPEAQWHSSLARTSSAEYNVNNLV

SPVLFQEALWHVPEHAVVLEIAPHALLQAVLKRGLKPSCTIIPLMKKDHRDNLEFFLA

GIGRLHLSGIDANPNALFPPVEFPAPRGTPLISPLIKWDHSLAWDVPAAEDFPNGSGS

PSAAIYNIDTSSESPDHYLVDHTLDGRVLFPATGYLSIVWKTLARALGLGVEQLPVVF

EDVVLHQATILPKTGTVSLEVRLLEASRAFEVSENGNLVVSGKVYQWDDPDPRLFDHP

ESPTPNPTEPLFLAQAEVYKELRLRGYDYGPHFQGILEASLEGDSGRLLWKDNWVSFM

DTMLQMSILGSAKHGLYLPTRVTAIHIDPATHRQKLYTLQDKAQVADVVVSRWLRVTV

AGGVHISGLHTESAPRRQQEQQVPILEKFCFTPHTEEGCLSERAALQEELQLCKGLVQ

ALQTKVTQQGLKMVVPGLDGAQIPRDPSQQELPRLLSAACRLQLNGNLQLELAQVLAQ

ERPKLPEDPLLSGLLDSPALKACLDTAVENMPSLKMKVVEVLAGHGHLYSRIPGLLSP

HPLLQLSYTATDRHPQALEAAQAELQQHDVAQGQWDPADPAPSALGSADLLVCNCAVA

ALGDPASALSNMVAALREGGFLLLHTLLRGHPLGDIVAFLTSTEPQYGQGILSQDAWE

SLFSRVSLRLVGLKKSFYGSTLFLCRRPTPQDSPIFLPVDDTSFRWVESLKGILADED

SSRPVWLKAINCATSGVVGLVNCLRREPGGNRLRCVLLSNLSSTSHVPEVDPGSAELQ

KVLQGDLVMNVYRDGAWGAFRHFLLEEDKPEEPTAHAFVSTLTRGDLSSIRWVCSSLR

HAQPTCPGAQLCTVYYASLNFRDIMLATGKLSPDAIPGKWTSQDSLLGMEFSGRDASG

KRVMGLVPAKGLATSVLLSPDFLWDVPSNWTLEEAASVPVVYSTAYYALVVRGRVRPG

ETLLIHSGSGGVGQAAIAIALSLGCRVFTTVGSAEKRAYLQARFPQLDSTSFANSRDT

FIG. 13-3

SFEQHVLWHTGGKGVDLVLNSLAEEKLQASVRCLATHGRFLEIGKFDLSQNHPLGMAI

FLKNVTFHGVLLDAFFNESSADWREVWALVQAGIRDGVVRPLKCTVFHGAQVEDAFRY

MAQGKHIGKVVVQVLAEEPEAVLKGAKPKLMSAISKTFCPAHKSYIIAGGLGGFGLEL

AQWLIQRGVQKLVLTSRSGIRTGYQAKQVRRWRRQGVQVQVSTSNISSLEGARGLIAE

AAQLGPVGGVFNLAVVLRDGLLENQTPEFFQDVCKPKYSGTLNLDRVTREACPELDYF

VVFSSVSCGRGNAGQSNYGFANSAMERICEKRRHEGLPGLAVQWGAIGDVGILVETMS

TNDTIVSGTLPQRMASCLEVLDLFLNQPHMVLSSFVLAEKAAAYRDRDSQRDLVEAVA

HILGIRDLAAVNLDSSLADLGLDSLMSVEVRQTLERELNLVLSVREVRQLTLRKLQEL

SSKADEASELACPTPKEDGLAQQQTQLNLRSLLVNPEGPTLMRLNSVQSSERPLFLVH

PIEGSTTVFHSLASRLSIPTYGLQCTRAAPLDSIHSLAAYYIDCIRQVQPEGPYRVAG

YSYGACVAFEMCSQLQAQQSPAPTHNSLFLFDGSPTYVLAYTQSYRAKLTPGCEAEAE

TEAICFFVQQFTDMEHNRVLEALLPLKGLEERVAAAVDLIIKSHQGLDRQELSFAARS

FYYKLRAAEQYTPKAKYHGNVMLLRAKTGGAYGEDLGADYNLSQVCDGKVSVHVIEGD

HRTLLEGSGLESIISIIHSSLAEPRVSVREG"

exon 245..397
/gene="FASN"
/gene_synonym="FAS; MGC14367; MGC15706; OA-519; SDR27X1"
/inference="alignment:Splign"
/number=3

STS 281..387
/gene="FASN"
/gene_synonym="FAS; MGC14367; MGC15706; OA-519; SDR27X1"
/standard_name="D17S1256"
/db_xref="UniSTS:149801"

exon 398..571

FIG. 13-4

/gene="FASN"
/gene_synonym="FAS; MGC14367; MGC15706; OA-519; SDR27X1"
/inference="alignment:Splign"
/number=4 exon 572..772
/gene="FASN"
/gene_synonym="FAS; MGC14367; MGC15706; OA-519; SDR27X1"
/inference="alignment:Splign"
/number=5 exon 773..895
/gene="FASN"
/gene_synonym="FAS; MGC14367; MGC15706; OA-519; SDR27X1"
/inference="alignment:Splign"
/number=6 exon 896..1011
/gene="FASN"
/gene_synonym="FAS; MGC14367; MGC15706; OA-519; SDR27X1"
/inference="alignment:Splign"
/number=7 exon 1012..1146
/gene="FASN"
/gene_synonym="FAS; MGC14367; MGC15706; OA-519; SDR27X1"
/inference="alignment:Splign"
/number=8 exon 1147..1609
/gene="FASN"
/gene_synonym="FAS; MGC14367; MGC15706; OA-519; SDR27X1"
/inference="alignment:Splign"
/number=9 exon 1610..1797
/gene="FASN"
/gene_synonym="FAS; MGC14367; MGC15706; OA-519; SDR27X1"
/inference="alignment:Splign"
/number=10 exon 1798..1987
/gene="FASN"

FIG. 13-5

```
                   /gene_synonym="FAS; MGC14367; MGC15706; OA-519; SDR27X1"
                   /inference="alignment:Splign"
                   /number=11
     exon          1988..2082
                   /gene="FASN"
                   /gene_synonym="FAS; MGC14367; MGC15706; OA-519; SDR27X1"
                   /inference="alignment:Splign"
                   /number=12
     exon          2083..2217
                   /gene="FASN"
                   /gene_synonym="FAS; MGC14367; MGC15706; OA-519; SDR27X1"
                   /inference="alignment:Splign"
                   /number=13
     exon          2218..2421
                   /gene="FASN"
                   /gene_synonym="FAS; MGC14367; MGC15706; OA-519; SDR27X1"
                   /inference="alignment:Splign"
                   /number=14
     exon          2422..2537
                   /gene="FASN"
                   /gene_synonym="FAS; MGC14367; MGC15706; OA-519; SDR27X1"
                   /inference="alignment:Splign"
                   /number=15
     exon          2538..2710
                   /gene="FASN"
                   /gene_synonym="FAS; MGC14367; MGC15706; OA-519; SDR27X1"
                   /inference="alignment:Splign"
                   /number=16
     exon          2711..2902
                   /gene="FASN"
                   /gene_synonym="FAS; MGC14367; MGC15706; OA-519; SDR27X1"
                   /inference="alignment:Splign"
                   /number=17
     exon          2903..2983
                   /gene="FASN"
                   /gene_synonym="FAS; MGC14367; MGC15706; OA-519; SDR27X1"
```

```
                     /inference="alignment:Splign"
                     /number=18
     exon            2984..3160
                     /gene="FASN"
                     /gene_synonym="FAS; MGC14367; MGC15706; OA-519; SDR27X1"
                     /inference="alignment:Splign"
                     /number=19
     exon            3161..3340
                     /gene="FASN"
                     /gene_synonym="FAS; MGC14367; MGC15706; OA-519; SDR27X1"
                     /inference="alignment:Splign"
                     /number=20
     exon            3341..3544
                     /gene="FASN"
                     /gene_synonym="FAS; MGC14367; MGC15706; OA-519; SDR27X1"
                     /inference="alignment:Splign"
                     /number=21
     exon            3545..3849
                     /gene="FASN"
                     /gene_synonym="FAS; MGC14367; MGC15706; OA-519; SDR27X1"
                     /inference="alignment:Splign"
                     /number=22
     exon            3850..4239
                     /gene="FASN"
                     /gene_synonym="FAS; MGC14367; MGC15706; OA-519; SDR27X1"
                     /inference="alignment:Splign"
                     /number=23
     exon            4240..4404
                     /gene="FASN"
                     /gene_synonym="FAS; MGC14367; MGC15706; OA-519; SDR27X1"
                     /inference="alignment:Splign"
                     /number=24
     exon            4405..4526
                     /gene="FASN"
                     /gene_synonym="FAS; MGC14367; MGC15706; OA-519; SDR27X1"
                     /inference="alignment:Splign"
```

FIG. 13-8

```
                    /number=25
exon                4527..4681
                    /gene="FASN"
                    /gene_synonym="FAS; MGC14367; MGC15706; OA-519; SDR27X1"
                    /inference="alignment:Splign"
                    /number=26
exon                4682..4885
                    /gene="FASN"
                    /gene_synonym="FAS; MGC14367; MGC15706; OA-519; SDR27X1"
                    /inference="alignment:Splign"
                    /number=27
exon                4886..5036
                    /gene="FASN"
                    /gene_synonym="FAS; MGC14367; MGC15706; OA-519; SDR27X1"
                    /inference="alignment:Splign"
                    /number=28
exon                5037..5215
                    /gene="FASN"
                    /gene_synonym="FAS; MGC14367; MGC15706; OA-519; SDR27X1"
                    /inference="alignment:Splign"
                    /number=29
exon                5216..5335
                    /gene="FASN"
                    /gene_synonym="FAS; MGC14367; MGC15706; OA-519; SDR27X1"
                    /inference="alignment:Splign"
                    /number=30
exon                5336..5458
                    /gene="FASN"
                    /gene_synonym="FAS; MGC14367; MGC15706; OA-519; SDR27X1"
                    /inference="alignment:Splign"
                    /number=31
exon                5459..5682
                    /gene="FASN"
                    /gene_synonym="FAS; MGC14367; MGC15706; OA-519; SDR27X1"
                    /inference="alignment:Splign"
                    /number=32
```

FIG. 13-9 exon 5683..5884
/gene="FASN"
/gene_synonym="FAS; MGC14367; MGC15706; OA-519; SDR27X1"
/inference="alignment:Splign"
/number=33
exon 5885..6036
/gene="FASN"
/gene_synonym="FAS; MGC14367; MGC15706; OA-519; SDR27X1"
/inference="alignment:Splign"
/number=34
exon 6037..6128
/gene="FASN"
/gene_synonym="FAS; MGC14367; MGC15706; OA-519; SDR27X1"
/inference="alignment:Splign"
/number=35
exon 6129..6280
/gene="FASN"
/gene_synonym="FAS; MGC14367; MGC15706; OA-519; SDR27X1"
/inference="alignment:Splign"
/number=36
exon 6281..6523
/gene="FASN"
/gene_synonym="FAS; MGC14367; MGC15706; OA-519; SDR27X1"
/inference="alignment:Splign"
/number=37
exon 6524..6712
/gene="FASN"
/gene_synonym="FAS; MGC14367; MGC15706; OA-519; SDR27X1"
/inference="alignment:Splign"
/number=38
exon 6713..6943
/gene="FASN"
/gene_synonym="FAS; MGC14367; MGC15706; OA-519; SDR27X1"
/inference="alignment:Splign"
/number=39
exon 6944..7164

FIG. 13-10

```
                     /gene="FASN"
                     /gene_synonym="FAS; MGC14367; MGC15706; OA-519; SDR27X1"
                     /inference="alignment:Splign"
                     /number=40
     exon            7165..7263
                     /gene="FASN"
                     /gene_synonym="FAS; MGC14367; MGC15706; OA-519; SDR27X1"
                     /inference="alignment:Splign"
                     /number=41
     exon            7264..7515
                     /gene="FASN"
                     /gene_synonym="FAS; MGC14367; MGC15706; OA-519; SDR27X1"
                     /inference="alignment:Splign"
                     /number=42
     exon            7516..8458
                     /gene="FASN"
                     /gene_synonym="FAS; MGC14367; MGC15706; OA-519; SDR27X1
                     /inference="alignment:Splign"
                     /number=43
     STS             7588..8358
                     /gene="FASN"
                     /gene_synonym="FAS; MGC14367; MGC15706; OA-519; SDR27X1
                     /standard_name="FASN_7242"
                     /db_xref="UniSTS:466167"
     polyA_signal    8437..8442
                     /gene="FASN"
                     /gene_synonym="FAS; MGC14367; MGC15706; OA-519; SDR27X1
     polyA_site      8458
                     /gene="FASN"
                     /gene_synonym="FAS; MGC14367; MGC15706; OA-519; SDR27X1
ORIGIN
        1 gagagacggc agcggccccg gcctccctct ccgccgcgct tcagcctccc gctccgccgc
       61 gctccagcct cgctctccgc cgcccgcacc gccgcccgcg ccctcaccag agcagccatg
      121 gaggaggtgg tgattgccgg catgtccggg aagctgccag agtcggagaa cttgcaggag
      181 ttctgggaca acctcatcgg cggtgtggac atggtcacgg acgatgaccg tcgctggaag
      241 gcggggctct acggcctgcc ccggcggtcc ggcaagctga aggacctgtc taggtttgat
```

FIG. 13-11

301 gcctccttct tcggagtcca ccccaagcag gcacacacga tggaccctca gctgcggctg
361 ctgctggaag tcacctatga agccatcgtg gacggaggca tcaacccaga ttcactccga
421 ggaacacaca ctggcgtctg ggtgggcgtg agcggctctg agacctcgga ggccctgagc
481 cgagaccccg agacactcgt gggctacagc atggtgggct gccagcgagc gatgatggcc
541 aaccggctct ccttcttctt cgacttcaga gggcccagca tcgcactgga cacagcctgc
601 tcctccagcc tgatggccct gcagaacgcc taccaggcca tccacagcgg gcagtgccct
661 gccgccatcg tgggggggcat caatgtcctg ctgaagccca acacctccgt gcagttcttg
721 aggctgggga tgctcagccc cgagggcacc tgcaaggcct tcgacacagc ggggaatggg
781 tactgccgct cggagggtgt ggtggccgtc ctgctgacca agaagtccct ggcccggcgg
841 gtgtacgcca ccatcctgaa cgccggcacc aatacagatg gcttcaagga gcaaggcgtg
901 accttcccct caggggatat ccaggagcag ctcatccgct cgttgtacca gtcggccgga
961 gtggcccctg agtcatttga atacatcgaa gcccacggca caggcaccaa ggtgggcgac
1021 ccccaggagc tgaatggcat caccccgagcc ctgtgcgcca cccgccagga gccgctgctc
1081 atcggctcca ccaagtccaa catggggcac ccggagccag cctcggggct ggcagccctg
1141 gccaaggtgc tgctgtccct ggagcacggg ctctgggccc ccaacctgca cttccatagc
1201 cccaaccctg agatcccagc gctgttggat gggcggctgc aggtggtgga ccagcccctg
1261 cccgtccgtg gcggcaacgt gggcatcaac tcctttggct tcgggggctc caacgtgcac
1321 atcatcctga ggcccaacac gcagccgccc cccgcacccg ccccacatgc caccctgccc
1381 cgtctgctgc gggccagcgg acgcacccct gaggccgtgc agaagctgct ggagcagggc
1441 ctccggcaca gccaggacct ggctttcctg agcatgctga acgacatcgc ggctgtcccc
1501 gccaccgcca tgcccttccg tggctacgct gtgctgggtg gtgagcgcgg tggcccagag
1561 gtgcagcagg tgcccgctgg cgagcgcccg ctctggttca tctgctctgg gatgggcaca
1621 cagtggcgcg ggatggggct gagcctcatg cgcctggacc gcttccgaga ttccatccta
1681 cgctccgatg aggctgtgaa gccattcggc ctgaaggtgt cacagctgct gctgagcaca
1741 gacgagagca cctttgatga catcgtccat tcgtttgtga gcctgactgc catccagata
1801 ggcctcatag acctgctgag ctgcatgggg ctgaggccag atggcatcgt cggccactcc
1861 ctgggggagg tggcctgtgg ctacgccgac ggctgcctgt cccaggagga ggccgtcctc
1921 gctgcctact ggaggggaca gtgcatcaaa gaagcccatc tcccgccggg cgccatggca
1981 gccgtgggct tgtcctggga ggagtgtaaa cagcgctgcc ccccgggcgt ggtgcccgcc
2041 tgccacaact ccaaggacac agtcaccatc tcgggacctc aggccccggt gtttgagttc
2101 gtggagcagc tgaggaagga gggtgtgttt gccaaggagg tgcggaccgg cggtatggcc
2161 ttccactcct acttcatgga ggccatcgca ccccccactgc tgcaggagct caagaaggtg
2221 atccgggagc cgaagccacg ttcagcccgc tggctcagca cctctatccc cgaggcccag
2281 tggcacagca gcctggcacg cacgtcctcc gccgagtaca atgtcaacaa cctggtgagc
2341 cctgtgctgt tccaggaggc cctgtggcac gtgcctgagc acgcggtggt gctggagatc
2401 gcgccccacg ccctgctgca ggctgtcctg aagcgtggcc tgaagccgag ctgcaccatc

FIG. 13-12

2461 atccccctga tgaagaagga tcacagggac aacctggagt tcttcctggc cgccatcggc
2521 aggctgcacc tctcaggcat cgacgccaac cccaatgcct tgttcccacc tgtggagttc
2581 ccagctcccc gaggaactcc cctcatctcc ccactcatca agtgggacca cagcctggcc
2641 tgggacgtgc cggccgccga ggacttcccc aacgcttcag gttcccccctc agccgccatc
2701 tacaacatcg acaccagctc cgagtctcct gaccactacc tggtggacca caccctcgac
2761 ggtcgcgtcc tcttccccgc cactggctac ctgagccatag tgtggaagac gctggcccgc
2821 gccctgggcc tgggcgtcga gcagctgcct gtggtgtttg aggatgtggt gctgcaccag
2881 gccaccatcc tgcccaagac tgggacagtg tccctggagg tacggctcct ggaggcctcc
2941 cgtgccttcg aggtgtcaga gaacggcaac ctggtagtga gtgggaaggt gtaccagtgg
3001 gatgaccctg accccaggct cttcgaccac ccggaaagcc ccaccccccaa ccccacggag
3061 cccctcttcc tggcccaggc tgaagtttac aaggagctgc gtctgcgtgg ctacgactac
3121 ggccctcatt tccagggcat cctggaggcc agcctggaag gtgactcggg gacgctgctg
3181 tggaaggata actgggtgag cttcatggac accatgctgc agatgtccat cctgggctcg
3241 gccaagcacg gcctgtacct gcccacccgt gtcaccgcca tccacatcga ccctgccacc
3301 cacaggcaga agctgtacac actgcaggac aaggcccaag tggctgacgt ggtgctgagc
3361 aggtggctga gggtcacagt ggccggaggc gtccacatct ccgggctcca cactgagtcg
3421 gccccgcggc ggcagcagga gcagcaggtg cccatcctgg agaagttttg cttcactccc
3481 cacacggagg aggggtgcct gtctgagcgc gctgccctgc aggaggagct gcaactgtgc
3541 aaggggctgg tgcaggcact gcagaccaag gtgacccagc aggggctgaa gatggtggtg
3601 cccggactgg atggggccca gatcccccgg gacccctcac agcaggaact gccccggctg
3661 ttgtcggctg cctgcaggct tcagctcaac gggaacctgc agctggagct ggcgcaggtg
3721 ctggcccagg agaggcccaa gctgccagag gaccctctgc tcagcggcct cctggactcc
3781 ccggcactca aggcctgcct ggacactgcc gtggagaaca tgcccagcct gaagatgaag
3841 gtggtggagg tgctggctgg ccacggtcac ctgtattccc gcatcccagg cctgctcagc
3901 ccccatcccc tgctgcagct gagctacacg gccaccgacc gccaccccca ggccctggag
3961 gctgcccagg ccgagctgca gcagcacgac gttgcccagg gccagtggga tcccgcagac
4021 cctgccccca gcgccctggg cagcgccgac ctcctggtgt gcaactgtgc tgtggctgcc
4081 ctcggggacc cggcctcagc tctcagcaac atggtggctg ccctgagaga agcgggcttt
4141 ctgctcctgc acacactgct ccgggggcac cccctcgggg acatcgtggc cttcctcacc
4201 tccactgagc cgcagtatgg ccagggcatc ctgagcccagg acgcgtggga gagcctcttc
4261 tccagggtgt cgctgcgcct ggtgggcctg aagaagtcct tctacggctc cacgctcttc
4321 ctgtgccgcc ggcccacccc gcaggacagc cccatcttcc tgccggtgga cgataccagc
4381 ttccgctggg tggagtctct gaagggcatc ctggctgacg aagactcttc ccggcctgtg
4441 tggctgaagg ccatcaactg tgccacctcg ggcgtggtgg gcttggtgaa ctctctccgc
4501 cgagagcccg gcgggaaccg cctccggtgt gtgctgctct ccaacctcag cagcacctcc
4561 cacgtcccgg aggtggaccc gggctccgca gaactgcaga aggtgttgca gggcagacctg

FIG. 13-13

4621 gtgatgaacg tctaccgcga cggggcctgg ggggctttcc gccacttcct gctgcaggag
4681 gacaagcctg aggagccgac ggcacatgcc tttgtgagca ccctcacccg gggggacctg
4741 tcctccatcc gctgggtctg ctcctcgctg cgccatgccc agcccacctg ccctggcgcc
4801 cagctctgca cggtctacta cgcctccctc aacttccgcg acatcatgct ggccactggc
4861 aagctgtccc ctgatgccat cccagggaag tggacctccc aggacagcct gctaggtatg
4921 gagttctcgg gccgagacgc cagcggcaag cgtgtgatgg gactggtgcc tgccaagggc
4981 ctggccacct ctgtcctgct gtcaccggac ttcctctggg atgtgccttc caactggacg
5041 ctggaggagg cggcctcggt gcctgtcgtc tacagcacgg cctactacgc gctggtggtg
5101 cgtgggcggg tgcgccccgg ggagacgctg ctcatccact cgggctcggg cggcgtgggc
5161 caggccgcca tcgccatcgc cctcagtctg ggctgccgcg tcttcaccac cgtggggtcg
5221 gctgagaagc gggcgtacct ccaggccagg ttcccccagc tcgacagcac cagcttcgcc
5281 aactcccggg acacatcctt cgagcagcat gtgctgtggc acacgggcgg gaagggcgtt
5341 gacctggtct tgaactcctt ggcggaagag aagctgcagg ccagcgtgag gtgcttggct
5401 acgcacggtc gcttcctgga aattggcaaa ttcgaccttt ctcagaacca cccgctcggc
5461 atggctatct tcctgaagaa cgtgacattc cacggggtcc tactggatgc gttcttcaac
5521 gagagcagtg ctgactggcg ggaggtgtgg gcgcttgtgc aggccggcat ccgggatggg
5581 gtggtacggc ccctcaagtg cacggtgttc catgggggccc aggtggagga cgccttccgc
5641 tacatggccc aagggaagca cattggcaaa gtcgtcgtgc aggtgcttgc ggagcagccg
5701 gaggcagtgc tgaacggggc caaaccccaag ctgatgtcgg ccatctccaa gaccttctgc
5761 ccggcccaca agagctacat catcgctggt ggtctgggtg gcttcggcct ggagttggcg
5821 cagtggctga tacagcgtgg ggtgcagaag ctcgtgttga cttctcgctc cgggatccgg
5881 acaggctacc aggccaagca ggtccgccgg tggaggcgcc agggcgtaca ggtgcaggtg
5941 tccaccagca acatcagctc actggagggg gcccgggccc tcattgccga ggcggcgcag
6001 cttgggcccg tgggcggcgt cttcaacctg gccgtggtct tgagagatgg cttgctggag
6061 aaccagaccc cagagttctt ccaggacgtc tgcaagccca agtacagcgg caccctgaac
6121 ctggacaggg tgacccgaga ggcgtgccct gagctggact actttgtggt cttctcctct
6181 gtgagctgcg ggcgtggcaa tgcgggacag agcaactacg gctttgccaa ttccgccatg
6241 gagcgtatct gtgacaaacg ccggcacgaa ggcctcccag gcctggccgt gcagtggggc
6301 gccatcggcg acgtcggcat tttggtggag acgatgagca ccaacgacac gatcgtcagt
6361 ggcacgctgc cccagcgcat ggcgtcctgc ctggaggtgc tggacctctt cctgaaccag
6421 ccccacatgg tcctcagcag ctttgtgctg gctgagaagg ctgcggccta tagggacagg
6481 gacagccagc gggacctggt ggaggccgtg gcacacatcc tgggcatccg cgacttggct
6541 gctgtcaacc tggacagctc actggcggac ctgggcctgg actcgctcat gagcgtggag
6601 gtgcgccaga cgctcgagcg tgagctcaac ctggtgctgt ccgtgcgcga ggtgcggcaa
6661 ctcacgctcc ggaaactgca ggagctgtcc tcaaaggcgg atgaggccag cgagctggca
6721 tgccccacgc ccaacgagga tggtctggcc cagcagcaga ctcagctgaa cctgcgctcc

FIG. 13-14

```
6781 ctgctggtga accccgaggg ccccaccctg atgcggctca actccgtgca gagctcggag
6841 cggcccctgt tcctcgtgca cccaatcgag ggctccacca ccgtgttcca cagcctggcc
6901 tcccggctca gcatccccac ctatggcctg cagtgcaccc gagctgcgcc ccttgacagc
6961 atccacagcc tggctgccta ctacatcgac tgcatcaggc aggtgcagcc cgagggcccc
7021 taccgcgtgg ccggctactc ctacggggcc tgcgtggcct ttgaaatgtg ctcccagctg
7081 caggcccagc agagcccagc ccccacccac aacagcctct tcctgttcga cggctcgccc
7141 acctacgtac tggcctacac ccagagctac cgggcaaagc tgaccccagg ctgtgaggct
7201 gaggctgaga cggacgccat atgcttcttc gtgcagcagt tcacggacat ggagcacaac
7261 agggtgctgg aggcgctgct gccgctgaag ggcctagagg agcgtgtggc agccgccgtg
7321 gacctgatca tcaagagcca ccagggcctg gaccgccagg agctgagctt tgcggcccgg
7381 tccttctact acaagctgcg tgccgctgag cagtacacac ccaaggccaa gtaccatggc
7441 aacgtgatgc tactgcgcgc caagacgggt ggcgcctacg gcgaggacct gggcgcggac
7501 tacaacctct cccacgtatg cgacgggaaa gtatccgtcc acgtcatcga gggtgaccac
7561 cgcacgctgc tggacggcag cggcctggag tccatcatca gcatcatcca cagctccctg
7621 gctgagccac gcgtgagcgt gcgggagggc taggcccgtg cccccgcctg ccaccggagg
7681 tcactccacc atccccaccc caccccaccc caccccccgcc atgcaacggg attgaagggt
7741 cctgccggtg ggaccctgtc cggcccagtg ccactgcccc ccgaggctgc tagatgtagg
7801 tgttaggcat gtcccaccca cccgccgcct cccacggcac ctcggggaca ccagagctgc
7861 cgacttggag actcctggtc tgtgaagagc cggtggtgcc cgtgcccgca ggaactgggc
7921 tgggcctcgt gcgcccgtgg ggtctgcgct tggtctttct gtgcttggat ttgcatattt
7981 attgcattgc tggtagagac ccccaggcct gtccaccctg ccaagactcc tcaggcagcg
8041 tgtgggtccc gcactctgcc cccatttccc cgatgtcccc tgcgggcgcg ggcagccacc
8101 caagcctgct ggctgcggcc ccctctcggc caggcattgg ctcagcccgc tgagtggggg
8161 gtcgtgggcc agtccccgag gagctgggcc cctgcacagg cacacagggc ccggccacac
8221 ccagcggccc cccgcacagc caccccgtggg gtgctgccct tatgcccggc gccgggcacc
8281 aactccatgt ttggtgtttg tctgtgtttg tttttcaaga aatgattcaa attgctgctt
8341 ggattttgaa atttactgta actgtcagtg tacacgtctg gaccccgttt catttttaca
8401 ccaatttggt aaaaatgctg ctctcagcct cccacaatta aaccgcatgt gatctccaaa
8461 aaaaaaaaaa aaaaaaaaaa a
//
```

ZDHHC1:

```
FEATURES             Location/Qualifiers
     source          1..2026
```

FIG. 13-15

```
                     /organism="Homo sapiens"
                     /mol_type="mRNA"
                     /db_xref="taxon:9606"
                     /chromosome="16"
                     /map="16q22.1"
     gene            1..2026
                     /gene="ZDHHC1"
                     /gene_synonym="C16orf1; HSU90653; ZNF377"
                     /note="zinc finger, DHHC-type containing 1"
                     /db_xref="GeneID:29800"
                     /db_xref="HGNC:17916"
                     /db_xref="HPRD:15707"
     exon            1..266
                     /gene="ZDHHC1"
                     /gene_synonym="C16orf1; HSU90653; ZNF377"
                     /inference="alignment:Splign"
                     /number=1
     exon            267..313
                     /gene="ZDHHC1"
                     /gene_synonym="C16orf1; HSU90653; ZNF377"
                     /inference="alignment:Splign"
                     /number=2
     CDS             305..1762
                     /gene="ZDHHC1"
                     /gene_synonym="C16orf1; HSU90653; ZNF377"
                     /note="DHHC-domain-containing cysteine-rich protein;
zinc
                     finger, DHHC domain containing 1; DHHC-1; zinc finger
                     protein 377; zinc finger DHHC domain-containing protein
1;
                     DHHC domain-containing cysteine-rich protein 1"
                     /codon_start=1
                     /product="probable palmitoyltransferase ZDHHC1"
                     /protein_id="NP_037436.1"
                     /db_xref="GI:24307963"
                     /db_xref="CCDS:CCDS10836.1"
```

/db_xref="GeneID:29800"
/db_xref="HGNC:17916"
/db_xref="HPRD:15707"

FIG. 13-16

/translation="MYKMNICNKPSNKTAPEKSVWTAPAQPSGPSPELQGQRSRRNGW

SKPPHPLQIVAWLLYLFFAVIGFGILVPLLPHHWVPAGYACMGAIFAGHLVVHLTAVS

IDPADANVRDKSYAGPLPIFNRSQHAHVIEDLHCNLCNVDVSARSKHCSACNKCVCGF

DHHCKWLNNCVGERNYRLFLHSVASALLGVLLLVLVATYVFVEFFVNPMRLRTNRHFE

VLKNHTDVWFVFLPAAPVETQAPAILALAALLILLGLLSTALLGHLLCFHIYLMWHKL

TTYEYIVQHRPPQEAKGVHRELESCPPKMRPIQEMEFYMRTFRHMRPEPPGQAGPAAV

NAKHSRPASPDPTPGRRDCAGPPVQVEWDRKKPLPWRSPLLLLAMWGPQAPPCLCRKR

GRGACIKCERLRPRIRRRGLGPPAAAPARRRIPRTPALCTPLALPAPTTRRRQSPWTR
FQWRRRAWAAPLWPPRGAGADSPRWRGRRVRPPFS"

exon 314..556
/gene="ZDHHC1"
/gene_synonym="C16orf1; HSU90653; ZNF377"
/inference="alignment:Splign"
/number=3 exon 557..732
/gene="ZDHHC1"
/gene_synonym="C16orf1; HSU90653; ZNF377"
/inference="alignment:Splign"
/number=4 exon 733..834
/gene="ZDHHC1"
/gene_synonym="C16orf1; HSU90653; ZNF377"
/inference="alignment:Splign"
/number=5 exon 835..959
/gene="ZDHHC1"
/gene_synonym="C16orf1; HSU90653; ZNF377"
/inference="alignment:Splign"
/number=6 exon 960..1118
/gene="ZDHHC1"

```
                          /gene_synonym="C16orf1; HSU90653; ZNF377"
                          /inference="alignment:Splign"
                          /number=7
          exon            1119..1231
                          /gene="ZDHHC1"
                          /gene_synonym="C16orf1; HSU90653; ZNF377"
                          /inference="alignment:Splign"
                          /number=8
          exon            1232..1314
                          /gene="ZDHHC1"
                          /gene_synonym="C16orf1; HSU90653; ZNF377"
                          /inference="alignment:Splign"
                          /number=9
          exon            1315..1534
                          /gene="ZDHHC1"
                          /gene_synonym="C16orf1; HSU90653; ZNF377"
                          /inference="alignment:Splign"
                          /number=10
          exon            1535..2009
                          /gene="ZDHHC1"
                          /gene_synonym="C16orf1; HSU90653; ZNF377"
                          /inference="alignment:Splign"
                          /number=11
ORIGIN
        1 gcccctccag cctgctggag ccggagccgg agccggagcc ggagccggag ccggagccag
       61 agccagagct cgaggactca ccggcccagt ctccgtccgg gatggggccc cgctcccggg
      121 cgcgttgccg cccagtcccg gggaccgtcc ctaccgcgag ggtctgaggc gcggctgccc
      181 cggggagggt ggaaggccag gcgtggggcc cgaacctctg gctgactttg gcagggccca
      241 tctggcacgg cctccgcggc gcgcagctgt tttcaagtca gcaaacattt actgaggatc
      301 tactatgtac aagatgaaca tctgcaacaa gccctccaac aagacggccc ctgagaagag
      361 tgtgtggacg gcaccggcac agccagcgg accctcccct gagctgcagg gccagcgatc
      421 ccgccggaat gggtggagct ggccccctca cccgctccag attgtggcct ggctgctgta
      481 cctcttcttt gctgtgatcg gctttgggat ccttgttccc ctcctgcctc accactgggt
      541 gcccgctggc tacgcttgca tgggcgccat ctttgctggc caccttgtgg tgcacctgac
      601 cgccgtctcc atcgatccag cagatgccaa cgtgcgggac aagagctatg cggggcccct
      661 gcccatcttc aaccgaagcc agcacgcaca tgtcattgaa gacctgcact gcaacttgtg
```

FIG. 13-18

```
 721 caacgtggat gtgagcgctc gctccaagca ctgcagcgcc tgcaacaagt gcgtgtgcgg
 781 tttcgaccac cactgcaagt ggctcaacaa ctgtgtgggc gagcggaact accggctctt
 841 tctacacagt gttgcatccg ctttactggg cgtcctgctc ctggtgctgg tggccacata
 901 tgtcttcgtg gagttctttg tcaaccccat gcgtctgcgc accaaccgac actttgaagt
 961 cctgaagaat cacacggatg tgtggttcgt gttcctgcct gccgcccccg tggagaccca
1021 ggcccctgcc atcctggccc tggccgccct gctcatcctt ctgggcctcc tgtccacagc
1081 cctcctgggg cacctgctct gcttccacat ttatctcatg tggcacaagc tcaccaccta
1141 tgagtacatc gtgcagcacc gcccaccaca ggaggccaag gggttcaca gggagctcga
1201 gtcatgtcct cccaagatgc ggcccattca ggagatggag ttctacatgc ggaccttcag
1261 acatatgcgc ccagagcccc ctggccaggc cgggccagca gcagtgaatg ccaaacactc
1321 tcgccctgcc tcccgggatc cgaccccagg taggagggac tgtgctgggc ctccggtcca
1381 ggtggagtgg gatagaaaga agcctctacc ctggcgctcg cctctgcttc ttttggcgat
1441 gtggggccct caggctcccc cgtgtctctg cagaaaaaga ggaagaggcg cgtgtataaa
1501 gtgcgaacgt ctgagacctc ggatccggcg tcggggccta gggcccccag ccgccgctcc
1561 agctcgtcga cggattccgc ggacgccagc cctgtgcacg ccgctggccc tgccggcgcc
1621 taccactcgg cgtcggcaga gtccgtggac gagattccag tggcgcagac gcgcctgggc
1681 agcgccgctc tggccgcccc gcggggccgg ggccgacagc ccacgctggc gcggcaggcg
1741 cgtgcgcccg ccgttttcgt gagcccgagc agcggcgagc ccagggcgcc gggcggccgg
1801 gaggctggtc tggcttagct gggccgagag gccggagggc cgagttagag cggccggcct
1861 gactctctat gcaacacccc atccttgccg caccgagtgc actttagggg cccctacggc
1921 cggcgggatc ggcctccctc ccccacgact cagcaatacc cgccccaccg gctgtgatgc
1981 tccaataaac ttttttatgc ttttgcggaa aaaaaaaaaa aaaaaa
//
```

ZDHHC2:

```
FEATURES             Location/Qualifiers
     source          1..4012
                     /organism="Homo sapiens"
                     /mol_type="mRNA"
                     /db_xref="taxon:9606"
                     /chromosome="8"
                     /map="8p21.3-p22"
```

FIG. 13-19 gene 1..4012
/gene="ZDHHC2"
/gene_synonym="DHHC2; ZNF372"
/note="zinc finger, DHHC-type containing 2"
/db_xref="GeneID:51201"
/db_xref="HGNC:18469"
/db_xref="HPRD:15715"
exon 1..527
/gene="ZDHHC2"
/gene_synonym="DHHC2; ZNF372"
/inference="alignment:Splign"
/number=1
CDS 398..1501
/gene="ZDHHC2"
/gene_synonym="DHHC2; ZNF372"
/note="rec; zinc finger, DHHC domain containing 2; ream; DHHC-2; zinc finger protein 372; reduced expression in cancer protein; zinc finger DHHC domain-containing
protein
2; reduced expression associated with metastasis
protein"
/codon_start=1
/product="palmitoyltransferase ZDHHC2"
/protein_id="NP_057437.1"
/db_xref="GI:7705949"
/db_xref="CCDS:CCDS47810.1"
/db_xref="GeneID:51201"
/db_xref="HGNC:18469"
/db_xref="HPRD:15715"

/translation="MAPSGPGSSARRRCRRVLYWIPVVFITLLLGWSYYAYAIQLCIV

SMENTGEQVVCLMAYHLLFAMFVWSYWKTIFTLPMNPSKEFHLSYAEKDLLEREPRGE

AHQEVLRRAAKDLPIYTRTMSGAIRYCDRCQLIKPDRCHHCSVCDKCILKMDHHCPWV

NNCVGFSNYKFFLLFLAYSLLYCLFIAATDLQYFIKFWTNGLPDTQAKFHIMFLFFAA

AMFSVSLSSLFGYHCWLVSKNKSTLEAFRSPVFRHGTDKNGFSLGFSKNMRQVFGDEK

KYWLLPIFSSLGDGCSFPTCLVNQDPEQASTPAGLNSTAKNLENHQFPAKPLRESQSH
LLTDSQSWTESSINPGKCKAGMSNPALTMENET"

exon 528..554
/gene="ZDHHC2"
/gene_synonym="DHHC2; ZNF372"
/inference="alignment:Splign"
/number=2 exon 555..649
/gene="ZDHHC2"
/gene_synonym="DHHC2; ZNF372"
/inference="alignment:Splign"
/number=3 exon 650..770
/gene="ZDHHC2"
/gene_synonym="DHHC2; ZNF372"
/inference="alignment:Splign"
/number=4 exon 771..840
/gene="ZDHHC2"
/gene_synonym="DHHC2; ZNF372"
/inference="alignment:Splign"
/number=5 exon 841..873
/gene="ZDHHC2"
/gene_synonym="DHHC2; ZNF372"
/inference="alignment:Splign"
/number=6 exon 874..994
/gene="ZDHHC2"
/gene_synonym="DHHC2; ZNF372"
/inference="alignment:Splign"
/number=7 exon 995..1127
/gene="ZDHHC2"
/gene_synonym="DHHC2; ZNF372"

```
                     /inference="alignment:Splign"
                     /number=8
     exon            1128..1254
                     /gene="ZDHHC2"
                     /gene_synonym="DHHC2; ZNF372"
                     /inference="alignment:Splign"
                     /number=9
     exon            1255..1347
                     /gene="ZDHHC2"
                     /gene_synonym="DHHC2; ZNF372"
                     /inference="alignment:Splign"
                     /number=10
     exon            1348..1460
                     /gene="ZDHHC2"
                     /gene_synonym="DHHC2; ZNF372"
                     /inference="alignment:Splign"
                     /number=11
     exon            1461..1535
                     /gene="ZDHHC2"
                     /gene_synonym="DHHC2; ZNF372"
                     /inference="alignment:Splign"
                     /number=12
     exon            1536..4012
                     /gene="ZDHHC2"
                     /gene_synonym="DHHC2; ZNF372"
                     /inference="alignment:Splign"
                     /number=13
     STS             1541..1660
                     /gene="ZDHHC2"
                     /gene_synonym="DHHC2; ZNF372"
                     /standard_name="RH36493"
                     /db_xref="UniSTS:4085"
ORIGIN
        1 gtgggagccc gcgaggtggc ccgagcgagg gcccccgcatc cccgcagagc ccgcccgagg
       61 gcgcagcctg ccacgccagg gcaggcggcc gggcggcggg gaacggcggg ggcggagcgc
      121 agcctcccga cgccgccgcc tcaccgcccc cctccgcctc ctcggcctcc gctcgcagcc
      181 gccgcctccg cctccgccgg gctgaggagc cgggagtccg ccgcgccggc tcggggctgc
```

FIG. 13-22

```
 241 gggatgggga gttagcgcca cggcggcggc agtggccgca gcgcaccccg ccgccgccca
 301 ggagcccgtc cagccagggg tgccgggccc gcccagcccg ccccggagcc aggcccgcgg
 361 gcggcggcgg agctgggcag gtggatgcgg ctggaagatg gcgccctcgg gcccgggcag
 421 cagcgccagg cggcggtgcc ggcgggtgct gtactggatc ccggtggtgt tcatcaccct
 481 cctgctcggc tggtcctact acgcctacgc catccagctg tgcatagtgt ccatggaaaa
 541 cactggcgaa caagttgtgt gcctgatggc ctatcatcta ctttttgcaa tgtttgtctg
 601 gtcatactgg aaaactatct ttacattacc aatgaatcct tcaaaagaat tccatctctc
 661 ttatgcagag aaagatttgt tggagagaga gccaagagga gaagcccatc aggaagttct
 721 taggcgagca gccaaggatc ttcccatcta taccaggacc atgtctggag ccatccgata
 781 ctgtgacaga tgccaactta taaaaccaga tcgctgccat cactgctccg tctgtgataa
 841 atgtattttg aagatggatc atcattgtcc atgggtgaac aattgtgttg gatttcaaa
 901 ttataagttc tttctccttt tcttggctta ttctctgctc tactgccttt ttattgcggc
 961 aacagattta cagtatttta tcaaattttg gacaaatggc ctacctgata ctcaagccaa
1021 gttccatatt atgtttttat tctttgctgc agctatgttt tctgtcagct tgtcttctct
1081 gtttggctat cattgttggc tagtcagcaa aaataaatct acattagagg cattcagaag
1141 tccagtattt cgacatggaa cagataagaa tggattcagc ttgggtttca gtaaaaacat
1201 gcgacaagtt tttggtgatg agaagaagta ctggttgcta cccatttttt caagtctagg
1261 tgatggctgc tcctttccaa cttgccttgt taaccaggat cctgaacaag catctactcc
1321 tgcagggctg aattccacag ctaaaaatct cgaaaaccat cagtttcctg caaagccatt
1381 gagagagtcc cagagccacc ttcttactga ttctcagtct tggacggaga gcagcataaa
1441 cccaggaaaa tgcaaagctg gtatgagcaa tcctgcatta accatggaaa atgagactta
1501 actcttcaag caagataaat tcatacttta taaaagtatc aatgctgtag atggatggaa
1561 gaggcttccc acaggaaggt gccaccagtc agttgtgcct atgtcccttt ggctggaaat
1621 gcagaatatg aattgattag ttctctccaa gccattgctt aaaatataac atgttttgga
1681 tccaatacac acattgttac aactaacaca aattcctatt aaatattaaa agtagttctg
1741 gtttattaat caacggggaa aacatcttct ccaaaaaact tggaataaat ccaaggacca
1801 gtttttaccc aaatatatgg gtagcacagt ttatcacata gaaactccat taatcatctg
1861 attttccgaa tctgaaaatt gagactatta agatattagg atttcagaga tttcaagtca
1921 cattataatg ataagcatta ttcataaaac ttgttacctt taagaaggtg gaagtggcaa
1981 accatacttc tttttttcc tctgatgtga atccagcctc agactgagtg aactgtaata
2041 attatgaatt cattacagag tccaggtggc ctgcagttga agatcatcaa ccatttttgc
2101 ctcacttaat tccagccttt tgttttctgc tggaaaataa gtgtggacat tgaagcttga
2161 gctctcaaag cagttggctg gaatactttt gtcagaatac ggtacatttc tattacatca
2221 gaaatatatt ttcatctctt cttgttaaat tgggaggaaa tttatgatag caattatgaa
2281 gattgtttta tgacattctt ttgtcagttt ggctttctaa aaatctcttt ttagattatt
2341 tctcctgttg aacatagtaa aactattgaa tttctcttaa gaattcctaa taggtcaata
2401 gatttaccct ccagtgatat ctatattatt tctttctcgt ctcatcaaaa tgatgacagg
```

FIG. 13-23

```
2461 taaactatat ttttccttaa acacctatta cagttaaatt atgcaaatca ttaaataaaa
2521 atcatacaac ttttggaaag ttagttcaac atgaactaaa atggcatgct atttggaaat
2581 ttagtttgag ataaactaaa gtgtgttgat gccagaatgt tcagcttcag taaatataat
2641 aagctcttgt gccttgtatg cactatttaa aaaaagtttt ttttatttga gtccagtata
2701 attcatgtaa atgttaacaa ttagaataat actctgtatg ctttttttgat actgattttg
2761 agaatttaaa gcagattacc ttttaaaact ggaccaacta agtaattggt atttaatcaa
2821 agagaaaatg gtaataaact tttcaaaatc tttgttaaac caaacattca acacaaaata
2881 aactagaagg ccagaggata atggaataaa agatcattgc aattacttat ccttcctaaa
2941 aatatagttt tatattaatt gtgcttatgg aagaaacaat gtcagccaag tccattttat
3001 agtttgagtg caattctttg aacaatagaa atatctgcag tctttcacag atttgtatta
3061 tgctgaagag tttcatctga caatctgctt caagaaatct cagaaaatat gataacattt
3121 taactttcat tttagagcac gttttggtca tttttaaaaa tacctaaagt gccagaccgg
3181 aacctatagc tactgctaga agtcttaaaa aaaccaacag cagcacagga tgtattaaga
3241 attatatgaa gtcaggtttg tttttttttt tttttttttt tcaaagcaca gtactgttag
3301 ctgtttttgt ggacaggatt cgattaagta ttccctcttg tcaaactgga agctagggga
3361 aaaagaggga tttttatcct ttactcttct agagtactgt taatgcccct ttcccacagt
3421 cttttatata attaaatata tgtcaataca cattagaatc agatttgaaa aagttaaaac
3481 aatttcattg ttgtaattgt tccctttctg ttttcatata gtgaataacc tttaaagggt
3541 tgttttgttt tgttttgaat tataggagtt ataatctttg gagatgattg catatctcat
3601 tagatatgca atataaattt atctgagtga acaaagtgct aaataaatag atctacattt
3661 tgtacatatt tatataaaat ttacctttaa gtatttactt taaaaaattt aatggcttaa
3721 ctcgaacttg aagacacata cttcaactgt ccttattgtc cattaaactg ataattttga
3781 tttttcttgc ttttatagat tttactatat aggaatcaag atttaagaaa ttttgcatta
3841 aaaatagtgt accaatgctt catatacgtt agttatttgc tattatgtag ggaagaggat
3901 tgttatttca aagatatatt aaagaacagt tgcatctgaa tataatcatg atgcattcaa
3961 tgaagttcat atccatgaat tcactcctaa tataccctaa taaagtggtt ga
//
```

ZDHHC3 (isoform 1 of 3):

```
FEATURES             Location/Qualifiers
     source          1..12630
                     /organism="Homo sapiens"
                     /mol_type="mRNA"
```

FIG. 13-24

```
                    /db_xref="taxon:9606"
                    /chromosome="3"
                    /map="3p21.31"
     gene           1..12630
                    /gene="ZDHHC3"
                    /gene_synonym="DKFZp313D2314; FLJ20209; FLJ45940; GODZ;
                    ZNF373"
                    /note="zinc finger, DHHC-type containing 3"
                    /db_xref="GeneID:51304"
                    /db_xref="HGNC:18470"
     exon           1..250
                    /gene="ZDHHC3"
                    /gene_synonym="DKFZp313D2314; FLJ20209; FLJ45940; GODZ;
                    ZNF373"
                    /inference="alignment:Splign"
                    /number=1
     exon           251..580
                    /gene="ZDHHC3"
                    /gene_synonym="DKFZp313D2314; FLJ20209; FLJ45940; GODZ;
                    ZNF373"
                    /inference="alignment:Splign"
                    /number=2
     CDS            275..1174
                    /gene="ZDHHC3"
                    /gene_synonym="DKFZp313D2314; FLJ20209; FLJ45940; GODZ;
                    ZNF373"
                    /note="isoform 1 is encoded by transcript variant 1;
Golgi
                    apparatus-specific protein with DHHC zinc finger domain;
                    DHHC1 protein; zinc finger, DHHC domain containing 3;
                    golgi-specific DHHC Zinc Finger Protein; DHHC-3; zinc
                    finger protein 373; zinc finger DHHC domain-containing
                    protein 3; palmitoyltransferase ZDHHC3"
                    /codon_start=1
                    /product="palmitoyltransferase ZDHHC3 isoform 1"
                    /protein_id="NP_001128651.1"
```

FIG. 13-25

/db_xref="GI:206597477"
/db_xref="CCDS:CCDS46811.1"
/db_xref="GeneID:51304"
/db_xref="HGNC:18470"

/translation="MMLIPTHHFRNIERKPEYLQPEKCVPPPYPGPVGTMWFIRDGCG

IACAIVTWFLVLYAEFVVLFVMLIPSRDYVYSIINGIVFNLLAFLALASHCRAMLTDP

GAVPKGNATKEFIESLQLKPGQVVYKCPKCCSIKPDRAHHCSVCKRCIRKMDHHCPWV

NNCVGENNQKYFVLFTMYIALISLHALIMVGFHFLHCFEEDWTKCSSFSPPTTVILLI

LLCFEGLLFLIFTSVMFGTQVHSICTDETGIEQLKKEERRWAKKTKWMNMKAVFGHPF

SLGWASPFATPDQGKADPYQYVV"

exon 581..705
/gene="ZDHHC3"
/gene_synonym="DKFZp313D2314; FLJ20209; FLJ45940; GODZ;
ZNF373"
/inference="alignment:Splign"
/number=3 exon 706..802
/gene="ZDHHC3"
/gene_synonym="DKFZp313D2314; FLJ20209; FLJ45940; GODZ;
ZNF373"
/inference="alignment:Splign"
/number=4 exon 803..884
/gene="ZDHHC3"
/gene_synonym="DKFZp313D2314; FLJ20209; FLJ45940; GODZ;
ZNF373"
/inference="alignment:Splign"
/number=5 exon 885..1015
/gene="ZDHHC3"
/gene_synonym="DKFZp313D2314; FLJ20209; FLJ45940; GODZ;

FIG. 13-26

```
                    ZNF373"
                    /inference="alignment:Splign"
                    /number=7
     exon           1016..12602
                    /gene="ZDHHC3"
                    /gene_synonym="DKFZp313D2314; FLJ20209; FLJ45940; GODZ;
                    ZNF373"
                    /inference="alignment:Splign"
                    /number=8a
     STS            1906..2764
                    /gene="ZDHHC3"
                    /gene_synonym="DKFZp313D2314; FLJ20209; FLJ45940; GODZ;
                    ZNF373"
                    /standard_name="ZDHHC3__4936"
                    /db_xref="UniSTS:462956"
     STS            2442..2560
                    /gene="ZDHHC3"
                    /gene_synonym="DKFZp313D2314; FLJ20209; FLJ45940; GODZ;
                    ZNF373"
                    /standard_name="A005027"
                    /db_xref="UniSTS:21034"
     STS            2442..2560
                    /gene="ZDHHC3"
                    /gene_synonym="DKFZp313D2314; FLJ20209; FLJ45940; GODZ;
                    ZNF373"
                    /standard_name="G20511"
                    /db_xref="UniSTS:21033"
     STS            2556..2694
                    /gene="ZDHHC3"
                    /gene_synonym="DKFZp313D2314; FLJ20209; FLJ45940; GODZ;
                    ZNF373"
                    /standard_name="D3S4221"
                    /db_xref="UniSTS:26874"
     polyA_signal   2673..2678
                    /gene="ZDHHC3"
                    /gene_synonym="DKFZp313D2314; FLJ20209; FLJ45940; GODZ;
                    ZNF373"
```

FIG. 13-27 polyA_site 2700
/gene="ZDHHC3"
/gene_synonym="DKFZp313D2314; FLJ20209; FLJ45940; GODZ; ZNF373"
polyA_signal 3807..3812
/gene="ZDHHC3"
/gene_synonym="DKFZp313D2314; FLJ20209; FLJ45940; GODZ; ZNF373"
polyA_site 3834
/gene="ZDHHC3"
/gene_synonym="DKFZp313D2314; FLJ20209; FLJ45940; GODZ; ZNF373"
STS 7507..7670
/gene="ZDHHC3"
/gene_synonym="DKFZp313D2314; FLJ20209; FLJ45940; GODZ; ZNF373"
/standard_name="RH103204"
/db_xref="UniSTS:97537"
STS 7527..7768
/gene="ZDHHC3"
/gene_synonym="DKFZp313D2314; FLJ20209; FLJ45940; GODZ; ZNF373"
/standard_name="STS-AA027089"
/db_xref="UniSTS:5753"
polyA_signal 7787..7792
/gene="ZDHHC3"
/gene_synonym="DKFZp313D2314; FLJ20209; FLJ45940; GODZ; ZNF373"
polyA_site 7813
/gene="ZDHHC3"
/gene_synonym="DKFZp313D2314; FLJ20209; FLJ45940; GODZ; ZNF373"
polyA_signal 7864..7869
/gene="ZDHHC3"
/gene_synonym="DKFZp313D2314; FLJ20209; FLJ45940; GODZ; ZNF373"

FIG. 13-28

```
     polyA_site      7884
                     /gene="ZDHHC3"
                     /gene_synonym="DKFZp313D2314; FLJ20209; FLJ45940; GODZ;
                     ZNF373"
     STS             9016..10454
                     /gene="ZDHHC3"
                     /gene_synonym="DKFZp313D2314; FLJ20209; FLJ45940; GODZ;
                     ZNF373"
                     /db_xref="UniSTS:484717"
     STS             12340..12477
                     /gene="ZDHHC3"
                     /gene_synonym="DKFZp313D2314; FLJ20209; FLJ45940; GODZ;
                     ZNF373"
                     /standard_name="RH98231"
                     /db_xref="UniSTS:92255"
     polyA_signal    12577..12582
                     /gene="ZDHHC3"
                     /gene_synonym="DKFZp313D2314; FLJ20209; FLJ45940; GODZ;
                     ZNF373"
     polyA_site      12602
                     /gene="ZDHHC3"
                     /gene_synonym="DKFZp313D2314; FLJ20209; FLJ45940; GODZ;
                     ZNF373"
ORIGIN
        1 gcgtcatcaa cctgcgcggc ggccgctcct gcagccgcgg ccgccgccac tgccggcaga
       61 gctcgatggg cttctcctgc gcgccgcccg gtgtctggcc gagtccagag agccgcggcg
      121 cctcgttccg aggagccatc gccgaagccc gaggccgggt cccgggttgg ggactgcagg
      181 ggaaggcagc ggcggcggcg gcgggagccc caccggggtc tgggactggg gaactgcctc
      241 cggcttcacg atgccagtat ggacagaata gcttatgatg cttatcccca cccaccactt
      301 ccgaaacatt gagcggaaac cagaatacct ccagccagag aagtgtgtcc caccccccta
      361 ccctggtcct gtgggaacca tgtggtttat ccgtgacggc tgtggcatcg cctgtgccat
      421 cgttacctgg tttctggtcc tctatgcgga gttcgtggtc ctctttgtca tgctgattcc
      481 atctcgagac tacgtgtata gcatcatcaa cggaattgtg ttcaacctgc tggccttctt
      541 ggccctggcc tcccactgcc gggccatgct gacggacccc ggggcagtgc ccaaaggaaa
      601 tgccactaaa gaattcatcg agagtttaca gttgaagcct gggcaggtgg tgtacaagtg
      661 ccccaaatgc tgcagcatca agcccgaccg agcccaccac tgcagtgttt gtaagcggtg
```

FIG. 13-29

721 cattcggaag atggaccacc actgtccctg ggtcaacaac tgtgtaggcg agaacaacca
781 gaagtacttc gtcctgttta caatgtacat agctctcatt tccttgcacg ccctcatcat
841 ggtgggattc cacttcctgc attgctttga agaagattgg acaaagtgca gctccttctc
901 tccacccacc acagtgattc tccttatcct gctgtgcttt gagggcctgc tcttcctcat
961 tttcacatca gtgatgtttg ggacccaggt gcactccatc tgcacagatg agacgggaat
1021 agaacaattg aaaaaggaag agagaagatg ggctaaaaaa acaaaatgga tgaacatgaa
1081 agccgttttt ggccacccct tctctctagg ctgggccagc ccctttgcca cgccagacca
1141 agggaaggca gaccccgtacc agtatgtggt ctgaaggacc ccgaccggca tggccactca
1201 gacacaagtc cacaccacag cactaccgtc ccatccgttc tcatgaatgt ttaaatcgaa
1261 aaagcaaaac aactactctt aaaacttttt ttatgtctca agtaaaatgg ctgagcattg
1321 cagagaaaaa aaaaagtccc cacattttat tttttaaaaa ccatcctttc gatttctttt
1381 ggtgaccgaa gctgctctct tttcctttta aaatcacttc tctggcctct ggtttctctc
1441 tgctgtctgt ctggcatgac taatgtagag ggcgctgtct cgcgctgtgc ccattctact
1501 aactgagtga gacatgacgc tgtgcgtgga tggaatagtc tggacacctg gtgggggatg
1561 catgggaaag ccaggagggc cctgacctcc cactgcccag gaggcagtgg cgggctcccc
1621 gatgggacat aaaacctcac cgaagatgga tgcttacccc ttgaggcctg agaagggcag
1681 gatcagaagg gaccttggca cagcgacctc atcccccaag tggacacggt ttgcctgcta
1741 actcgcaaag caattgcctg ccttgtactt tatgggcttg ggtgtgtag aatgattttg
1801 cgggggagtg ggagagaaga tgaaagaggt cttatttgta ttctgaatca gcaattatat
1861 tccctgtgat tatttggaag agtgtgtagg aaagacgttt ttccagttca aaatgcctta
1921 tacaatcaag aggaaaaaaa attacacaat ttcaggcaag ctacgttttc ctttgtttca
1981 tctgcttcct ctctcaccac cccatctccc tctcttcccc agcaagatgt caattaagca
2041 gtgtgaattc tgactgcaat aggcaccagt gcccaacaca tacagcccca ccatcatccc
2101 cttctcattt tataaacctc aaagtggatt cactttctga tagttaaccc ccataaatgt
2161 gcacgtacct gtgtcttatc tatattttaa cctgggagac tgttgtcctg gcatggagat
2221 gaccatgatg ctggggttac ctcacagtcc ccaccctttc aaagttgaca tatggccatc
2281 ccattggcca gaatccacag acacacctaa gcctgtggca ctgggacaga atagattttc
2341 catttgagag gcacttcctg tgtcagtctt gtttgaagga ggtggtgatg gtggatagag
2401 gtgaaggagg tagggagtgc cctccaagtg caaaaataac aaatatgatt attgaccatc
2461 ggggaattct cacacattga tttgtttttt aagcaattgc cagaaacccc ctttttagc
2521 ttttgcttgg ggtgggggta ggagttaagg tttattcaat cctgtcctgg gtagggcgaa
2581 agttaatcta gccatgtgat ttttcagaaa agtaagtgga acatgctgcc acttttcaat
2641 tctgtcagtg cttccacatg gaaacaaaat gcaataaaat ttttccaaaa cctgttctga
2701 tttagctctc tcttgaggtg ttacccttag tgggaggccg actatccaca atctacttga
2761 gttttctctg gttgggtgtt tgtttcattg ctctgtctct tgaatgagga tactttattt
2821 tttttgtttt aaaatgcatt tatggtccct ctcttgaacc agcttgcccc accaggcctc

FIG. 13-30

2881 tttcctttgc tttctgcagc ctgaatcaat tcctttgtgc tgatgggctc tcctaagagc
2941 tttcctgagt cagttaactt tacctcgtgt ctacggtgct attcatgcga tacgggcgag
3001 gctgagatgc taagattaaa aagaaaagaa tgctgtttta gatcaagttg atagcatttg
3061 ttttccatat gcttttttaa aatttttca taacatacag ctcagttagg tgtatgaaag
3121 aagtgttatt gtattaaata actagagcag ggctacagct ctggccctcc cctaggggga
3181 agagattggt aatactccat cttccagggc attttttaaa gtgagccagg ttagctcttt
3241 tcccctggca tttctcagga atgcagtaga tagtgctgaa gatgcactga cttttttta
3301 gtcctaaaaa tagaaactcc tcctttaaag ctgtgcatac tatgcttatc tttccaatag
3361 agtggggttc cttcagatat cctataggat tctgcctctg gttttgtata ggccttggct
3421 agaaagagtc aatgtttctg agctctcaaa ccagttgctc tcagaagata ggaatacccc
3481 aaggttcctg gcatttttcc tatttcattt ttgttcagac tgatattttg ccaagagcac
3541 aatgactgag gaatgtagcc atcatttgca gggtagtgat tggttcccag cctggcttcc
3601 acacaggaca ggaagggaaa gcatccctga gctctcctca gtatttccgg atgtaatgaa
3661 agaggacatc tttctacaca aagtcagccc caacttttgg cttggtcaca ggagttctga
3721 tagtactgtt tggtgcactc atgggaaatt gaaccagtcg tagccacagt ctttcagagc
3781 ctgggctctg gggagtggaa gtgaaaaata aagatgtggc ttgttggatt gtgatcccca
3841 gcttgctttc cttctgtcaa ctctgtcagg tttgtgttca tagcaactag actgaatatg
3901 caaaaggctt agatccaagc aaatctataa tctatgcata tttgcatggg cttggtaata
3961 tcatgtacac aaaacacatt tgggtagaag tgcatgtgct aaatctcctt ttagtcccac
4021 cattttgtct tcttcatact gtacttcctc ttttttgttt gagacaaggt cttgctctgt
4081 cacccaggct ggaatgcagt ggcacaatta gagctcactg cagccttgaa ctcctgggct
4141 caagtgattc ttgtgccttg gcctcctgaa tatccagggc tacaggcacg tactaccatg
4201 cctggctaat ttttttgttt tttaatagag tcagggtctc actgtgttgc cctagctagt
4261 ctcaaatgcc cggcctccag caattttcct gccttagcct ccccaaagtcc tgggattaca
4321 ggcgtgagcc actgggccca gccctgtact tcttgaaaaa gccccaagta ttagcttttg
4381 ctcatctggc taggccactt aaatagttag aatccaccgt cccctaatgc agaaaccgtt
4441 taggtgaggt aaattaacaa acattttaag ccgggcgcgg acacttctca ctgtggacat
4501 ccctcacgcc tgtaatccca gcactttggg aggccgaggc gggcagatca cgaggtcaag
4561 agatcgagat catcctggct aacacggtga aaccctgtct ctactaaaaa tataaaaaaa
4621 ttagctgggc gtggtggcag gcgtctgtag tcccagctac ttgggaggct gaggcaggag
4681 aatggcgtga acccgggaag tggagcttgc agtgagccaa gatcgcacca ctgcactcca
4741 gcctgggcga cagagtgaga ctccgtctca aaaaaaaaaa acaaacattt taaacatgta
4801 tgtgaggttg gcattacaca gaaactcctc tccgggtggg ctgggatggg ctttctcagc
4861 caggctaatg ggttttaaat ttctctcttt tcaagacttg cagtgcatca gcttaaaggg
4921 tgagccagcc agtagagggg aaggcgcccc acctagaagg tgcccttaga tatcaaagaa
4981 atgtgaaaag agaaagattt tgctagaatc ctcctcaaag gtgttcttga ggttgccaga

FIG. 13-31

5041 ccagcaacgt caacatcagc atcacctgag aacttgttag aaatgcacat tctcggtccc
5101 caccccaggc taccgaacca gaaaccgagc ggggcccagc agcccgtgtc ttaacagccc
5161 tccaggtgat tctgactatc aagtttgaga atccagttgg ggctagcagg agtccccccct
5221 caggtggtcc ctgatgcctg ctggtgatat gggtcttgtg tgctgctggg ctcagcatag
5281 tgcagttggg gtgtgctgat tgtgagacag gcacgtgttc cctccgcgga gaagccactg
5341 agactgcctt ccctcataag ctgcggcctc cccaacaaac aactgccaag acatcaaaga
5401 aagtctgtat gaagcagatc caaattatta gcctgcccac cactccttgt gcatctcatc
5461 agtggaaccc atctctagac caagggccct ttgggtgaag aagcagcccg gaagggaaag
5521 agaaaagagt agaaccaagg gacctccaga tgggagcggc ggccggtgag tagtctagag
5581 ccaggggcat tgtagcagcc tggatacatg acctgaacac gtcttgacct ttgctttcta
5641 cgtgtgggtt tcaacaccca tgtggctttt tcttgtattc tttaaatatg tatctggctt
5701 aggatcacct catagaagag aaagaattca cagtgaagca gaaacaagcc actgaccagc
5761 gtactcccaa cctgaacctt ctttttctca ccctctccct caagtaaaca tcttgctgac
5821 ttgagcagtg tgattgccgt agcaaagcag agtggccccc agggatcccg ctctgttggg
5881 cccacaggag gagccgatga agctgatcca aggagtgagg acaagcgctg cagagggacg
5941 ttcgctaaaa gccttctagg ggccgcacat gctctaacac ggacataagg atgccctgaa
6001 tttctgcagc tgaggccata tagtctggtg accaagtatt tgggtcctgg cttcagtctt
6061 tggttgaaat gtctgcttgg ctacttatta ccgcacctac taccaaaata tgaccttgag
6121 cagtaacttc tttaagcctc agtttttcca tctgaaaacg ggaatgataa tctaaatcac
6181 aaagttaatg gaaggattaa atgagggtga tgaataggaa tgtatagcgt ctggccctgg
6241 tatggcttta taaatgttag ctgtgttgga gctgtgcttt tcaaaccatt ggtcacagcc
6301 attcatggtt tgcaaccagc atgtttttca agaaaaatgt ttaatgcatt acatattgca
6361 ggataagtat tgttttatga agcttaggga gttgtgtgta tatgtgttct ggaatgcaac
6421 agaaaaatgt ttcctcttgt gggttacaat atagaggtat gaaatctctg atgaggagag
6481 acagtgttat ctggcccgct atgaagagac acatttgcat aggctgctcc ctgaggctct
6541 ggctttctac atctgatgat acagggagca gggaacagcc tgttctcgtt ctgtggggct
6601 cagctgagtc tgttctgcac agactcttcc ttcctcggga gccttagtcc taatacattc
6661 attttggagt gttggtgagt ttgttcacag atcacagctc atgtgtcacc cagactgacc
6721 tgggccaaaa ggcccatcac acaccctgca agagcttctg gtgtcgacta tgaccccctt
6781 accaggcatc aaccattttt gttcgttctc ttgagcctga agctactatt actgctcctc
6841 tgcaaacctc aagcttaaga actttgcctg caggatccct ttaaatccac acaaaactca
6901 aaattgagtc ctaccaggaa aaagcagccc tcagccccatt tttatacatc ggatttgttt
6961 gcaatatttt ctttctagac tcaaaagtca acactccctg aaagtttgtc gactttactg
7021 ctgaagacct ctggtagaca ggccaggctc tgtctggaat actttatgag gttggtgagg
7081 aggttgagta taatccaaga gtgcctatct gggagcatgc cacatgaatg gcaaataatc
7141 atcctgtggg ctcttggctt cattcccctt ctctctgact gagctcagcc tgggcacagt

FIG. 13-32

7201 ggtgatttgc agtagaactg gaaacctgtt gggcagaaaa aaagacacta gttctggttc
7261 cagttctgat acataacaag ctagatgagc cttgcccacc gtcatggcct cttggaactt
7321 ctgtttcttc cccatctgcc aatcatcaat actcatacco acctcctcac aaggaggcca
7381 taaaaaccta tggtcatggc tttgagtcca agtcagtgtg gatgcagcca gtctgtcatt
7441 tttgggtgtt tcctctgtag ccgggtctgc catatgctga tgtcccagct ctcgtgctat
7501 gaagttaaag cctctttctc aacaggctgc agatgatcac ccaggaagag aatgcagaat
7561 gcccaaagca aaccatctca gctggtcact gcttctgtgc caagaaggga ggcctggcga
7621 ggggccagtc aggaagcagc atggcatcac atgctcatga cccacatgaa ggtcccttta
7681 gacttgtgtc aacaagatcc atttctgaa acaactattt ttgttctgat tataaaagta
7741 acattggctc attggtaaaa cttggattgt gtgacaagtc tacagaaata aatacaaatc
7801 ctctagaatt ccatccccaa aagtaaccac tcagacaaat gttctaatgt catgtaaaac
7861 catattaaac catcttttct agctgcatag tgttatagaa tcatttgctt aaccatcatt
7921 attgggcatt tctcatttcc agctttgcat tattataatt cagtgttcaa gtttgtattg
7981 cataaatctt tgtctcagat tattgattat ttttaaactt tttgtgaaat cagacttaca
8041 aaaatgtgac aaaaacagta caaagagttc ccatctacct ttcagtcagt ctcaccaaag
8101 gtaaacattt tatacaacca taatacaaat ataaaaccct ggacattggc aacaccatac
8161 ccttaactaa tgtatgtacc ttattcacat ttctccagtt gtcccattaa caccctttc
8221 tgttccagga tcccacactg catcatttgc gatgtctcct tagtctcctc cagtttgtga
8281 cagttcctca gtcttccttt gtctttcatg accttgaccc tttttaaaaa tcgaggtgaa
8341 attcctgtaa cacaaaatta gccattttaa agtgtacatt taatgcattc acaatgtttt
8401 gtaaccacca ggtctgtctg gttccaaaat cttttcatca atctttgacc cttttgaaga
8461 ttgtagggca ggtattctgt aggctgtcct tcagattgtg tttttgatgt ttttctcatg
8521 attagattga ggttaggcat ttggggcagg agcactgctg aagcaatgtg tcctcgttgc
8581 accgtatcag gaggcatatg gtgttgatac gtttcattat tgtgatgtta actttgatca
8641 ttgggtgaag gtggtacgtg caatgtttct tccctgctat taaggtactg tttttccctt
8701 tgtaattgat aagtatctta tgaggatata cttttgagat ccaatttttt taacttagaa
8761 tttattcaaa agtcaagaat cttaaatctc tgaaatggcg tgggaagaaa aagtgctaga
8821 tacacagaga tcttcttga gtcatgtgaa ggagcagtgc ccaagcccag caaacccaca
8881 gcaaattccc ttggcttcca gaagagatgg agaaagcagt gcccccagtg gaggtcaaa
8941 ggcctctgtg cagggtgttg tgggcctgga gagctggcct ggccatgtct ttacctcctc
9001 tgggcatctc cccaccccaa caccctttct gtggcctggt ggctgagttg cagccgacac
9061 ccagaggcag gtgagttgac agcttggaag aggctgcagg gtggatctgc tgcatgagca
9121 ggcctgagcc cagccttacc tccccacagt ggtcctgtgt gccctccggc tgcctaatgc
9181 atgttggcac ttgctgtacg agcacccgct tcttcacctc gcatgctgtt tgtgtcctgc
9241 actccttcct taaccccatc gtccttctgc tgtgtttgca gcccctatct accctggtgg
9301 gagtggccaa aaatatttag gaggggatca ccagtttgta gtggcctcag aggatgtgtg

FIG. 13-33

9361 gtccccctta tgcctcagcc actcatcagc ctagcccctg cccatcatct ggcattgcac
9421 ttgtggaagg aaagaagggg agggctgggt ggtgggtgga gaacacgtca gtccaccagg
9481 cgggccctgc ttgctgtgtt cctccacgct gctgtccacc cacaccccag cagtcctctg
9541 agggacctcc cgggggtgac ctgggccaca acagactgcc cactcagacc ccatcttacc
9601 catgccgtgg acaccccgcc cccccccccg ccactgctat gctatagctg ggggtgtcta
9661 tgtgagctgt acagcccagc accacgctga cgatgttctt catccccttc tccctgcagg
9721 gcatcgagcg cctcaaacga aagaaccagc ccagggagca catggggagc tggcagtcag
9781 taaaggagac ctttggtggg gacttctccc tgaactggtt caaccccttc tccagaccgt
9841 gtcagccaga gatccccagt gacaaagaca tggtgcggca ggtgacatcg ctgtcagaca
9901 ccgaaacaat ggaggatcca tcagaggaga caaaggacga ggactctgtg gaggtgacag
9961 atgaatagat gctgctgtgg ggagagaagc aaacactaaa aagtgctgtc aaccttcatc
10021 ctggggtttt ggctaaaggg gcttatgggc atggtgcgct cccagcaccc ccagtgcttc
10081 ccttagccac tcgcttggcc ttgccatttc ccctccttct tctctccatg ttgggccagg
10141 tctgggggtc gggagtaggc tggggacatc agaggaggat gggggctttc tcagagttca
10201 tctaagaaga gtctgcactg agacggctca tcaagaaccg ttctccaaga ctgggtggct
10261 ttcacattct ccgcccagca aagggagctt ttgaacaggg catcccaggg gcagaaaaga
10321 gcttgccttt ggctttcccc aggatttctg tcttctcttg ggaaggctgg gcccctggct
10381 cctggctttg agaagtaagg ttgtgacaga aggaccgggc agggcttgcc ttggggacct
10441 gggttgggac actgacatca ggggagacta gcctggaaag actgcagagc tgccagctac
10501 tccctggaaa gggcttcccc atgctgcctg ccgaaattag gaggtagagg tggctgccac
10561 atctacctgc aagggccagg catggttcaa agaggaccct gcattaagct ctacacacac
10621 atgtgcagga catgtccagc atggacagag ccagagttaa gacagtagca ccgaaaatga
10681 gcccccattc cacagacact ggagtcttca ctgagcgaga cagctgggag ctgtcctgcc
10741 tgtggctaca tatctagcca ttcacagatg tggatatggg aaggacctct ttggagctac
10801 tggggactcc ctaaccactc gcatgagaac ttaattgaat gttacctctt ggagggagtc
10861 taataacaca tgtaggtaga actgaccata aaccctgcct gtgtgtttga aaaggccagt
10921 tctcccaaat tggtgcccat cttgtctctg aaaagatggg tgatggccag ggtctgctga
10981 ttgatgaatc agatgaatca ggaagataga caaacacaca cacacacaca cacaccccac
11041 caggatgagt ctgccctcta ttcaccccat ttgaagcctg tggtgtctgt gaccactgct
11101 gaaggtctga gcagcgttct ggtgctccta aaccccattc cagtggttgc tgaagcagca
11161 tcttctgcac aaagcccaac agaagggttc ttatccccgt ttggtataag aagtggattc
11221 accaccccact ccctccacgt gcctttgttc ctctctttgg cccatttccc cagcgtctac
11281 tggcgtcagg attggcagga gcacaggcac tcagcagagc atgcccctgc aagacctcag
11341 tgttagggcc ccccttccag ctccaggcaa aagggcatga gtcctggccc caaggggcct
11401 ctggctgcag ttcagaggag aagaaggtca gtgtttggag gtgcagcctc aggatgctga
11461 gaaaggaaac tggcgaccgt gagaaagaaa agagccaagc agcatcctgg ttcttggaca

```
11521 gcatctttgg acactctgtg aagggcaacg atcctgccag agaccgtctc tctacaactg
11581 atgacccact agggcctggg gttaattgct caaagggccc agtgttcaca aagccacctc
11641 tgccctaacc cttgccagag ctctccaact atgacccacg agaggggtga tggtggcatt
11701 ctaacatcaa cagagcaacc agaaagacat tgggcctccc acactcaggc tgcaggccca
11761 ctttcttggt ccttatcagc tttaatattt attaatgacg acataggagc ccgagtcagc
11821 tgtaaaggcc attaacttgc aatctggaca ggaagttgac gctcaccact ttgggtaaga
11881 gctgctctga ctgtagggcc ccctatttgt tgtcctaacc cagaagcagc tctgggctgc
11941 caggatggtg gatggaatac cagagagttc acactaggga ggaagcaatg cctgccccct
12001 ggagtctcct agggggcagc agttagaata agggaagagg atttgctggt cactgtttgc
12061 tgacatgggt ttccatggtg agttcaggcc tgaggacagc agtgtctgca aaaccacatg
12121 gcccttgaga aatgtccttg cacattgggc ttcaaactcc tcttctaggg aatccatctt
12181 ggcctgaaag cagaggtaca acaccagccc caaaggcaat tctgttttca gattggttgc
12241 tctggaaagg aaggctgggg tgagggggca ttttacttgc acagaggctg accctgcctc
12301 ccctcttcac tgaccccatc tccaaggtag acctcagcca tgtcagtccc tgttctggga
12361 ggtgctgggc tgggccacag ccagggttat gtaggtaatt aacctgtcca accctgagcc
12421 tcgcctcccc acaccagcaa cacagtggtc tctctgtggt gaccattcac agcataacat
12481 tctgcttagc ctcagactga aagcattgca actgatgtca aaaccagatg agatcttaca
12541 gggagagaga ttgggtgcaa tttgcctctt tctttgaata aaaagctctt tgctcaccct
12601 caaaaaaaaa aaaaaaaaaa aaaaaaaaaa
//
```

ZDHHC4:

```
FEATURES             Location/Qualifiers
     source          1..1570
                     /organism="Homo sapiens"
                     /mol_type="mRNA"
                     /db_xref="taxon:9606"
                     /chromosome="7"
                     /map="7p22.1"
     gene            1..1570
                     /gene="ZDHHC4"
                     /gene_synonym="FLJ10479; ZNF374"
                     /note="zinc finger, DHHC-type containing 4"
                     /db_xref="GeneID:55146"
```

FIG. 13-34

/db_xref="HGNC:18471"
exon 1..287
/gene="ZDHHC4"
/gene_synonym="FLJ10479; ZNF374"
/inference="alignment:Splign"
/number=1b
exon 288..442
/gene="ZDHHC4"
/gene_synonym="FLJ10479; ZNF374"
/inference="alignment:Splign"
/number=2b
exon 443..566
/gene="ZDHHC4"
/gene_synonym="FLJ10479; ZNF374"
/inference="alignment:Splign"
/number=3
CDS 450..1484
/gene="ZDHHC4"
/gene_synonym="FLJ10479; ZNF374"
/note="zinc finger, DHHC domain containing 4; DHHC-4;
zinc
finger protein 374; zinc finger DHHC domain-containing
protein 4"
/codon_start=1
/product="probable palmitoyltransferase ZDHHC4"
/protein_id="NP_001127859.1"
/db_xref="GI:197304686"
/db_xref="CCDS:CCDS5352.1"
/db_xref="GeneID:55146"
/db_xref="HGNC:18471"

/translation="MDFLVLFLFYLASVLMGLVLICVCSKTHSLKGLARGGAQIFSCI

IPECLQRAVHGLLHYLFHTRNHTFIVLHLVLQGMVYTEYTWEVFGYCQELELSLHYLL

LPYLLLGVNLFFFTLTCGTNPGIITKANELLFLHVYEFDEVMFPKNVRCSTCDLRKPA

FIG. 13-35

RSKHCSVCNWCVHRFDHHCVWVNNCIGAWNIRYFLIYVLTLTASAATVAIVSTTFLVH

LVVMSDLYQETYIDDLGHLHVMDTVFLIQYLFLTFPRIVFMLGFVVVLSFLLGGYLLF

VLYLAATNQTTNEWYRGDWAWCQRCPLVAWPPSAEPQVHRNIHSHGLRSNLQEIFLPA
FPCHERKKQE"

exon 567..640
/gene="ZDHHC4"
/gene_synonym="FLJ10479; ZNF374"
/inference="alignment:Splign"
/number=4 exon 641..819
/gene="ZDHHC4"
/gene_synonym="FLJ10479; ZNF374"
/inference="alignment:Splign"
/number=5 exon 820..945
/gene="ZDHHC4"
/gene_synonym="FLJ10479; ZNF374"
/inference="alignment:Splign"
/number=6 exon 946..1190
/gene="ZDHHC4"
/gene_synonym="FLJ10479; ZNF374"
/inference="alignment:Splign"
/number=7

STS 1079..1215
/gene="ZDHHC4"
/gene_synonym="FLJ10479; ZNF374"
/standard_name="RH93371"
/db_xref="UniSTS:90991"

exon 1191..1553
/gene="ZDHHC4"
/gene_synonym="FLJ10479; ZNF374"
/inference="alignment:Splign"
/number=8

```
     STS             1300..1494
                     /gene="ZDHHC4"
                     /gene_synonym="FLJ10479; ZNF374"
                     /standard_name="A008D23"
                     /db_xref="UniSTS:27450"
     STS             1434..1490
                     /gene="ZDHHC4"
                     /gene_synonym="FLJ10479; ZNF374"
                     /standard_name="STS-Z41394"
                     /db_xref="UniSTS:25243"
     STS             1439..1542
                     /gene="ZDHHC4"
                     /gene_synonym="FLJ10479; ZNF374"
                     /standard_name="D7S2646"
                     /db_xref="UniSTS:34431"
ORIGIN
        1 gatgtcacga gcccgcacga agtctcgtat cgcgcccggg aggcgccgga gcccagcggc
       61 tggcggtaag gccgcctccg cggggctgtg ggaagcttgg gctgtcccag gaccgtcagt
      121 ctcctcctct gaccctccct ttccccttgt gtgtagggcc gccgtcccac ccccacctcg
      181 cccgagtccg gggcggcccc ggtgtcccct ccgagcctgc tgcactccac gtccccctac
      241 cagggctcca gcccccacgg aaatctccga ccaggcccgc ccaggagcca gatccaggct
      301 cctggaagaa ccatgtccgg cagctactgg tcatgccagg cacacactgc tgcccaagag
      361 gagctgctgt ttgaattatc tgtgaatgtt gggaagagga atgccagagc tgccggctga
      421 aaattaccca accaagacaa atctgcagga tggactttct ggtcctcttc ttgttctacc
      481 tggcttcggt gctgatggcgt cttgttctta tctgcgtctg ctcgaaaacc catagcttga
      541 aaggcctggc caggggacga gcacagatat ttcctgtat aattccagaa tgtcttcaga
      601 gagccgtgca tggattgctt cattaccttt tccatacgag aaaccacacc ttcattgtcc
      661 tgcacctggt cttgcaacgg atggtttata ctgagtacac ctgggaagta tttggctact
      721 gtcaggagct ggagttgtcc ttgcattacc ttcttctgcc ctatctgctg ctaggtgtaa
      781 acctgttttt tttcaccctg acttgtggaa ccaatcctgg cattataaca aaagcaaatg
      841 aattattatt tcttcatgtt tatgaatttg atgaagtgat gtttccaaag aacgtgaggt
      901 gctctacttg tgatttaagg aaaccagctc gatccaagca ctgcagtgtg tgtaactggt
      961 gtgtgcaccg tttcgaccat cactgtgttt gggtgaacaa ctgcatcggg gcctggaaca
     1021 tcaggtactt cctcatctac gtcttgacct tgacggcctc ggctgccacc gtcgccattg
     1081 tgagcaccac ttttctggtc cacttggtgg tgatgtcaga tttataccag gagacttaca
     1141 tcgatgacct tggacacctc catgttatgg acacggtctt tcttattcag tacctgttcc
```

FIG. 13-38

```
1201 tgacttttcc acggattctc ttcatgctgg gctttgtcgt ggttctgagc ttcctcctgg
1261 gtggctacct gttgtttctc ctgtatctgg cggccaccaa ccagactact aacgagtggt
1321 acagaggtga ctgggcctgg tgccagcgtt gtccccttgt ggcctggcct ccgtcagcag
1381 agccccaagt ccaccggaac attcactccc atgggcttcg gagcaacctt caagagatct
1441 ttctacctgc ctttccatgt catgagagga agaaacaaga atgacaagtg tatgactgcc
1501 tttgagctgt agttcccgtt tatttacaca tgtggatcct cgttttccaa gcaaaaaaaa
1561 aaaaaaaaaa
//
```

ZDHHC5:

```
FEATURES             Location/Qualifiers
     source          1..4582
                     /organism="Homo sapiens"
                     /mol_type="mRNA"
                     /db_xref="taxon:9606"
                     /chromosome="11"
                     /map="11q12.1"
     gene            1..4582
                     /gene="ZDHHC5"
                     /gene_synonym="DKFZp586K0524; KIAA1748; ZNF375"
                     /note="zinc finger, DHHC-type containing 5"
                     /db_xref="GeneID:25921"
                     /db_xref="HGNC:18472"
                     /db_xref="HPRD:15720"
     exon            1..186
                     /gene="ZDHHC5"
                     /gene_synonym="DKFZp586K0524; KIAA1748; ZNF375"
                     /inference="alignment:Splign"
                     /number=1
     exon            187..1360
                     /gene="ZDHHC5"
                     /gene_synonym="DKFZp586K0524; KIAA1748; ZNF375"
                     /inference="alignment:Splign"
```

FIG. 13-39

/number=2
CDS 1257..3404
/gene="ZDHHC5"
/gene_synonym="DKFZp586K0524; KIAA1748; ZNF375"
/note="zinc finger, DHHC domain containing 5;
membrane-associated DHHC5 zinc finger protein; DHHC-5;
zinc finger protein 375; zinc finger DHHC
domain-containing protein 5"
/codon_start=1
/product="probable palmitoyltransferase ZDHHC5"
/protein_id="NP_056272.2"
/db_xref="GI:41152072"
/db_xref="CCDS:CCDS7965.1"
/db_xref="GeneID:25921"
/db_xref="HGNC:18472"
/db_xref="HPRD:15720"

/translation="MPAESGKRFKPSKYVPVSAAAIFLVGATTLFFAFTCPGLSLYVS

PAVPIYNAIMFLFVLANFSMATFMDPGIFPRAEEDEDKEDDFRAPLYKTVEIKGIQVR

MKWCATCRFYRPPRCSHCSVCDNCVEEFDHHCPWVNNCIGRRNYRYFFLFLLSLTAHI

MGVFGFGLLYVLYHIEELSGVRTAVTMAVMCVAGLFFIPVAGLTGFHVVLVARGRTTN

EQVTGKFRGGVNPFTNGCCNNVSRVLCSSPAPRYLGRPKKEKTIVIRPPFLRPEVSDG

QITVKIMDNGIQGELRRTKSKGSLEITESQSADAEPPPPPKPDLSRYTGLRTHLGLAT

NEDSSLLAKDSPPTPTMYKYRPGYSSSSTSAAMPHSSSAKLSRGDSLKEPTSIAESSR

HPSYRSEPSLEPESFRSPTFGKSFHFDPLSSGSRSSSLKSAQGTGFELGQLQSIRSEG

TTSTSYKSLANQTRNGSLSYDSLLTPSDSPDFESVQAGPEPDPPLGYTSPFLSARLAQ

QREAERHPRLVPTGPTHREPSPVRYDNLSRHIVASLQEREKLLRQSPPLPGREEEPGL

GDSGIQSTPGSGHAPRTSSSSDDSKRSPLGKTPLGRPAVPRFGKPDGLRGRGVGSPEP

GPTAPYLGRSMSYSSQKAQPGVSETEEVALQPLLTPKDEVQLKTTYSKSNGQPKSLGS
ASPGPGQPPLSSPTRGGVKKVSGVGGTTYEISV"

exon 1361..1482
/gene="ZDHHC5"
/gene_synonym="DKFZp586K0524; KIAA1748; ZNF375"
/inference="alignment:Splign"
/number=3 exon 1483..1640
/gene="ZDHHC5"
/gene_synonym="DKFZp586K0524; KIAA1748; ZNF375"
/inference="alignment:Splign"
/number=4 exon 1641..1813
/gene="ZDHHC5"
/gene_synonym="DKFZp586K0524; KIAA1748; ZNF375"
/inference="alignment:Splign"
/number=5 exon 1814..1916
/gene="ZDHHC5"
/gene_synonym="DKFZp586K0524; KIAA1748; ZNF375"
/inference="alignment:Splign"
/number=6 exon 1917..2008
/gene="ZDHHC5"
/gene_synonym="DKFZp586K0524; KIAA1748; ZNF375"
/inference="alignment:Splign"
/number=7 exon 2009..2141
/gene="ZDHHC5"
/gene_synonym="DKFZp586K0524; KIAA1748; ZNF375"
/inference="alignment:Splign"
/number=8 exon 2142..2265
/gene="ZDHHC5"

```
                /gene_synonym="DKFZp586K0524; KIAA1748; ZNF375"
                /inference="alignment:Splign"
                /number=9
exon            2266..2378
                /gene="ZDHHC5"
                /gene_synonym="DKFZp586K0524; KIAA1748; ZNF375"
                /inference="alignment:Splign"
                /number=10
exon            2379..3238
                /gene="ZDHHC5"
                /gene_synonym="DKFZp586K0524; KIAA1748; ZNF375"
                /inference="alignment:Splign"
                /number=11
exon            3239..4560
                /gene="ZDHHC5"
                /gene_synonym="DKFZp586K0524; KIAA1748; ZNF375"
                /inference="alignment:Splign"
                /number=12
STS             4251..4532
                /gene="ZDHHC5"
                /gene_synonym="DKFZp586K0524; KIAA1748; ZNF375"
                /standard_name="D11S4384"
                /db_xref="UniSTS:33107"
STS             4254..4463
                /gene="ZDHHC5"
                /gene_synonym="DKFZp586K0524; KIAA1748; ZNF375"
                /standard_name="A003A41"
                /db_xref="UniSTS:32856"
STS             4294..4458
                /gene="ZDHHC5"
                /gene_synonym="DKFZp586K0524; KIAA1748; ZNF375"
                /standard_name="D11S2272E"
                /db_xref="UniSTS:76902"
polyA_site      4557
                /gene="ZDHHC5"
                /gene_synonym="DKFZp586K0524; KIAA1748; ZNF375"
```

FIG. 13-42

ORIGIN

```
   1 gagacccggc actgagggca acggccgcgc gccggctccg agacgagcga cgcctggcgg
  61 gagcgcgcgg cagcggggcg ggcgtggagc gtgcgggggc cgcgcgctgc ttctctgagg
 121 caggacggca ctgccgggag gcggcggtga caacgacggc ggtggtgacg ggcaccgcgc
 181 tcgcgggtga gacacagtaa cctggttgaa ctctgcatct ggaaagctga agactgaaga
 241 aagataagag acattgacta gtctggaaac agggacatct ttggaacttc gttttcatcc
 301 acagtaaact tttgaagtgt catcaattgg aattgatttc ttcatcttat tctgcctatt
 361 gggaagaaca tggcttcaag gattttaagt ttccctttag ttttacatga actttgtagg
 421 aaacagagcc cttaaagggc ttgggaataa caagaagaga ttgaagacag agaagcttgc
 481 cctgttttcc ttgccccttc aaagaaaagg atttacagct caaacttaga acagctgttg
 541 tccagcttta gccatcaaga gagaaataaa ttaaaccacc attgccagac tacaagccct
 601 ggtgaagtca gggtgtggga gtggtggcat tgagaagact acctaaaaga gacaaagact
 661 gcagtaaaca aagctcctct ttaaagttgg aaggggcctc aggttccttc ttggattgaa
 721 atagaaatag aaacacaggg cacacctctt ttaggtgcag ctcacatttt atggaactgt
 781 agtcgtggag gtactatagt atctcagaag aatttttctt tgcccaaagt ttttttgcca
 841 taccctgata ttctctcctt cttttgaaga cctgcctcca tccatgagct gtatcttgat
 901 ctgtctgact gtccatgttt tccacctgca accatttgca tgtgtacagc ctactgtttg
 961 tctccagttt ttaaactgta caagttgtgt ttcttaatct tcccttctgc cttgttctgg
1021 ggaggtggtt attcatcatt tggaatcacc tttccccctc ccatgtgctt tccttcattt
1081 gagatctttt gacctttggc tttatttggg agggggaagg gtgataaagt tttctgtttc
1141 cctggttttc ttttgtactc ctctctgttg cttccctcct cccattttct tgtctgttct
1201 gccgctgtgt gggcctgggc tatgcggcag ggcagatttc ccatcagagc tccaacatgc
1261 ccgcagagtc tggaaagaga ttcaaaccca gcaagtatgt cccggtctct gcagccgcca
1321 tcttcctagt gggagctacg acactcttct ttgcctttac gtgtccagga ctaagcctgt
1381 atgtgtcacc tgcagtgccc atctacaatg caattatgtt tctctttgtg ttggccaact
1441 tcagcatggc caccttcatg gacccaggga ttttccctcg agctgaggag gatgaggaca
1501 aggaagatga tttccgagct cccctttaca aaacagtgga gataaagggc atccaggtgc
1561 gcatgaaatg gtgtgccacc tgccgctttt accgtccccc tcgatgttcc cactgcagtg
1621 tctgtgacaa ctgtgtggag gaatttgatc atcactgccc ctgggtgaat aactgtattg
1681 gtcgccggaa ctaccgctat tttttccttt tcctcctttc cctgacagcc cacattatgg
1741 gtgtgtttgg ctttggcctc ctttatgtcc tctaccacat agaggaactc tcaggggtcc
1801 gcacggctgt cacaatggca gtaatgtgtg tggctggctt attcttcatc cctgtagctg
1861 gcctcacggg atttcacgtg gttctggtgg ccaggggacg cacaaccaat gaacaggtta
1921 cgggtaaatt ccgggggagt gtgaacccct tcaccaatgg ctgctgtaac aatgtcagcc
1981 gtgttctctg cagttctcca gcacccaggt atttggggag accaaagaaa gagaagacaa
2041 ttgtaatcag acctcccttc cttcgaccag aagtttcaga tgggcagata actgtgaaga
```

FIG. 13-43

2101 tcatggataa tggcatccag ggagagctga ggagaacaaa gtctaaggga agcctggaga
2161 taacagagag ccagtctgca gatgctgaac ctccacctcc tcctaagcca gacctgagcc
2221 gttacacagg gttgcgaaca cacctcggct tggctactaa tgaggatagt agcttattgg
2281 ccaaggacag ccccccgaca cctaccatgt acaagtatcg gccgggttac agtagcagca
2341 gtacgtcagc tgccatgccg cattcctcca gcgccaagtt gagtcgtggg gacagcttga
2401 aggagccaac ctcaattgca gagagcagcc gtcaccccag ctaccgctca gagcccagct
2461 tggaaccaga gagcttccgt tctcctacct ttggcaaaag ttttcacttc gatccactat
2521 ccagtggctc acgctcctcc agcctcaagt cagcccaggg cacaggcttt gagctgggcc
2581 agttgcaatc cattcgttca gagggcacca cctccacctc ctataagagc ctggccaacc
2641 agacacgcaa tggaagccta tcttatgaca gcttgctcac accttcagac agccctgatt
2701 ttgagtcagt gcaggcaggg cctgagccag acccaccttt aggctatacc tctcccttcc
2761 tgtcagccag gctggcccag caacgggaag ctgagaggca cccacgtttg gtgccaactg
2821 gcccaacaca ccgagagccc tcaccagtcc gttacgacaa tctgtcgcgc cacattgtgg
2881 cctctctcca ggaacgagag aagttgctgc gccagtcacc cccactcccg ggccgtgagg
2941 aagaaccagg cttgggggac tcaggcattc agtcaacacc aggctcgggc catgcccctc
3001 gtactagttc ctcctcagat gattcaaaga gatcaccttt gggcaagact ccactgggac
3061 gcccagctgt cccccgtttt ggcaagccag atgggctaag ggccgggga gtagggtccc
3121 ctgaaccagg cccaacagcc ccatacctgg gccgatcgat gtcttacagc agccaaaaag
3181 cccaacctgg tgtctctgag acagaagaag tggccttgca gccattactg acacccaaag
3241 atgaagtaca gctgaagacc acctacagca aatccaacgg gcagcccaag agcttaggct
3301 cagcctcccc tggcccaggc cagccacctc tcagtagccc cacgagggga ggagtcaaga
3361 aggtgtcagg ggttggtggt accacctatg agatttcggt gtgagccttc ggcacctccc
3421 ctccccaacg cctctgcgcc tacaccaaag ggccccaggt ggccaccttc cttccctcaa
3481 ggggctcccc tcccgtgcat ggacattttt taaaccaccg attccaagag gatgaggagt
3541 gtttctaaa atgcagtagg cttggggagt cggagagttg ggccctgag actggggtag
3601 caaccccccc ttttatcttt taagaccttc ccttccttga tccctggacc agactcagtg
3661 gacatttgtg caattgctcg ccctggaggg aaccagatca tttttaaacc agaaataatt
3721 ttttttatta ttgttacgga ttctattttt ttcctcttct gcgttaccag gtgtgtgtgt
3781 acatataata tatatatata tatattataa atatcaaaga aattatatat ctatcctggg
3841 atgggaaaat gagggaggga tacatatacg gagggggatc ttactcttcc cattcctcag
3901 accagcagga aaagaggggga gacgtcagtc tttttcctgt ggttccctct catttgtccc
3961 agttactaac tacggaaata gcatcctctg ctggtgctaa gtgtgattag gaagaagcct
4021 ggggagaggt gagtctggaa ttttggtcac aagagggaag gacttggaga ggagaattag
4081 ttttctaggc tcattggcat ttagtttccc taggaaaggg gtcaaaactt caagacactg
4141 gtggtggtgg gagatcagga aaataacttg gcctagctca aacaatattg gataatcccc
4201 tccttggggg agagggatta gagtgtgctc ctactggccc cttggagcct cccctagctt

FIG. 13-44

```
4261 acacagttaa cttgatttta aaatccaagg ccaggagaga agaatccaaa aagcaatatt
4321 tttcatcaca tgccaaaaac gggggataga gagaaggagt ggcaggccta ggcccctccg
4381 attgtccctt gggggttacc cctcagccca cctcactatg gtgctgggta gaggggatac
4441 ctgggttcta acctctaaat aggggagatc ccagcctcca caaagaggcc cttttatttt
4501 ttattctgat tagccatttt aaaccaacga ggaataaaaa gaaatcctga tctaaccagc
4561 aaaaaaaaaa aaaaaaaaaa aa
//
```

ZDHHC6:

```
FEATURES             Location/Qualifiers
     source          1..2187
                     /organism="Homo sapiens"
                     /mol_type="mRNA"
                     /db_xref="taxon:9606"
                     /chromosome="10"
                     /map="10q25.2"
     gene            1..2187
                     /gene="ZDHHC6"
                     /gene_synonym="FLJ21952; ZNF376"
                     /note="zinc finger, DHHC-type containing 6"
                     /db_xref="GeneID:64429"
                     /db_xref="HGNC:19160"
                     /db_xref="HPRD:15721"
     exon            1..210
                     /gene="ZDHHC6"
                     /gene_synonym="FLJ21952; ZNF376"
                     /inference="alignment:Splign"
                     /number=1
     exon            211..691
                     /gene="ZDHHC6"
                     /gene_synonym="FLJ21952; ZNF376"
                     /inference="alignment:Splign"
```

FIG. 13-45

/number=2
CDS 425..1666
/gene="ZDHHC6"
/gene_synonym="FLJ21952; ZNF376"
/note="zinc finger, DHHC domain containing 6; DHHC-6;
zinc
finger protein 376; transmembrane protein H4; zinc
finger
DHHC domain-containing protein 6"
/codon_start=1
/product="probable palmitoyltransferase ZDHHC6"
/protein_id="NP_071939.1"
/db_xref="GI:11968053"
/db_xref="CCDS:CCDS7574.1"
/db_xref="GeneID:64429"
/db_xref="HGNC:19160"
/db_xref="HPRD:15721"

/translation="MGTFCSVIKFENLQELKRLCHWGPIIALGVIAICSTMAMIDSVL

WYWPLHTTGGSVNFIMLINWTVMILYNYFNAMFVGPGFVPLGWKPEISQDTMYLQYCK

VCQAYKAPRSHHCRKCNRCVMKMDHHCPWINNCCGYQNHASFTLFLLLAPLGCIHAAF

IFVMTMYTQLYHRLSFGWNTVKIDMSAARRDPLPIVPFGLAAFATTLFALGLALGTTI

AVGMLFFIQMKIILRNKTSIESWIEEKAKDRIQYYQLDEVFVFPYDMGSRWRNFKQVF

TWSGVPEGDGLEWPVREGCHQYSLTIEQLKQKADKRVRSVRYKVIEDYSGACCPLNKG

IKTFFTSPCTEEPRIQLQKGEFILATRGLRYWLYGDKILDDSFIEGVSRIRGWFPRKC
VEKCPCDAETDQAPEGEKKNR"
exon 692..783
/gene="ZDHHC6"
/gene_synonym="FLJ21952; ZNF376"

FIG. 13-46

```
                    /inference="alignment:Splign"
                    /number=3
STS                 783..942
                    /gene="ZDHHC6"
                    /gene_synonym="FLJ21952; ZNF376"
                    /standard_name="D10S1390E"
                    /db_xref="UniSTS:151387"
exon                784..943
                    /gene="ZDHHC6"
                    /gene_synonym="FLJ21952; ZNF376"
                    /inference="alignment:Splign"
                    /number=4
exon                944..1105
                    /gene="ZDHHC6"
                    /gene_synonym="FLJ21952; ZNF376"
                    /inference="alignment:Splign"
                    /number=5
exon                1106..1159
                    /gene="ZDHHC6"
                    /gene_synonym="FLJ21952; ZNF376"
                    /inference="alignment:Splign"
                    /number=6
exon                1160..1327
                    /gene="ZDHHC6"
                    /gene_synonym="FLJ21952; ZNF376"
                    /inference="alignment:Splign"
                    /number=7
exon                1328..1369
                    /gene="ZDHHC6"
                    /gene_synonym="FLJ21952; ZNF376"
                    /inference="alignment:Splign"
                    /number=8
exon                1370..1515
                    /gene="ZDHHC6"
                    /gene_synonym="FLJ21952; ZNF376"
                    /inference="alignment:Splign"
                    /number=9
```

FIG. 13-47

```
     exon            1516..1562
                     /gene="ZDHHC6"
                     /gene_synonym="FLJ21952; ZNF376"
                     /inference="alignment:Splign"
                     /number=10
     exon            1563..2170
                     /gene="ZDHHC6"
                     /gene_synonym="FLJ21952; ZNF376"
                     /inference="alignment:Splign"
                     /number=11
     STS             1903..2103
                     /gene="ZDHHC6"
                     /gene_synonym="FLJ21952; ZNF376"
                     /standard_name="A006C33"
                     /db_xref="UniSTS:2005"
     STS             1903..2103
                     /gene="ZDHHC6"
                     /gene_synonym="FLJ21952; ZNF376"
                     /standard_name="G20705"
                     /db_xref="UniSTS:2004"
ORIGIN
        1 agagtcctgg cgagggcgct ggccgagagg tgctcggctt gtagcaggtc ccgcactcca
       61 gcctctcgct gccagggttt gctctctgct tgtcctgggc tgaggtgtcc atgacggagt
      121 catccaagga ggaaaaaatc tgttccgggt gagcccaggc cgccccggat atgcgatggc
      181 tgaggagcag acaccaggga ccacactgag gttgggtttc agaccaagac actggattct
      241 cctagttaag ataaagagct ttgggtgcct gacagtgaaa atggtgtaat ctgcgttaac
      301 agttcacagc ttgaaggcat gacaattaaa gaacacacat ggacttgtgg cacatggaaa
      361 tgtgcgcaca gaaaaaggaa atctataatt cttttaaagt aggaaggcat tcttccttgc
      421 caaaatgggt acgttctgtt cggttatcaa gtttgaaaat ctacaagaat taaagagact
      481 gtgtcactgg ggtcccatca tagcccttgg tgttatagca atatgttcta ccatggccat
      541 gattgactct gtgttgtggt attggcccct acatacaact ggaggaagtg tgaatttcat
      601 catgttgata aattggactg tcatgattct ttataattac ttcaatgcca tgtttgtcgg
      661 tccgggcttt gtccctctgg ggtggaaacc ggaaatttct caggatacca tgtatctcca
      721 gtattgtaaa gtctgccaag catacaaggc accacgttca catcactgca gaaagtgtaa
      781 cagatgtgtg atgaagatgg accatcactg tccttggatc aacaactgtt gtggttacca
      841 aaatcatgct tcgttcacac tgtttctcct tttagcacca ctgggttgta tccatgctgc
```

FIG. 13-48

```
 901 tttcattttt gtgatgacta tgtacacaca gctttatcat cggctctcct ttgggtggaa
 961 cacagtgaag atcgacatga gtgcagcccg gagagatcct cttccaattg ttccatttgg
1021 attagctgca tttgctacca ccttgtttgc cttgggatta gctttaggaa caaccatagc
1081 tgttgggatg ttgtttttta tccagatgaa aataattctc agaaacaaaa cttctattga
1141 gtcatggatt gaagagaagg ctaaagatcg aattcagtat tatcaactag atgaagtctt
1201 tgtttttcca tatgatatgg gaagtagatg gaggaacttt aaacaggtat ttacgtggtc
1261 aggggtccct gaaggagatg gacttgagtg gccagtaaga gaaggctgtc accaatacag
1321 cttaacaata gaacagttga aacaaaaagc agataagaga gtcagaagtg ttcgctataa
1381 agtaatagaa gattatagtg gtgcctgctg ccctctgaat aaaggaatca aaaccttctt
1441 cacaagtccc tgcaccgaag agcctcgaat acagctgcaa aaagggggaat tcattttagc
1501 cacaagaggt ttacgatact ggttatatgg agacaaaatt cttgatgatt cctttataga
1561 aggtgtttca agaataaggg gttggttccc tagaaaatgt gtggaaaagt gtccctgtga
1621 tgctgaaaca gatcaagccc cagaggggga gaagaaaaat agatagctgc tgttaaaaca
1681 aaattatcct ttaagtctgc ttaattactt gaaaattgta catattacta aagaattatg
1741 caatgagcct actctggtta agatgttctt ttcctcaaag gtgccctagt gccatgattt
1801 aaatattttt attaccattt tgaaatggag aagccattct gcatatgcct ttgaattcct
1861 gcccttcttt accacctctt cctccccctc aaaggaaaaa catttcatcc aagtaagtta
1921 acggcatttt ctgtaggatt ttcttatgca ctgcacactc tggacctcac ctgcagatac
1981 agttcccccc ttgccaggag catctgcatg tggtacttct cttttccctc agttgatatt
2041 tcttatatga tattctagat actatagaac tcaatttgtc agattcagta taacctcaga
2101 ttttgttacc tgtcttttaa aaatgcagat tttgtcaaat caaataaaga tcaatggatg
2161 ttgggtataa aaaaaaaaaa aaaaaaa
//
```

ZDHHC7:

```
FEATURES             Location/Qualifiers
     source          1..3279
                     /organism="Homo sapiens"
                     /mol_type="mRNA"
                     /db_xref="taxon:9606"
                     /chromosome="16"
                     /map="16q24.1"
```

FIG. 13-49

```
     gene            1..3279
                     /gene="ZDHHC7"
                     /gene_synonym="FLJ10792; FLJ20279; SERZ-B; SERZ1;
ZNF370"
                     /note="zinc finger, DHHC-type containing 7"
                     /db_xref="GeneID:55625"
                     /db_xref="HGNC:18459"
     exon            1..250
                     /gene="ZDHHC7"
                     /gene_synonym="FLJ10792; FLJ20279; SERZ-B; SERZ1;
ZNF370"
                     /inference="alignment:Splign"
                     /number=1
     exon            251..336
                     /gene="ZDHHC7"
                     /gene_synonym="FLJ10792; FLJ20279; SERZ-B; SERZ1;
ZNF370"
                     /inference="alignment:Splign"
                     /number=2
     exon            337..668
                     /gene="ZDHHC7"
                     /gene_synonym="FLJ10792; FLJ20279; SERZ-B; SERZ1;
ZNF370"
                     /inference="alignment:Splign"
                     /number=3
     CDS             354..1391
                     /gene="ZDHHC7"
                     /gene_synonym="FLJ10792; FLJ20279; SERZ-B; SERZ1;
ZNF370"
                     /note="isoform 1 is encoded by transcript variant 1;
zinc
                     finger, DHHC domain containing 7; Sertoli cell gene with
                     zinc finger domain-β DHHC-7; zinc finger protein 370;
                     zinc finger DHHC domain-containing protein 7;
                     palmitoyltransferase ZDHHC7"
                     /codon_start=1
```

FIG. 13-50

```
                    /product="palmitoyltransferase ZDHHC7 isoform 1"
                    /protein_id="NP_001139020.1"
                    /db_xref="GI:224493964"
                    /db_xref="CCDS:CCDS45538.1"
                    /db_xref="GeneID:55625"
                    /db_xref="HGNC:18459"

/translation="MQPSGHRLRDVEHHPLLAENDNYDSSSSSSSEADVADRVWFIRD

GCGMICAVMTWLLVAYADFVVTFVMLLPSKDFWYSVVNGVIFNCLAVLALSSHLRTML

TDPEKSSDCRPSACTVKTGLDPTLVGICGEGTESVQSLLLGAVPKGNATKEYMESLQL

KPGEVIYKCPKCCCIKPERAHHCSICKRCIRKMDHHCPWVNNCVGEKNQRFFVLFTMY

IALSSVHALILCGFQFISCVRGQWTECSDFSPPITVILLIFLCLEGLLFFTFTAVMFG

TQIHSICNDETEIERLKSEKPTWERRLRWEGMKSVFGGPPSLLWMNPFVGFRFRRLPT
                    RPRKGGPEFSV"
     exon           669..779
                    /gene="ZDHHC7"
                    /gene_synonym="FLJ10792; FLJ20279; SERZ-B; SERZ1;
ZNF370"
                    /inference="alignment:Splign"
                    /number=4
     exon           780..904
                    /gene="ZDHHC7"
                    /gene_synonym="FLJ10792; FLJ20279; SERZ-B; SERZ1;
ZNF370"
                    /inference="alignment:Splign"
                    /number=5
     exon           905..1001
                    /gene="ZDHHC7"
                    /gene_synonym="FLJ10792; FLJ20279; SERZ-B; SERZ1;
ZNF370"
                    /inference="alignment:Splign"
```

FIG. 13-51

```
                     /number=6
     exon            1002..1083
                     /gene="ZDHHC7"
                     /gene_synonym="FLJ10792; FLJ20279; SERZ-B; SERZ1;
ZNF370"
                     /inference="alignment:Splign"
                     /number=7
     exon            1084..1214
                     /gene="ZDHHC7"
                     /gene_synonym="FLJ10792; FLJ20279; SERZ-B; SERZ1;
ZNF370"
                     /inference="alignment:Splign"
                     /number=8
     exon            1215..3274
                     /gene="ZDHHC7"
                     /gene_synonym="FLJ10792; FLJ20279; SERZ-B; SERZ1;
ZNF370"
                     /inference="alignment:Splign"
                     /number=9
     STS             3031..3161
                     /gene="ZDHHC7"
                     /gene_synonym="FLJ10792; FLJ20279; SERZ-B; SERZ1;
ZNF370"
                     /standard_name="D16S3320"
                     /db_xref="UniSTS:8792"
ORIGIN
        1 acttccggcg ctcgcaccgc cccgctctcc agccaaggct ccgggctgag gcatttgctt
       61 ggctgcagcc tccttccgac ctgccccggcg ggacccaggg gaccaagccg agccgagccg
      121 cggggcccgc tccagcccgg ccatgagcgc ggccgcatga tgcgtccctg cctcggccgc
      181 tgcagtcgcc gccgccgccg ccgcaggccg ggaggagccg cagcgccggg cgaccccgcc
      241 cgggcctcgg atccgatcac ataggacagt atgcacctta agatcctgaa gaaacggcac
      301 aaaatgttca agtgatgttt agaaataact tgtgagggtg cgtcagggaa atcatgcagc
      361 catcaggaca caggctccgg gacgtcgagc atcatcctct cctggctgaa aatgacaact
      421 atgactcttc atcgtcctcc tcctccgagg ctgacgtggc tgaccgggtc tggttcatcc
      481 gtgacggctg cggcatgatc tgtgctgtca tgacgtggct tctggtcgcc tatgcagact
      541 tcgtggtgac tttcgtcatg ctcctgcctt ccaaagactt ctggtactct gtggtcaacg
```

FIG. 13-52

601 gggtcatctt taactgcttg gccgtgcttg ccctgtcatc ccacctgaga accatgctca
661 ccgaccctga aaaatccagt gactgccgac catctgcctg cacagtgaaa actgggctgg
721 acccaaccct tgtgggcatt tgtggtgagg gaaccgagtc tgtgcaaagc ctcctgcttg
781 gggcagtacc caaaggaaac gctacgaaag aatacatgga gagcttgcag ctgaagcccg
841 gggaagtcat ctacaagtgc cccaagtgct gctgtattaa acccgagcgc gcccaccact
901 gcagtatttg caaaagatgt attcggaaaa tggatcatca ctgcccgtgg gtgaacaatt
961 gtgtaggaga aaagaatcaa agatttttg tgctcttcac tatgtatata gctctgtctt
1021 cagtccatgc tctgatcctt tgtggatttc agttcatctc ctgtgtccga gggcagtgga
1081 ctgaatgcag tgatttttca cctccgataa ctgtaatcct gttgatcttc ctgtgccttg
1141 agggtcttct gtttttcact ttcactgcag ttatgtttgg cacccaaatc cactccatat
1201 gcaacgacga gacggagatc gagcgattga aaagtgagaa gcccacatgg gagcggaggc
1261 tgcgatggga agggatgaag tccgtctttg gggggccccc ctcactcctc tggatgaatc
1321 cctttgtggg cttccgattt aggcgactgc ccacgagacc cagaaaaggt ggcccggagt
1381 tctcagtgtg aggcgtggct catcagactg aaacttgctc acagacttcc agttatttat
1441 ttggggtctg aaggatatca acagctcatc tgtgaccaac agggcaactg gaacctacac
1501 aaaccaattg cttgcagcaa gcagagtttt atatatttat agtcacagat ggcagaggaa
1561 gaggctctca gtccccacct gtacaacaac ggaaaggtgt gtggccacac gaagaagcca
1621 aacgccgtgg cctcctgcag agctggggct tctgtggaga atacttcggg ttattacatg
1681 ggttattcaa atcctgggtc ctgagctgct gtttccaatc atgaagaaaa acagtgaatc
1741 cagtgaacag ggattctcca agcagtcatt tcaggggggct cctgctgacc ccgccactca
1801 gcagtgcact ccccggatca cagcagggcg tttacataga aagacgtttt ggtctcgatt
1861 agctccgatg ctttgcactg aagttgcaaa agatctgtgc actgaacagt gaaggtggct
1921 tccggcacac tccccgctgc cccggaagag acatcctttg accctctcag caagtctgtg
1981 tgtgtgcgtg tctgtgcgtg tgcgcgcgtg tgtgcatgtg tgtcaaaatt gccagtgttg
2041 tttaggcaat gtaacattta ccggctgtgt acagcaaaca agctattttt tagaaaccga
2101 cgtttcaggg aagaggggag agagccgcgg ggtcctgccc gtggttacta tgaatgtatt
2161 gctgttggag gacatctcga tccaaagaac agccgttcct gtgcggccct tcgttgccct
2221 cctgctttca tttttaaag aaatcttgag tgcttgaggg ccttggaact gattttttt
2281 ttttgttcca gccaaattag cagtgtataa atggcaccta ggtaagagca gagctgcggc
2341 tcggtgactt gatacttggg gcagcccgat gctgtgtgtg gggcagggga ggcatcctta
2401 ctggagaggc agggcccagc cattgggcac ctctgggaag gggaggggac catgaggcag
2461 ccagcccctg gcaggggcga ctgtgccacc gcaggcagcg ctccagtcgg gaatggccag
2521 gatggcgccc tcttgttgga gtttttggtt agcttttacg ttttcttctc cacccacggc
2581 acaggtgata aaataggatc cttggtgcgg agcttaaaat tatgccagaa agccaacagc
2641 tcccctcgtg gggccttgcc ttaaacttgc ctggtttgta catttttgc cggacgcatc
2701 aagaagcaat ctgtgacaaa gtctgagggt cttcctttat gcttgccctc cacactaaga

FIG. 13-53

```
2761 gaagttggcg tctccctcct gggaattgtt ttgcctttct gttcatctgt gaactgtttt
2821 ttgtttttaa ttactctgta ccccatccga atcagggctt ctaccactgc tgatgcaaaa
2881 ccacaaaggg acctacctga gccaccgtcc tagccaagcg agcaaacctg caggggggttt
2941 ggaagtggac ttggtcaccg cagaagcgtg tgcgccgttg ggggaagagc tgcgtcacag
3001 ccagagggac aaagtgtggg tgatcctgga gacgccagtt tccgagattg ttctgcatat
3061 tcatttgcac attgttgtct gggttggaca tgcgtgtggg cttcagtgtg aggcttttaa
3121 tatgtatatc ctgttatcaa taaaacaatt atccaagtgg ttgaatcctg tgagacttgg
3181 caagtgtgtg caaatcaagt atacttgact tttcaacctc ttctttcaat gtaactttta
3241 tatgaaataa agtaatcaat taacagttct caaaaaaaa
//
```

ZDHHC8:

```
FEATURES             Location/Qualifiers
     source          1..3520
                     /organism="Homo sapiens"
                     /mol_type="mRNA"
                     /db_xref="taxon:9606"
                     /chromosome="22"
                     /map="22q11.21"
     gene            1..3520
                     /gene="ZDHHC8"
                     /gene_synonym="ZDHHCL1; ZNF378"
                     /note="zinc finger, DHHC-type containing 8"
                     /db_xref="GeneID:29801"
                     /db_xref="HGNC:18474"
                     /db_xref="HPRD:12298"
                     /db_xref="MIM:608784"
     exon            1..210
                     /gene="ZDHHC8"
                     /gene_synonym="ZDHHCL1; ZNF378"
                     /inference="alignment:Splign"
                     /number=1
```

FIG. 13-54

CDS 107..2404
/gene="ZDHHC8"
/gene_synonym="ZDHHCL1; ZNF378"
/note="zinc finger, DHHC domain containing 8; DHHC-8;
zinc
finger protein 378; zinc finger DHHC domain-containing
protein 8; zinc finger, DHHC domain like containing 1;
membrane-associated DHHC8 zinc finger protein"
/codon_start=1
/product="probable palmitoyltransferase ZDHHC8"
/protein_id="NP_037505.1"
/db_xref="GI:32698692"
/db_xref="CCDS:CCDS13776.1"
/db_xref="GeneID:29801"
/db_xref="HGNC:18474"
/db_xref="HPRD:12298"
/db_xref="MIM:608784"

/translation="MPRSPGTRLKPAKYIPVATAAALLVGSSTLFFVFTCPWLTRAVS

PAVPVYNGIIFLFVLANFSMATFMDPGVFPRADEDEDKEDDFRAPLYKNVDVRGIQVR

MKWCATCHFYRPPRCSHCSVCDNCVEDFDHHCPWVNNCIGRRNYRYFFLFLLSLSAHM

VGVVAFGLVYVLNHAEGLGAAHTTITMAVMCVAGLFFIPVIGLTGFHVVLVTRGRTTN

EQVTGKFRGGVNPFTRGCCGNVEHVLCSPLAPRYVVEPPRLPLAVSLKPPFLRPELLD

RAAPLKVKLSDNGLKAGLGRSKSKGSLDRLDEKPLDLGPPLPPKIEAGTFSSDLQTPR

PGSAESALSVQRTSPPTPAMYKFRPAFPTGPKVPFCGPGEQVPGPDSLTLGDDSIRSL

DFVSEPSLDLPDYGPGGLHAAYPPSPPLSASDAFSGALRSLSLKASSRRGGDHVALQP

LRSEGGPPTPHRSIFAPHALPNRNGSLSYDSLLNPGSPGGHACPAHPAVGVAGYHSPY

LHPGATGDPPRPLPRSFSPVLGPRPREPSPVRYDNLSRTIMASIQERKDREERERLLR

SQADSLFGDSGVYDAPSSYSLQQASVLSEGPRGPALRYGSRDDLVAGPGFGGARNPAL

QTSLSSLSSSVSRAPRTSSSSLQADQASSNAPGPRPSSGSHRSPARQGLPSPPGTPHS

PSYAGPKAVAFIHTDLPEPPPSLTVQRDHPQLKTPPSKLNGQSPGLARLGPATGPPGP

SASPTRHTLVKKVSGVGGTTYEISV"

exon 211..332
/gene="ZDHHC8"
/gene_synonym="ZDHHCL1; ZNF378"
/inference="alignment:Splign"
/number=2 exon 333..490
/gene="ZDHHC8"
/gene_synonym="ZDHHCL1; ZNF378"
/inference="alignment:Splign"
/number=3 exon 491..663
/gene="ZDHHC8"
/gene_synonym="ZDHHCL1; ZNF378"
/inference="alignment:Splign"
/number=4 exon 664..766
/gene="ZDHHC8"
/gene_synonym="ZDHHCL1; ZNF378"
/inference="alignment:Splign"
/number=5 exon 767..858
/gene="ZDHHC8"
/gene_synonym="ZDHHCL1; ZNF378"
/inference="alignment:Splign"
/number=6 exon 859..1000
/gene="ZDHHC8"
/gene_synonym="ZDHHCL1; ZNF378"
/inference="alignment:Splign"
/number=7

```
     exon            1001..1121
                     /gene="ZDHHC8"
                     /gene_synonym="ZDHHCL1; ZNF378"
                     /inference="alignment:Splign"
                     /number=8
     exon            1122..1231
                     /gene="ZDHHC8"
                     /gene_synonym="ZDHHCL1; ZNF378"
                     /inference="alignment:Splign"
                     /number=9
     exon            1232..2232
                     /gene="ZDHHC8"
                     /gene_synonym="ZDHHCL1; ZNF378"
                     /inference="alignment:Splign"
                     /number=10
     exon            2233..3455
                     /gene="ZDHHC8"
                     /gene_synonym="ZDHHCL1; ZNF378"
                     /inference="alignment:Splign"
                     /number=11
     STS             3191..3322
                     /gene="ZDHHC8"
                     /gene_synonym="ZDHHCL1; ZNF378"
                     /standard_name="RH91790"
                     /db_xref="UniSTS:87197"
     polyA_signal    3437..3442
                     /gene="ZDHHC8"
                     /gene_synonym="ZDHHCL1; ZNF378"
     polyA_site      3455
                     /gene="ZDHHC8"
                     /gene_synonym="ZDHHCL1; ZNF378"
ORIGIN
        1 ccgcgggtcc tgcgccgcgt ccagcccgcc cgcccgaccc cggcccgacc ccggccggcc
       61 ctgcccgccc ggcccccggg agggatgcgg cggcgcggcg cccaggatgc cccgcagccc
      121 cgggacgcgc ctcaaacccg ccaagtacat cccggtggcc acggccgccg cgctgctggt
      181 cggctccagc accctcttct tcgtgttcac gtgcccgtgg ttgacacgag ctgtgtcccc
```

FIG. 13-57

241 agctgttccc gtctacaatg gcatcatctt cctctttgtc ctggccaact tcagcatggc
301 cactttcatg gaccctggtg ttttcccccg agcggatgag gatgaggaca aggaggacga
361 cttccgggct ccgctgtaca agaacgtgga tgtgcgaggt atccaggtcc gcatgaagtg
421 gtgtgccacg tgccacttct accgcccgcc gcgctgctcc cactgcagcg tctgtgacaa
481 ctgtgtagag gactttgacc accactgccc ctgggtcaac aactgcatcg ggcgtcgaaa
541 ctatcgctac ttcttcctgt tcctgctgtc actcagtgca cacatggtgg gcgtcgtggc
601 cttcggcctg gtctacgtgc tgaaccacgc tgaggggctg ggagccgcgc acaccaccat
661 caccatggct gtcatgtgtg tggccggcct cttcttcatc cctgtcattg gcctcactgg
721 cttccatgtg gtgctggtca ctcgggggcg caccaccaac gagcaggtga ctgggaagtt
781 ccgcgggggt gtgaaccctt tcacccgagg ctgctgtggg aatgtggagc acgtgctgtg
841 tagccccctg gcgccccggt acgtggtgga gccacccegg ctgccgctcg cggtgagttt
901 gaagccgcct ttccttaggc ctgaactcct ggaccgagct gcaccgctca aggtcaagct
961 tagtgacaac gggctgaagg ctggcctggg ccgtagcaag tccaagggca gcctggaccg
1021 gctggatgag aagccactgg acttggggcc accactgccc cccaagatag aggctggcac
1081 gttcagcagt gacctgcaga ccccgcgccc aggcagtgct gagagtgccc tgtcggtgca
1141 gaggaccagc ccccgacac ctgccatgta caagtttagg ccggctttcc ccacgggtcc
1201 caaggtgccc ttctgtggac caggcgagca ggttccaggc cctgattccc tgaccctggg
1261 ggacgacagc atccgtagcc tggactttgt gtccgagccg agcctggacc tccctgacta
1321 tgggccaggg ggcctgcatg cagcctaccc gccatcccca ccgctcagcg cctctgatgc
1381 cttctcgggc gctttgcgct ccctgagcct caaggcctcg agccggcggg gcggggatca
1441 tgtggccctg cagcccctgc gctctgaggg gggccccccc acgccccacc gtagcatttt
1501 tgccccccat gcactgccca accgcaacgg cagcctgtcc tatgacagcc tgctcaatcc
1561 tggctcgcct ggtggccacg cctgccctgc ccacccagca gttggcgtgg ccggatacca
1621 ctcaccctac ctgcatcctg ggggcaacggg cgacccgcca cggcccctac cccgcagctt
1681 cagccccgtg ctgggccccc gcccccggga gccctcgcct gtgcgctacg acaacctgtc
1741 caggaccatc atggcatcca tccaggagcg caaggacagg gaggagcgtg agcgcctgct
1801 gcgctcccag gccgactcac tcttcggcga ctcaggcgtc tatgacgctc ccagctccta
1861 cagcctgcag caggccagtg tgctgtccga gggcccccga ggtcccgcgc tgcgctatgg
1921 ctccagagac gaccttgtgg ctgggcccgg cttcggtggc gcccgcaacc ctgccctgca
1981 gacgtcactg tcctcgctgt ccagctccgt gagccgtgca ccgcggacgt cgtcctcctc
2041 cctgcaggct gatcaggcca gcagcaacgc cccggggccc cggcccagca gtggctcaca
2101 caggtcacct gcacgccagg gcctgccctc cccgcccggc actccccact caccatccta
2161 cgcgggcccc aaagctgtcg ccttcatcca cacggacctc ccagagccac cgccctcgct
2221 gaccgtgcag agggaccacc ctcagctgaa gactccccca agtaagctta atgggcagtc
2281 cccgggcctg gcccggctgg gacctgccac cggcccccca gggccctctg ccagccctac
2341 acggcacacg ctggttaaga aggtgtccgg cgtgggtggg accacctacg agatctcggt

FIG. 13-58

```
2401 gtgaggactg actgccacac atccgccatg gtgccacggg gaccaggacc ccacagcgca
2461 cccccccctcc ccaccaactt ctctgcccca gggacccgag gccaccccag cctggtgtgg
2521 acccatcggc gggagagagt gccacgcctc cacagcttgc cccaagcgct ctgcctgccc
2581 gtccactcat ctgcccatgg ggaagtcggc tcactgggac aagggccact gggctggtct
2641 gtgtctgggc ctgtcccatg gctggggcag tgagggggcc cagtcagcct ctttggggca
2701 ccctctctca gccaggcttg gcccactgcc atcacccagc accccagatc accgccaggc
2761 cagcccccaa tggtcccctt acggacacgt cccagagatg gacagaggca cccagggccc
2821 ccaccgtcct tctgacacag cctgtgggct cccggaccga gtgtcccccg ccaggctact
2881 cctaactaac gcgttgcctt tcacggaccc cgctggaagc ttgtagcttg gcaaggctga
2941 tgcttctgcc ctggcctgct ctgggtgctg gtggataggt ggacagacgg ccagccagcc
3001 agctgtggcc gggggcccgg ctccatgtgt cccgtgtctg tgtgctgtgc tgccgcgccg
3061 tgtctgatgt gtcagtgctc cggccgccgc tgtccctttc atcaaagcct taacctttgc
3121 tttatgctct tgtgggaggc gacgggggcgg caggcgggag caggcacggg ggtgatgctg
3181 ccacaggggg ctggtgacac ccagagcccc ctccccagcc ctcaggccct ccctgccaaa
3241 ctggagaacc ccaccccaag gcatgccacg tccgcagccc cggcctggct gcggtgctcg
3301 cgccgtggga aagcacactg ggagggctc agtgcttccc ttggtgtcag ggacctgaga
3361 gtaagcacat gacagcgtct gcttgcgttg tgtctgtttt atgtttttat atctacatct
3421 atatatctat aattttatta aaaaaaacaa aaagaaaaaa aaaaaaaaaa aaaaaaaaaa
3481 aaaaaaaaaa aaaaaaaaaa aaaaaaaaaa aaaaaaaaaa
```

//

ZDHHC9:

```
FEATURES             Location/Qualifiers
     source          1..2949
                     /organism="Homo sapiens"
                     /mol_type="mRNA"
                     /db_xref="taxon:9606"
                     /chromosome="X"
                     /map="Xq26.1"
     gene            1..2949
                     /gene="ZDHHC9"
                     /gene_synonym="CGI-89; CXorf11; DHHC9; MMSA-1; MRXSZ;
                     ZDHHC10; ZNF379; ZNF380"
                     /note="zinc finger, DHHC-type containing 9"
```

FIG. 13-59

```
                    /db_xref="GeneID:51114"
                    /db_xref="HGNC:18475"
                    /db_xref="HPRD:06759"
                    /db_xref="MIM:300646"
     exon           1..202
                    /gene="ZDHHC9"
                    /gene_synonym="CGI-89; CXorf11; DHHC9; MMSA-1; MRXSZ;
                    ZDHHC10; ZNF379; ZNF380"
                    /inference="alignment:Splign"
                    /number=1
     exon           203..270
                    /gene="ZDHHC9"
                    /gene_synonym="CGI-89; CXorf11; DHHC9; MMSA-1; MRXSZ;
                    ZDHHC10; ZNF379; ZNF380"
                    /inference="alignment:Splign"
                    /number=2b
     exon           271..572
                    /gene="ZDHHC9"
                    /gene_synonym="CGI-89; CXorf11; DHHC9; MMSA-1; MRXSZ;
                    ZDHHC10; ZNF379; ZNF380"
                    /inference="alignment:Splign"
                    /number=3
     STS            282..431
                    /gene="ZDHHC9"
                    /gene_synonym="CGI-89; CXorf11; DHHC9; MMSA-1; MRXSZ;
                    ZDHHC10; ZNF379; ZNF380"
                    /standard_name="ZDHHC9"
                    /db_xref="UniSTS:506676"
     CDS            406..1500
                    /gene="ZDHHC9"
                    /gene_synonym="CGI-89; CXorf11; DHHC9; MMSA-1; MRXSZ;
                    ZDHHC10; ZNF379; ZNF380"
                    /note="Asp-His-His-Cys domain containing protein 9; zinc
                    finger, DHHC domain containing 9; zinc finger, DHHC-type
                    containing 10; zinc finger, DHHC domain containing 10;
                    antigen MMSA-1; DHHC-9; zinc finger protein 379; zinc
```

FIG. 13-60 finger DHHC domain-containing protein 9"
/codon_start=1
/product="palmitoyltransferase ZDHHC9"
/protein_id="NP_057116.2"
/db_xref="GI:56682972"
/db_xref="CCDS:CCDS35395.1"
/db_xref="GeneID:51114"
/db_xref="HGNC:18475"
/db_xref="HPRD:06759"
/db_xref="MIM:300646"

/translaticn="MSVMVVRKKVTRKWEKLPGRNTFCCDGRVMMARQKGIFYLTLFL

ILGTCTLFFAFECRYLAVQLSPAIPVFAAMLFLFSMATLLRTSFSDPGVIPRALPDEA

AFIEMEIEATNGAVPQGQRPPPRIKNFQINNQIVKLKYCYTCKIFRPPRASHCSICDN

CVERFDHHCPWVGNCVGKRNYRYFYLFILSLSLLTIYVFAFNIVYVALKSLKIGFLET

LKETPGTVLEVLICFFTLWSVVGLTGFHTFLVALNQTTNEDIKGSWTGKNRVQNPYSH

GNIVKNCCEVLCGPLPPSVLDRRGILPLEESGSRPPSTQETSSSLLPQSPAPTEHLNS
NEMPEDSSTPEEMPPPEPPEPPQEAAEAEK"

exon 573..733
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=4 exon 734..892
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=5 exon 893..1030

FIG. 13-61

/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=6 exon 1031..1079
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=7 exon 1080..1182
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=8 exon 1183..1286
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=9 exon 1287..1383
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=10 exon 1384..2934
/gene="ZDHHC9"
/gene_synonym="CGI-89; CXorf11; DHHC9; MMSA-1; MRXSZ; ZDHHC10; ZNF379; ZNF380"
/inference="alignment:Splign"
/number=11

STS 2744..2895

FIG. 13-62

```
                     /gene="ZDHHC9"
                     /gene_synonym="CGI-89; CXorf11; DHHC9; MMSA-1; MRXSZ;
                     ZDHHC10; ZNF379; ZNF380"
                     /standard_name="STS-R49987"
                     /db_xref="UniSTS:1743"
     polyA_signal    2913..2918
                     /gene="ZDHHC9"
                     /gene_synonym="CGI-89; CXorf11; DHHC9; MMSA-1; MRXSZ;
                     ZDHHC10; ZNF379; ZNF380"
     polyA_site      2934
                     /gene="ZDHHC9"
                     /gene_synonym="CGI-89; CXorf11; DHHC9; MMSA-1; MRXSZ;
                     ZDHHC10; ZNF379; ZNF380"
ORIGIN
        1 tgaggagcgt tccatttggc cagtggtggg cggttgccac agctggttta gggccccgac
       61 cactggggcc ccttgtcagg aggagacagc ctcccggccc ggggaggaca agtcgctgcc
      121 acctttggct gccgacgtga ttccctggga cggtccgttt cctgccgtca gctgccggcc
      181 gagttgggtc tccgtggttc aggccggctc ccccttcctg gtctcccttc tcccgctggg
      241 ccggtttatc gggaggagat tgtcttccag ggctagcaat tggacttttg atgatgtttg
      301 acccagcggc aggaatagca ggcaacgtga tttcaaagct gggctcagcc tctgtttctt
      361 ctctcgtgta atcgcaaaac ccattttgga gcaggaattc caatcatgtc tgtgatggtg
      421 gtgagaaaga aggtgacacg gaaatgggag aaactcccag gcaggaacac cttttgctgt
      481 gatggccgcg tcatgatggc ccggcaaaag ggcattttct acctgaccct tttcctcatc
      541 ctggggacat gtacactctt cttcgccttt gagtgccgct acctggctgt tcagctgtct
      601 cctgccatcc ctgtatttgc tgccatgctc ttccttttct ccatggctac actgttgagg
      661 accagcttca gtgaccctgg agtgattcct cgggcgctac cagatgaagc agctttcata
      721 gaaatggaga tagaagctac caatggtgcg gtgccccagg gccagcgacc accgcctcgt
      781 atcaagaatt tccagataaa caaccagatt gtgaaactga aatactgtta cacatgcaag
      841 atcttccggc ctccccgggc ctcccattgc agcatctgtg acaactgtgt ggagcgcttc
      901 gaccatcact gcccctgggt ggggaattgt gttggaaaga ggaactaccg ctacttctac
      961 ctcttcatcc tttctctctc cctcctcaca atctatgtct tcgccttcaa catcgtctat
     1021 gtggccctca aatctttgaa aattggcttc ttggagacat tgaaagaaac tcctggaact
     1081 gttctagaag tcctcatttg cttctttaca ctctggtccg tcgtgggact gactggattt
     1141 catactttcc tcgtggctct caaccagaca accaatgaag acatcaaagg atcatggaca
     1201 gggaagaatc gcgtccagaa tccctacagc catggcaata ttgtgaagaa ctgctgtgaa
     1261 gtgctgtgtg gccccttgcc ccccagtgtg ctggatcgaa ggggtatttt gccactggag
```

FIG. 13-63

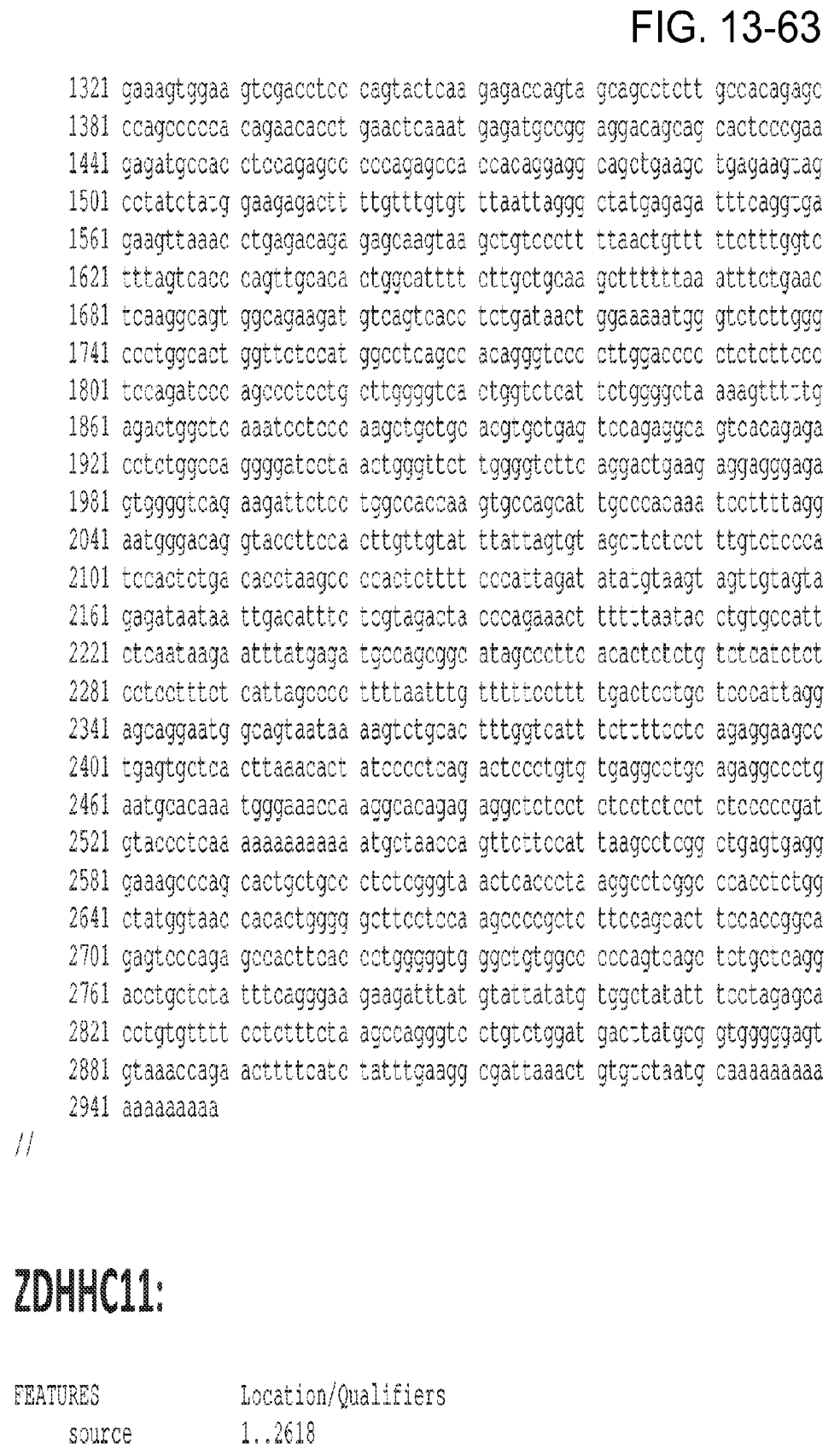

```
1321 gaaagtggaa gtcgacctcc cagtactcaa gagaccagta gcagcctctt gccacagagc
1381 ccagccccca cagaacacct gaactcaaat gagatgccgg aggacagcag cactcccgaa
1441 gagatgccac ctccagagcc cccagagcca ccacaggagg cagctgaagc tgagaagtag
1501 cctatctatg gaagagactt ttgtttgtgt ttaattaggg ctatgagaga tttcaggtga
1561 gaagttaaac ctgagacaga gagcaagtaa gctgtccctt ttaactgttt ttctttggtc
1621 tttagtcacc cagttgcaca ctggcatttt cttgctgcaa gcttttttaa atttctgaac
1681 tcaaggcagt ggcagaagat gtcagtcacc tctgataact ggaaaaatgg gtctcttggg
1741 ccctggcact ggttctccat ggcctcagcc acagggtccc cttggacccc ctctcttccc
1801 tccagatccc agccctcctg cttggggtca ctggtctcat tctggggcta aaagtttttg
1861 agactggctc aaatcctccc aagctgctgc acgtgctgag tccagaggca gtcacagaga
1921 cctctggcca ggggatccta actgggttct tggggtcttc aggactgaag aggagggaga
1981 gtggggtcag aagattctcc tggccaccaa gtgccagcat tgcccacaaa tccttttagg
2041 aatgggacag gtaccttcca cttgttgtat ttattagtgt agcttctcct ttgtctccca
2101 tccactctga cacctaagcc ccactctttt cccattagat atatgtaagt agttgtagta
2161 gagataataa ttgacatttc tcgtagacta cccagaaact ttttaatac ctgtgccatt
2221 ctcaataaga atttatgaga tgccagcggc atagcccttc acactctctg tctcatctct
2281 cctcctttct cattagcccc ttttaatttg tttttccttt tgactcctgc tcccattagg
2341 agcaggaatg gcagtaataa aagtctgcac tttggtcatt tcttttcctc agaggaagcc
2401 tgagtgctca cttaaacact atcccctcag actccctgtg tgaggcctgc agaggccctg
2461 aatgcacaaa tgggaaacca aggcacagag aggctctcct ctcctctcct ctcccccgat
2521 gtaccctcaa aaaaaaaaaa atgctaacca gttcttccat taagcctcgg ctgagtgagg
2581 gaaagcccag cactgctgcc ctctcgggta actcacccta aggcctcggc ccacctctgg
2641 ctatggtaac cacactgggg gcttcctcca agccccgctc ttccagcact tccaccggca
2701 gagtcccaga gccacttcac cctgggggtg ggctgtggcc cccagtcagc tctgctcagg
2761 acctgctcta tttcagggaa gaagatttat gtattatatg tggctatatt tcctagagca
2821 cctgtgtttt cctctttcta agccagggtc ctgtctggat gacttatgcg gtgggggagt
2881 gtaaaccaga acttttcatc tatttgaagg cgattaaact gtgtctaatg caaaaaaaaa
2941 aaaaaaaaa
//
```

ZDHHC11:

```
FEATURES             Location/Qualifiers
     source          1..2618
```

FIG. 13-64

```
                    /organism="Homo sapiens"
                    /mol_type="mRNA"
                    /db_xref="taxon:9606"
                    /chromosome="5"
                    /map="5p15.33"
     gene           1..2618
                    /gene="ZDHHC11"
                    /gene_synonym="FLJ13153; ZNF399"
                    /note="zinc finger, DHHC-type containing 11"
                    /db_xref="GeneID:79844"
                    /db_xref="HGNC:19158"
                    /db_xref="HPRD:15708"
     exon           1..606
                    /gene="ZDHHC11"
                    /gene_synonym="FLJ13153; ZNF399"
                    /inference="alignment:Splign"
                    /number=1
     CDS            385..1623
                    /gene="ZDHHC11"
                    /gene_synonym="FLJ13153; ZNF399"
                    /note="zinc finger, DHHC domain containing 11; DHHC-11;
                    zinc finger protein 399; zinc finger DHHC
                    domain-containing protein 11"
                    /codon_start=1
                    /product="probable palmitoyltransferase ZDHHC11"
                    /protein_id="NP_079062.1"
                    /db_xref="GI:13376150"
                    /db_xref="CCDS:CCDS3857.1"
                    /db_xref="GeneID:79844"
                    /db_xref="HGNC:19158"
                    /db_xref="HPRD:15708"

/translation="MDTRSGSQCSVTPEAILNNEKLVLPPRISRVNGWSLPLHYFQVV

TWAVFVGLSSATFGIFIPFLPHAWKYIAYVVTGGIFSFHLVVHLIASCIDPADSNVRL

MKNYSQPMPLFDRSKHAHVIQNQFCHLCKVTVNKKTKHCISCNKCVSGFDHHCKWINN
```

FIG. 13-65

CVGSRNYWFFFSTVASATAGMLCLIAILLYVLVQYLVNPGVLRTDPRYEDVKNMNIWL

LFLPLFPVQVQTLIVVIIGMLVLLLDFLGLVHLGQLLIFHIYLKAKKMTTFEYLINNR

KEESSKHQAVRKDPYVQMDKGVLQQGAGALGSSAQGVKAKSSLLIHKHLCHFCTSVNQ

DGDSTAREGDEDPCPSALGAKARNSRLICRRLCQFSTRVHPDGGSMAQEADDAPSIST

LGLQQETTEPMKTDSAESED"

exon 607..785
/gene="ZDHHC11"
/gene_synonym="FLJ13153; ZNF399"
/inference="alignment:Splign"
/number=2 exon 786..887
/gene="ZDHHC11"
/gene_synonym="FLJ13153; ZNF399"
/inference="alignment:Splign"
/number=3 exon 888..1012
/gene="ZDHHC11"
/gene_synonym="FLJ13153; ZNF399"
/inference="alignment:Splign"
/number=4 exon 1013..1168
/gene="ZDHHC11"
/gene_synonym="FLJ13153; ZNF399"
/inference="alignment:Splign"
/number=5 exon 1169..1284
/gene="ZDHHC11"
/gene_synonym="FLJ13153; ZNF399"
/inference="alignment:Splign"
/number=6 exon 1285..1319
/gene="ZDHHC11"
/gene_synonym="FLJ13153; ZNF399"

FIG. 13-66

```
                    /inference="alignment:Splign"
                    /number=7
     exon           1320..1407
                    /gene="ZDHHC11"
                    /gene_synonym="FLJ13153; ZNF399"
                    /inference="alignment:Splign"
                    /number=8
     exon           1408..1442
                    /gene="ZDHHC11"
                    /gene_synonym="FLJ13153; ZNF399"
                    /inference="alignment:Splign"
                    /number=9
     exon           1443..1530
                    /gene="ZDHHC11"
                    /gene_synonym="FLJ13153; ZNF399"
                    /inference="alignment:Splign"
                    /number=10
     exon           1531..1565
                    /gene="ZDHHC11"
                    /gene_synonym="FLJ13153; ZNF399"
                    /inference="alignment:Splign"
                    /number=11
     exon           1566..1630
                    /gene="ZDHHC11"
                    /gene_synonym="FLJ13153; ZNF399"
                    /inference="alignment:Splign"
                    /number=12
     exon           1631..2606
                    /gene="ZDHHC11"
                    /gene_synonym="FLJ13153; ZNF399"
                    /inference="alignment:Splign"
                    /number=13
     STS            1688..1887
                    /gene="ZDHHC11"
                    /gene_synonym="FLJ13153; ZNF399"
                    /standard_name="A008P27"
                    /db_xref="UniSTS:55169"
```

FIG. 13-67

ORIGIN

```
   1 gtgaacgggt tgtgggacct gtcgctgtgt gggggctgtc gagcactccc cagaacgtaa
  61 caaatcctca ggggaactga tgggcggtcg cgcgggcact gggtcctcca caccctggag
 121 agccgttttc cgttgccact cggctctggc cggggtcaca ttctgcagca tgtctgttca
 181 ttcccctggg cggggccctg caccgactcc agcccagccc ctgctccctc tgcggggaac
 241 gtggccccag gcagtgctgg gccattggct gtcagtgctg gtcctggcgg ctgcattccc
 301 agtccccttg gtctctgtga cagtgggcgg ggccggccct cccaggatct gacggcgcag
 361 gtcctcccct tctgtgtcct gcagatggac acccgctccg ggagccagtg ttccgtcacc
 421 ccagaagcca tactcaataa tgaaaagctg gtcttgccgc cccgcatctc cagagtgaac
 481 ggctggtcgt taccccctgca ctacttccag gtggtgacct gggctgtctt cgtgggcctt
 541 tcctcggcca ccttcgggat cttcattccc ttcctgcctc acgcgtggaa atacattgcc
 601 tacgtggtga ccgggggggat cttctcgttc cacctcgtcg tccacctgat cgcgtcctgc
 661 atcgacccgg ccgactccaa tgtcagactc atgaagaact attctcagcc catgcccctc
 721 ttcgacagat caaaacatgc acacgtgatc cagaatcagt tctgccacct gtgcaaggtc
 781 accgtgaaca agaaaaccaa acactgcatt tcctgcaata agtgtgtgtc cggcttcgac
 841 caccactgca aatggatcaa caactgcgtg ggaagccgga attattggtt cttcttcagc
 901 actgtggcct cggccacagc tggcatgctc tgcctgatcg ccatcctgct gtatgtcctc
 961 gtccagtacc tcgtgaaccc cggggtgctc cgcacggacc ccaggtatga agatgtcaag
1021 aatatgaaca cgtggctgct gttcctcccc ctgttcccgg tgcaggtgca gaccctgata
1081 gtcgtgatca tcgggatgct cgtgctcctg ctggactttc ttggcttggt gcacctgggc
1141 cagctgctca tcttccacat ctacctgaag gccaagaaga tgaccacctt tgagtatctc
1201 attaataacc gcaaagaaga gagttcaaaa catcaagcag tgaggaaaga tccatacgtg
1261 caaatggaca aaggagttct ccagcaagga gctggcgccc tgggctcatc tgcacaggga
1321 gtcaaagcca agagctccct gctgattcac aagcacttat gtcacttctg cacttcagta
1381 aaccaggatg gggattcgac ggcacgggaa ggggatgaag acccgtgtcc atctgcactt
1441 ggagccaagg ccaggaactc ccggctgatt tgcaggcgcc tgtgtcagtt ctccactcgt
1501 gtacacccag acgggggctc gatggcacag gaagcagatg atgccccgag tatatctaca
1561 cttgggctgc aacaagaaac aacagagccc atgaaaactg acagtgctga aagtgaagac
1621 tgagattcag gagctcaggt gcccctgtga tccaggtctt ctaccctgaa accccaccct
1681 ccatcaaggt cctgcctgta gagtctacct tgcaaagcct cctgctccta cccatgctac
1741 aggccaggaa ccagagccca tcatctcaga ggcccctgga tgtccttcga aggaaccagg
1801 accctcagag cccagcatcc atctctgtca tcatcttcat cacacccaca gaagagccag
1861 ccttgcagga gggtttacat ctccaggaag atgggctgcc agcaactgca gaggatgcag
1921 ccacctgctt aactgtgctg tccagccagc cagccagctg cagggcctct tgctgcttaa
1981 gagctgatgg gccgggcatg ttggctcaca cctgtgagca cagtactggg aaatgggagc
2041 acagtactag gaaatgggag cacagtactg ggaaatggga gcacagtact gggaaatggg
2101 ggctcacagc actgcaaaat gggagcacag tattgggaaa tgggagcaca gtactgggaa
```

FIG. 13-68

```
2161 gtgggagcac agtactgaga agtgggagca cagtactgag aaatgggagt acactactga
2221 gaaatgggag cacagtactg ggaaatgggc atacagtact gagaaatcgg agcacacagt
2281 actgggaaat gggagcacag tactgggaaa tgggagccca cagtactcgg aaaggggagt
2341 tcacagtact cggaaatggg agcatagtac tgggaaatgg gagcacacta ctgggaaatg
2401 ggagcatagt actgggaaac cccagacctg gattctgagt ttttcagcct agcccagact
2461 tcttatctta gtagacaaaa agagtcaata ccagagaacc agaggcatcc tctgtatttt
2521 aatgaactct gcattttaat ctgtttagta gtcatttttt aaaagataat cagttttcca
2581 aatatatcta taagttacta cgtgcaaaaa aaaaaaaa
//
```

ZDHHC11B:

```
FEATURES             Location/Qualifiers
     source          1..1621
                     /organism="Homo sapiens"
                     /mol_type="mRNA"
                     /db_xref="taxon:9606"
                     /chromosome="5"
     gene            1..1621
                     /gene="ZDHHC11B"
                     /note="Derived by automated computational analysis using
                     gene prediction method: GNOMON. Supporting evidence
                     includes similarity to: 4 ESTs, 2 Proteins"
                     /db_xref="GeneID:653082"
                     /db_xref="HGNC:32962"
     CDS             1..1083
                     /gene="ZDHHC11B"
                     /codon_start=1
                     /product="zinc finger, DHHC-type containing 11B isoform
1"
                     /protein_id="XP_931146.2"
                     /db_xref="GI:239742476"
                     /db_xref="GeneID:653082"
                     /db_xref="HGNC:32962"
```

FIG. 13-69

/translation="MDTRSGSQCSVTPEAIRNNEELVLPPRISRVNGWSLPLHYFRVV

TWAVFVGLSLATFRIFIPLLPHSWKYIAYVVTGGIFSFHLVVHLIASCIDPADSNVRL

MKNYSQPMPLFDRSKHAHVIQNQFCHLCKVTVNKKTKHCISCNKCVSGFDHHCKWINN

CVGSRNYWFFFSTVASATAGMLCLIAILLYVLVQYLVNPRVLRTDPRYEDVKNMNTWL

LFLPLFPVQVQTLIVVIIRMLVLLLDLLGLVQLGQLLIFHIYLKAKKMTTFEYLINTR

KEESSKHQAVRKDPYVQMDKGFLQQGAGALGSSAQGVKAKSSLLIYKCPCHFCTSVNQ
DGDSKAQGRLTALPQDFREQAPVTWK"

ORIGIN 1 atggacaccc gctccgggag ccagtgttcc gtcaccccag aagccatacg caacaatgaa
61 gagctggtct tgccgccccg catctccaga gtgaacggct ggtcgttacc cctgcactac
121 ttccgggtgg tgacttgggc tgtcttcgtt ggcctttcct tggccacctt caggatcttc
181 attcccctcc tgcctcactc gtggaaatac atcgcctatg tggtgaccgg ggggatcttc
241 tcgttccacc tcgtcgtcca cctgatcgcg tcctgcatcg accccgccga ctccaatgtc
301 agactcatga agaactattc tcagcccatg cccctcttcg acagatcaaa acatgcacac
361 gtgatccaga atcagttctg ccacctgtgc aaggtcaccg tgaacaagaa aaccaaacac
421 tgcatttcct gcaataagtg tgtgtccggc ttcgaccacc actgcaaatg gatcaacaac
481 tgcgtgggaa gccggaatta ttggttcttc ttcagcactg tggcctcggc cacagctggc
541 atgctctgcc tgatcgccat cctgctgtat gtcctcgtcc agtacctcgt gaaccccagg
601 gtgctccgca cggaccccag gtatgaagat gtcaagaata tgaacacgtg gctgctgttc
661 ctcccccctgt tcccggtgca ggtgcagact ctgatagtcg tgatcatcag gatgctcgtg
721 ctcctgctgg accttcttgg cttggtgcag ctgggccagc tgctcatctt ccacatctac
781 ctgaaggcca agaagatgac cacctttgag tatctcatta atacccgcaa agaagagagt
841 tcaaaacatc aagcagtgag gaaagatcca tacgtgcaaa tggacaaagg atttctccag
901 caaggagctg gcgccctggg ctcatctgca cagggagtca aggccaagag ctccctgctg
961 atttacaaat gcccatgtca cttctgcact tcagtaaacc aggacgggga ttcgaaggca
1021 cagggccgcc tcaccgcact tccccaggat ttcagggaac aggctcctgt gacttggaaa
1081 tgaaaatgga tcacccaacc tggaggaaca gtgaggctgg tgtccaagac ttgccccttg
1141 cctgcacttc cagcaaagat ttggagacac tcagtggaaa ccaatcgagc cccagccca
1201 cccccgccca gactcagcca ccaaagttcc ctcactgcat gtggcacacg ggctcatggg
1261 agtttctctg cctgcgattg tccacgttga caccttctgc acagctgcat ttgtgagtcc
1321 cctcggtgtc tctgcagcat ctatgtgtgg atgaatagtg aagccacatg aggcctggtc
1381 tgaagcagag aagatccgct cagcatcacg ttgaatccca agcccgcatc tccgtgggct

FIG. 13-70

```
    1441 ccaggacaat cctatgaaaa tgacaccgtc ggttcattgt tcacatcggg gaggagaatt
    1501 ccgtctgaaa atgagcgtga cttcactgac acccaagtcc gtggcacagc cctgtgctga
    1561 gctccacaga cctacagtcc atcgcctccc cttcgagtgg gcccagggct gcagacagca
    1621 t
//
```

ZDHHC12:

```
FEATURES             Location/Qualifiers
     source          1..1184
                     /organism="Homo sapiens"
                     /mol_type="mRNA"
                     /db_xref="taxon:9606"
                     /chromosome="9"
                     /map="9q34.11"
     gene            1..1184
                     /gene="ZDHHC12"
                     /gene_synonym="FLJ14524; MGC13153; MGC54050; ZNF400"
                     /note="zinc finger, DHHC-type containing 12"
                     /db_xref="GeneID:84885"
                     /db_xref="HGNC:19159"
                     /db_xref="HPRD:15709"
     exon            1..136
                     /gene="ZDHHC12"
                     /gene_synonym="FLJ14524; MGC13153; MGC54050; ZNF400"
                     /inference="alignment:Splign"
                     /number=1
     CDS             37..840
                     /gene="ZDHHC12"
                     /gene_synonym="FLJ14524; MGC13153; MGC54050; ZNF400"
                     /note="zinc finger, DHHC domain containing 12; DHHC-12;
                     zinc finger protein 400; zinc finger DHHC
```

FIG. 13-71 domain-containing protein 12"
/codon_start=1
/product="probable palmitoyltransferase ZDHHC12"
/protein_id="NP_116188.2"
/db_xref="GI:21361910"
/db_xref="CCDS:CCDS6909.1"
/db_xref="GeneID:84885"
/db_xref="HGNC:19159"
/db_xref="HPRD:15709"

/translation="MAPWALLSPGVLVRTGHTVLTWGITLVLFLHDTELRQWEEQGEL

LLPLTFLLLVLGSLLLYLAVSLMDPGYVNVQPQPQEELKEEQTAMVPPAIPLRRCRYC

LVLQPLRARHCRECRRCVRRYDHHCPWMENCVGERNHPLFVVYLALQLVVLLWGLYLA

WSGLRFFQPWGLWLRSSGLLFATFLLLSLFSLVASLLLVSHLYLVASNTTTWEFISSH
RIAYLRQRPSNPFDRGLTRNLAHFFCGWPSGSWETLWAEEEEEGSSPAV"

exon 137..273
/gene="ZDHHC12"
/gene_synonym="FLJ14524; MGC13153; MGC54050; ZNF400"
/inference="alignment:Splign"
/number=2 exon 274..351
/gene="ZDHHC12"
/gene_synonym="FLJ14524; MGC13153; MGC54050; ZNF400"
/inference="alignment:Splign"
/number=3 exon 352..518
/gene="ZDHHC12"
/gene_synonym="FLJ14524; MGC13153; MGC54050; ZNF400"
/inference="alignment:Splign"
/number=4 exon 519..1152
/gene="ZDHHC12"
/gene_synonym="FLJ14524; MGC13153; MGC54050; ZNF400"

FIG. 13-72

```
                  /inference="alignment:Splign"
                  /number=5
ORIGIN
        1 gggcgcttct tccgggtggg gccccgggcc gaggcgatgg cgccctgggc gctcctcagc
       61 cctggggtcc tggtgcggac cgggcacacc gtgctgacct ggggaatcac gctggtgctc
      121 ttcctgcacg ataccgagct gcggcaatcg gaggagcagg gggagctgct cctgcccctc
      181 accttcctgc tcctggtgct gggctccctg ctgctctacc tcgctgtgtc actcatggac
      241 cctggctacg tgaatgtgca gccccagcct caggaggagc tcaaagagga gcagacagcc
      301 atggttcctc cagccatccc tcttcggcgc tgcagatact gcctggtgct gcagcccctg
      361 agggctcggc actgccgtga gtgccgccgt tgcgtccgcc gctacgacca ccactgcccc
      421 tggatggaga actgtgtggg agagcgcaac cacccactct ttgtggtcta cctggcgctg
      481 cagctggtgg tgcttctgtg gggcctgtac ctggcatggt caggcctccg gttcttccag
      541 ccctggggtc tgtggttgcg gtccagcggg ctcctgttcg ccaccttcct gctgctgtcc
      601 ctcttctcgt tggtggccag cctgctcctc gtctcgcacc tctacctggt ggccagcaac
      661 accaccacct gggaattcat ctcctcacac cgcatcgcct atctccgcca gcgccccagc
      721 aacccettcg accgaggcct gacccgcaac ctggcccact tcttctgtgg atggccctca
      781 gggtcctggg agaccctctg ggctgaggag gaggaagagg gcagcagccc agctgtttag
      841 ggttgctgga ggccgggcta ccgtcttgtg cctgaaaacc acggggcctg tccccagctg
      901 gggtgagcgc tcagagggcc tggggccctc actcctgccc acgcctccca gaccccagaa
      961 cggagcttca agtcagacag atccctgcct tggtggcag ttctgccttc caaggaagaa
     1021 ggggaagaaa aggacctgtg ggtggctcag gcccaagcag accccgggct ccaccccagc
     1081 cccgcccagg ctgctgccag tgcacacttt tacaaattta atataaagca agtccagtct
     1141 taaaaagaca aaaaaaaaaa aaaaaaaaaa aaaaaaaaaa aaaa
//
```

ZDHHC13:

```
FEATURES             Location/Qualifiers
     source          1..2448
                     /organism="Homo sapiens"
                     /mol_type="mRNA"
                     /db_xref="taxon:9606"
                     /chromosome="11"
                     /map="11p15.1"
```

FIG. 13-73

```
     gene            1..2448
                     /gene="ZDHHC13"
                     /gene_synonym="FLJ10852; FLJ10941; HIP14L; HIP3RP;
                     MGC64994"
                     /note="zinc finger, DHHC-type containing 13"
                     /db_xref="GeneID:54503"
                     /db_xref="HGNC:18413"
                     /db_xref="HPRD:15710"
                     /db_xref="MIM:612815"
     CDS             106..1974
                     /gene="ZDHHC13"
                     /gene_synonym="FLJ10852; FLJ10941; HIP14L; HIP3RP;
                     MGC64994"
                     /note="isoform 1 is encoded by transcript variant 1;
                     huntingtin interacting protein HIP3RP; HIP14-like;
                     HIP14-related protein; zinc finger, DHHC domain
containing
                     13; DHHC-13; huntingtin-interacting protein HIP3RP;
                     putative MAPK-activating protein PM03; putative
                     NF-kappa-B-activating protein 209; zinc finger DHHC
                     domain-containing protein 13; huntingtin-interacting
                     protein 14-related protein; probable
palmitoyltransferase
                     ZDHHC13"
                     /codon_start=1
                     /product="probable palmitoyltransferase ZDHHC13 isoform
1"
                     /protein_id="NP_061901.2"
                     /db_xref="GI:47933346"
                     /db_xref="CCDS:CCDS44550.1"
                     /db_xref="GeneID:54503"
                     /db_xref="HGNC:18413"
                     /db_xref="HPRD:15710"
                     /db_xref="MIM:612815"

/translation="MEGPGLGSQCRNHSHGPHPPGFGRYGICAHENKELANAREALPL
```

FIG. 13-74

IEDSSNCDIVKATQYGIFERCKELVEAGYDVRQPDKENVSLLHWAAINNRLDLVKFYI

SKGAVVDQLGGDLNSTPLHWAIRQGHLPMVILLLQHGADPTLIDGEGFSSIHLAVLFQ

HMPIIAYLISKGQSVNMTDVNGQTPLMLSAHKVIGPEPTGFLLKFNPSLNVVDKIHQN

TPLHWAVAAGNVNAVDKLLEAGSSLDIQNVKGETPLDMALQNKNQLIIHMLKTEAKMR

ANQKFRLWRWLQKCELFLLLMLSVITMWAIGYILDFNSDSWLLKGCLLVTLFFLTSLF

PRFLVGYKNLVYLPTAFLLSSVFWIFMTWFILFFPDLAGAPFYFSFIFSIVAFLYFFY

KTWATDPGFTKASEEEKKVNIITLAETGSLDFRTFCTSCLIRKPLRSLHCHVCNCCVA

RYDQHCLWTGRCIGFGNHHYYIFFLFFLSMVCGWIIYGSFIYLSSHCATTFKEDGLWT

YLNQIVACSPWVLYILMLATFHFSWSTFLLLNQLFQIAFLGLTSHERISLQKQSKHMK

QTLSLRKTPYNLGFMQNLADFFQCGCFGLVKPCVVDWTSQYTMVFHPAREKVLRSV"

polyA_site 2428
/gene="ZDHHC13"
/gene_synonym="FLJ10852; FLJ10941; HIP14L; HIP3RP;
MGC64994"

ORIGIN 1 gggcgccagc aggaagtggg agaagaggcg acccaaggcg ggctggcggg ctggcggcag
61 tcgctacttg cctagtagcc tcagccgctg tgggctcctg gggagatgga ggggccgggg
121 ctgggctcgc agtgcaggaa tcacagccat ggccccccacc ctccaggatt tggtcgatat
181 ggcatctgtg cacatgaaaa caaagaactt gccaatgcaa gagaagctct tcctcttata
241 gaggactcta gtaactgtga cattgtcaaa gctactcaat acggaatttt tgaacgatgt
301 aaagagttgg tagaagcagg atatgatgtc aggcaaccag ataaagaaaa tgtgtcgctt
361 cttcattggg ctgctattaa caacagactg gatcttgtaa agttttatat ttcaaaaggt
421 gctgttgtag atcagttggg tggagattta aattcaactc ctcttcactg ggccatccga
481 caaggacatt tacctatggt catattatta ctccagcatg gtgcagaccc cactcttatt
541 gatggagagg gattcagcag catccacctg gcagtattgt ttcaacacat gcctattata
601 gcatatctca tctcaaaggg acagagtgtg aatatgacag atgtaaatgg gcagacacct
661 ctcatgttat cagctcacaa agtaattggg ccagaaccaa ctggatttct tttaaagttt

```
 721 aatccttctc tcaatgtggt tgataaaata caccaaaaca ctccacttca ctgggcagtt
 781 gcagcaggaa atgttaatgc agttgataag cttttggaag ctggttctag cctggatatc
 841 cagaatgtta agggagaaac acctcttgat atggctctac aaaacaaaaa tcagctcatt
 901 attcatatgc taaaaacaga agccaaaatg agagccaacc aaaagttcag actttggagg
 961 tggctgcaga aatgcgagct cttcctgctg ctgatgcttt ctgtgattac catgtgggct
1021 attggataca tattggactt caattcagat tcttggcttt taaaaggatg tcttctagta
1081 acactgtttt ttctgacatc tttgtttcca aggttcttgg ttgggtataa gaaccttgta
1141 tacttaccaa cagcctttct gctaagttct gtttttttgga tatttatgac ttggttcatc
1201 ttattttttc ctgatttagc aggagcccct ttctatttca gtttcatttt cagcatagta
1261 gcctttctat actttttcta taagacttgg gcaactgatc caggcttcac taaggcttct
1321 gaagaagaaa agaaagtgaa tatcatcacc cttgcagaaa ctggctctct ggacttcaga
1381 acattttgta catcatgtct tataaggaag ccattaaggt cactccactg ccatgtatgc
1441 aactgctgtg tggctcgata tgatcaacac tgcctgtgga ctggacggtg cataggtttt
1501 ggcaaccatc actattacat attcttcttg tttttccttt ccatggtatg tggctggatt
1561 atatatggat ctttcatcta tttgtccagt cattgtgcca caacattcaa agaagatgga
1621 ttatggactt acctcaatca gattgtggcc tgttcccctt gggttttata tatcttgatg
1681 ctagcaactt tccatttctc atggtcaaca tttttattat taaatcaact ctttcagatt
1741 gcctttctgg gcctgacctc ccatgagaga atcagcctgc agaagcagag caagcatatg
1801 aaacagacgt tgtccctcag gaagacacca tacaatcttg gattcatgca gaacctggca
1861 gatttctttc agtgtggctg ctttggcttg gtgaagccct gtgtggtaga ttggacatca
1921 cagtacacca tggtctttca cccagccagg gagaaggttc ttcgctcagt atgaagaaaa
1981 gcaacccaaa actctcaatc tgatttgttt ttgtttatgt cgatgccctg tagtttgaaa
2041 gtgaagtaaa gatttagaat tcacctaagt ccaaaggaaa acacgtggtt tttaaagcca
2101 ttaggtaaaa aaagttctca ataaaggcat tacaattttt taggtttaga aagatggact
2161 tttctgataa atcttggcag acatctaaaa aaaaaaccat atttttcaca agaaaatgca
2221 agttactttt tttggaaata atactcactg attatggata aaatggaata ttttcagata
2281 ctatattggc tgtttcaaaa tagtactatt ctttaaactt gtaatttttg ctaagttatt
2341 tgtctttgtt gtatctataa atatgtaaaa aatatttaaa tagatgtacc tgttttgctt
2401 tcacacttaa taaaaaattt tttttgtag ttgaaaaaaa aaaaaaaa
//
```

ZDHHC14:

FEATURES Location/Qualifiers

FIG. 13-75

```
     source          1..2821
                     /organism="Homo sapiens"
                     /mol_type="mRNA"
                     /db_xref="taxon:9606"
                     /chromosome="6"
                     /map="6q25.3"
     gene            1..2821
                     /gene="ZDHHC14"
                     /gene_synonym="FLJ20984; NEW1CP"
                     /note="zinc finger, DHHC-type containing 14"
                     /db_xref="GeneID:79683"
                     /db_xref="HGNC:20341"
                     /db_xref="HPRD:15711"
     exon            1..742
                     /gene="ZDHHC14"
                     /gene_synonym="FLJ20984; NEW1CP"
                     /inference="alignment:Splign"
                     /number=1
     CDS             498..1964
                     /gene="ZDHHC14"
                     /gene_synonym="FLJ20984; NEW1CP"
                     /note="isoform 1 is encoded by transcript variant 1;
NEW1
                     domain containing protein; zinc finger, DHHC domain
                     containing 14; DHHC-14; NEW1 domain-containing protein;
                     zinc finger DHHC domain-containing protein 14; probable
                     palmitoyltransferase ZDHHC14"
                     /codon_start=1
                     /product="probable palmitoyltransferase ZDHHC14 isoform
1"
                     /protein_id="NP_078906.2"
                     /db_xref="GI:24371241"
                     /db_xref="CCDS:CCDS5252.1"
                     /db_xref="GeneID:79683"
                     /db_xref="HGNC:20341"
                     /db_xref="HPRD:15711"
```

FIG. 13-76

/translation="MPPGGGGPMKDCEYSQISTHSSSPMESPHKKKKIAARRKWEVFP
GRNKFFCNGRIMMARQTGVFYLTLVLILVTSGLFFAFDCPYLAVKITPAIPAVAGILF
FFVMGTLLRTSFSDPGVLPRATPDEAADLERQIDIANGTSSGGYRPPPRTKEVIINGQ
TVKLKYCFTCKIFRPPRASHCSLCDNCVERFDHHCPWVGNCVGKRNYRFFYMFILSLS
FLTVFIFAFVITHVILRSQQTGFLNALKDSPASVLEAVVCFFSVWSIVGLSGFHTYLI
SSNQTTNEDIKGSWSNKRGKENYNPYSYGNIFTNCCVALCGPISPSLIDRRGYIQPDT
PQPAAPSNGITMYGATQSQSDMCDQDQCIQSTKFVLQAAATPLLQSEPSLTSDELHLP
GKPGLGTPCASLTLGPPTPPASMPNLAEATLADVMPRKDEHMGHQFLTPDEAPSPPRL
LAAGSPLAHSRTMHVLGLASQDSLHEDSVRGLVKLSSV"

exon 743..903
/gene="ZDHHC14"
/gene_synonym="FLJ20984; NEW1CP"
/inference="alignment:Splign"
/number=2 exon 904..1062
/gene="ZDHHC14"
/gene_synonym="FLJ20984; NEW1CP"
/inference="alignment:Splign"
/number=3 exon 1063..1200
/gene="ZDHHC14"
/gene_synonym="FLJ20984; NEW1CP"
/inference="alignment:Splign"
/number=4 exon 1201..1249
/gene="ZDHHC14"
/gene_synonym="FLJ20984; NEW1CP"
/inference="alignment:Splign"
/number=5

```
exon            1250..1352
                /gene="ZDHHC14"
                /gene_synonym="FLJ20984; NEW1CP"
                /inference="alignment:Splign"
                /number=6
exon            1353..1462
                /gene="ZDHHC14"
                /gene_synonym="FLJ20984; NEW1CP"
                /inference="alignment:Splign"
                /number=7
exon            1463..1565
                /gene="ZDHHC14"
                /gene_synonym="FLJ20984; NEW1CP"
                /inference="alignment:Splign"
                /number=8
exon            1566..2787
                /gene="ZDHHC14"
                /gene_synonym="FLJ20984; NEW1CP"
                /inference="alignment:Splign"
                /number=9a
STS             2210..2333
                /gene="ZDHHC14"
                /gene_synonym="FLJ20984; NEW1CP"
                /standard_name="SHGC-34375"
                /db_xref="UniSTS:56404"
STS             2524..2660
                /gene="ZDHHC14"
                /gene_synonym="FLJ20984; NEW1CP"
                /standard_name="RH46611"
                /db_xref="UniSTS:4850"
STS             2654..2780
                /gene="ZDHHC14"
                /gene_synonym="FLJ20984; NEW1CP"
                /standard_name="WI-14340"
                /db_xref="UniSTS:60432"
```

FIG. 13-79

ORIGIN

```
   1 gaaggagtgg acccaacctg gccgcgccgc agaagtggct cccgaggaag ccggcgccgg
  61 ggccgccgcc tcgtgtcccc tcggggcgca gtgctcgggg gtcggcgcgc cagagccgag
 121 gcgcggccgg ggagccgggg gctgcggggc cgagcgggca gccgcgccag gggcgggcg
 181 ctcggcgacc cgggggccgg ccgggctgag ccccgcgccc cgggacgcgg gctggaagcg
 241 acggaggagt gctgccgcgg gctgcggacc agcgccgtcc cctcacgcag cggggattct
 301 gctatgacag ttgggctccc ccgagggtta acctgggtgt cctcggcaaa gttgtcgccg
 361 agccgggagc ccgtgtaggg gccgcggcgc cgcggctcgg ggggcggccg ggcggccggc
 421 ggcggtcgtg gctcggcggg gccccgcgg ccgggggggct cctggggctg tgcgccccca
 481 gccggctgcc ctcgtggatg cctcccggcg gcggcgggcc catgaaagac tgcgagtaca
 541 gccagatcag cacccacagc tcctccccca tggagtcgcc ccacaagaag aagaaaatcg
 601 cggcccggag gaaatgggag gtgttcccgg gaagaaacaa gttcttctgt aacgggagga
 661 tcatgatggc ccggcagacg ggcgtcttct acctgacgct cgtcctcatc ctggtcacta
 721 gcggactctt cttcgccttc gactgtccgt acctggcggt gaaaatcacc cctgccatcc
 781 ctgcagtcgc tggcatcctg ttcttctttg tgatggggac cctgctccgc accagcttca
 841 gcgaccccgg agtcctccca ccagccacgc ctgatgaagc cgccgatctg gaaaggcaaa
 901 tagatatcgc aaacggcacc agttcagggg ggtaccgccc gcctcccaga accaaagaag
 961 tcatcatcaa tggccagacc gtgaaactta aatactgttt cacctgcaag attttccggc
1021 cccctcgcgc ctcccattgc agcctttgtg ataactgcgt agaacggttt gatcaccact
1081 gtccctgggt aggcaactgt gtggggaaaa gaaactacag attttttat atgtttattt
1141 tatctctgtc ttttctgaca gtctttatat ttgcattcgt tatcacccac gtcattcttc
1201 gttcacagca aacaggattc ctaaatgccc ttaaggacag tcctgcaagc gtcctggagg
1261 ctgtggtgtg cttcttctct gtctggtcca tcgttggcct ctcaggattc cacacctact
1321 tgatcagctc caaccagaca acaaatgagg acattaaagg atcctggtca aataaaagag
1381 gtaaagaaaa ttacaatccc tacagctacg gaaatatctt taccaactgc tgtgttgccc
1441 tgtgtgggcc catctcacca agcctgatcg acagaagagg gtacatccag cccgacacgc
1501 cgcagccagc agcaccctcc aatggcatca ccatgtacgg ggccacgcag tcacagagtg
1561 acatgtgcga ccaagaccag tgcattcaga gcaccaaatt cgttttgcag gctgcagcca
1621 cgcccctgct gcagagcgag cccagcctca ccagcgacga gctgcacctg cccgggaagc
1681 ctggcctggg cacgccctgc gccagcctca cactgggccc gcccacaccg cccgcctcca
1741 tgcccaacct cgccgaggcc acgctcgcgg acgtgatgcc ccggaaagat gagcacatgg
1801 gccaccagtt cctgacgccc gatgaggcgc cctcgccccc caggctactg gcggcgggca
1861 gccccctggc gcacagccgc accatgcacg tgctgggcct ggccagccag gactccctgc
1921 atgaggactc tgtgcgcggc ctggtgaagc tcagctccgt gtgacccaca tggccccagg
1981 ccgggggaca ccagaggctc ctccatgggc agcaggagtg agcggagcgg tgtgtcccac
2041 agcgactttc ccagccaatg ccacggtgga gatgacagcc ccaggtctgg ggtacagaga
```

FIG. 13-80

```
2101 ccacttagga tggcacaggg tggctggccc cggatgctga gagcttggtt tcatttgaat
2161 tttcttcccc aacctgagtg ctttgacaac aatggaaata gagaagtggc tgctttcttt
2221 tggtgaccct ccaggggtgg aatcggagtg tgtctgcccg cccttgtgac agacacacgg
2281 aaggcttctg acgcttgtgg ccagactgca attgcactta tgtgttatgc tactaatatt
2341 tgaaacagac ctgccattcc atttgttaat taaaaaaaaa aaaaatccta aagggaaaaa
2401 accgaccagg tgtggatctg catgccacgc tgccgtctgt gttacagtgg tgttgctatt
2461 tccaaggaag tgctgctttc tttttctttt tttaattttg tgaattttca agtgctgttt
2521 tgttggaaga cagtgcaacg aactgagact aatggacagt gtcatcactc agcttactgg
2581 gctgaggcgt ctgtggagag gtggcaccgg cgctgcagag ggcggctggg gttccgtcgt
2641 gtcgggtgtc acttcacctt ctgtttggcc cctcgatgag gtctcgtgtt gagatattgt
2701 gtgccacaac ccccacagtc ttcacctccg tgtgtgatga aacttcccgt ggacagccaa
2761 taaaatgacg tcctctgtta ttttggaaaa aaaaaaaaaa aaaaaaaaaa aaaaaaaaaa
2821 a
//
```

ZDHHC15:

```
FEATURES             Location/Qualifiers
     source          1..1782
                     /organism="Homo sapiens"
                     /mol_type="mRNA"
                     /db_xref="taxon:9606"
                     /chromosome="X"
                     /map="Xq13.3"
     gene            1..1782
                     /gene="ZDHHC15"
                     /gene_synonym="FLJ31812; MGC119974; MGC119975;
MGC119976;
                     MRX91"
                     /note="zinc finger, DHHC-type containing 15"
                     /db_xref="GeneID:158866"
```

FIG. 13-81

```
                    /db_xref="HGNC:20342"
                    /db_xref="HPRD:06758"
                    /db_xref="MIM:300576"
     STS            1..1106
                    /gene="ZDHHC15"
                    /gene_synonym="FLJ31812; MGC119974; MGC119975;
MGC119976;
                    MRX91"
                    /db_xref="UniSTS:482995"
     exon           1..152
                    /gene="ZDHHC15"
                    /gene_synonym="FLJ31812; MGC119974; MGC119975;
MGC119976;
                    MRX91"
                    /inference="alignment:Splign"
                    /number=1
     CDS            17..1030
                    /gene="ZDHHC15"
                    /gene_synonym="FLJ31812; MGC119974; MGC119975;
MGC119976;
                    MRX91"
                    /note="zinc finger, DHHC domain containing 15"
                    /codon_start=1
                    /product="zinc finger, DHHC-type containing 15"
                    /protein_id="NP_659406.1"
                    /db_xref="GI:21450653"
                    /db_xref="CCDS:CCDS14430.1"
                    /db_xref="GeneID:158866"
                    /db_xref="HGNC:20342"
                    /db_xref="HPRD:06758"
                    /db_xref="MIM:300576"
```

/translation="MRRGWKMALSGGLRCCRRVLSWVPVLVIVLVVLWSYYAYVFELC

LVTVLSPAEKVIYLILYHAIFVFFTWTYWKSIFTLPQQPNQKFHLSYTDKERYENEER

PEVQKQMLVDMAKKLPVYTRTGSGAVRFCDRCHLIKPDRCHHCSVCAMCVLKMDHHCP

FIG. 13-82

WVNNCIGFSNYKFFLQFLAYSVLYCLYIATTVFSYFIKYWRGELPSVRSKFHVLFLLF

VACMFFVSLVILFGYHCWLVSRNKTTLEAFCTPVFTSGPEKNGFNLGFIKNIQQVFGD

KKKFWLIPIGSSPGDGHSFPMRSMNESQNPLLANEETWEDNEDDNQDYPEGSSSLAVE
TET"
<u>exon</u> 153..179
/gene="ZDHHC15"
/gene_synonym="FLJ31812; MGC119974; MGC119975;
MGC119976;
MRX91"
/inference="alignment:Splign"
/number=2
<u>exon</u> 180..274
/gene="ZDHHC15"
/gene_synonym="FLJ31812; MGC119974; MGC119975;
MGC119976;
MRX91"
/inference="alignment:Splign"
/number=3
<u>exon</u> 275..395
/gene="ZDHHC15"
/gene_synonym="FLJ31812; MGC119974; MGC119975;
MGC119976;
MRX91"
/inference="alignment:Splign"
/number=4
<u>exon</u> 396..465
/gene="ZDHHC15"
/gene_synonym="FLJ31812; MGC119974; MGC119975;
MGC119976;
MRX91"
/inference="alignment:Splign"
/number=5
<u>exon</u> 466..498
/gene="ZDHHC15"

FIG. 13-83

/gene_synonym="FLJ31812; MGC119974; MGC119975;
MGC119976;
MRX91"
/inference="alignment:Splign"
/number=6
exon 499..619
/gene="ZDHHC15"
/gene_synonym="FLJ31812; MGC119974; MGC119975;
MGC119976;
MRX91"
/inference="alignment:Splign"
/number=7
exon 620..752
/gene="ZDHHC15"
/gene_synonym="FLJ31812; MGC119974; MGC119975;
MGC119976;
MRX91"
/inference="alignment:Splign"
/number=8
exon 753..879
/gene="ZDHHC15"
/gene_synonym="FLJ31812; MGC119974; MGC119975;
MGC119976;
MRX91"
/inference="alignment:Splign"
/number=9
exon 880..983
/gene="ZDHHC15"
/gene_synonym="FLJ31812; MGC119974; MGC119975;
MGC119976;
MRX91"
/inference="alignment:Splign"
/number=10
exon 984..1062
/gene="ZDHHC15"
/gene_synonym="FLJ31812; MGC119974; MGC119975;

MGC119976;

FIG. 13-84

MRX91"
/inference="alignment:Splign"
/number=11
exon 1063..1782
/gene="ZDHHC15"
/gene_synonym="FLJ31812; MGC119974; MGC119975;
MGC119976;
MRX91"
/inference="alignment:Splign"
/number=12
ORIGIN

```
   1 gatcttcgag ccaaagatgc ggcgaggctg gaagatggct ctgtctgggg ggctgcggtg
  61 ctgccgccgg gtactgtcct gggtgccagt gctcgttatt gtcctcgtcg tgctctggtc
 121 ctactatgcc tacgtctttg aactctgcct ggtgactgtt ttgagcccag cagaaaaagt
 181 tatttacctc atactctacc atgccatctt tgtgttcttt acctggacct actggaagtc
 241 tatctttaca ctcccacagc agccaaacca gaagttccac ttgtcctaca cagacaagga
 301 gcgctatgaa aatgaagaaa gacctgaggt ccagaagcag atgcttgttg atatggccaa
 361 aaagctaccg gtttacacaa gaactggaag tggagctgta cgattctgtg accggtgtca
 421 tctgatcaag ccagaccgct gccaccactg ctctgtctgt gctatgtgtg tgttaaaaat
 481 ggatcatcac tgcccttggg ttaataactg cattggattt tccaactaca aattcttcct
 541 tcaattctta gcttactctg ttctctactg cctgtacatt gctacgacag tcttcagcta
 601 tttcatcaaa tactggagag gggaattacc cagtgttcgc tctaagttcc atgtcctttt
 661 tcttctcttt gtggcctgca tgtttttttgt cagccttgtg attctctttg gttaccattg
 721 ttggcttgtc agcagaaaca aaaccacctt agaggccttc tgcactccag tgtttacaag
 781 tggcccagag aaaaatgggt tcaaccttgg cttcatcaag aatatccagc aggtgtttgg
 841 agataagaag aagttctggt taatacctat tggttccagc cctggtgatg gacactcctt
 901 ccctatgagg tctatgaatg agtcacagaa cccactgcta gcaaatgaag aaacctggga
 961 agacaacgag gatgacaacc aagattatcc agaaggctca tcatctcttg ctgtggaaac
1021 ggaaacatag cagttttcac atttcctgca tctctcagac aggactcacc atctctgcct
1081 cccatgaggc ttacagagtt caatgttgga aatcattgta atcttcaaaa taagtcaccg
1141 tgttggattg aaagcttcaa aatttgaaag aattccatca aatacttgct gtgtaaatgt
1201 ttctggactt tatgttattt aatttactga ctgaaatcca atttggaatt tggtagcagt
1261 taattcaagc caattttttt tgtttcttca tttcccctcc cccaatccat gaaagcctaa
1321 atgtaaaata tatcttttca ttcatcttat caggtaaaag gaaattcaga aaatttcctt
1381 agagtcttta attcccccac aaagattatt aatcacatat atagggcctt tttggtgttg
1441 aagggaatca aactacattt gctgcttgtg tgcgtgtgca tttgtgaaca cgtacagcat
```

FIG. 13-85

```
1501 atctatacaa aattctgcta tagtgtgaaa atcagggcta aaaacctgaa gcctttgttt
1561 aattatgctt ttcctctaaa tagcaactta aatatttgct agactttgaa tcatcgctat
1621 atcaagtatc taaaatttgg gagggtgaat cagtacactg tgaccaaggt cctcaaattg
1681 gaatttgaac aacaatgtaa aacctgttct gtcacaaatg ttcctgaaag caccacagct
1741 actcaagaag atcaaattca ggacataaac tttattgaac at
//
```

ZDHHC16:

```
FEATURES             Location/Qualifiers
     source          1..1816
                     /organism="Homo sapiens"
                     /mol_type="mRNA"
                     /db_xref="taxon:9606"
                     /chromosome="10"
                     /map="10q24.1"
     gene            1..1816
                     /gene="ZDHHC16"
                     /gene_synonym="APH2; MGC2993"
                     /note="zinc finger, DHHC-type containing 16"
                     /db_xref="GeneID:84287"
                     /db_xref="HGNC:20714"
                     /db_xref="HPRD:15712"
     exon            1..181
                     /gene="ZDHHC16"
                     /gene_synonym="APH2; MGC2993"
                     /inference="alignment:Splign"
                     /number=1a
     exon            182..429
                     /gene="ZDHHC16"
                     /gene_synonym="APH2; MGC2993"
                     /inference="alignment:Splign"
                     /number=3
```

FIG. 13-86

```
     CDS             187..1320
                     /gene="ZDHHC16"
                     /gene_synonym="APH2; MGC2993"
                     /note="isoform 1 is encoded by transcript variant 1;
                     Abl-philin 2; zinc finger, DHHC domain containing 16;
                     DHHC-16; zinc finger DHHC domain-containing protein 16;
                     probable palmitoyltransferase ZDHHC16"
                     /codon_start=1
                     /product="probable palmitoyltransferase ZDHHC16 isoform
1"
                     /protein_id="NP_115703.2"
                     /db_xref="GI:37594455"
                     /db_xref="CCDS:CCDS7460.1"
                     /db_xref="GeneID:84287"
                     /db_xref="HGNC:20714"
                     /db_xref="HPRD:15712"

/translation="MRGQRSLLLGPARLCLRLLLLLGYRRRCPPLLRGLVQRWRYGKV

CLRSLLYNSFGGSDTAVDAAFEPVYWLVDNVIRWFGVVFVVLVIVLTGSIVAIAYLCV

LPLILRTYSVPRLCWHFFYSHWNLILIVFHYYQAITTPPGYPPQGRNDIATVSICKKC

IYPKPARTHHCSICNRCVLKMDHHCPWLNNCVGHYNHRYFFSFCFFMTLGCVYCSYGS

WDLFREAYAAIEKMKQLDKNKLQAVANQTYHQTPPPTFSFRERMTHKSLVYLWFLCSS

VALALGALTVWHAVLISRGETSIERHINKKERRRLQAKGRVFRNPYNYGCLDNWKVFL
                     GVDTGRHWLTRVLLPSSHLPHGNGMSWEPPPWVTAHSASVMAV"
     exon            430..624
                     /gene="ZDHHC16"
                     /gene_synonym="APH2; MGC2993"
                     /inference="alignment:Splign"
                     /number=4
     exon            625..713
                     /gene="ZDHHC16"
                     /gene_synonym="APH2; MGC2993"
```

FIG. 13-87

```
                     /inference="alignment:Splign"
                     /number=5
     exon            714..742
                     /gene="ZDHHC16"
                     /gene_synonym="APH2; MGC2993"
                     /inference="alignment:Splign"
                     /number=6
     exon            743..876
                     /gene="ZDHHC16"
                     /gene_synonym="APH2; MGC2993"
                     /inference="alignment:Splign"
                     /number=7a
     exon            877..924
                     /gene="ZDHHC16"
                     /gene_synonym="APH2; MGC2993"
                     /inference="alignment:Splign"
                     /number=8
     exon            925..1010
                     /gene="ZDHHC16"
                     /gene_synonym="APH2; MGC2993"
                     /inference="alignment:Splign"
                     /number=9
     exon            1011..1134
                     /gene="ZDHHC16"
                     /gene_synonym="APH2; MGC2993"
                     /inference="alignment:Splign"
                     /number=10
     exon            1135..1205
                     /gene="ZDHHC16"
                     /gene_synonym="APH2; MGC2993"
                     /inference="alignment:Splign"
                     /number=11
     exon            1206..1799
                     /gene="ZDHHC16"
                     /gene_synonym="APH2; MGC2993"
                     /inference="alignment:Splign"
```

FIG. 13-88

```
                     /number=12
     STS             1504..1682
                     /gene="ZDHHC16"
                     /gene_synonym="APH2; MGC2993"
                     /standard_name="A002I07"
                     /db_xref="UniSTS:56306"
     STS             1633..1782
                     /gene="ZDHHC16"
                     /gene_synonym="APH2; MGC2993"
                     /standard_name="SHGC-31924"
                     /db_xref="UniSTS:61660"
     STS             1633..1753
                     /gene="ZDHHC16"
                     /gene_synonym="APH2; MGC2993"
                     /standard_name="RH11297"
                     /db_xref="UniSTS:75220"
ORIGIN
        1 gtgtcgttga ggatgggctg gcggcgggtc cgggtccgct gcctggcgct gcgggcgccg
       61 ggccatggtg gtttggattg agccgggccc ggccggggcg ccgagtcgga gggggtgcca
      121 gtgagcggcg gcagaggcta cggggctcgg tttggctgac tggggagtcg gcaggcgcca
      181 ggaaccatgc gaggccagcg gagcctgctg ctgggcccgg cccgcctctg cctccgcctc
      241 cttctgctgc tgggttacag gcgcccgctgt ccacctctac tccggggtct agtacagcgc
      301 tggcgctacg gcaaggtctg cctgcgctcc ctgctctaca actcctttgg gggcagtcac
      361 accgctgttg atgctgcctt tgagcctgtc tactggctgg tagacaacgt gatccgctgg
      421 tttggagtgg tgttcgtggt cctggtgatc gtgctgacag gctccattgt agctatcgcc
      481 tacctgtgtg tcctgcctct catcctccga acctactcag tgccacgact ctgctggcat
      541 ttcttctata gccactggaa tctgatcctg attgtcttcc actactacca ggccatcacc
      601 actccgcctg ggtacccacc ccagggcagg aatgatatcg ccaccgtctc catctgtaag
      661 aagtgcattt accccaagcc agcccgaaca caccactgca gcatctgcaa caggtgtctg
      721 ctgaagatgg atcaccactg cccctggcta aacaattgtg tgggccacta taaccatcgg
      781 tacttcttct ctttctgctt tttcatgact ctgggctgtg tctactgcag ctatggaagt
      841 tgggaccttt tccgggaggc ttatgctgcc attgagaaaa tgaaacagct cgacaagaac
      901 aaactacagg cggttgccaa ccagacttat caccagaccc caccacccac cttctccttt
      961 cgagaaagga tgactcacaa gagtcttgtc tacctctggt tcctgtgcag ttctgtggca
     1021 cttgccctgg gtgccctaac tgtatggcat gctgttctca tcagtcgagg tgagactagc
     1081 atcgaaaggc acatcaacaa gaaggagaga cgtcggctac aggccaaggg cagagtattt
```

FIG. 13-89

```
1141 aggaatcctt acaactacgg ctgcttggac aactggaagg tattcctggg tgtggataca
1201 ggaaggcact ggcttactcg ggtgctctta ccttctagtc acttgcccca tgggaatgga
1261 atgagctggg agccccctcc ctgggtgact gctcactcag cctctgtgat ggcagtgtga
1321 gctggactgt gtcagccacg actcgagcac tcattctgct ccctatgtta tttcaagggc
1381 ctccaagggc agcttttctc agaatccttg atcaaaaaga gccagtgggc ctgccttagg
1441 gtaccatgca ggacaattca aggaccagcc tttttaccac tgcagaagaa agacacaatg
1501 tggagaaatc ttaggactga catcccttta ctcaggcaaa cagaagttcc aaccccagac
1561 taggggtcag gcagctagct acctaccttg cccagtgctg acccggacct cctccaggat
1621 acagcactgg agttggccac cacctcttct acttgctgtc tgaaaaaaca cctgactagt
1681 acagctgaga tcttggcttc tcaacagggc aaagatacca ggcctgctgc tgaggtcact
1741 gccacttctc acatgctgct taagggagca caaataaagg tattcgattt ttaaagataa
1801 aaaaaaaaaa aaaaaa
//
```

ZDHHC17:

```
FEATURES             Location/Qualifiers
     source          1..4771
                     /organism="Homo sapiens"
                     /mol_type="mRNA"
                     /db_xref="taxon:9606"
                     /chromosome="12"
                     /map="12q21.2"
     gene            1..4771
                     /gene="ZDHHC17"
                     /gene_synonym="HIP14; HIP3; HSPC294; HYPH; KIAA0946"
                     /note="zinc finger, DHHC-type containing 17"
                     /db_xref="GeneID:23390"
                     /db_xref="HGNC:18412"
                     /db_xref="HPRD:09697"
                     /db_xref="MIM:607799"
     exon            1..256
                     /gene="ZDHHC17"
```

FIG. 13-90

/gene_synonym="HIP14; HIP3; HSPC294; HYPH; KIAA0946"
/inference="alignment:Splign"
/number=1
CDS 164..2062
/gene="ZDHHC17"
/gene_synonym="HIP14; HIP3; HSPC294; HYPH; KIAA0946"
/note="Huntingtin interacting protein H; huntingtin interacting protein 3; huntingtin interacting protein 14;
zinc finger, DHHC domain containing 17; HIP-3; HIP-14; DHHC-17; huntingtin yeast partner H; huntingtin-interacting protein 3; huntingtin-interacting protein H; huntingtin-interacting protein 14; putative MAPK-activating protein PM11; putative NF-kappa-B-activating protein 205; zinc finger DHHC domain-containing protein 17"
/codon_start=1
/product="palmitoyltransferase ZDHHC17"
/protein_id="NP_056151.2"
/db_xref="GI:103471993"
/db_xref="CCDS:CCDS44946.1"
/db_xref="GeneID:23390"
/db_xref="HGNC:18412"
/db_xref="HPRD:09697"
/db_xref="MIM:607799"

/translation="MQREEGFNTKMADGPDEYDTEAGCVPLLHPEEIKPQSHYNHGYG

EPLGRKTHIDDYSTWDIVKATQYGIYERCRELVEAGYDVRQPDKENVTLLHWAAINNR

IDLVKYYISKGAIVDQLGGDLNSTPLHWATRQGHLSMVVQLMKYGADPSLIDGEGCSC

IHLAAQFGHTSIVAYLIAKGQDVDMMDQNGMTPLMWAAYRTHSVDPTRLLLTFNVSVN

LGDKYHKNTALHWAVLAGNTTVISLLLEAGANVDAQNIKGESALDLAKQRKNVWMINH

LQEARQAKGYDNPSFLRKLKADKEFRQKVMLGTPFLVIWLVGFIADLNIDSWLIKGLM

FIG. 13-91

YGGVWATVQFLSKSFFDHSMHSALPLGIYLATKFWMYVTWFFWFWNDLNFLFIHLPFL

ANSVALFYNFGKSWKSDPGIIKATEEQKKKTIVELAETGSLDLSIFCSTCLIRKPVRS

KHCGVCNRCIAKFDHHCPWVGNCVGAGNHRYFMGYLFFLLFMICWMIYGCISYWGLHC

ETTYTKDGFWTYITQIATCSPWMFWMFLNSVFHFMWVAVLLMCQMYQISCLGITTNER

MNARRYKHFKVTTTSIESPFNHGCVRNIIDFFEFRCCGLFRPVIVDWTRQYTIEYDQI

SGSGYQLV"

exon 257..360
/gene="ZDHHC17"
/gene_synonym="HIP14; HIP3; HSPC294; HYPH; KIAA0946"
/inference="alignment:Splign"
/number=2 exon 361..483
/gene="ZDHHC17"
/gene_synonym="HIP14; HIP3; HSPC294; HYPH; KIAA0946"
/inference="alignment:Splign"
/number=3 exon 484..561
/gene="ZDHHC17"
/gene_synonym="HIP14; HIP3; HSPC294; HYPH; KIAA0946"
/inference="alignment:Splign"
/number=4 exon 562..706
/gene="ZDHHC17"
/gene_synonym="HIP14; HIP3; HSPC294; HYPH; KIAA0946"
/inference="alignment:Splign"
/number=5 exon 707..771
/gene="ZDHHC17"
/gene_synonym="HIP14; HIP3; HSPC294; HYPH; KIAA0946"
/inference="alignment:Splign"
/number=6

FIG. 13-92

```
exon            772..934
                /gene="ZDHHC17"
                /gene_synonym="HIP14; HIP3; HSPC294; HYPH; KIAA0946"
                /inference="alignment:Splign"
                /number=7
exon            935..1060
                /gene="ZDHHC17"
                /gene_synonym="HIP14; HIP3; HSPC294; HYPH; KIAA0946"
                /inference="alignment:Splign"
                /number=8
exon            1061..1203
                /gene="ZDHHC17"
                /gene_synonym="HIP14; HIP3; HSPC294; HYPH; KIAA0946"
                /inference="alignment:Splign"
                /number=9
exon            1204..1304
                /gene="ZDHHC17"
                /gene_synonym="HIP14; HIP3; HSPC294; HYPH; KIAA0946"
                /inference="alignment:Splign"
                /number=10
exon            1305..1429
                /gene="ZDHHC17"
                /gene_synonym="HIP14; HIP3; HSPC294; HYPH; KIAA0946"
                /inference="alignment:Splign"
                /number=11
exon            1430..1492
                /gene="ZDHHC17"
                /gene_synonym="HIP14; HIP3; HSPC294; HYPH; KIAA0946"
                /inference="alignment:Splign"
                /number=12
exon            1493..1586
                /gene="ZDHHC17"
                /gene_synonym="HIP14; HIP3; HSPC294; HYPH; KIAA0946"
                /inference="alignment:Splign"
                /number=13
exon            1587..1670
```

FIG. 13-93

```
                     /gene="ZDHHC17"
                     /gene_synonym="HIP14; HIP3; HSPC294; HYPH; KIAA0946"
                     /inference="alignment:Splign"
                     /number=14
     exon            1671..1828
                     /gene="ZDHHC17"
                     /gene_synonym="HIP14; HIP3; HSPC294; HYPH; KIAA0946"
                     /inference="alignment:Splign"
                     /number=15
     STS             1698..1798
                     /gene="ZDHHC17"
                     /gene_synonym="HIP14; HIP3; HSPC294; HYPH; KIAA0946"
                     /standard_name="SHGC-44319"
                     /db_xref="UniSTS:24567"
     exon            1829..1923
                     /gene="ZDHHC17"
                     /gene_synonym="HIP14; HIP3; HSPC294; HYPH; KIAA0946"
                     /inference="alignment:Splign"
                     /number=16
     exon            1924..4771
                     /gene="ZDHHC17"
                     /gene_synonym="HIP14; HIP3; HSPC294; HYPH; KIAA0946"
                     /inference="alignment:Splign"
                     /number=17
     STS             4414..4679
                     /gene="ZDHHC17"
                     /gene_synonym="HIP14; HIP3; HSPC294; HYPH; KIAA0946"
                     /standard_name="WI-19323"
                     /db_xref="UniSTS:79247"
     STS             4557..4679
                     /gene="ZDHHC17"
                     /gene_synonym="HIP14; HIP3; HSPC294; HYPH; KIAA0946"
                     /standard_name="RH11174"
                     /db_xref="UniSTS:79246"
ORIGIN
        1 agaaacccgc gccctccgag gggggagggg acagaggggg cgtcacgggg gcaggagaag
```

FIG. 13-94

```
  61 aaggaggagg aggcccgcgt cgcctccggc ggggctcgcg ctcgccccgc gctcgccctc
 121 cgcctcgccc gagccccggg agggtgaaac gctttctccc agcatgcagc gggaggaggg
 181 atttaacacc aagatggcgg acggcccgga tgagtacgat accgaagcgg gctgtgtgcc
 241 ccttctccac ccagaggaaa tcaaacccca aagccattat aaccatggat atggtgaacc
 301 tcttggacgg aaaactcata ttgatgatta cagcacatgg gacatagtca aggctacaca
 361 atatggaata tatgaacgct gtcgagaatt ggtggaagca ggttatgatg tacggcaacc
 421 ggacaaagaa aatgttaccc tcctccattg ggctgccatc aataacagaa tagatttagt
 481 caaatactat atttcgaaag gtgctattgt ggatcaactt ggaggggacc tgaattcaac
 541 tccattgcac tgggccacaa gacaaggcca tctatccatg gttgtgcaac taatgaaata
 601 tggtgcagat ccttcattaa ttgatggaga aggatgtagc tgtattcatc tggctgctca
 661 gttcggacat acctcaattg ttgcttatct catagcaaaa ggacaggatg tagatatgat
 721 ggatcagaat ggaatgacgc ctttaatgtg ggcagcatat agaacacata gtgtggatcc
 781 aactagattg cttttaacat tcaatgtttc agttaacctt ggtgacaagt atcacaaaaa
 841 cactgctctg cattgggcag tgctagcagg gaataccaca gtcattagcc ttcttctgga
 901 agctggagct aatgttgatg cccagaatat caagggcgaa tcagcgcttg atttggcaaa
 961 acagagaaaa aatgtgtgga tgatcaacca cttacaagag gcaaggcaag caaaaggata
1021 tgacaatccg tccttcctta gaaagctgaa agctgataag gaatttcggc agaaagtaat
1081 gttaggaact cctttcctag ttatttggct ggtgggtttt atagcagacc taaatattga
1141 ttcttggctc attaaagggc taatgtatgg tggtgtttgg gctacagtac agtttctttc
1201 aaaatccttt ttcgatcatt caatgcatag tgcattgccc cttgggatat atttggcaac
1261 caaattctgg atgtatgtga cgtggttctt ctggttttgg aatgatctca actttttatt
1321 tatccatctt ccattccttg ccaatagtgt tgcacttttc tacaattttg gaaaatcttg
1381 gaaatcagat ccagggatta ttaaagcaac agaagagcaa aagaaaaaga caatagttga
1441 acttgcagag acaggaagtc tggacctcag tatattctgc agtacctgtt tgatacgaaa
1501 accggtgagg tccaaacatt gtggtgtgtg caacccgctgt atagcaaaat ttgatcatca
1561 ttgcccatgg gtgggtaact gtgtaggtgc aggcaaccat agatatttta tgggctacct
1621 attcttcttg ctttttatga tctgctggat gatttatggt tgtatatctt actggggact
1681 ccactgtgag accacttaca ccaaggatgg attttggaca tacattactc agattgccac
1741 gtgttcacct tggatgtttt ggatgttcct gaacagtgtt ttccacttca tgtgggtggc
1801 tgtattactc atgtgtcaga tgtaccagat atcatgttta ggtattacta caaatgaaag
1861 aatgaatgcc aggagataca agcactttaa agtcacaaca acgtctattg aaagcccatt
1921 caaccatgga tgtgtaagaa atattataga cttctttgaa tttcgatgct gtggcctctt
1981 tcgtcctgtt atcgtggact ggaccaggca gtatacaata gaatatgacc aaatatcagg
2041 atctgggtac cagctggtgt agcgacatct tatcctatga agcatattgc tgagtggtgc
2101 ctgaaaattg tgtctgtccg tgtctttctc acactcgaat ccacatcctt tgaacaagag
2161 catgctatgt gtagggctaa tggtgaattt tacagtcttt ttttcaacac ttttattaac
```

FIG. 13-95

2221 aaaagtaaac atggacagaa cacactgcca tttctgggaa gagtaaagat gataaaaaat
2281 aattttaatg gttcttaatg tggaaattca caacatactc aacttttggg ttttgttctc
2341 acagtatttt tcacaaaaaa agggtaaact tattctattg acagacatgg tgtactgatc
2401 agaaatgttc agttttaact aaaactaaat ttatgttatt tggctaaatg ttatgatgca
2461 gtctagtacg agtattgcat ctaattccag gagcattgtt ttaagttgat tgactagtta
2521 ttatgtacat ttcagaatgt acacataaat actgtgatga aaatcatgtg attgggatct
2581 actgtgatgt tgtcttcaaa ggcaggagaa aataatgttc acaataaaat gtgctaacaa
2641 tgttttgttt ctatcagctg ttgcaatgct gatatatttc tagttcagtg aaataatttg
2701 tagtaacctt actctgaggt tttacggtct gataatgaag cacttgcatg agtatagtaa
2761 gtcatgtttt tttgttcaaa tttaaaagcc ctgctaattg catgacacac cacatagaat
2821 gtatactagc agatactatc cagtgaagca taaattagaa tttaatttga tgttcaaaaa
2881 cagttccatt tttaagggtt aaggtggtat tttcaagaaa aggcagaaca aataatgcaa
2941 aattctcagt aatagtgata catggatata cttcctttta aattctcagc tgcaaaataa
3001 ttgtagacaa aataatggca tttaactaaa gatggagcat gatctaagta catagcacat
3061 gtgaataaaa gaaaagctga cagtatattc tggtttcaat aaaatgacct atcagaaagt
3121 agaatttcat ccccaagagt atttcagttt atccaatatt gagtaagttc tgaaacagtt
3181 ttagaaaaaa ttttcttttt gttaaatgtg atgcactgat caatttttgt cacagcattt
3241 tcataccttc atggtggact actagtcact gcttccataa atattgttta cagggtgaga
3301 tttggtttat tcatcttaag tgctgtagca aactgtggtt cgagcaacct gtgggaaatc
3361 tgtgagaggg aatggggtgg gagatgtggg ggaatggtgg tcagactgat gacagatcct
3421 agaccaatgt aaagaatgtg tatctgtata taaataattt atcaaatagt tttctctttg
3481 tgtctgtgtt agtgttttta aagctgctca tttcattttg tccaaccaaa aagaaaaggg
3541 agataactaa tgagcttcta gtgatgttca aaattgctgt taataggcat tataccctgc
3601 aagttcactg catgtctgat gcttggtaaa actagtcttc cctgtaaaat gcagattaca
3661 ggtattaaag caatctagtg gtataccccgc cccttgcctt agtaagagga gcagtgaaat
3721 gtatatagtt gatgttcagt atttccaagt accattttta tatagtagct tatttgacca
3781 taagtcacac atcaaaaaaa gattaccctt agtgtatgtg ttttaatatt agaaaattgg
3841 catatgtact ttatttttga aaagggaaga gatgggtgtg gggtggcaat agcattgtgc
3901 cattttgtca tagaatgtaa aaattggtta actttacaaa tgtcagctag ttttgactac
3961 taattggggg aaattttaga taatttttaa attcaaagtt atttataaaa tgctagaatt
4021 tgttttaatt ttttgtattt tgagccactt cacatgaaga ctcagttgca tttttatcga
4081 atacattttt atcaacagtt aaagactatg gtggtttttt cagagtttgg ctaagaatgt
4141 tgttaccatc ttctttgttt gtggtacaat attttcagtg caaaagagat gtcattcagt
4201 taaaaagaca aacctctaga tgtgtaatta catggaaaat actagcaatg tgaatgcttt
4261 tgtagtaacc atcttgtagt acctgtgaaa tctataactc agaaatggtc agatggtcag

FIG. 13-96

```
4321 gagccagcta tgcagcagta taccatctgt ttaattattt tgtaggtcct gtgtgtggaa
4381 ccaactataa acccagttct aaagttgtgt atgatggtga acctttggga atagttctta
4441 tcaacttaat tggatacttt tagcaaatag gaacttaatt ctcagcactg aacatgaatt
4501 acttccttgg agttttttt cattcatatt tttgttgttt ccaggaattt atttgatatt
4561 aatgggcgta aaacagcatc attgtactta agctatggat gtttttattt tatattttct
4621 ttatttataa ctgtgccaag tattattttg ctacttaccg tgttattctg tggaaagaaa
4681 aacctgtaaa gtgtttaata aattagccct ccttacataa attaaatgtc aaaattttgt
4741 aaaatattaa tcagaataaa tactgactct t
//
```

ZDHHC18:

```
FEATURES             Location/Qualifiers
     source          1..3163
                     /organism="Homo sapiens"
                     /mol_type="mRNA"
                     /db_xref="taxon:9606"
                     /chromosome="1"
                     /map="1p36.11"
     gene            1..3163
                     /gene="ZDHHC18"
                     /gene_synonym="DKFZp66702416"
                     /note="zinc finger, DHHC-type containing 18"
                     /db_xref="GeneID:84243"
                     /db_xref="HGNC:20712"
                     /db_xref="HPRD:15713"
     exon            1..430
                     /gene="ZDHHC18"
                     /gene_synonym="DKFZp66702416"
                     /inference="alignment:Splign"
                     /number=1
     CDS             96..1262
                     /gene="ZDHHC18"
```

FIG. 13-97

/gene_synonym="DKFZp667O2416"
/note="zinc finger, DHHC domain containing 18; DHHC-18;
zinc finger DHHC domain-containing protein 18"
/codon_start=1
/product="palmitoyltransferase ZDHHC18"
/protein_id="NP_115659.1"
/db_xref="GI:45433499"
/db_xref="CCDS:CCDS30650.1"
/db_xref="GeneID:84243"
/db_xref="HGNC:20712"
/db_xref="HPRD:15713"

/translation="MKDCEYQQISPGAAPLPASPGARRPGPAASPTPGPGPAPPAAPA

PPRWSSSGSGSGSGSGSLGRRPRRKWEVFPGRNRFYCGGRLMLAGHGGVFALTLLLIL

TTTGLFFVFDCPYLARKLTLAIPIIAAILFFFVMSCLLQTSFTDPGILPRATVCEAAA

LEKQIDNTGSSTYRPPPRTREVLINGQMVKLKYCFTCKMFRPPRTSHCSVCDNCVERF

DHHCPWVGNCVGRRNYRFFYAFILSLSFLTAFIFACVVTHLTLRAQGSNFLSTLKETP

ASVLELVICFFSIWSILGLSGFHTYLVASNLTTNEDIKGSWSSKRGGEASVNPYSHKS

IITNCCAVLCGPLPPSLIDRRGFVQSDTVLPSPIRSDEPACRAKPDASMVGGHP"

exon 431..591
/gene="ZDHHC18"
/gene_synonym="DKFZp667O2416"
/inference="alignment:Splign"
/number=2 exon 592..741
/gene="ZDHHC18"
/gene_synonym="DKFZp667O2416"
/inference="alignment:Splign"
/number=3 exon 742..879
/gene="ZDHHC18"

FIG. 13-98

```
                     /gene_synonym="DKFZp66702416"
                     /inference="alignment:Splign"
                     /number=4
     exon            880..928
                     /gene="ZDHHC18"
                     /gene_synonym="DKFZp66702416"
                     /inference="alignment:Splign"
                     /number=5
     exon            929..1031
                     /gene="ZDHHC18"
                     /gene_synonym="DKFZp66702416"
                     /inference="alignment:Splign"
                     /number=6
     exon            1032..1144
                     /gene="ZDHHC18"
                     /gene_synonym="DKFZp66702416"
                     /inference="alignment:Splign"
                     /number=7
     exon            1145..3136
                     /gene="ZDHHC18"
                     /gene_synonym="DKFZp66702416"
                     /inference="alignment:Splign"
                     /number=8
     STS             1976..2118
                     /gene="ZDHHC18"
                     /gene_synonym="DKFZp66702416"
                     /standard_name="SHGC-74485"
                     /db_xref="UniSTS:44073"
     STS             2828..3097
                     /gene="ZDHHC18"
                     /gene_synonym="DKFZp66702416"
                     /standard_name="A002B28"
                     /db_xref="UniSTS:17559"
     STS             2828..3097
                     /gene="ZDHHC18"
                     /gene_synonym="DKFZp66702416"
```

FIG. 13-99

```
                     /standard_name="G19894"
                     /db_xref="UniSTS:17558"
     STS             2911..3065
                     /gene="ZDHHC18"
                     /gene_synonym="DKFZp66702416"
                     /standard_name="RH12522"
                     /db_xref="UniSTS:32019"
ORIGIN
        1 gcgcgcgccg ccgctgccac ctccgctgct cggcccggtc ccggagtggc ccggccggcc
       61 cgcggggcgc ggagccgagg cccgcggctg gctgcatgaa ggactgcgag taccagcaga
      121 tcagcccccgg ggccgccccg ctgcccgcct ccccgggggc gcgccgtccc ggccccgccg
      181 cgtccccgac tccgggcccc gggcccgcgc cgcccgccgc ccccgccccg ccgcgctgga
      241 gcagcagcgg cagcggcagc ggcagcggga gcgggagcct cggccgccgc ccacggcgca
      301 agtgggaggt gttcccgggt cgcaatcgct tctactgcgg cggccgcctc atgctggccg
      361 gccacggcgg cgtcttcgcg ctcacgctgc tgctcatcct caccaccacc ggcctcttct
      421 tcgtctttga ctgtccctac ctggctcgca agctgaccct tgccatcccc atcatcgctg
      481 ccatcctctt cttcttcgtc atgagctgcc tgctgcagac aagcttcacc gaccctggga
      541 tcctgccccg ggccactgtc tgtgaagcag ccgccctgga gaaacagatc gacaacacag
      601 gcagttctac ataccggcca ccccctcgga cccgggaggt gctgatcaac gggcagatgg
      661 tgaagctgaa gtactgcttc acctgcaaga tgttccggcc accccgaacc tcacactgca
      721 gtgtctgcga caactgtgtg gaacgatttg accatcactg cccctgggtg ggcaactgtg
      781 tggggagacg gaactatcgc ttcttctacg cgtttattct ctccctctca ttcctgacgg
      841 ccttcatctt cgcctgtgtg gtcacccacc tgacgttgcg cgctcaggga agcaacttcc
      901 tctccactct gaaggagaca ccagcaagcg tgctggagtt ggtgatctgc ttcttctcca
      961 tctggtccat tctgggcctc tcagggtttc acacgtacct cgtcgcctcc aacctgacta
     1021 ctaatgaaga catcaaaggc tcgtggtcca gcaagagggg cggtgaggcc tctgtcaacc
     1081 cctacagcca taaaagtatt atcaccaact gctgtgctgt gctctgtggc cccctacctc
     1141 ccagcctaat tgaccggagg ggatttgtgc agtccgacac cgtgttgccc tcacccatca
     1201 gaagcgatga gccagcctgc agagccaagc ctgatgccag catggtagga ggccacccct
     1261 gaccacggct cagtacttgc cacctgctgg cctgtctgac cctccgcact cacctgccgg
     1321 gaccctccct attccatcca agggaagcag aactgccaaa gactcaagtc ttttcatatt
     1381 tatttcccat cctgcgtggc tttccctgaa ctgttccgtg gctgtgccct ctgctcccca
     1441 aacccaggtt cccacagcct tgggccctag gtaccccagc tgatcagtgc caggagagac
     1501 cagagcctct ggaggctacc caggggacca caccaagtcc ttgcctgtgc cgggcgagcc
     1561 ctgtgtgagt gaggctgtga actgagcgtg aggcctccca ggtgggggaa ctgcttgggc
     1621 cttgctgagc cagggtcctc agggtgaagc aggactgagg agtggccagc tctggatagc
```

FIG. 13-100

```
1681 tggctgtgga gaggaagcct ccatgggctg ctttcgtctg tgggctcctt cattcccttg
1741 gtgataattt ccctttcttc tgtgggattt ttggtggggt tttccccccct tttttatgga
1801 gttggccaat aggattgagt tggggctcca gtagagaagg cagggttggt ggtgggtggg
1861 ggcagcctgt atcagacaaa ggtaaatcag ccagccaggc acccacagcc tcagctcctg
1921 tgcagttcct gggcagcaca gtggaagtgg gagcctggtc cttcccctgc ccatggagag
1981 ctctttaagg gatcccagcc tgcccctcca cttctctccc aagccaggtc ccggcatggg
2041 tgggttatgc tcatgctggc aatacttgaa acggctttat taatgctggg tattttgcac
2101 aattttatag acctcttttc tacatagtct tttttaaatg gaaggagaaa atgtcagcca
2161 cattactgtc tgtgtagtgc caggtgaagg gttatcagaa ggctggttgg ttttaataag
2221 tttattccaa gagaccttct ggctggaatg agtgagagtg tgtgtgcatg tgtgtgtgtg
2281 ttcatgtgtg ccctgtatga atgtggctgg ctcccatatc ccctgggctg ccccctgccc
2341 catccccttt gagtatcaga agcactctga gccaagggga caggggggcac gtgcactggt
2401 cacgagaaaa ccctcggctc ccactggggc tcagcccagc ctcctatctt tccttcttct
2461 atggacttca gacagccagt gtctggggac tctgccactc tacccccagc cctacccacc
2521 agcccccagg tgaggcttcc agctgggacc tgcccagaca ggctgagcct gggcgtggtg
2581 ggtggggtga tggctctggg gagcggctgc catcctacaa gccacacccc ctcctctgag
2641 ctctgaatat gggacccagt gccaggagct ggaagacaag gtgtttctgc caaacgggga
2701 cctccatcca gagaaaagga agaaggtgca gggtcggcca agaggcaagt gaaggttggc
2761 ctgagtctgg gccggaaact cagaggatgt ttctcctctg ctgggagctg tagtttctta
2821 tcaaaataga tattcttcca ccatccccct ccttcgccct tcaagtgggc tgaagccctt
2881 ggaaagtgac ataggaagtc cccagatctt gcccttctca ctccagaggc tagtggtcac
2941 agacagctgg gaatggcagc cacagagggt cccctctggg agaaacagct tcaccccagc
3001 ctcagggccc tgggccatca ctgcagtggc cctgcgaggt gaggaagaag ctggctagag
3061 gagggggctc ccacctacct tttatttaag ccagtattct ttgttcctgc ttgtaataaa
3121 acttcagttt ataagaaaaa aaaaaagaaa aaaaaaaaaa aaa
//
```

ZDHHC19:

```
FEATURES             Location/Qualifiers
     source          1..1370
                     /organism="Homo sapiens"
                     /mol_type="mRNA"
                     /db_xref="taxon:9606"
                     /chromosome="3"
```

FIG. 13-101

/map="3q29"
gene 1..1370
/gene="ZDHHC19"
/gene_synonym="DHHC19; MGC33345"
/note="zinc finger, DHHC-type containing 19"
/db_xref="GeneID:131540"
/db_xref="HGNC:20713"
exon 1..260
/gene="ZDHHC19"
/gene_synonym="DHHC19; MGC33345"
/inference="alignment:Splign"
/number=1
CDS 115..1044
/gene="ZDHHC19"
/gene_synonym="DHHC19; MGC33345"
/note="zinc finger, DHHC domain containing 19; DHHC-19; zinc finger DHHC domain-containing protein 19"
/codon_start=1
/product="probable palmitoyltransferase ZDHHC19"
/protein_id="NP_001034706.1"
/db_xref="GI:88900493"
/db_xref="CCDS:CCDS43190.1"
/db_xref="GeneID:131540"
/db_xref="HGNC:20713"

/translation="MTLLTDATPLVKEPHPLPLVPRPWFLPSLFAAFNVVLLVFFSGL

FFAFPCRWLAQNGEWAFPVITGSLFVLTFFSLVSLNFSDPGILHQGSAEQGPLTVHVV

WVNHGAFRLQWCPKCCFHRPPRTYHCPWCNICVEDFDHHCKWVNNCIGHRNFRFFMLL

VLSLCLYSGAMLVTCLIFLVRTTHLPFSTDKAIAIVVAVSAAGLLVPLSLLLLIQALS

VSSADRTYKGKCRHLQGYNPFDQGCASNWYLTICAPLGPKYMAEAVQLQRVVGPDWTS
MPNLHPPMSPSALNPPAPTSGSLQSREGTPGAW"
exon 261..382

FIG. 13-102

```
                     /gene="ZDHHC19"
                     /gene_synonym="DHHC19; MGC33345"
                     /inference="alignment:Splign"
                     /number=2
     exon            383..522
                     /gene="ZDHHC19"
                     /gene_synonym="DHHC19; MGC33345"
                     /inference="alignment:Splign"
                     /number=3
     exon            523..695
                     /gene="ZDHHC19"
                     /gene_synonym="DHHC19; MGC33345"
                     /inference="alignment:Splign"
                     /number=4
     exon            696..801
                     /gene="ZDHHC19"
                     /gene_synonym="DHHC19; MGC33345"
                     /inference="alignment:Splign"
                     /number=5
     exon            802..887
                     /gene="ZDHHC19"
                     /gene_synonym="DHHC19; MGC33345"
                     /inference="alignment:Splign"
                     /number=6
     exon            888..1063
                     /gene="ZDHHC19"
                     /gene_synonym="DHHC19; MGC33345"
                     /inference="alignment:Splign"
                     /number=7
     exon            1064..1337
                     /gene="ZDHHC19"
                     /gene_synonym="DHHC19; MGC33345"
                     /inference="alignment:Splign"
                     /number=8
     STS             1214..1332
                     /gene="ZDHHC19"
```

FIG. 13-103

```
                     /gene_synonym="DHHC19; MGC33345"
                     /standard_name="RH92567"
                     /db_xref="UniSTS:89484"
ORIGIN
        1 ctttcaccct gggctgcggc tctgaggctg ccgtggccat ggagctctgg aagctgggct
       61 gggggaggaa gcctggtggc tctgacctcc cctggaggcg aaggaggccc agccatgaca
      121 ctcttaacgg atgccacgcc gctggtgaag gagcccccatc ccctgcctct ggtcccacgt
      181 ccctggttcc tccctagcct ctttgctgcc ttcaatgtgg tgctgctggt ctttttcagt
      241 ggcctcttct tcgcattccc ttgcaggtgg ctggctcaga acggggagtg ggcctttcct
      301 gttatcacag gctccctctt tgtccttacc ttcttcagtc ttgtttcact caacttctca
      361 gaccctggca tcttacatca aggctccgct gagcagggcc ccttgacggt gcacgtggtg
      421 tgggtgaacc acggggcctt ccgcctgcaa tggtgtccaa agtgctgctt ccaccgcccg
      481 ccccggactt accactgccc ctggtgcaac atctgtgtgg aggactttga ccaccactgc
      541 aagtgggtca ataactgcat cggtcaccgc aacttccgct tcttcatgct gcttgtcctg
      601 tccctgtgcc tctactcggg cgccatgctg gtcacctgtc tcatcttcct ggtgcgcaca
      661 acccacctgc ccttctccac cgacaaggcc atcgccatcg tggtggccgt gtccgccgcg
      721 ggcctcctgg tgccgctgtc cctcctgctg ctgatccagg cactgtccgt gagctcggcc
      781 gaccgcacct acaagggcaa gtgcagacac cttcagggat acaacccctt cgaccagggc
      841 tgtgccagca actggtattt aacaatttgt gcaccactgg gacccaagta catggctgaa
      901 gctgtccagc tgcagagagt ggtggggcct gactggacat ccatgccgaa tctgcaccct
      961 ccaatgtccc cctctgctct caacccccca gccccaacct ctgggtccct acaaagcagg
     1021 gaagggaccc ccgggggcgtg gtgaggctgc agctctccag gagttccaca cgggcccagt
     1081 gctgcccctg ctgctgcagg agcccccagg cgaggttcgg ccttcctctc gcccctgtgc
     1141 acccggagat gcccacagca ccagcacctg agctcacctc cgaacccgcc tcctgaaccc
     1201 gcctcctgaa cctgcctcct tacctcccac ttcctgagcc ctgagtggaa gcctttctgt
     1261 gccttgccct ttgcccactc ccctggtggg actgccaaga ccctcaatgc ccattaaata
     1321 ctcttgcctg cctcttaaaa aaaaaaaaaa aaaaaaaaaa aaaaaaaaaa
//
```

ZDHHC20:

```
FEATURES             Location/Qualifiers
     source          1..1514
                     /organism="Homo sapiens"
```

FIG. 13-104

```
                /mol_type="mRNA"
                /db_xref="taxon:9606"
                /chromosome="13"
                /map="13q12.11"
     gene       1..1514
                /gene="ZDHHC20"
                /gene_synonym="FLJ25952; MGC126005"
                /note="zinc finger, DHHC-type containing 20"
                /db_xref="GeneID:253832"
                /db_xref="HGNC:20749"
                /db_xref="HPRD:08078"
     exon       1..231
                /gene="ZDHHC20"
                /gene_synonym="FLJ25952; MGC126005"
                /inference="alignment:Splign"
                /number=1
     STS        34..1337
                /gene="ZDHHC20"
                /gene_synonym="FLJ25952; MGC126005"
                /db_xref="UniSTS:490024"
     CDS        114..1178
                /gene="ZDHHC20"
                /gene_synonym="FLJ25952; MGC126005"
                /note="DHHC-containing protein 20; 4933421L13Rik; zinc
                finger, DHHC domain containing 20; DHHC-20; zinc finger
                DHHC domain-containing protein 20"
                /codon_start=1
                /product="probable palmitoyltransferase ZDHHC20"
                /protein_id="NP_694983.2"
                /db_xref="GI:49457851"
                /db_xref="CCDS:CCDS45017.1"
                /db_xref="GeneID:253832"
                /db_xref="HGNC:20749"
                /db_xref="HPRD:08078"
/translation="MAPWTLWRCCQRVVGWVPVLFITFVVVWSYYAYVVELCVFTIFG
```

NEENGKTVVYLVAFHLFFVMFVWSYWMTIFTSPASPSKEFYLSNSEKERYEKEFSQER

QQEILRRAARALPIYTTSASKTIRYCEKCQLIKPDRAHHCSACDSCILKMDHHCPWVN

NCVGFSNYKFFLLFLLYSLLYCLFVAATVLEYFIKFWTNELTDTRAKFHVLFLFFVSA

MFFISVLSLFSYHCWLVGKNRTTIESFRAPTFSYGPDGNGFSLGCSKNWRQVFGDEKK

YWLLPIFSSLGDGCSFPTRLVGMDPEQASVTNQNEYARSGSNQPFPIKPLSESKNRLL

DSESQWLENGAEEGIVKSGV"

exon 232..258
/gene="ZDHHC20"
/gene_synonym="FLJ25952; MGC126005"
/inference="alignment:Splign"
/number=2

STS 257..383
/gene="ZDHHC20"
/gene_synonym="FLJ25952; MGC126005"
/standard_name="RH69325"
/db_xref="UniSTS:72733"

exon 259..362
/gene="ZDHHC20"
/gene_synonym="FLJ25952; MGC126005"
/inference="alignment:Splign"
/number=3 exon 363..483
/gene="ZDHHC20"
/gene_synonym="FLJ25952; MGC126005"
/inference="alignment:Splign"
/number=4 exon 484..553
/gene="ZDHHC20"
/gene_synonym="FLJ25952; MGC126005"
/inference="alignment:Splign"
/number=5 exon 554..586

```
                     /gene="ZDHHC20"
                     /gene_synonym="FLJ25952; MGC126005"
                     /inference="alignment:Splign"
                     /number=6
     exon            587..707
                     /gene="ZDHHC20"
                     /gene_synonym="FLJ25952; MGC126005"
                     /inference="alignment:Splign"
                     /number=7
     exon            708..840
                     /gene="ZDHHC20"
                     /gene_synonym="FLJ25952; MGC126005"
                     /inference="alignment:Splign"
                     /number=8
     exon            841..967
                     /gene="ZDHHC20"
                     /gene_synonym="FLJ25952; MGC126005"
                     /inference="alignment:Splign"
                     /number=9
     exon            968..1057
                     /gene="ZDHHC20"
                     /gene_synonym="FLJ25952; MGC126005"
                     /inference="alignment:Splign"
                     /number=10
     exon            1058..1170
                     /gene="ZDHHC20"
                     /gene_synonym="FLJ25952; MGC126005"
                     /inference="alignment:Splign"
                     /number=11
     exon            1171..1457
                     /gene="ZDHHC20"
                     /gene_synonym="FLJ25952; MGC126005"
                     /inference="alignment:Splign"
                     /number=12
ORIGIN
        1 cggacgcggg ggagctggac cagcagccgc ctggagcgtc cgagtcaccg tcgccggggc
```

FIG. 13-107

```
  61 tcccgcgctc cccagaacgg tgggacgcgg ggctcggcag ccgccagcgg aacatggcgc
 121 cctggacgct gtggcgctgc tgccagcgcg tcgtgggctg ggtgccggtg ctcttcatca
 181 ccttcgtggt cgtctggtcc tactacgcgt acgtggtgga gctctgcgtg tttactattt
 241 ttggaaatga agaaaatgga aagaccgttg tttaccttgt ggctttccat ctgttctttg
 301 ttatgtttgt atggtcctat tggatgacaa ttttcacatc tcccgcttcc ccctccaaag
 361 agttctactt gtccaattct gaaaaggaac gttatgaaaa agaattcagc caagaaagac
 421 aacaagaaat tttgagaaga gcagcaagag ctttacctat ctataccaca tcagcttcaa
 481 aaactatcag atattgtgaa aaatgtcagc tgattaaacc tgatcgggcg catcactgct
 541 cagcctgtga ctcatgtatt cttaagatgg atcatcactg tccttgggtg aataactgtg
 601 tgggatttc taattacaaa ttcttcctgc tgtttttatt gtattcccta ttatattgcc
 661 ttttcgtggc tgcaacagtt ttagagtact ttataaaatt ttggacgaat gaactgacag
 721 atacacgtgc aaaattccac gtactttttc ttttctttgt gtctgcaatg ttcttcatca
 781 gcgtcctctc acttttcagc taccactgct ggctagttgg aaaaaataga acaacaatag
 841 aatcattccg cgcacccacg ttttcatacg gacctgatgg aaatggtttc tctcttggat
 901 gcagtaaaaa ttggagacaa gtctttggtg atgaaaagaa atattggcta cttccaatat
 961 tttcaagctt gggtgatggt tgcagttttc caactcgcct tgtggggatg gatccagaac
1021 aagcttctgt tacaaaccag aatgagtatg ccagaagtgg ctcaaatcaa ccttttccta
1081 tcaaaccact tagtgaatca aaaaaccgct tgttggacag tgaatctcag tggctggaga
1141 atggagctga agaaggcatc gtcaaatcag gtgtatgaaa acattataga ctggtatttt
1201 caattttcat ttgcaagaaa atgatcagtg gaatgaaata actgaagtat aacagaagat
1261 atatttttta aaacggaaag cctttgtaca gttcctggga ttcacagaag cactactcca
1321 gagcagaatg atgccttaat cttaagtgtc catttgtgca gcattgactt agagctacaa
1381 aagtgactta atgttattct ggaaataata cttacctgtt atgagttgct ataatatgag
1441 ctgtcatcac attttaaaaa aaaaaaaaaa aaaaaaaaaa aaaaaaaaaa aaaaaaaaaa
1501 aaaaaaaaaa aaaa
//
```

DHHC21:

```
FEATURES             Location/Qualifiers
     source          1..3265
                     /organism="Homo sapiens"
                     /mol_type="mRNA"
```

FIG. 13-108

```
                    /db_xref="taxon:9606"
                    /chromosome="9"
                    /map="9p22.3"
     gene           1..3265
                    /gene="ZDHHC21"
                    /gene_synonym="DHHC-21; DNZ1"
                    /note="zinc finger, DHHC-type containing 21"
                    /db_xref="GeneID:340481"
                    /db_xref="HGNC:20750"
                    /db_xref="HPRD:15716"
     exon           1..246
                    /gene="ZDHHC21"
                    /gene_synonym="DHHC-21; DNZ1"
                    /inference="alignment:Splign"
                    /number=1
     exon           247..295
                    /gene="ZDHHC21"
                    /gene_synonym="DHHC-21; DNZ1"
                    /inference="alignment:Splign"
                    /number=2
     exon           296..425
                    /gene="ZDHHC21"
                    /gene_synonym="DHHC-21; DNZ1"
                    /inference="alignment:Splign"
                    /number=3
     exon           426..624
                    /gene="ZDHHC21"
                    /gene_synonym="DHHC-21; DNZ1"
                    /inference="alignment:Splign"
                    /number=4
     CDS            471..1268
                    /gene="ZDHHC21"
                    /gene_synonym="DHHC-21; DNZ1"
                    /EC_number="2.3.1.-"
                    /note="9130404H11Rik; HSPC097; zinc finger, DHHC domain
                    containing 21; zinc finger DHHC domain-containing
```

protein

FIG. 13-109

21"
/codon_start=1
/product="probable palmitoyltransferase ZDHHC21"
/protein_id="NP_848661.1"
/db_xref="GI:30425538"
/db_xref="CCDS:CCDS6475.1"
/db_xref="GeneID:340481"
/db_xref="HGNC:20750"
/db_xref="HPRD:15716"

/translation="MGLRIHFVVDPHGWCCMGLIVFVWLYNIVLIPKIVLFPHYEEGH

IPGILIIIFYGISIFCLVALVRASITDPGRLPENPKIPHGEREFWELCNKCNLMRPKR

SHHCSRCGHCVRRMDHHCPWINNCVGEDNHWLFLQLCFYTELLTCYALMFSFCHYYYF

LPLKKRNLDLFVFRHELAIMRLAAFMGITMLVGITGLFYTQLIGIITDTTSIEKMSNC
CEDISRPRKPWQQTFSEVFGTRWKILWFIPFRQRQPLRVPYHFANHV"

exon 625..723
/gene="ZDHHC21"
/gene_synonym="DHHC-21; DNZ1"
/inference="alignment:Splign"
/number=5 exon 724..835
/gene="ZDHHC21"
/gene_synonym="DHHC-21; DNZ1"
/inference="alignment:Splign"
/number=6 exon 836..974
/gene="ZDHHC21"
/gene_synonym="DHHC-21; DNZ1"
/inference="alignment:Splign"
/number=7 exon 975..1091
/gene="ZDHHC21"

FIG. 13-110

```
                     /gene_synonym="DHHC-21; DNZ1"
                     /inference="alignment:Splign"
                     /number=8
     exon            1092..1135
                     /gene="ZDHHC21"
                     /gene_synonym="DHHC-21; DNZ1"
                     /inference="alignment:Splign"
                     /number=9
     exon            1136..3204
                     /gene="ZDHHC21"
                     /gene_synonym="DHHC-21; DNZ1"
                     /inference="alignment:Splign"
                     /number=10
ORIGIN
        1 ccgtcgcggc tcccgggagc taagcgagac ggcgacggcg gcagtcgtcc ctccccacgc
       61 gggcgcgcgg gcatgcggac acccactcgg ccggtccagg ccctcaggct cccggaagcg
      121 gaaggggaga gcggcccggc ctggcggcg gcgccggagg aggcggaggt ggcgcggcag
      181 gaggagggga aagagctgct ggtggtcggg agagcggcgg cagcgagagg cgagccagcg
      241 gcgacgaatg aagaactttt tcacttactg caggattttc agcttcagca agcaggttct
      301 catggagaac tgttattgaa gagagatcca tttggtggga tataattaaa aaaaatgaat
      361 caaaagaaaa tctctaaatg cagattccag aaaaattaca gcacatctca gtgaatttgc
      421 aagtggatca tccttccttg tgggttagca ggcagttata agattgcaaa atgggtctcc
      481 ggattcactt tgttgttgac ccacatggtt ggtgctgcat gggtttgatt gtctttgttt
      541 ggttatacaa tattgtttta attcccaaaa ttgtcctctt tcctcactat gaagaaggac
      601 atattccagg catattaata ataatattct atggcatttc catattctgt ctggttgcct
      661 tagtgagggc ctccataact gatccaggaa gactccctga gaaccccaag atcccacatg
      721 gagaaaggga gttctgggaa ttatgtaaca agtgtaattt gatgagacca aagcgttccc
      781 atcactgcag ccgctgcggc cactgtgtga ggagaatgga tcatcactgt ccatggatta
      841 acaattgtgt tggtgaagat aatcattggc tctttctgca gttgtgtttc tacactgaac
      901 ttcttacttg ctacgcactg atgttttctt tctgccacta ttactatttt cttccactaa
      961 aaaagcgtaa tttggacctc tttgttttta gacatgaatt ggccataatg agactagcag
     1021 cctttatggg cattactatg ttagttggaa taactggact cttttacact caactaattg
     1081 gcatcatcac agatacaaca tctattgaaa agatgtcaaa ctgttgtgaa gatatatcga
     1141 ggccccgaaa gccatggcag cagaccttct cagaagtttt tggcactcgt tggaagatcc
     1201 tgtggttcat tcctttcagg cagaggcaac cactgcgagt tccctaccac tttgccaatc
     1261 atgtctaaac agatggatgg tgggcacaga tgggtcctcc atgctggcaa tgcgttacag
```

FIG. 13-111

1321 gttttatgat aatagaacta tgacagtctt caagtcaatt aaaatccacc caccaatctt
1381 aggcatcata atgtgcccca ggctttattt taatagtgat cttgatcctg ttgtgggact
1441 aatacaagat ctatatttaa gttttaaagc atgtttactt tcaaattagc tttccacagg
1501 gatttcttga aatgcttttg ttattaaact caaaaggcag tgattaggat gaaataattg
1561 tacataattt attttagtac tgacagtgtt acagattcta atttatggta aatttcagat
1621 gtttatttaa aattttcact tttaaacagt aaccaaatct aaatttaatt attcaggttt
1681 tacaaaagtt gatacacctt cttatagtat aggtaaattt tctttttcaa atccaattta
1741 aaataacctt tccttttaaa tgtgctgcaa cgtttttaaa aatgcagcag cataggagtg
1801 aacaacagca acacaaaacg ggcattggtt tcttaggagt ggcttgctta cgttttcttc
1861 tttttcttc accaaaacca acatgaaagt accactgaag taaaacacca actacctacc
1921 ttactataaa ggaaatgtta aaattttttt cacaataatt ttttcaattt tcactattac
1981 tgttgtaatt attgattgtg attaaaatat ttgctcccag gagaactcct gaccagtggg
2041 catgtattcc tattttatcc taagatttta atgagcaaaa aggggagaga atttgcaata
2101 acttcacaat taccttttct agtgcagtta tattagaatg catatgtttt taaaatgcta
2161 gtataactag atagtatata atgtacagta taaagaggaa tattgtgctt ttgaaaagag
2221 tatacttttt acttttattt atgtactagt agatgtaaaa tttcgcattg aaggtttata
2281 tatattggcc aactcatata gaaattttat ttataggaag ctactactaa aaaaagtcac
2341 taactttgtg tacctataat ccctaaatta aaattaaatt ttaattggct ggctgtaatt
2401 tgcattgaga gacctttac tagtagctag tgttaggaag tgaacctaaa ataagaaaat
2461 ataatgatct gtgtttatca ttagccttgt acaaatgtaa attactaata gtgatgttct
2521 tttgcaaggc atagaacatt tgtatgaaaa gacatttagt atgctttgaa aaaaactcag
2581 cttttagttt ttttccatta gaatactgca aaacccatat atctttttaa aaaatttatg
2641 tactcacagt ctttcccttg aagagaagat tgaaaaagtc tactgttcat aaaccatgct
2701 aacattttcc ttttagctag ttttgaaagt aaggaacaat acctgggaaa taataaaaca
2761 gaaggttacc attgtcagcc agttggctat actgtggtta gttctttcag aaattgtaaa
2821 tatcttgtag catattctga aataatagag taagttcttc tcagagatgt taatatcatg
2881 tttttcatgt tctaattaga atactttatt acttacaaac tcagaaatac gaacagaaat
2941 acagcagacg aacatattta ttggtactga aaagagatgt agtaaattaa atagaagaaa
3001 tatatttata aagcttagtg aaacacaaaa ttagaatgtt catgtcaggc acaagggttt
3061 ggattttgtg caagctaatt tggccacatt tggcctggtg acagaactgt tcataaggaa
3121 gtaatatata gataaggtag gtagatatca gttgaatgcc ttatattgta tacattcctt
3181 tcaaataaag accttgagaa aacaaaaaaa aaaaaaaaaa aaaaaaaaaa aaaaaaaaaa
3241 aaaaaaaaac aaaaaaaaaa aaaaa

//

DHHC22:

FIG. 13-112

```
FEATURES             Location/Qualifiers
     source          1..3408
                     /organism="Homo sapiens"
                     /mol_type="mRNA"
                     /db_xref="taxon:9606"
                     /chromosome="14"
                     /map="14q24.3"
     gene            1..3408
                     /gene="ZDHHC22"
                     /gene_synonym="C14orf59"
                     /note="zinc finger, DHHC-type containing 22"
                     /db_xref="GeneID:283576"
                     /db_xref="HGNC:20106"
                     /db_xref="HPRD:12655"
     exon            1..189
                     /gene="ZDHHC22"
                     /gene_synonym="C14orf59"
                     /inference="alignment:Splign"
                     /number=1
     exon            190..729
                     /gene="ZDHHC22"
                     /gene_synonym="C14orf59"
                     /inference="alignment:Splign"
                     /number=2
     CDS             204..995
                     /gene="ZDHHC22"
                     /gene_synonym="C14orf59"
                     /note="zinc finger, DHHC domain containing 22; DHHC-22;
                     zinc finger DHHC domain-containing protein 22"
                     /codon_start=1
                     /product="putative palmitoyltransferase ZDHHC22"
                     /protein_id="NP_777636.2"
                     /db_xref="GI:145046234"
```

FIG. 13-113

/db_xref="CCDS:CCDS45140.1"
/db_xref="GeneID:283576"
/db_xref="HGNC:20106"
/db_xref="HPRD:12655"

/translation="MLALRLLNVVAPAYFLCISLVTFVLQLFLFLPSMREDPAAARLF

SPALLHGALFLFLSANALGNYVLVIQNSPDDLGACQGASARKTPCPSPSTHFCRVCAR

VTLRHDHHCFFTGNCIGSRNMRNFVLFCLYTSLACLYSMVAGVAYISAVLSISFAHPL

AFLTLLPTSISQFFSGAVLGSEMFVILMLYLWFAIGLACAGFCCHQLLLILRGQIRHQ

VRKGVAVRARPWRKNLQEVFGKRWLLGLLVPMFNVGSESSKQQDK"

exon 730..3408
/gene="ZDHHC22"
/gene_synonym="C14orf59"
/inference="alignment:Splign"
/number=3

ORIGIN

```
  1 ccttactcgc tggcgcccaa gtgggaagcc agcagctgcc cgctccctcc tccccacatc
 61 cccgctactt gcccagttcc cgaagcgaag cgcaggctgc gagccagccg ggccgagtcc
121 acaactttgc agcctcgggc agggcgagag ccggcgtccg gggctcctct tgtcggcgac
181 cagagctcgg aatgtaatcg aggatgctgg ccctgcggct gctcaacgtg gtggcccccg
241 cctacttctt gtgcatctcc ctggtgacct tcgtgctgca gctcttcctc ttcctgccca
301 gcatgcgcga ggacccccgcg gccgcccggc tcttctcgcc cgccctgctc cacggggcgc
361 tcttcctatt cctctcggcc aacgccctgg gcaattacgt ccttgtcatc cagaactccc
421 cagacgacct gggggcctgc caggggggcct cggccaggaa gactccatgc ccctcaccta
481 gcacccactt ctgccgagtg tgcgccagag tcaccctgag gcacgaccat cactgtttct
541 tcaccggcaa ctgcatcggc agcaggaaca tgcgcaactt cgtcctgttc tgcctctaca
601 cctccctggc ctgcctctac tccatggtgg ccggcgtggc ctacatctcc gctgtccttt
661 ccatctcctt cgcccacccc ttggccttcc tcacgctcct gcccacctcc atcagccagt
721 tcttctccgg agctgtcctg ggttctgaaa tgttcgtcat cctcatgctc tacctctggt
781 tcgccatcgg cctggcctgc gccggcttct gctgccacca gctgctgttg atcctccgcg
841 ggcagacccg ccaccaggtg cggaaggggg tggcagtgag ggcccggccc tggcgcaaga
901 acttacaaga ggtcttcgga aagaggtggc tgctgggcct gctggtcccc atgttcaatg
961 tcggaagtga gagctccaag cagcaggata agtagtagac actcccgtca tttatctctc
```

FIG. 13-114

1021 tgtctctgtc ttgactcctc ctgagcataa aaccatggca gccttgtctc caccccatgac
1081 tcactacaac cttgtgctgg taaggtccta gcatcttccc ctcaccttcc acccatgaga
1141 acagcgtgag ctggtggatc atgacaagga ggaaaaatgt ccccccaggc atttctaggc
1201 tcctcacgag ccagccaggt ggctgctagc tgttaggctg cctctgcttt ctttccgtcc
1261 ccttgggatc cctgctttcc ccctcttcct ggctcatcca ttctccaccg tgtctcattc
1321 atcactgctg tctgctagag cccttcctct cagcccccat gttgggagag gggagtggat
1381 tcttgctgct ggtatgagac tccctgggac ctagaggctg gcaaatgttt aaaatcacca
1441 cgtgtaagag gcagccaagt cagctctgcc aactgctagg ggagttggga aagagtgggt
1501 gtgtgtccgc atcccctctg taggaaaaag aacttagtag cttgctgctc cctcaccacc
1561 ccccaccagg ttcaagaccc tttttctggg agacagcaat caatggcctg ctttttccaa
1621 atgttattcc ctgtccaccc tgccccatct ggccggccca gcccagtcca ggacctggct
1681 ggatgcttcc tgtccctgga actcttccag cctttctact tgatctccag cccccaggtc
1741 tttgccagat gatgggaagg caaggaagaa gggacaggga aagataatta ctgataaatg
1801 aaggggatat tcgactgtat aaccatatgg aagtgtgtgt gtgtgtgtgt gtgtgtgtgt
1861 gagagagaga gagagagaga tgggtggtgg tgagaagtgt tgttagaaac atataggaat
1921 aatgcctagg ggaaagggag aagtgagagg gacaattggg ttcatttatg ccctatacaa
1981 agggcattcc agcagctgaa actcttcaat gtttgaatgg ctgcctgtga aggtagtgag
2041 tgccccatca ctggaggtat tccagcagag tctaggcagt cgtctgccag gcatgctgtg
2101 gaagggattt ctgtacaggg tcattctagg tgagcttaca cattccttcc aaccccaagg
2161 ttctgatgtc ctggttgtga ttgctggacc cagaggcaag atctgcagag atgcctgtga
2221 gatatttgct ttcctagagg ggagtgtggg catgggaggg gtctgaaaat caggacccaa
2281 cccagccact gaagagagag tctctgcaga gacagggcta cctgggtggt tgaggggact
2341 gacatttgag gacagggaga tggagcagtg tcattgtcag tggcagggca tgggggggcag
2401 tggtgagcta aggctgagga gtggagatga ccagaatata agggtgcaat tcccagacca
2461 tccctgcgca tctgactgac tccggtggag gcactgctgt gtgttttctg aaacctagag
2521 gaccagacct ctggggcata taagggagta gggacaacac aagtgccccc tcctgactgg
2581 gtcccaaagc caatatgaca tccatgcagg cagcagtgct gaatccatgc cctgcaatgt
2641 ccaaccgcca actgcagtga cccgctgata gctgcgcaac agcctgggtt cttgagcaga
2701 gattgggagg actttactgt ggttctgcct tcacaccccc tagagagcta atgtagtatt
2761 ggctccacct gctcacattt ctccctccca tactcattcc ttcactcatc catcctacgt
2821 atatttattg agtgccaacc acgttcccag cctcttccag gcactggcaa tgcagtgatg
2881 aacaggatga caagattcat gccatcaggg gcaccttgtc actgccgtct gtgcactgat
2941 tcacactccc tgcaaaatgg tcactctgcc atcttggtgg ttggtggggc aggtcatttg
3001 gaaataaaga atgtgataga gatggctgaa gaggggaagc ctaggctgcc tcaatcgagg
3061 agtcgctggg ggcattttca cccacaattc tggccatact taagcaatgg gagggagagg
3121 gaggagggga agatctgggc aattttggcc ttgactcttt cctggctcca gagctcaagc

FIG. 13-115

```
    3181 ttagaagcca gccctgctat ttccagcctc ctgaaggctc agcacggtga ggcctgacat
    3241 cctggggaag ggcaacaggg agacctacag gatgttggct gcttgcagac tggtcaatgg
    3301 gggatgacgg tggggaggtt gccagatgtg agacttgagt agcatttgta cacatggccc
    3361 tgtattgtcc ttgaagaaca tcaataaaat atatggtttt aaattgga
//
```

ZDHHC23:

```
FEATURES             Location/Qualifiers
     source          1..3778
                     /organism="Homo sapiens"
                     /mol_type="mRNA"
                     /db_xref="taxon:9606"
                     /chromosome="3"
                     /map="3q13.31"
     gene            1..3778
                     /gene="ZDHHC23"
                     /gene_synonym="MGC42530; NIDD"
                     /note="zinc finger, DHHC-type containing 23"
                     /db_xref="GeneID:254887"
                     /db_xref="HGNC:28654"
                     /db_xref="HPRD:15717"
     exon            1..290
                     /gene="ZDHHC23"
                     /gene_synonym="MGC42530; NIDD"
                     /inference="alignment:Splign"
                     /number=1
     exon            291..460
                     /gene="ZDHHC23"
                     /gene_synonym="MGC42530; NIDD"
                     /inference="alignment:Splign"
                     /number=2
     CDS             300..1529
```

FIG. 13-116

/gene="ZDHHC23"
/gene_synonym="MGC42530; NIDD"
/note="zinc finger, DHHC domain containing 23; DHHC-23;
zinc finger DHHC domain-containing protein 23"
/codon_start=1
/product="probable palmitoyltransferase ZDHHC23"
/protein_id="NP_775841.2"
/db_xref="GI:50234886"
/db_xref="CCDS:CCDS33827.1"
/db_xref="GeneID:254887"
/db_xref="HGNC:28654"
/db_xref="HPRD:15717"

/translation="MTQKGSMKPVKKKKTEEPELEPLCCCEYIDRNGEKNHVATCLCD

CQDLDEGCDRWITCKSLQPETCERIMDTISDRLRIPWLRGAKKVNISIIPPLVLLPVF

LHVASWHFLLGVVVLTSLPVLALWYYYLTHRRKEQTLFFLSLGLFSLGYMYYVFLQEV

VPKGRVGPVQLAVLTCGLFLILLALHRAKKNPGYLSNPASGDRSLSSSQLECLSRKGQ

EKTKGFPGADMSGSLNNRTTKDDPKGSSKMPAGSPTKAKEDWCAKCQLVRPARAWHCR

ICGICVRRMDHHCVWINSCVGESNHQAFILALLIFLLTSVYGITLTLDTICRDRSVFT

ALFYCPGVYANYSSALSFTCVWYSVIITAGMAYIFLIQLINISYNVTEREVQQALRQK

TGRRLLCGLIVDTGLLG"

exon 461..1171
/gene="ZDHHC23"
/gene_synonym="MGC42530; NIDD"
/inference="alignment:Splign"
/number=3 exon 1172..1339
/gene="ZDHHC23"
/gene_synonym="MGC42530; NIDD"
/inference="alignment:Splign"
/number=4

FIG. 13-117

```
exon            1340..1515
                /gene="ZDHHC23"
                /gene_synonym="MGC42530; NIDD"
                /inference="alignment:Splign"
                /number=5
exon            1516..3778
                /gene="ZDHHC23"
                /gene_synonym="MGC42530; NIDD"
                /inference="alignment:Splign"
                /number=6
STS             2422..2578
                /gene="ZDHHC23"
                /gene_synonym="MGC42530; NIDD"
                /standard_name="RH12338"
                /db_xref="UniSTS:74454"
STS             3544..3659
                /gene="ZDHHC23"
                /gene_synonym="MGC42530; NIDD"
                /standard_name="A005A39"
                /db_xref="UniSTS:55346"
STS             3544..3659
                /gene="ZDHHC23"
                /gene_synonym="MGC42530; NIDD"
                /standard_name="G20226"
                /db_xref="UniSTS:55345"
STS             3551..3750
                /gene="ZDHHC23"
                /gene_synonym="MGC42530; NIDD"
                /standard_name="D3S3313"
                /db_xref="UniSTS:28853"
STS             3645..3744
                /gene="ZDHHC23"
                /gene_synonym="MGC42530; NIDD"
                /standard_name="D3S2836E"
```

FIG. 13-118

/db_xref="UniSTS:150866"

ORIGIN 1 ggggcacccg gaagcgcgcg tggacctggc gcaccgagcc gggcgggcgg aggggcggtt
61 gggacggcgc ggggaggcgg gcgcgccgcc cgggccgcgg cgggctgtgg tcacaggtgg
121 gcggctgcgg cgagggagcg gccgagcgga gcccgggtcc cggagactcc tgccgtcacg
181 cccggggctc cgcgtagcag agatcgggag acgcgtctgt gcctccgggg aagccgaccc
241 atctcccctc cgcctctttg gctgcagttg cacctcccgc cagagggcag gtgcaaatca
301 tgacacagaa gggcagtatg aagcctgtga agaaaaagaa aaccgaagaa cctgaattgg
361 agcccctgtg ctgctgcgag tacatagatc ggaatgggga aaagaaccac gtggctactt
421 gtttgtgtga ttgtcaagat ctggatgaag ggtgtgatcg atggattaca tgtaaatctt
481 tacagccaga gacttgtgaa agaatcatgg atacaatttc tgatcgcctc cgaattcctt
541 ggcttagggg agccaaaaaa gtgaacatca gcatcatccc tccgcttgtc ctgctgcctg
601 tcttccttca tgtggcttcc tggcatttcc tcctgggcgt ggtggttttg acctcccttc
661 ctgtgctggc actgtggtac tactacctca ctcacagaag gaaagaacag accctgtttt
721 tcctgagcct tggactgttc tctctgggct acatgtacta tgtgttcctg caggaagtgg
781 tccccaaagg gcgtgtgggt cccgttcagc tggcggttct tacctgcggg ttatttctga
841 tactcttagc cttgcacaga gccaagaaga atccaggcta cctcagcaat ccagcaagcg
901 gtgacagatc tctaagcagc agccagctgg agtgcctgag cagaaaaggg caggagaaga
961 ccaaagggtt ccctggggca gacatgtcgg gcagtctcaa caatcgcaca acaaaggatg
1021 accccaaggg ctcttccaag atgccagctg gaagccccac caaagcgaag gaggactggt
1081 gtgccaagtg ccagctggtg cgaccagccc gggcatggca ctgccggata tgtggcatct
1141 gtgtgaggag aatggatcat cattgtgtct ggataaatag ctgcgttgga gaatcaaatc
1201 atcaagcatt tatacttgcc cttttgatct tcttgctcac ctcggtgtat gggatcacac
1261 tgaccttgga caccatttgt agagacagaa gtgtcttcac agctctttte tattgtcctg
1321 gagtttatgc aaattacagc tcggctctgt ccttcacctg cgtgtggtac tctgtgatca
1381 tcacagcagg catggcctac atcttcctga tccagctgat caacatcagc tacaatgtga
1441 ctgagcggga agtccagcag gccctccgac agaagactgg gcgccggctc ctctgcgggc
1501 tcatcgtgga cacagggtta cttggatgag ccaactccgc ttccttccca tggataggaa
1561 gggactctgt gtattattca ggtttattgg cacgaagata cttgttttaa gttccttgag
1621 aacccatgat ggacagttga cagaatgctt aaacctgtca aaagatgagt gatcttgtgt
1681 gggaaaagcc ttcccaggcg tctgtaccga aaggagcagc aaacaagggg ctaatccatg
1741 agcagtgttc tgtaggctct gtgacatctt tggtttatag gattttggag cctttttatga
1801 tctggaacta tttgaggggt ttcattatag gccttggttc tctccagggg ccagatgagt
1861 ttattgtgga atctttgaaa ggacaaggcc tctgtgaatg aatcagtccc agggaagcat
1921 ttggtggtgg cggcagtgga ggattgcccg gtgaacctat aaatcagcag tctcttgggc
1981 agaggagcaa gcccctcgaa catgatttca aacaagcagg tcctcttctc tcatctcacg

FIG. 13-119

```
2041 tccttagtct ctgttaatga acatactgga tgtggagttt aataaattac ctactatcat
2101 ctggccactt agattattat cacaccactg tggactgttc ctgggggcag aagaacacac
2161 cgatttgaaa gattcaaggg agaaagatta aggatcagga ttgcatgaaa gaagaaaatc
2221 cttcaatatt taaaatgttt cttacaatac ccacggagca cttttatcgt tccagcccag
2281 cgttcctgaa atgaactgac cattaacagc gcctctttga taggttaccc tgatgctcct
2341 aaagtaaagc cttaagtgtg tttttgggac aacgtgctgc ttattccacc tcagccacat
2401 atgtgtttgt gtttaggata ttgtaaatct ttgctaagta gtgttttcct tggtgaatga
2461 agtcattgtt gtcttcaagt gtaccatctg cctagcaaaa aattgctaca aactttctct
2521 tatgcaatag tccttggtac ttctaatatt tttagcaaga gacaattttc tgtactacaa
2581 tcttccactg ccagaaaaca cagtgccagt aaggttctac ataccactga ccatctgctt
2641 aatagacatg tatttccttt gagtaggaca ttagcttttg attataaagc tcaactacta
2701 taagcaaaaa tataacatct agaagcacag ttttagccag gatgtttaaa aattacactt
2761 ttgtgagact taagggtctt tttaacctag gtaagtttat atgacctaac ttaattgtag
2821 ccatattctg gtaccttcca ttttgaaaag tagaggttgc ttaagcaagc aatggataat
2881 aagagacttt tcctgaggca cctgtttgga atctggtttt ctcagcgcca gcttgacatg
2941 tgcacccttt tgtattaaac actgcaaggg tgatgcaggg gagcaggaaa gccatcctaa
3001 actcactact gagtacgatt cagtatgttc ctgtggatgt ctgctgtgac taatataaat
3061 ttcttgcaga atcagctaca cttaattatg ttgctgatag acaagcatcc acgcttcagc
3121 tggcactaag tgttttcatt gtaggatcag cagcaggtta aagactgaac ggttagtcaa
3181 gacaaatgtc ttaagaggct gcgatgtcta ggttgggctt gtgacttctt agtggcctag
3241 ccttcttgat ggcaccttga aagtgaactt ctagaaatct acatttaaaa ggcaaagctt
3301 taaaagcaga gctagtctat tctagttact gatgcaacta aaattctgta tttcttaaga
3361 tggagccact gacgagatgt cacagtatag agcctgcagt ctcaactcat tgtgatccta
3421 atggtctggg tgattggatg gtttgagttg ttagggattt tgagtttttc attttattgc
3481 atatctgggt tggatgttag actaaaggaa acccaggaat atttacctgg tgttacattt
3541 aatatttaat gtaactggtc tagcaacatt aagggggatt tctgaagcca actccggagg
3601 ctgtgggctg cacattttgc actgttttta tatacttgta ttcatatcct cttatcacct
3661 cagactcaga cacaaggcct tttacatgga aattttacaa attacttcca tttatgtaaa
3721 ataacgtcct gtgaccaagt tgtttaaatg gaaaataaag tgctttcttt aaggaaaa
//
```

ZDHHC24:

FEATURES Location/Qualifiers

FIG. 13-120

```
source          1..1319
                /organism="Homo sapiens"
                /mol_type="mRNA"
                /db_xref="taxon:9606"
                /chromosome="11"
                /map="11q13.2"
gene            1..1319
                /gene="ZDHHC24"
                /note="zinc finger, DHHC-type containing 24"
                /db_xref="GeneID:254359"
                /db_xref="HGNC:27387"
                /db_xref="HPRD:17325"
exon            1..478
                /gene="ZDHHC24"
                /inference="alignment:Splign"
                /number=1
CDS             198..1052
                /gene="ZDHHC24"
                /note="zinc finger, DHHC domain containing 24; DHHC-24;
                zinc finger DHHC domain-containing protein 24"
                /codon_start=1
                /product="probable palmitoyltransferase ZDHHC24"
                /protein_id="NP_997223.1"
                /db_xref="GI:46409316"
                /db_xref="CCDS:CCDS8143.1"
                /db_xref="GeneID:254359"
                /db_xref="HGNC:27387"
                /db_xref="HPRD:17325"
```

/translation="MGQPWAAGSTDGAPAQLPLVLTALWAAAVGLELAYVLVLGPGPP

PLGPLARALQLALAAFQLLNLLGNVGLFLRSDPSIRGVMLAGRGLGQGWAYCYQCQSQ

VPPRSGHCSACRVCILRRDHHCRLLGRCVGFGNYRPFLCLLLHAAGVLLHVSVLLGPA

LSALLRAHTPLHMAALLLLPWLMLLTGRVSLAQFALAFVTDTCVAGALLCGAGLLFHG

FIG. 13-121

```
MLLLRGQTTWEWARGQHSYDLGPCHNLQAALGPRWALVWLWPFLASPLPGDGITFQTT
                     ADVGHTAS"
     exon            479..756
                     /gene="ZDHHC24"
                     /inference="alignment:Splign"
                     /number=2
     exon            757..1317
                     /gene="ZDHHC24"
                     /inference="alignment:Splign"
                     /number=3
ORIGIN
        1 gattccgagc gcctccactg ctggtccgtt ggccagatca actcgccgcg tgggccggcc
       61 gttccctgag agtctgagcg ctcgccgcac ccccttccga gcttctattg gccgtagcag
      121 acgtccgtct gccgctatct ccgccccaat acggaagcgg cctagtcctc cggctccgac
      181 agctgggtgt ccaggccatg gggcagccct gggcggctgg gagcacggac ggggcgcccg
      241 cgcagctgcc tctcgtgctc accgcgctgt gggccgcggc cgtgggcctg gagctggctt
      301 acgtgctggt gctcggtccc gggccgccgc cgctgggacc cctggcccgg gccttgcagc
      361 tggcgctggc cgccttccag ctgctcaacc tgctgggcaa cgtggggctc ttcctgcgct
      421 cggatcccag catccgtggc gtgatgctgg ccggccgcgg tctgggccag ggctgggctt
      481 actgctacca atgccaaagc caggtgccgc cacgcagcgg acactgctct gcctgccgcg
      541 tctgcatcct gcgtcgggac caccactgcc gcctgctggg ccgctgcgtg ggcttcggca
      601 actaccggcc cttcctgtgc ctgctgcttc atgccgccgg cgtcctgctc cacgtctctg
      661 tgctgctggg ccctgcactg tcggccctgc tgcgagccca cacgcccctc cacatggctg
      721 ccctcctcct gcttccctgg ctcatgttgc tcacaggcag agtgtctctg gcacagtttg
      781 ccttggcctt cgtgacggac acgtgcgtgg cgggtgcgct gctgtgcggg gctgggctgc
      841 tcttccatgg gatgctgctg ctgcggggcc agaccacatg ggagtgggct cggggccagc
      901 actcctatga cctgggtccc tgccacaacc tgcaggcagc cctggggccc cgctgggccc
      961 tcgtctggct ctggcccttc ctggcctccc cattgcctgg ggatgggatc accttccaga
     1021 ccacagcaga tgtgggacac acagcctcct gactccagga agagccagag ctgtgcaggg
     1081 aggaaggggt gagagggggg cccccacacc tagactcagt aaggaagtcg ggttggacct
     1141 taacatctgc attggacaac tccacccctt ccttggcctt gcccctgccc gcctacactc
     1201 ctacgtgtcc agggcttggg ccgtgactta ggcagaggag tgcagaggag ggtctggcag
     1261 gggctgctca ggccgcctag ctgccccttt gccaggttaa taaagcactg acttgttaa
//
```

CANCER THERAPY

RELATED APPLICATIONS

This application claims priority to U.S. Provisional Application No. 61/357,845, entitled Cancer Therapy, filed Jun. 23, 2010, the entire contents of which are incorporated herein by reference.

GOVERNMENT SUPPORT

The United States Government has provided grant support utilized in the development of the present invention. In particular, National Institutes of Health contract number R01 HL083515 has supported development of this invention. The United States Government may have certain rights in the invention.

SEQUENCE LISTING

The instant application contains a Sequence Listing which has been submitted electronically in ASCII format and is hereby incorporated by reference in its entirety. Said ASCII copy, created on Aug. 13, 2014, is named 2004952-0026_SL.txt and is 221,903 bytes in size.

BACKGROUND OF THE INVENTION

The American Cancer Society reports that cancer caused almost 25% of the deaths in the United States in 2006. Although the cancer death rate has decreased since its peak of more than 215 per 100,000, reached in 1991, there remains a powerful need for new therapies and novel approaches to their identification and development.

SUMMARY OF THE INVENTION

The present invention encompasses the finding that inhibiting palmitoylation of RAS proteins can dominantly suppress cancer transformations directed by mediators upstream of RAS. According to the present invention, RAS palmitoylation modulators can be useful in medicine as described herein, and particularly in treatment and/or prevention of certain cancers.

Thus, among other things, the present invention provides systems for treating certain cancers with agents that modulate RAS palmitoylation. In some embodiments, the present invention provides systems for treating certain cancers with agents that modulate one or more RAS palmitoyl-acyl transferases. In some such embodiments, the agents inhibit (e.g., reduce level and/or activity of) a RAS palmitoyl-acyl transferase. In some embodiments, a provided agent is or comprises an siRNA agent specific to a RAS palmitoyl-acyl transferase.

In some embodiments, the present invention provides systems for treating certain cancers with agents that modulate one or more enzymes involved in palmitate production (e.g., fatty acid synthases). In some such embodiments, the agents reduce production of palmitate. In certain specific embodiments, a provided agent is or comprises an siRNA agent specific to a fatty acid synthase.

In some embodiments, the present invention provides systems for identifying individuals who are suffering from or susceptible to particular cancers and who are or are not likely to respond to therapy with one or more RAS palmitoylation modulating agents as described herein. In some such embodiments, individuals with elevated levels of serum palmitate and/or elevated levels and/or activity of palmitoylated RAS and/or elevated levels and/or activity of RAS palmitoyl-acyl transferase and/or elevated levels and/or activity of fatty acid synthase are determined to be good candidates for treatment with one or more RAS palmitoylation inhibitors (and not with RAS palmitoylation activators) as described herein; the converse is also true.

In some embodiments, the present invention provides systems for identifying RAS palmitoylation modulators.

In some embodiments, the present invention provides systems for identifying therapeutic agents effective in cancers. In some embodiments, provided such methods involve characterizing ability of candidate agents to inhibit RAS palmitoylation; in some embodiments, candidate agents are known to inhibit palmitoylation of RAS. In some embodiments, provided such methods involve contacting cells with a plurality of test agents and identifying those agents for which (i) transformation and/or proliferation of the cells is reduced; (ii) cell death is increased; (iii) level an/or activity of palmitoylated RAS is reduced; and/or (iv) localization of RAS is altered when the agent is present as compared with otherwise identical conditions when it is absent.

In some embodiments, a relevant property is increased or reduced by at least 5%, 10%, 15%, 20%, 25%, 30%, 35%, 40%, 45%, 50%, 55%, 60%, 65%, 70%, 75%, 80%, 85%, 90%, 95%, 100% or more when the agent is present than under otherwise identical conditions when it is absent. In some embodiments, a relevant property is increased or reduced by at least 1.5 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold or more when the agent is present than under otherwise identical conditions when it is absent. In some embodiments, cells with which candidate agents are contacted do not contain a RAS mutation.

According to the present invention, in some embodiments, RAS palmitoylation modulators as identified and/or discussed herein are useful in the treatment and/or prevention of certain cancers, including of cancers that are associated with oncogenes upstream of RAS, and/or of cancers that are not mediated by RAS mutation. In some embodiments, cancers are treated that have previously been treated with another agent. In some embodiments, RAS palmitoylation modulators are administered in combination with one or more other anti-cancer therapies or agents. In some embodiments, relevant cancers are hematological cancers. In some embodiments, relevant cancers are selected from the group consisting of BCR/ABL-positive cancers, B-acute lymphoblastic leukemia (B-ALL), and/or chronic myelogenous leukemia (CML).

In some particular embodiments, the present invention provides a method of treating cancer by administering to a patient in need thereof an agent that inhibits palmitoylation of NRAS.

In some particular embodiments, the present invention provides a method of identifying agents useful in the treatment of cancer, the method comprising steps of: (i) providing one or more agents that inhibit RAS palmitoylation; and (ii) assessing ability of the agents to inhibit proliferation of cancer cells.

In some particular embodiments, the present invention provides a method of treating cancers associated with activated RAS that requires palmitoylation, the method comprising steps of: (i) administering a FASN inhibitor to a subject suffering from a cancer that is associated with activated RAS requiring palmitoylation.

In some particular embodiments, the present invention provides a method for treating cancer comprising administering a FASN inhibitor and a RAS palmitoylation inhibitor in combination.

In some particular embodiments, the present invention provides a method comprising steps of: (i) identifying in a cancer patient suffering from or susceptible to a cancer associated with an activated RAS that requires palmitoylation; (ii) determining, based on the identification, that the patient is a good candidate for therapy with a FASN inhibitor and/or a RAS palmitoylation inhibitor.

BRIEF DESCRIPTION OF THE DRAWING

FIG. 11B. Non-lipid inhibitors of protein palmitoylation.

FIG. 12 presents GenBank records for certain representative palmitoyl-acyl transferase polypeptides. FIG. 12 discloses SEQ ID NOS 2, 46, 3, 47, 4, 48, 5, 49, 6, 50, 7, 51, 8, 52, 9, 53, 10, 54, 11, 55, 12, 56, 13, 57, 14, 58, 15, 59, 16, 60, 17, 61, 18, 62, 19, 63, 20, 64, 21, 65, 22, 66, 23, 67, 24, 68, 25 and 69, respectively, in order of appearance. FIG. 12 discloses 'DHHC' as SEQ ID NO: 1.

FIG. 13 presents GenBank records for certain representative fatty acid synthase polypeptides. FIG. 13 discloses SEQ ID NOS 26, 70, 2, 46, 3, 47, 4, 48, 5, 49, 6, 50, 7, 51, 8, 52, 9, 53, 10, 54, 11, 55, 12, 56, 13, 57, 14, 58, 15, 59, 16, 60, 17, 61, 18, 62, 19, 63, 20, 64, 21, 65, 22, 66, 23, 67, 24, 68, 25 and 69, respectively, in order of appearance. FIG. 13 discloses 'DHHC' as SEQ ID NO: 1.

DEFINITIONS

Figure 1A:
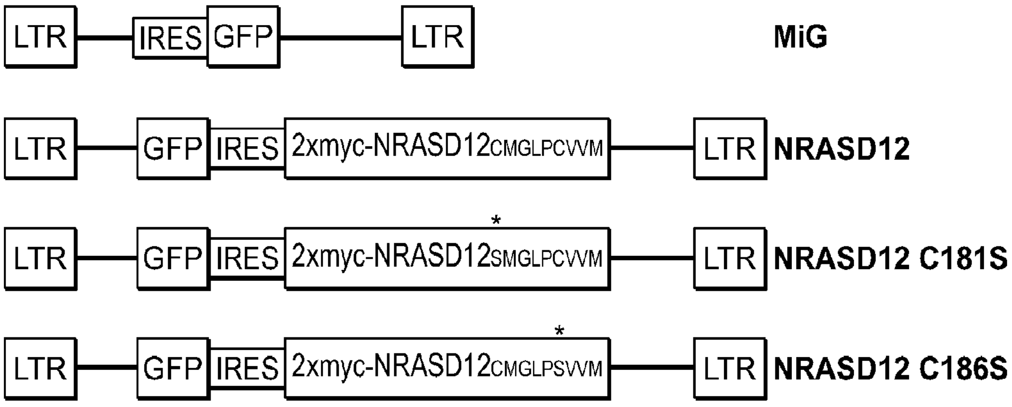
FIG. 1. Expression and localization of oncogenic NRAS and its PTM mutants. (A) Schematic diagram of retroviral expression vectors used to transduce NRASD12 (SEQ ID NO: 43), NRASD12$^{C181S}$ (SEQ ID NO: 44), or NRASD12$^{C186S}$ (SEQ ID NO: 45). (B) Immunoblot of lysates of NIH3T3 cells stably expressing the proteins listed above with a pan anti-RAS antibody (top band represents 2 times Myc-tagged-NRAS; and bottom band, endogenous RAS). (C) NIH3T3 cells expressing GFP-fused NRASD12, NRASD12$^{C181S}$, or NRASD12$^{C186S}$, contained with fluorescence-conjugated antibodies against Golgi (Golga-7) ER (BIP) resident proteins, were visualized on a Leica TCS SP2 Sprectral Confocal Microscope (original magnification× 630).

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Combination Therapy: The term "combination therapy", as used herein, refers to those situations in which two or more different pharmaceutical agents are administered in overlapping regimens so that the subject is simultaneously exposed to both agents.

Corresponding to: As used herein, the term "corresponding to" is often used to designate the position/identity of an amino acid residue in a polypeptide. Those of ordinary skill will appreciate that, for purposes of simplicity, a canonical numbering system is typically used when referring to positions in a polypeptide chain, so that an amino acid "corresponding to" a residue at position 190, for example, need not actually be the $190^{th}$ amino acid in a particular amino acid chain but rather corresponds to the residue found at 190 in a reference polypeptide (e.g., a wild type polypeptide); those of ordinary skill in the art readily appreciate how to identify corresponding amino acids.

Direct: The term "direct" may be used herein to refer to a physical interaction between two entities. Typically, a "direct" interaction is a non-covalent interaction that does not require intermediating entities. In some embodiments, a direct interaction is one that occurs in the absence of one or more other entities (e.g., of entities not participating in the interaction and/or in its detection). In some embodiments, a direct interaction is one that occurs in the absence of any other entities.

High throughput: The term "high throughput", is used herein with its art-understood meaning referring to substantially simultaneous analysis of a large number of agents (e.g., test compounds). In some embodiments, simultaneous analysis of as few as about 10 agents can be considered to be "high throughput". In many embodiments, however, simultaneous analysis of about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 300, about 350, about 400, about 450, about 500, about 550, about 600, about 650, about 700, about 750, about 800, about 850, about 900, about 950, about 1000, about 1500, about 2000, about 2500, about 3000, about 3500, about 4000, about 4500, about 5000, about 5500, about 6000, about 6500, about 7000, about 7500, about 8000, about 8500, about 9000, about 10,000, about 15,000, about 20,000, about 25,000, about 30,000, about 35,000, about 40,000, about 45,000, about 50,000, about 55,000, about 60,000, about 65,000, about 70,000, about 75,000, about 8000, about 85,000, about 90,000, about 95,000, about 100,000 or more agents is required for an analysis to be considered to be "high throughput" herein.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Inhibit: In general, an agent is said to "inhibit" a target if level and/or activity of the target is reduced in a system producing and/or containing the target when the agent is present as compared to otherwise identical conditions when it is absent. In some embodiments, level and/or activity of the target is reduced at least 5%, 10%, 15%, 20%, 25%, 30%, 35%, 40%, 45%, 50%, 55%, 60%, 65%, 70%, 75%, 80%, 85%, 90%, 95%, 100% or more when the agent is present; in some embodiments, level and/or activity of the target is reduced at least 1.5 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold or more when the agent is present as compared with when it is absent.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, 20%, 30%, 40%, 50%, 60%, 70%, 80%, 90%, or more of the other components with which they were initially associated. In some embodiments, isolated agents are more than 90%, 91%, 92%, 93%, 94%, 95%, 96%, 97%, 98%, 99% pure. In some embodiments, calculation of percent purity of isolated substances and/or entities does not include excipients (e.g., buffer, solvent, water, etc.) Non-natural amino acid: The phrase "non-natural amino acid" refers to an entity having the chemical structure of an amino acid (i.e.:

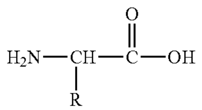

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally. Those of ordinary skill in the art will further appreciate that particular classes of polypeptides can be defined based on a designated degree of structural and/or functional similarity. In general, polypeptides of a particular class may be defined as having a specified degree of overall sequence identitiy (e.g., at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%<87%, 88%, 89%, 90%, 91%, 92%, 93%, 94%, 95%, 96%, 97%, 98%, 99%, or more) and/or as sharing one or more characteristic sequence elements. In some embodiments, such a characteristic sequence element is one whose presence correlates with a particular biological activity.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, 92%, 93%, 94%, 95%, 96%, 97%, 98%, or 99% pure.

RAS-mediated tumors: The term "RAS-mediated tumors", as used herein, refers to tumors whose transformed state is mediated by mutation of RAS. For example, activating mutations of NRAS are common in acute lymphoblastic leukemia (ALL; 10-20% carry N-RAS and/or K-RAS mutations); acute myelogenous leukemia (AML; 20-40% carry N- and/or K-RAS mutations) cells, chronic myelogenous leukemia (CML) cells, chronic myelomonocytic leukemia (CMML; 50-70% carry N- and/or K-RAS mutations) cells, juvenile chronic myelogenous leukemia (JCML; 20-30% carry N- and/or K-RAS mutations) cells, myelodysplastic syndrome (MDS; 10-30% carry N-RAS mutations) cells, multiple myeloma (MM; 10-40% carry N- and/or K-RAS mutations) and/or refractory anemia with excess blasts (RAEBt; 50% carry N- and/or K-RAS mutations) cells. RAS mutations are also common in certain melanoma cells (e.g., melanoma cells carrying RAS mutations; 25% of melanomas carry NRAS mutations). RAS mutations may also be common in neuroblastoma cells. In some embodiments, relevant cancer cells are cancer cells carrying HRAS mutations. In some embodiments, relevant cancer cells are bladder cancer cells (e.g., bladder cancer cells carrying HRAS mutations). In some embodiments, relevant cancer cells are cancer cells carrying KRAS mutations. KRAS has two alternative spliced forms—4B and 4A. KRAS4A and 4B differ only the COOH-terminal regions. When oncogenic mutations occur, both 4A and 4B become activated. KRAS4A undergoes palmitoylation, but 4B is the predominant form in cells and it does not undergo palmitoylation. In some embodiments, relevant cancer cells are lung cancer cells (e.g., lung cancer cells carrying KRAS mutations).

RAS palmitoylation modulator: The term "RAS palmitoylation modulator" is used herein to refer to agents for which the level and/or activity of palmitoylated RAS is altered when the agent is present than under otherwise identical conditions lacking the agent. Level and/or activity of palmitoylated RAS may be assessed according to any appropriate method including, for example, those described herein. In some embodiments, level and/or activity of palmitoylated RAS is at least 5%, 10%, 15%, 20%, 25%, 30%, 35%, 40%, 45%, 50%, 55%, 60%, 65%, 70%, 75%, 80%, 85%, 90%, 95%, 100% or more different when the agent is present than under otherwise identical conditions when it is absent. In some embodiments, level and/or activity of palmitoylated RAS is at least 1.5 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold or more different when the agent is present than under otherwise identical conditions when it is absent. In some embodiments, a RAS palmitoylation modulator is a RAS palmitoylation inhibitor. In some embodiments, a RAS palmitoylation modulator interacts directly with an enzyme that palmitoylates RAS (e.g., with a RAS palmitoyl-acyl transferase). In some embodiments, a RAS palmitoylation modulator interacts directly with an enzyme that participates in production of palmitate; in some such embodiments, a RAS palmitoylation modulator interacts directly with a fatty acid synthase.

RAS palmitoylation inhibitor: The term "RAS palmitoylation inhibitor" is used herein to refer to any agent for which the level and/or activity of palmitoylated RAS is lower when the agent is present than under otherwise identical conditions lacking the agent. Level and/or activity of palmitoylated RAS may be assessed according to any appropriate method including, for example, those described herein. In some embodiments, level and/or activity of palmitoylated RAS is at least 5%, 10%, 15%, 20%, 25%, 30%, 35%, 40%, 45%, 50%, 55%, 60%, 65%, 70%, 75%, 80%, 85%, 90%, 95%, 100% or more lower when the agent is present than under otherwise identical conditions when it is absent. In some embodiments, level and/or activity of palmitoylated RAS is at least 1.5 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold or more lower when the agent is present than under otherwise identical conditions when it is absent. In some embodiments, a RAS palmitoylation inhibitor acts on (in some embodiments directly; in some embodiments indirectly) a RAS palmitoyl-acetyl transferase. In some embodiments, a RAS palmitoylation inhibitor acts (in some embodiments directly; in some embodiments indirectly) on a fatty acid synthase, for example on a fatty acid synthase whose activity results in production of palmitate.

RNAi-inducing agent: The term "RNAi-inducing agent" is used to refer to siRNAs, shRNAs, and other double-stranded structures (e.g., dsRNA) that can be processed to yield an siRNA or shRNA or other small RNA species that inhibits expression of a target transcript by RNA interference. In certain embodiments of the invention an RNAi-inducing agent inhibits expression of a target RNA via an RNA interference pathway that involves translational repression.

RNAi-inducing entity: The term "RNAi-inducing entity", encompasses RNA molecules and vectors whose presence within a cell results in RNAi and leads to reduced expression of a transcript to which the RNAi-inducing entity is targeted. The RNAi-inducing entity may be, for example, an RNAi-inducing agent such as an siRNA, shRNA, or an RNAi-inducing vector. Use of the terms "RNAi-inducing entity", "RNAi-inducing agent", or "RNAi-inducing vector" is not intended to imply that the entity, agent, or vector upregulates or activates RNAi in general, though it may do so, but simply to indicate that presence of the entity, agent, or vector within the cell results in RNAi-mediated reduction in expression of a target transcript. An "RNAi-inducing entity" as used herein is an entity that has been modified or generated by the hand of man and/or whose presence in a cell is a result of human intervention as distinct, e.g., from endogenous RNA species or RNA species that are produced in a cell during the natural course of viral infection.

RNA-inducing vector: An "RNAi-inducing vector" is a vector whose presence within a cell results in transcription of one or more RNAs that hybridize to each other or self-hybridize to form an RNAi-inducing agent such as an siRNA or shRNA. In various embodiments of the invention this term encompasses plasmids or viruses whose presence within a cell results in production of one or more RNAs that self-hybridize or hybridize to each other to form an RNAi-inducing agent. In general, the vector comprises a nucleic acid operably linked to expression signal(s) so that one or more RNA molecules that hybridize or self-hybridize to form an RNAi-inducing agent is transcribed when the vector is present in a cell. Thus the vector provides a template for intracellular synthesis of the RNAi-inducing agent. For purposes of inducing RNAi, presence of a viral genome in a cell constitutes presence of the virus within the cell. A vector is considered to be present within a cell if it is introduced into the cell, enters the cell, or is inherited from a parental cell, regardless of whether it is subsequently modified or processed within the cell. An RNAi-inducing vector is considered to be targeted to a transcript if the vector comprises a template for transcription of an RNAi-inducing agent that is targeted to the transcript. Such vectors have a number of other uses in addition to transcript inhibition in a cell. For example, they may be used for in vitro production of an RNAi-inducing agent and/or for production of the agent in a cell that may or may not contain a transcript to which the vector is targeted.

Short, interfering RNA: A "short, interfering RNA" comprises a double-stranded (duplex) RNA that is between 15 and approximately 29 nucleotides in length or any other subrange or specific value within the interval between 15 and 29, e.g., 16-18, 17-19, 21-23, 24-27, 27-29 nt long and optionally further comprises one or two single-stranded overhangs, e.g., a 3' overhang on one or both strands. In certain embodiments the duplex is approximately 19 nt long. The overhang may be, e.g., 1-6 residues in length, e.g., 2 nt. An siRNA may be formed from two RNA molecules that hybridize together or may alternatively be generated from an shRNA. In certain embodiments of the invention one or both of the 5' ends of an siRNA has a phosphate group while in other embodiments one or more of the 5' ends lacks a phosphate group. In certain embodiments of the invention one or both of the 3' ends has a hydroxyl group while in other embodiments they do not. One strand of an siRNA, which is referred to as the "antisense strand" or "guide strand" includes a portion that hybridizes with a target transcript. In certain preferred embodiments of the invention, the antisense strand of the siRNA is 100% complementary with a region of the target transcript, i.e., it hybridizes to the target transcript without a single mismatch or bulge over a target region between 15 and approximately 29 nt in length, preferably at least 16 nt in length, more preferably 18-20, e.g., 19 nt in length. The region of complementarity may be any subrange or specific value within the interval between 17 and 29, e.g., 17-18, 19-21, 21-23, 19-23, 24-27, 27-29. In other embodiments the antisense strand is substantially complementary to the target region, i.e., one or more mismatches and/or bulges exists in the duplex formed by the antisense strand and a target transcript. The two strands of an siRNA are substantially complementary, preferably 100% complementary to each other within the duplex portion.

Short hairpin RNA: The term "short hairpin RNA" refers to an RNA molecule comprising at least two complementary portions hybridized or capable of hybridizing to form a double-stranded (duplex) structure sufficiently long to mediate RNAi (as described for siRNA duplexes), and at least one single-stranded portion that forms a loop connecting the regions of the shRNA that form the duplex. The structure is also referred to as a stem/loop structure, with the stem being the duplex portion. The structure may further comprise an overhang (e.g., as described for siRNA) on the 5' or 3' end. Preferably, the loop is about 1-20, more preferably about 4-10, and most preferably about 6-9 nt long and/or the overhang is about 1-20, and more preferably about 2-15 nt long. The loop may be located at either the 5' or 3' end of the region that is complementary to the target transcript whose inhibition is desired (i.e., the antisense portion of the shRNA). In certain embodiments the overhang comprises one or more U residues, e.g., between 1 and 5 Us. As described further below, shRNAs are processed into siRNAs by the conserved cellular RNAi machinery. Thus shRNAs are precursors of siRNAs and are, in general, similarly capable of inhibiting expression of a target transcript that is complementary to a portion of the shRNA (referred to as the antisense or guide strand of the shRNA). In general, the features of the duplex formed between the antisense strand of the shRNA and a target transcript are similar to those of the duplex formed between the guide strand of an siRNA and a target transcript. In certain embodiments of the invention the 5' end of an shRNA has a phosphate group while in other embodiments it does not. In certain embodiments of the invention the 3' end of an shRNA has a hydroxyl group while in other embodiments it does not.

Specificity: As is known in the art, "specificity" is a measure of the ability of a particular ligand or agent to distinguish its binding and/or reaction partner from other potential binding and/or reaction partners in its environment. In some embodiments, a ligand or agent is considered to show "specificity" for its binding and/or reaction partner if it shows at least a 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000, 9000, 10000 fold preference or more for its binding and/or reaction partner over other potential binding and/or reaction partners in its environment.

Subject: The term "subject", as used herein, refers to an individual susceptible to infection with a virus, e.g., influenza virus. The term includes birds and animals, e.g., domesticated birds and animals (such as chickens, mammals, including swine, horse, dogs, cats, etc.), and wild animals, non-human primates, and humans.

Suffering from: An individual who is "suffering from" a disease, disorder, and/or condition has been diagnosed with and/or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Targeted: The term "targeted" may be used herein to refer, for example, to an RNAi-inducing agent directed to a particular transcript. An RNAi-inducing agent is considered to be "targeted" to a target transcript for the purposes described herein if (1) the RNAi-inducing agent comprises a strand that is at least 80%, preferably at least about 85%, more preferably at least about 90%, 91%, 92%, 93%, 94%, 95%, 96%, 97%, 98%, 99%, or 100% complementary with the target transcript for a stretch of at least about 15, more preferably at least about 17, yet more preferably at least about 18 or 19 to about 21-23, or 24-29 nucleotides in length; and/or (2) one strand of the RNAi-inducing agent hybridizes to the target transcript. Suitable hybridization conditions are those typically found within the cytoplasm or nucleus of mammalian cells and/or in a *Drosophila* lysate as described, e.g., in US Pubs. 20020086356 and 20040229266 and in refs 21 and 28. In certain embodiments of the invention a GU or UG base pair in a duplex formed by an antisense strand and a target transcript is not considered a mismatch for purposes of determining whether an RNAi-inducing agent is targeted to the transcript. An RNA-inducing vector whose presence within a cell results in production of an RNAi-inducing agent that is targeted to a transcript is also considered to be targeted to the transcript. An RNAi-inducing agent targeted to a transcript is also considered to target the gene that directs synthesis of the transcript. A "target portion" is a region of a target transcript that hybridizes with an antisense strand of an RNAi-inducing agent.

Target transcript: The term "target transcript" refers to any RNA that is a target for RNAi. Messenger RNA is a preferred target. The terms "target RNA" and "target transcript" are used interchangeably herein.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of and/or reduce incidence of one or more symptoms or features of influenza infection.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treatment: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

Unit Dose: The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

Variant: As used herein, the term "variant" is a relative term that describes the relationship between a particular polypeptide of interest and a reference polypeptide to which its sequence is being compared. A polypeptide of interest is considered to be a "variant" of a reference polypeptide if the polypeptide of interest has an amino acid sequence that is identical to that of the reference but for a small number of sequence alterations at particular positions. Typically, fewer than 20%, 15%, 10%, 9%, 8%, 7%, 6%, 5%, 4%, 3%, 2% of the residues in the variant are substituted as compared with the reference. In some embodiments, a variant has 10, 9, 8, 7, 6, 5, 4, 3, 2, or 1 substituted residue as compared with a reference. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the reference. Moreover, any additions or deletions are typically fewer than about 25, 20, 19, 18, 17, 16, 15, 14, 13, 10, 9, 8, 7, 6, and commonly are fewer than about 5, 4, 3, or 2 residues. In some embodiments, the reference polypeptide is one found in nature.

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic or prokaryotic cell. Vectors capable of directing the expression of operatively linked genes are referred to herein as "expression vectors."

Wild type: As is understood in the art, the phrase "wild type" generally refers to a normal form of a protein or nucleic acid, as is found in nature.

DETAILED DESCRIPTION OF CERTAIN EMBODIMENTS

NRAS

RAS proteins are small GTPases that act as molecular switches, transducing signals from activated receptors that regulate cell proliferation, survival, and differentiation (Ulku, *Cancer Treat Res.* 15:189, 2003). RAS proteins also play a central role in tumorigenesis. Activating mutation of RAS are found in about 30% of all human cancers (Bos, *Cancer Res.* 49(17):4682, 1989). RAS activation is particularly common in certain hematological tumors. For example, expression of oncogenic NRAS, which is the predominant oncogenic RAS isoform found in hematological malignancies, efficiently induces chromic myelomonocytic leukemia (CMML)-like or acute myeloid leukemia (AML)-like disease in mice (Parikh, *Blood.* 108(7):2349, 2006). RAS can also be activated in tumors with mutations of the RAS regulator neurofibromin 1 (NF1) (Weiss, *Am J Med Genet.* 89(1):14, 1999). Additionally, a variety of well characterized oncogenes function upstream of RAS, relying on RAS to relay oncogenic signals (Downward, *Nat Rev Cancer.* 3(1):11, 2003). Indeed, it is well known that chronic up-regulation of the RAS signalling pathway occurs in many cancers in the absence of mutations in RAS itself (see, for example, Vajtek et al., *J. Biol. Chem.* 273:19925, 1998, and references cited therein).

Since the enzymatic activity of RAS is used to turn itself off and is inactive in oncogenic RAS, RAS proteins are often considered in the field to be "non-targetable" for developing cancer therapies. The present invention encompasses the recognition that identification of alternative (i.e., non-RAS) targets in order to block RAS signaling is critical for the development of therapies for RAS-related cancers (i.e., for cancers mediated by RAS).

The mammalian genome contains three RAS genes that encode four highly homologous RAS proteins: HRAS, NRAS, and the splice variants KRAS4A and KRAS4B (Ulku, *Cancer Treat Res.* 15:189, 2003). These RAS family proteins are highly homologous but divers at hypervariable regions (HVRs) at their C-temini, though all terminate in a -CAAX motif (where C represents cysteine, A represents an aliphatic amino acid, and X represents serine or threonine). The HVRs are subjected to post-translational modifications, including both farnesylation and palmitoylation, that anchor the proteins to cellular membranes and target the specific RAS isoforms to functionally distinct microdomains of the plasma membrane or endomembranes, allowing for interaction with specific pools of activator and effector proteins to generate distinct signal outputs (Hancock, *Nat Rev Mol Cell Biol.* 4(5):373, 2003).

Farnesylation is the obligatory first step in RAS post-translational modification. Specifically, an isoprenoid lipid is added to the cysteine residue of the -CAAX motif by farnesyl protein transferase (FTase) or geranylgeranyl transferase (GGTase) in the cytosol, followed by removal of the -AAX tripeptide by RAS converting enzyme (Rce1), and methylation of the newly exposed terminal farnesylated cysteine residue by isoprenylcysteine carboxyl methyltransferase on the cytosolic face of the endoplasmic reticulum. Prenylation is the minimal post-translational modification that is required for membrane association.

After -AAX cleavage and methylation, NRAS, HRAS, and KRAS4A are singly or doubly palmitoylated at cysteine residues immediately upstream of the CAAX motif. This palmitoylation is performed by palmitoyltransferases in the Gogli. Palmitoylated RAS species travel through the classic secretory pathway to the plasma membrane, whereas KRAS4B traffics directly from the endoplastmic reticulum to the plasma membrane, relying on a polybasic lysine tract in its HVR as a second means of membrane association/subdomain localization. Hancock et al *Cell.* 1989; 57(7): 1167-1177. Wright et al. *J. Lipid Res.* 2006; 47(5): 883-891. The palmitoylation of H, N, and KRAS4A is reversible; palmitoylated RAS at the plasma membrane can be depalmitoylated by a putative acylprotein thioesterase, in which case it will recycle back to the Golgi. Rocks et al. *Science.* 2005; 307(5716): 1746-1752. Consequently, a pool of depalmitoylated RAS exists at the Golgi and in transit in the case of both normal and oncogenic forms of the protein.

Various studies have examined the roles of post translational modifications in RAS localization and neoplastic transformation. Because, as noted above, prenylation by FTase is the obligate first post-translational modification for all RAS isoforms and has been shown to be essential for RAS membrane association and neoplastic transformation, significant efforts have been made to target RAS farnesylation in order to identify anti-cancer agents. However, to date, such efforts have met with only modest success.

Because farnesyl transferase inhibitors have not proven to be as successful as initially hoped, some studies have investigated downstream modifications as potential anti-cancer targets, but prior to work by the present inventors, the roles played by posttranslational modifications downstream of farnesylation in cancer development have remained unclear. For example, an Rce1 conditional knockout mouse displays a significantly more rapid disease progression in a KRAS leukemic mouse model, a conditional knockout if ICmt in a similar model delayed by did not prevent disease progression. Wahlstrom et al. *Blood.* 2007; 109(2): 763-768. Wahlstrom et al *Blood.* 2008; 112(4): 1357-1365.

Similarly, while palmitoylation has been mentioned as a possible target for the development of anti-cancer therapies, based in large part on its being required for localization of NRAS, HRAS, and KRAS4A to the inner face of the plasma membrane, which is a location previously thought to be exclusive for RAS signaling. Ducker et al *Mol Cancer Ther.* 2006; 5(7): 1647-1659. However, now that important roles for RAS signaling from the Golgi, ER, and mitochonfrial membranes have been described (see, for example, Bivona et al. *Nature.* 2003; 424(6949): 694-698. Chui et al *Nat Cell Biol.* 2002; 4(5): 343-350. Eungdamrong et al. *Biophys J.* 2007; 92(3): 808-815. Perez de Castro et al. *Mol Cell Biol.* 2004; 24(8): 3485-3496. Quatela et al *Curr Opin Cell Biol.* 2006; 18(2): 162-167.), prior to the present invention, the relevance of palmitoylation as a target has been unclear. Furthermore, evidence exists indicating that blocking palmitoylation may in fact not significantly inhibit RAS transforming activity. For example, mutations that block palmitoylation sites in oncogenic versions of RAS (specifically C181S and C184S mutations in the oncogenic RAS protein HRAS61L) generate a protein that localizes to the Golgi and internal membranes and, moreover, transforms NIH3T3 cells with good efficiency (75% of that observed with fully palmitoylation-competent HRAS61L. Chiu V K, Bivona T, Hach A, et al. RAS signalling on the endoplasmic reticulum and the Golgi. *Nat. Cell Biol.* 2002; 4(5): 343-350.

Protein Palmitoylation

Palmitoylation affects the localization and/or activity of the proteins thatit affects. Protein palmitoylation involves linkage of a palmitate to a amino acid (particularly cysteine) via either an amide linkage (N-palmitoylation) or a thioester linkage (S-palmitoylation). Typically, the palmitate linkage is relatively labile, and the palmitate on proteins turns over rapidly.

Palmitoyl-acyl transferase polypeptides typically contain a cysteine-rich domain that includes the sequence element Asp-His-His-Cys (SEQ ID NO: 1); for this reason, the domain is often referred to as a "DHHC domain" (SEQ ID NO: 1). Mutations in this domain often abolish palmitoyl-acyl transferase activity. 23 putative palmitoyl-acyl transferase polypeptides have been identified in human and mouse genomes (see, for example, Fukata et al., *Methods* 40:177, 2006; see also Table 1 and FIG. 12).

TABLE 1

Exemplary Human Palmitoyl-Acyl Transferase Polypeptides

| Name | SEQ ID NO: | Amino Acid Sequence |
|---|---|---|
| ZDHHC1 | 2 | MYKMNICNKPSNKTAPEKSVWTAPAQPSGPSPELQGQRSRRNGW<br>SWPPHPLQIVAWLLYLFFAVIGFGILVPLLPHHWVPAGYACMGAIFAGHLVVHLTAVS<br>IDPADANVRDKSYAGPLPIFNRSQHAHVIEDLHCNLCNVDVSARSKHCSACNKCVCGF<br>DHHCKWLNNCVGERNYRLFLHSVASALLGVLLLVLVATYVFVEFFVNPMRLRTNRHFE<br>VLKNHTDVWFVFLPAAPVETQAPAILALAALLILLGLLSTALLGHLLCFHIYLMWHKL<br>TTYEYIVQHRPPQEAKGVHRELESCPPKMRPIQEMEFYMRTFRHMRPEPPGQAGPAAV<br>NAKHSRPASPDPTPGRRDCAGPPVQVEWDRKKPLPWRSPLLLLAMWGPQAPPCLCRKR<br>GRGACIKCERLRPRIRRRGLGPPAAAPARRRIPRTPALCTPLALPAPTTRRRQSPWTR<br>FQWRRRAWAAPLWPPRGAGADSPRWRGRRVRPPFS |
| ZDHHC2 | 3 | MAPSGPGSSARRRCRRVLYWIPVVFITLLLGWSYYAYAIQLCIV<br>SMENTGEQVVCLMAYHLLFAMFVWSYWKTIFTLPMNPSKEFHLSYAEKDLLEREPRGE<br>AHQEVLRRAAKDLPIYTRTMSGAIRYCDRCQLIKPDRCHHCSVCDKCILKMDHHCPWV<br>NNCVGFSNYKFFLLFLAYSLLYCLFIAATDLQYFIKFWTNGLPDTQAKFHIMFLFFAA<br>AMFSVSLSSLFGYHCWLVSKNKSTLEAFRSPVFRHGTDKNGFSLGFSKNMRQVFGDEK<br>KYWLLPIFSSLGDGCSFPTCLVNQDPEQASTPAGLNSTAKNLENHQFPAKPLRESQSH<br>LLTDSQSWTESSINPGKCKAGMSNPALTMENET |
| ZDHHC3 | 4 | MMLIPTHHFRNIERKPEYLQPEKCVPPPYPGPVGTMWFIRDGCG<br>IACAIVTWFLVLYAEFVVLFVMLIPSRDYVYSIINGIVFNLLAFLALASHCRAMLTDP<br>GAVPKGNATKEFIESLQLKPGQVVYKCPKCCSIKPDRAHHCSVCKRCIRKMDHHCPWV<br>NNCVGENNQKYFVLFTMYIALISLHALIMVGFHFLHCFEEDWTKCSSFSPPTTVILLI<br>LLCFEGLLFLIFTSVMFGTQVHSICTDETGIEQLKKEERRWAKKTKWMNMKAVFGHPF<br>SLGWASPFATPDQGKADPYQYVV |
| ZDHHC4 | 5 | MDFLVLFLFYLASVLMGLVLICVCSKTHSLKGLARGGAWIFSCI<br>IPECLQRAVHGLLHYLFHTRNHTFIVLHLVLQGMVYTEYTWEVFGYCQELELSLHYLL<br>LPYLLLGVNLFFFTLTCGTNPGIITKANELLFLHVYEFDEVMFPKNVRCSTCDLRKPA<br>RSKHCSVCNWCVHRFDHHCVWVNNCIGAWNIRYFLIYVLTLTASAATVAIVSTTFLVH<br>LVVMSDLYQETYIDDLGHLHVMDTVFLIQYLFLTFPRIVFMLGFVVVLSFLLGGYLLF<br>VLYLAATNQTTNEWYRGDWAWCQRCPLVAWPPSAEPQVHRNIHSHGLRSNLQEIFLPA<br>FPCHERKKQE |
| ZDHHC5 | 6 | MPAESGKRFKPSKYVPVSAAAIFLVGATTLFFAFTCPGLSLYVS<br>PAVPIYNAIMFLFVLANFSMATFMDPGIFPRAEEDEDKEDDFRAPLYKTVEIKGIQVR<br>MKWCATCRFYRPPRCSHCSVCDNCVEEFDHHCPWVNNCIGRRNYRYFFLFLLSLTAHI<br>MGVFGFGLLYVLYHIEELSGVRTAVTMAVMCVAGLFFIPVAGLTFGHVVLVARGRTTN<br>EQVTGKFRGGVNPFTNGCCNNVSRVLCSSPARRYLGRPKKEKTIVIRPPFLRPEVSDG<br>QITVKIMDNGIQGELRRTKSKGSLEITESQSADAEPPPPPKPDLSRYTGLRTHLGLAT<br>NEDSSLLAKDSPPTPTMYKYRPGYSSSSTSAAMPHSSSAKLSRGDSLKEPTSIAESSR<br>HPSYRSEPSLEPESFRSPTFGKSFHFDPLSSGSRSSSLKSAQGTGFELGQLQSIRSEG<br>TTSTSYKSLANQTRNGSLSYDSLLTPSDSPDFESVQAGPEPDPPLGYTSPFLSARLAQ<br>QREAERHPRLVPTGPTHREPSPVRYDNLSRHIVASLQEREKLLRQSPPLPGREEEPGL<br>GDSGIQSTPGSGHAPRTSSSSDDSKRSPLGKTPLGRPAVPRFGKPDGLRGRGVGSPEP<br>GPTAPYLGRSMSYSSQKAQPGVSETEEVALQPLLTPKDEVQLKTTYSKSNGQPKSLGS<br>ASPGPGQPPLSSPTRGGVKKVSGVGGTTYEISV |
| ZDHHC6 | 7 | MGTFCSVIKFENLQELKRLCHWGPIIALGVIAICSTMAMIDSVL<br>WYWPLHTTGGSVMFIMLINWTVMILYNYFNAMFVGPGFVPLGWKPEISQDTMYLQYCK<br>VCQAYKAPRSHHCRKCNRCVMKMDHHCPWINNCCGYQWHASFTLFLLLAPLGCIHAAF<br>IFVMTMYTQLYHRLSFGWNTVKIDMSAARRDPLPIVPFGLAAFATTLFALGLALGTTI<br>AVGMLFFIQMKIILRNKTSIESWIEEKAKDRIQYYQLDEVFVFPYDMGSRWRNFKQVF<br>TWSGVPEGDGLEWPVREGCHQYSLTIEQLKQKADKRVRSVRYKVIEDYSGACCPLNKG<br>IKTFFTSPCTEEPRIQLQKGEFILATRGLRYWLYGDKILDDSFIEGVSRIRGWFPRKC<br>VEKCPCDAETDQAPEGEKKNR |
| ZDHHC7 | 8 | MQPSGHRLRDVEHHPLLAENDNYDSSSSSSSEADVADRVWFIRD<br>GCGMICAVMTWLLVAYADFVVTFVMLLPSKDFWYSVVNGVIFNCLAVLALSSHLRTML<br>TDPEKSSDCRPSACTVKTGLDPTLVGICGEGTESVQSLLLGAVPKGMATKEYMESLQL<br>KPGEVIYKCPKCCCIKPERAHHCSICKRCIRKMDHHCPWVNNCVGEKNQRFFVLFTMY<br>IALSSVHALILCGFQFISCVRGQWTECSDFSPPITVILLIFLCLEGLLFFTFTAVMFG<br>TQIHSICNDETEIERLKSEKPTWERRLRWEGMKSVFGGPPSLLWMMPFVGFRFRRLPT<br>RPRKGGPEFSV |
| ZDHHC8 | 9 | MPRSPGTRLKPAKYIPVATAAALLVGSSTLFFVFTCPWLTRAVS<br>PAVPVYNGIIFLFVLANFSMATFMDPGVFPRADEDEDKEDDFRAPLYKNVDVRGIQVR<br>MKWCATCHFYRPPRCSHCSVCDNCVEDFDHHCPWVNNCIGRRNYRYFFLFLLSLSAHM<br>VGVVAFGLVYVLNHAEGLGAAHTTITMAVMCVAGLFFIPVIGLTGFHVVLVTRGRTTN<br>EQVTGKFRGGVNPFTRGCCGNVEHVLCSPLAPRYVVEPPRLPLAVSLKPPFLRPELLD<br>RAAPLKVKLSDNGLKAGLGRSKSKGSLDRLDEKPLDLGPPLPPKIEAGTFSSDLQTPR<br>PGSAESALSVQRTSPPTPAMYKFRPAFPTGPKVPFCGPGEQVPGPDSLTLGDDSIRSL<br>DFVSEPSLDLPDYGPGGLHAAYPPSPPLSASDAFSGALRSLSLKASSRRGGDHVALQP<br>LRSEGGPPTPHRSIFAPHALPNRNGSLSYDSLLNPGSPGGHACPAHPAVGVAGYHSPY<br>LHPGATGDPPRPLPRSFSPVLGPRPREPSPVRYDNLSRTIMASIQERKDREERERLLR<br>SQADSLFGDSGVYDAPSSYSLQQASVLSEGPRGPALRYGSRDDLVAGPGFGGARNPAL<br>QTSLSSLSSSVSRAPRTSSSSLQADQASSMAPGPRPSSGSHRSPARQGLPSPPGTPHS |

TABLE 1-continued

| Exemplary Human Palmitoyl-Acyl Transferase Polypeptides | | |
|---|---|---|
| Name | SEQ ID NO: | Amino Acid Sequence |
| | | PSYAGPKAVAFIHTDLPEPPPSLTVQRDHPQLKTPPSKLNGQSPGLARLGPATGPPGP SASPTRHTLVKKVSGVGGTTYEISV |
| ZDHHC9 | 10 | MSVMVVRKKVTRKWEKLPGRNTFCCDGRVMMARQKGIFYLTLFL ILGTCTLFFAFECRYLAVQLSPAIPVFAAMLFLFSMATLLRTSFSDPGVIPRALPDEA AFIEMEIEATNGAVPQGQRPPPRIKNFQINNQIVKLKYCYTCKIFRPPRASHCSICDN CVERFDHHCPWVGNCVGKRNYRYFYLFILSLSLLTIYVFAFNIVYVALKSLKIGFLET LKETPGTVLEVLICFFTLWSVVGLTGFHTFLVALNQTTNEDIKGSWTGKNRVQNPYSH GNIVKNCCEVLCGPLPPSVLDRRGILPLEESGSRPPSTQETSSSLLPQSPAPTEHLNS NEMPEDSSTPEEMPPPEPPEPPQEAAEAEK |
| ZDHHC11 | 11 | MDTRSGSQCSVTPEAILNNEKLVLPPRISRVNGWSLPLHYFQVV TWAVFVGLSSATFGIFIPFLPHAWKYIAYVVTGGIFSFHLVVHLIASCIDPADSNVRL MKNYSQPMPLFDRSKHAHVIQNQFCHLCKVTVNKKTKHCISCNKCVSGFDHHCKWINN CVGSRNYWFFFSTVASATAGMLCLIAILLYVLVQYLVNPGVLRTDPRYEDVKNMNTWL LFLPLFPVQVQTLIVVIIGMLVLLLDFLGLVHLGQLLIFHIYLKAKKMTTFEYLINNR KEESSKHQAVRKDPYVQMDKGVLQQGAGALGSSAQGVKAKSSLLIHKHLCHFCTSVNQ DGDSTAREGDEDPCPSALGAKARNSRLICRRLCQFSTRVHPDGGSMAQEADDAPSIST LGLQQETTEPMKTDSAESED |
| ZDHHC11B | 12 | MDTRSGSQCSVTPEAIRNNEELVLPPRISRVNGWSLPLHYFRVV TWAVFVGLSLATFRIFIPLLPHSWKYIAYVVTGGIFSFHLVVHLIASCIDPADSNVRL MKNYSQPMPLFDRSKHAHVIQNQFCHLCKVTVNKKTKHCISCNKCVSGFDHHCKWINN CVGSRNYWFFFSTVASATAGMLCLIAILLYVLVQYLVNPRVLRTDPRYEDVKNMNTWL LFLPLFPVQVQTLIVVIIRMLVLLLDLLGLVQLGQLLIFHIYLKAKKMTTFEYLINTR KEESSKHQAVRKDPYVQMDKGFLQQGAGALGSSAQGVKAKSSLLIYKCPCHFCTSVNQ DGDSKAQGRLTALPQDREQAPVTWK |
| ZDHHC12 | 13 | MAPWALLSPGVLVRTGHTVLTWGITLVLFLHDTELRQWEEQGEL LLPLTFLLLVLGSLLLYLAVSLMDPGYVNVQPQPQEELKEEQTAMVPPAIPLRRCRYC LVLQPLRARHCRECRRCVRRYDHHCPWMENCVGERNHPLFVVYLALQLVVLLWGLYLA WSGLRFFQPWGLWLRSSGLLFATFLLLSLFSLVASLLLVSHLYLVASNTTTWEFISSH RIAYLRQRPSNPFDRGLTRNLAHFFCGWPSGSWETLWAEEEEEGSSPAV |
| ZDHHC13 | 14 | MEGPGLGSQCRNHSHGPHPPGFGRYGICAHENKELANAREALPL IEDSSNCDIVKATQYGIFERCKELVEAGYDVRQPDKENVSLLHWAAINNRLDLVKFYI SKGAVVDQLGGDLNSTPLHWAIRQGHLPMVILLLQHGADPTLIDGEGFSSIHLAVLFQ HMPIIAYLISKGQSVNMTDVNGQTPLMLSAHKVIGPEPTGFLLKFNPSLNVVDKDIHQN TPLHWAVAAGNVNAVDKLLEAGSSLDIQNVKGETPLDMALQNKNQLIIHMLKTEAKMR ANQKFRLWRWLQKCELFLLLMLSVITMWAIGYILDFNSDSWLLKGCLLVTLFFLTSLF PRFLVGYKNLVYLPTAFLLSSVFWIFMTWFILFFPDLAGAPFYFSFIFSIVAFLYFFY KTWATDPGFTKASEEEKKVNIITLAETGSLDFRTFCTSCLIRKPLRSLHCHVCNCCVA RYDQHCLWTGRCIGFGNHHYYIFFLFFLSMVCGWIIYGSFIYLSSHCATTFKEDGLWT YLNQIVACSPWVLYILMLATFHFSWSTFLLLNQLFQIAFLGLTSHERISLQKQSKHMK QTLSLRKTPYNLGFMQNLADFFQCGCFGLVKPCVVDWTSQYTMVFHPAREKVLRSV |
| ZDHHC14 | 15 | MPPGGGGPMKDCEYSQISTHSSSPMESPHKKKKIAARRKWEVFP GRNKFFCNGRIMMARQTGVFYLTLVLILVTSGLFFAFDCPYLAVKITPAIPAVAGILF FFVMGTLLRTSFSDPGVLPRATPDEAADLERQIDIANGTSSGGYRPPPRTKEVIINGQ TVKLKYCFTCKIFRPPRASHCSLCDNCVERFDHHCPWVGNCVGKRNYRFFYMFILSLS FLTVFIFAFVITHVILRSQQTGFLNALKDSPASVLEAVVCFFSVWSIVGLSGFHTYLI SSNQTTNEDIKGSWSNKRGKENYNPYSYGNIFTNCCVALCGPISPSLIDRRGYIQPDT PQPAAPSNGITMYGATQSQSDMCDQDQCIQSTKFVLQAAATPLLQSEPSLTSDELHLP GKPGLGTPCASLTLGPPTPPASMPNLAEATLADVMPRKDEHMGHQFLTPDEAPSPPRL LAAGSPLAHSRTMHVLGLASQDSLHEDSVRGLVKLSSV |
| ZDHHC15 | 16 | MRRGWKMALSGGLRCCRRVLSWVPVLVIVLVVLWSYYAYVFELC LVTVLSPAEKVIYLILYHAIFVFFTWTYWKSIFTLPQQPNQKFHLSYTDKERYENEER PEVQKQMLVDMAKKLPVYTRTGSGAVRFCDRCHLIKPDRCHHCSVCAMCVLKMDHHCP WVNNCIGFSNYKFFLQFLAYSVLYCLYIATTVFSYFIKYWRGELPSVRSKFHVLFLLF VACMFFVSLVILFGYHCWLVSRNKTTLEAFCTPVFTSGPEKNGFNLGFIKNIQQVFGD KKKFWLIPIGSSPGDGHSFPMRSMNESQNPLLANEETWEDNEDDNQDYPEGSSSLAVE TET |
| ZDHHC16 | 17 | MRGQRSLLLGPARLCLRLLLLLGYRRRCPPLLRGLVQRWRYGKV CLRSLLYNSFGGSDTAVDAAFEPVYWLVDNVIRWFGVVFVVLVIVLTGSIVAIAYLCV LPLILRTYSVPRLCWHFFYSHWNLILIVFHYYQAITTPPGYPPQGRNDIATVSICKKC IYPKPARTHHCSICNRCVLKMDHHCPWLNNCVGHYNHRYFFSFCFFMTLGCVYCSYGS WDLFREAYAAIEKMKQLDKNKLQAVANQTYHQTPPPTFSFRERMTHKSLVYLWFLCSS VALALGALTVWHAVLISRGETSIERHINKKERRRLQAKGRVFRNPYNYGCLDNWKVFL GVDTGRHWLTRVLLPSSHLPHGNGMSWEPPPWVTAHSASVMAV |
| ZDHHC17 | 18 | MQREEGFNTKMADGPDEYDTEAGCVPLLHPEEIKPQSHYNHGYG EPLGRKTHIDDYSTWDIVKATQYGIYERCRELVEAGYDVRQPDKENVTLLHWAAINNR IDLVKYYISKGAIVDQLGGDLNSTPLHWATRQGHLSMVVQLMKYGADPSLIDGEGCSC IHLAAQFGHTSIVAYLIAKGQDVDMMDQNGMTPLMWAAYRTHSVDPTRLLLTFNVSVN |

TABLE 1-continued

Exemplary Human Palmitoyl-Acyl Transferase Polypeptides

| Name | SEQ ID NO: | Amino Acid Sequence |
|---|---|---|
| | | LGDKYHKNTALHWAVLAGNTTVISLLLEAGANVDAQNIKGESALDLAKQRKNVWMINH LQEARQAKGYDNPSFLRKLKADKEFRQKVMLGTPFLVIWLVGFIADLNIDSWLIKGLM YGGVWATVQFLSKSFFDHSMHSALPLGIYLATKFWMYVTWFFWFWNDLNFLFIHLPFL ANSVALFYNFGKSWKSDPGIIKATEEQKKKTIVELAETGSLDLSIFCSTCLIRKPVRS KHCGVCNRCIAKFDHHCPWVGNCVGAGNHRYFMGYLFFLLFMICWMIYGCISYWGLHC ETTYTKDGFWTYITQIATCSPWMFWMFLNSVFHFMWVAVLLMCQMYQISCLGITTNER MNARRYKHFKVTTTSIESPFNHGCVRNIIDFFEFRCCGLFRPVIVDWTRQYTIEYDQI SGSGYQLV |
| ZDHHC18 | 19 | MKDCEYQQISPGAAPLPASPGARRPGPAASPTPGPGPAPPAAPA PPRWSSSGSGSGSGSGSLGRRPRRKWEVFPGRNRFYCGGRLMLAGHGGVFALTLLLIL TTTGLFFVFDCPYLARKLTLAIPIIAAILFFFVMSCLLQTSFTDPGILPRATVCEAAA LEKQIDNTGSSTYRPPPRTREVLINGQMVKLKYCFTCKMFRPPRTSHCSVCDNCVERF DHHCPWVGNCVGRRNYRFFYAFILSLSFLTAFIFACVVTHLTLRAQGSNFLSTLKETP ASVLELVICFFSIWSILGLSGFHTYLVASNLTTNEDIKGSWSSKRGGEASVNPYSHKS IITNCCAVLCGPLPPSLIDRRGFVQSDTVLPSPIRSDEPACRAKPDASMVGGHP |
| ZDHHC19 | 20 | MTLLTDATPLVKEPHPLPLVPRPWFLPSLFAAFNVVLLVFFSGL FFAFPCRWLAQNGEWAFPVITGSLFVLTFFSLVSLNFSDPGILHQGSAEQGPLTVHVV WVNHGAFRLQWCPKCCFHRPPRTYHCPWCNICVEDFDHHCKWVNNCIGHRNFRFFMLL VLSLCLYSGAMLVTCLIFLVRTTHLPFSTDKAIAIVVAVSAAGLLVPLSLLLLIQALS VSSADRTYKGKCRHLQGYNPFDQGCASNWYLTICAPLGPKYMAEAVQLQRVVGPDWTS MPNLHPPMSPSALNPPAPTSGSLQSREGTPGAW |
| ZDHHC20 | 21 | MAPWTLWRCCQRVVGWVPVLFITFVVVWSYYAYVVELCVFTIFG NEENGKTVVYLVAFHLFFVMFVWSYWMTIFTSPASPSKEFYLSNSEKERYEKEFSQER QQEILRRAARALPIYTTSASKTIRYCEKCQLIKPDRAHHCSACDSCILKMDHHCPWVN NCVGFSNYKFFLLFLLYSLLYCLFVAATVLEYFIKFWTNELTDTRAKFHVLFLFFVSA MFFISVLSLFSYHCWLVGKNRTTIESFRAPTFSYGPDGNGFSLGCSKNWRQVFGDEKK YWLLPIFSSLGDGCSFPTRLVGMDPEQASVTNQNEYARSGSNQPFPIKPLSESKNRLL DSESQWLENGAEEGIVKSGV |
| DHHC21 | 22 | MGLRIHFVVDPHGWCCMGLIVFVWLYNIVLIPKIVLFPHYEEGH IPGILIIIFYGISIFCLVALVRASITDPGRLPENPKIPHGEREFWELCNKCNLMRPKR SHHCSRCGHCVRRMDHHCPWINNCVGEDNHWLFLQLCFYTELLTCYALMFSFCHYYYF LPLKKRNLDLFVFRHELAIMRLAAFMGITMLVGITGLFYTQLIGIITDTTSIEKMSNC CEDISRPRKPWQQTFSEVFGTRWKILWFIPFRQRQPLRVPYHFANHV |
| DHHC22 | 23 | MLALRLLNVVAPAYFLCISLVTFVLQLFLFLPSMREDPAAARLF SPALLHGALFLFLSANALGNYVLVIQNSPDDLGACQGASARKTPCPSPSTHFCRVCAR VTLRHDHHCFFTGNCIGSRNMRNFVLFCLYTSLACLYSMVAGVAYISAVLSISFAHPL AFLTLLPTSISQFFSGAVLGSEMFVILMLYLWFAIGLACAGFCCHQLLLILRGQTRHQ VRKGVAVRARPWRKNLQEVFGKRWLLGLLVPMFNVGSESSKQQDK |
| ZDHHC23 | 24 | MTQKGSMKPVKKKKTEEPELEPLCCCEYIDRNGEKNHVATCLCD CQDLDEGCDRWITCKSLQPETCERIMDTISDRLRIPWLRGAKKVNISIIPPLVLLPVF LHVASWHFLLGVVVLTSLPVLALWYYYLTHRRKEQTLFFLSLGLFSLGYMYYVFLQEV VPKGRVGPVQLAVLTCGLFLILLALHRAKKNPGYLSNPASGDRSLSSSQLECLSRKGQ EKTKGFPGADMSGSLNNRTTKDDPKGSSKMPAGSPTKAKEDWCAKCQLVRPARAWHCR ICGICVRRMDHHCVWINSCVGESNHQAFILALLIFLLTSVYGITLTLDTICRDRSVFT ALFYCPGVYANYSSALSFTCVWYSVIITAGMAYIFLIQLINISYNVTEREVQQALRQK TGRRLLCGLIVDTGLLG |
| ZDHHC24 | 25 | MGQPWAAGSTDGAPAQLPLVLTALWAAAVGLELAYVLVLGPGPP PLGPLARALQLALAAFQLLNLLGNVGLFLRSDPSIRGVMLAGRGLGQGWAYCYQCQSQ VPPRSGHCSACRVCILRRDHHCRLLGRCVGFGNYRPFLCLLLHAAGVLLHVSVLLGPA LSALLRAHTPLHMAALLLLPWLMLLTGRVSLAQFALAFVTDTCVAGALLCGAGLLFHG MLLLRGQTTWEWARGQHSYDLGPCHNLQAALGPRWALVWLWPFLASPLPGDGITFQTT ADVGHTAS |

As can be seen with reference to Table 1, sequence similarity between and among the presented palmitoyl-acyl transferase polypeptides is highest in the DHHC domain (SEQ ID NO: 1); each depicted palmitoyl-acyl transferase polypeptide also has several (at least 4) transmembrane domains.

Two palmitoyl-acyl transferase polypeptides (DHHC-9 (SEQ ID NO: 10) and DHHC-18 (SEQ ID NO: 19) in Table 1) have been reported to show apparent palmitoyl-aceyl transferase activity only toward HRAS and NRAS (Fukata et al., *Methods* 40:177, 2006).

Palmitate Synthesis

Those of ordinary skill in the art reading the present disclosure will appreciate that protein palmitoylation may be modified by, for example, affecting level or activity of one or more palmitate-acyl transferase polypeptides as described herein and/or by affecting the level of palmitate substrate available to such palmitoyl-acyl transferase polypeptides.

In some embodiments of the present invention, palmitate levels can be modulated, for example, by modulating one or more enzymes involved in palmitate synthesis. Table 2 presents representative sequences of known fatty acid synthases and other enzymes involved in production of palmitate.

TABLE 2

Exemplary Human Polypeptides Involved in Palmitate Production

| Name | Amino Acid Sequence |
|---|---|
| FASN (SEQ ID NO: 26) | MEEVVIAGMSGKLPESENLQEFWDNLIGGVDMVTDDDRRWKAGL<br>YGLPRRSGKLKDLSRFDASFFGVHPKQAHTMDPQLRLLLEVTYEAIVDGGINPDSLRG<br>THTGVWVGVSGSETSEALSRDPETLVGYSMVGCQRAMMANRLSFFFDFRGPSIALDTA<br>CSSSLMALQNAYQAIHSGQCPAAIVGGINVLLKPNTSVQFLRLGMLSPEGTCKAFDTA<br>GNGYCRSEGVVAVLLTKKSLARRVYATILNAGTNTDGFKEQGVTFPSGDIQEQLIRSL<br>YQSAGVAPESFEYIEAHGTGTKVGDPQELNGITRALCATRQEPLLIGSTKSNMGHPEP<br>ASGLAALAKVLLSLEHGLWAPNLHFHSPNPEIPALLDGRLQVVDQPLPVRGGNVGINS<br>FGFGGSNVHIILRPNTQPPPAPAPHATLPRLLRASGRTPEAVQKLLEQGLRHSQDLAF<br>LSMLNDIAAVPATAMPFRGYAVLGGERGGPEVQQVPAGERPLWFICSGMGTQWRGMGL<br>SLMRLDRFRDSILRSDEAVKPFGLKVSQLLLSTDESTFDDIVHSFVSLTAIQIGLIDL<br>LSCMGLRPDGIVGHSLGEVACGYADGCLSQEEAVLAAYWRGQCIKEAHLPPGAMAAVG<br>LSWEECKQRCPPGVVPACHNSKDTVTISGPQAPVFEFVEQLRKEGVFAKEVRTGGMAF<br>HSYFMEAIAPPLLQELKKVIREPKPRSARWLSTSIPEAQWHSSLARTSSAEYNVNNLV<br>SPVLFQEALWHVPEHAVVLEIAPHALLQAVLKRGLKPSCTIIPLMKKDHRDNLEFFLA<br>GIGRLHLSGIDANPNALFPPVEFPAPRGTPLISPLIKWDHSLAWDVPAAEDFPNGSGS<br>PSAAIYNIDTSSESPDHYLVDHTLDGRVLFPATGYLSIVWKTLARALGLGVEQLPVVF<br>EDVVLHQATILPKTGTVSLEVRLLEASRAFEVSENGNLVVSGKVYQWDDPDPRLFDHP<br>ESPTPNPTEPLFLAQAEVYKELRLRGYDYGPHFQGILEASLEGDSGRLLWKDNWVSFM<br>DTMLQMSILGSAKHGLYLPTRVTAIHIDPATHRQKLYTLQDKAQVADVVVSRWLRVTV<br>AGGVHISGLHTESAPRRQQEQQVPILEKFCFTPHTEEGCLSERAALQEELQLCKGLVQ<br>ALQTKVTQQGLKMVVPGLDGAQIPRDPSQQELPRLLSAACRLQLNGNLQLELAQVLAQ<br>ERPKLPEDPLLSGLLDSPALKACLDTAVENMPSLKMKVVEVLAGHGHLYSRIPGLLSP<br>HPLLQLSYTATDRHPQALEAAQAELQQHDVAQGQWDPADPAPSALGSADLLVCNCAVA<br>ALGDPASALSNMVAALREGGFLLLHTLLRGHPLGDIVAFLTSTEPQYGQGILSQDAWE<br>SLFSRVSLRLVGLKKSFYGSTLFLCRRPTPQDSPIFLPVDDTSFRWVESLKGILADED<br>SSRPVWLKAINCATSGVVGLVNCLRREPGGNRLRCVLLSNLSSTSHVPEVDPGSAELQ<br>KVLQGDLVMNVYRDGAWGAFRHFLLEEDKPEEPTAHAFVSTLTRGDLSSIRWVCSSLR<br>HAQPTCPGAQLCTVYYASLNFRDIMLATGKLSPDAIPGKWTSQDSLLGMEFSGRDASG<br>KRVMGLVPAKGLATSVLLSPDFLWDVPSNWTLEEAASVPVVYSTAYYALVVRGRVRPG<br>ETLLIHSGSGGVGQAAIAIALSLGCRVFTTVGSAEKRAYLQARFPQLDSTSFANSRDT<br>SFEQHVLWHTGGKGVDLVLNSLAEEKLQASVRCLATHGRFLEIGKFDLSQNHPLGMAI<br>FLKNVTFHGVLLDAFFNESSADWREVWALVQAGIRDGVVRPLKCTVFHGAQVEDAFRY<br>MAQGKHIGKVVVQVLAEEPEAVLKGAKPKLMSAISKTFCPAHKSYIIAGGLGGFGLEL<br>AQWLIQRGVQKLVLTSRSGIRTGYQAKQVRRWRRQGVQVQVSTSNISSLEGARGLIAE<br>AAQLGPVGGVFNLAVVLRDGLLENQTPEFFQDVCKPKYSGTLNLDRVTREACPELDYF<br>VVFSSVSCGRGNAGQSNYGFANSAMERICEKRRHEGLPGLAVQWGAIGDVGILVETMS<br>TNDTIVSGTLPQRMASCLEVLDLFLNQPHMVLSSFVLAEKAAAYRDRDSQRDLVEAVA<br>HILGIRDLAAVNLDSSLADLGLDSLMSVEVRQTLERELNLVLSVREVRQLTLRKLQEL<br>SSKADEASELACPTPKEDGLAQQQTQLNLRSLLVNPEGPTLMRLNSVQSSERPLFLVH<br>PIEGSTTVFHSLASRLSIPTYGLQCTRAAPLDSIHSLAAYYIDCIRQVQPEGPYRVAG<br>YSYGACVAFEMCSQLQAQQSPAPTHNSLFLFDGSPTYVLAYTQSYRAKLTPGCEAEAE<br>TEAICFFVQQFTDMEHNRVLEALLPLKGLEERVAAAVDLIIKSHQGLDRQELSFAARS<br>FYYKLRAAEQYTPKAKYHGNVMLLRAKTGGAYGEDLGADYNLSQVCDGKVSVHVIEGD<br>HRTLLEGSGLESIISIIHSSLAEPRVSVREG |

Palmitoylation Modulators

As described herein, the present invention provides systems for identifying, characterizing, and/or using modulators of NRAS palmitoylation, for example as relevant to the diagnosis and/or treatment of cancer.

In some embodiments, a palmitoylation modulator as described herein specifically modulates palmitoylation of RAS, e.g., of NRAS. In some embodiments, a palmitoylation modulator as described herein modulates activity of a palmitoyl-acyl transferase polypeptide. In some embodiments, a palmitoylation modulator modulates level and/or activity of a palmitoyl-acyl transferase polypeptide that is specific to RAS, e.g., to NRAS. In some embodiments, a palmitoylation modulator modulates level and/or activity of only one palmitoyl-acyl transferase polypeptide that acts on RAS. In some embodiments, a palmitoylation modulator modulates level and/or activity of more than one palmitoyl-acyl transferase polypeptide that acts on RAS. In some embodiments, a palmitoylation modulator modulates level and/or activity of all palmitoyl-acyl transferase polypeptides in a given system that act on RAS.

In some embodiments, a palmitoylation modulator as described herein modulates activity of one or more enzymes involved in production of palmitate. In some embodiments, a palmitoylation modulator as described herein modulates activity of one or more fatty acid synthases.

A variety of assay systems are know for the assessment of protein palmitoylation (see, for example, Draper et al., *Mol Membr Biol* 26:5, 2009). For example, some assays involve metabolic labeling of cultured cells with radioactive forme of palmitate (s.g., [$^{3}$H]palmitate or $^{123}$I-IC16palmitate (see, for example, Lobo et al., *J Biol Chem* 277:41368, 2002; Roth et al., *J Cell Biol* 159:23, 2002; Swarthout et al., *J Biol Chem* 280:31148, 2005; Resh et al., *Sci STKE* 2006:re14, 2006; Drisdel et al, *Methods* 40:127, 2006; Fernandez-Hernando *J Cell Biol* 174:369, 2006; Fukata et al., *Neuron* 44:987, 2004; Berthiaume et al., *Methods Enzymol* 250:454, 1995; Peseckis et al., *J Biol Chem* 268:5107, 1993; Hensel et al., *Eir J Biochem* 232:373, 1995). The labeled palmitate is metabolically incorporated into palmitoylation sites on proteins. Cells are lysed, and labeled proteins are purified, for example by gel electrophoresis (e.g., SDS-PAGE). This approach allows assessment of palmitoylation in live cells, and also can permit palmitoylation/depalmitoylation studies.

Alternatively or additionally, assay systems have been developed that utilize matrix-assisted laser desorption ionization time-of-flight mass spectrometry (MALDI-TOF MS) (see, for example, Resh et al., *Sci SKTE* 2006:re14, 2006;

Drisdel et al., *Methods* 40:127, 2006; Hensel et al., *Eir J Biochem* 232:373, 1995; Liang et al., *J Biol Chem* 276:30987, 2001). In such assays, palmitoylated proteins are typically fragmented (e.g., by digestion with a protease) so that peptide fingerprints can be prepared before and after addition or removal of palmitate groups. Palmitate groups can be removed, for example, by treatment with hydroxylamine. This approach can allow characterization of particular palmitoylation sites and/or estimation of palmitoylation stoichiometry.

Alternatively or additionally, assay systems have been developed that utilize fatty acyl exchange chemistry (see, for example, Drisdel et al., *Methods* 40:127, 2006) to assess palmitoylation of proteins. Typically, these assays involve blocking free sulfyhdryl groups (e.g., with N-ethylmaleimide; NEM), and then palmitate groups are released, for example by hydroxylamine cleavage, thereby creating free sulfyhdryl groups on cysteine residues to which palmitate had been attached. These free sulfhydryl groups are then available for labeling, for example with thiol-specific reagents such as [$^3$H]NEM or biotin-conjugated 1-biotinamido-4-[4-(maleimidomethyl)cyclohexanecarboxamido]butane (Btn-BMCC) for ready detection. This approach can provide particularly high sensitivity, and therefore, in some embodiments, is particularly useful for assessment of low abundance events.

Alternatively or additionally, assay systems have been developed that permit assessment of protein palmitoylation by labeling target proteins for example with w-azido-fatty acids (see, for example, Hang et al., *J Am Chem Soc* 129: 2744, 2007). Such w-azido fatty acids can be added to live cells, which take them up and incorporate them into proteins at sites of S-palmitoylation or N-myristoylation. Incorporated fatty acids can then be detected, for example by labeling with biotin and binding to streptavidin.

Alternatively or additionally, protein palmitoylation can be assessed in vitro, for example using labeled lipopeptides that mimic palmitoylation motifs in systems that include isolated palmitoyl-acyl transferase enzymes (optionally in the context of membrane fractions).

Alternatively or additionally, assays systems have been developed for assessment of protein palmitoylation that utilize labeled lipopeptides provided to intact cells that have endogenous palmitoyl-CoA (see, for example, Draper et al., *J Lipid Res* 48:1873, 2007). Peptides that are taken up and palmitoylated inside cells can then be released from the cells and detected, for example, based on their altered hydrophobicity. This method may be particularly useful, for example, when it is desirable to quantitatively assess different types (e.g., Type 1 and Type 2) palmitoyl-acyl transferase activity. This assay may also be particularly amenable to higher throughput formats.

According to the present invention, any such palmitoylation assays, or other appropriate assays as may be developed, identified, or otherwise utilized by those of ordinary skill in the art in light of the guidance provided herein, may be utilized to identify, characterize, detect, or otherwise assess one or more palmitoylation modulators as described herein. In some embodiments, palmitoylation modulators are identified and/or characterized by being contacted with a palmitoylation assay system so that their effects on protein palmitoylation, and/or particularly on palmitoylation of NRAS are determined. In some embodiments, activity of one or more test agents is compared with that of a reference agent (e.g., one or more known palmitoylation modulators) and/or reference set of conditions (e.g., absence of the test agent, presence of mutant palmitoylation substrate, presence of mutant palmitoyl-acyl transferase polypeptide, presence of mutant enzyme involved in palmitate synthesis, etc.).

In some embodiments, the present invention provides and/or relates to palmitoylation modulators that are or comprise RNAi-inducing entities. In some such embodiments, the RNAi-inducing entities are targeted to one or more palmitoyl-acyl transferase transcripts as described herein; in some such embodiments, the RNAi-inducing entities are targeted to one or more transcripts encoding a polypeptide involved in palmitate production as described herein. Those of ordinary skill in the art, guided by the teachings presented herein, are readily able to design, prepare and use specific RNAi-inducing agents in accordance with the present invention.

In some embodiments, the present invention provides and/or relates to palmitoylation modulators that are or comprise antibodies. In some such embodiments, the antibodies specifically bind to one or more palmitoyl-acyl transferase polypeptides as described herein; in some such embodiments, the antibodies specifically bind to one or more polypeptides involved in palmitate production as described herein. Those of ordinary skill in the art, guided by the teachings presented herein, are readily able to design, prepare and use specific antibodies that are palmitoylation modulators in accordance with the present invention.

In some embodiments, the present invention provides and/or relates to palmitoylation modulators that are or comprise small molecules. In some such embodiments, the small molecules specifically interact with one or more palmitoyl-acyl transferase polypeptides as described herein; in some such embodiments, the small molecules specifically interact with one or more polypeptides involved in palmitate production as described herein. In some embodiments, relevant small molecules are known in modulate (e.g., inhibit) one or more palmitoyl-acyl transferase polypeptides and/or one or more polypeptides involved in palmitate synthesis.

In some embodiments, the present invention provides and/or relates to palmitoylation modulators that are or comprise lipid based compounds (e.g., 2-bromopalmitate, tunicamycin, cerlenin analogs, and related compounds; see, for example, FIG. 11. In some particular embodiments, lipid-based compounds that show specificity for NRAS-specific palmitoyl-acyl transferases are identified, characterized, and/or utilized in accordance with the present invention.

Identification and/or Characterization of Anti-Cancer Agents

As described herein, the present invention relates to inhibiting transformation and/or proliferation of certain cancer cells, and/or to the identification, characterization, and/or use of agents that inhibit transformation and/or proliferation of certain cancer cells. Such inhibition may be assessed and/or performed in vivo (i.e., in the context of an organism) or in vitro (i.e., with proliferating isolated cells).

In some embodiments, relevant cancer cells are cells of hematologic cancers. In some embodiments, relevant cancer cells are transformed by mutation and/or activation of RAS. In some embodiments, relevant cancer cells are not transformed by mutation and/or activation of RAS. That is, in some embodiments, relevant cancer cells do not carry RAS mutations.

In some embodiments, relevant cancer cells are transformed through mutation and/or activation of one or more oncogenes upstream of RAS (e.g., which result in hyperactivation of RAS). In some embodiments, relevant cancer cells are those that involve activated RAS that requires palmitoylation. In some embodiments, relevant cancer cells show elevated levels of BCR/ABL as compared with non-cancer cells. In some embodiments, relevant cancer cells show sensitivity to FASN inhibitors and/or to other palmitoylation modulators. In some embodiments, relevant cancer cells are cancer cells with NRAS mutations; in some embodiments, relevant cancer cells do not carry NRAS mutations. In some embodiments, relevant cancer cells are hematological cancer cells (e.g., carrying RAS mutations).

In some embodiments, relevant cancer cells are selected from the group consisting of acute lymphoblastic leukemia (ALL; 10-20% carry N-RAS and/or K-RAS mutations); acute myelogenous leukemia (AML; 20-40% carry N- and/or K-RAS mutations) cells, chronic myelogenous leukemia (CML) cells, chronic myelomonocytic leukemia (CMML; 50-70% carry N- and/or K-RAS mutations) cells, juvenile chronic myelogenous leukemia (JCML; 20-30% carry N- and/or K-RAS mutations) cells, myelodysplastic syndrome (MDS; 10-30% carry N-RAS mutations) cells, multiple myeloma (MM; 10-40% carry N- and/or K-RAS mutations) and/or refractory anemia with excess blasts (RAEBt; 50% carry N- and/or K-RAS mutations) cells.

In some embodiments, relevant cancer cells are melanoma cells (e.g., melanoma cells carrying RAS mutations; 25% of melanomas carry NRAS mutations). In some embodiments, relevant cancer cells are neuroblastoma cells.

In some embodiments, relevant cancer cells are cancer cells carrying HRAS mutations. In some embodiments, relevant cancer cells are bladder cancer cells (e.g., bladder cancer cells carrying HRAS mutations)

In some embodiments, relevant cancer cells are cancer cells carrying KRAS mutations. KRAS has two alternative spliced forms—4B and 4A. KRAS4A and 4B differ only the COOH-terminal regions. When oncogenic mutations occur, both 4A and 4B become activated. KRAS4A undergoes palmitoylation, but 4B is the predominant form in cells and it does not undergo palmitoylation. In some embodiments, relevant cancer cells are lung cancer cells (e.g., lung cancer cells carrying KRAS mutations.

In some embodiments, relevant cancer cells are cancer cells carrying NF1 mutations. In some embodiments, relevant cancer cells are neurofibromatosis or JMML cells (e.g., neurofibromatosis or JMML cells carrying NF1 mutations). In particular, data presented herein (see, for example, Example 2) demonstrates that palmitoylation-deficient activated NRAS can function as a dominant negative regulator for the RAS signaling pathways and suggests that NF1 related cancers would benefit from inhibition of RAS palmitoylation).

The vast majority of CML patients, as well as about 15% of all B-ALL patients, carry a reciprocal translocation t(9;22) (q34;q11) known as the Philadelphia chromosome (Ph) that generates the BCR/ABL fusion protein (Deininger, *Blood.* 96(10):3343, 2000; Apostolidou, *Drugs* 67(15):2153, 2007). ABL tyrosine kinase activity is elevated in BCR/ABL. While significant advances have been made in the treatment of CML by targeting the kinase activity of BCR/ABL, these treatments do not constitute a cure, as BCR/ABL-positive cells persist and eventually develop mutations that cause resistance to kinase inhibitors (reviewed in Ren, *Nat Rev Cancer.* 5(3):172, 2005). Great advances have also been achieved in the treatment of Ph+ B-ALL through the use of the ABL kinase inhibitor (imatinib) in combination with other chemotherapy agents. Patient prognosis and survival rates have improved 40-50% (Gokbuget, *Semin Hematol.* 46(1):64, 2009; Labarth, *Blood* 109(4):1408, 2007). However, Ph+ B-ALL continues to pose a huge challenge; tumors are or become refractory to imatinib, and remail the least treatable subtype of ALL (Talpaz, *N Engl J Med.* 354(24):2531, 2006; Alvarado, *Expert Opin Emerg Drugs.* 12(1):165, 2007; Apostolidou, *Drugs.* 67(15):2153, 2007). The present invention encompasses the recognition that there remains a need for the identification of new pathways to be targeted for the treatment of Ph+ patients.

The present invention further encompasses the recognition that RAS plays an important role in transducing oncogenic signals of BCR/ABL (reviewed in Ren, *Nat Rev Cancer.* 5(3):172, 2005; Deininger, *Blood.* 96(10):3343, 2000). Furthermore, the present invention encompasses the observation that hyperactivation of RAS in common in ALL (see, for, example, Nakao, *Leukemia* 14(2):312, 2000; Neri, *Proc Natl Acad Sci USA.* 85(23):9268, 1988; Tyner, *Proc Natl Acad Sci USA.* 106(21):8695, 2009; Yokota, *Int J Hematol.* 67(4):379, 1998; Case, *Cancer Res.* 68(16):6803, 2008). Without wishing to be bound by any particular theory, the present inventors propose that RAS palmitoylation may be relevant to transduction of BCR/ABL signaling. The present invention further encompasses the insight that RAS palmitoylation constitutes a novel target for the identification, characterization, and use of agents that can have therapeutic effect in cancers mediated by BCR/ABL, including for example CML and ALL.

As described in Example 1, we have demonstrated that palmitoylation-deficient oncogenic NRAS is mislocalized away from the plasma membrane but is still capable of binding GTP in cells.

Without wishing to be bound by any particular theory, the present invention proposes that palmitoylation-deficient derivatives of oncogenic NRAS proteins may in fact have a dominant negative effect on RAS signaling. Thus, the present invention provides methods of identifying, characterizing, and/or using agents that inhibit RAS palmitoylation with respect to the treatment of cancers that involve RAS signaling, even if the transformation is not mediated by RAS. The present invention therefore provides methods of identifying, characterizing, and/or using agents that inhibit RAS palmitoylation in the treatment of cancers that do not carry a mutant RAS (e.g., that do carry wild type RAS). In some embodiments, the present invention specifically contemplates use of palmitoylation deficient RAS derivatives themselves to treat such cancers.

The present invention further and specifically demonstrates that palmitoylation-deficient derivatives of oncogenic NRAS proteins can impede the development of B-ALL and CML-like diseases that are induced by expression of the BCR/ABL oncogene (see, for example, Example 2).

Treating Cancer

According to the present invention, RAS palmitoylation modulators are useful, among other things, in the treatment of cancer. Those of ordinary skill in the art will appreciate that such agents can be administered according to any appropriate route and/or administration schedule, in the context of any appropriate composition, without departing from the spirit or scope of the present invention.

Those of ordinary skill in the art will further appreciate that RAS palmitoylation modulators as described herein may be administered in combination with one or more other agents useful in the treatment of the relevant cancer and/or in amelioration of one or more symptoms or diseases, disorders, or conditions from which the relevant subject is suffering or to which the relevant subject is susceptible. In some particular embodiments, RAS palmitoylation modulators as described herein is/are administered in combination with one or more other agents useful in the treatment of one or more hematological cancers including, for example, chronic myelogenous leukemia. In some embodiments, one or more RAS palmitoylation modulators as described herein is/are administered in combination with one or more therapies useful in the treatment of a cancer associated with an oncogene upstream of RAS (e.g., BCR-ABL). In some particular embodiments, one or more RAS palmitoylation modulators as described herein is/are administered in combination with imatinib.

In some embodiments of the present invention, RAS palmitoylation inhibitors are administered in combination with one or more FASN inhibitors to treat cancer.

In some embodiments, one or more FASN inhibitors is administered in the treatment of a cancer associated with activation of a RAS that requires palmitoylation for activity.

Still further, those of ordinary skill in the art, reading the present disclosure, will appreciate that the present invention provides systems for identifying subjects who are suffering from or susceptible to cancer and are good (or bad) candidates for treatment with a RAS palmitoylation modulator as described herein. In some embodiments, such subjects are suffering from or susceptible to a cancer that does not result from mutation of RAS. In some embodiments, such subjects show high levels of serum palmitate and/or of palmitoylated RAS (e.g., NRAS) protein. In some embodiments, such subjects show elevated levels and/or activity of one or more palmitoyl-acyl transferase polypeptides as described herein. In some embodiments, such subjects show elevated levels and/or activity of one or more polypeptides involved in palmitate production.

EXEMPLIFICATION

Example 1

Palmitoylation of Oncogenic NRAS is Essential for Leukemogenesis

The present Example demonstrates that palmitoylation of NRAS is essential for leukemogenesis by oncogenic NRAS. These findings suggest that targeting palmitoylation of RAS may be an effective strategy for treating malignancies associated with NRAS activation. However, the role of RAS palmitoylation in cancers not mediated by NRAS activation (e.g., cancers that do not contain a RAS mutation) remains unclear in light of this Example.

Methods

Construction of Retroviral Expression Vectors

Construction of the murine stem cell virus (MSCV)-GFP-ires-2xmyc-tag-NRASD12 vector has been described previously (Quatela, *Cur. Opin Cell Biol.* 18(2):162, 2006) and was used as template to produce all additional constructs described here. NRASD12$^{C181S}$ and NRASD12$^{C186S}$ were created using a mutational 2-step polymerase chain reaction (PCR) system using nested primers to introduce point mutations individually to sense and antisense complimentary overhangs. Subsequently, these individual products were combined as an annealed template in a second PCR reaction to amplify the completed NRASD12 gene containing the desired point mutation.

Mutational primers used in separate individual reactions for NRASD12$^{C181S}$ were: 5' CTC AGG GTA GTA TGG GAT (SEQ ID NO: 27) and 5' ATC CCA TAC TAC CCT GAG (SEQ ID NO: 28). For NRASD12$^{C186S}$ they were: 5' CAC CAC ACT TGG CAA TCC (SEQ ID NO: 29) and 5' GAT TGC GTG TGG TGA TG (SEQ ID NO: 30). Each mutational primer was paired in its reaction with either 5' TGA CTG ACT GAA TCG ATG (SEQ ID NO: 31) or 5' CAG GTG GGG TCT TTC ATT (SEQ ID NO: 32), to that anneal to the complimentary strand to amplify. The second PCR reaction used the products of the first round of reactions as the template and used the primers 5' ATG GAC GAG CTG TAC AAG (SEQ ID NO: 33) and 5' GTC GGA TGC AAC TGC AAG (SEQ ID NO: 34) to amplify both products containing the individual new point mutations.

Final PCR products and introduced mutations were confirmed by DNA sequencing before subsequent cloning. Sequenced PCR products were first ligated into pCR2.1 TA cloning vector before being excised with NotI and ClaI and inserted into MSCV at these sites. Finally, GFP-ires was isolated from MSCV-GFP-ires-2xmyc-tag-NRASD12 by NotI and inserted into each MSCV-2xmyc-tag-NRASD12$^{C181S}$ or NRASD12$^{C186S}$ to create the final bicistronic expression vector.

Plasmids expressing NRASD12 and NRASD12 PTM mutants as N-terminal GFP-fusion proteins were created by taking advantage of a digestion by NcoI of GFP at amino acid 234 found in an earlier sequenced miniprep, which resulted in a NcoI flanked green fluorescent protein (GFP) lacking the most C-terminal 5 amino acids. This was inserted into an Nca-digested MSCV-GFP-ires-2xmyc-tag-NRASD12 construct. All cDNAs were reconfirmed by DNA sequencing before expression.

Retrovirus Production and Tittering

Retroviruses were produced in BOSC23 cells, cultured, and titered as previously described (Gross, *Mol Cell Biol.* 19(10):6918, 1999). The viral titer was calculated in transducing units (TUs) by multiplying the percentage of NIH3T3 cells expressing GFP and the total number of cells on the dish at the time of infection. Retroviral titers were matched before bone marrow infection at $1.3\times10^5+0.3\times10^5$ TUs.

Cell Culture

NIH3T3 and 32D cl-3 cell lines stably expressing NRASD12, NRASD12$^{C181S}$, NRASD12$^{C186S}$, or the control GFP were created by retroviral transduction as described (Gross, *Mol Cell Biol.* 19(10):6918, 1999; Parikh, *Cancer Res.* 67(15):7139, 2007). All cell lines were sorted by GFP expression to more than 95% homogeneity by fluorescence-activated cell sorting (FACS) using a FACSAria (BD Biosciences). Cell lines were cultured as previously described (Gross, *Mol Cell Biol.* 19(10):6918, 1999).

Cell Photographs and Serial Growth Curves

Equal numbers ($5\times10^5$) of NIH3T3 cells expressing vector alone, NRASD12, NRASD12$^{C181S}$, or NRASD12$^{C186S}$ were plated onto plastic 100-mm tissue culture dishes. Cells were cultured for 6 days (media was changed every 2 days) and photographed using an Olympus E-Volt E500 digital camera attached to an Olympus IX70 inverted microscope (Olympus; original magnification×100). For serial growth curves, $2\times10^5$ cells were plated in 60-mm culture dishes at day 0. Media was changed every 2 days. Cells, in triplicate, were stained with trypan blue to exclude nonviable cells and counted manually under a light microscope each day. NRASD12-expressing cells formed tight spheres after 6 days in culture, making it difficult to determine the cell numbers. For this reason, the growth curve was ended at day 6. The Student t test was used for statistical analysis.

Soft-Agar Colony-Forming Assay

A total of 1 mL of 0.6% bottom agar (mixing 1.2% agar with concentrated media [2 times Dulbecco modified Eagle media+40% Dulbecco buffered saline+2 times Pen-Strep] with 1:1 ratio) was prepared and introduced to each well of a 6-well tissue culture plate. FACS-purified NIH3T3 cell lines expressing GFP, NRASD12, NRASD12$^{C181S}$, or NRASD12$^{C186S}$ were diluted to $10^5$ cells/mL, $10^4$ cells/mL, or $10^3$ cells/mL in 1 times Dulbecco modified Eagle medium+10% Dulbecco buffered saline+1 times Pen-Strep. Triplicate 3-mL cells suspended in soft agar were added to the bottom agar for each cell line and incubated in a 37° C. $CO_2$ incubator. Colonies were counted under a light microscope at day 15 after plating.

Bone Marrow Transduction/Transplantation

Mouse bone marrow transduction and transplantation experiments were performed as previously described (Zhang, *Blood.* 92(10):3829, 1998). Briefly, bone marrow (BM) cells from 5-fluorouracil (250 mg/kg)-treated 6- to 8-week-old male donor BALB/c mice (Taconic Farms) were infected with retroviruses each day for 2 days before $4\times10^5$ cells were injected into the tail vein of each lethally irradiated (2×4.5 Gy, 4 hours between each dose) female recipient BALB/c mouse as described (Zhang, *Blood.* 92(10):3829, 1998). Retroviral titers were matched before BM infection. Recipient mice were monitored weekly for signs of disease beginning on day 14 after transplantation.

Mice used in this project are housed in the Association for Assessment and Accreditation of Laboratory Animal Care International accredited Foster Animal Research Facility at Brandeis University. All experiments involving mice are approved the Institutional Animal Care and Use Committee of Brandeis University.

Hematopathologic Analysis

Blood was collected from mice by tail bleed and 34 was diluted in 3 mL of Isoton II (Fisher Scientific). White blood cell (WBC) counts were measured using the Coulter Counter model Z1 (Coulter), after lysing the red blood cells with ZAP-O-Globin (Beckman Coulter). Hematocrit was measured by capillary centrifugation on a micro-hematocrit centrifuge (StatSpin). Smears, cytospin, and touch preparation of blood and other murine tissues were stained with Hema 3 stain set (Fisher Scientific) for routine identification of cell morphology. Flow cytrometric analysis of GFP-positive WBCs and immunophenotyping of leukemic cells were performed as previously described (Parikh, *Blood.* 108(7):2349, 2006).

Subcellular Localization Analysis of RAS Proteins

NIH3T3 cell lines expressing NRASD12 with GFP fused to its N-terminus (GFP-NRASD12) or expressing GFP-fusion versions of NRASD12 PTM mutant proteins (GFP-NRASD12$^{c181S}$, GFP-NRASD12$^{c186S}$) were grown overnight on fibronectin-coated (50 μg/mL for 30 minutes at room temperature) glass coverslips. Fresh media was supplanted with 100 μg/mL cycloheximide 3 hours before fixation with 4% paraformaldehyde in phosphate-buffered saline (PBS) for 20 minutes at room temperature. Cells were permeablized in 0.1% Triton X-100 for 15 minutes at room temperature and blocked with 2% bovine serum albumin in PBS for 30 minutes at room temperature before primary antibody (anti-BIP; Cell Signaling Technologyl anti-GOLGA7; ABNOVA) was added at 1:250 dilution in 2% bovine serum albumin/PBS and incubated overnight at 4° C. Alexa Fluor 635-conjugated secondary antibody (Invitrogen) was added to 5 μg/mL final concentration for 1 hour at room temperature. Cells were washed 3×10 minutes in PBS after each step. Coverslips were mounted onto slides using Vectashield mounting medium with 4,6-diamidino-2-phenylindole (Vector Laboratories) and fluorescence visualized on a Leica TCS SP2 Spectral Confocal Microscope.

Western Blot Analysis

Cell lysates were prepared from 90% confluent NIH3T3 cell lines serum started for 22 hours. Similar lysates were prepared from 32D cl-3 cell-lines starved of serum and WEHI-3B conditional media (as a source of interleukin-3) for 13 hours. Cells were counted and lysed in 1 times sodium dodecyl sulfate-polyacrylamide gel electrophoresis running buffer, sonicated briefly to break up DNA, heated at 100° C. for 10 minutes, and centrifuged to remove debris. Lysates were resolved on 6% to 18% gradient polyacrylamide gels, transferred to nitrocellulose membranes, and blotted with the following primary antibodies overnight at 4° C.: anti-RAS (RAS10; Upstate Biotechnology), antiactin (AC40; Sigma-Aldrich), anti-myc tag 9E10 monoclonal antibody (from conditional media of 9E10 hybridoma cell line), and pAkt, Akt, pMek1/2, Mek1/2, pErk42/44, Erk42/44, pS6rp, and S6rp (all 1:1000; Cell Signaling Technology). Horseradish peroxidase-labeled goat anti-mouse IgG or goat anti-rabbit IgG (Pierce Biotechnology) was used as a secondary antibody. Densitometry ratios of expressed NRAS to endogenous RAS were performed using Adobe Photoshop 7.0 (Adobe Systems).

RAS-GTP and Ral-GTP Detection Assays

Activated RAS and Ral were detected using affinity purification kits (Upstate Biotechnology) according to the manufacturer's instructions. Human RAS-guanosine triphosphate (GTP) or murine Ral-GTP was immobilized on glutathione-agarose beads bound with GST-Raf-1-RAS-binding domain (RBD) or GST-Ral Binding Protein 1 (RalBP1), respectively, then run on 15% sodium dodecyl sulfate-polyacrylamide gel electrophoresis gels, transferred to nitrocellulose, and detected using RAS or Ral specific antibodies. Total RAS was similarly probed as a loading control in these assays.

Results

Figure 1B:
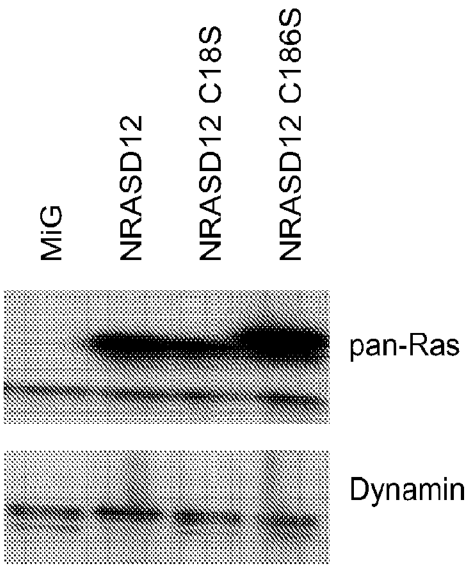
Figure 1C:
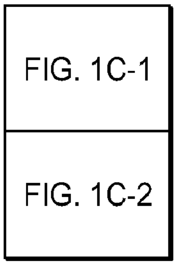
Figures 1, 1C:
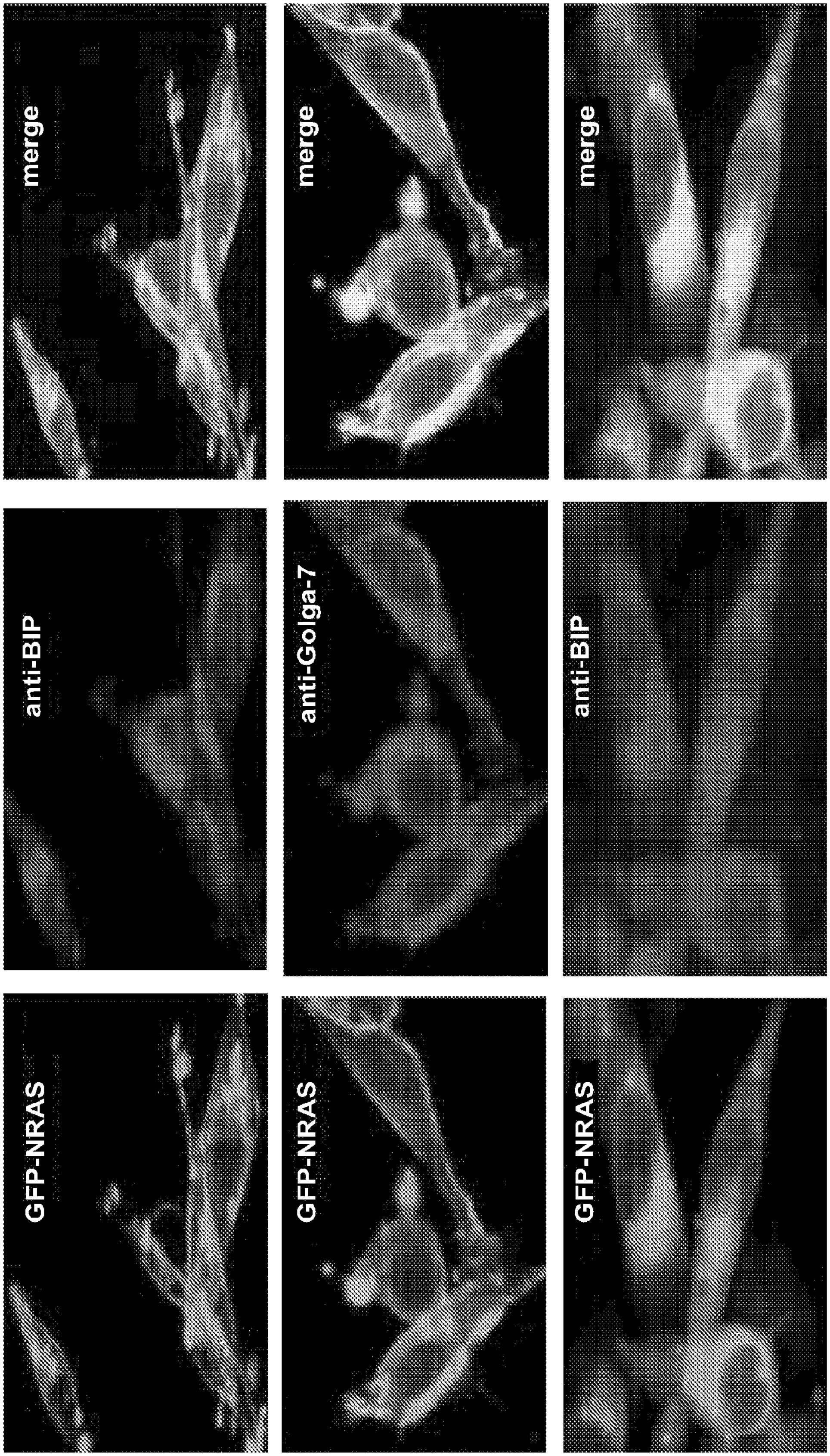
Figures 1, 1C, 2:
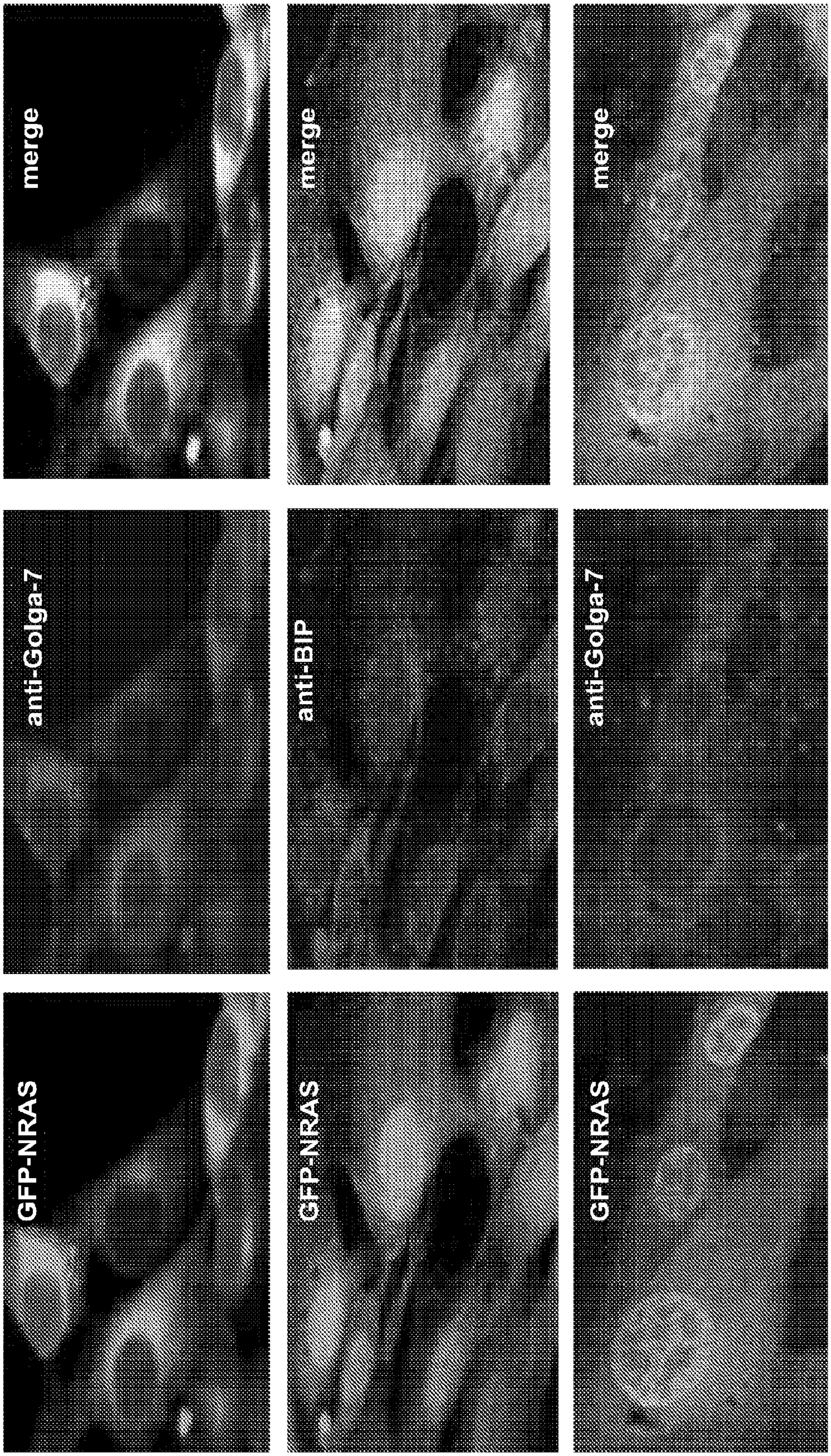
FIG. 2. NIH3T3 cell lines expressing NRAD12 or NRASD12 PTM mutants result in phenotypic changes in morphology and density-dependent inhibition of growth. (A) Morphology of cultured NIH3T3 cells stably expressing the proteins indicated. Equal numbers ($5\times10^5$) of NIH3T3 cells expressing vector alone, NRASD12, NRASD12$^{C181S}$, or NRASD12$^{C186S}$ were plated onto 100-mm plates and were cultured for 6 days before the pictures were taken (original magnification×100). (B) Total numbers of viable cells per plate (means with error bars) for NIH3T3 cells expressing vector alone, NRASD12, NRASD12$^{C181S}$, or NRASD12$^{C186S}$ were plotted versus time (days). NRASD12$^{C186S}$ cells grew significantly slower than the vector control cells at day 4 (P=0.01). NRASD12 and NRASD12$^{C181S}$ cells grew significantly faster than the vector control cells at day 6 (P=0.005 and P=0.02, respectively).

Stable Expression of Palmitoylation-Deficient NRASD12 Confers Morphologic Changes and Abrogates Cell Density-Dependent Inhibition of Growth but does not Confer Anchorage-Independent Growth to NIH3T3 Cells To determine whether palmitoylation is required for NRAS leukemogenesis and similarly confirm the requirement for prenylation, we constructed retroviral vectors expressing myc-tagged NRASD12$^{C181S}$ or NRASD12$^{C186S}$ (well-characterized palmitoylation-defective and prenylation-defective mutants of NRAS, respectively (Hancock, *Cell.* 57(7):1167, 1989); FIG. 1A). We first characterized the PTM mutants of oncogenic NRAS in vitro. NIH3T3 cells were infected by retroviruses, containing GFP alone (MiG), NRASD12, NRASD12$^{C181S}$ or NRASD12$^{C186S}$. Infected cells (GFP$^+$) were isolated by FACS. The expression of NRAS mutants in NIH3T3 cells was confirmed by Western blotting with an anti-RAS antibody. Each NRAS mutant was expressed at similar levels (FIG. 1B). To confirm loss of plasma membrane association of the PTM deficient NRAS mutants, we constructed N-terminal GFP-fusion versions of NRASD12, NRASD12$^{C181S}$, or NRASD12$^{C186S}$ retroviral vectors and expressed them in both 32D cl-3 cells (data not shown) and NIH3T3 cells. As expected, GFP-NRASD12 localized primarily to the plasma membrane and internal membranes that colocalized with immunostained Golgi-resident (Golga-7) and ER-resident (BIP) proteins (FIG. 1C). GFP-NRASD12$^{C181S}$ localized entirely to internal membranes, whereas GFP-NRASD12$^{C186S}$ diffused in the cytoplasm and, interestingly, in the nucleus (FIG. 1C). These results confirm that for NRAS palmitoylation is required for the association with the plasma membrane and that prenylation is required for any membrane association. This observation itself provides a basis for identifying RAS palmitoylation modulators as described herein. for example, test agents can be contacted with cells and their effects on RAS (e.g., NRAS localization assessed, for example by tracking a marked RAS protein. In some embodiments, RAS can be marked by fusion with a detectable protein (e.g., to give but one specific example, GFP-RAS; those of ordinary skill in the art would be well aware of a plethora of other relevant approaches). It will be appreciated by those of skill in the art, reading the present disclosure, that such an approach could readily be adapted to high throughput formats, so that the present invention, among other things, provides high throughput systems for identifying and/or characterizing RAS palmitoylation modulators by assessing their effects on RAS localization.

It has been observed that oncogenic KRAS and NRAS have greatly reduced transformation activity compared with oncogenic HRAS in NIH3T3 focus-forming assays (Li, *J Biol. Chem.* 279(36):37398, 2004). Consistent with this finding, we observed that minority populations of NRASD12-expressing cells grown in close proximity to normal NIH3T3 fibroblasts hardly formed foci (data not shown). In addition, NRASD12 did not permit 32D cl-3 myeloid progenitor cells to grow in a factor-independent manner (data not shown).

Figure 2A:
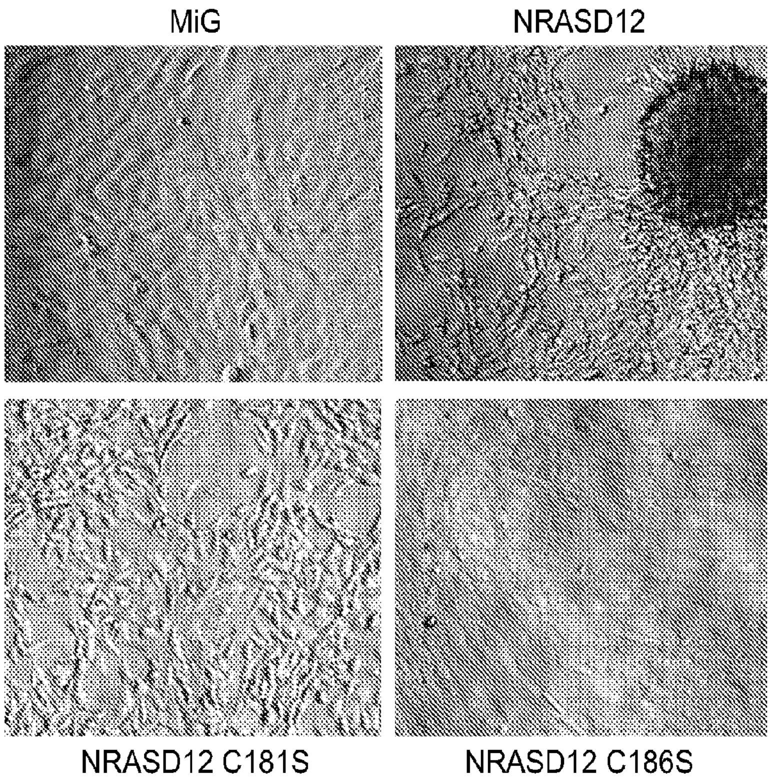

However, we observed a changed morphology for sorted NRASD12-expressing NIH3T3 cells (FIG. 2A). Approximately one week after FACS sorting, NRASD12-expressing cells in culture appeared smaller, more spindle-shaped, and began to grow in a lattice that produced spheres protruding from the flat plane of adherent cells at the lattice nodules. These spheres grew to various sizes before detaching from the dish. Cells from spheres were viable and could merge with other spheres in suspension to form amorphous cell clumps. Interestingly, nonpalmitoylated NRASD12$^{C181S}$-expressing cells also appeared spindle-shaped and grew in a lattice similar to NRASD12 cells, although these did not produce spheres. In contRASt, the prenylation-deficient NRASD12$^{C186S}$-expressing cells appeared larger and less spindle-shaped, morphologically similar to the MiG control cells.

Figure 2B:
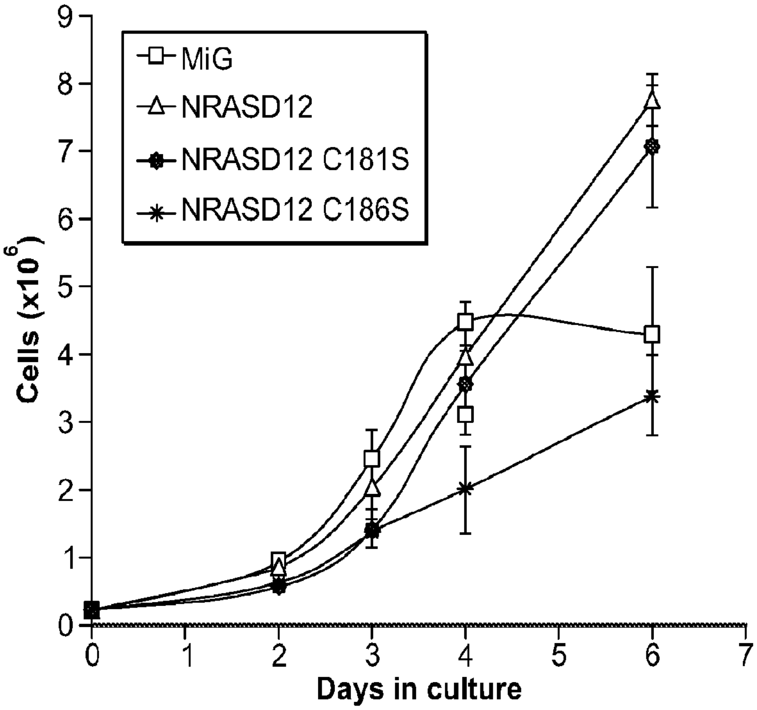

To characterize any changes in proliferation or cell density-mediated inhibition of growth conferred by blocking PTMs of oncogenic NRAS, we compared growth of NIH3T3 cells stably expressing vector alone, NRASD12, NRASD12$^{C181S}$, or NRASD12$^{C186S}$ in liquid culture (FIG. 2B). Growth of MiG-expressing cells stopped after 4 days in culture because of cell density-dependent inhibition, whereas cells expressing NRASD12 continued to proliferate. Interestingly, cells expressing NRASD12$^{C181S}$, such as cells expressing NRASD12, were able to overcome normal density-dependent growth controls and continue to proliferate. Cells expressing NRASD12$^{C186S}$, on the other hand, displayed a significantly reduced proliferation compared with control cells, suggesting that expression of prenylation-defective NRASD12 is toxic to NIH3T3 cells.

To further assess the transforming potential of NRASD12 and its PTM mutants, we performed a soft-agar colony assay. Sorted GFP$^+$ cells were seeded in soft-agar and colonies were counted at day 14 (Table 1). NRASD12-expressing cells formed numerous colonies in soft agar, indicating that oncogenic NRAS can abrogate the anchorage-dependent growth of NIH3T3 cells. In contrast, cells expressing nonpalmitoylated NRASD12$^{C181S}$ formed only a few clusters equivalent to cells expressing NRASD12$^{C186S}$ or GFP alone. These observations demonstrate that expression of palmitoylation-defective NRASD12 causes NIH3T3 cells to display some characteristics of transformation, including morphologic changes and loss of normal density-dependent growth inhibition but cannot confer anchorage-independent growth to these cells.

Palmitoylation and Prenylation are Each Required for NRAS Leukemogenesis

We next examined the role of palmitoylation in NRAS leukemogenesis using a mouse bone marrow transduction and transplantation model. We also tested the leukemogenic potential of the prenylation-defective mutant of NRAS because, although prenylation of RAS is the obligate initial PTM and has been shown to be essential for RAS transformation in vitro, the role of prenylation in NRAS leukemogenesis in vivo has not yet been directly tested.

Figure 3A:
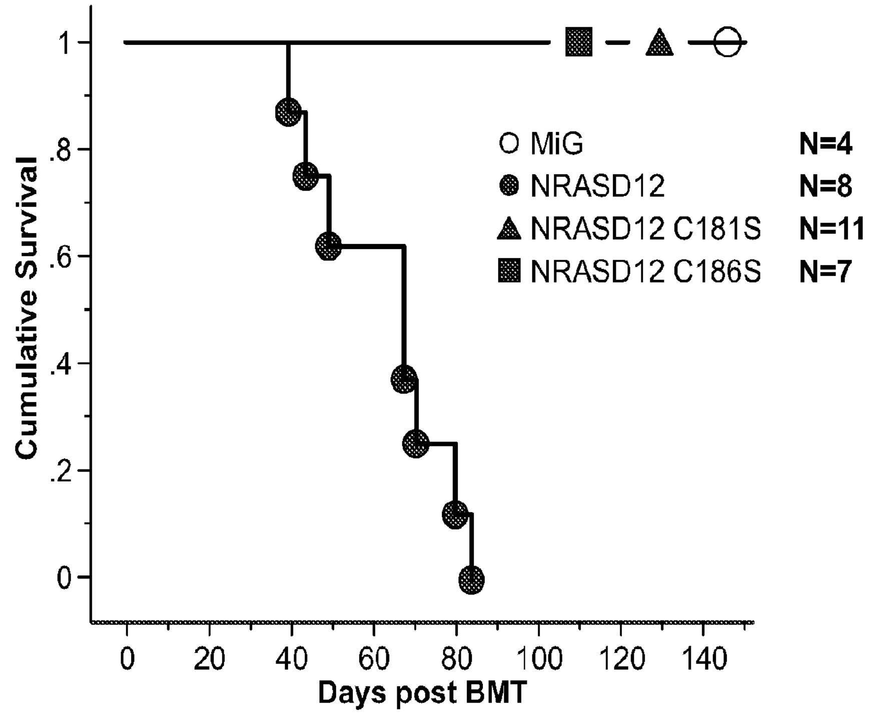
FIG. 3. Palmitoylation and prenylation are each essential for NRAS leukemogenesis in vivo. (A) Kaplan-Meier plot of cumulative survival of recipient mice transplanted with BM cells infected by NRASD12, NRASD12$^{C181S}$, or NRASD12$^{C186S}$ containing retroviruses, or the MiG vector. (B) FACS analysis of GFP$^+$ cells in peripheral blood of NRASD12, NRASD12$^{C181S}$, NRASD12$^{C186S}$, or GFP vector bone marrow transduction and transplantation model mice.

We infected BM cells isolated from 5-fluorouracil-treated mice with titer-matched retroviruses containing NRASD12. NRASD12$^{C181S}$, NRASD12$^{C186S}$, or vector control and then transplanted these cells into lethally irradiated syngeneic recipient mice, as previously described (Parikh, *Blood.* 108 (7):2349, 2006). As shown previously, all mice receiving NRASD12-transduced BM cells developed a fatal AML (~35%)- or CMML (~65%)-like disease and died in 30 to 90 days after bone marrow transplantation (FIG. 3A; and data not shown). However, mice receiving NRASD12$^{C181S}$ or NRASD12$^{C186S}$-transduced BM cells did not develop any disease and remained healthy for more than 2 years, similar to MiG control mice (FIG. 3A; and data not shown). Peripheral blood (PB) collected weekly from these animals displayed to abnormal expansion of any cell type when cell morphologies were examined after differential staining with Hema-3 stain (Fisher; data not shown). Livers and spleens of animals receiving NRASD12$^{C181S}$- or NRASD12$^{C186S}$-transduced BM cells were of normal size and weight, similar to MiG mice (data not shown). Cells isolated from livers, spleens, PB, and BM of these animals were assessed by FACS analysis with a panel of myeloid and lymphoid markers. (Gr-1, B220, CD19, Thy-1.2, CD86, CD31, CD115 [M-CSFR], Ter-119, Mac-1, CD34, CD38, CD16/32, and c-Kit) and displayed no abnormal hematopoietic expansion, as did MiG mice. Identical results were seen in 2 independent experiments.

Figure 3B:
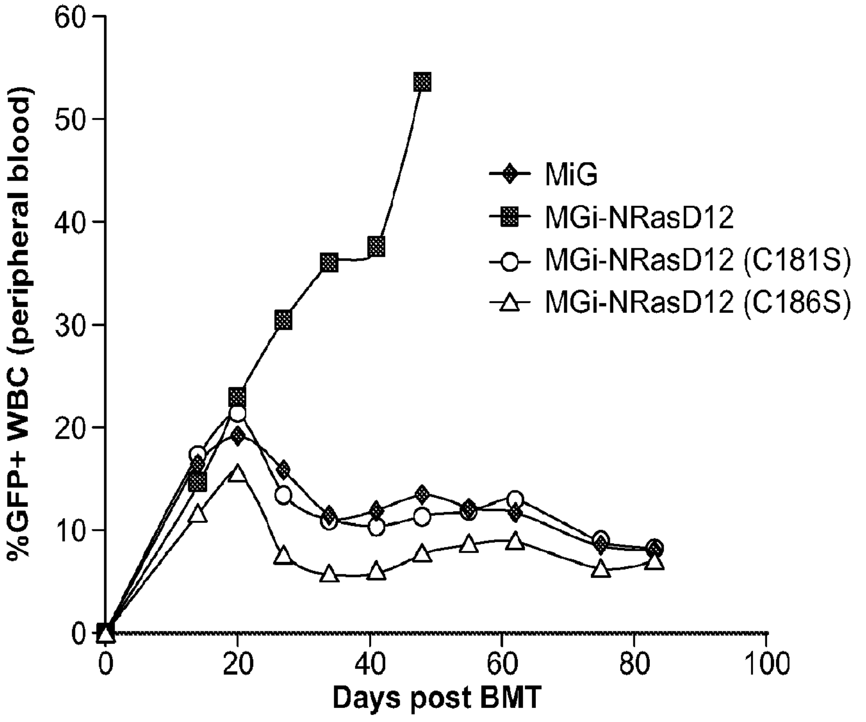

Weekly analysis of PB of animals receiving NRASD12$^{C181S}$ or NRASD12$^{C186S}$-transduced BM revealed a limited increase (analogous to MiG control) in the percentage of GFP$^+$ WBCs over the first 3 weeks after bone marrow transplantation, peaking at 15% to 20% GFP$^+$ WBCs. This result indicates that NRASD12$^{C181S}$ or NRASD12$^{C186S}$-transduced BM cells are not deficient for homing to hematopoietic niches (FIG. 3B). After 3 weeks, the percentage of GFP$^+$ PB WBCs isolated from MiG, NRASD12$^{C181S}$, and NRASD12$^{C186S}$ mice began to decline, with similar rates of decline in NRASD12$^{C181S}$ and NRASD12$^{C186S}$ mice as MiG mice, suggesting that expression of palmitoylation- or prenylation-defective NRASD12 is not significantly toxic to hematopoietic cells. These experiments show that palmitoylation and are essential for NRAS leukemogenesis.

Figure 4C:
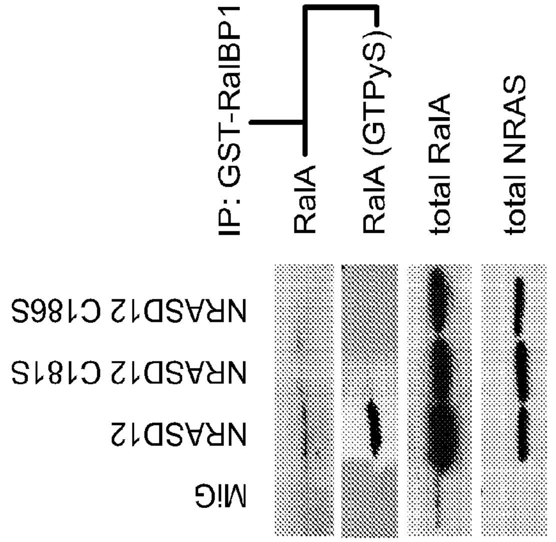
FIG. 4. Oncogenic signaling downstream of NRASD12 is disrupted by blocking palmitoylation. Serum-starved lysates of NIH3T3 cells expressing vector, NRASD12, NRASD12$^{C181S}$, or NRASD12$^{C186S}$ were analyzed by Western blotting. (A) Effect of palmitoylation and prenylation of NRASD12 on phosphorylation of Akt and S6 ribosomal protein. (B) Effect of palmitoylation and prenylation of NRASD12 on phosphorylation of Erk. (C) Effect of palmitoylation and prenylation of NRASD12 on Ral activation. Ral-GTP precipitated from serum-starved NIH3T3 cells expressing vector control, NRASD12, NRASD12$^{C181S}$, or NRASD12$^{C186S}$ with GST-RalBP1 glutathione agarose beads with or without addition of GTPγS were analyzed by Western blotting with an anti-RalA antibody. Total Ral was also probed. RAS expression was detected as a loading control.
Figure 4B:
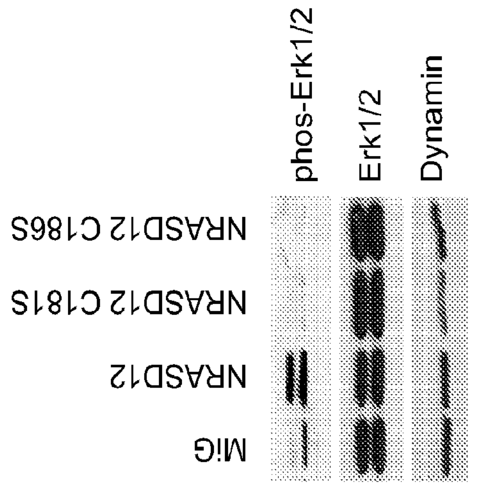
Figure 4A:
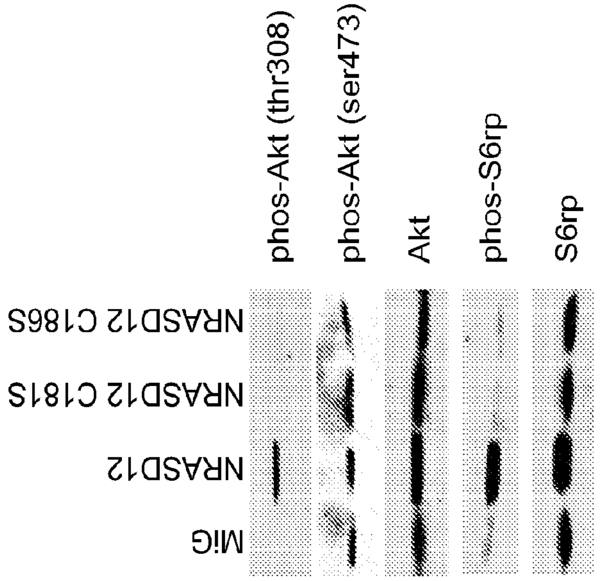

Palmitoylation is Required for Activation of Multiple Downstream Signaling Pathways by Oncogenic NRAS RAS activates multiple downstream signaling pathways, including the phosphoinositide-3 kinase (P13K), mitogen-activated protein kinase (MAPK) Erk and Ral pathways. To determine whether and how these signaling pathways are affected by lack of palmitoylation of NRASD12, we examined known activating phosphorylation sites on well-established signaling proteins in the P13K and MAPK pathways in NIH3T3 cells expressing MiG, NRASD12, NRASD12$^{C181S}$ or NRASD12$^{C186S}$ by Western blotting with phospho-specific antibodies (FIG. 4A-B).

Cells were serum-starved for 22 hours before lysis to minimize RAS signaling because of receptor tyrosine kinase activation by serum growth factors. In the P13K pathway, Akt is a central regulator of cell survival, proliferation, and metabolism (Engelman, *Nat Rev Genet.* 7(8):606, 2006; Manning, *Cell.* 129(77):1261, 2007). We detected little or no basal phosphorylation at Akt Thr308, an activating phosphorylation site of Akt and target of PDK1 downstream of P13K in MiG vector lysates, whereas NRASD12 expression triggered marked phosphorylation at this site (FIG. 4A). In contrast, cell lysates isolated from both NRASD12$^{C186S}$- and $NRASD12^{C181S}$-expressing cells did not induce phosphorylation at Akt Thr308. Akt phosphorylation at Ser473 contributes to full activation of Akt and is the target of the mTORC2 complex (Kresko, *J Biol. Chem.* 280(49):40406, 2005; Sarbassov, *Science.* 307(5712):1098, 2005). We observed that Akt Ser473 was constitutively phosphorylated in miG cell lysates, and this remained unchanged in lysates of cells expressing NRASD12 or PTM mutants of NRASD12 (FIG. 4A).

Activating phosphorylation of S6rp, a ribosomal protein, is often increased in cells transformed by oncogenic RAS (Holland, *Oncogene.* 23(18):3138, 2004). We observed little or no basal activation of S6rp in MiG cell lysates but marked activation of S6rp in lysates of cells expressing NRASD12 (FIG. 4A). NRASD12-mediated hyperactivation of S6rp was not seen in lysates of cells expressing NRASD12 cis's or $NRASD12^{C186S}$. Similarly, marked phosphorylation of Erk1/2 was observed in lysates from NRASD12 cells, whereas in $NRASD12^{C186S}$ and $NRASD12^{C181S}$ cell lysates we did not observe activating phosphorylation of Erk1/2 (FIG. 4B).

Ral GTPase activation has also been implicated as an important pathway downstream of RAS (Bodemann, *Nat Rev Cancer.* 8(2):133, 2008). To assess whether NRAS palmitoylation is necessary for Ral activation, we ran Ral-GTP detection assays using lysates of the cell lines described above (FIG. 4C). In this assay, active RalA (GTP bound) is precipitated with glutathione-agarose beads bound GST-tagged RalBP1. The precipitates were then analyzed by Western blotting using an anti-RalA antibody. Once again, we observed marked activation of Ral by NRASD12, and this activity was abolished by either the prenylation or palmitoylation mutation. Lysates treated with a nonhydrolyzable form of GTP (GTPγS) showed similar results, suggesting that non-palmitoylation, like prenylation, is essential for NRASD12 to activate downstream signaling pathways that are important for cell transformation.

Prenylation, but not Palmitoylation, Affects FTP Loading of Oncogenic NRAS

Figure 5:
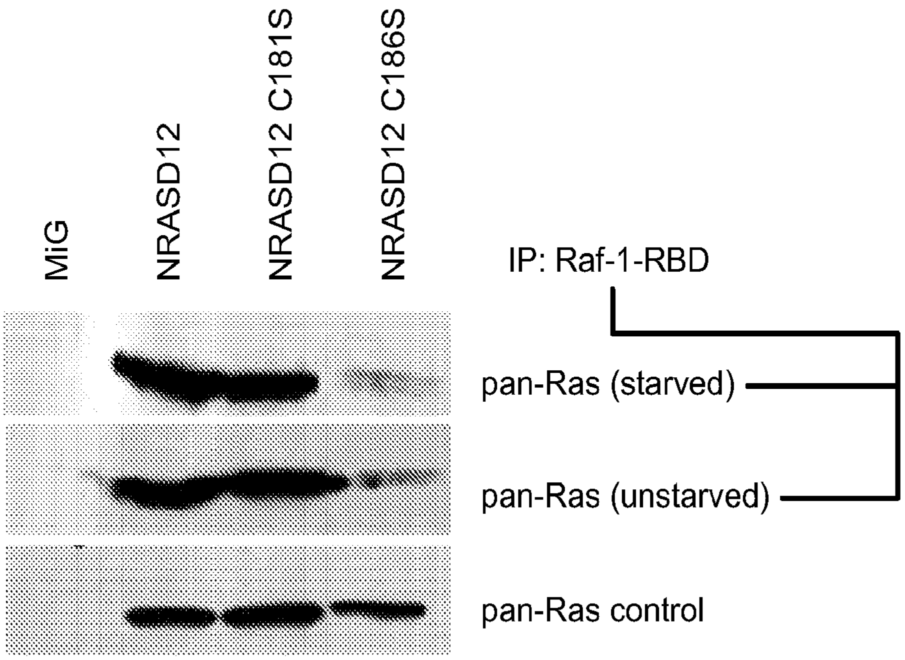
FIG. 5. Palmitoylation-defective NRASD12$^{C181S}$ retains the ability to bind Raf-1-RBD. RAS-GTP precipitated with glutathione-agarose beads bound GST-fused RAS-binding domain (residues 1-149) of Raf-1 from serum-starved or unstarved NIH3T3 cells expressing GFP alone, NRASD12, nonpalmitoylable NRASD12$^{C181S}$, or nonprenylable NRASD12$^{C186S}$ were analyzed by Western blotting with an anti-pan-RAS (RAS10) antibody. RAS from the same lysates was probed as a loading control.

Having observed that multiple oncogenic signaling pathways were not activated by palmitoylation-defective NRASD12, we wondered whether NRASD12 cis's retained the ability to bind GTP. GTP-bound RAS proteins from lysates of serum-starved and unstarved NIH3T3 cells expressing NRASD12, $NRASD12^{C181S}$, $NRASD12^{C186S}$, or GFP control were analyzed by a RAS-FTP detection assay. We observed that NRASD12 binds GTP in both serum-starved and unstarved lysates, indicating that NRASD12 is constitutively activated (FIG. 5; and data not shown). We also found that levels of RAS-GTP from cells expressing NRASD12 (FIG. 5). Interestingly, prenylation-defective NRASD12 showed markedly reduced levels of RAS-GTP, perhaps because the lack of membrane association prevents it from accessing to RASGEFs. These results indicate that although prenylation is important for FTP loading of NRASD12, palmitoylation is not required for optimal GTP loading NRASD12 or for its binding the RBD of Raf-1.

Discussion

In this Example, we demonstrate that palmitoylation is essential for leukemogenesis by oncogenic NRAS, raising the possibility that therapeutics targeting NRAS palmitoylation may be effective in treating NRAS-associated hematologic malignancies as well as other NRAS-related cancers. Palmitoylation-defective NRASD12 localizes entirely to internal membranes in cells and can be activated by GTP binding. Although defective in activating the P13K, Erk, and Ral pathways, the NRASD12 palmitoylation mutant retains the ability to alter morphology and to abrogate normal density-dependent growth controls when stably expressed in NIH3T3 fibroblast cells. However, this residual activity had no apparent effects in hematopoietic cells.

In addition, we show that prenylation is essential for leukemogenesis by oncogenic NRAS, confirming the importance of this process in RAS oncogenesis in vivo. Prenylation-defective NRASD12 completely loses the ability to associate with cellular membranes, is inefficiently activated by GTP loading, cannot activate downstream oncogenic signaling pathways, and does not transform cells in vitro or in vivo. In addition, NIH373 cells express prenylation-defective NRASD12 proliferate at a slower rate than control cells expressing GFP only, suggesting that prenylation-defective NRASD12 is toxic to cells. Interestingly, a GFP-tagged version of this mutant localized predominately to the nucleus, although this fusion protein is too large to enter the nucleus by passive diffusion. This observation suggests that unmodified RAS might be actively targeted to the nucleus and may serve a yet unknown nuclear function.

It is previously shown that G418-selected NIH3T3 cells stably expressing NRASV12 were not capable of growing in an anchorage-independent manner in soft agar (Li, *J Biol. Chem.* 279(36):37398, 2004). We show here that FACS-purified NRASD12-expressing NIH3T3 cells form spheres in liquid culture, and form colonies in soft agar. This discrepancy may be the result of different NIH3T3 sub-lines used. The same oncogene may have different transforming abilities in different NIH3T3 sub lines. For example, it has been found that there are permissive and nonpermissive sub-lines of NIH3T3 cells for transformation of abl oncogenes (Gross, *Mol Cell Biol.* 19(10):6918, 1999; Daley, *Science.* 237(4814):532, 1987; Renshaw, *EMBO J.* 11(11):3941, 1992). The NIH3T3 cell line we used can be transformed by various abl oncogenes (Gross, *Mol Cell Biol.* 19(10):6918, 1999).

The observation that active RAS signaling occurs not only on the plasma membrane but also on internal membranes, including the ER and Golgi, has significantly altered the way we view RAS signaling (Bivona, *Nature.* 424(6949):694, 2003; Chiu, *Nat Cell Biol.* 4(5):343, 2002; Perez, *Mol Cell Biol.* 24(80:3485, 2004; Quatela, *Curr Opin Cell Biol.* 18(2): 162, 2006); it has brought to light the idea of compartmentalized signaling, with different resident pools of activators and effectors becoming accessible to RAS at different subcellular locales. Whereas pools of constitutively active H— and NRAS are found on internal membranes and engage Raf-1, only HRAS was reported to retain much of its transforming capacity regardless of palmitoylation status and to become activated in response to growth factors from internal membranes in cultured cell lines (Chiu, *Nat Cell Biol.* 4(5): 343, 2002). Although it is not known whether palmitoylation is also required for leukemogenesis by oncogenic HRAS, we found here that palmitoylation-deficit NRASD12 does not activate the PI3K, Erk, and Ral pathways and loses much of its transforming activity in NIH3T3 cells. The different roles of palmitoylation in H- and NRAS transformation may rely on additional differences between the 2 RAS oncoproteins.

Interestingly, nonpalmitoylated NRASD12 remains constitutively GTP-bound and thus retains its capacity to engage the RAS-binding domain of Raf kinase. However, we found that nonpalmitoylated NRASD12 is incapable of activating Erk. Activation of Raf requires more than simple engagement of its RBD by RAS-GTP. We have noted that, in myeloid progenitor 32Dcl-3 cells stably expressing NRASD12, Raf-1 is phosphorylated on Ser259 (data not shown), a site that has been shown to be phosphorylated by Akt to produce an inhibitory 14-3-3 binding site and block downstream MAPK signaling (Zimmermann, *Science.* 286(5445):1741, 1999). It is thought that this inhibitory binding site must be dephosphorylated by growth factor-induced phosphatases, such as PP1 and PP2A, which may require association of NRAS with the plasma membrane (Jaumot, *Oncogene* 20(30):3949, 2001). Similarly, activation of the PI3K and Ral pathways by oncogenic NRAS may also require association with the plasma membrane.

Although targeting prenylation has proven difficult (targeting one of the 2 enzymes responsible for this modification is insufficient, yet targeting both is too toxic), there is reason to think that targeting RAS palmitoylation may prove more successful. Thus far, 23 putative palmitoyl-acyltransferases, each exhibiting a high degree of enzyme-substrate specificity, have been identified (Fukata, *Methods.* 40(2):177, 2006; Iwanaga, *Prog Lipid Res.* 48(3):117, 2009; Swarthout, *J Biol chem.* 280(35):31141, 2005). As such inhibited RAS-specific palmitoyl-acyltransferases could prove an effective therapy for leukemias and other cancers involving NRAS.

Example 2

Palmitoylation-Deficient Activated NRAS Functions as a Dominant Negative Suppressor for Leukemogenesis by BCR/ABL The present Example demonstrates that activated NRAS (i.e., NRAS that binds to GTP) acts as a dominant negative suppressor of leukemogenesis mediated by an upstream oncogene (i.e., BCR/ABL). These findings establish the proof of principle that inhibiting NRAS palmitoylation is beneficial in the treatment of cancer, even when the relevant cancer does not involve NRAS mutation. Additionally, among other things, these findings establish that partial inhibition of NRAS palmitoylation can prove an effective therapy. Without wishing to be bound by any particular theory, we propose that such partial inhibition could effectively convert oncogenic NRAS into cancer cell poison, such that the activated oncoprotein participates in cancer destruction when palmitoylation inhibitors are administered.

Materials and Methods

Construction of Retroviral Expression Vectors

MSCV-p210-IRES-GFP (Zhang, *Blood.* 92(10):3829, 1998) was used as a template to create the plasmids used here. To generate MSCV-p210GFP-IRES and MSCV-p210GFP-IRES-2xmyc-tag-NRASD12 retroviral vectors, we first fused GFP to p210 with an engineered Note site. 2xmyc-tag-NRASD12 was then inserted downstream of the encephalomyocarditis virus' internal ribosomal entry site (IRES) between NcoI and ClaI. MSCV-p210GFP-IRES-NRASD12$^{C181S}$ was created by excising 2xMyc-tag-NRASD12$^{C181S}$ from MSCV-GFP-IRES-2xmyc-tagNRASD12$^{C181S}$ with Note and ClaI. MSCV-p210GFP-IRES-NRASD12 was also cut with Note and ClaI and MSCV-p210 was isolated. The 2xmyc-tag-NRASD12$^{C181S}$ fragment was subcloned into MSCV-p210 to create MSCV-p210-2xmyc-tag-NRASD12$^{C181S}$. GFP-IRES was isolated from MSCV-p210GFP-IRES-2xmyc-tagNRASD12 by excision using Note. Finally, MSCV-p210-2xmyctag-NRASD12$^{C181S}$ was linearized with Note and GFP-IRES was subcloned into Note non-directionally. All cDNA was sequenced (Genewiz Inc., South Plainfield, N.J.) to confirm identity before use.

Retrovirus Production and Titering

Retroviruses were produced in BOSC23 cells; cultured and titered as previously described (Gross, *Mol Cell Biol.* 19(10): 6918, 1999). The viral titer was calculated in transducing units (TUs) by multiplying the percentage of NIH3T3 cells expressing GFP and the total number of cells on the dish at the time of infection. Retroviral titers were matched prior to bone marrow infection at approximately $6.56\times10^{6}\pm4.28\times10^{5}$ TU for transduction under lymphoid growth promoting conditions and approximately $6.93\times10^{6}\pm3.86\times10^{5}$ TU for the transduction under myeloid conditions.

Cell Lines and Culture.

E2A, an interleukin-7 (IL-7)-dependent B-precursor cell line (Acquaviva, *Blood* 112(9):3798, 2008). E2A cells expressing NRASD12, p210GFP, p210GFP-IRES-NRASD12, p210GFP-IRES-NRASD12$^{C181S}$ or GFP alone (MiG) were created by retroviral transduction as described (Acquaviva, *Blood* 112(9):3798, 2008). All cell lines were sorted by GFP expression to >95% homogeneity by fluorescence-activated cell sorting (FACS) using a FACSAria (Becton, Dickinson and Company, Franklin Lakes, N.J.). All E2A cells were maintained in culture in the presence of IL-7 (from media of E2A cells transduced with retrovirus to overexpress IL-7), 50 nM 2-mercaptoethanol (2-ME) and 2 mM L-glutamine added to the culture media (RPMI with 10% FBS and 1× penicillin/streptomycin). Similar cell lines were created using 32D cl-3 cells.

Bone Marrow Transduction/Transplantation.

Mouse bone marrow transduction and transplantation (BMT) experiments under myeloid or lymphoid growth conditions were performed as previously described (Zhang *Blood.* 92(10):3829, 1998; Roumiantsev, *Blood.* 97(1):4, 2001). Briefly, for myeloid conditions, bone marrow (BM) cells from 5-fluorouracil (5-FU; 250 mg/kg) treated 6-8 week old male donor BALB/c mice (Taconic Farms, Germantown, N.Y.) were infected with retroviruses each day for 2 days in the presence of stem cell factor, IL-3, and IL-6. Approximately 24 hrs after the 2$^{nd}$ infection, $4\times10^{5}$ cells were injected into the tail vein of each lethally irradiated (2×4.5Gy, 4 hours between each dose) female recipient BALB/c mice as described. For lymphoid conditions, BM was isolated from mice without 5-FU treatment and a single retroviral infection carried out for ~6 hrs in the presence of IL-7 and IL-3 before $1\times10^{6}$ cells were injected into mice lethally irradiated as described above. In both conditions, retroviral titers were matched prior to BM infection. Recipient mice were monitored weekly as described below beginning day 14 post-transplantation.

Mice used in this project are housed in the Association for Assessment and Accreditation of Laboratory Animal Care International (AAALAC) accredited Foster Animal Research Facility at Brandeis University. All experiments involving mice are approved by the Institutional Animal Care and Use Committee (IACUC) of Brandeis University.

Hematopathological Analysis.

Hematopathological analysis was performed weekly (unless otherwise noted) until mice became moribund as previously described (Parikh, *Blood.* 108(7):2349, 2006).

Immunophenotyping.

Cells isolated peripheral blood, bone marrow, liver, spleen and pleural effusion (where applicable) of moribund mice were analyzed by FACS after staining with PE- or APC-conjugated antibodies as previously described (Parikh, *Blood.* 108(7):2349, 2006). For myeloid conditions, the following panel of antibodies was used: PE-conjugated Gr-1, CD19, Ter119, F4/80, CD86, MOMA-2, and CD115; APC-conjugated Mac-1, B220, Thy1.2, c-kit, and CD31; biotinylated CD38 and CD16/32 and APC-conjugated streptavidin. For lymphoid conditions: PE-conjugated Gr-1, Teri 19, CD19, BP-1, and IgM; APC-conjugated Mac-1, Thy1.2, B220, and C-kit; biotinylated CD24 and APC-conjugated streptavidin. All antibodies used for FACS immunophenotyping were purchased from BD Pharmingen, San Jose, Calif.

Immunoblotting.

Cell lysates were prepared from 90% confluent E2A cell lines starved of IL-7 and serum for ~16 hrs. Similar lysates were prepared from 32D cl-3 cell-lines starved of serum and WEHI-3B conditional media (as a source of IL-3) for ~16 hrs. Cells were counted and lysed in Lysis Buffer A (0.5% NP40, 150 mM NaCl, 50 mM Tris-HCl (pH 8.0) 1 mM EDTA) on ice for 15 minutes and centrifuged to remove debris. Total protein levels were equalized for loading by Bradford assay. Lysates were boiled for 5 minutes at 100° C., and 20 ug of total protein were resolved on 6-18% gradient polyacrylamide gels, transferred to nitrocellulose membranes, and blotted with the following primary antibodies overnight at 4° C.: anti-RAS (RAS10; used at 1:2000 dilution; Upstate Biotechnology/Millipore, Billerica, Mass.), anti-actin (AC40; 1:1000; Sigma, St Louis, Mo.), antibodies specific for phosphorylation of Stat5A/B (anti-pStat5A/B; 1:1000 Upstate Biotechnology/Millipore Billerica, Mass.), anti-pAkt, anti-pMek1/2, anti-pErk42/44, anti-total Akt, anti-Mek1/2, anti-Erk42/44, (all 1:1000; Cell Signaling Technologies, Beverly, Mass.), anti-total Stat5, (1:1000, BD Pharmingen, San Jose, Calif.) anti-p16$^{INK4A}$ (1:500, Cell Signaling Technologies, Beverly, Mass.), and anti-Bcl-x (1:1000, BD Pharmingen, San Jose, Calif.). HRP-labeled goat anti-mouse IgG or goat anti-rabbit IgG (Pierce Biotechnology, Rockford, Ill.) was used as a secondary antibody. Densitometry ratios were performed using Adobe Photoshop 7.0 (Adobe Systems Inc., San Jose, Calif.).

Results

Palmitoylation-Deficient NRASD12 Suppresses Progression of BCR/ABL Induced B-ALL in Mice.

Figure 6A:
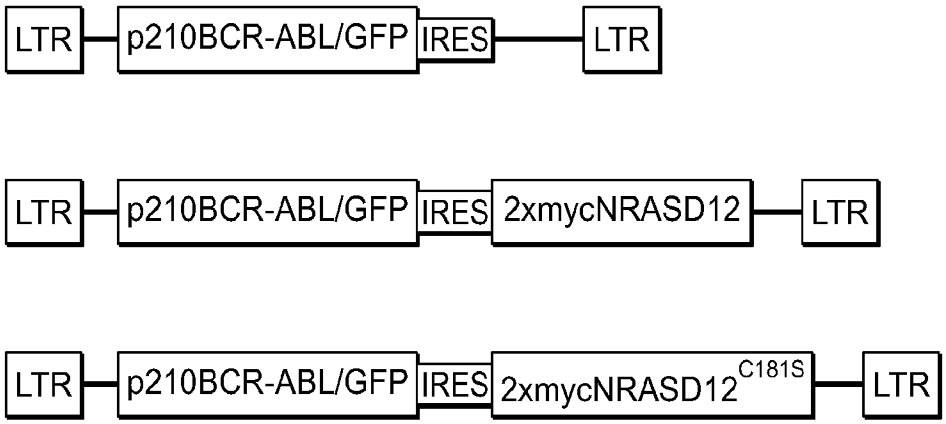
FIG. 6. Expression of BCR/ABL and NRASD12 or palmitoylation-deficient NRASD12 by retroviral vectors. A. Schematic diagram of MSCV-p210GFP-ires, MSCV-p210GFP-ires-NRAD12 and MSCV-p210GFP-ires-NRAD12$^{C181S}$ retroviral vectors. B. Titer and expression levels of BCR/ABL/GFP in p210GFP, p210GFP-ires-NRAD12 or p210GFP-ires-NRAD12$^{C181S}$ infected NIH 3T3 cells. GFP fluorescence x-axis) was measured by FACS analysis of NIH3T3 cells transduced with the retroviral vectors indicated. C. Relative expression levels of NRASD12 induced by the retroviral vectors. Immunoblot from whole cell lysates isolated from E2A B-precursor cells transduced by retroviral vectors containing GFP-ires-NRASD12, GFP alone (MiG) or the BCR/ABL containing vectors shown in A.
Figure 6B:
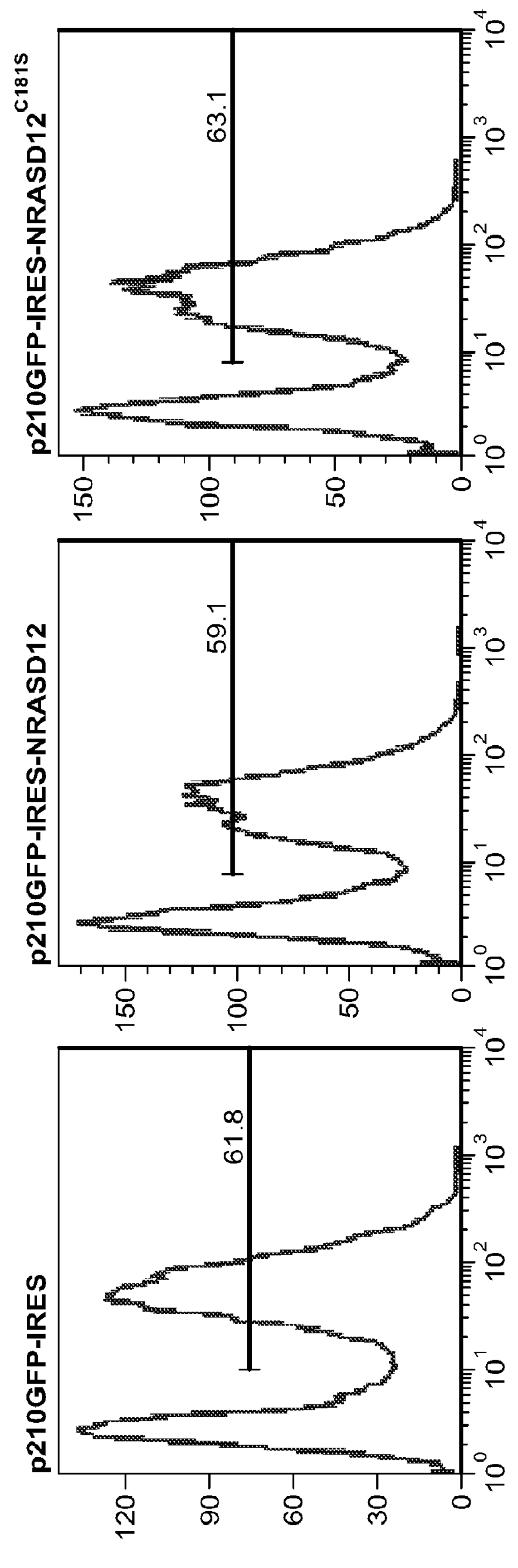
Figure 6C:
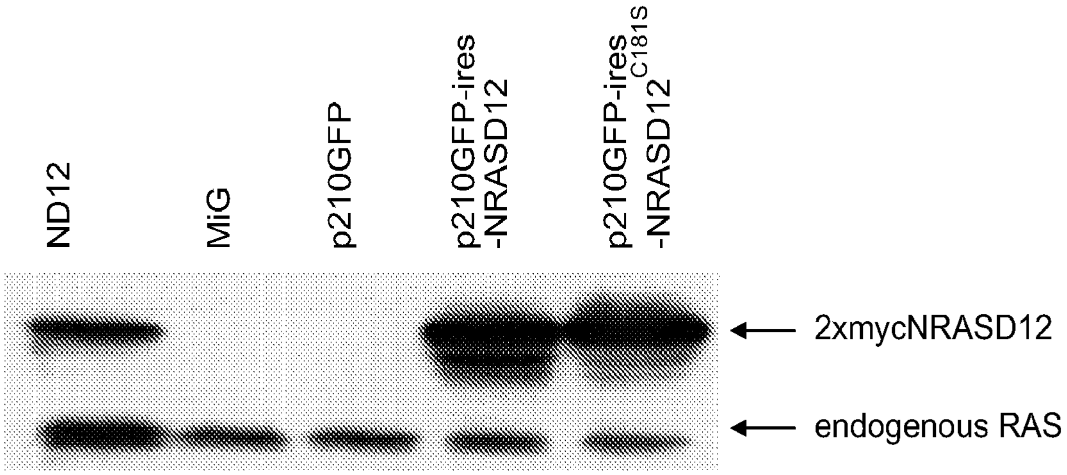

To assess the importance of NRAS palmitoylation in BCR/ABL induced B-ALL we employed a bicistronic murine stem cell virus (MSCV) retroviral vector to transduce BCR/ABL/GFP fusion oncogenes (p210GFP) with oncogenic NRAS (NRASD12) or palmitoylation mutant of NRASD12 (NRASD12$^{C181S}$) downstream of an internal ribosomal entry site (p210GFP-ires-NRAD12; p210GFP-ires-NRASD12$^{C181S}$) (FIG. 6A). Titers of MSCV-p210GFP-ires, MSCV-p210GFP-ires-NRAD12 and MSCV-p210GFP-ires-NRAD12$^{C181S}$ were determined in NIH 3T3 cells by FACS analysis (FIG. 6B). As shown in FIG. 6B, p210GFP expression levels are not affected by co-expressing NRAS mutants. Oncogenic NRAS and the palmitoylation mutant of NRASD12 are also expressed similarly in MSCV-p210GFP-ires-NRAD12 and MSCV-p210GFP-ires-NRAD12$^{C181S}$ infected E2A pro-B cell lines that were purified by FACS sorting of GFP$^{hi}$ cells (E2A cells express low levels of GFP) respectively (FIG. 6C).

Bone marrow (BM) isolated from Balb/c donor mice was transduced with titer-matched retroviruses under lymphoid growth conditions (see Methods) and $1\times10^6$ infected BM cells were transplanted into lethally irradiated Balb/c recipient mice as previously described (Acquaviva, *Blood.* 112(9): 3798, 2008; Roumiantsev, *Blood.* 97(1):4, 2001). Disease progression was monitored weekly 14 days after bone marrow transplantation by checking peripheral blood (PB) white blood cell (WBC) counts, blood cell morphology (blood smear) and FACS analysis of GFP-positive WBCs in PB. Moribund mice were euthanized and cells were isolated from PB, livers, spleens and pleural effusion and analyzed by FACS. Liver and spleen weights were also measured.

Figure 7A:
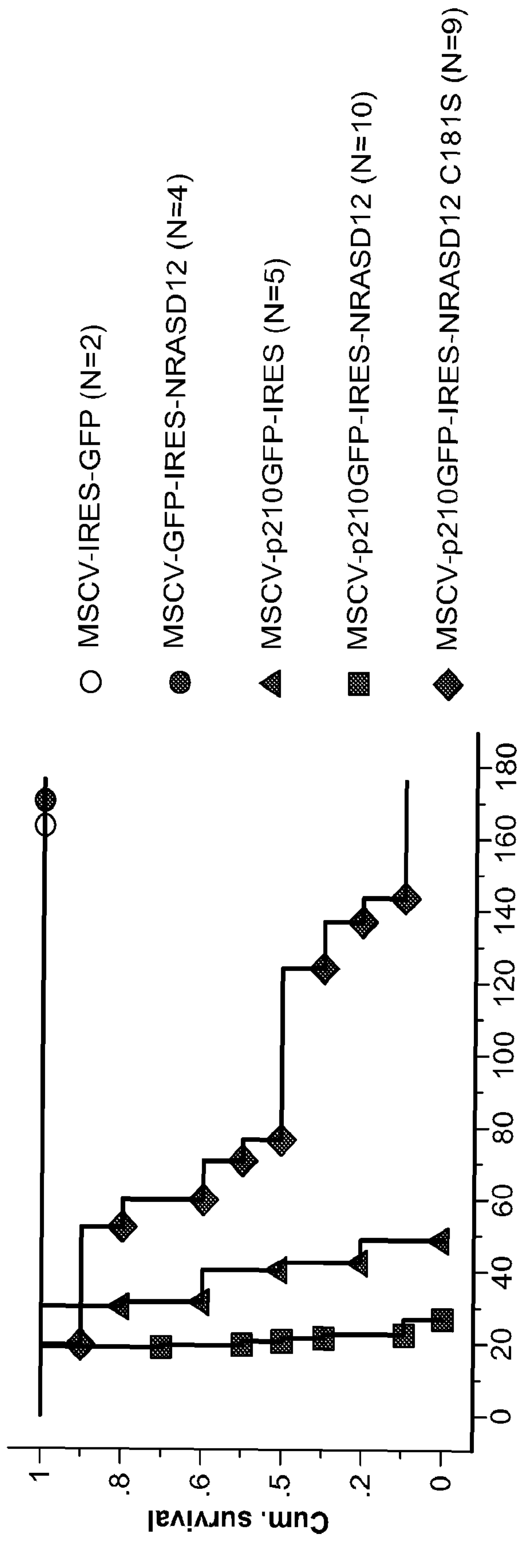
FIG. 7. Palmitoylation-deficient NRASD12 suppresses progression of BCR/ABL induced B-ALL in mice. A. Kaplan-Meyer survival analysis of mice transplanted with BM cells infected by p210GFP, p210GFP-ires-NRAD12 or p210GFP-ires-NRAD12$^{C181S}$ retroviruses, or the MiG and MiG-NRAD12 vectors. B. Changes of white blood cell counts over time in peripheral blood of GFP, NRASD12, p210GFP, p210GFP-ires-NRAD12 or p210GFP-ires-NRAD12$^{C181S}$ BMTT mice. C. Percentages of GFP-positive white blood cells over time in peripheral blood of GFP, NRASD12, p210GFP, p210GFP-ires-NRAD12 or p210GFP-ires-NRAD12$^{C181S}$ BMTT mice, assessed by FACS analysis.

As expected, mice receiving BM cells transduced with GFP alone (MiG mice) did not develop any disease (FIG. 7A). Additionally, mice receiving BM cells transduced with NRASD12, which induces an AML- or CMML-like diseases with 100% efficiency in a BMT model when transduced under conditions promoting transduction and growth of hematopoietic stem cells (HSCs) (Parikh, *Blood.* 108(7):2349,2006), did not develop any disease in the BMT model under lymphoid conditions.

As previously reported (Acquaviva, *Blood.* 112(9):3798, 2008), mice receiving BM transduced with p210GFP succumbed to B-ALL between days 30-49 post-BMT (7A). GFP+ cells from BM, spleens and livers of p210GFP mice express B-lymphoblastic markers (B220$^{+}$; CD19$^{+}$; CD43$^{+}$; BP-1$^{+}$; IgM$^{-/lo}$) (data not shown).

All mice receiving BM cells transduced with p210GFP-ires-NRASD12 succumbed to B-ALL with significantly shorter latency (P=<0.0001) (FIG. 7A). Nearly all of the p210GFP-ires-NRASD12 mice developed hind limb paralysis. Additionally these mice showed a nearly 4-fold increase in spleen weight and increased liver weight (data not shown) compared to p210GFP mice. These data demonstrate that co-expression of oncogenic NRAS exacerbates BCR/ABL induced B-ALL.

In contrast, only 50% mice receiving BM cells transduced with p210GFP-ires-NRASD12$^{C181S}$ succumbed to B-ALL, and the disease progression was significantly delayed compared with p210GFP mice (P=0.0358). We could not detect any signs of hematopoietic disease in the remaining p210GFP-ires-NRASD12$^{C181S}$ mice through day 104 when one mouse was sacrificed and BM, spleen and liver were analyzed by flow cytometry. However, 3 of 4 remaining mice of this group died between day 124-143 from unknown causes. One p210GFP-ires-NRASD12$^{C181S}$ mouse was still alive at day 197 after BM transplantation, with <1% PB GFP+ cells seen at day 178.

While p210GFP, p210GFP-ires-NRASD12, and p210GFP-ires-NRASD12$^{C181S}$ mice displayed an expansion of GFP+ cell in PB compared to MiG or NRASD12 transduced mice, this expansion was most rapid for p210GFP-ires-NRASD12 mice although expansion p210GFP GFP+ cells in PB was also significantly more rapid compared to p210GFP-ires-NRASD12$^{C181S}$ mice (7B and C). The decline of PB WBC counts and the amounts of GFP+ cells correlates with the appearance of bloody pleural effusion consisting of B-lymphoblasts in these mice.

The above results show that oncogenic NRAS can cooperate with BCR/ABL to induce a more aggressive B-ALL than BCR/ABL alone. Importantly, co-transduction of palmitoylation-deficient NRASD12 inhibited progression of BCR/ABL induced B-ALL.

Palmitoylation-deficient NRASD12 suppresses progression of BCR/ABL induced CML-like disease in mice.

Figure 8A:
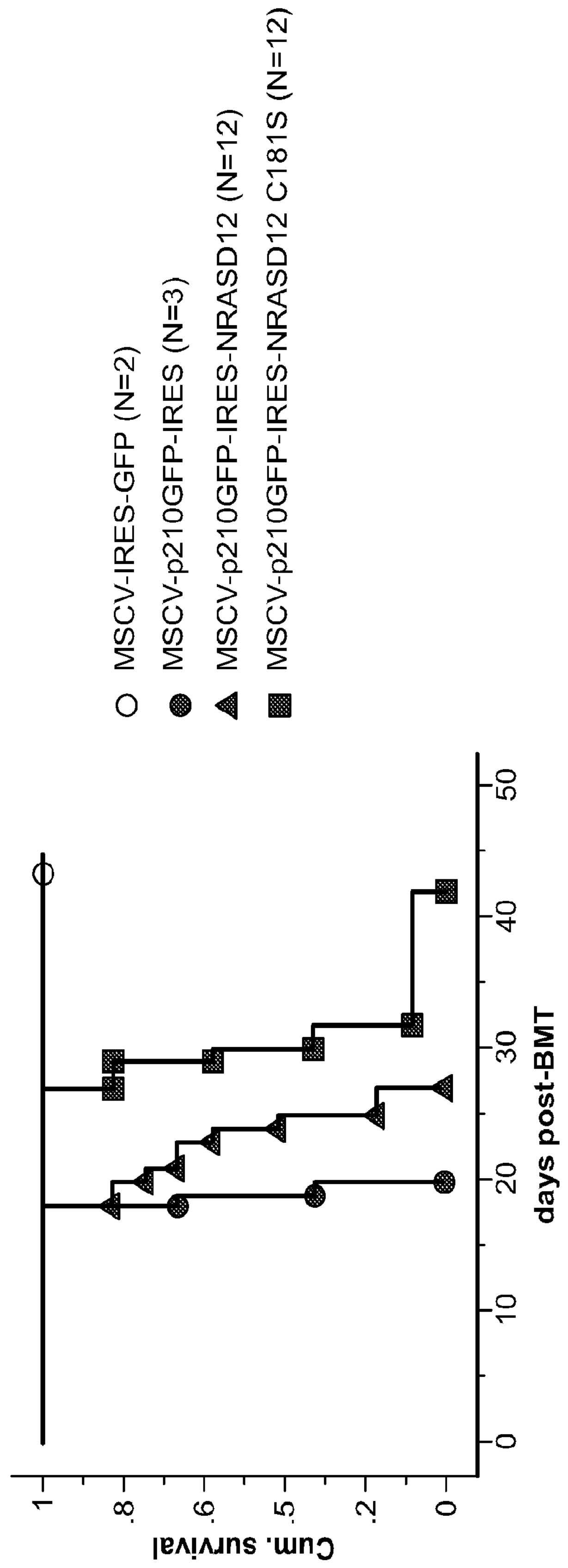
FIG. 8. Palmitoylation-deficient NRASD12 suppresses progression of BCR/ABL induced CML-like disease in mice. A. Kaplan-Meyer survival analysis of mice transplanted with 5-FU treated BM cells infected by p210GFP, p210GFP-ires-NRAD12 or p210GFP-ires-NRAD12$^{C181S}$ retroviruses, or the MiG control vectors. B. Percentages of GFP-positive white blood cells in peripheral blood from GFP, p210GFP, p210GFP-ires-NRAD12 or p210GFP-ires-NRAD12$^{C181S}$ BMTT mice, assessed by FACS analysis.

In order to assess the effect of palmitoylation-deficient, activated NRAS in the progression of BCR/ABL+ CML, we tested the effect of coexpression of palmitoylation-deficient NRASD12 in BCR/ABL induced CML-like disease using a BMT model under myeloid conditions that promotes retroviral transduction of HSCs. Mice receiving BCR/ABL infected BM succumbed to a lethal CML-like myeloproliferative disease within 3 weeks as previously reported (Zhang, *Blood,* 92(10):3829, 1998). However, mice receiving p210GFP-ires-NRASD12$^{C181S}$ transduced BM developed a significantly delayed CML (P=0.0002) (FIG. 8A). This was also reflected by a delayed expansion of GFP+ PB WBCs (8B). These results demonstrate that blocking palmitoylation of activated NRAS can also suppress BCR/ABL induced myeloid disease.

BCR/ABL and NRASD12 Cooperate in the Induction of B-ALL, Even Under Myeloid Conditions.

Interestingly, mice receiving p210GFP-ires-NRASD12 transduced BM cells under myeloid conditions did not develop a CML-like disease, but instead manifested a lethal B-ALL disease with 100% efficiency. This disease had identical latency to the aggressive B-ALL resulting from transduction of the same retroviral vector under lymphoid conditions [mice became moribund at day 18-27 under both myeloid and lymphoid conditions (FIGS. 8A and 7A)]. However, this aggressive B-ALL still has a longer latency compared to BCR/ABL induced CML-like disease (FIG. 8A).

Figure 9:
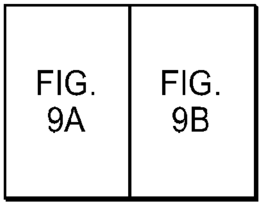
FIG. 9. Immunophenotyping of bone marrow cells isolated from mice transplanted with 5-FU treated BM cells infected by p210GFP, p210GFP-ires-NRAD12 or p210GFP-ires-NRAD12$^{C181S}$ retroviruses. The expression of GFP is shown along the X-axis, while the Y-axis shows the expression of cell surface markers specified over each column.
Figure 9A:
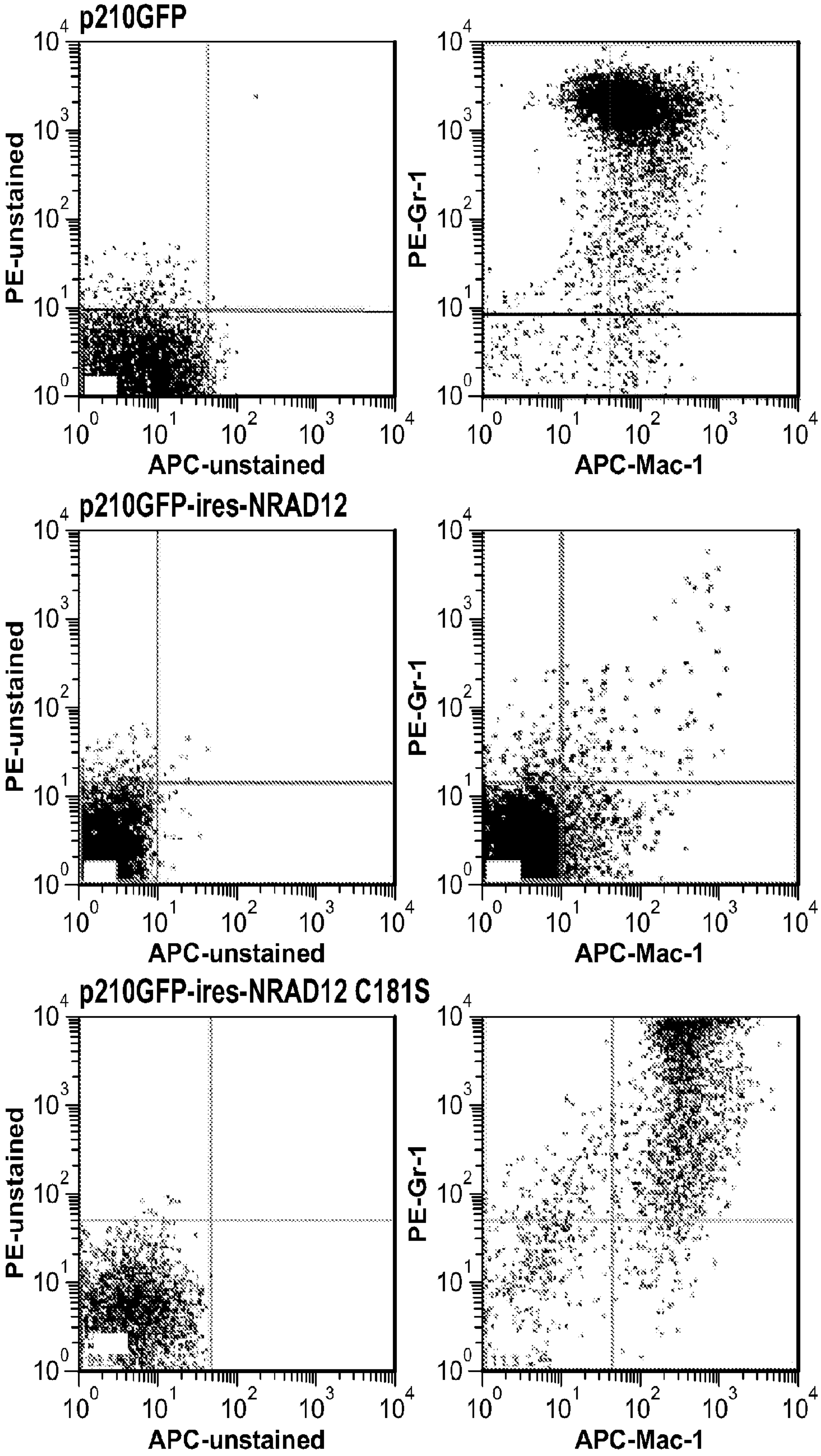
Figure 9B:
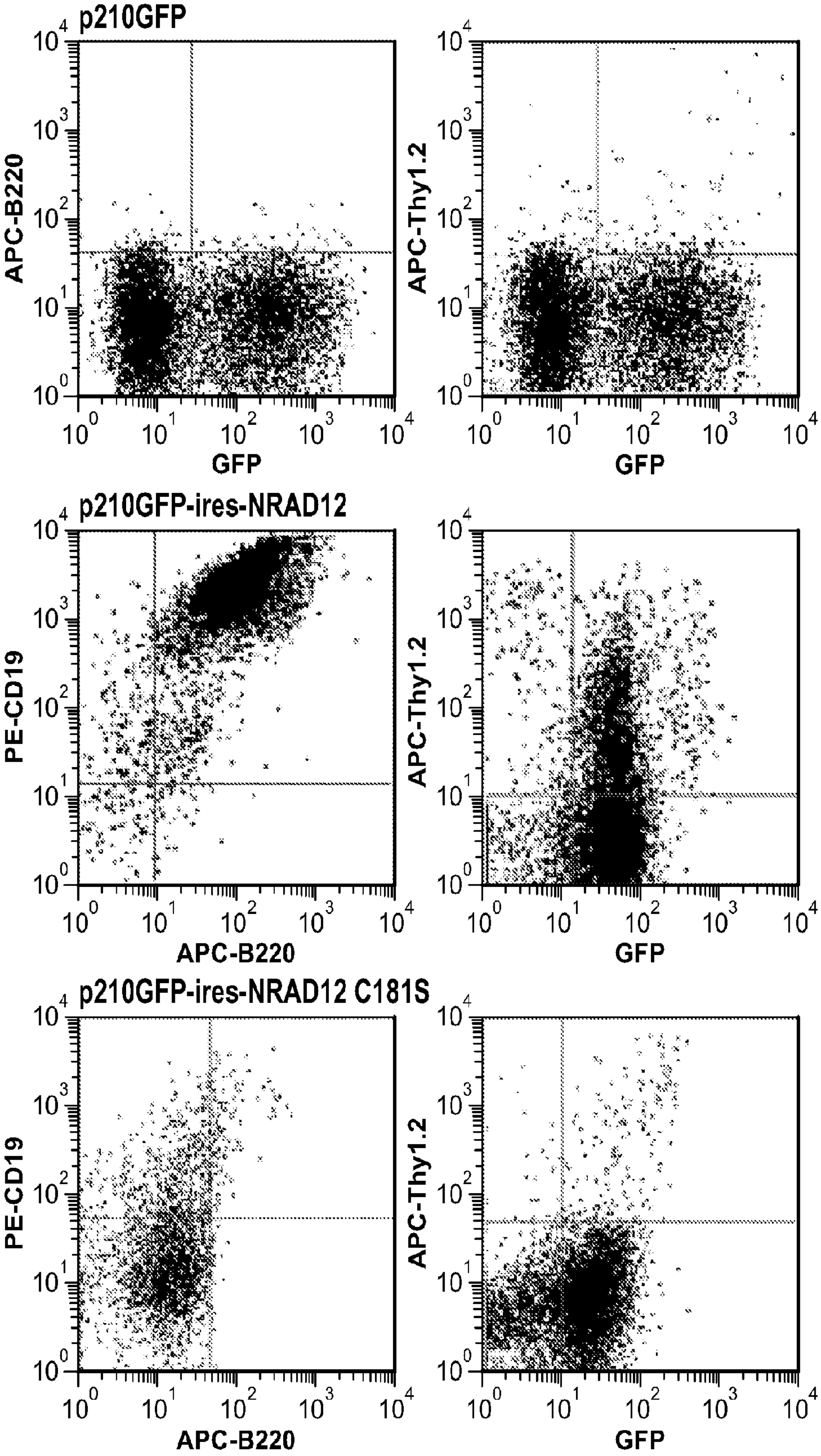

Flow cytometry analysis of BM, liver, spleen, and pleural effusions of moribund mice confirmed that the immunophenotype of lymphoblasts in p210GFP-ires-NRASD12 mice was the same as that in mice with BCR/ABL induced B-ALL under lymphoid BMT conditions (FIG. 9). This result suggests that cooperative signaling by NRASD12 and BCR/ABL not only drives a B-ALL in mice but also prevents the development of the myeloid disease driven by BCR/ABL or NRASD12 alone.

Mice transduced with p210GFP-ires-NRASD12$^{C181S}$ did not develop B-ALL, but developed a delayed CML-like disease (FIG. 9). This result indicates that palmitoylation is required for NRASD12 to cooperate with BCR/ABL in lymphoid lineage-specific transformation.

Coexpression of BCR/ABL and Oncogenic NRAS Alters Downstream Signaling Compared to Expression of Either Alone in a Cell-Context Dependent Manner, while Disruption Palmitoylation of NRASD12 Abrogates the RAS Signaling.

To gain insights into the underlying mechanisms of the dominant negative effect of palmitoylation-deficient NRASD12 in BCR/ABL leukemogenesis and the cooperation of BCR/ABL and oncogenic NRAS in lymphoid lineage-specific transformation, we expressed MiG, NRASD12, p210GFP, p210GFP-ires-NRASD12, or p210GFP-ires-NRASD12$^{C181S}$ in E2A, an IL-7 dependent B-lymphoid precursor cell line (Acquaviva, *Blood.* 112(9):3798, 2008) and 32D cl-3, an IL-3 dependent myeloid progenitor cell line by retroviral transduction followed by FACS sorting. Since STATS and RAS signaling have been shown to play critical roles in BCR/ABL transformation (Ren, *Nat Rev Cancer.* 5(3):172, 2005; Deininger, *Blood.* 96(10):3343, 2000; Hoelbl, *EMBO Mol. Med.* 2(3):98, 2010; Hoover, *Oncogene* 20(41):5826, 2001), we examined the activation of these two pathways by immunoblotting analyses.

Figure 10A:
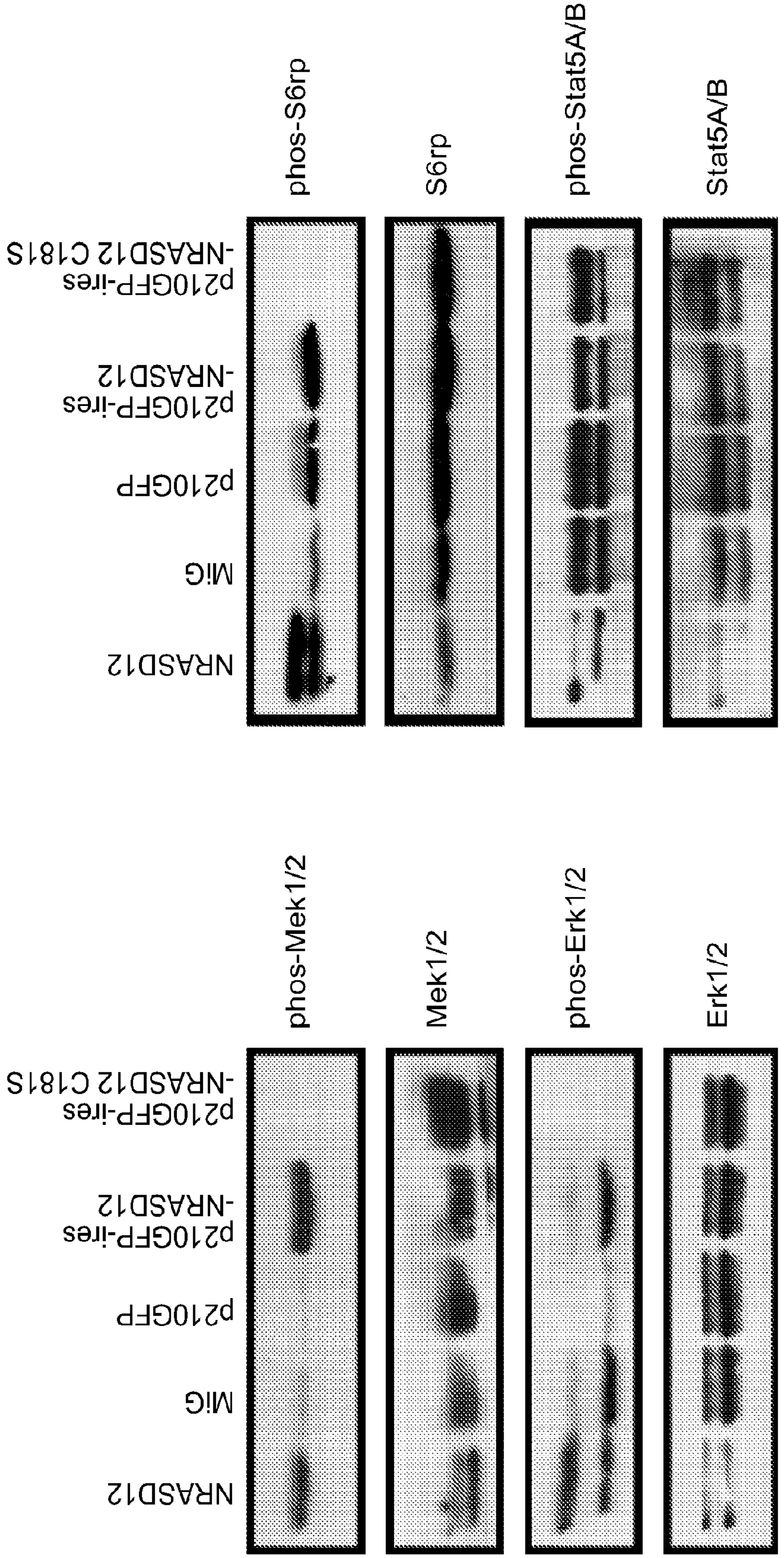
FIG. 10. Effects of coexpression of BCR/ABL and NRASD12 or NRASD12$^{C181S}$ on selected signaling pathways. A. Western blot analysis of signaling proteins in E2A B-precursor cells expressing NRASD12, GFP, p210GFP, p210GFP-ires-NRAD12 or p210GFP-ires-NRAD12$^{C181S}$. B. A. Western blot analysis of signaling proteins in 32D cl-3 myeloid progenitor cells expressing NRASD12, GFP, p210GFP, p210GFP-ires-NRAD12 or p210GFP-ires-NRAD12$^{C181S}$.

Immunoblots of lysates of IL-7 starved E2A cells transduced with MiG retrovirus (E2A-MiG), reveals a basal level of phosphorylation of Mek, Erk and S6rp (FIG. 10A). Phosphorylation of Mek, Erk and S6rp is significantly increased in E2A-NRASD12 cells, even though the overall Mek, Erk and S6rp expression levels are reduced compared to those in E2A-MiG cells. Expression of BCR/ABL in E2A B-lymphoid precursor cells does not activate Mek and Erk, and appears to reduce their activation compared to the vector control cells. But BCR/ABL does activate S6rp above the vector control level. Co-expression of BCR/ABL and NRASD12 restored the activation of Erk, Mek, and S6rp to or above the basal levels, respectively. The increased activation of Mek, Erk, and S6rp by coexpression of NRASD12 with BCR/ABL compared to BCR/ABL alone may contribute to the more aggressive B-ALL induced by the two oncogenes. Interestingly, coexpression of palmitoylation-deficient NRASD12 with BCR/ABL abolished the activation of Mek, Erk and S6rp, suggesting an underlying mechanism for the dominant negative effect of the palmitoylation-deficient NRASD12 in BCR/ABL induced B-ALL.

Although IL-7 starved, E2A-MiG cells contain a high level of phosphorylated Stat5A/B (FIG. 10A). Stat5A/B are slightly more activated in E2A-p210GFP cells. However, E2A-NRASD12 lysates displayed drastically reduced levels of phospho-Stat5A/B. While loading controls indicate similar protein loading (shown here by probing for total Akt protein), levels of overall Stat5A/B were also diminished in E2A-NRASD12 cells, suggesting that expression of oncogenic NRAS results in reduced expression of Stat5A/B in B-precursor cells. The activation of Stat5A/B is largely restored by coexpression of NRASD12 with BCR/ABL. These results suggest opposing effects of these oncogenes on activation of Stat5 signaling in B-precursor cells, with BCR/ABL expression enhancing signaling through Stat5 and oncogenic NRAS diminishing Stat5 signaling.

In summary, coexpression of BCR/ABL and NRASD12 result in a slightly less Stat5A/B activation, but much more Mek and Erk activation compared to BCR/ABL alone. The sum of these signaling pathways may underlie the more aggressive progression of B-ALL. On the other hand, the dominant negative effect of palmitoylation-deficient NRASD12 on RAS signaling may underlie the repression of B-ALL development in p210GFP-ires-NRASD12$^{C181S}$ mice.

Figure 10B:
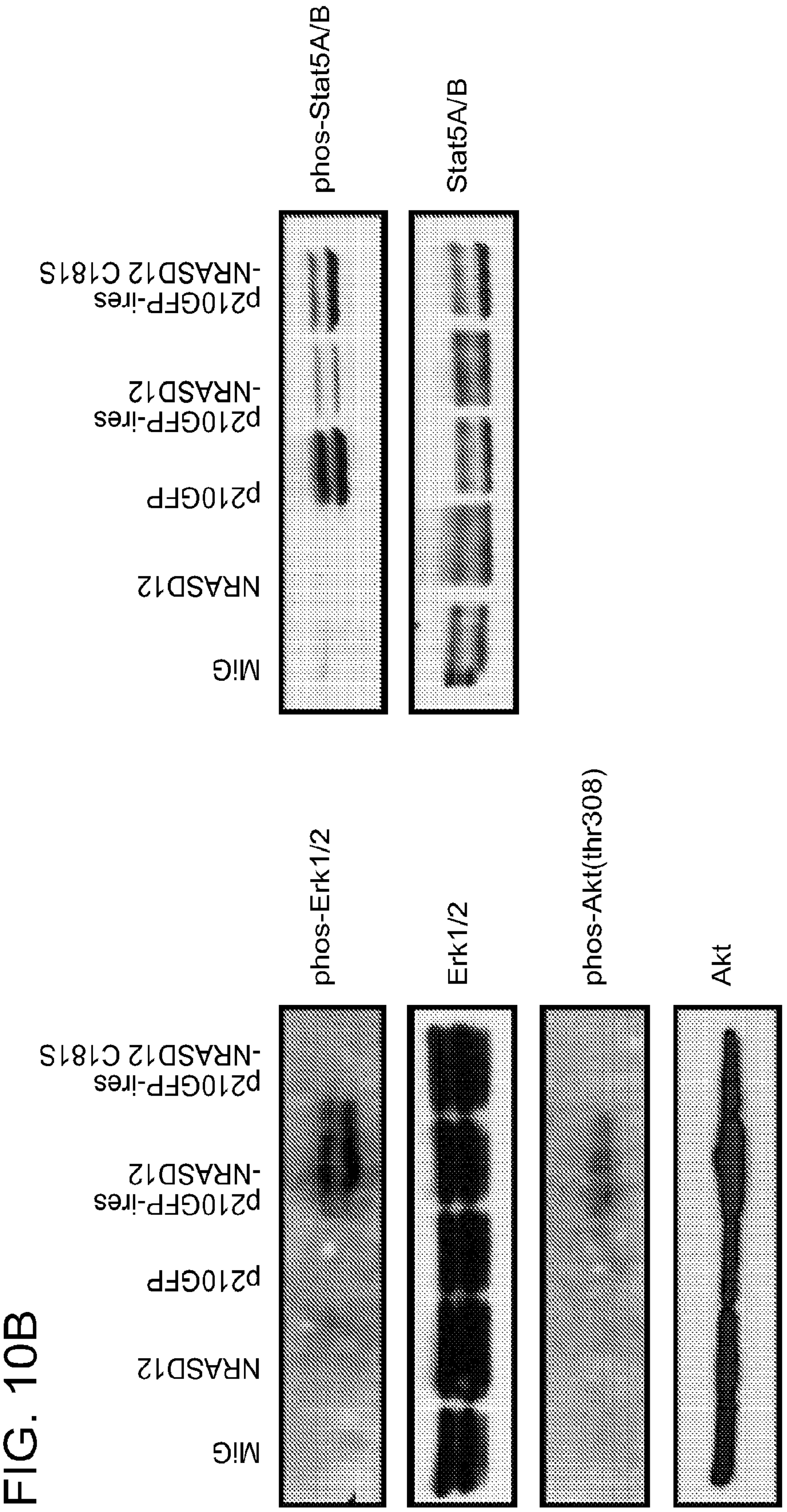
Figure 11A:
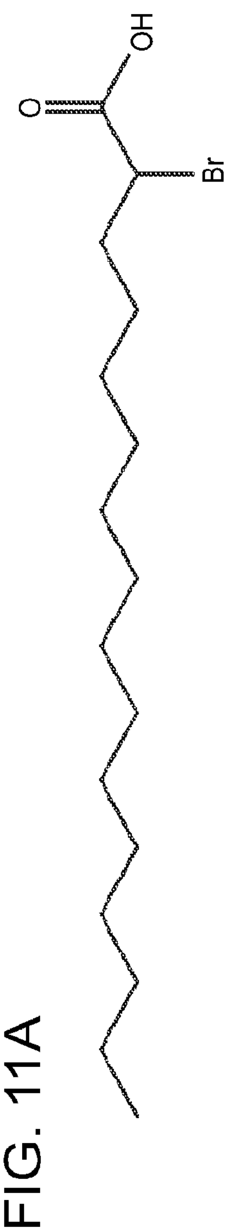
FIG. 11A. Lipid-based inhibitors of protein palmitoylation.
Figure 11A:
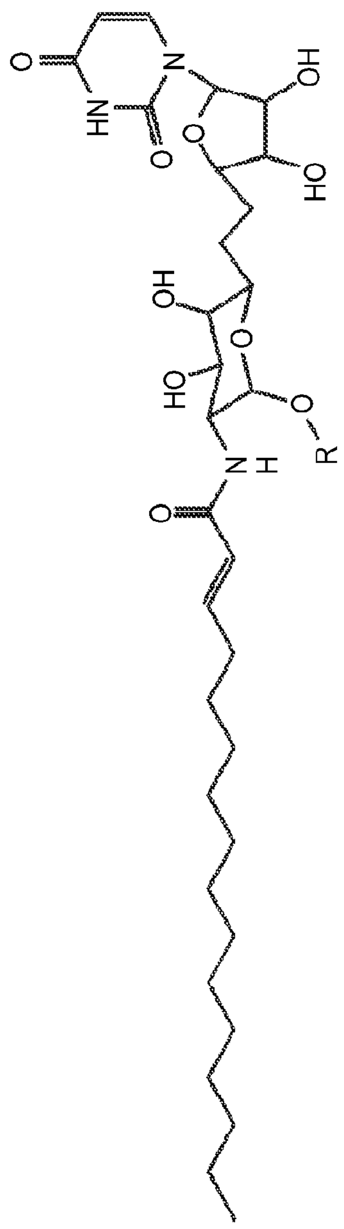
Figure 11A:
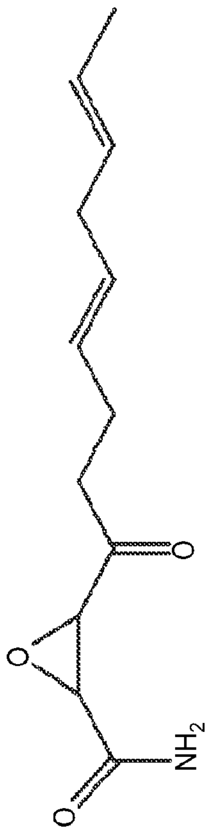
Figure 11A:
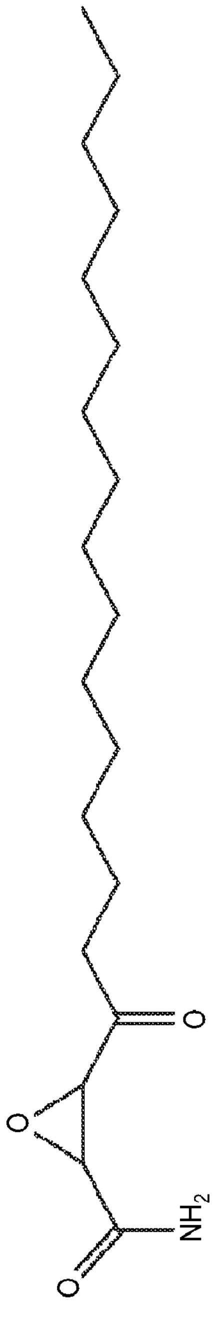

In 32D cl-3 myeloid precursor cells, constitutive RAS activation is not sufficient to permit IL-3 independent growth or activate MAPK or PI3K signaling pathways (Mavilio, *Oncogene* 4(3):301, 1989). However, BCR/ABL can confer factor independence to 32D cells, likely due to the fact that BCR/ABL induces robust activation of Stats, as these cells rely heavily on the Jak-Stat pathway for proliferative signaling (Parikh, *Cancer Res.* 67(15):7139, 2007; Hara, *Stem Cells* 14(6):605, 1996). We found that, unlike the results seen in E2A cells, only lysates from 32D cells coexpressing BCR/ABL and NRASD12 contain a high level phosphorylated Erk1/2 (FIG. 10B). Likewise, phosphorylation of Akt downstream of PI3K is also seen in cells coexpressing BCR/ABL and NRASD12.

As expected, BCR/ABL activates Stat5A/B in 32D cells (FIG. 10B). However, coexpression of NRASD12 dramatically reduces Stat5A/B activation by BCR/ABL. Since Stat5A/B play an essential role in BCR/ABL leukemogenesis (Hoelbl, *EMBO Mol. Med.* 2(3):98, 2010), the strong repression of Stat5A/B activation by NRASD12 may cause or at least contribute to the failure of induction of CML-like disease by coexpression of BCR/ABL and NRASD12, even though the RAS signaling pathways are more activated in cells expressing the two oncogenes. Coexpression of palmitoylation-deficient NRASD12 also reduces BCR/ABL induced Stat5A/B activation, albeit to a lesser extent than that by NRASD12. This effect of palmitoylation-deficient NRASD12 may contribute to the slower progression of BCR/ABL induced CML-like disease in mice.

Discussion

Figure 7B:
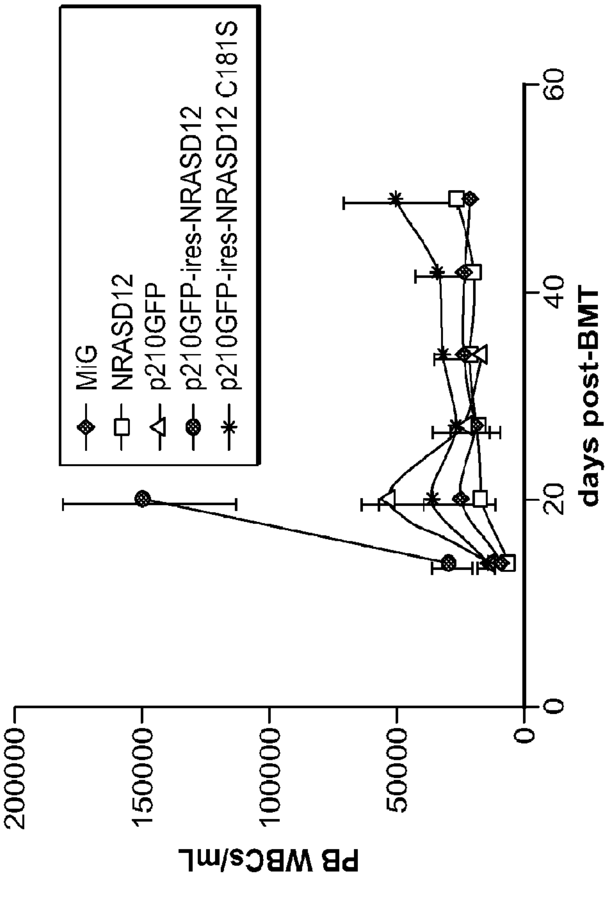
Figure 7C:
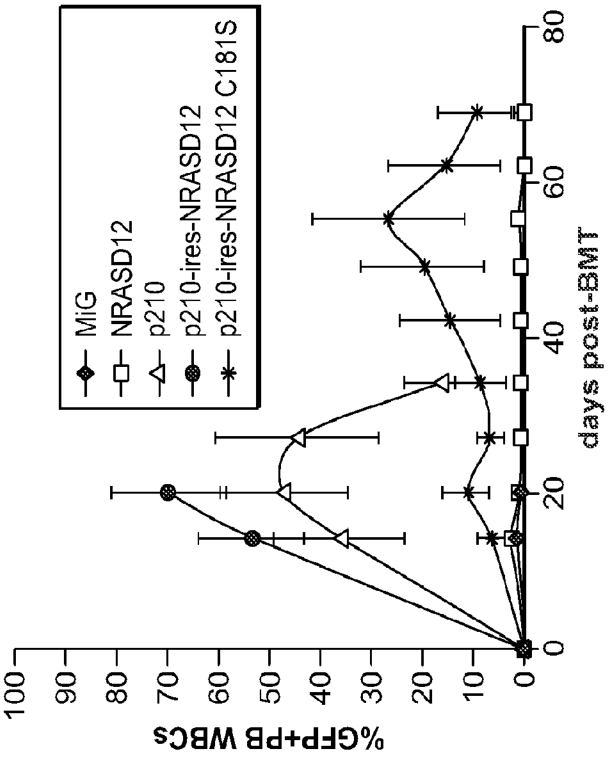
Figure 8B:
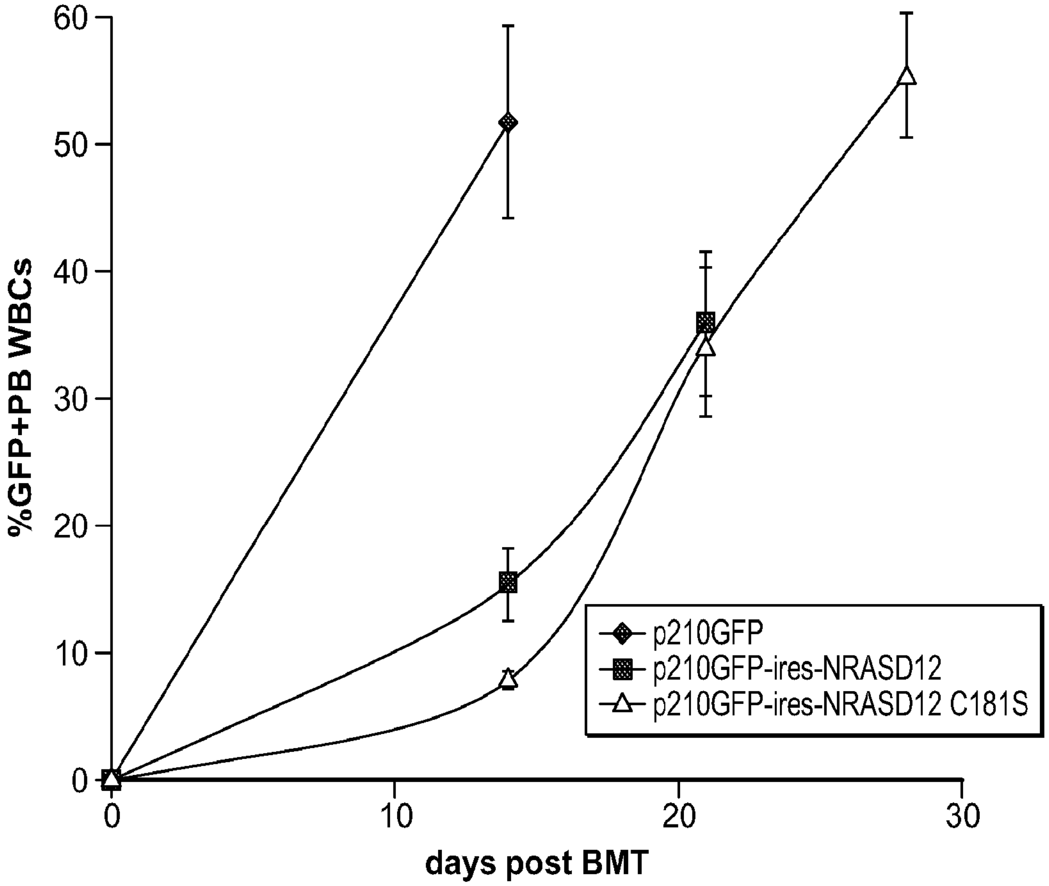

In this study, we found that palmitoylation-deficient oncogenic NRAS (NRASD12$^{C181S}$) not only loses the ability to activate Mek, Erk and S6rp, but also suppresses the basal activation of these signaling proteins (FIG. 10A) and that coexpression of NRASD12$^{C181S}$ with BCR/ABL suppresses the leukemogenesis induced by BCR/ABL (FIGS. 7 and 8). These data demonstrate that palmitoylation-deficient active NRAS has a dominant negative effect on RAS signaling and the leukemogenic signaling by BCR/ABL. We have previously shown that palmitoylation-deficient oncogenic NRAS is mislocalized away from the plasma membrane yet still capable of binding GTP and the RAS binding domain of the RAS effector Raf in cells. Since activation of PI3K and MAPK signaling cascades require activators other than RAS-GTP (Jimenez, *J Biol. Chem.* 277(44):41556, 2002; Matheny, *J Biol. Chem.* 284(17):11007, 2009; Rajakulendran, *Nature* 461(7263):542, 2009), it is likely that palmitoylation-deficient active NRAS interferes with RAS signaling by sequestrating RAS effectors away from the plasma membrane, and hence away from plasma membrane-associated activators.

Ph+ B-ALL is highly refractory to treatment with first and second-generation BCR/ABL kinase inhibitors (Talpaz, *N Engl J Med.* 354(24):2531, 2006; Ottmann, *Blood.* 100(6): 1965, 2002). Our data show that palmitoylation-deficient, activated RAS acts as a dominant negative regulator for BCR/ABL signaling and dramatically suppresses the progression of B-ALL induced by BCR/ABL in mice. The results suggest that therapies targeting RAS palmitoylation may be effective in treating Ph+ B-ALL. The same principle may also apply to a broad range of cancers driven by oncogenes that rely upon RAS as a central transducer of oncogenic signaling. These may include oncogenic KRAS and numerous upstream activators of RAS, though these will need to be directly tested.

We have previously shown that BCR/ABL and oncogenic NRAS are each capable of inducing myeloid malignancies in mice (Zhang, *Blood.* 92(10):3829, 1998; Parikh, *Blood.* 108 (7):2349, 2006). Interestingly, we found here that coexpression of oncogenic NRAS with BCR/ABL fails to induce myeloid malignancies under conditions where either oncogene alone could. Our data show that in the 32D myeloid cell line, coexpression of oncogenic NRAS dramatically suppresses the activation of Stat5 by BCR/ABL (FIG. 10B). This phenomenon underscores the cross talk/regulations between different signaling pathways. Recent studies have shown that Stat5A/B play an essential role in both initiation and maintenance of BCR/ABL+ leukemia (Hoelbl, *EMBO Mol. Med.* 2(3):98, 2010). The surprise finding that activated RAS suppresses the activation of Stat5 by BCR/ABL provides an explanation of the failed myeloid leukemogenesis from BM cells expressing both oncogenes. Further studies of the mechanism by which activated NRAS suppresses the activation of Stat5 by BCR/ABL may help to design therapeutic strategies targeting Stat5.

It is not clear how expression of BCR/ABL interferes with myeloid leukemogenesis by oncogenic NRAS, since coexpression of BCR/ABL did not block the activation of downstream effectors of NRASD12. Since NRASD12 induces myeloid tumors with a much longer latency than that by BCR/ABL (Parikh, *Blood.* 108(7):2349, 2006), it is possible that the rapid induction of B-ALL by BCR/ABL+ NRASD12 might have masked the myeloid diseases driven by the activated RAS signaling pathways.

We have shown here that oncogenic NRAS is incapable of inducing B-ALL even under the BM transduction condition that favors the targeting of lymphoic cells (FIG. 7A). RAS exerts distinct functions in different cellular context (Karnoub, *Nat Rev Mol Cell Biol.* 9(7):517, 2008). Recent studies showed that activation of RAS by the pre-B cell receptor orchestrates exit from the cell cycle and light-chain recombination during early B cell development Mandal, *Nat. Immunol.* 10(10):1110, 2009). Therefore, in the context of pre-B cells, activated RAS promotes cell differentiation instead of proliferation. Coexpression of BCR/ABL with NRASD12 must have overcome the cell cycle block and with the presence of BCR/ABL, the activated RAS turns around to facilitate neoplastic transformation.

Deletions of the CDKN2A/B tumor suppressor locus and of the IKAROS and PAX5 genes that promote B-lineage development occur frequently in Ph+ B-ALL Mullighan, *Genes Dev.* 22(11):1411, 2008). Our finding that BCR/ABL and NRASD12 cooperate in the induction of B-ALL suggests that some of the effects of deletion of the CDKN2A/B tumor suppressor locus and of the IKAROS and PAX5 genes may be achieved by enhanced RAS signaling (FIG. 10A). The significance of hyperactivation of RAS in the pathogenesis of B-ALL should be further investigated.

Our data also show that unlike oncogenic NRAS, palmitoylation-deficient NRASD12 no longer prohibits BCR/ABL induced myeloproliferative disease and no longer exacerbates BCR/ABL induced B-ALL, suggesting that the effects of oncogenic NRAS on BCR/ABL leukemogenesis rely upon the plasma membrane association.

Palmitoylation-deficient NRASD12 also inhibits the progress of BCR/ABL induced CML-like disease, although to a lesser extent than its effect on BCR/ABL induced B-ALL. Although palmitoylation-deficient NRASD12 also inhibits the activation of Stat5 by BCR/ABL, this inhibition is much weaker than that by NRASD12. It is possible that the remaining activated Stat5 can still drive the myeloproliferation. The therapeutic effect of blocking RAS palmitoylation may be more dramatic in cancers that rely more upon the RAS signaling.

Blocking RAS palmitoylation could be achieved by inhibiting RAS palmitoyl-acyl transferases (PATs). Thus far, 23 putative PATs, each exhibiting a high degree of enzyme-substrate specificity, have been identified (Fukata, *Methods* 40(2):177, 2006; Iwanaga, *Prog Lipid Res.* 48(3-4):117, 2009; Swarthout, *J Biol. Chem.* 280(35):31141, 2005). In addition, other aspects of palmitoylation, such as synthesis of the palmitic acid substrate, may also serve as targets for therapies. Future experiments testing the effects of these targets in tumorigenesis are warranted.

Example 3

Sensitivity of Cancers Involving Palmitoylation-Dependent Activated RAS to Inhibition of FASN The present Example demonstrates, among other things, that cancers involving activated RAS that is dependent upon palmitoylation are particularly sensitive to therapy with FASN inhibitors.

Introduction

One hallmark of cancer is the shift in cell metabolism from oxidative phosphorylation to aerobic glycolysis ("the Warburg effect") [1]. Another hallmark of cancer that is functionally related to the glycolytic pathway but not so well known is an increase of de novo fatty acid (FA) synthesis. FAs are essential for cell membrane formation, energy metabolism, signal transduction and lipid based post-translational modifications of proteins.

There are two sources of FAs for cells—exogenously derived (dietary) and endogenously synthesized. Fatty acid synthase (FASN) is a large homodimeric protein with seven catalytic domains that condenses Malonyl-CoA and Acetyl-CoA and utilizes NADPH to reduce the product into the 16-carbon fatty acid, palmitate [2]. FASN was originally identified from sequence homology to an antigen found in abundance in breast cancer patients with poor prognosis [3]. Palmitate is the base fatty acid from which all other de novo fatty acids are produced in the cell. FASN is essential for embryonic development [4]. But, in most normal adult cells, FASN expression is usually silenced or is expressed only at very low levels, as cells preferentially use the exogenous FAs [5]. Cancer cells, on the other hand, no longer acquire and process exogenous FAs, but instead rely almost entirely upon synthesis of de novo FAs [6].

Activation of FASN is intricately connected to metabolic changes in cancer cells, so FASN may in fact be a key metabolic mediator of oncogenesis, linking metabolism, energy, and lipogenesis [7, 8]. A wide variety of solid tumors show dramatic upregulation of FASN as an early event in oncogenesis [8-11]. More recently, studies have shown that FASN is also important for leukemia cells in culture [12]. Due to its minor importance for normal cell function but great importance for cancer cells, inhibition of FASN has for some time been an attractive target for treatment or chemoprevention of a number of cancers with promising results [13-23].

RAS proteins are small GTPases that act as molecular switches, transducing signals from many activated receptors that regulate cell proliferation, survival and differentiation [24]. Members of the RAS family include three cellular RAS genes, which encode four highly homologous proteins: H-, N-, and K-RAS4A and 4B, the latter two being alternatively spliced forms differing only at the carboxyl terminus (with alternative $4^{th}$ exon) [25]. Mutations that result in constitutive activation of RAS proteins are associated with approximately 30% of all human cancers, including approximately 30% myeloid malignancies [26]. Since the enzymatic activity of RAS is used to turn itself off and is inactive in oncogenic RAS, RAS proteins are considered to be "non-targetable" for developing cancer therapies. Identification of alternative targets that block RAS signaling is critical for the development of therapies for RAS-related cancer.

We have found that expression of oncogenic NRAS (NRASD12) efficiently induces chronic myelomonocytic leukemia (CMML)-like or acute myeloid leukemia (AML)-like disease in mice [27]. Using the in vivo model, we examined the role of PTMs in NRAS leukemogenesis and found for the first time that palmitoylation is essential for NRAS leukemogenesis [28]. As described herein, these findings suggest, among other things, that targeting palmitoylation may be an effective therapy for hematological malignancies as well as other NRAS related cancers.

In addition to the direct activation by mutations, RAS can also be functionally activated by other oncogenic mutations, including many oncogenes encoding activated protein tyrosine kinases such as BCR/ABL. We have found that palmitoylation-deficient oncogenic NRAS is mislocalized away from the plasma membrane yet still capable of binding GTP in cells [28]. This finding suggests that palmitoylation-deficient, activated RAS may have a dominant negative effect on RAS signaling. As a proof-of-concept study for treating cancers driven by RAS regulators through blocking RAS palmitoylation, we evaluated the effect of blocking RAS palmitoylation on BCR/ABL leukemogenesis and found that expression of palmitoylation-deficient NRASD12 significantly impeded progression of BCR/ABL-induced B-acute lymphoblastic lymphoma (B-ALL)- and chronic myeloid leukemia (CML)-like diseases in mice. As described herein, these results suggested that palmitoylation-deficient, activated RAS acts as a dominant negative regulator for BCR/ABL signaling, and that targeting RAS palmitoylation may also constitute an effective therapy in hematological malignancies and other cancers driven by oncogenes upstream of RAS.

In the studies described above, we blocked oncogenic NRAS palmitoylation by mutating the palmitoylation site in NRASD12. Therapeutic intervention of oncogenic NRAS' palmitoylation requires targeting the trans-acting factors—enzymes that mediate NRAS palmitoylation. One candidate target for RAS palmitoylation—is FASN that is responsible for the production of the palmitic acid substrate for palmitoylation. The present Example describes our analysis of the role of FASN in RAS transformation.

Results and Discussion

Oncogenic NRAS and KRAS4B Upregulate FASN.

Figure 14:
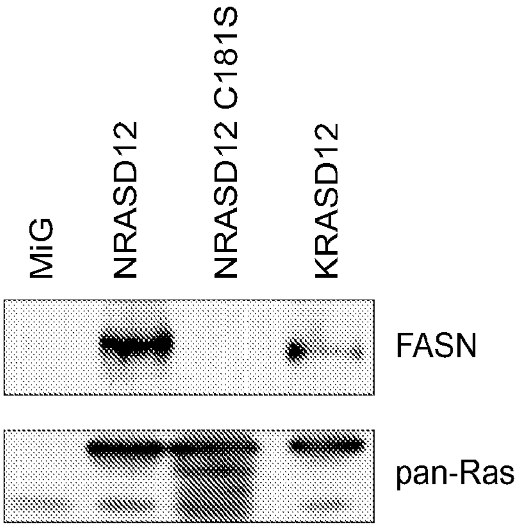
FIG. 14 shows data from NIH3T3 cells that were transduced with retroviral vectors MSCV-GFP-ires-2xmyc-tag-NRASD12, MSCV-GFP-ires-2xmyc-tag-NRASD12$^{C181S}$ MSCV-GFP-ires-2xmyc-tag-KRAS4BD12, or MIG vector control, followed by FACS sorting for GFP$^+$ cells. The lysates of 3T3-NRASD12, 3T3—NRASD12$^{C181S}$, 3T3-KRAS4BD12, or 3T3-MiG cells were immunoblotted with an anti-FASN antibody (Cell Signaling Technologies, Beverly, Mass.) or a pan-RAS antibody (Upstate Biotechnology, Lake Placid, N.Y.).

It has been shown that FASN can be upregulated by ERK and PI3K, downstream effectors of RAS, through activation of the sterol regulatory element binding protein 1 (SREBP-1) transcription factor [29]. To assess the role of FASN in RAS transformation, we first examined FASN expression in NIH3T3 cells expressing NRASD12, NRASD12$^{C181S}$, KRAS4BD12 or GFP control (FIG. 14). Western blot analysis of whole cell lysates from these cell lines indicated that FASN expression was induced by stable expression of oncogenic NRAS and KRAS, but not by the palmitoylation mutant of NRASD12. RAS expression was confirmed by probing with a pan-RAS antibody.

Silencing of FASN Expression Selectively Mislocalizes NRASD12 but not KRAS4BD12 Away from the Plasma Membrane.

We then examined the effect of knocking down FASN expression on RAS localization by the RNA interference (RNAi) approach. RNAi is endogenously mediated by microRNA (miRNA) [30]. miRNAs are generated from primary transcripts (pri-miRNAs) and processed into pre-miRNA and eventually mature miRNA. Artificial miRNAs are natural pri-miRNA in which the stem sequence of a miRNA has been substituted with a sequence targeting the gene of interest. In target cells, artificial miRNA undergoes the same processing steps of the parental pri-miRNA. A FASN specific small hairpin (sh) RNA (Open-Biosystems) was cloned into a MSCV-based retroviral shRNAmir (pSM2; Open-Biosystems) vector to generate an artificial miRNA for FASN (the cloning oligo for the FASN shRNA: 5' TGC TGT TGA CAG TGA GCG CCG CTT CTT AGA GAT TGG CAA ATA GTG AAG CCA CAG ATG TAT TTG CCA ATC TCT AAG AAG CGA TGC CTA CTG CCT CGG A 3' (SEQ ID NO: 35)). The miRNA is under the control a U6 promoter and the vector includes a puromycin resistance gene under the control of phosphoglycerate kinase (PGK) eukaryotic promoter [31]. A scrambled shRNA (the cloning oligo: 5' TGC TGT TGA CAG TGA GCG CTT CCT CTC TTT CTC TCC CTT TA GTG AAG CCA CAG ATG TAC AAG GGA GAG AAA GAG AGG AAG GAT GCC TAC TGC CTC GGA 3' (SEQ ID NO: 36)) was similarly cloned into pSM2 as a control. These vectors were then transduced into NIH3T3 cells lines stably expressing the GFP-NRASD12 or GFP-KRAS4BD12 fusion protein. Cells were selected with puromycin (1 ug/mL).

Figure 15:
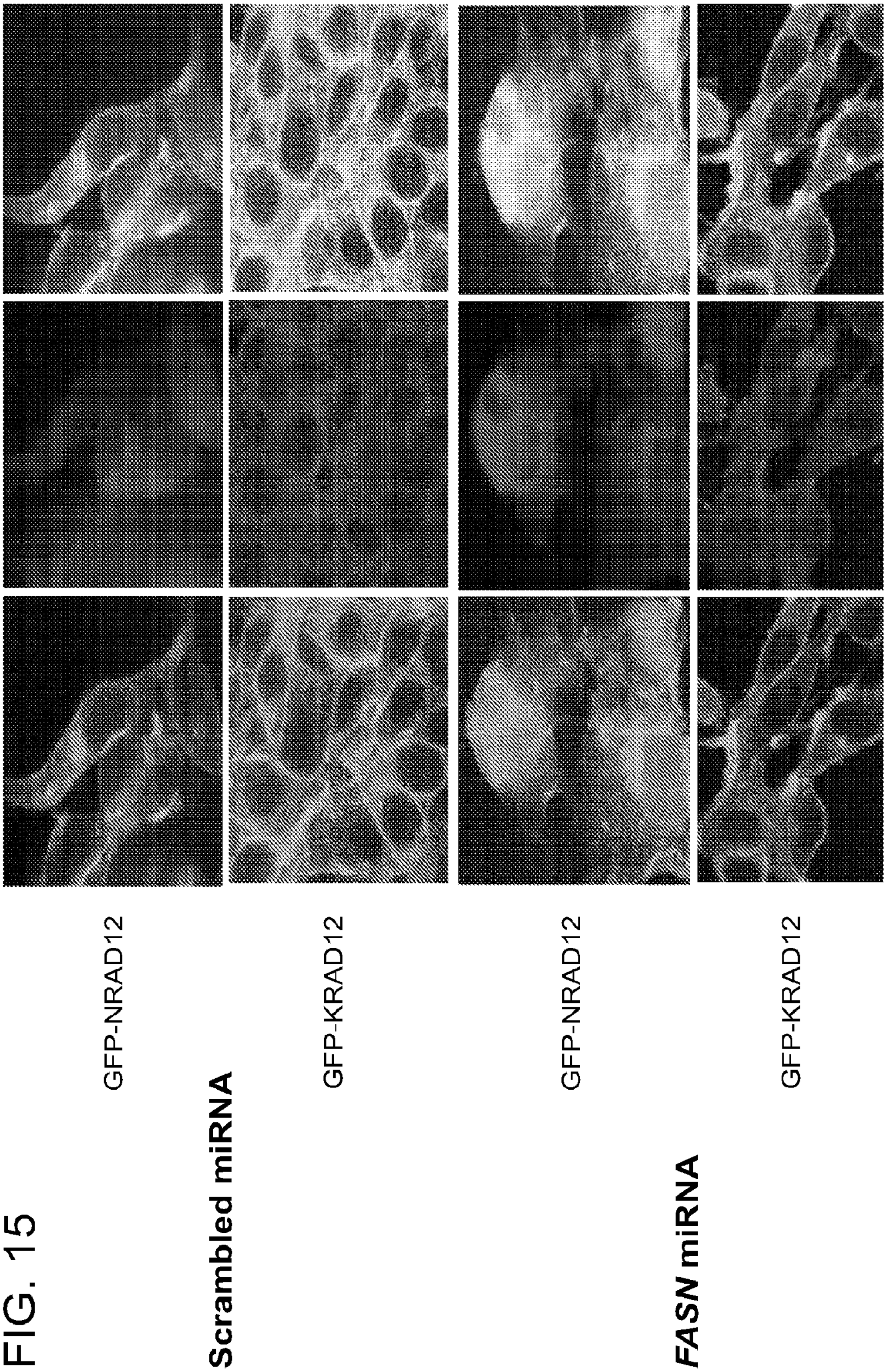
FIG. 15 shows NIH3T3 cell lines expressing GFP-fused versions of the oncogenic NRAS and KRAS4B that were transduced with scrambled miRNA or miRNA specific for FASN. Fixed and permeablized cells were stained with an anti-BIP antibody, followed by an alexafluor 635-conjugated secondary antibody, and visualized on a Leica TCS SP2 Spectral Confocal Microscope. Original magnification was 630×.

Western blot analysis confirmed that FASN expression was largely abolished by the FASN specific miRNA (data not shown). The above cell lines were then fixed, permeablized, stained with an endoplasmic reticulum (ER) marker, and mounted on coverslips to be visualized by confocal microscopy. FIG. 15 shows that GFP-NRAS mislocalized to endomembranes in 3T3-GFP-NRASD12 cells transduced by FASN miRNA, but not by the scrambled miRNA, while GFP-KRAS4BD12 localized to both the plasma membrane and internal membranes in cells regardless the presence of scrambled or FASN miRNA.

Silencing of FASN Inhibits Transformation in Cells Stably Expressing NRASD12 but not KRAS4BD12.

Figure 16:
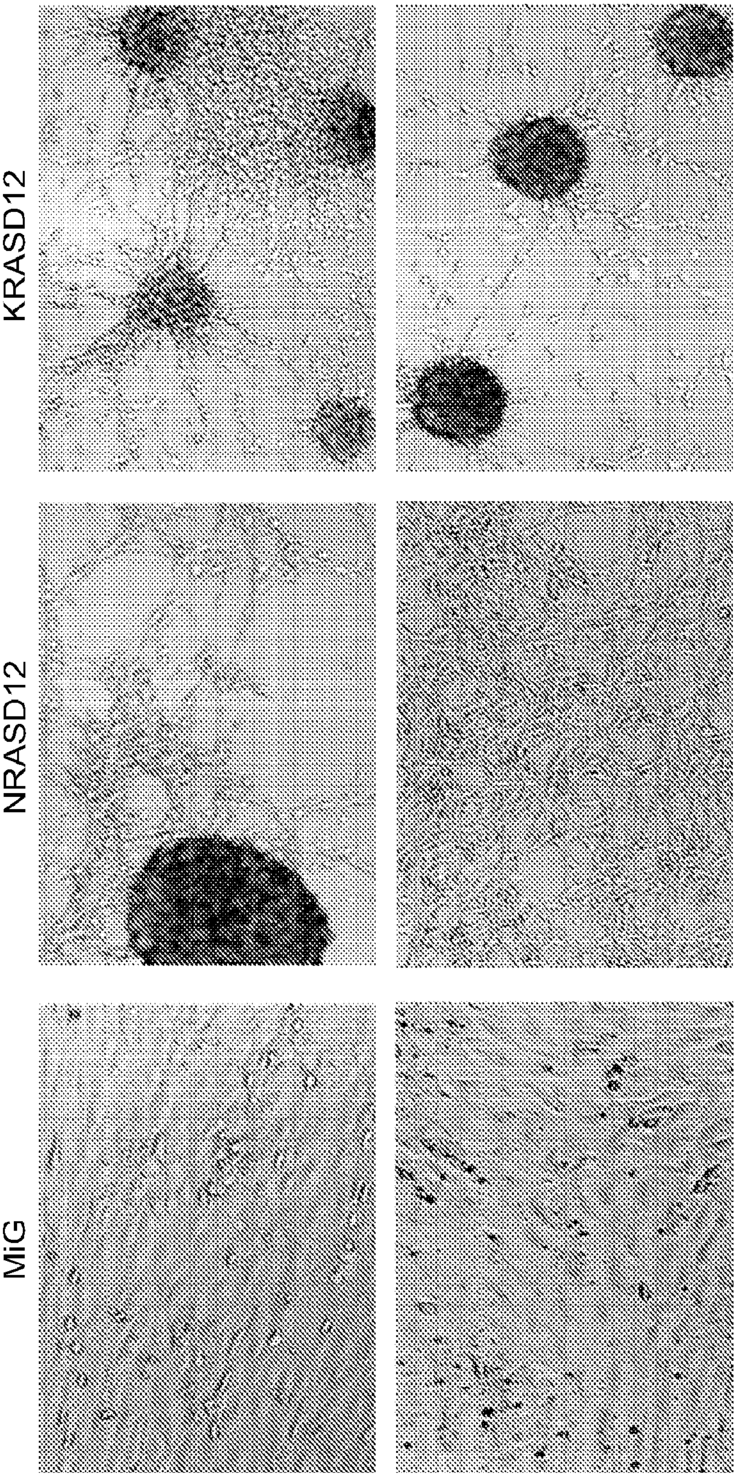
FIG. 16 illustrates the morphology of cultured NIH3T3 cells stably expressing the proteins and miRNAs indicated. Equal numbers ($5\times10^5$) of cells were plated onto 100-mm plates after puromycin selection and were cultured for 6 days before representative pictures were taken (original magnification 100×)

Both 3T3-NRASD12 [28] and 3T3-KRAS4BD12 form sphere-like foci in culture, while 3T3-MiG cells grow as normal NIH3T3 cells (FIG. 16). 3T3-NRASD12$^{C181S}$ cells do not form spheres, but have a somewhat changed morphology [28]. We plated equal cell numbers of scrambled or FASN miRNA-transduced, puromycin-selected 3T3-NRASD12 or 3T3-KRASD12 cell lines cultured for 6 days and observed cell morphology and foci formation (FIG. 16). 3T3-KRASD12 cells formed spheres regardless the presence of scrambled or FASN miRNA. 3T3-NRASD12 cells transduced with scrambled miRNA were able to form spheres as usual, but cells transduced with FASN miRNA no longer formed spheres and grew in a flat monolayer. However, these cells had somewhat altered morphology, similar to those observed in 3T3-NRASD12$^{C181S}$ cells.

Together, these results indicate that oncogenic NRAS transformation is particularly sensitive to FASN inhibition and suggest that cancers involving activated RAS that needs palmitoylation are particularly sensitive to FASN inhibition. These include, for example, 1) Hematological malignancies with NRAS mutations; 2) Melanoma with NRAS mutations (25% of all melanoma); 3) Neuroblastoma, where NRAS was firstly identified; 4) Other cancers with NRAS mutations; 5) Cancers, such as bladder carcinoma, with HRAS mutations (HRAS undergoes palmitoylation); 6) Cancers with KRAS4A mutations—KRAS mutations are predominant in cancers with RAS mutations. KRAS has two alternative spliced forms—4B and 4A. KRAS4A and 4B differ only the COOH-terminal regions. When oncogenic mutations occur, both 4A and 4B becomes activated. KRAS4A undergoes palmitoylation, but 4B is the predominant form in cells and it does not undergo palmitoylation. Recent studies have shown that KRAS4A is required for lung cancer development. So it is likely that inhibition of palmitoylation would impact on cancers with KRAS mutations; 7) Cancers, such as neuroblastoma and JMML, with NF1 mutations (a negative regulator for RAS, deletion of which leads to hyperactivation of RAS proteins); and 8) Cancers with oncogenic mutations in upstream regulators of RAS.

FASN Inhibitors Selectively Mislocalize NRASD12 but not KRAS4BD12 Away from the Plasma Membrane.

A number of small-molecules are known to inhibit FASN, including Cerulenin, a naturally occurring antibiotic isolated from the fungus *Cephalosporium caerulens*, the anti-obesity drug Orlistat, and Epigallocatechin-3-gallate (EGCG) the major polyphenol found in green tea [32]. The antineoplastic effects of cerulenin have been tested previously, however the molecule has proven to be of limited efficacy due to innate instability caused by its highly reactive epoxy group [22, 23]. For this reason, more stable synthetic derivatives of cerulenin have been developed. One of synthetic derivatives of cerulenin is C75, which lacks the reactive epoxy group. However, treatment of mice with C75 resulted in increased metabolism, rapid and significant weight loss, and fasting [33, 34], precluding its development as an anti-cancer agent.

An improved analogue of cerulenin, C93, has been developed recently [35]. This inhibitor is more specific and does not raise metabolism, induce fasting or cause rapid weight loss. However, it is not yet commercially available and we were unable to obtain this molecule for our studies.

Figure 17:
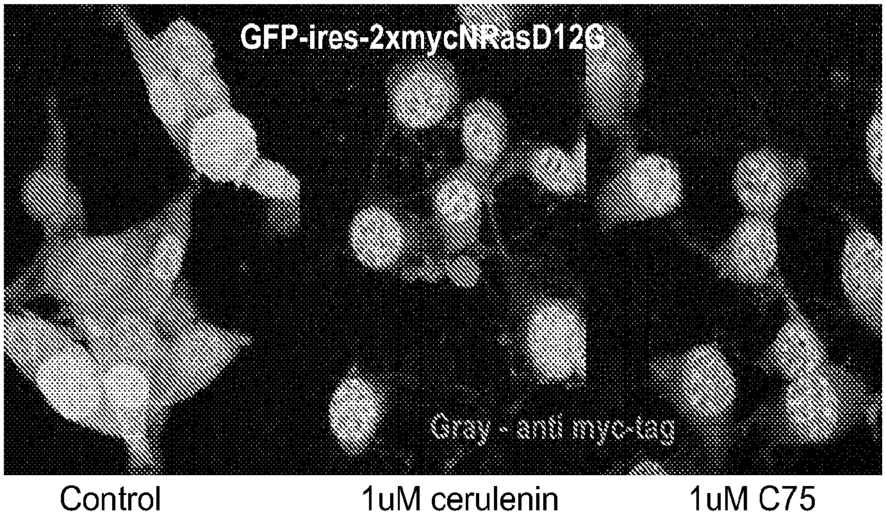
FIG. 17 illustrates that FASN inhibitors cause mislocalization of NRASD12 to internal membranes. Localization of myc-tagged NRASD12 in MSCV-GFP-ires-2xmycN-RASD12 infected NIH3T3 cells 3 hrs post-treatment with 1 uM cerulenin or 1 uM C75. NRASD12 were visualized by confocal microscope after probing with anti-myc-tag (9E10) antibody overnight at 4° C. and AlexaFluor-conjugated secondary antibody (red). Original magnification: 630×.

As a proof of principle studies of the effect of FASN inhibitors on NRAS palmitoylation/localization, we examined the effect of cerulenin and C75 on NRASD12 expressing NIH3T3 cells. Drugs were applied at previously characterized pharmacologically active concentrations with cytotoxicity <25% in similar cell-culture models [36-38]. Immunofluorescence study shows that cerulenin and C75 causes NRASD12 to be mislocalized to internal membranes (FIG. 17).

These studies demonstrate that FASN inhibitors can be effective to treat cancers involving activated RAS that needs palmitoylation. These studies further demonstrate that such cancers can likely be effectively treated with combination therapy involving a FASN inhibitor in combination with at least one RAS palmitoylation inhibitor.

REFERENCES

1. Vander Heiden M G, Cantley L C, Thompson C B. Understanding the Warburg effect: the metabolic requirements of cell proliferation. *Science*. May 22, 2009; 324(5930): 1029-1033.
2. Chirala S S, Wakil S J. Structure and function of animal fatty acid synthase. *Lipids*. November 2004; 39(11):1045-1053.
3. Kuhajda F P, Jenner K, Wood F D, et al. Fatty acid synthesis: a potential selective target for antineoplastic therapy. *Proc Natl Acad Sci USA*. Jul. 5, 1994; 91(14):6379-6383.
4. Chirala S S, Chang H, Matzuk M, et al. Fatty acid synthesis is essential in embryonic development: fatty acid synthase null mutants and most of the heterozygotes die in utero. *Proc Natl Acad Sci USA*. May 27, 2003; 100(11):6358-6363.
5. Weiss L, Hoffmann G E, Schreiber R, et al. Fatty-acid biosynthesis in man, a pathway of minor importance. Purification, optimal assay conditions, and organ distribution of fatty-acid synthase. *Biol Chem Hoppe Seyler*. September 1986; 367(9):905-912.
6. Medes G, Thomas A, Weinhouse S. Metabolism of neoplastic tissue. IV. A study of lipid synthesis in neoplastic tissue slices in vitro. *Cancer Res*. January 1953; 13(1):27-29.
7. Menendez J A. Fine-tuning the lipogenic/lipolytic balance to optimize the metabolic requirements of cancer cell growth: molecular mechanisms and therapeutic perspectives. *Biochim Biophys Acta*. March 2010; 1801(3):381-391.
8. Menendez J A, Lupu R. Fatty acid synthase and the lipogenic phenotype in cancer pathogenesis. *Nat Rev Cancer*. October 2007; 7(10):763-777.
9. Milgraum L Z, Witters L A, Pasternack G R, Kuhajda F P. Enzymes of the fatty acid synthesis pathway are highly expressed in in situ breast carcinoma. *Clin Cancer Res*. November 1997; 3(11):2115-2120.
10. Pizer E S, Kurman R J, Pasternack G R, Kuhajda F P. Expression of fatty acid synthase is closely linked to proliferation and stromal decidualization in cycling endometrium. *Int J Gynecol Pathol*. January 1997; 16(1): 45-51.
11. Rashid A, Pizer E S, Moga M, et al. Elevated expression of fatty acid synthase and fatty acid synthetic activity in colorectal neoplasia. *Am J. Pathol*. January 1997; 150(1): 201-208.
12. Samudio I, Harmancey R, Fiegl M, et al. Pharmacologic inhibition of fatty acid oxidation sensitizes human leukemia cells to apoptosis induction. *J Clin Invest*. Jan. 4, 2010; 120(1):142-156.
13. Alli P M, Pinn M L, Jaffee E M, McFadden J M, Kuhajda F P. Fatty acid synthase inhibitors are chemopreventive for mammary cancer in neu-N transgenic mice. *Oncogene*. Jan. 6, 2005; 24(1):39-46.
14. Brusselmans K, De Schrijver E, Heyns W, Verhoeven G, Swinnen J V. Epigallocatechin-3-gallate is a potent natural inhibitor of fatty acid synthase in intact cells and selectively induces apoptosis in prostate cancer cells. *Int J. Cancer*. Oct. 10, 2003; 106(6):856-862.
15. De Schrijver E, Brusselmans K, Heyns W, Verhoeven G, Swinnen J V. RNA interference-mediated silencing of the fatty acid synthase gene attenuates growth and induces morphological changes and apoptosis of LNCaP prostate cancer cells. *Cancer Res*. Jul. 1, 2003; 63(13):3799-3804.
16. Kridel S J, Lowther W T, Pemble C Wt. Fatty acid synthase inhibitors: new directions for oncology. *Expert Opin Investig Drugs*. November 2007; 16(11):1817-1829.
17. Kuhajda F P. Fatty acid synthase and cancer: new application of an old pathway. *Cancer Res*. Jun. 15, 2006; 66(12):5977-5980.
18. Menendez J A, Mehmi I, Verma V A, Teng P K, Lupu R. Pharmacological inhibition of fatty acid synthase (FAS): a novel therapeutic approach for breast cancer chemoprevention through its ability to suppress Her-2/neu (erbB-2) oncogene-induced malignant transformation. *Mol. Carcinog*. November 2004; 41(3):164-178.
19. Menendez J A, Vellon L, Mehmi I, et al. Inhibition of fatty acid synthase (FAS) suppresses HER2/neu (erbB-2) oncogene overexpression in cancer cells. *Proc Natl Acad Sci USA*. Jul. 20, 2004; 101(29):10715-10720.
20. Orita H, Coulter J, Lemmon C, et al. Selective inhibition of fatty acid synthase for lung cancer treatment. *Clin Cancer Res*. Dec. 1, 2007; 13(23):7139-7145.
21. Orita H, Coulter J, Tully E, Kuhajda F P, Gabrielson E. Inhibiting fatty acid synthase for chemoprevention of chemically induced lung tumors. *Clin Cancer Res*. Apr. 15, 2008; 14(8):2458-2464.
22. Pizer E S, Jackisch C, Wood F D, Pasternack G R, Davidson N E, Kuhajda F P. Inhibition of fatty acid synthesis induces programmed cell death in human breast cancer cells. *Cancer Res*. Jun. 15, 1996; 56(12):2745-2747.
23. Pizer E S, Wood F D, Heine H S, Romantsev F E, Pasternack G R, Kuhajda F P. Inhibition of fatty acid synthesis delays disease progression in a xenograft model of ovarian cancer. *Cancer Res*. Mar. 15, 1996; 56(6):1189-1193.
24. Ulku A S, Der C J. RAS signaling, deregulation of gene expression and oncogenesis. *Cancer Treat Res*. 2003; 115: 189-208.
25. Barbacid M. RAS genes. *Annu Rev Biochem*. 1987; 56:779-827.
26. Bos J L. RAS oncogenes in human cancer: a review. *Cancer Res*. Sep. 1, 1989; 49(17):4682-4689.
27. Parikh C, Subrahmanyam R, Ren R. Oncogenic NRAS rapidly and efficiently induces CMML- and AML-like diseases in mice. *Blood*. Oct. 1, 2006; 108(7):2349-2357.
28. Cuiffo B, Ren R. Palmitoylation of oncogenic NRAS is essential for leukemogenesis. *Blood*. Apr. 29, 2010; 115 (17):3598-3605.
29. Yang Y A, Han W F, Morin P J, Chrest F J, Pizer E S. Activation of fatty acid synthesis during neoplastic transformation: role of mitogen-activated protein kinase and phosphatidylinositol 3-kinase. *Exp Cell Res*. Sep. 10, 2002; 279(1):80-90.
30. Bartel D P. MicroRNAs: genomics, biogenesis, mechanism, and function. *Cell*. Jan. 23, 2004; 116(2):281-297.
31. Paddison P J, Hannon G J. RNA interference: the new somatic cell genetics? *Cancer Cell*. July 2002; 2(1):17-23.
32. Lupu R, Menendez J A. Pharmacological inhibitors of Fatty Acid Synthase (FASN)—catalyzed endogenous fatty acid biogenesis: a new family of anti-cancer agents? *Curr Pharm Biotechnol*. December 2006; 7(6):483-493.
33. Loftus T M, Jaworsky D E, Frehywot G L, et al. Reduced food intake and body weight in mice treated with fatty acid synthase inhibitors. *Science*. Jun. 30, 2000; 288(5475): 2379-2381.
34. Wortman M D, Clegg D J, D'Alessio D, Woods S C, Seeley R J. C75 inhibits food intake by increasing CNS glucose metabolism. *Nat. Med*. May 2003; 9(5):483-485.
35. McFadden J M, Medghalchi S M, Thupari J N, et al. Application of a flexible synthesis of (5R)-thiolactomycin to develop new inhibitors of type I fatty acid synthase. *J Med. Chem*. Feb. 24, 2005; 48(4):946-961.
36. De Vos M L, Lawrence D S, Smith C D. Cellular pharmacology of cerulenin analogs that inhibit protein palmitoylation. *Biochem Pharmacol*. Oct. 15, 2001; 62(8):985-995.
37. Lawrence D S, Zilfou J T, Smith C D. Structure-activity studies of cerulenin analogues as protein palmitoylation inhibitors. *J Med. Chem*. Dec. 2, 1999; 42(24):4932-4941.
38. Webb Y, Hermida-Matsumoto L, Resh M D Inhibition of protein palmitoylation, raft localization, and T cell signaling by 2-bromopalmitate and polyunsaturated fatty acids. *J Biol. Chem*. Jan. 7, 2000; 275(1):261-270.

Example 4

Silencing Expression of Palmitoyl-Acyl Tranferase DHHC9 (SEQ ID NO: 10) Results in Mislocalization of Oncogenic NRAS to Endomembranes The present Example demonstrates, among other things, that inhibition of a palmitoyl-acyl transferase results in mislocalization of palmitoylation-dependent activated RAS.

The Erf2/Erf4 complex is one of the two palmitoyl-acyl transferases (PATs) first identified and is required for RAS palmitoylation in yeast [1]. Erf2 contains an Asp-His-His-Cys (DHHC) motif (SEQ ID NO: 1) embedded in a cysteine-rich domain (CRD). This domain is believed to be important for PAT activity for RAS in vitro and for RAS function in yeast [2]. To date 23 human DHHC-CRD family ('DHHC' disclosed as SEQ ID NO: 1) of PATs have been found. The zinc finger, DHHC-containing 9 (SEQ ID NO: 10) (ZDHHC9 (SEQ ID NO: 10) or simply DHHC9 (SEQ ID NO: 10)) and GCP16 are functional orthologs of Erf2 and Erf4 and constitute a human PAT with specificity for H and NRAS [3].

Figure 18A:
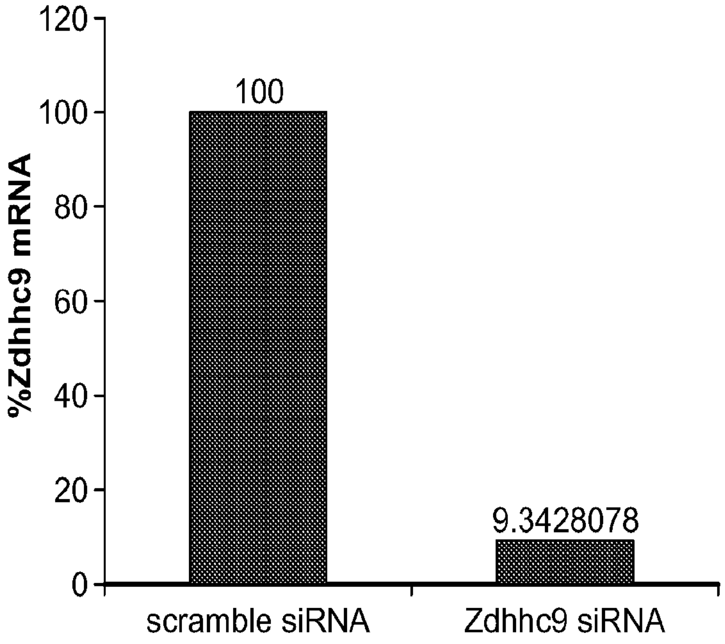
FIG. 18 shows that downregulation of DHHC9 (SEQ ID NO: 10) transcripts by a DHHC9 (SEQ ID NO: 10) siRNA and its effect on the cellular localization of the GFP-NRASD12 fusion protein. (A) Relative DHHC9 (SEQ ID NO: 10) mRNA levels in NIH3T3 cells transfected by either DHHC9 (SEQ ID NO: 10) siRNA or control siRNA were determined by real-time RT-PCR. (B) GFP-NRASD12 expressing NIH3T3 cells transfected by either DHHC9 (SEQ ID NO: 10) siRNA or control siRNA were visualized by confocal microscope. Original magnification was 630×.
Figure 18B:
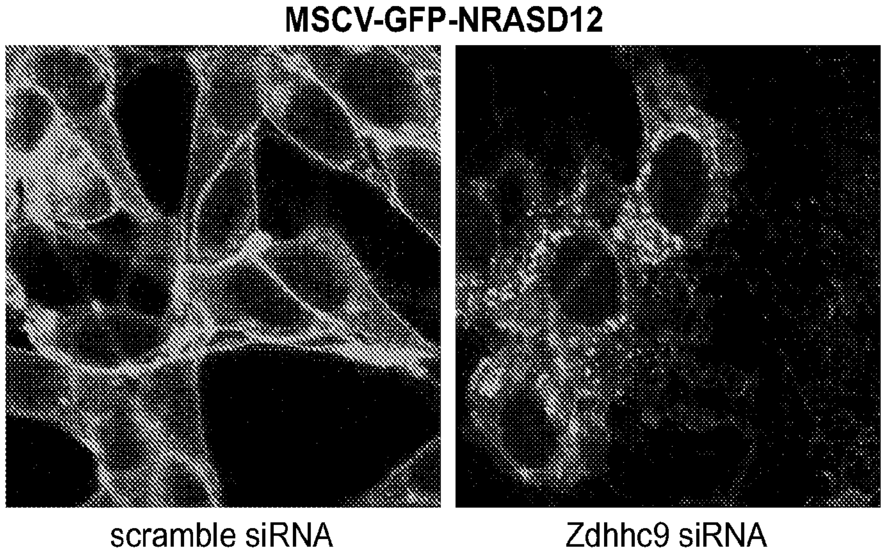

To determine the role of DHHC9 (SEQ ID NO: 10) in NRAS biology, we first examined the effect of DHHC9 (SEQ ID NO: 10) downregulation on cellular localization of oncogenic NRAS (NRASD12). RNA interference (RNAi) is a powerful tool for gene function studies and holds promise for the development of new molecular medicines. RNAi usually downregulate but often not abolish the target mRNAs, which mimic therapies more than gene-knockout. In addition, since DHHC9 (SEQ ID NO: 10) may have substrates other than RAS, knocking out the DHHC9 (SEQ ID NO: 10) gene might be toxic to cells. For these reasons we tested several small interference RNA (siRNA) specific to murine DHHC9 (SEQ ID NO: 10) for their ability to downregulate the DHHC9 (SEQ ID NO: 10) mRNA. As shown in FIG. 18, one DHHC9 (SEQ ID NO: 10) siRNA (sense: 5' GGA AGA AGA ACU AUG UAU UAU AUG T 3' (SEQ ID NO: 37); antisense: 5' A CAU AUA AUA CAU AGU UCU UCU UCC CU 3' (SEQ ID NO: 38)) dramatically reduced the levels of DHHC9 (SEQ ID NO: 10) mRNA, comparing to scrambled siRNA (sense: 5' CUU CCU CUC UUU CUC UCC CUU GUG A 3' (SEQ ID NO: 39); antisense: 5' U CAC AAG GGA GAG AAA GAG AGG AAG GA 3' (SEQ ID NO: 40)). Introducing the DHHC9 (SEQ ID NO: 10) siRNA into NIH3T3 cells expressing the GFP-NRASD12 fusion protein causes mislocalization of GFP-NRASD12 to internal membranes (Figure XX7B). Similar result was obtained for another DHHC9 (SEQ ID NO: 10) siRNA (sense: 5' ACU AAU CAG UAC UUC CAU UAA GCC T 3' (SEQ ID NO: 41); antisense: 5' A GGC UUA AUG GAA GUA CUG AUU AGU CU 3' (SEQ ID NO: 42)). The results suggest, among other things, that targeting DHHC9 (SEQ ID NO: 10), such as by RNAi, is an effective therapy for cancers involving activated RAS that needs palmitoylation. Furthermore, the results suggest that identification of tumors associated with palmitoylation-dependent activated RAS are likely to be responsive to therapy with a palmitoyl-acyl transferase inhibitor. Still further, the present invention provides systems for identifying cancer patients likely to respond to therapy that includes administration of one or more palmitoyl-acyl transferase inhibitors. Specifically, the present invention demonstrates that patients suffering from a cancer that relies upon an activated, palmitoylated RAS that requires palmitoylation, and determining, based on the identification, that the patient is a positive candidate for therapy.

REFERENCES

1. Bartels D J, Mitchell D A, Dong X, Deschenes R J. Erf2, a novel gene product that affects the localization and palmitoylation of RAS2 in *Saccharomyces cerevisiae. Mol Cell Biol.* October 1999; 19(10):6775-6787.

2. Nadolski M J, Linder M E. Protein lipidation. *Febs J.* October 2007; 274(20):5202-5210.

3. Swarthout J T, Lobo S, Farh L, et al. DHHC9 (SEQ ID NO: 10) and GCP16 constitute a human protein fatty acyltransferase with specificity for H- and N-RAS. *J Biol. Chem.* Sep. 2, 2005; 280(35):31141-31148.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating cancer by administering to a patient in need thereof an agent that directly inhibits activity of a RAS palmitoyl-acyl transferase and reduces palmitoylation of NRAS, wherein the agent blocks a RAS palmitoylation site.

2. The method of claim 1, wherein the cancer is associated with an oncogene that acts upstream of RAS.

3. The method of claim 1 or claim 2, wherein the cancer is not associated with a mutation of NRAS.

4. A method of treating cancer by administering to a patient in need thereof an agent that directly inhibits activity of a RAS palmitoyl-acyl transferase and reduces palmitoylation of NRAS, wherein the agent comprises a RAS polypeptide variant that dominantly suppresses palmitoylation of an oncogenic RAS.

5. The method of claim 1, wherein the RAS palmitoyl-acyl transferase is selected from the group consisting of SEQ ID NO: 2-25 and combinations thereof.

6. The method of claim 4, wherein the RAS polypeptide variant comprises at least one non-natural amino acid.

7. The method of claim 4, wherein the cancer is associated with an oncogene that acts upstream of RAS.

8. The method of claim 4 or 7, wherein the cancer is not associated with a mutation of NRAS.

9. The method of claim 4, wherein the RAS palmitoyl-acyl transferase is selected from the group consisting of SEQ ID NO: 2-25 and combinations thereof.

* * * * *

SEQUENCE LISTING

```
<160> NUMBER OF SEQ ID NOS: 70

<210> SEQ ID NO 1
<211> LENGTH: 4
<212> TYPE: PRT
<213> ORGANISM: Homo sapiens

<400> SEQUENCE: 1

Asp His His Cys
1


<210> SEQ ID NO 2
<211> LENGTH: 485
<212> TYPE: PRT
<213> ORGANISM: Homo sapiens

<400> SEQUENCE: 2

Met Tyr Lys Met Asn Ile Cys Asn Lys Pro Ser Asn Lys Thr Ala Pro
1               5                   10                  15

Glu Lys Ser Val Trp Thr Ala Pro Ala Gln Pro Ser Gly Pro Ser Pro
            20                  25                  30

Glu Leu Gln Gly Gln Arg Ser Arg Arg Asn Gly Trp Ser Trp Pro Pro
        35                  40                  45

His Pro Leu Gln Ile Val Ala Trp Leu Leu Tyr Leu Phe Phe Ala Val
    50                  55                  60

Ile Gly Phe Gly Ile Leu Val Pro Leu Leu Pro His His Trp Val Pro
65                  70                  75                  80

Ala Gly Tyr Ala Cys Met Gly Ala Ile Phe Ala Gly His Leu Val Val
                85                  90                  95

His Leu Thr Ala Val Ser Ile Asp Pro Ala Asp Ala Asn Val Arg Asp
            100                 105                 110

Lys Ser Tyr Ala Gly Pro Leu Pro Ile Phe Asn Arg Ser Gln His Ala
        115                 120                 125

His Val Ile Glu Asp Leu His Cys Asn Leu Cys Asn Val Asp Val Ser
    130                 135                 140

Ala Arg Ser Lys His Cys Ser Ala Cys Asn Lys Cys Val Cys Gly Phe
145                 150                 155                 160

Asp His His Cys Lys Trp Leu Asn Asn Cys Val Gly Glu Arg Asn Tyr
                165                 170                 175

Arg Leu Phe Leu His Ser Val Ala Ser Ala Leu Leu Gly Val Leu Leu
```

-continued

```
            180                 185                 190

Leu Val Leu Val Ala Thr Tyr Val Phe Val Glu Phe Phe Val Asn Pro
        195                 200                 205

Met Arg Leu Arg Thr Asn Arg His Phe Glu Val Leu Lys Asn His Thr
    210                 215                 220

Asp Val Trp Phe Val Phe Leu Pro Ala Ala Pro Val Glu Thr Gln Ala
225                 230                 235                 240

Pro Ala Ile Leu Ala Leu Ala Ala Leu Leu Ile Leu Leu Gly Leu Leu
                245                 250                 255

Ser Thr Ala Leu Leu Gly His Leu Leu Cys Phe His Ile Tyr Leu Met
            260                 265                 270

Trp His Lys Leu Thr Thr Tyr Glu Tyr Ile Val Gln His Arg Pro Pro
        275                 280                 285

Gln Glu Ala Lys Gly Val His Arg Glu Leu Glu Ser Cys Pro Pro Lys
    290                 295                 300

Met Arg Pro Ile Gln Glu Met Glu Phe Tyr Met Arg Thr Phe Arg His
305                 310                 315                 320

Met Arg Pro Glu Pro Pro Gly Gln Ala Gly Pro Ala Ala Val Asn Ala
                325                 330                 335

Lys His Ser Arg Pro Ala Ser Pro Asp Pro Thr Pro Gly Arg Arg Asp
            340                 345                 350

Cys Ala Gly Pro Pro Val Gln Val Glu Trp Asp Arg Lys Lys Pro Leu
        355                 360                 365

Pro Trp Arg Ser Pro Leu Leu Leu Leu Ala Met Trp Gly Pro Gln Ala
    370                 375                 380

Pro Pro Cys Leu Cys Arg Lys Arg Gly Arg Gly Ala Cys Ile Lys Cys
385                 390                 395                 400

Glu Arg Leu Arg Pro Arg Ile Arg Arg Arg Gly Leu Gly Pro Pro Ala
                405                 410                 415

Ala Ala Pro Ala Arg Arg Arg Ile Pro Arg Thr Pro Ala Leu Cys Thr
            420                 425                 430

Pro Leu Ala Leu Pro Ala Pro Thr Thr Arg Arg Arg Gln Ser Pro Trp
        435                 440                 445

Thr Arg Phe Gln Trp Arg Arg Arg Ala Trp Ala Ala Pro Leu Trp Pro
    450                 455                 460

Pro Arg Gly Ala Gly Ala Asp Ser Pro Arg Trp Arg Gly Arg Arg Val
465                 470                 475                 480

Arg Pro Pro Phe Ser
                485
```

<210> SEQ ID NO 3
<211> LENGTH: 367
<212> TYPE: PRT
<213> ORGANISM: Homo sapiens

<400> SEQUENCE: 3

```
Met Ala Pro Ser Gly Pro Gly Ser Ser Ala Arg Arg Arg Cys Arg Arg
1               5                   10                  15

Val Leu Tyr Trp Ile Pro Val Val Phe Ile Thr Leu Leu Leu Gly Trp
            20                  25                  30

Ser Tyr Tyr Ala Tyr Ala Ile Gln Leu Cys Ile Val Ser Met Glu Asn
        35                  40                  45

Thr Gly Glu Gln Val Val Cys Leu Met Ala Tyr His Leu Leu Phe Ala
    50                  55                  60
```

-continued

```
Met Phe Val Trp Ser Tyr Trp Lys Thr Ile Phe Thr Leu Pro Met Asn
65                  70                  75                  80

Pro Ser Lys Glu Phe His Leu Ser Tyr Ala Glu Lys Asp Leu Leu Glu
                85                  90                  95

Arg Glu Pro Arg Gly Glu Ala His Gln Glu Val Leu Arg Arg Ala Ala
            100                 105                 110

Lys Asp Leu Pro Ile Tyr Thr Arg Thr Met Ser Gly Ala Ile Arg Tyr
        115                 120                 125

Cys Asp Arg Cys Gln Leu Ile Lys Pro Asp Arg Cys His His Cys Ser
    130                 135                 140

Val Cys Asp Lys Cys Ile Leu Lys Met Asp His His Cys Pro Trp Val
145                 150                 155                 160

Asn Asn Cys Val Gly Phe Ser Asn Tyr Lys Phe Phe Leu Leu Phe Leu
                165                 170                 175

Ala Tyr Ser Leu Leu Tyr Cys Leu Phe Ile Ala Ala Thr Asp Leu Gln
            180                 185                 190

Tyr Phe Ile Lys Phe Trp Thr Asn Gly Leu Pro Asp Thr Gln Ala Lys
        195                 200                 205

Phe His Ile Met Phe Leu Phe Phe Ala Ala Ala Met Phe Ser Val Ser
    210                 215                 220

Leu Ser Ser Leu Phe Gly Tyr His Cys Trp Leu Val Ser Lys Asn Lys
225                 230                 235                 240

Ser Thr Leu Glu Ala Phe Arg Ser Pro Val Phe Arg His Gly Thr Asp
                245                 250                 255

Lys Asn Gly Phe Ser Leu Gly Phe Ser Lys Asn Met Arg Gln Val Phe
            260                 265                 270

Gly Asp Glu Lys Lys Tyr Trp Leu Leu Pro Ile Phe Ser Ser Leu Gly
        275                 280                 285

Asp Gly Cys Ser Phe Pro Thr Cys Leu Val Asn Gln Asp Pro Glu Gln
    290                 295                 300

Ala Ser Thr Pro Ala Gly Leu Asn Ser Thr Ala Lys Asn Leu Glu Asn
305                 310                 315                 320

His Gln Phe Pro Ala Lys Pro Leu Arg Glu Ser Gln Ser His Leu Leu
                325                 330                 335

Thr Asp Ser Gln Ser Trp Thr Glu Ser Ser Ile Asn Pro Gly Lys Cys
            340                 345                 350

Lys Ala Gly Met Ser Asn Pro Ala Leu Thr Met Glu Asn Glu Thr
        355                 360                 365


<210> SEQ ID NO 4
<211> LENGTH: 299
<212> TYPE: PRT
<213> ORGANISM: Homo sapiens

<400> SEQUENCE: 4

Met Met Leu Ile Pro Thr His His Phe Arg Asn Ile Glu Arg Lys Pro
1               5                   10                  15

Glu Tyr Leu Gln Pro Glu Lys Cys Val Pro Pro Pro Tyr Pro Gly Pro
            20                  25                  30

Val Gly Thr Met Trp Phe Ile Arg Asp Gly Cys Gly Ile Ala Cys Ala
        35                  40                  45

Ile Val Thr Trp Phe Leu Val Leu Tyr Ala Glu Phe Val Val Leu Phe
    50                  55                  60

Val Met Leu Ile Pro Ser Arg Asp Tyr Val Tyr Ser Ile Ile Asn Gly
65                  70                  75                  80
```

```
Ile Val Phe Asn Leu Leu Ala Phe Leu Ala Leu Ala Ser His Cys Arg
                85                  90                  95

Ala Met Leu Thr Asp Pro Gly Ala Val Pro Lys Gly Asn Ala Thr Lys
            100                 105                 110

Glu Phe Ile Glu Ser Leu Gln Leu Lys Pro Gly Gln Val Val Tyr Lys
        115                 120                 125

Cys Pro Lys Cys Cys Ser Ile Lys Pro Asp Arg Ala His His Cys Ser
    130                 135                 140

Val Cys Lys Arg Cys Ile Arg Lys Met Asp His His Cys Pro Trp Val
145                 150                 155                 160

Asn Asn Cys Val Gly Glu Asn Asn Gln Lys Tyr Phe Val Leu Phe Thr
                165                 170                 175

Met Tyr Ile Ala Leu Ile Ser Leu His Ala Leu Ile Met Val Gly Phe
            180                 185                 190

His Phe Leu His Cys Phe Glu Glu Asp Trp Thr Lys Cys Ser Ser Phe
        195                 200                 205

Ser Pro Pro Thr Thr Val Ile Leu Leu Ile Leu Leu Cys Phe Glu Gly
    210                 215                 220

Leu Leu Phe Leu Ile Phe Thr Ser Val Met Phe Gly Thr Gln Val His
225                 230                 235                 240

Ser Ile Cys Thr Asp Glu Thr Gly Ile Glu Gln Leu Lys Lys Glu Glu
                245                 250                 255

Arg Arg Trp Ala Lys Lys Thr Lys Trp Met Asn Met Lys Ala Val Phe
            260                 265                 270

Gly His Pro Phe Ser Leu Gly Trp Ala Ser Pro Phe Ala Thr Pro Asp
        275                 280                 285

Gln Gly Lys Ala Asp Pro Tyr Gln Tyr Val Val
    290                 295


<210> SEQ ID NO 5
<211> LENGTH: 344
<212> TYPE: PRT
<213> ORGANISM: Homo sapiens

<400> SEQUENCE: 5

Met Asp Phe Leu Val Leu Phe Leu Phe Tyr Leu Ala Ser Val Leu Met
1               5                   10                  15

Gly Leu Val Leu Ile Cys Val Cys Ser Lys Thr His Ser Leu Lys Gly
            20                  25                  30

Leu Ala Arg Gly Gly Ala Gln Ile Phe Ser Cys Ile Ile Pro Glu Cys
        35                  40                  45

Leu Gln Arg Ala Val His Gly Leu Leu His Tyr Leu Phe His Thr Arg
    50                  55                  60

Asn His Thr Phe Ile Val Leu His Leu Val Leu Gln Gly Met Val Tyr
65                  70                  75                  80

Thr Glu Tyr Thr Trp Glu Val Phe Gly Tyr Cys Gln Glu Leu Glu Leu
                85                  90                  95

Ser Leu His Tyr Leu Leu Leu Pro Tyr Leu Leu Leu Gly Val Asn Leu
            100                 105                 110

Phe Phe Phe Thr Leu Thr Cys Gly Thr Asn Pro Gly Ile Ile Thr Lys
        115                 120                 125

Ala Asn Glu Leu Leu Phe Leu His Val Tyr Glu Phe Asp Glu Val Met
    130                 135                 140

Phe Pro Lys Asn Val Arg Cys Ser Thr Cys Asp Leu Arg Lys Pro Ala
```

145 150 155 160

Arg Ser Lys His Cys Ser Val Cys Asn Trp Cys Val His Arg Phe Asp
165 170 175

His His Cys Val Trp Val Asn Asn Cys Ile Gly Ala Trp Asn Ile Arg
180 185 190

Tyr Phe Leu Ile Tyr Val Leu Thr Leu Thr Ala Ser Ala Ala Thr Val
195 200 205

Ala Ile Val Ser Thr Thr Phe Leu Val His Leu Val Val Met Ser Asp
210 215 220

Leu Tyr Gln Glu Thr Tyr Ile Asp Asp Leu Gly His Leu His Val Met
225 230 235 240

Asp Thr Val Phe Leu Ile Gln Tyr Leu Phe Leu Thr Phe Pro Arg Ile
245 250 255

Val Phe Met Leu Gly Phe Val Val Val Leu Ser Phe Leu Leu Gly Gly
260 265 270

Tyr Leu Leu Phe Val Leu Tyr Leu Ala Ala Thr Asn Gln Thr Thr Asn
275 280 285

Glu Trp Tyr Arg Gly Asp Trp Ala Trp Cys Gln Arg Cys Pro Leu Val
290 295 300

Ala Trp Pro Pro Ser Ala Glu Pro Gln Val His Arg Asn Ile His Ser
305 310 315 320

His Gly Leu Arg Ser Asn Leu Gln Glu Ile Phe Leu Pro Ala Phe Pro
325 330 335

Cys His Glu Arg Lys Lys Gln Glu
340

<210> SEQ ID NO 6
<211> LENGTH: 715
<212> TYPE: PRT
<213> ORGANISM: Homo sapiens

<400> SEQUENCE: 6

Met Pro Ala Glu Ser Gly Lys Arg Phe Lys Pro Ser Lys Tyr Val Pro
1 5 10 15

Val Ser Ala Ala Ala Ile Phe Leu Val Gly Ala Thr Thr Leu Phe Phe
20 25 30

Ala Phe Thr Cys Pro Gly Leu Ser Leu Tyr Val Ser Pro Ala Val Pro
35 40 45

Ile Tyr Asn Ala Ile Met Phe Leu Phe Val Leu Ala Asn Phe Ser Met
50 55 60

Ala Thr Phe Met Asp Pro Gly Ile Phe Pro Arg Ala Glu Glu Asp Glu
65 70 75 80

Asp Lys Glu Asp Asp Phe Arg Ala Pro Leu Tyr Lys Thr Val Glu Ile
85 90 95

Lys Gly Ile Gln Val Arg Met Lys Trp Cys Ala Thr Cys Arg Phe Tyr
100 105 110

Arg Pro Pro Arg Cys Ser His Cys Ser Val Cys Asp Asn Cys Val Glu
115 120 125

Glu Phe Asp His His Cys Pro Trp Val Asn Asn Cys Ile Gly Arg Arg
130 135 140

Asn Tyr Arg Tyr Phe Phe Leu Phe Leu Leu Ser Leu Thr Ala His Ile
145 150 155 160

Met Gly Val Phe Gly Phe Gly Leu Leu Tyr Val Leu Tyr His Ile Glu
165 170 175

-continued

```
Glu Leu Ser Gly Val Arg Thr Ala Val Thr Met Ala Val Met Cys Val
            180                 185                 190

Ala Gly Leu Phe Phe Ile Pro Val Ala Gly Leu Thr Gly Phe His Val
        195                 200                 205

Val Leu Val Ala Arg Gly Arg Thr Thr Asn Glu Gln Val Thr Gly Lys
    210                 215                 220

Phe Arg Gly Gly Val Asn Pro Phe Thr Asn Gly Cys Cys Asn Asn Val
225                 230                 235                 240

Ser Arg Val Leu Cys Ser Ser Pro Ala Pro Arg Tyr Leu Gly Arg Pro
                245                 250                 255

Lys Lys Glu Lys Thr Ile Val Ile Arg Pro Pro Phe Leu Arg Pro Glu
            260                 265                 270

Val Ser Asp Gly Gln Ile Thr Val Lys Ile Met Asp Asn Gly Ile Gln
        275                 280                 285

Gly Glu Leu Arg Arg Thr Lys Ser Lys Gly Ser Leu Glu Ile Thr Glu
    290                 295                 300

Ser Gln Ser Ala Asp Ala Glu Pro Pro Pro Pro Pro Lys Pro Asp Leu
305                 310                 315                 320

Ser Arg Tyr Thr Gly Leu Arg Thr His Leu Gly Leu Ala Thr Asn Glu
                325                 330                 335

Asp Ser Ser Leu Leu Ala Lys Asp Ser Pro Pro Thr Pro Thr Met Tyr
            340                 345                 350

Lys Tyr Arg Pro Gly Tyr Ser Ser Ser Ser Thr Ser Ala Ala Met Pro
        355                 360                 365

His Ser Ser Ser Ala Lys Leu Ser Arg Gly Asp Ser Leu Lys Glu Pro
    370                 375                 380

Thr Ser Ile Ala Glu Ser Ser Arg His Pro Ser Tyr Arg Ser Glu Pro
385                 390                 395                 400

Ser Leu Glu Pro Glu Ser Phe Arg Ser Pro Thr Phe Gly Lys Ser Phe
                405                 410                 415

His Phe Asp Pro Leu Ser Ser Gly Ser Arg Ser Ser Ser Leu Lys Ser
            420                 425                 430

Ala Gln Gly Thr Gly Phe Glu Leu Gly Gln Leu Gln Ser Ile Arg Ser
        435                 440                 445

Glu Gly Thr Thr Ser Thr Ser Tyr Lys Ser Leu Ala Asn Gln Thr Arg
    450                 455                 460

Asn Gly Ser Leu Ser Tyr Asp Ser Leu Leu Thr Pro Ser Asp Ser Pro
465                 470                 475                 480

Asp Phe Glu Ser Val Gln Ala Gly Pro Glu Pro Asp Pro Pro Leu Gly
                485                 490                 495

Tyr Thr Ser Pro Phe Leu Ser Ala Arg Leu Ala Gln Gln Arg Glu Ala
            500                 505                 510

Glu Arg His Pro Arg Leu Val Pro Thr Gly Pro Thr His Arg Glu Pro
        515                 520                 525

Ser Pro Val Arg Tyr Asp Asn Leu Ser Arg His Ile Val Ala Ser Leu
    530                 535                 540

Gln Glu Arg Glu Lys Leu Leu Arg Gln Ser Pro Pro Leu Pro Gly Arg
545                 550                 555                 560

Glu Glu Glu Pro Gly Leu Gly Asp Ser Gly Ile Gln Ser Thr Pro Gly
                565                 570                 575

Ser Gly His Ala Pro Arg Thr Ser Ser Ser Ser Asp Asp Ser Lys Arg
            580                 585                 590

Ser Pro Leu Gly Lys Thr Pro Leu Gly Arg Pro Ala Val Pro Arg Phe
```

```
        595                 600                 605

Gly Lys Pro Asp Gly Leu Arg Gly Arg Gly Val Gly Ser Pro Glu Pro
    610                 615                 620

Gly Pro Thr Ala Pro Tyr Leu Gly Arg Ser Met Ser Tyr Ser Ser Gln
625                 630                 635                 640

Lys Ala Gln Pro Gly Val Ser Glu Thr Glu Glu Val Ala Leu Gln Pro
                645                 650                 655

Leu Leu Thr Pro Lys Asp Glu Val Gln Leu Lys Thr Thr Tyr Ser Lys
            660                 665                 670

Ser Asn Gly Gln Pro Lys Ser Leu Gly Ser Ala Ser Pro Gly Pro Gly
        675                 680                 685

Gln Pro Pro Leu Ser Ser Pro Thr Arg Gly Gly Val Lys Lys Val Ser
    690                 695                 700

Gly Val Gly Gly Thr Thr Tyr Glu Ile Ser Val
705                 710                 715


<210> SEQ ID NO 7
<211> LENGTH: 413
<212> TYPE: PRT
<213> ORGANISM: Homo sapiens

<400> SEQUENCE: 7

Met Gly Thr Phe Cys Ser Val Ile Lys Phe Glu Asn Leu Gln Glu Leu
1               5                   10                  15

Lys Arg Leu Cys His Trp Gly Pro Ile Ile Ala Leu Gly Val Ile Ala
            20                  25                  30

Ile Cys Ser Thr Met Ala Met Ile Asp Ser Val Leu Trp Tyr Trp Pro
        35                  40                  45

Leu His Thr Thr Gly Gly Ser Val Asn Phe Ile Met Leu Ile Asn Trp
    50                  55                  60

Thr Val Met Ile Leu Tyr Asn Tyr Phe Asn Ala Met Phe Val Gly Pro
65                  70                  75                  80

Gly Phe Val Pro Leu Gly Trp Lys Pro Glu Ile Ser Gln Asp Thr Met
                85                  90                  95

Tyr Leu Gln Tyr Cys Lys Val Cys Gln Ala Tyr Lys Ala Pro Arg Ser
            100                 105                 110

His His Cys Arg Lys Cys Asn Arg Cys Val Met Lys Met Asp His His
        115                 120                 125

Cys Pro Trp Ile Asn Asn Cys Cys Gly Tyr Gln Asn His Ala Ser Phe
    130                 135                 140

Thr Leu Phe Leu Leu Leu Ala Pro Leu Gly Cys Ile His Ala Ala Phe
145                 150                 155                 160

Ile Phe Val Met Thr Met Tyr Thr Gln Leu Tyr His Arg Leu Ser Phe
                165                 170                 175

Gly Trp Asn Thr Val Lys Ile Asp Met Ser Ala Ala Arg Arg Asp Pro
            180                 185                 190

Leu Pro Ile Val Pro Phe Gly Leu Ala Ala Phe Ala Thr Thr Leu Phe
        195                 200                 205

Ala Leu Gly Leu Ala Leu Gly Thr Thr Ile Ala Val Gly Met Leu Phe
    210                 215                 220

Phe Ile Gln Met Lys Ile Ile Leu Arg Asn Lys Thr Ser Ile Glu Ser
225                 230                 235                 240

Trp Ile Glu Glu Lys Ala Lys Asp Arg Ile Gln Tyr Tyr Gln Leu Asp
                245                 250                 255
```

-continued

```
Glu Val Phe Val Phe Pro Tyr Asp Met Gly Ser Arg Trp Arg Asn Phe
            260                 265                 270

Lys Gln Val Phe Thr Trp Ser Gly Val Pro Glu Gly Asp Gly Leu Glu
        275                 280                 285

Trp Pro Val Arg Glu Gly Cys His Gln Tyr Ser Leu Thr Ile Glu Gln
    290                 295                 300

Leu Lys Gln Lys Ala Asp Lys Arg Val Arg Ser Val Arg Tyr Lys Val
305                 310                 315                 320

Ile Glu Asp Tyr Ser Gly Ala Cys Cys Pro Leu Asn Lys Gly Ile Lys
                325                 330                 335

Thr Phe Phe Thr Ser Pro Cys Thr Glu Glu Pro Arg Ile Gln Leu Gln
            340                 345                 350

Lys Gly Glu Phe Ile Leu Ala Thr Arg Gly Leu Arg Tyr Trp Leu Tyr
        355                 360                 365

Gly Asp Lys Ile Leu Asp Asp Ser Phe Ile Glu Gly Val Ser Arg Ile
    370                 375                 380

Arg Gly Trp Phe Pro Arg Lys Cys Val Glu Lys Cys Pro Cys Asp Ala
385                 390                 395                 400

Glu Thr Asp Gln Ala Pro Glu Gly Glu Lys Lys Asn Arg
                405                 410


<210> SEQ ID NO 8
<211> LENGTH: 345
<212> TYPE: PRT
<213> ORGANISM: Homo sapiens

<400> SEQUENCE: 8

Met Gln Pro Ser Gly His Arg Leu Arg Asp Val Glu His His Pro Leu
1               5                   10                  15

Leu Ala Glu Asn Asp Asn Tyr Asp Ser Ser Ser Ser Ser Ser Ser Glu
            20                  25                  30

Ala Asp Val Ala Asp Arg Val Trp Phe Ile Arg Asp Gly Cys Gly Met
        35                  40                  45

Ile Cys Ala Val Met Thr Trp Leu Leu Val Ala Tyr Ala Asp Phe Val
    50                  55                  60

Val Thr Phe Val Met Leu Leu Pro Ser Lys Asp Phe Trp Tyr Ser Val
65                  70                  75                  80

Val Asn Gly Val Ile Phe Asn Cys Leu Ala Val Leu Ala Leu Ser Ser
                85                  90                  95

His Leu Arg Thr Met Leu Thr Asp Pro Glu Lys Ser Ser Asp Cys Arg
            100                 105                 110

Pro Ser Ala Cys Thr Val Lys Thr Gly Leu Asp Pro Thr Leu Val Gly
        115                 120                 125

Ile Cys Gly Glu Gly Thr Glu Ser Val Gln Ser Leu Leu Leu Gly Ala
    130                 135                 140

Val Pro Lys Gly Asn Ala Thr Lys Glu Tyr Met Glu Ser Leu Gln Leu
145                 150                 155                 160

Lys Pro Gly Glu Val Ile Tyr Lys Cys Pro Lys Cys Cys Cys Ile Lys
                165                 170                 175

Pro Glu Arg Ala His His Cys Ser Ile Cys Lys Arg Cys Ile Arg Lys
            180                 185                 190

Met Asp His His Cys Pro Trp Val Asn Asn Cys Val Gly Glu Lys Asn
        195                 200                 205

Gln Arg Phe Phe Val Leu Phe Thr Met Tyr Ile Ala Leu Ser Ser Val
    210                 215                 220
```

His Ala Leu Ile Leu Cys Gly Phe Gln Phe Ile Ser Cys Val Arg Gly
225 230 235 240

Gln Trp Thr Glu Cys Ser Asp Phe Ser Pro Pro Ile Thr Val Ile Leu
245 250 255

Leu Ile Phe Leu Cys Leu Glu Gly Leu Leu Phe Phe Thr Phe Thr Ala
260 265 270

Val Met Phe Gly Thr Gln Ile His Ser Ile Cys Asn Asp Glu Thr Glu
275 280 285

Ile Glu Arg Leu Lys Ser Glu Lys Pro Thr Trp Glu Arg Arg Leu Arg
290 295 300

Trp Glu Gly Met Lys Ser Val Phe Gly Gly Pro Pro Ser Leu Leu Trp
305 310 315 320

Met Asn Pro Phe Val Gly Phe Arg Phe Arg Arg Leu Pro Thr Arg Pro
325 330 335

Arg Lys Gly Gly Pro Glu Phe Ser Val
340 345

<210> SEQ ID NO 9
<211> LENGTH: 765
<212> TYPE: PRT
<213> ORGANISM: Homo sapiens

<400> SEQUENCE: 9

Met Pro Arg Ser Pro Gly Thr Arg Leu Lys Pro Ala Lys Tyr Ile Pro
1 5 10 15

Val Ala Thr Ala Ala Ala Leu Leu Val Gly Ser Ser Thr Leu Phe Phe
20 25 30

Val Phe Thr Cys Pro Trp Leu Thr Arg Ala Val Ser Pro Ala Val Pro
35 40 45

Val Tyr Asn Gly Ile Ile Phe Leu Phe Val Leu Ala Asn Phe Ser Met
50 55 60

Ala Thr Phe Met Asp Pro Gly Val Phe Pro Arg Ala Asp Glu Asp Glu
65 70 75 80

Asp Lys Glu Asp Asp Phe Arg Ala Pro Leu Tyr Lys Asn Val Asp Val
85 90 95

Arg Gly Ile Gln Val Arg Met Lys Trp Cys Ala Thr Cys His Phe Tyr
100 105 110

Arg Pro Pro Arg Cys Ser His Cys Ser Val Cys Asp Asn Cys Val Glu
115 120 125

Asp Phe Asp His His Cys Pro Trp Val Asn Asn Cys Ile Gly Arg Arg
130 135 140

Asn Tyr Arg Tyr Phe Phe Leu Phe Leu Leu Ser Leu Ser Ala His Met
145 150 155 160

Val Gly Val Val Ala Phe Gly Leu Val Tyr Val Leu Asn His Ala Glu
165 170 175

Gly Leu Gly Ala Ala His Thr Thr Ile Thr Met Ala Val Met Cys Val
180 185 190

Ala Gly Leu Phe Phe Ile Pro Val Ile Gly Leu Thr Gly Phe His Val
195 200 205

Val Leu Val Thr Arg Gly Arg Thr Thr Asn Glu Gln Val Thr Gly Lys
210 215 220

Phe Arg Gly Gly Val Asn Pro Phe Thr Arg Gly Cys Cys Gly Asn Val
225 230 235 240

Glu His Val Leu Cys Ser Pro Leu Ala Pro Arg Tyr Val Val Glu Pro

```
                245                 250                 255

Pro Arg Leu Pro Leu Ala Val Ser Leu Lys Pro Pro Phe Leu Arg Pro
            260                 265                 270

Glu Leu Leu Asp Arg Ala Ala Pro Leu Lys Val Lys Leu Ser Asp Asn
        275                 280                 285

Gly Leu Lys Ala Gly Leu Gly Arg Ser Lys Ser Lys Gly Ser Leu Asp
    290                 295                 300

Arg Leu Asp Glu Lys Pro Leu Asp Leu Gly Pro Pro Leu Pro Pro Lys
305                 310                 315                 320

Ile Glu Ala Gly Thr Phe Ser Ser Asp Leu Gln Thr Pro Arg Pro Gly
                325                 330                 335

Ser Ala Glu Ser Ala Leu Ser Val Gln Arg Thr Ser Pro Pro Thr Pro
            340                 345                 350

Ala Met Tyr Lys Phe Arg Pro Ala Phe Pro Thr Gly Pro Lys Val Pro
        355                 360                 365

Phe Cys Gly Pro Gly Glu Gln Val Pro Gly Pro Asp Ser Leu Thr Leu
    370                 375                 380

Gly Asp Asp Ser Ile Arg Ser Leu Asp Phe Val Ser Glu Pro Ser Leu
385                 390                 395                 400

Asp Leu Pro Asp Tyr Gly Pro Gly Gly Leu His Ala Ala Tyr Pro Pro
                405                 410                 415

Ser Pro Pro Leu Ser Ala Ser Asp Ala Phe Ser Gly Ala Leu Arg Ser
            420                 425                 430

Leu Ser Leu Lys Ala Ser Ser Arg Arg Gly Gly Asp His Val Ala Leu
        435                 440                 445

Gln Pro Leu Arg Ser Glu Gly Gly Pro Pro Thr Pro His Arg Ser Ile
    450                 455                 460

Phe Ala Pro His Ala Leu Pro Asn Arg Asn Gly Ser Leu Ser Tyr Asp
465                 470                 475                 480

Ser Leu Leu Asn Pro Gly Ser Pro Gly Gly His Ala Cys Pro Ala His
                485                 490                 495

Pro Ala Val Gly Val Ala Gly Tyr His Ser Pro Tyr Leu His Pro Gly
            500                 505                 510

Ala Thr Gly Asp Pro Pro Arg Pro Leu Pro Arg Ser Phe Ser Pro Val
        515                 520                 525

Leu Gly Pro Arg Pro Arg Glu Pro Ser Pro Val Arg Tyr Asp Asn Leu
    530                 535                 540

Ser Arg Thr Ile Met Ala Ser Ile Gln Glu Arg Lys Asp Arg Glu Glu
545                 550                 555                 560

Arg Glu Arg Leu Leu Arg Ser Gln Ala Asp Ser Leu Phe Gly Asp Ser
                565                 570                 575

Gly Val Tyr Asp Ala Pro Ser Ser Tyr Ser Leu Gln Gln Ala Ser Val
            580                 585                 590

Leu Ser Glu Gly Pro Arg Gly Pro Ala Leu Arg Tyr Gly Ser Arg Asp
        595                 600                 605

Asp Leu Val Ala Gly Pro Gly Phe Gly Gly Ala Arg Asn Pro Ala Leu
    610                 615                 620

Gln Thr Ser Leu Ser Ser Leu Ser Ser Ser Val Ser Arg Ala Pro Arg
625                 630                 635                 640

Thr Ser Ser Ser Ser Leu Gln Ala Asp Gln Ala Ser Ser Asn Ala Pro
                645                 650                 655

Gly Pro Arg Pro Ser Ser Gly Ser His Arg Ser Pro Ala Arg Gln Gly
            660                 665                 670
```

```
Leu Pro Ser Pro Pro Gly Thr Pro His Ser Pro Ser Tyr Ala Gly Pro
        675                 680                 685

Lys Ala Val Ala Phe Ile His Thr Asp Leu Pro Glu Pro Pro Pro Ser
    690                 695                 700

Leu Thr Val Gln Arg Asp His Pro Gln Leu Lys Thr Pro Pro Ser Lys
705                 710                 715                 720

Leu Asn Gly Gln Ser Pro Gly Leu Ala Arg Leu Gly Pro Ala Thr Gly
                725                 730                 735

Pro Pro Gly Pro Ser Ala Ser Pro Thr Arg His Thr Leu Val Lys Lys
            740                 745                 750

Val Ser Gly Val Gly Gly Thr Thr Tyr Glu Ile Ser Val
        755                 760                 765


<210> SEQ ID NO 10
<211> LENGTH: 364
<212> TYPE: PRT
<213> ORGANISM: Homo sapiens

<400> SEQUENCE: 10

Met Ser Val Met Val Val Arg Lys Lys Val Thr Arg Lys Trp Glu Lys
1               5                   10                  15

Leu Pro Gly Arg Asn Thr Phe Cys Cys Asp Gly Arg Val Met Met Ala
            20                  25                  30

Arg Gln Lys Gly Ile Phe Tyr Leu Thr Leu Phe Leu Ile Leu Gly Thr
        35                  40                  45

Cys Thr Leu Phe Phe Ala Phe Glu Cys Arg Tyr Leu Ala Val Gln Leu
    50                  55                  60

Ser Pro Ala Ile Pro Val Phe Ala Ala Met Leu Phe Leu Phe Ser Met
65                  70                  75                  80

Ala Thr Leu Leu Arg Thr Ser Phe Ser Asp Pro Gly Val Ile Pro Arg
                85                  90                  95

Ala Leu Pro Asp Glu Ala Ala Phe Ile Glu Met Glu Ile Glu Ala Thr
            100                 105                 110

Asn Gly Ala Val Pro Gln Gly Gln Arg Pro Pro Pro Arg Ile Lys Asn
        115                 120                 125

Phe Gln Ile Asn Asn Gln Ile Val Lys Leu Lys Tyr Cys Tyr Thr Cys
    130                 135                 140

Lys Ile Phe Arg Pro Pro Arg Ala Ser His Cys Ser Ile Cys Asp Asn
145                 150                 155                 160

Cys Val Glu Arg Phe Asp His His Cys Pro Trp Val Gly Asn Cys Val
                165                 170                 175

Gly Lys Arg Asn Tyr Arg Tyr Phe Tyr Leu Phe Ile Leu Ser Leu Ser
            180                 185                 190

Leu Leu Thr Ile Tyr Val Phe Ala Phe Asn Ile Val Tyr Val Ala Leu
        195                 200                 205

Lys Ser Leu Lys Ile Gly Phe Leu Glu Thr Leu Lys Glu Thr Pro Gly
    210                 215                 220

Thr Val Leu Glu Val Leu Ile Cys Phe Phe Thr Leu Trp Ser Val Val
225                 230                 235                 240

Gly Leu Thr Gly Phe His Thr Phe Leu Val Ala Leu Asn Gln Thr Thr
                245                 250                 255

Asn Glu Asp Ile Lys Gly Ser Trp Thr Gly Lys Asn Arg Val Gln Asn
            260                 265                 270

Pro Tyr Ser His Gly Asn Ile Val Lys Asn Cys Cys Glu Val Leu Cys
```

-continued

```
        275                 280                 285

Gly Pro Leu Pro Pro Ser Val Leu Asp Arg Arg Gly Ile Leu Pro Leu
    290                 295                 300

Glu Glu Ser Gly Ser Arg Pro Pro Ser Thr Gln Glu Thr Ser Ser Ser
305                 310                 315                 320

Leu Leu Pro Gln Ser Pro Ala Pro Thr Glu His Leu Asn Ser Asn Glu
                325                 330                 335

Met Pro Glu Asp Ser Ser Thr Pro Glu Glu Met Pro Pro Pro Glu Pro
            340                 345                 350

Pro Glu Pro Pro Gln Glu Ala Ala Glu Ala Glu Lys
        355                 360


<210> SEQ ID NO 11
<211> LENGTH: 412
<212> TYPE: PRT
<213> ORGANISM: Homo sapiens

<400> SEQUENCE: 11

Met Asp Thr Arg Ser Gly Ser Gln Cys Ser Val Thr Pro Glu Ala Ile
1               5                   10                  15

Leu Asn Asn Glu Lys Leu Val Leu Pro Pro Arg Ile Ser Arg Val Asn
            20                  25                  30

Gly Trp Ser Leu Pro Leu His Tyr Phe Gln Val Val Thr Trp Ala Val
        35                  40                  45

Phe Val Gly Leu Ser Ser Ala Thr Phe Gly Ile Phe Ile Pro Phe Leu
    50                  55                  60

Pro His Ala Trp Lys Tyr Ile Ala Tyr Val Val Thr Gly Gly Ile Phe
65                  70                  75                  80

Ser Phe His Leu Val Val His Leu Ile Ala Ser Cys Ile Asp Pro Ala
                85                  90                  95

Asp Ser Asn Val Arg Leu Met Lys Asn Tyr Ser Gln Pro Met Pro Leu
            100                 105                 110

Phe Asp Arg Ser Lys His Ala His Val Ile Gln Asn Gln Phe Cys His
        115                 120                 125

Leu Cys Lys Val Thr Val Asn Lys Lys Thr Lys His Cys Ile Ser Cys
    130                 135                 140

Asn Lys Cys Val Ser Gly Phe Asp His His Cys Lys Trp Ile Asn Asn
145                 150                 155                 160

Cys Val Gly Ser Arg Asn Tyr Trp Phe Phe Phe Ser Thr Val Ala Ser
                165                 170                 175

Ala Thr Ala Gly Met Leu Cys Leu Ile Ala Ile Leu Leu Tyr Val Leu
            180                 185                 190

Val Gln Tyr Leu Val Asn Pro Gly Val Leu Arg Thr Asp Pro Arg Tyr
        195                 200                 205

Glu Asp Val Lys Asn Met Asn Thr Trp Leu Leu Phe Leu Pro Leu Phe
    210                 215                 220

Pro Val Gln Val Gln Thr Leu Ile Val Val Ile Ile Gly Met Leu Val
225                 230                 235                 240

Leu Leu Leu Asp Phe Leu Gly Leu Val His Leu Gly Gln Leu Leu Ile
                245                 250                 255

Phe His Ile Tyr Leu Lys Ala Lys Lys Met Thr Thr Phe Glu Tyr Leu
            260                 265                 270

Ile Asn Asn Arg Lys Glu Glu Ser Ser Lys His Gln Ala Val Arg Lys
        275                 280                 285
```

```
Asp Pro Tyr Val Gln Met Asp Lys Gly Val Leu Gln Gln Gly Ala Gly
    290                 295                 300

Ala Leu Gly Ser Ser Ala Gln Gly Val Lys Ala Lys Ser Ser Leu Leu
305                 310                 315                 320

Ile His Lys His Leu Cys His Phe Cys Thr Ser Val Asn Gln Asp Gly
                325                 330                 335

Asp Ser Thr Ala Arg Glu Gly Asp Glu Asp Pro Cys Pro Ser Ala Leu
            340                 345                 350

Gly Ala Lys Ala Arg Asn Ser Arg Leu Ile Cys Arg Arg Leu Cys Gln
        355                 360                 365

Phe Ser Thr Arg Val His Pro Asp Gly Gly Ser Met Ala Gln Glu Ala
    370                 375                 380

Asp Asp Ala Pro Ser Ile Ser Thr Leu Gly Leu Gln Gln Glu Thr Thr
385                 390                 395                 400

Glu Pro Met Lys Thr Asp Ser Ala Glu Ser Glu Asp
                405                 410


<210> SEQ ID NO 12
<211> LENGTH: 360
<212> TYPE: PRT
<213> ORGANISM: Homo sapiens

<400> SEQUENCE: 12

Met Asp Thr Arg Ser Gly Ser Gln Cys Ser Val Thr Pro Glu Ala Ile
1               5                   10                  15

Arg Asn Asn Glu Glu Leu Val Leu Pro Pro Arg Ile Ser Arg Val Asn
            20                  25                  30

Gly Trp Ser Leu Pro Leu His Tyr Phe Arg Val Val Thr Trp Ala Val
        35                  40                  45

Phe Val Gly Leu Ser Leu Ala Thr Phe Arg Ile Phe Ile Pro Leu Leu
    50                  55                  60

Pro His Ser Trp Lys Tyr Ile Ala Tyr Val Val Thr Gly Gly Ile Phe
65                  70                  75                  80

Ser Phe His Leu Val Val His Leu Ile Ala Ser Cys Ile Asp Pro Ala
                85                  90                  95

Asp Ser Asn Val Arg Leu Met Lys Asn Tyr Ser Gln Pro Met Pro Leu
            100                 105                 110

Phe Asp Arg Ser Lys His Ala His Val Ile Gln Asn Gln Phe Cys His
        115                 120                 125

Leu Cys Lys Val Thr Val Asn Lys Lys Thr Lys His Cys Ile Ser Cys
    130                 135                 140

Asn Lys Cys Val Ser Gly Phe Asp His His Cys Lys Trp Ile Asn Asn
145                 150                 155                 160

Cys Val Gly Ser Arg Asn Tyr Trp Phe Phe Phe Ser Thr Val Ala Ser
                165                 170                 175

Ala Thr Ala Gly Met Leu Cys Leu Ile Ala Ile Leu Leu Tyr Val Leu
            180                 185                 190

Val Gln Tyr Leu Val Asn Pro Arg Val Leu Arg Thr Asp Pro Arg Tyr
        195                 200                 205

Glu Asp Val Lys Asn Met Asn Thr Trp Leu Leu Phe Leu Pro Leu Phe
    210                 215                 220

Pro Val Gln Val Gln Thr Leu Ile Val Val Ile Ile Arg Met Leu Val
225                 230                 235                 240

Leu Leu Leu Asp Leu Leu Gly Leu Val Gln Leu Gly Gln Leu Leu Ile
                245                 250                 255
```

Phe His Ile Tyr Leu Lys Ala Lys Lys Met Thr Thr Phe Glu Tyr Leu
260 265 270

Ile Asn Thr Arg Lys Glu Glu Ser Ser Lys His Gln Ala Val Arg Lys
275 280 285

Asp Pro Tyr Val Gln Met Asp Lys Gly Phe Leu Gln Gln Gly Ala Gly
290 295 300

Ala Leu Gly Ser Ser Ala Gln Gly Val Lys Ala Lys Ser Ser Leu Leu
305 310 315 320

Ile Tyr Lys Cys Pro Cys His Phe Cys Thr Ser Val Asn Gln Asp Gly
325 330 335

Asp Ser Lys Ala Gln Gly Arg Leu Thr Ala Leu Pro Gln Asp Phe Arg
340 345 350

Glu Gln Ala Pro Val Thr Trp Lys
355 360

<210> SEQ ID NO 13
<211> LENGTH: 267
<212> TYPE: PRT
<213> ORGANISM: Homo sapiens

<400> SEQUENCE: 13

Met Ala Pro Trp Ala Leu Leu Ser Pro Gly Val Leu Val Arg Thr Gly
1 5 10 15

His Thr Val Leu Thr Trp Gly Ile Thr Leu Val Leu Phe Leu His Asp
20 25 30

Thr Glu Leu Arg Gln Trp Glu Glu Gln Gly Glu Leu Leu Leu Pro Leu
35 40 45

Thr Phe Leu Leu Leu Val Leu Gly Ser Leu Leu Leu Tyr Leu Ala Val
50 55 60

Ser Leu Met Asp Pro Gly Tyr Val Asn Val Gln Pro Gln Pro Gln Glu
65 70 75 80

Glu Leu Lys Glu Glu Gln Thr Ala Met Val Pro Pro Ala Ile Pro Leu
85 90 95

Arg Arg Cys Arg Tyr Cys Leu Val Leu Gln Pro Leu Arg Ala Arg His
100 105 110

Cys Arg Glu Cys Arg Arg Cys Val Arg Arg Tyr Asp His His Cys Pro
115 120 125

Trp Met Glu Asn Cys Val Gly Glu Arg Asn His Pro Leu Phe Val Val
130 135 140

Tyr Leu Ala Leu Gln Leu Val Val Leu Leu Trp Gly Leu Tyr Leu Ala
145 150 155 160

Trp Ser Gly Leu Arg Phe Phe Gln Pro Trp Gly Leu Trp Leu Arg Ser
165 170 175

Ser Gly Leu Leu Phe Ala Thr Phe Leu Leu Leu Ser Leu Phe Ser Leu
180 185 190

Val Ala Ser Leu Leu Leu Val Ser His Leu Tyr Leu Val Ala Ser Asn
195 200 205

Thr Thr Thr Trp Glu Phe Ile Ser Ser His Arg Ile Ala Tyr Leu Arg
210 215 220

Gln Arg Pro Ser Asn Pro Phe Asp Arg Gly Leu Thr Arg Asn Leu Ala
225 230 235 240

His Phe Phe Cys Gly Trp Pro Ser Gly Ser Trp Glu Thr Leu Trp Ala
245 250 255

Glu Glu Glu Glu Glu Gly Ser Ser Pro Ala Val 260 265

<210> SEQ ID NO 14
<211> LENGTH: 622
<212> TYPE: PRT
<213> ORGANISM: Homo sapiens

<400> SEQUENCE: 14

Met Glu Gly Pro Gly Leu Gly Ser Gln Cys Arg Asn His Ser His Gly
1 5 10 15

Pro His Pro Pro Gly Phe Gly Arg Tyr Gly Ile Cys Ala His Glu Asn
20 25 30

Lys Glu Leu Ala Asn Ala Arg Glu Ala Leu Pro Leu Ile Glu Asp Ser
35 40 45

Ser Asn Cys Asp Ile Val Lys Ala Thr Gln Tyr Gly Ile Phe Glu Arg
50 55 60

Cys Lys Glu Leu Val Glu Ala Gly Tyr Asp Val Arg Gln Pro Asp Lys
65 70 75 80

Glu Asn Val Ser Leu Leu His Trp Ala Ala Ile Asn Asn Arg Leu Asp
85 90 95

Leu Val Lys Phe Tyr Ile Ser Lys Gly Ala Val Val Asp Gln Leu Gly
100 105 110

Gly Asp Leu Asn Ser Thr Pro Leu His Trp Ala Ile Arg Gln Gly His
115 120 125

Leu Pro Met Val Ile Leu Leu Leu Gln His Gly Ala Asp Pro Thr Leu
130 135 140

Ile Asp Gly Glu Gly Phe Ser Ser Ile His Leu Ala Val Leu Phe Gln
145 150 155 160

His Met Pro Ile Ile Ala Tyr Leu Ile Ser Lys Gly Gln Ser Val Asn
165 170 175

Met Thr Asp Val Asn Gly Gln Thr Pro Leu Met Leu Ser Ala His Lys
180 185 190

Val Ile Gly Pro Glu Pro Thr Gly Phe Leu Leu Lys Phe Asn Pro Ser
195 200 205

Leu Asn Val Val Asp Lys Ile His Gln Asn Thr Pro Leu His Trp Ala
210 215 220

Val Ala Ala Gly Asn Val Asn Ala Val Asp Lys Leu Leu Glu Ala Gly
225 230 235 240

Ser Ser Leu Asp Ile Gln Asn Val Lys Gly Glu Thr Pro Leu Asp Met
245 250 255

Ala Leu Gln Asn Lys Asn Gln Leu Ile Ile His Met Leu Lys Thr Glu
260 265 270

Ala Lys Met Arg Ala Asn Gln Lys Phe Arg Leu Trp Arg Trp Leu Gln
275 280 285

Lys Cys Glu Leu Phe Leu Leu Leu Met Leu Ser Val Ile Thr Met Trp
290 295 300

Ala Ile Gly Tyr Ile Leu Asp Phe Asn Ser Asp Ser Trp Leu Leu Lys
305 310 315 320

Gly Cys Leu Leu Val Thr Leu Phe Phe Leu Thr Ser Leu Phe Pro Arg
325 330 335

Phe Leu Val Gly Tyr Lys Asn Leu Val Tyr Leu Pro Thr Ala Phe Leu
340 345 350

Leu Ser Ser Val Phe Trp Ile Phe Met Thr Trp Phe Ile Leu Phe Phe
355 360 365

```
Pro Asp Leu Ala Gly Ala Pro Phe Tyr Phe Ser Phe Ile Phe Ser Ile
    370                 375                 380

Val Ala Phe Leu Tyr Phe Phe Tyr Lys Thr Trp Ala Thr Asp Pro Gly
385                 390                 395                 400

Phe Thr Lys Ala Ser Glu Glu Glu Lys Lys Val Asn Ile Ile Thr Leu
                405                 410                 415

Ala Glu Thr Gly Ser Leu Asp Phe Arg Thr Phe Cys Thr Ser Cys Leu
            420                 425                 430

Ile Arg Lys Pro Leu Arg Ser Leu His Cys His Val Cys Asn Cys Cys
        435                 440                 445

Val Ala Arg Tyr Asp Gln His Cys Leu Trp Thr Gly Arg Cys Ile Gly
    450                 455                 460

Phe Gly Asn His His Tyr Tyr Ile Phe Phe Leu Phe Phe Leu Ser Met
465                 470                 475                 480

Val Cys Gly Trp Ile Ile Tyr Gly Ser Phe Ile Tyr Leu Ser Ser His
                485                 490                 495

Cys Ala Thr Thr Phe Lys Glu Asp Gly Leu Trp Thr Tyr Leu Asn Gln
            500                 505                 510

Ile Val Ala Cys Ser Pro Trp Val Leu Tyr Ile Leu Met Leu Ala Thr
        515                 520                 525

Phe His Phe Ser Trp Ser Thr Phe Leu Leu Leu Asn Gln Leu Phe Gln
    530                 535                 540

Ile Ala Phe Leu Gly Leu Thr Ser His Glu Arg Ile Ser Leu Gln Lys
545                 550                 555                 560

Gln Ser Lys His Met Lys Gln Thr Leu Ser Leu Arg Lys Thr Pro Tyr
                565                 570                 575

Asn Leu Gly Phe Met Gln Asn Leu Ala Asp Phe Phe Gln Cys Gly Cys
            580                 585                 590

Phe Gly Leu Val Lys Pro Cys Val Val Asp Trp Thr Ser Gln Tyr Thr
        595                 600                 605

Met Val Phe His Pro Ala Arg Glu Lys Val Leu Arg Ser Val
    610                 615                 620


<210> SEQ ID NO 15
<211> LENGTH: 488
<212> TYPE: PRT
<213> ORGANISM: Homo sapiens

<400> SEQUENCE: 15

Met Pro Pro Gly Gly Gly Gly Pro Met Lys Asp Cys Glu Tyr Ser Gln
1               5                   10                  15

Ile Ser Thr His Ser Ser Ser Pro Met Glu Ser Pro His Lys Lys Lys
            20                  25                  30

Lys Ile Ala Ala Arg Arg Lys Trp Glu Val Phe Pro Gly Arg Asn Lys
        35                  40                  45

Phe Phe Cys Asn Gly Arg Ile Met Met Ala Arg Gln Thr Gly Val Phe
    50                  55                  60

Tyr Leu Thr Leu Val Leu Ile Leu Val Thr Ser Gly Leu Phe Phe Ala
65                  70                  75                  80

Phe Asp Cys Pro Tyr Leu Ala Val Lys Ile Thr Pro Ala Ile Pro Ala
                85                  90                  95

Val Ala Gly Ile Leu Phe Phe Phe Val Met Gly Thr Leu Leu Arg Thr
            100                 105                 110

Ser Phe Ser Asp Pro Gly Val Leu Pro Arg Ala Thr Pro Asp Glu Ala
        115                 120                 125
```

```
Ala Asp Leu Glu Arg Gln Ile Asp Ile Ala Asn Gly Thr Ser Ser Gly
    130                 135                 140

Gly Tyr Arg Pro Pro Pro Arg Thr Lys Glu Val Ile Ile Asn Gly Gln
145                 150                 155                 160

Thr Val Lys Leu Lys Tyr Cys Phe Thr Cys Lys Ile Phe Arg Pro Pro
                165                 170                 175

Arg Ala Ser His Cys Ser Leu Cys Asp Asn Cys Val Glu Arg Phe Asp
            180                 185                 190

His His Cys Pro Trp Val Gly Asn Cys Val Gly Lys Arg Asn Tyr Arg
        195                 200                 205

Phe Phe Tyr Met Phe Ile Leu Ser Leu Ser Phe Leu Thr Val Phe Ile
    210                 215                 220

Phe Ala Phe Val Ile Thr His Val Ile Leu Arg Ser Gln Gln Thr Gly
225                 230                 235                 240

Phe Leu Asn Ala Leu Lys Asp Ser Pro Ala Ser Val Leu Glu Ala Val
                245                 250                 255

Val Cys Phe Phe Ser Val Trp Ser Ile Val Gly Leu Ser Gly Phe His
            260                 265                 270

Thr Tyr Leu Ile Ser Ser Asn Gln Thr Thr Asn Glu Asp Ile Lys Gly
        275                 280                 285

Ser Trp Ser Asn Lys Arg Gly Lys Glu Asn Tyr Asn Pro Tyr Ser Tyr
    290                 295                 300

Gly Asn Ile Phe Thr Asn Cys Cys Val Ala Leu Cys Gly Pro Ile Ser
305                 310                 315                 320

Pro Ser Leu Ile Asp Arg Arg Gly Tyr Ile Gln Pro Asp Thr Pro Gln
                325                 330                 335

Pro Ala Ala Pro Ser Asn Gly Ile Thr Met Tyr Gly Ala Thr Gln Ser
            340                 345                 350

Gln Ser Asp Met Cys Asp Gln Asp Gln Cys Ile Gln Ser Thr Lys Phe
        355                 360                 365

Val Leu Gln Ala Ala Ala Thr Pro Leu Leu Gln Ser Glu Pro Ser Leu
    370                 375                 380

Thr Ser Asp Glu Leu His Leu Pro Gly Lys Pro Gly Leu Gly Thr Pro
385                 390                 395                 400

Cys Ala Ser Leu Thr Leu Gly Pro Pro Thr Pro Pro Ala Ser Met Pro
                405                 410                 415

Asn Leu Ala Glu Ala Thr Leu Ala Asp Val Met Pro Arg Lys Asp Glu
            420                 425                 430

His Met Gly His Gln Phe Leu Thr Pro Asp Glu Ala Pro Ser Pro Pro
        435                 440                 445

Arg Leu Leu Ala Ala Gly Ser Pro Leu Ala His Ser Arg Thr Met His
    450                 455                 460

Val Leu Gly Leu Ala Ser Gln Asp Ser Leu His Glu Asp Ser Val Arg
465                 470                 475                 480

Gly Leu Val Lys Leu Ser Ser Val
                485
```

<210> SEQ ID NO 16
<211> LENGTH: 337
<212> TYPE: PRT
<213> ORGANISM: Homo sapiens

<400> SEQUENCE: 16

```
Met Arg Arg Gly Trp Lys Met Ala Leu Ser Gly Gly Leu Arg Cys Cys
```

```
1               5                   10                  15

Arg Arg Val Leu Ser Trp Val Pro Val Leu Val Ile Val Leu Val Val
            20                  25                  30

Leu Trp Ser Tyr Tyr Ala Tyr Val Phe Glu Leu Cys Leu Val Thr Val
        35                  40                  45

Leu Ser Pro Ala Glu Lys Val Ile Tyr Leu Ile Leu Tyr His Ala Ile
    50                  55                  60

Phe Val Phe Phe Thr Trp Thr Tyr Trp Lys Ser Ile Phe Thr Leu Pro
65                  70                  75                  80

Gln Gln Pro Asn Gln Lys Phe His Leu Ser Tyr Thr Asp Lys Glu Arg
                85                  90                  95

Tyr Glu Asn Glu Glu Arg Pro Glu Val Gln Lys Gln Met Leu Val Asp
            100                 105                 110

Met Ala Lys Lys Leu Pro Val Tyr Thr Arg Thr Gly Ser Gly Ala Val
        115                 120                 125

Arg Phe Cys Asp Arg Cys His Leu Ile Lys Pro Asp Arg Cys His His
    130                 135                 140

Cys Ser Val Cys Ala Met Cys Val Leu Lys Met Asp His His Cys Pro
145                 150                 155                 160

Trp Val Asn Asn Cys Ile Gly Phe Ser Asn Tyr Lys Phe Phe Leu Gln
                165                 170                 175

Phe Leu Ala Tyr Ser Val Leu Tyr Cys Leu Tyr Ile Ala Thr Thr Val
            180                 185                 190

Phe Ser Tyr Phe Ile Lys Tyr Trp Arg Gly Glu Leu Pro Ser Val Arg
        195                 200                 205

Ser Lys Phe His Val Leu Phe Leu Leu Phe Val Ala Cys Met Phe Phe
    210                 215                 220

Val Ser Leu Val Ile Leu Phe Gly Tyr His Cys Trp Leu Val Ser Arg
225                 230                 235                 240

Asn Lys Thr Thr Leu Glu Ala Phe Cys Thr Pro Val Phe Thr Ser Gly
                245                 250                 255

Pro Glu Lys Asn Gly Phe Asn Leu Gly Phe Ile Lys Asn Ile Gln Gln
            260                 265                 270

Val Phe Gly Asp Lys Lys Lys Phe Trp Leu Ile Pro Ile Gly Ser Ser
        275                 280                 285

Pro Gly Asp Gly His Ser Phe Pro Met Arg Ser Met Asn Glu Ser Gln
    290                 295                 300

Asn Pro Leu Leu Ala Asn Glu Glu Thr Trp Glu Asp Asn Glu Asp Asp
305                 310                 315                 320

Asn Gln Asp Tyr Pro Glu Gly Ser Ser Ser Leu Ala Val Glu Thr Glu
                325                 330                 335

Thr


<210> SEQ ID NO 17
<211> LENGTH: 377
<212> TYPE: PRT
<213> ORGANISM: Homo sapiens

<400> SEQUENCE: 17

Met Arg Gly Gln Arg Ser Leu Leu Leu Gly Pro Ala Arg Leu Cys Leu
1               5                   10                  15

Arg Leu Leu Leu Leu Leu Gly Tyr Arg Arg Arg Cys Pro Pro Leu Leu
            20                  25                  30

Arg Gly Leu Val Gln Arg Trp Arg Tyr Gly Lys Val Cys Leu Arg Ser
```

```
        35                  40                  45

Leu Leu Tyr Asn Ser Phe Gly Gly Ser Asp Thr Ala Val Asp Ala Ala
    50                  55                  60

Phe Glu Pro Val Tyr Trp Leu Val Asp Asn Val Ile Arg Trp Phe Gly
65                  70                  75                  80

Val Val Phe Val Val Leu Val Ile Val Leu Thr Gly Ser Ile Val Ala
                85                  90                  95

Ile Ala Tyr Leu Cys Val Leu Pro Leu Ile Leu Arg Thr Tyr Ser Val
            100                 105                 110

Pro Arg Leu Cys Trp His Phe Phe Tyr Ser His Trp Asn Leu Ile Leu
        115                 120                 125

Ile Val Phe His Tyr Tyr Gln Ala Ile Thr Thr Pro Pro Gly Tyr Pro
    130                 135                 140

Pro Gln Gly Arg Asn Asp Ile Ala Thr Val Ser Ile Cys Lys Lys Cys
145                 150                 155                 160

Ile Tyr Pro Lys Pro Ala Arg Thr His His Cys Ser Ile Cys Asn Arg
                165                 170                 175

Cys Val Leu Lys Met Asp His His Cys Pro Trp Leu Asn Asn Cys Val
            180                 185                 190

Gly His Tyr Asn His Arg Tyr Phe Phe Ser Phe Cys Phe Phe Met Thr
        195                 200                 205

Leu Gly Cys Val Tyr Cys Ser Tyr Gly Ser Trp Asp Leu Phe Arg Glu
    210                 215                 220

Ala Tyr Ala Ala Ile Glu Lys Met Lys Gln Leu Asp Lys Asn Lys Leu
225                 230                 235                 240

Gln Ala Val Ala Asn Gln Thr Tyr His Gln Thr Pro Pro Pro Thr Phe
                245                 250                 255

Ser Phe Arg Glu Arg Met Thr His Lys Ser Leu Val Tyr Leu Trp Phe
            260                 265                 270

Leu Cys Ser Ser Val Ala Leu Ala Leu Gly Ala Leu Thr Val Trp His
        275                 280                 285

Ala Val Leu Ile Ser Arg Gly Glu Thr Ser Ile Glu Arg His Ile Asn
    290                 295                 300

Lys Lys Glu Arg Arg Arg Leu Gln Ala Lys Gly Arg Val Phe Arg Asn
305                 310                 315                 320

Pro Tyr Asn Tyr Gly Cys Leu Asp Asn Trp Lys Val Phe Leu Gly Val
                325                 330                 335

Asp Thr Gly Arg His Trp Leu Thr Arg Val Leu Leu Pro Ser Ser His
            340                 345                 350

Leu Pro His Gly Asn Gly Met Ser Trp Glu Pro Pro Pro Trp Val Thr
        355                 360                 365

Ala His Ser Ala Ser Val Met Ala Val
    370                 375


<210> SEQ ID NO 18
<211> LENGTH: 632
<212> TYPE: PRT
<213> ORGANISM: Homo sapiens

<400> SEQUENCE: 18

Met Gln Arg Glu Glu Gly Phe Asn Thr Lys Met Ala Asp Gly Pro Asp
1               5                   10                  15

Glu Tyr Asp Thr Glu Ala Gly Cys Val Pro Leu Leu His Pro Glu Glu
            20                  25                  30
```

-continued

```
Ile Lys Pro Gln Ser His Tyr Asn His Gly Tyr Gly Glu Pro Leu Gly
        35                  40                  45

Arg Lys Thr His Ile Asp Asp Tyr Ser Thr Trp Asp Ile Val Lys Ala
    50                  55                  60

Thr Gln Tyr Gly Ile Tyr Glu Arg Cys Arg Glu Leu Val Glu Ala Gly
65                  70                  75                  80

Tyr Asp Val Arg Gln Pro Asp Lys Glu Asn Val Thr Leu Leu His Trp
                85                  90                  95

Ala Ala Ile Asn Asn Arg Ile Asp Leu Val Lys Tyr Tyr Ile Ser Lys
            100                 105                 110

Gly Ala Ile Val Asp Gln Leu Gly Gly Asp Leu Asn Ser Thr Pro Leu
        115                 120                 125

His Trp Ala Thr Arg Gln Gly His Leu Ser Met Val Val Gln Leu Met
    130                 135                 140

Lys Tyr Gly Ala Asp Pro Ser Leu Ile Asp Gly Glu Gly Cys Ser Cys
145                 150                 155                 160

Ile His Leu Ala Ala Gln Phe Gly His Thr Ser Ile Val Ala Tyr Leu
                165                 170                 175

Ile Ala Lys Gly Gln Asp Val Asp Met Met Asp Gln Asn Gly Met Thr
            180                 185                 190

Pro Leu Met Trp Ala Ala Tyr Arg Thr His Ser Val Asp Pro Thr Arg
        195                 200                 205

Leu Leu Leu Thr Phe Asn Val Ser Val Asn Leu Gly Asp Lys Tyr His
    210                 215                 220

Lys Asn Thr Ala Leu His Trp Ala Val Leu Ala Gly Asn Thr Thr Val
225                 230                 235                 240

Ile Ser Leu Leu Leu Glu Ala Gly Ala Asn Val Asp Ala Gln Asn Ile
                245                 250                 255

Lys Gly Glu Ser Ala Leu Asp Leu Ala Lys Gln Arg Lys Asn Val Trp
            260                 265                 270

Met Ile Asn His Leu Gln Glu Ala Arg Gln Ala Lys Gly Tyr Asp Asn
        275                 280                 285

Pro Ser Phe Leu Arg Lys Leu Lys Ala Asp Lys Glu Phe Arg Gln Lys
    290                 295                 300

Val Met Leu Gly Thr Pro Phe Leu Val Ile Trp Leu Val Gly Phe Ile
305                 310                 315                 320

Ala Asp Leu Asn Ile Asp Ser Trp Leu Ile Lys Gly Leu Met Tyr Gly
                325                 330                 335

Gly Val Trp Ala Thr Val Gln Phe Leu Ser Lys Ser Phe Phe Asp His
            340                 345                 350

Ser Met His Ser Ala Leu Pro Leu Gly Ile Tyr Leu Ala Thr Lys Phe
        355                 360                 365

Trp Met Tyr Val Thr Trp Phe Phe Trp Phe Trp Asn Asp Leu Asn Phe
    370                 375                 380

Leu Phe Ile His Leu Pro Phe Leu Ala Asn Ser Val Ala Leu Phe Tyr
385                 390                 395                 400

Asn Phe Gly Lys Ser Trp Lys Ser Asp Pro Gly Ile Ile Lys Ala Thr
                405                 410                 415

Glu Glu Gln Lys Lys Lys Thr Ile Val Glu Leu Ala Glu Thr Gly Ser
            420                 425                 430

Leu Asp Leu Ser Ile Phe Cys Ser Thr Cys Leu Ile Arg Lys Pro Val
        435                 440                 445

Arg Ser Lys His Cys Gly Val Cys Asn Arg Cys Ile Ala Lys Phe Asp
```

```
    450                 455                 460

His His Cys Pro Trp Val Gly Asn Cys Val Gly Ala Gly Asn His Arg
465                 470                 475                 480

Tyr Phe Met Gly Tyr Leu Phe Phe Leu Leu Phe Met Ile Cys Trp Met
                485                 490                 495

Ile Tyr Gly Cys Ile Ser Tyr Trp Gly Leu His Cys Glu Thr Thr Tyr
            500                 505                 510

Thr Lys Asp Gly Phe Trp Thr Tyr Ile Thr Gln Ile Ala Thr Cys Ser
        515                 520                 525

Pro Trp Met Phe Trp Met Phe Leu Asn Ser Val Phe His Phe Met Trp
    530                 535                 540

Val Ala Val Leu Leu Met Cys Gln Met Tyr Gln Ile Ser Cys Leu Gly
545                 550                 555                 560

Ile Thr Thr Asn Glu Arg Met Asn Ala Arg Arg Tyr Lys His Phe Lys
                565                 570                 575

Val Thr Thr Thr Ser Ile Glu Ser Pro Phe Asn His Gly Cys Val Arg
            580                 585                 590

Asn Ile Ile Asp Phe Phe Glu Phe Arg Cys Cys Gly Leu Phe Arg Pro
        595                 600                 605

Val Ile Val Asp Trp Thr Arg Gln Tyr Thr Ile Glu Tyr Asp Gln Ile
    610                 615                 620

Ser Gly Ser Gly Tyr Gln Leu Val
625                 630


<210> SEQ ID NO 19
<211> LENGTH: 388
<212> TYPE: PRT
<213> ORGANISM: Homo sapiens

<400> SEQUENCE: 19

Met Lys Asp Cys Glu Tyr Gln Gln Ile Ser Pro Gly Ala Ala Pro Leu
1               5                   10                  15

Pro Ala Ser Pro Gly Ala Arg Arg Pro Gly Pro Ala Ala Ser Pro Thr
            20                  25                  30

Pro Gly Pro Gly Pro Ala Pro Pro Ala Ala Pro Ala Pro Pro Arg Trp
        35                  40                  45

Ser Ser Ser Gly Ser Gly Ser Gly Ser Gly Ser Gly Ser Leu Gly Arg
    50                  55                  60

Arg Pro Arg Arg Lys Trp Glu Val Phe Pro Gly Arg Asn Arg Phe Tyr
65                  70                  75                  80

Cys Gly Gly Arg Leu Met Leu Ala Gly His Gly Gly Val Phe Ala Leu
                85                  90                  95

Thr Leu Leu Leu Ile Leu Thr Thr Thr Gly Leu Phe Phe Val Phe Asp
            100                 105                 110

Cys Pro Tyr Leu Ala Arg Lys Leu Thr Leu Ala Ile Pro Ile Ile Ala
        115                 120                 125

Ala Ile Leu Phe Phe Phe Val Met Ser Cys Leu Leu Gln Thr Ser Phe
    130                 135                 140

Thr Asp Pro Gly Ile Leu Pro Arg Ala Thr Val Cys Glu Ala Ala Ala
145                 150                 155                 160

Leu Glu Lys Gln Ile Asp Asn Thr Gly Ser Ser Thr Tyr Arg Pro Pro
                165                 170                 175

Pro Arg Thr Arg Glu Val Leu Ile Asn Gly Gln Met Val Lys Leu Lys
            180                 185                 190
```

```
Tyr Cys Phe Thr Cys Lys Met Phe Arg Pro Pro Arg Thr Ser His Cys
        195                 200                 205

Ser Val Cys Asp Asn Cys Val Glu Arg Phe Asp His His Cys Pro Trp
    210                 215                 220

Val Gly Asn Cys Val Gly Arg Arg Asn Tyr Arg Phe Phe Tyr Ala Phe
225                 230                 235                 240

Ile Leu Ser Leu Ser Phe Leu Thr Ala Phe Ile Phe Ala Cys Val Val
                245                 250                 255

Thr His Leu Thr Leu Arg Ala Gln Gly Ser Asn Phe Leu Ser Thr Leu
            260                 265                 270

Lys Glu Thr Pro Ala Ser Val Leu Glu Leu Val Ile Cys Phe Phe Ser
        275                 280                 285

Ile Trp Ser Ile Leu Gly Leu Ser Gly Phe His Thr Tyr Leu Val Ala
    290                 295                 300

Ser Asn Leu Thr Thr Asn Glu Asp Ile Lys Gly Ser Trp Ser Ser Lys
305                 310                 315                 320

Arg Gly Gly Glu Ala Ser Val Asn Pro Tyr Ser His Lys Ser Ile Ile
                325                 330                 335

Thr Asn Cys Cys Ala Val Leu Cys Gly Pro Leu Pro Pro Ser Leu Ile
            340                 345                 350

Asp Arg Arg Gly Phe Val Gln Ser Asp Thr Val Leu Pro Ser Pro Ile
        355                 360                 365

Arg Ser Asp Glu Pro Ala Cys Arg Ala Lys Pro Asp Ala Ser Met Val
    370                 375                 380

Gly Gly His Pro
385


<210> SEQ ID NO 20
<211> LENGTH: 309
<212> TYPE: PRT
<213> ORGANISM: Homo sapiens

<400> SEQUENCE: 20

Met Thr Leu Leu Thr Asp Ala Thr Pro Leu Val Lys Glu Pro His Pro
1               5                   10                  15

Leu Pro Leu Val Pro Arg Pro Trp Phe Leu Pro Ser Leu Phe Ala Ala
            20                  25                  30

Phe Asn Val Val Leu Leu Val Phe Phe Ser Gly Leu Phe Phe Ala Phe
        35                  40                  45

Pro Cys Arg Trp Leu Ala Gln Asn Gly Glu Trp Ala Phe Pro Val Ile
    50                  55                  60

Thr Gly Ser Leu Phe Val Leu Thr Phe Phe Ser Leu Val Ser Leu Asn
65                  70                  75                  80

Phe Ser Asp Pro Gly Ile Leu His Gln Gly Ser Ala Glu Gln Gly Pro
                85                  90                  95

Leu Thr Val His Val Val Trp Val Asn His Gly Ala Phe Arg Leu Gln
            100                 105                 110

Trp Cys Pro Lys Cys Cys Phe His Arg Pro Pro Arg Thr Tyr His Cys
        115                 120                 125

Pro Trp Cys Asn Ile Cys Val Glu Asp Phe Asp His His Cys Lys Trp
    130                 135                 140

Val Asn Asn Cys Ile Gly His Arg Asn Phe Arg Phe Phe Met Leu Leu
145                 150                 155                 160

Val Leu Ser Leu Cys Leu Tyr Ser Gly Ala Met Leu Val Thr Cys Leu
                165                 170                 175
```

```
Ile Phe Leu Val Arg Thr Thr His Leu Pro Phe Ser Thr Asp Lys Ala
            180                 185                 190

Ile Ala Ile Val Val Ala Val Ser Ala Ala Gly Leu Leu Val Pro Leu
        195                 200                 205

Ser Leu Leu Leu Leu Ile Gln Ala Leu Ser Val Ser Ser Ala Asp Arg
    210                 215                 220

Thr Tyr Lys Gly Lys Cys Arg His Leu Gln Gly Tyr Asn Pro Phe Asp
225                 230                 235                 240

Gln Gly Cys Ala Ser Asn Trp Tyr Leu Thr Ile Cys Ala Pro Leu Gly
                245                 250                 255

Pro Lys Tyr Met Ala Glu Ala Val Gln Leu Gln Arg Val Val Gly Pro
            260                 265                 270

Asp Trp Thr Ser Met Pro Asn Leu His Pro Pro Met Ser Pro Ser Ala
        275                 280                 285

Leu Asn Pro Pro Ala Pro Thr Ser Gly Ser Leu Gln Ser Arg Glu Gly
    290                 295                 300

Thr Pro Gly Ala Trp
305


<210> SEQ ID NO 21
<211> LENGTH: 354
<212> TYPE: PRT
<213> ORGANISM: Homo sapiens

<400> SEQUENCE: 21

Met Ala Pro Trp Thr Leu Trp Arg Cys Cys Gln Arg Val Val Gly Trp
1               5                   10                  15

Val Pro Val Leu Phe Ile Thr Phe Val Val Val Trp Ser Tyr Tyr Ala
            20                  25                  30

Tyr Val Val Glu Leu Cys Val Phe Thr Ile Phe Gly Asn Glu Glu Asn
        35                  40                  45

Gly Lys Thr Val Val Tyr Leu Val Ala Phe His Leu Phe Phe Val Met
    50                  55                  60

Phe Val Trp Ser Tyr Trp Met Thr Ile Phe Thr Ser Pro Ala Ser Pro
65                  70                  75                  80

Ser Lys Glu Phe Tyr Leu Ser Asn Ser Glu Lys Glu Arg Tyr Glu Lys
                85                  90                  95

Glu Phe Ser Gln Glu Arg Gln Gln Glu Ile Leu Arg Arg Ala Ala Arg
            100                 105                 110

Ala Leu Pro Ile Tyr Thr Thr Ser Ala Ser Lys Thr Ile Arg Tyr Cys
        115                 120                 125

Glu Lys Cys Gln Leu Ile Lys Pro Asp Arg Ala His His Cys Ser Ala
    130                 135                 140

Cys Asp Ser Cys Ile Leu Lys Met Asp His His Cys Pro Trp Val Asn
145                 150                 155                 160

Asn Cys Val Gly Phe Ser Asn Tyr Lys Phe Phe Leu Leu Phe Leu Leu
                165                 170                 175

Tyr Ser Leu Leu Tyr Cys Leu Phe Val Ala Ala Thr Val Leu Glu Tyr
            180                 185                 190

Phe Ile Lys Phe Trp Thr Asn Glu Leu Thr Asp Thr Arg Ala Lys Phe
        195                 200                 205

His Val Leu Phe Leu Phe Phe Val Ser Ala Met Phe Phe Ile Ser Val
    210                 215                 220

Leu Ser Leu Phe Ser Tyr His Cys Trp Leu Val Gly Lys Asn Arg Thr
```

```
225                 230                 235                 240

Thr Ile Glu Ser Phe Arg Ala Pro Thr Phe Ser Tyr Gly Pro Asp Gly
                245                 250                 255

Asn Gly Phe Ser Leu Gly Cys Ser Lys Asn Trp Arg Gln Val Phe Gly
            260                 265                 270

Asp Glu Lys Lys Tyr Trp Leu Leu Pro Ile Phe Ser Ser Leu Gly Asp
        275                 280                 285

Gly Cys Ser Phe Pro Thr Arg Leu Val Gly Met Asp Pro Glu Gln Ala
    290                 295                 300

Ser Val Thr Asn Gln Asn Glu Tyr Ala Arg Ser Gly Ser Asn Gln Pro
305                 310                 315                 320

Phe Pro Ile Lys Pro Leu Ser Glu Ser Lys Asn Arg Leu Leu Asp Ser
                325                 330                 335

Glu Ser Gln Trp Leu Glu Asn Gly Ala Glu Glu Gly Ile Val Lys Ser
            340                 345                 350

Gly Val


<210> SEQ ID NO 22
<211> LENGTH: 265
<212> TYPE: PRT
<213> ORGANISM: Homo sapiens

<400> SEQUENCE: 22

Met Gly Leu Arg Ile His Phe Val Val Asp Pro His Gly Trp Cys Cys
1               5                   10                  15

Met Gly Leu Ile Val Phe Val Trp Leu Tyr Asn Ile Val Leu Ile Pro
            20                  25                  30

Lys Ile Val Leu Phe Pro His Tyr Glu Glu Gly His Ile Pro Gly Ile
        35                  40                  45

Leu Ile Ile Ile Phe Tyr Gly Ile Ser Ile Phe Cys Leu Val Ala Leu
    50                  55                  60

Val Arg Ala Ser Ile Thr Asp Pro Gly Arg Leu Pro Glu Asn Pro Lys
65                  70                  75                  80

Ile Pro His Gly Glu Arg Glu Phe Trp Glu Leu Cys Asn Lys Cys Asn
                85                  90                  95

Leu Met Arg Pro Lys Arg Ser His His Cys Ser Arg Cys Gly His Cys
            100                 105                 110

Val Arg Arg Met Asp His His Cys Pro Trp Ile Asn Asn Cys Val Gly
        115                 120                 125

Glu Asp Asn His Trp Leu Phe Leu Gln Leu Cys Phe Tyr Thr Glu Leu
    130                 135                 140

Leu Thr Cys Tyr Ala Leu Met Phe Ser Phe Cys His Tyr Tyr Tyr Phe
145                 150                 155                 160

Leu Pro Leu Lys Lys Arg Asn Leu Asp Leu Phe Val Phe Arg His Glu
                165                 170                 175

Leu Ala Ile Met Arg Leu Ala Ala Phe Met Gly Ile Thr Met Leu Val
            180                 185                 190

Gly Ile Thr Gly Leu Phe Tyr Thr Gln Leu Ile Gly Ile Ile Thr Asp
        195                 200                 205

Thr Thr Ser Ile Glu Lys Met Ser Asn Cys Cys Glu Asp Ile Ser Arg
    210                 215                 220

Pro Arg Lys Pro Trp Gln Gln Thr Phe Ser Glu Val Phe Gly Thr Arg
225                 230                 235                 240

Trp Lys Ile Leu Trp Phe Ile Pro Phe Arg Gln Arg Gln Pro Leu Arg
```

245 250 255

Val Pro Tyr His Phe Ala Asn His Val
260 265

<210> SEQ ID NO 23
<211> LENGTH: 263
<212> TYPE: PRT
<213> ORGANISM: Homo sapiens

<400> SEQUENCE: 23

Met Leu Ala Leu Arg Leu Leu Asn Val Val Ala Pro Ala Tyr Phe Leu
1 5 10 15

Cys Ile Ser Leu Val Thr Phe Val Leu Gln Leu Phe Leu Phe Leu Pro
20 25 30

Ser Met Arg Glu Asp Pro Ala Ala Ala Arg Leu Phe Ser Pro Ala Leu
35 40 45

Leu His Gly Ala Leu Phe Leu Phe Leu Ser Ala Asn Ala Leu Gly Asn
50 55 60

Tyr Val Leu Val Ile Gln Asn Ser Pro Asp Asp Leu Gly Ala Cys Gln
65 70 75 80

Gly Ala Ser Ala Arg Lys Thr Pro Cys Pro Ser Pro Ser Thr His Phe
85 90 95

Cys Arg Val Cys Ala Arg Val Thr Leu Arg His Asp His His Cys Phe
100 105 110

Phe Thr Gly Asn Cys Ile Gly Ser Arg Asn Met Arg Asn Phe Val Leu
115 120 125

Phe Cys Leu Tyr Thr Ser Leu Ala Cys Leu Tyr Ser Met Val Ala Gly
130 135 140

Val Ala Tyr Ile Ser Ala Val Leu Ser Ile Ser Phe Ala His Pro Leu
145 150 155 160

Ala Phe Leu Thr Leu Leu Pro Thr Ser Ile Ser Gln Phe Phe Ser Gly
165 170 175

Ala Val Leu Gly Ser Glu Met Phe Val Ile Leu Met Leu Tyr Leu Trp
180 185 190

Phe Ala Ile Gly Leu Ala Cys Ala Gly Phe Cys Cys His Gln Leu Leu
195 200 205

Leu Ile Leu Arg Gly Gln Thr Arg His Gln Val Arg Lys Gly Val Ala
210 215 220

Val Arg Ala Arg Pro Trp Arg Lys Asn Leu Gln Glu Val Phe Gly Lys
225 230 235 240

Arg Trp Leu Leu Gly Leu Leu Val Pro Met Phe Asn Val Gly Ser Glu
245 250 255

Ser Ser Lys Gln Gln Asp Lys
260

<210> SEQ ID NO 24
<211> LENGTH: 409
<212> TYPE: PRT
<213> ORGANISM: Homo sapiens

<400> SEQUENCE: 24

Met Thr Gln Lys Gly Ser Met Lys Pro Val Lys Lys Lys Lys Thr Glu
1 5 10 15

Glu Pro Glu Leu Glu Pro Leu Cys Cys Cys Glu Tyr Ile Asp Arg Asn
20 25 30

Gly Glu Lys Asn His Val Ala Thr Cys Leu Cys Asp Cys Gln Asp Leu

```
        35                  40                  45

Asp Glu Gly Cys Asp Arg Trp Ile Thr Cys Lys Ser Leu Gln Pro Glu
    50                  55                  60

Thr Cys Glu Arg Ile Met Asp Thr Ile Ser Asp Arg Leu Arg Ile Pro
65                  70                  75                  80

Trp Leu Arg Gly Ala Lys Lys Val Asn Ile Ser Ile Ile Pro Pro Leu
                85                  90                  95

Val Leu Leu Pro Val Phe Leu His Val Ala Ser Trp His Phe Leu Leu
            100                 105                 110

Gly Val Val Val Leu Thr Ser Leu Pro Val Leu Ala Leu Trp Tyr Tyr
        115                 120                 125

Tyr Leu Thr His Arg Arg Lys Glu Gln Thr Leu Phe Phe Leu Ser Leu
    130                 135                 140

Gly Leu Phe Ser Leu Gly Tyr Met Tyr Tyr Val Phe Leu Gln Glu Val
145                 150                 155                 160

Val Pro Lys Gly Arg Val Gly Pro Val Gln Leu Ala Val Leu Thr Cys
                165                 170                 175

Gly Leu Phe Leu Ile Leu Leu Ala Leu His Arg Ala Lys Lys Asn Pro
            180                 185                 190

Gly Tyr Leu Ser Asn Pro Ala Ser Gly Asp Arg Ser Leu Ser Ser Ser
        195                 200                 205

Gln Leu Glu Cys Leu Ser Arg Lys Gly Gln Glu Lys Thr Lys Gly Phe
    210                 215                 220

Pro Gly Ala Asp Met Ser Gly Ser Leu Asn Asn Arg Thr Thr Lys Asp
225                 230                 235                 240

Asp Pro Lys Gly Ser Ser Lys Met Pro Ala Gly Ser Pro Thr Lys Ala
                245                 250                 255

Lys Glu Asp Trp Cys Ala Lys Cys Gln Leu Val Arg Pro Ala Arg Ala
            260                 265                 270

Trp His Cys Arg Ile Cys Gly Ile Cys Val Arg Arg Met Asp His His
        275                 280                 285

Cys Val Trp Ile Asn Ser Cys Val Gly Glu Ser Asn His Gln Ala Phe
    290                 295                 300

Ile Leu Ala Leu Leu Ile Phe Leu Leu Thr Ser Val Tyr Gly Ile Thr
305                 310                 315                 320

Leu Thr Leu Asp Thr Ile Cys Arg Asp Arg Ser Val Phe Thr Ala Leu
                325                 330                 335

Phe Tyr Cys Pro Gly Val Tyr Ala Asn Tyr Ser Ser Ala Leu Ser Phe
            340                 345                 350

Thr Cys Val Trp Tyr Ser Val Ile Ile Thr Ala Gly Met Ala Tyr Ile
        355                 360                 365

Phe Leu Ile Gln Leu Ile Asn Ile Ser Tyr Asn Val Thr Glu Arg Glu
    370                 375                 380

Val Gln Gln Ala Leu Arg Gln Lys Thr Gly Arg Arg Leu Leu Cys Gly
385                 390                 395                 400

Leu Ile Val Asp Thr Gly Leu Leu Gly
                405


<210> SEQ ID NO 25
<211> LENGTH: 284
<212> TYPE: PRT
<213> ORGANISM: Homo sapiens

<400> SEQUENCE: 25
```

Met Gly Gln Pro Trp Ala Ala Gly Ser Thr Asp Gly Ala Pro Ala Gln
1               5                   10                  15

Leu Pro Leu Val Leu Thr Ala Leu Trp Ala Ala Ala Val Gly Leu Glu
            20                  25                  30

Leu Ala Tyr Val Leu Val Leu Gly Pro Gly Pro Pro Pro Leu Gly Pro
        35                  40                  45

Leu Ala Arg Ala Leu Gln Leu Ala Leu Ala Ala Phe Gln Leu Leu Asn
    50                  55                  60

Leu Leu Gly Asn Val Gly Leu Phe Leu Arg Ser Asp Pro Ser Ile Arg
65                  70                  75                  80

Gly Val Met Leu Ala Gly Arg Gly Leu Gly Gln Gly Trp Ala Tyr Cys
                85                  90                  95

Tyr Gln Cys Gln Ser Gln Val Pro Pro Arg Ser Gly His Cys Ser Ala
            100                 105                 110

Cys Arg Val Cys Ile Leu Arg Arg Asp His His Cys Arg Leu Leu Gly
        115                 120                 125

Arg Cys Val Gly Phe Gly Asn Tyr Arg Pro Phe Leu Cys Leu Leu Leu
    130                 135                 140

His Ala Ala Gly Val Leu Leu His Val Ser Val Leu Leu Gly Pro Ala
145                 150                 155                 160

Leu Ser Ala Leu Leu Arg Ala His Thr Pro Leu His Met Ala Ala Leu
                165                 170                 175

Leu Leu Leu Pro Trp Leu Met Leu Leu Thr Gly Arg Val Ser Leu Ala
            180                 185                 190

Gln Phe Ala Leu Ala Phe Val Thr Asp Thr Cys Val Ala Gly Ala Leu
        195                 200                 205

Leu Cys Gly Ala Gly Leu Leu Phe His Gly Met Leu Leu Leu Arg Gly
    210                 215                 220

Gln Thr Thr Trp Glu Trp Ala Arg Gly Gln His Ser Tyr Asp Leu Gly
225                 230                 235                 240

Pro Cys His Asn Leu Gln Ala Ala Leu Gly Pro Arg Trp Ala Leu Val
                245                 250                 255

Trp Leu Trp Pro Phe Leu Ala Ser Pro Leu Pro Gly Asp Gly Ile Thr
            260                 265                 270

Phe Gln Thr Thr Ala Asp Val Gly His Thr Ala Ser
        275                 280

<210> SEQ ID NO 26
<211> LENGTH: 2511
<212> TYPE: PRT
<213> ORGANISM: Homo sapiens

<400> SEQUENCE: 26

Met Glu Glu Val Val Ile Ala Gly Met Ser Gly Lys Leu Pro Glu Ser
1               5                   10                  15

Glu Asn Leu Gln Glu Phe Trp Asp Asn Leu Ile Gly Gly Val Asp Met
            20                  25                  30

Val Thr Asp Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
    50                  55                  60

Phe Gly Val His Pro Lys Gln Ala His Thr Met Asp Pro Gln Leu Arg
65                  70                  75                  80

Leu Leu Leu Glu Val Thr Tyr Glu Ala Ile Val Asp Gly Gly Ile Asn
                85                  90                  95

```
Pro Asp Ser Leu Arg Gly Thr His Thr Gly Val Trp Val Gly Val Ser
            100                 105                 110

Gly Ser Glu Thr Ser Glu Ala Leu Ser Arg Asp Pro Glu Thr Leu Val
        115                 120                 125

Gly Tyr Ser Met Val Gly Cys Gln Arg Ala Met Met Ala Asn Arg Leu
    130                 135                 140

Ser Phe Phe Phe Asp Phe Arg Gly Pro Ser Ile Ala Leu Asp Thr Ala
145                 150                 155                 160

Cys Ser Ser Ser Leu Met Ala Leu Gln Asn Ala Tyr Gln Ala Ile His
                165                 170                 175

Ser Gly Gln Cys Pro Ala Ala Ile Val Gly Gly Ile Asn Val Leu Leu
            180                 185                 190

Lys Pro Asn Thr Ser Val Gln Phe Leu Arg Leu Gly Met Leu Ser Pro
        195                 200                 205

Glu Gly Thr Cys Lys Ala Phe Asp Thr Ala Gly Asn Gly Tyr Cys Arg
    210                 215                 220

Ser Glu Gly Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Phe
                245                 250                 255

Lys Glu Gln Gly Val Thr Phe Pro Ser Gly Asp Ile Gln Glu Gln Leu
            260                 265                 270

Ile Arg Ser Leu Tyr Gln Ser Ala Gly Val Ala Pro Glu Ser Phe Glu
        275                 280                 285

Tyr Ile Glu Ala His Gly Thr Gly Thr Lys Val Gly Asp Pro Gln Glu
    290                 295                 300

Leu Asn Gly Ile Thr Arg Ala Leu Cys Ala Thr Arg Gln Glu Pro Leu
305                 310                 315                 320

Leu Ile Gly Ser Thr Lys Ser Asn Met Gly His Pro Glu Pro Ala Ser
                325                 330                 335

Gly Leu Ala Ala Leu Ala Lys Val Leu Leu Ser Leu Glu His Gly Leu
            340                 345                 350

Trp Ala Pro Asn Leu His Phe His Ser Pro Asn Pro Glu Ile Pro Ala
        355                 360                 365

Leu Leu Asp Gly Arg Leu Gln Val Val Asp Gln Pro Leu Pro Val Arg
    370                 375                 380

Gly Gly Asn Val Gly Ile Asn Ser Phe Gly Phe Gly Gly Ser Asn Val
385                 390                 395                 400

His Ile Ile Leu Arg Pro Asn Thr Gln Pro Pro Pro Ala Pro Ala Pro
                405                 410                 415

His Ala Thr Leu Pro Arg Leu Leu Arg Ala Ser Gly Arg Thr Pro Glu
            420                 425                 430

Ala Val Gln Lys Leu Leu Glu Gln Gly Leu Arg His Ser Gln Asp Leu
        435                 440                 445

Ala Phe Leu Ser Met Leu Asn Asp Ile Ala Ala Val Pro Ala Thr Ala
    450                 455                 460

Met Pro Phe Arg Gly Tyr Ala Val Leu Gly Gly Glu Arg Gly Gly Pro
465                 470                 475                 480

Glu Val Gln Gln Val Pro Ala Gly Glu Arg Pro Leu Trp Phe Ile Cys
                485                 490                 495

Ser Gly Met Gly Thr Gln Trp Arg Gly Met Gly Leu Ser Leu Met Arg
            500                 505                 510
```

-continued

```
Leu Asp Arg Phe Arg Asp Ser Ile Leu Arg Ser Asp Glu Ala Val Lys
        515                 520                 525

Pro Phe Gly Leu Lys Val Ser Gln Leu Leu Leu Ser Thr Asp Glu Ser
    530                 535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
                565                 570                 575

Ile Val Gly His Ser Leu Gly Glu Val Ala Cys Gly Tyr Ala Asp Gly
            580                 585                 590

Cys Leu Ser Gln Glu Glu Ala Val Leu Ala Ala Tyr Trp Arg Gly Gln
        595                 600                 605

Cys Ile Lys Glu Ala His Leu Pro Pro Gly Ala Met Ala Ala Val Gly
    610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
                645                 650                 655

Pro Val Phe Glu Phe Val Glu Gln Leu Arg Lys Glu Gly Val Phe Ala
            660                 665                 670

Lys Glu Val Arg Thr Gly Gly Met Ala Phe His Ser Tyr Phe Met Glu
        675                 680                 685

Ala Ile Ala Pro Pro Leu Leu Gln Glu Leu Lys Lys Val Ile Arg Glu
    690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
                725                 730                 735

Asn Asn Leu Val Ser Pro Val Leu Phe Gln Glu Ala Leu Trp His Val
            740                 745                 750

Pro Glu His Ala Val Val Leu Glu Ile Ala Pro His Ala Leu Leu Gln
        755                 760                 765

Ala Val Leu Lys Arg Gly Leu Lys Pro Ser Cys Thr Ile Ile Pro Leu
    770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
            820                 825                 830

Leu Ile Lys Trp Asp His Ser Leu Ala Trp Asp Val Pro Ala Ala Glu
        835                 840                 845

Asp Phe Pro Asn Gly Ser Gly Ser Pro Ser Ala Ala Ile Tyr Asn Ile
    850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
                885                 890                 895

Lys Thr Leu Ala Arg Ala Leu Gly Leu Gly Val Glu Gln Leu Pro Val
            900                 905                 910

Val Phe Glu Asp Val Val Leu His Gln Ala Thr Ile Leu Pro Lys Thr
        915                 920                 925

Gly Thr Val Ser Leu Glu Val Arg Leu Leu Glu Ala Ser Arg Ala Phe
```

-continued

```
    930                 935                 940

Glu Val Ser Glu Asn Gly Asn Leu Val Val Ser Gly Lys Val Tyr Gln
945                 950                 955                 960

Trp Asp Asp Pro Asp Pro Arg Leu Phe Asp His Pro Glu Ser Pro Thr
                965                 970                 975

Pro Asn Pro Thr Glu Pro Leu Phe Leu Ala Gln Ala Glu Val Tyr Lys
            980                 985                 990

Glu Leu Arg Leu Arg Gly Tyr Asp  Tyr Gly Pro His Phe  Gln Gly Ile
        995                 1000                 1005

Leu Glu  Ala Ser Leu Glu Gly  Asp Ser Gly Arg Leu  Leu Trp Lys
    1010                 1015                 1020

Asp Asn  Trp Val Ser Phe Met  Asp Thr Met Leu Gln  Met Ser Ile
    1025                 1030                 1035

Leu Gly  Ser Ala Lys His Gly  Leu Tyr Leu Pro Thr  Arg Val Thr
    1040                 1045                 1050

Ala Ile  His Ile Asp Pro Ala  Thr His Arg Gln Lys  Leu Tyr Thr
    1055                 1060                 1065

Leu Gln  Asp Lys Ala Gln Val  Ala Asp Val Val Val  Ser Arg Trp
    1070                 1075                 1080

Leu Arg  Val Thr Val Ala Gly  Gly Val His Ile Ser  Gly Leu His
    1085                 1090                 1095

Thr Glu  Ser Ala Pro Arg Arg  Gln Gln Glu Gln Gln  Val Pro Ile
    1100                 1105                 1110

Leu Glu  Lys Phe Cys Phe Thr  Pro His Thr Glu Glu  Gly Cys Leu
    1115                 1120                 1125

Ser Glu  Arg Ala Ala Leu Gln  Glu Glu Leu Gln Leu  Cys Lys Gly
    1130                 1135                 1140

Leu Val  Gln Ala Leu Gln Thr  Lys Val Thr Gln Gln  Gly Leu Lys
    1145                 1150                 1155

Met Val  Val Pro Gly Leu Asp  Gly Ala Gln Ile Pro  Arg Asp Pro
    1160                 1165                 1170

Ser Gln  Gln Glu Leu Pro Arg  Leu Leu Ser Ala Ala  Cys Arg Leu
    1175                 1180                 1185

Gln Leu  Asn Gly Asn Leu Gln  Leu Glu Leu Ala Gln  Val Leu Ala
    1190                 1195                 1200

Gln Glu  Arg Pro Lys Leu Pro  Glu Asp Pro Leu Leu  Ser Gly Leu
    1205                 1210                 1215

Leu Asp  Ser Pro Ala Leu Lys  Ala Cys Leu Asp Thr  Ala Val Glu
    1220                 1225                 1230

Asn Met  Pro Ser Leu Lys Met  Lys Val Val Glu Val  Leu Ala Gly
    1235                 1240                 1245

His Gly  His Leu Tyr Ser Arg  Ile Pro Gly Leu Leu  Ser Pro His
    1250                 1255                 1260

Pro Leu  Leu Gln Leu Ser Tyr  Thr Ala Thr Asp Arg  His Pro Gln
    1265                 1270                 1275

Ala Leu  Glu Ala Ala Gln Ala  Glu Leu Gln Gln His  Asp Val Ala
    1280                 1285                 1290

Gln Gly  Gln Trp Asp Pro Ala  Asp Pro Ala Pro Ser  Ala Leu Gly
    1295                 1300                 1305

Ser Ala  Asp Leu Leu Val Cys  Asn Cys Ala Val Ala  Ala Leu Gly
    1310                 1315                 1320

Asp Pro  Ala Ser Ala Leu Ser  Asn Met Val Ala Ala  Leu Arg Glu
    1325                 1330                 1335
```

-continued

```
Gly Gly  Phe Leu Leu Leu His  Thr Leu Leu Arg Gly  His Pro Leu
    1340                 1345                 1350

Gly Asp  Ile Val Ala Phe Leu  Thr Ser Thr Glu Pro  Gln Tyr Gly
    1355                 1360                 1365

Gln Gly  Ile Leu Ser Gln Asp  Ala Trp Glu Ser Leu  Phe Ser Arg
    1370                 1375                 1380

Val Ser  Leu Arg Leu Val Gly  Leu Lys Lys Ser Phe  Tyr Gly Ser
    1385                 1390                 1395

Thr Leu  Phe Leu Cys Arg Arg  Pro Thr Pro Gln Asp  Ser Pro Ile
    1400                 1405                 1410

Phe Leu  Pro Val Asp Asp Thr  Ser Phe Arg Trp Val  Glu Ser Leu
    1415                 1420                 1425

Lys Gly  Ile Leu Ala Asp Glu  Asp Ser Ser Arg Pro  Val Trp Leu
    1430                 1435                 1440

Lys Ala  Ile Asn Cys Ala Thr  Ser Gly Val Val Gly  Leu Val Asn
    1445                 1450                 1455

Cys Leu  Arg Arg Glu Pro Gly  Gly Asn Arg Leu Arg  Cys Val Leu
    1460                 1465                 1470

Leu Ser  Asn Leu Ser Ser Thr  Ser His Val Pro Glu  Val Asp Pro
    1475                 1480                 1485

Gly Ser  Ala Glu Leu Gln Lys  Val Leu Gln Gly Asp  Leu Val Met
    1490                 1495                 1500

Asn Val  Tyr Arg Asp Gly Ala  Trp Gly Ala Phe Arg  His Phe Leu
    1505                 1510                 1515

Leu Glu  Glu Asp Lys Pro Glu  Glu Pro Thr Ala His  Ala Phe Val
    1520                 1525                 1530

Ser Thr  Leu Thr Arg Gly Asp  Leu Ser Ser Ile Arg  Trp Val Cys
    1535                 1540                 1545

Ser Ser  Leu Arg His Ala Gln  Pro Thr Cys Pro Gly  Ala Gln Leu
    1550                 1555                 1560

Cys Thr  Val Tyr Tyr Ala Ser  Leu Asn Phe Arg Asp  Ile Met Leu
    1565                 1570                 1575

Ala Thr  Gly Lys Leu Ser Pro  Asp Ala Ile Pro Gly  Lys Trp Thr
    1580                 1585                 1590

Ser Gln  Asp Ser Leu Leu Gly  Met Glu Phe Ser Gly  Arg Asp Ala
    1595                 1600                 1605

Ser Gly  Lys Arg Val Met Gly  Leu Val Pro Ala Lys  Gly Leu Ala
    1610                 1615                 1620

Thr Ser  Val Leu Leu Ser Pro  Asp Phe Leu Trp Asp  Val Pro Ser
    1625                 1630                 1635

Asn Trp  Thr Leu Glu Glu Ala  Ala Ser Val Pro Val  Val Tyr Ser
    1640                 1645                 1650

Thr Ala  Tyr Tyr Ala Leu Val  Val Arg Gly Arg Val  Arg Pro Gly
    1655                 1660                 1665

Glu Thr  Leu Leu Ile His Ser  Gly Ser Gly Gly Val  Gly Gln Ala
    1670                 1675                 1680

Ala Ile  Ala Ile Ala Leu Ser  Leu Gly Cys Arg Val  Phe Thr Thr
    1685                 1690                 1695

Val Gly  Ser Ala Glu Lys Arg  Ala Tyr Leu Gln Ala  Arg Phe Pro
    1700                 1705                 1710

Gln Leu  Asp Ser Thr Ser Phe  Ala Asn Ser Arg Asp  Thr Ser Phe
    1715                 1720                 1725
```

```
Glu Gln  His Val Leu Trp His  Thr Gly Gly Lys Gly  Val Asp Leu
    1730                 1735                 1740

Val Leu  Asn Ser Leu Ala Glu  Glu Lys Leu Gln Ala  Ser Val Arg
    1745                 1750                 1755

Cys Leu  Ala Thr His Gly Arg  Phe Leu Glu Ile Gly  Lys Phe Asp
    1760                 1765                 1770

Leu Ser  Gln Asn His Pro Leu  Gly Met Ala Ile Phe  Leu Lys Asn
    1775                 1780                 1785

Val Thr  Phe His Gly Val Leu  Leu Asp Ala Phe Phe  Asn Glu Ser
    1790                 1795                 1800

Ser Ala  Asp Trp Arg Glu Val  Trp Ala Leu Val Gln  Ala Gly Ile
    1805                 1810                 1815

Arg Asp  Gly Val Val Arg Pro  Leu Lys Cys Thr Val  Phe His Gly
    1820                 1825                 1830

Ala Gln  Val Glu Asp Ala Phe  Arg Tyr Met Ala Gln  Gly Lys His
    1835                 1840                 1845

Ile Gly  Lys Val Val Val Gln  Val Leu Ala Glu Glu  Pro Glu Ala
    1850                 1855                 1860

Val Leu  Lys Gly Ala Lys Pro  Lys Leu Met Ser Ala  Ile Ser Lys
    1865                 1870                 1875

Thr Phe  Cys Pro Ala His Lys  Ser Tyr Ile Ile Ala  Gly Gly Leu
    1880                 1885                 1890

Gly Gly  Phe Gly Leu Glu Leu  Ala Gln Trp Leu Ile  Gln Arg Gly
    1895                 1900                 1905

Val Gln  Lys Leu Val Leu Thr  Ser Arg Ser Gly Ile  Arg Thr Gly
    1910                 1915                 1920

Tyr Gln  Ala Lys Gln Val Arg  Arg Trp Arg Arg Gln  Gly Val Gln
    1925                 1930                 1935

Val Gln  Val Ser Thr Ser Asn  Ile Ser Ser Leu Glu  Gly Ala Arg
    1940                 1945                 1950

Gly Leu  Ile Ala Glu Ala Ala  Gln Leu Gly Pro Val  Gly Gly Val
    1955                 1960                 1965

Phe Asn  Leu Ala Val Val Leu  Arg Asp Gly Leu Leu  Glu Asn Gln
    1970                 1975                 1980

Thr Pro  Glu Phe Phe Gln Asp  Val Cys Lys Pro Lys  Tyr Ser Gly
    1985                 1990                 1995

Thr Leu  Asn Leu Asp Arg Val  Thr Arg Glu Ala Cys  Pro Glu Leu
    2000                 2005                 2010

Asp Tyr  Phe Val Val Phe Ser  Ser Val Ser Cys Gly  Arg Gly Asn
    2015                 2020                 2025

Ala Gly  Gln Ser Asn Tyr Gly  Phe Ala Asn Ser Ala  Met Glu Arg
    2030                 2035                 2040

Ile Cys  Glu Lys Arg Arg His  Glu Gly Leu Pro Gly  Leu Ala Val
    2045                 2050                 2055

Gln Trp  Gly Ala Ile Gly Asp  Val Gly Ile Leu Val  Glu Thr Met
    2060                 2065                 2070

Ser Thr  Asn Asp Thr Ile Val  Ser Gly Thr Leu Pro  Gln Arg Met
    2075                 2080                 2085

Ala Ser  Cys Leu Glu Val Leu  Asp Leu Phe Leu Asn  Gln Pro His
    2090                 2095                 2100

Met Val  Leu Ser Ser Phe Val  Leu Ala Glu Lys Ala  Ala Ala Tyr
    2105                 2110                 2115

Arg Asp  Arg Asp Ser Gln Arg  Asp Leu Val Glu Ala  Val Ala His
```

```
    2120                2125                2130

Ile Leu  Gly Ile Arg Asp Leu  Ala Ala Val Asn Leu  Asp Ser Ser
    2135                2140                2145

Leu Ala  Asp Leu Gly Leu Asp  Ser Leu Met Ser Val  Glu Val Arg
    2150                2155                2160

Gln Thr  Leu Glu Arg Glu Leu  Asn Leu Val Leu Ser  Val Arg Glu
    2165                2170                2175

Val Arg  Gln Leu Thr Leu Arg  Lys Leu Gln Glu Leu  Ser Ser Lys
    2180                2185                2190

Ala Asp  Glu Ala Ser Glu Leu  Ala Cys Pro Thr Pro  Lys Glu Asp
    2195                2200                2205

Gly Leu  Ala Gln Gln Gln Thr  Gln Leu Asn Leu Arg  Ser Leu Leu
    2210                2215                2220

Val Asn  Pro Glu Gly Pro Thr  Leu Met Arg Leu Asn  Ser Val Gln
    2225                2230                2235

Ser Ser  Glu Arg Pro Leu Phe  Leu Val His Pro Ile  Glu Gly Ser
    2240                2245                2250

Thr Thr  Val Phe His Ser Leu  Ala Ser Arg Leu Ser  Ile Pro Thr
    2255                2260                2265

Tyr Gly  Leu Gln Cys Thr Arg  Ala Ala Pro Leu Asp  Ser Ile His
    2270                2275                2280

Ser Leu  Ala Ala Tyr Tyr Ile  Asp Cys Ile Arg Gln  Val Gln Pro
    2285                2290                2295

Glu Gly  Pro Tyr Arg Val Ala  Gly Tyr Ser Tyr Gly  Ala Cys Val
    2300                2305                2310

Ala Phe  Glu Met Cys Ser Gln  Leu Gln Ala Gln Gln  Ser Pro Ala
    2315                2320                2325

Pro Thr  His Asn Ser Leu Phe  Leu Phe Asp Gly Ser  Pro Thr Tyr
    2330                2335                2340

Val Leu  Ala Tyr Thr Gln Ser  Tyr Arg Ala Lys Leu  Thr Pro Gly
    2345                2350                2355

Cys Glu  Ala Glu Ala Glu Thr  Glu Ala Ile Cys Phe  Phe Val Gln
    2360                2365                2370

Gln Phe  Thr Asp Met Glu His  Asn Arg Val Leu Glu  Ala Leu Leu
    2375                2380                2385

Pro Leu  Lys Gly Leu Glu Glu  Arg Val Ala Ala Ala  Val Asp Leu
    2390                2395                2400

Ile Ile  Lys Ser His Gln Gly  Leu Asp Arg Gln Glu  Leu Ser Phe
    2405                2410                2415

Ala Ala  Arg Ser Phe Tyr Tyr  Lys Leu Arg Ala Ala  Glu Gln Tyr
    2420                2425                2430

Thr Pro  Lys Ala Lys Tyr His  Gly Asn Val Met Leu  Leu Arg Ala
    2435                2440                2445

Lys Thr  Gly Gly Ala Tyr Gly  Glu Asp Leu Gly Ala  Asp Tyr Asn
    2450                2455                2460

Leu Ser  Gln Val Cys Asp Gly  Lys Val Ser Val His  Val Ile Glu
    2465                2470                2475

Gly Asp  His Arg Thr Leu Leu  Glu Gly Ser Gly Leu  Glu Ser Ile
    2480                2485                2490

Ile Ser  Ile Ile His Ser Ser  Leu Ala Glu Pro Arg  Val Ser Val
    2495                2500                2505

Arg Glu  Gly
    2510
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
ctcagggtag tatgggat 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
atcccatact accctgag 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
caccacactt ggcaatcc 18

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
gattgcgtgt ggtgatg 17

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
tgactgactg aatcgatg 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
caggtggggt ctttcatt 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atggacgagc tgtacaag 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gtcggatgca actgcaag 18

<210> SEQ ID NO 35
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
tgctgttgac agtgagcgcc gcttcttaga gattggcaaa tagtgaagcc acagatgtat 60
ttgccaatct ctaagaagcg atgcctactg cctcgga 97

<210> SEQ ID NO 36
<211> LENGTH: 98
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
tgctgttgac agtgagcgct tcctctcttt ctctcccttt agtgaagcca cagatgtaca 60
agggagagaa agagaggaag gatgcctact gcctcgga 98

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 37
ggaagaagaa cuauguauua uaugt 25

<210> SEQ ID NO 38
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
acauauaaua cauaguucuu cuucccu 27

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
cuuccucucu uucucucccu uguga 25

<210> SEQ ID NO 40
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
ucacaaggga gagaaagaga ggaagga 27

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 41
acuaaucagu acuuccauua agcct 25

<210> SEQ ID NO 42
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 42
aggcuuaaug gaaguacuga uuagucu 27

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Cys Met Gly Leu Pro Cys Val Val Met
1 5

<210> SEQ ID NO 44
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 44

Ser Met Gly Leu Pro Cys Val Val Met
1 5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Cys Met Gly Leu Pro Ser Val Val Met
1 5

<210> SEQ ID NO 46
<211> LENGTH: 2026
<212> TYPE: DNA
<213> ORGANISM: Homo sapiens

<400> SEQUENCE: 46
gcccctccag cctgctggag ccggagccgg agccggagcc ggagccggag ccggagccag 60
agccagagct cgaggactca ccggcccagt ctccgtccgg gatggggccc cgctcccggg 120
cgcgttgccg cccagtcccg gggaccgtcc ctaccgcgag ggtctgaggc gcggctgccc 180
cggggagggt ggaaggccag gcgtggggcc cgaacctctg gctgactttg gcagggccca 240
tctggcacgg cctccgcggc gcgcagctgt tttcaagtca gcaaacattt actgaggatc 300
tactatgtac aagatgaaca tctgcaacaa gccctccaac aagacggccc ctgagaagag 360
tgtgtggacg gcaccggcac agcccagcgg accctcccct gagctgcagg gccagcgatc 420
ccgccggaat gggtggagct ggccccctca cccgctccag attgtggcct ggctgctgta 480
cctcttcttt gctgtgatcg gctttgggat ccttgttccc ctcctgcctc accactgggt 540
gcccgctggc tacgcttgca tgggcgccat ctttgctggc caccttgtgg tgcacctgac 600
cgccgtctcc atcgatccag cagatgccaa cgtgcgggac aagagctatg cggggcccct 660
gcccatcttc aaccgaagcc agcacgcaca tgtcattgaa gacctgcact gcaacttgtg 720
caacgtggat gtgagcgctc gctccaagca ctgcagcgcc tgcaacaagt gcgtgtgcgg 780
tttcgaccac cactgcaagt ggctcaacaa ctgtgtgggc gagcggaact accggctctt 840
tctacacagt gttgcatccg ctttactggg cgtcctgctc ctggtgctgg tggccacata 900
tgtcttcgtg gagttctttg tcaaccccat gcgtctgcgc accaaccgac actttgaagt 960
cctgaagaat cacacggatg tgtggttcgt gttcctgcct gccgcccccg tggagaccca 1020
ggcccctgcc atcctggccc tggccgccct gctcatcctt ctgggcctcc tgtccacagc 1080
cctcctgggg cacctgctct gcttccacat ttatctcatg tggcacaagc tcaccaccta 1140
tgagtacatc gtgcagcacc gcccaccaca ggaggccaag gggggttcaca gggagctcga 1200 gtcatgtcct cccaagatgc ggcccattca ggagatggag ttctacatgc ggaccttcag 1260
acatatgcgc ccagagcccc ctggccaggc cgggccagca gcagtgaatg ccaaacactc 1320
tcgccctgcc tccccggatc cgaccccagg taggagggac tgtgctgggc ctccggtcca 1380
ggtggagtgg gatagaaaga agcctctacc ctggcgctcg cctctgcttc ttttggcgat 1440
gtggggccct caggctcccc cgtgtctctg cagaaaaaga ggaagaggcg cgtgtataaa 1500
gtgcgaacgt ctgagacctc ggatccggcg tcggggccta gggcccccag ccgccgctcc 1560
agctcgtcga cggattccgc ggacgccagc cctgtgcacg ccgctggccc tgccggcgcc 1620
taccactcgg cgtcggcaga gtccgtggac gagattccag tggcgcagac gcgcctgggc 1680
agcgccgctc tggccgcccc gcggggccgg ggccgacagc ccacgctggc gcggcaggcg 1740
cgtgcgcccg ccgttttcgt gagcccgagc agcggcgagc ccagggcgcc gggcggccgg 1800
gaggctggtc tggcttagct gggccgagag gccggagggc cgagttagag cggccggcct 1860
gactctctat gcaacacccc atccttgccg caccgagtgc actttagggg cccctacggc 1920
cggcgggatc ggcctccctc ccccacgact cagcaatacc cgccccaccg gctgtgatgc 1980
tccaataaac ttttttatgc ttttgcggaa aaaaaaaaaa aaaaaa 2026

<210> SEQ ID NO 47
<211> LENGTH: 4012
<212> TYPE: DNA
<213> ORGANISM: Homo sapiens

<400> SEQUENCE: 47
gtgggagccc gcgaggtggc ccgagcgagg gccccgcatc cccgcagagc ccgcccgagg 60
gcgcagcctg ccacgccagg ggaggcggcc gggcggcggg gaacggcggg ggcggagcgc 120
agcctcccga cgccgccgcc tcaccgcccc cctccgcctc ctcggcctcc gctcgcagcc 180
gccgcctccg cctccgccgg gctgaggagc cgggagtccg ccgcgccggc tcggggctgc 240
gggatgggga gttagcgcca cggcggcggc agtggccgca gcgcaccccg ccgccgccca 300
ggagcccgtc cagccagggg tgccgggccc gcccagcccg ccccggagcc aggcccgcgg 360
gcggcggcgg agctgggcag gtggatgcgg ctggaagatg gcgccctcgg gcccgggcag 420
cagcgccagg cggcggtgcc ggcgggtgct gtactggatc ccggtggtgt tcatcaccct 480
cctgctcggc tggtcctact acgcctacgc catccagctg tgcatagtgt ccatggaaaa 540
cactggcgaa caagttgtgt gcctgatggc ctatcatcta ctttttgcaa tgtttgtctg 600
gtcatactgg aaaactatct ttacattacc aatgaatcct tcaaaagaat tccatctctc 660
ttatgcagag aaagatttgt tggagagaga gccaagagga gaagcccatc aggaagttct 720
taggcgagca gccaaggatc ttcccatcta taccaggacc atgtctggag ccatccgata 780
ctgtgacaga tgccaactta taaaaccaga tcgctgccat cactgctccg tctgtgataa 840
atgtattttg aagatggatc atcattgtcc atgggtgaac aattgtgttg gattttcaaa 900
ttataagttc tttctccttt tcttggctta ttctctgctc tactgccttt ttattgcggc 960
aacagattta cagtatttta tcaaattttg gacaaatggc ctacctgata ctcaagccaa 1020
gttccatatt atgtttttat tctttgctgc agctatgttt tctgtcagct tgtcttctct 1080
gtttggctat cattgttggc tagtcagcaa aaataaatct acattagagg cattcagaag 1140
tccagtattt cgacatggaa cagataagaa tggattcagc ttgggtttca gtaaaaacat 1200
gcgacaagtt tttggtgatg agaagaagta ctggttgcta cccatttttt caagtctagg 1260
tgatggctgc tcctttccaa cttgccttgt taaccaggat cctgaacaag catctactcc 1320
tgcagggctg aattccacag ctaaaaatct cgaaaaccat cagtttcctg caaagccatt 1380
gagagagtcc cagagccacc ttcttactga ttctcagtct tggacggaga gcagcataaa 1440
cccaggaaaa tgcaaagctg gtatgagcaa tcctgcatta accatggaaa atgagactta 1500

-continued

```
actcttcaag caagataaat tcatacttta taaaagtatc aatgctgtag atggatggaa   1560
gaggcttccc acaggaaggt gccaccagtc agttgtgcct atgtcccttt ggctggaaat   1620
gcagaatatg aattgattag ttctctccaa gccattgctt aaaatataac atgttttgga   1680
tccaatacac acattgttac aactaacaca aattcctatt aaatattaaa agtagttctg   1740
gtttattaat caacggggaa aacatcttct ccaaaaaact tggaataaat ccaaggacca   1800
gtttttaccc aaatatatgg gtagcacagt ttatcacata gaaactccat taatcatctg   1860
attttccgaa tctgaaaatt gagactatta agatattagg atttcagaga tttcaagtca   1920
cattataatg ataagcatta ttcataaaac ttgttacctt taagaaggtg gaagtggcaa   1980
accatacttc ttttttttcc tctgatgtga atccagcctc agactgagtg aactgtaata   2040
attatgaatt cattacagag tccaggtggc ctgcagttga agatcatcaa ccatttttgc   2100
ctcacttaat tccagccttt tgttttctgc tggaaaataa gtgtggacat tgaagcttga   2160
gctctcaaag cagttggctg gaatactttt gtcagaatac ggtacatttc tattacatca   2220
gaaatatatt ttcatctctt cttgttaaat tgggaggaaa tttatgatag caattatgaa   2280
gattgtttta tgacattctt ttgtcagttt ggctttctaa aaatctcttt ttagattatt   2340
tctcctgttg aacatagtaa aactattgaa tttctcttaa gaattcctaa taggtcaata   2400
gatttaccct ccagtgatat ctatattatt tctttctcgt ctcatcaaaa tgatgacagg   2460
taaactatat ttttccttaa acacctatta cagttaaatt atgcaaatca ttaaataaaa   2520
atcatacaac ttttggaaag ttagttcaac atgaactaaa atggcatgct atttggaaat   2580
ttagtttgag ataaactaaa gtgtgttgat gccagaatgt tcagcttcag taaatataat   2640
aagctcttgt gccttgtatg cactatttaa aaaaagtttt ttttatttga gtccagtata   2700
attcatgtaa atgttaacaa ttagaataat actctgtatg ctttttttgat actgattttg   2760
agaatttaaa gcagattacc ttttaaaact ggaccaacta agtaattggt atttaatcaa   2820
agagaaaatg gtaataaact tttcaaaatc tttgttaaac caaacattca acacaaaata   2880
aactagaagg ccagaggata atggaataaa agatcattgc aattacttat ccttcctaaa   2940
aatatagttt tatattaatt gtgcttatgg aagaaacaat gtcagccaag tccattttat   3000
agtttgagtg caattctttg aacaatagaa atatctgcag tctttcacag atttgtatta   3060
tgctgaagag tttcatctga caatctgctt caagaaatct cagaaaatat gataacattt   3120
taactttcat tttagagcac gttttggtca tttttaaaaa tacctaaagt gccagaccgg   3180
aacctatagc tactgctaga agtcttaaaa aaaccaacag cagcacagga tgtattaaga   3240
attatatgaa gtcaggtttg tttttttttt tttttttttt tcaaagcaca gtactgttag   3300
ctgtttttgt ggacaggatt cgattaagta ttccctcttg tcaaactgga agctagggga   3360
aaaagaggga tttttatcct ttactcttct agagtactgt taatgcccct ttcccacagt   3420
cttttatata attaaatata tgtcaataca cattagaatc agatttgaaa aagttaaaac   3480
aatttcattg ttgtaattgt tccctttctg ttttcatata gtgaataacc tttaaagggt   3540
tgttttgttt tgttttgaat tataggagtt ataatctttg gagatgattg catatctcat   3600
tagatatgca atataaattt atctgagtga acaaagtgct aaataaatag atctacattt   3660
tgtacatatt tatataaaat ttacctttaa gtatttactt taaaaaattt aatggcttaa   3720
ctcgaacttg aagacacata cttcaactgt ccttattgtc cattaaactg ataattttga   3780
tttttcttgc ttttatagat tttactatat aggaatcaag atttaagaaa ttttgcatta   3840
aaaatagtgt accaatgctt catatacgtt agttatttgc tattatgtag ggaagaggat   3900
```

tgttatttca aagatatatt aaagaacagt tgcatctgaa tataatcatg atgcattcaa 3960
tgaagttcat atccatgaat tcactcctaa tataccctaa taaagtggtt ga 4012

<210> SEQ ID NO 48
<211> LENGTH: 12630
<212> TYPE: DNA
<213> ORGANISM: Homo sapiens

<400> SEQUENCE: 48
gcgtcatcaa cctgcgcggc ggccgctcct gcagccgcgg ccgccgccac tgccgggaga 60
gctcgatggg cttctcctgc gcgccgcccg gtgtctggcc gagtccagag agccgcggcg 120
cctcgttccg aggagccatc gccgaagccc gaggccgggt cccgggttgg ggactgcagg 180
ggaaggcagc ggcggcggcg gcgggagccc caccggggtc tgggactggg gaactgcctc 240
cggcttcacg atgccagtat ggacagaata gcttatgatg cttatcccca cccaccactt 300
ccgaaacatt gagcggaaac cagaatacct ccagccagag aagtgtgtcc cacccccccta 360 ccctggtcct gtgggaacca tgtggtttat ccgtgacggc tgtggcatcg cctgtgccat 420
cgttacctgg tttctggtcc tctatgcgga gttcgtggtc ctctttgtca tgctgattcc 480
atctcgagac tacgtgtata gcatcatcaa cggaattgtg ttcaacctgc tggccttctt 540
ggccctggcc tcccactgcc gggccatgct gacggacccc ggggcagtgc ccaaaggaaa 600
tgccactaaa gaattcatcg agagtttaca gttgaagcct gggcaggtgg tgtacaagtg 660
ccccaaatgc tgcagcatca agcccgaccg agcccaccac tgcagtgttt gtaagcggtg 720
cattcggaag atggaccacc actgtccctg ggtcaacaac tgtgtaggcg agaacaacca 780
gaagtacttc gtcctgttta caatgtacat agctctcatt tccttgcacg ccctcatcat 840
ggtgggattc cacttcctgc attgctttga agaagattgg acaaagtgca gctccttctc 900
tccacccacc acagtgattc tccttatcct gctgtgcttt gagggcctgc tcttcctcat 960
tttcacatca gtgatgtttg ggacccaggt gcactccatc tgcacagatg agacgggaat 1020
agaacaattg aaaaaggaag agagaagatg ggctaaaaaa acaaaatgga tgaacatgaa 1080
agccgttttt ggccacccct tctctctagg ctgggccagc ccctttgcca cgccagacca 1140
agggaaggca gacccgtacc agtatgtggt ctgaaggacc ccgaccggca tggccactca 1200
gacacaagtc cacaccacag cactaccgtc ccatccgttc tcatgaatgt ttaaatcgaa 1260
aaagcaaaac aactactctt aaaacttttt ttatgtctca agtaaaatgg ctgagcattg 1320
cagagaaaaa aaaaagtccc cacattttat tttttaaaaa ccatcctttc gatttctttt 1380
ggtgaccgaa gctgctctct tttcctttta aaatcacttc tctggcctct ggtttctctc 1440
tgctgtctgt ctggcatgac taatgtagag ggcgctgtct cgcgctgtgc ccattctact 1500
aactgagtga gacatgacgc tgtgcgtgga tggaatagtc tggacacctg gtgggggatg 1560
catgggaaag ccaggagggc cctgacctcc cactgcccag gaggcagtgg cgggctcccc 1620
gatgggacat aaaacctcac cgaagatgga tgcttacccc ttgaggcctg agaagggcag 1680
gatcagaagg gaccttggca cagcgacctc atcccccaag tggacacggt ttgcctgcta 1740
actcgcaaag caattgcctg ccttgtactt tatgggcttg ggtgtgtag aatgattttg 1800 cgggggagtg gggagaaaga tgaaagaggt cttatttgta ttctgaatca gcaattatat 1860
tccctgtgat tatttggaag agtgtgtagg aaagacgttt ttccagttca aaatgcctta 1920
tacaatcaag aggaaaaaaa attacacaat ttcaggcaag ctacgtttc ctttgtttca 1980

-continued

```
tctgcttcct ctctcaccac cccatctccc tctcttcccc agcaagatgt caattaagca   2040
gtgtgaattc tgactgcaat aggcaccagt gcccaacaca tacagcccca ccatcatccc   2100
cttctcattt tataaacctc aaagtggatt cactttctga tagttaaccc ccataaatgt   2160
gcacgtacct gtgtcttatc tatattttaa cctgggagac tgttgtcctg gcatggagat   2220
gaccatgatg ctggggttac ctcacagtcc ccaccctttc aaagttgaca tatggccatc   2280
ccattggcca gaatccacag acacacctaa gcctgtggca ctgggacaga atagattttc   2340
catttgagag gcacttcctg tgtcagtctt gtttgaagga ggtggtgatg gtggatagag   2400
gtgaaggagg tagggagtgc cctccaagtg caaaaataac aaatatgatt attgaccatc   2460
ggggaattct cacacattga tttgtttttt aagcaattgc cagaaacccc ctttttttagc   2520
ttttgcttgg ggtgggggta ggagttaagg tttattcaat cctgtcctgg gtagggcgaa   2580
agttaatcta gccatgtgat ttttcagaaa agtaagtgga acatgctgcc acttttcaat   2640
tctgtcagtg cttccacatg gaaacaaaat gcaataaaat ttttccaaaa cctgttctga   2700
tttagctctc tcttgaggtg ttacccttag tgggaggccg actatccaca atctacttga   2760
gttttctctg gttgggtgtt tgtttcattg ctctgtctct tgaatgagga tactttattt   2820
tttttgtttt aaaatgcatt tatggtccct ctcttgaacc agcttgcccc accaggcctc   2880
tttcctttgc tttctgcagc ctgaatcaat tcctttgtgc tgatgggctc tcctaagagc   2940
tttcctgagt cagttaactt tacctcgtgt ctacggtgct attcatgcga tacgggcgag   3000
gctgagatgc taagattaaa aagaaaagaa tgctgtttta gatcaagttg atagcatttg   3060
ttttccatat gctttttttaa aatttttttca taacatacag ctcagttagg tgtatgaaag   3120
aagtgttatt gtattaaata actagagcag ggctacagct ctggccctcc cctaggggga   3180
agagattggt aatactccat cttccagggc atttttttaaa gtgagccagg ttagctcttt   3240
tcccctggca tttctcagga atgcagtaga tagtgctgaa gatgcactga ctttttttta   3300
gtcctaaaaa tagaaactcc tcctttaaag ctgtgcatac tatgcttatc tttccaatag   3360
agtggggttc cttcagatat cctataggat tctgcctctg gttttgtata ggccttggct   3420
agaaagagtc aatgtttctg agctctcaaa ccagttgctc tcagaagata ggaatacccc   3480
aaggttcctg gcatttttcc tatttcattt ttgttcagac tgatattttg ccaagagcac   3540
aatgactgag gaatgtagcc atcatttgca gggtagtgat tggttcccag cctggcttcc   3600
acacaggaca ggaagggaaa gcatccctga gctctcctca gtatttccgg atgtaatgaa   3660
agaggacatc tttctacaca aagtcagccc caactttttgg cttggtcaca ggagttctga   3720
tagtactgtt tggtgcactc atgggaaatt gaaccagtcg tagccacagt ctttcagagc   3780
ctgggctctg gggagtggaa gtgaaaaata aagatgtggc ttgttggatt gtgatcccca   3840
gcttgctttc cttctgtcaa ctctgtcagg tttgtgttca tagcaactag actgaatatg   3900
caaaaggctt agatccaagc aaatctataa tctatgcata tttgcatggg cttggtaata   3960
tcatgtacac aaaacacatt tgggtagaag tgcatgtgct aaatctcctt ttagtcccac   4020
cattttgtct tcttcatact gtacttcctc ttttttgttt gagacaaggt cttgctctgt   4080
cacccaggct ggaatgcagt ggcacaatta gagctcactg cagccttgaa ctcctgggct   4140
caagtgattc ttgtgccttg gcctcctgaa tatccagggc tacaggcacg tactaccatg   4200
cctggctaat ttttttgttt tttaatagag tcagggtctc actgtgttgc cctagctagt   4260
ctcaaatgcc cggcctccag caattttcct gccttagcct cccaaagtcc tgggattaca   4320
ggcgtgagcc actgggccca gccctgtact tcttgaaaaa gccccaagta ttagcttttg   4380
```

ctcatctggc taggccactt aaatagttag aatccaccgt cccctaatgc agaaaccgtt 4440
taggtgaggt aaattaacaa acattttaag ccgggcgcgg acacttctca ctgtggacat 4500
ccctcacgcc tgtaatccca gcactttggg aggccgaggc gggcagatca cgaggtcaag 4560
agatcgagat catcctggct aacacggtga aaccctgtct ctactaaaaa tataaaaaaa 4620
ttagctgggc gtggtggcag gcgtctgtag tcccagctac ttgggaggct gaggcaggag 4680
aatggcgtga acccgggaag tggagcttgc agtgagccaa gatcgcacca ctgcactcca 4740
gcctgggcga cagagtgaga ctccgtctca aaaaaaaaaa acaaacattt taaacatgta 4800
tgtgaggttg gcattacaca gaaactcctc tccgggtggg ctgggatggg ctttctcagc 4860
caggctaatg ggttttaaat ttctctcttt tcaagacttg cagtgcatca gcttaaaggg 4920
tgagccagcc agtagagggg aaggcgcccc acctagaagg tgcccttaga tatcaaagaa 4980
atgtgaaaag agaaagattt tgctagaatc ctcctcaaag gtgttcttga ggttgccaga 5040
ccagcaacgt caacatcagc atcacctgag aacttgttag aaatgcacat tctcggtccc 5100
caccccaggc taccgaacca gaaaccgagc ggggcccagc agcccgtgtc ttaacagccc 5160
tccaggtgat tctgactatc aagtttgaga atccagttgg ggctagcagg agtcccccct 5220
caggtggtcc ctgatgcctg ctggtgatat gggtcttgtg tgctgctggg ctcagcatag 5280
tgcagttggg gtgtgctgat tgtgagacag gcacgtgttc cctccgcgga gaagccactg 5340
agactgcctt ccctcataag ctgcggcctc cccaacaaac aactgccaag acatcaaaga 5400
aagtctgtat gaagcagatc caaattatta gcctgcccac cactccttgt gcatctcatc 5460
agtggaaccc atctctagac caagggccct ttgggtgaag aagcagcccg gaagggaaag 5520
agaaaagagt agaaccaagg gacctccaga tgggagcggc ggccggtgag tagtctagag 5580
ccaggggcat tgtagcagcc tggatacatg acctgaacac gtcttgacct ttgctttcta 5640
cgtgtgggtt tcaacaccca tgtggctttt tcttgtattc tttaaatatg tatctggctt 5700
aggatcacct catagaagag aaagaattca cagtgaagca gaaacaagcc actgaccagc 5760
gtactcccaa cctgaacctt ctttttctca ccctctccct caagtaaaca tcttgctgac 5820
ttgagcagtg tgattgccgt agcaaagcag agtggccccc agggatcccg ctctgttggg 5880
cccacaggag gagccgatga agctgatcca aggagtgagg acaagcgctg cagagggacg 5940
ttcgctaaaa gccttctagg ggccgcacat gctctaacac ggacataagg atgccctgaa 6000
tttctgcagc tgaggccata tagtctggtg accaagtatt tgggtcctgg cttcagtctt 6060
tggttgaaat gtctgcttgg ctacttatta ccgcacctac taccaaaata tgaccttgag 6120
cagtaacttc tttaagcctc agtttttca tctgaaaacg ggaatgataa tctaaatcac 6180
aaagttaatg gaaggattaa atgagggtga tgaataggaa tgtatagcgt ctggccctgg 6240
tatggcttta taaatgttag ctgtgttgga gctgtgcttt tcaaaccatt ggtcacagcc 6300
attcatggtt tgcaaccagc atgtttttca agaaaaatgt ttaatgcatt acatattgca 6360
ggataagtat tgttttatga agcttaggga gttgtgtgta tatgtgttct ggaatgcaac 6420
agaaaaatgt ttcctcttgt gggttacaat atagaggtat gaaatctctg atgaggagag 6480
acagtgttat ctggcccgct atgaagagac acatttgcat aggctgctcc ctgaggctct 6540
ggctttctac atctgatgat acagggagca gggaacagcc tgttctcgtt ctgtggggct 6600
cagctgagtc tgttctgcac agactcttcc ttcctcggga gccttagtcc taatacattc 6660
attttggagt gttggtgagt ttgttcacag atcacagctc atgtgtcacc cagactgacc 6720

-continued

```
tgggccaaaa ggcccatcac acaccctgca agagcttctg gtgtcgacta tgaccccctt   6780
accaggcatc aaccattttt gttcgttctc ttgagcctga agctactatt actgctcctc   6840
tgcaaacctc aagcttaaga actttgcctg caggatccct ttaaatccac acaaaactca   6900
aaattgagtc ctaccaggaa aaagcagccc tcagcccatt tttatacatc ggatttgttt   6960
gcaatatttt ctttctagac tcaaaagtca acactccctg aaagtttgtc gactttactg   7020
ctgaagacct ctggtagaca ggccaggctc tgtctggaat actttatgag gttggtgagg   7080
aggttgagta taatccaaga gtgcctatct gggagcatgc cacatgaatg gcaaataatc   7140
atcctgtggg ctcttggctt cattcccctt ctctctgact gagctcagcc tgggcacagt   7200
ggtgatttgc agtagaactg gaaacctgtt gggcagaaaa aaagacacta gttctggttc   7260
cagttctgat acataacaag ctagatgagc cttggccacc gtcatggcct cttggaactt   7320
ctgtttcttc cccatctgcc aatcatcaat actcataccc acctcctcac aaggaggcca   7380
taaaaaccta tggtcatggc tttgagtcca agtcagtgtg gatgcagcca gtctgtcatt   7440
tttgggtgtt tcctctgtag ccgggtctgc catatggtga tgtcccagct ctcgtgctat   7500
gaagttaaag cctctttctc aacaggctgc agatgatcac ccaggaagag aatgcagaat   7560
gcccaaagca aaccatctca gctggtcact gcttctgtgc caagaaggga ggcctggcga   7620
ggggccagtc aggaagcagc atggcatcac atgctcatga cccacatgaa ggtcccttta   7680
gacttgtgtc aacaagatcc attttctgaa acaactattt ttgttctgat tataaaagta   7740
acattggctc attggtaaaa cttggattgt gtgagaagtc tacagaaata aatacaaatc   7800
ctctagaatt ccatccccaa aagtaaccac tcagacaaat gttctaatgt catgtaaaac   7860
catattaaac catcttttct agctgcatag tgttatagaa tcatttgctt aaccatcatt   7920
attgggcatt tctcatttcc agctttgcat tattataatt cagtgttcaa gtttgtattg   7980
cataaatctt tgtctcagat tattgattat ttttaaactt tttgtgaaat cagacttaca   8040
aaaatgtgac aaaaacagta caaagagttc ccatgtacct ttcagtcagt ctcaccaaag   8100
gtaaacattt tatacaacca taatacaaat ataaaaccct ggacattggc aacaccatac   8160
ccttaactaa tgtatgtacc ttattcacat ttctccagtt gtcccattaa caccctttc    8220
tgttccagga tcccacactg catcatttgc gatgtctcct tagtctcctc cagtttgtga   8280
cagttcctca gtcttccttt gtctttcatg accttgaccc tttttaaaaa tcgaggtgaa   8340
attcctgtaa cacaaaatta gccattttaa agtgtacatt taatgcattc acaatgtttt   8400
gtaaccacca ggtctgtctg gttccaaaat cttttcatca atctttgacc cttttgaaga   8460
ttgtagggca ggtattctgt aggctgtcct tcagattgtg tttttgatgt ttttctcatg   8520
attagattga ggttaggcat ttggggcagg agcactgctg aagcaatgtg tcctcgttgc   8580
accgtatcag gaggcatatg gtgttgatac gtttcattat tgtgatgtta actttgatca   8640
ttgggtgaag gtggtacgtg caatgtttct tccctgctat taaggtactg tttttccctt   8700
tgtaattgat aagtatctta tgaggatata cttttgagat ccaatttttt taacttagaa   8760
tttattcaaa agtcaagaat cttaaatctc tgaaatggcg tgggaagaaa aagtgctaga   8820
tacacagaga tctttcttga gtcatgtgaa ggagcagtgc ccaagcccag caaacccaca   8880
gcaaattccc ttggcttcca gaagagatgg agaaagcagt gcccccagtg gagggtcaaa   8940
ggcctctgtg cagggtgttg tgggcctgga gagctggcct ggccatgtct ttacctcctc   9000
tgggcatctc cccaccccaa caccctttct gtggcctggt ggctgagttg cagccgacac   9060
ccagaggcag gtgagttgac agcttggaag aggctgcagg gtggatctgc tgcatgagca   9120
```

-continued

```
ggcctgagcc cagccttacc tccccacagt ggtcctgtgt gccctccggc tgcctaatgc   9180
atgttggcac ttgctgtacg agcacccgct tcttcacctc gcatgctgtt tgtgtcctgc   9240
actccttcct taaccccatc gtccttctgc tgtgtttgca gcccctatct accctggtgg   9300
gagtggccaa aaatatttag gaggggatca ccagtttgta gtggcctcag aggatgtgtg   9360
gtccccctta tgcctcagcc actcatcagc ctagcccctg cccatcatct ggcattgcac   9420
ttgtggaagg aaagaagggg agggctgggt ggtgggtgga gaacacgtca gtccaccagg   9480
cgggccctgc ttgctgtgtt cctccacgct gctgtccacc cacaccccag cagtcctctg   9540
agggacctcc cgggggtgac ctgggccaca acagactgcc cactcagacc ccatcttacc   9600
catgccgtgg acaccccgcc cccccccccg ccactgctat gctatagctg ggggtgtcta   9660
tgtgagctgt acagcccagc accacgctga cgatgttctt catccccttc tccctgcagg   9720
gcatcgagcg cctcaaacga aagaaccagc ccagggagca catggggagc tggcagtcag   9780
taaaggagac ctttggtggg gacttctccc tgaactggtt caaccccttc tccagaccgt   9840
gtcagccaga gatccccagt gacaaagaca tggtgcggca ggtgacatcg ctgtcagaca   9900
ccgaaacaat ggaggatcca tcagaggaga caaaggacga ggactctgtg gaggtgacag   9960
atgaatagat gctgctgtgg ggagagaagc aaacactaaa aagtgctgtc aaccttcatc  10020
ctggggtttt ggctaaaggg gcttatgggc atggtgcgct cccagcaccc ccagtgcttc  10080
ccttagccac tcgcttggcc ttgccatttc ccctccttct tctctccatg ttgggccagg  10140
tctgggggtc gggagtaggc tggggacatc agaggaggat gggggctttc tcagagttca  10200
tctaagaaga gtctgcactg agacggctca tcaagaaccg ttctccaaga ctgggtggct  10260
ttcacattct ccgcccagca aagggagctt ttgaacaggg catcccaggg gcagaaaaga  10320
gcttgccttt ggctttcccc aggatttctg tcttctcttg ggaaggctgg gcccctggct  10380
cctggctttg agaagtaagg ttgtgacaga aggaccgggc agggcttgcc ttggggacct  10440
gggttgggac actgacatca ggggagacta gcctggaaag actgcagagc tgccagctac  10500
tccctggaaa gggcttcccc atgctgcctg ccgaaattag gaggtagagg tggctgccac  10560
atctacctgc aagggccagg catggttcaa agaggaccct gcattaagct ctacacacac  10620
atgtgcagga catgtccagc atggacagag ccagagttaa gacagtagca ccgaaaatga  10680
gcccccattc cacagacact ggagtcttca ctgagcgaga cagctgggag ctgtcctgcc  10740
tgtggctaca tatctagcca ttcacagatg tggatatggg aaggacctct ttggagctac  10800
tggggactcc ctaaccactc gcatgagaac ttaattgaat gttacctctt ggagggagtc  10860
taataacaca tgtaggtaga actgaccata aaccctgcct gtgtgtttga aaaggccagt  10920
tctcccaaat tggtgcccat cttgtctctg aaaagatggg tgatggccag ggtctgctga  10980
ttgatgaatc agatgaatca ggaagataga caaacacaca cacacacaca cacaccccac  11040
caggatgagt ctgccctcta ttcaccccat ttgaagcctg tggtgtctgt gaccactgct  11100
gaaggtctga gcagcgttct ggtgctccta aaccccattc cagtggttgc tgaagcagca  11160
tcttctgcac aaagcccaac agaagggttc ttatccccgt ttggtataag aagtggattc  11220
accacccact ccctccacgt gcctttgttc ctctctttgg cccatttccc cagcgtctac  11280
tggcgtcagg attggcagga gcacaggcac tcagcagagc atgcccctgc aagacctcag  11340
tgttagggcc ccccttccag ctccaggcaa aagggcatga gtcctggccc caaggggcct  11400
gtggctgcag ttcagaggag aagaaggtca gtgtttggag gtgcagcctc aggatgctga  11460
```

-continued gaaaggaaac tggcgaccgt gagaaagaaa agagccaagc agcatcctgg ttcttggaca 11520
gcatctttgg acactctgtg aagggcaacg atcctgccag agaccgtctc tctacaactg 11580
atgacccact agggcctggg gttaattgct caaagggccc agtgttcaca aagccacctc 11640
tgccctaacc cttgccagag ctctccaact atgacccacg agaggggtga tggtgggatt 11700
ctaacatcaa cagagcaacc agaaagacat tgggcctccc acactcaggc tgcaggccca 11760
ctttcttggt ccttatcagc tttaatattt attaatgacg acataggagc ccgagtcagc 11820
tgtaaaggcc attaacttgc aatctggaca ggaagttgac gctcaccact ttgggtaaga 11880
gctgctctga ctgtagggcc ccctatttgt tgtcctaacc cagaagcagc tctgggctgc 11940
caggatggtg gatggaatac cagagagttc acactaggga ggaagcaatg cctgcccccct 12000 ggagtctcct agggggcagc agttagaata agggaagagg atttgctggt cactgtttgc 12060
tgacatgggt ttccatggtg agttcaggcc tgaggacagc agtgtctgca aaaccacatg 12120
gcccttgaga aatgtccttg cacattgggc ttcaaactcc tcttctaggg aatccatctt 12180
ggcctgaaag cagaggtaca acaccagccc caaaggcaat tctgttttca gattggttgc 12240
tctggaaagg aaggctgggg tgagggggca ttttacttgc acagaggctg accctgcctc 12300
ccctcttcac tgaccccatc tccaaggtag acctcagcca tgtcagtccc tgttctggga 12360
ggtgctgggc tgggccacag ccagggttat gtaggtaatt aacctgtcca accctgagcc 12420
tcgcctcccc acaccagcaa cacagtggtc tctctgtggt gaccattcac agcataacat 12480
tctgcttagc ctcagactga aagcattgca actgatgtca aaaccagatg agatcttaca 12540
gggagagaga ttgggtgcaa tttgcctctt tctttgaata aaaagctctt tgctcaccct 12600
caaaaaaaaa aaaaaaaaaa aaaaaaaaaa 12630

<210> SEQ ID NO 49
<211> LENGTH: 1570
<212> TYPE: DNA
<213> ORGANISM: Homo sapiens

<400> SEQUENCE: 49
gatgtcacga gcccgcagga agtctcgtat cgcgcccggg aggcgccgga gcccagcggc 60
tggcggtaag gccgcctccg cggggctgtg ggaagcttgg gctgtcccag gaccgtcagt 120
ctcctcctct gaccctccct ttccccttgt gtgtagggcc gccgtcccac ccccacctcg 180
cccgagtccg gggcggcccc ggtgtcccct ccgagcctgc tgcactccac gtccccctac 240
cagggctcca gcccccaggg aaatctccga ccaggcccgc ccaggagcca gatccaggct 300
cctggaagaa ccatgtccgg cagctactgg tcatgccagg cacacactgc tgcccaagag 360
gagctgctgt ttgaattatc tgtgaatgtt gggaagagga atgccagagc tgccggctga 420
aaattaccca accaagagaa atctgcagga tggactttct ggtcctcttc ttgttctacc 480
tggcttcggt gctgatgggt cttgttctta tctgcgtctg ctcgaaaacc catagcttga 540
aaggcctggc caggggagga gcacagatat tttcctgtat aattccagaa tgtcttcaga 600
gagccgtgca tggattgctt cattaccttt tccatacgag aaaccacacc ttcattgtcc 660
tgcacctggt cttgcaaggg atggtttata ctgagtacac ctgggaagta tttggctact 720
gtcaggagct ggagttgtcc ttgcattacc ttcttctgcc ctatctgctg ctaggtgtaa 780
acctgttttt tttcaccctg acttgtggaa ccaatcctgg cattataaca aaagcaaatg 840
aattattatt tcttcatgtt tatgaatttg atgaagtgat gtttccaaag aacgtgaggt 900
gctctacttg tgatttaagg aaaccagctc gatccaagca ctgcagtgtg tgtaactggt 960

```
gtgtgcaccg tttcgaccat cactgtgttt gggtgaacaa ctgcatcggg gcctggaaca   1020

tcaggtactt cctcatctac gtcttgacct tgacggcctc ggctgccacc gtcgccattg   1080

tgagcaccac ttttctggtc cacttggtgg tgatgtcaga tttataccag gagacttaca   1140

tcgatgacct tggacacctc catgttatgg acacggtctt tcttattcag tacctgttcc   1200

tgacttttcc acggattgtc ttcatgctgg gctttgtcgt ggttctgagc ttcctcctgg   1260

gtggctacct gttgtttgtc ctgtatctgg cggccaccaa ccagactact aacgagtggt   1320

acagaggtga ctgggcctgg tgccagcgtt gtccccttgt ggcctggcct ccgtcagcag   1380

agccccaagt ccaccggaac attcactccc atgggcttcg gagcaacctt caagagatct   1440

ttctacctgc ctttccatgt catgagagga agaaacaaga atgacaagtg tatgactgcc   1500

tttgagctgt agttcccgtt tatttacaca tgtggatcct cgttttccaa gcaaaaaaaa   1560

aaaaaaaaaa                                                          1570
```

<210> SEQ ID NO 50
<211> LENGTH: 4582
<212> TYPE: DNA
<213> ORGANISM: Homo sapiens

<400> SEQUENCE: 50

```
gagacccggc actgagggca acggccgcgc gccggctccg agacgagcga cgcctggcgg     60

gagcgcgcgg cagcggggcg ggcgtggagc gtgcgggggc cgcgcgctgc ttctctgagg    120

caggacggca ctgccgggag gcggcggtga caacgacggc ggtggtgacg ggcaccgggc    180

tcgcgggtga gacacagtaa cctggttgaa ctctgcatct ggaaagctga agactgaaga    240

aagataagag acattgacta gtctggaaac agggacatct ttggaacttc gttttcatcc    300

acagtaaact tttgaagtgt catcaattgg aattgatttc ttcatcttat tctgcctatt    360

gggaagaaca tggcttcaag gattttaagt ttccctttag ttttacatga actttgtagg    420

aaacagagcc cttaaagggc ttgggaataa caagaagaga ttgaagacag agaagcttgc    480

cctgttttcc ttgccccttc aaagaaaagg atttacagct caaacttaga acagctgttg    540

tccagcttta gccatcaaga gagaaataaa ttaaaccacc attgccagac tacaagccct    600

ggtgaagtca gggtgtggga gtggtggcat tgagaagact acctaaaaga gacaaagact    660

gcagtaaaca aagctcctct ttaaagttgg aaggggcctc aggttccttc ttggattgaa    720

atagaaatag aaacacaggg cacacctctt ttaggtgcag ctcacatttt atggaactgt    780

agtcgtggag gtactatagt atctcagaag aatttttctt tgcccaaagt ttttttgcca    840

taccctgata ttctctcctt cttttgaaga cctgcctcca tccatgagct gtatcttgat    900

ctgtctgact gtccatgttt tccacctgca accatttgca tgtgtacagc ctactgtttg    960

tctccagttt ttaaactgta caagttgtgt ttcttaatct tcccttctgc cttgttctgg   1020

ggaggtggtt attcatcatt tggaatcacc tttccccctc ccatgtgctt tccttcattt   1080

gagatctttt gacctttggc tttatttggg agggggaagg gtgataaagt tttctgtttc   1140

cctggttttc ttttgtactc ctctctgttg cttccctcct cccattttct tgtctgttct   1200

gccgctgtgt gggcctgggc tatgcggcag ggcagatttc ccatcagagc tccaacatgc   1260

ccgcagagtc tggaaagaga ttcaaaccca gcaagtatgt cccggtctct gcagccgcca   1320

tcttcctagt gggagctacg acactcttct ttgcctttac gtgtccagga ctaagcctgt   1380

atgtgtcacc tgcagtgccc atctacaatg caattatgtt tctctttgtg ttggccaact   1440
```

-continued

```
tcagcatggc caccttcatg gacccaggga ttttccctcg agctgaggag gatgaggaca   1500
aggaagatga tttccgagct cccctttaca aaacagtgga gataaagggc atccaggtgc   1560
gcatgaaatg gtgtgccacc tgccgctttt accgtccccc tcgatgttcc cactgcagtg   1620
tctgtgacaa ctgtgtggag gaatttgatc atcactgccc ctgggtgaat aactgtattg   1680
gtcgccggaa ctaccgttat tttttccttt tcctcctttc cctgacagcc cacattatgg   1740
gtgtgtttgg ctttggcctc ctttatgtcc tctaccacat agaggaactc tcaggggtcc   1800
gcacggctgt cacaatggca gtaatgtgtg tggctggctt attcttcatc cctgtagctg   1860
gcctcacggg atttcacgtg gttctggtgg ccaggggacg cacaaccaat gaacaggtta   1920
cgggtaaatt ccggggaggt gtgaacccct tcaccaatgg ctgctgtaac aatgtcagcc   1980
gtgttctctg cagttctcca gcacccaggt atttggggag accaaagaaa gagaagacaa   2040
ttgtaatcag acctcccttc cttcgaccag aagtttcaga tgggcagata actgtgaaga   2100
tcatggataa tggcatccag ggagagctga ggagaacaaa gtctaaggga agcctggaga   2160
taacagagag ccagtctgca gatgctgaac ctccacctcc tcctaagcca gacctgagcc   2220
gttacacagg gttgcgaaca cacctcggct tggctactaa tgaggatagt agcttattgg   2280
ccaaggacag ccccccgaca cctaccatgt acaagtatcg gccgggttac agtagcagca   2340
gtacgtcagc tgccatgccg cattcctcca gcgccaagtt gagtcgtggg gacagcttga   2400
aggagccaac ctcaattgca gagagcagcc gtcaccccag ctaccgctca gagcccagct   2460
tggaaccaga gagcttccgt tctcctacct ttggcaaaag ttttcacttc gatccactat   2520
ccagtggctc acgctcctcc agcctcaagt cagcccaggg cacaggcttt gagctgggcc   2580
agttgcaatc cattcgttca gagggcacca cctccacctc ctataagagc ctggccaacc   2640
agacacgcaa tggaagccta tcttatgaca gcttgctcac accttcagac agccctgatt   2700
ttgagtcagt gcaggcaggg cctgagccag acccaccttt aggctatacc tctcccttcc   2760
tgtcagccag gctggcccag caacgggaag ctgagaggca cccacgtttg gtgccaactg   2820
gcccaacaca ccgagagccc tcaccagtcc gttacgacaa tctgtcgcgc cacattgtgg   2880
cctctctcca ggaacgagag aagttgctgc gccagtcacc cccactcccg ggccgtgagg   2940
aagaaccagg cttgggggac tcaggcattc agtcaacacc aggctcgggc catgcccctc   3000
gtactagttc ctcctcagat gattcaaaga gatcaccttt gggcaagact ccactgggac   3060
gcccagctgt cccccgtttt ggcaagccag atgggctaag gggccgggga gtagggtccc   3120
ctgaaccagg cccaacagcc ccatacctgg gccgatcgat gtcttacagc agccaaaaag   3180
cccaacctgg tgtctctgag acagaagaag tggccttgca gccattactg acacccaaag   3240
atgaagtaca gctgaagacc acctacagca aatccaacgg gcagcccaag agcttaggct   3300
cagcctcccc tggcccaggc cagccacctc tcagtagccc cacgagggga ggagtcaaga   3360
aggtgtcagg ggttggtggt accacctatg agatttcggt gtgagccttc ggcacctccc   3420
ctccccaacg cctctgcgcc tacaccaaag ggccccaggt ggccaccttc cttccctcaa   3480
ggggctcccc tcccgtgcat ggacattttt taaaccaccg attccaagag gatgaggagt   3540
gttttctaaa atgcagtagg cttggggagt cggagagttg gggccctgag actggggtag   3600
caaccccccc ttttatcttt taagaccttc ccttccttga tccctggacc agactcagtg   3660
gacatttgtg caattgctcg ccctggaggg aaccagatca tttttaaacc agaaataatt   3720
ttttttatta ttgttacgga ttctattttt ttcctcttct gcgttaccag gtgtgtgtgt   3780
acatataata tatatatata tatattataa atatcaaaga aattatatat ctatcctggg   3840
```

```
atgggaaaat gagggaggga tacatatacg gaggggggatc ttactcttcc cattcctcag   3900

accagcagga aaagagggga gacgtcagtc tttttcctgt ggttccctct catttgtccc   3960

agttactaac tacggaaata gcatcctctg ctggtgctaa gtgtgattag gaagaagcct   4020

ggggagaggt gagtctggaa ttttggtcac aagagggaag gacttggaga ggagaattag   4080

ttttctaggc tcattggcat ttagtttccc taggaaaggg gtcaaaactt caagacactg   4140

gtggtggtgg gagatcagga aaataacttg gcctagctca aacaatattg gataatcccc   4200

tccttggggg agagggatta gagtgtgctc ctactggccc cttggagcct cccctagctt   4260

acacagttaa cttgatttta aaatccaagg ccaggagaga agaatccaaa aagcaatatt   4320

tttcatcaca tgccaaaaac gggggataga gagaaggagt ggcaggccta ggcccctccg   4380

attgtccctt gggggttacc cctcagccca cctcactatg gtgctgggta gaggggatac   4440

ctgggttcta acctctaaat aggggagatc ccagcctcca caaagaggcc cttttatttt   4500

ttattctgat tagccatttt aaaccaacga ggaataaaaa gaaatcctga tctaaccagc   4560

aaaaaaaaaa aaaaaaaaaa aa                                             4582


<210> SEQ ID NO 51
<211> LENGTH: 2187
<212> TYPE: DNA
<213> ORGANISM: Homo sapiens

<400> SEQUENCE: 51

agagtcctgg cgagggcgct ggccgagagg tgctcggctt gtagcaggtc ccgcactcca     60

gcctctcgct gccagggttt gctctctgct tgtcctgggc tgaggtgtcc atgacggagt    120

catccaagga ggaaaaaatc tgttccgggt gagcccaggc cgccccggat atgcgatggc    180

tgaggagcag acaccaggga ccacactgag gttgggtttc agaccaagac actggattct    240

cctagttaag ataaagagct ttgggtgcct gacagtgaaa atggtgtaat ctgcgttaac    300

agttcacagc ttgaaggcat gacaattaaa gaacacacat ggacttgtgg cacatggaaa    360

tgtgcgcaca gaaaaaggaa atctataatt cttttaaagt aggaaggcat tcttccttgc    420

caaaatgggt acgttctgtt cggttatcaa gtttgaaaat ctacaagaat taaagagact    480

gtgtcactgg ggtcccatca tagcccttgg tgttatagca atatgttcta ccatggccat    540

gattgactct gtgttgtggt attggccctt acatacaact ggaggaagtg tgaatttcat    600

catgttgata aattggactg tcatgattct ttataattac ttcaatgcca tgtttgtcgg    660

tccgggcttt gtccctctgg ggtggaaacc ggaaatttct caggatacca tgtatctcca    720

gtattgtaaa gtctgccaag catacaaggc accacgttca catcactgca gaaagtgtaa    780

cagatgtgtg atgaagatgg accatcactg tccttggatc aacaactgtt gtggttacca    840

aaatcatgct tcgttcacac tgtttctcct tttagcacca ctgggttgta tccatgctgc    900

tttcattttt gtgatgacta tgtacacaca gctttatcat cggctctcct ttgggtggaa    960

cacagtgaag atcgacatga gtgcagcccg gagagatcct cttccaattg ttccatttgg   1020

attagctgca tttgctacca ccttgtttgc cttgggatta gctttaggaa caaccatagc   1080

tgttgggatg ttgtttttta tccagatgaa aataattctc agaaacaaaa cttctattga   1140

gtcatggatt gaagagaagg ctaaagatcg aattcagtat tatcaactag atgaagtctt   1200

tgtttttcca tatgatatgg gaagtagatg gaggaacttt aaacaggtat ttacgtggtc   1260

aggggtccct gaaggagatg gacttgagtg gccagtaaga gaaggctgtc accaatacag   1320
```

```
cttaacaata gaacagttga aacaaaaagc agataagaga gtcagaagtg ttcgctataa   1380

agtaatagaa gattatagtg gtgcctgctg ccctctgaat aaaggaatca aaaccttctt   1440

cacaagtccc tgcaccgaag agcctcgaat acagctgcaa aaaggggaat tcattttagc   1500

cacaagaggt ttacgatact ggttatatgg agacaaaatt cttgatgatt cctttataga   1560

aggtgtttca agaataaggg gttggttccc tagaaaatgt gtggaaaagt gtccctgtga   1620

tgctgaaaca gatcaagccc cagaggggga gaagaaaaat agatagctgc tgttaaaaca   1680

aaattatcct ttaagtctgc ttaattactt gaaaattgta catattacta aagaattatg   1740

caatgagcct actctggtta agatgttctt ttcctcaaag gtgccctagt gccatgattt   1800

aaatattttt attaccattt tgaaatggag aagccattct gcatatgcct ttgaattcct   1860

gcccttcttt accacctctt cctccccctc aaaggaaaaa catttcatcc aagtaagtta   1920

acggcatttt ctgtaggatt ttcttatgca ctgcacactc tggacctcac ctgcagatac   1980

agttcccccc ttgccaggag catctgcatg tggtacttct cttttccctc agttgatatt   2040

tcttatatga tattctagat actatagaac tcaatttgtc agattcagta taacctcaga   2100

ttttgttacc tgtcttttaa aaatgcagat tttgtcaaat caaataaaga tcaatggatg   2160

ttgggtataa aaaaaaaaaa aaaaaaa                                       2187
```

<210> SEQ ID NO 52
<211> LENGTH: 3279
<212> TYPE: DNA
<213> ORGANISM: Homo sapiens

<400> SEQUENCE: 52

```
acttccggcg ctcgcaccgc cccgctctcc agccaaggct ccgggctgag gcatttgctt     60

ggctgcagcc tccttccgac ctgcccggcg ggacccaggg gaccaagccg agccgagccg    120

cggggcccgc tccagcccgg ccatgagcgc ggccgcatga tgcgtccctg cctcggccgc    180

tgcagtcgcc gccgccgccg ccgcaggccg ggaggagccg cagcgccggg cgaccccgcc    240

cgggcctcgg atccgatcac ataggacagt atgcacctta agatcctgaa gaaacggcac    300

aaaatgttca agtgatgttt agaaataact tgtgagggtg cgtcagggaa atcatgcagc    360

catcaggaca caggctccgg gacgtcgagc atcatcctct cctggctgaa aatgacaact    420

atgactcttc atcgtcctcc tcctccgagg ctgacgtggc tgaccgggtc tggttcatcc    480

gtgacggctg cggcatgatc tgtgctgtca tgacgtggct tctggtcgcc tatgcagact    540

tcgtggtgac tttcgtcatg ctgctgcctt ccaaagactt ctggtactct gtggtcaacg    600

gggtcatctt taactgcttg gccgtgcttg ccctgtcatc ccacctgaga accatgctca    660

ccgaccctga aaaatccagt gactgccgac catctgcctg cacagtgaaa actgggctgg    720

acccaaccct tgtgggcatt tgtggtgagg gaaccgagtc tgtgcaaagc ctcctgcttg    780

gggcagtacc caaaggaaac gctacgaaag aatacatgga gagcttgcag ctgaagcccg    840

gggaagtcat ctacaagtgc cccaagtgct gctgtattaa acccgagcgc gcccaccact    900

gcagtatttg caaaagatgt attcggaaaa tggatcatca ctgcccgtgg gtgaacaatt    960

gtgtaggaga aaagaatcaa agattttttg tgctcttcac tatgtatata gctctgtctt   1020

cagtccatgc tctgatcctt tgtggatttc agttcatctc ctgtgtccga gggcagtgga   1080

ctgaatgcag tgatttttca cctccgataa ctgtaatcct gttgatcttc ctgtgccttg   1140

agggtcttct gtttttcact ttcactgcag ttatgtttgg cacccaaatc cactccatat   1200

gcaacgacga gacggagatc gagcgattga aaagtgagaa gcccacatgg gagcggaggc   1260
```

-continued

```
tgcgatggga agggatgaag tccgtctttg gggggccccc ctcactcctc tggatgaatc   1320

cctttgtggg cttccgattt aggcgactgc ccacgagacc cagaaaaggt ggcccggagt   1380

tctcagtgtg aggcgtggct catcagactg aaacttgctc acagacttcc agttatttat   1440

ttggggtctg aaggatatca acagctcatc tgtgaccaac agggcaactg gaacctacac   1500

aaaccaattg cttgcagcaa gcagagtttt atatatttat agtcacagat ggcagaggaa   1560

gaggctctca gtccccacct gtacaacaac ggaaaggtgt gtggccacac gaagaagcca   1620

aacgccgtgg cctcctgcag agctggggct tctgtggaga atacttcggg ttattacatg   1680

ggttattcaa atcctgggtc ctgagctgct gtttccaatc atgaagaaaa acagtgaatc   1740

cagtgaacag ggattctcca agcagtcatt tcagggggct cctgctgacc ccgccactca   1800

gcagtgcact ccccggatca cagcagggcg tttacataga aagacgtttt ggtctcgatt   1860

agctccgatg ctttgcactg aagttgcaaa agatctgtgc actgaacagt gaaggtggct   1920

tccggcacac tccccgctgc ccggaagag acatcctttg accctctcag caagtctgtg   1980

tgtgtgcgtg tctgtgcgtg tgcgcgcgtg tgtgcatgtg tgtcaaaatt gccagtgttg   2040

tttaggcaat gtaacattta ccggctgtgt acagcaaaca agctattttt tagaaaccga   2100

cgtttcaggg aagaggggag agagccgcgg ggtcctgccc gtggttacta tgaatgtatt   2160

gctgttggag gacatctcga tccaaagaac agccgttcct gtgcggccct tcgttgccct   2220

cctgctttca ttttttaaag aaatcttgag tgcttgaggg ccttggaact gatttttttt   2280

ttttgttcca gccaaattag cagtgtataa atggcaccta ggtaagagca gagctgcggc   2340

tcggtgactt gatacttggg gcagcccgat gctgtgtgtg gggcagggga ggcatcctta   2400

ctggagaggc agggcccagc cattgggcac ctctgggaag gggaggggac catgaggcag   2460

ccagcccctg gcaggggcga ctgtgccacc gcaggcagcg ctccagtcgg gaatggccag   2520

gatggcgccc tcttgttgga gtttttggtt agcttttacg ttttcttctc cacccacggc   2580

acaggtgata aaataggatc cttggtgcgg agcttaaaat tatgccagaa agccaacagc   2640

tcccctcgtg gggccttgcc ttaaacttgc ctggtttgta catttttttgc cggacgcatc   2700

aagaagcaat ctgtgacaaa gtctgagggt cttcctttat gcttgccctc cacactaaga   2760

gaagttggcg tctccctcct gggaattgtt ttgcctttct gttcatctgt gaactgtttt   2820

ttgtttttaa ttactctgta ccccatccga atcagggctt ctaccactgc tgatgcaaaa   2880

ccacaaaggg acctacctga gccaccgtcc tagccaagcg agcaaacctg caggggggttt   2940

ggaagtggac ttggtcaccg cagaagcgtg tgcgccgttg gggggaagagc tgcgtcacag   3000

ccagagggac aaagtgtggg tgatcctgga gacgccagtt tccgagattg ttctgcatat   3060

tcatttgcac attgttgtct gggttggaca tgcgtgtggg cttcagtgtg aggcttttaa   3120

tatgtatatc ctgttatcaa taaaacaatt atccaagtgg ttgaatcctg tgagacttgg   3180

caagtgtgtg caaatcaagt atacttgact tttcaacctc ttctttcaat gtaactttta   3240

tatgaaataa agtaatcaat taacagttct caaaaaaaa                          3279
```

<210> SEQ ID NO 53
<211> LENGTH: 3520
<212> TYPE: DNA
<213> ORGANISM: Homo sapiens

<400> SEQUENCE: 53

```
ccgcgggtcc tgcgccgcgt ccagcccgcc cgcccgaccc cggcccgacc ccggccggcc     60
```

-continued

```
ctgcccgccc ggccccgggg agggatgcgg cggcgcggcg cccaggatgc cccgcagccc    120
cgggacgcgc ctcaaacccg ccaagtacat cccggtggcc acggccgccg cgctgctggt    180
cggctccagc accctcttct tcgtgttcac gtgcccgtgg ttgacacgag ctgtgtcccc    240
agctgttccc gtctacaatg gcatcatctt cctctttgtc ctggccaact tcagcatggc    300
cactttcatg gaccctggtg ttttcccccg agcggatgag gatgaggaca aggaggacga    360
cttccgggct ccgctgtaca agaacgtgga tgtgcgaggt atccaggtcc gcatgaagtg    420
gtgtgccacg tgccacttct accgcccgcc gcgctgctcc cactgcagcg tctgtgacaa    480
ctgtgtagag gactttgacc accactgccc ctgggtcaac aactgcatcg ggcgtcgaaa    540
ctatcgctac ttcttcctgt tcctgctgtc actcagtgca cacatggtgg gcgtcgtggc    600
cttcggcctg gtctacgtgc tgaaccacgc tgaggggctg ggagccgcgc acaccaccat    660
caccatggct gtcatgtgtg tggccggcct cttcttcatc cctgtcattg gcctcactgg    720
cttccatgtg gtgctggtca ctcgggggcg caccaccaac gagcaggtga ctgggaagtt    780
ccgcgggggt gtgaaccctt tcacccgagg ctgctgtggg aatgtggagc acgtgctgtg    840
tagcccctg gcgccccggt acgtggtgga gccaccccgg ctgccgctcg cggtgagttt    900
gaagccgcct ttccttaggc ctgaactcct ggaccgagct gcaccgctca aggtcaagct    960
tagtgacaac gggctgaagg ctggcctggg ccgtagcaag tccaagggca gcctggaccg   1020
gctggatgag aagccactgg acttggggcc accactgccc cccaagatag aggctggcac   1080
gttcagcagt gacctgcaga ccccgcgccc aggcagtgct gagagtgccc tgtcggtgca   1140
gaggaccagc cccccgacac ctgccatgta caagtttagg ccggctttcc ccacgggtcc   1200
caaggtgccc ttctgtggac caggcgagca ggttccaggc cctgattccc tgaccctggg   1260
ggacgacagc atccgtagcc tggactttgt gtccgagccg agcctggacc tccctgacta   1320
tgggccaggg ggcctgcatg cagcctaccc gccatcccca ccgctcagcg cctctgatgc   1380
cttctcgggc gctttgcgct ccctgagcct caaggcctcg agccggcggg gcggggatca   1440
tgtggccctg cagcccctgc gctctgaggg ggggcccccc acgccccacc gtagcatttt   1500
tgccccccat gcactgccca accgcaacgg cagcctgtcc tatgacagcc tgctcaatcc   1560
tggctcgcct ggtggccacg cctgccctgc ccacccagca gttggcgtgg ccggatacca   1620
ctcaccctac ctgcatcctg ggcaacgggg cgacccgcca cggcccctac cccgcagctt   1680
cagccccgtg ctgggccccc gcccccggga gccctcgcct gtgcgctacg acaacctgtc   1740
caggaccatc atggcatcca tccaggagcg caaggacagg gaggagcgtg agcgcctgct   1800
gcgctcccag gccgactcac tcttcggcga ctcaggcgtc tatgacgctc ccagctccta   1860
cagcctgcag caggccagtg tgctgtccga gggcccccga ggtcccgcgc tgcgctatgg   1920
ctccagagac gaccttgtgg ctgggcccgg cttcggtggc gcccgcaacc ctgccctgca   1980
gacgtcactg tcctcgctgt ccagctccgt gagccgtgca ccgcggacgt cgtcctcctc   2040
cctgcaggct gatcaggcca gcagcaacgc cccggggccc cggcccagca gtggctcaca   2100
caggtcacct gcacgccagg gcctgccctc cccgcccggc actccccact caccatccta   2160
cgcgggcccc aaagctgtcg ccttcatcca cacggacctc ccagagccac cgccctcgct   2220
gaccgtgcag agggaccacc ctcagctgaa gactccccca agtaagctta atgggcagtc   2280
cccgggcctg gcccggctgg gacctgccac cggcccccca gggccctctg ccagccctac   2340
acggcacacg ctggttaaga aggtgtccgg cgtgggtggg accacctacg agatctcggt   2400
gtgaggactg actgccacac atccgccatg gtgccacggg gaccaggacc ccacagcgca   2460
```

```
ccccccctcc ccaccaactt ctctgcccca gggacccgag gccaccccag cctggtgtgg   2520
acccatcggc gggagagagt gccacgcctc cacagcttgc cccaagcgct ctgcctgccc   2580
gtccactcat ctgcccatgg ggaagtcggc tcactgggac aagggccact gggctggtct   2640
gtgtctgggc ctgtcccatg gctggggcag tgagggggcc cagtcagcct ctttggggca   2700
ccctctctca gccaggcttg gcccactgcc atcacccagc accccagatc accgccaggc   2760
cagcccccaa tggtcccctt acggacaggt cccagagatg gacagaggca cccagggccc   2820
ccaccgtcct tctgacacag cctgtgggct cccggaccga gtgtccccg ccaggctact    2880
cctaactaac gcgttgcctt tcacggaccc cgctggaagc ttgtagcttg gcaaggctga   2940
tgcttctgcc ctggcctgct ctgggtggtg gtggataggt ggacagacgg ccagccagcc   3000
agctgtggcc gggggcccgg ctccatgtgt cccgtgtctg tgtgctgtgc tgccgcgccg   3060
tgtctgatgt gtcagtgctc cggccgccgc tgtccctttc atcaaagcct taacctttgc   3120
tttatgctct tgtgggaggc gacgggggg caggcgggag caggcacggg ggtgatgctg    3180
ccacaggggg ctggtgacac ccagagcccc ctccccagcc ctcaggccct ccctgccaaa   3240
ctggagaacc ccaccccaag gcatgccacg tccgcagccc cggcctggct gcggtgctcg   3300
cgccgtggga aagcacactg gggaggggtc agtgcttccc ttggtgtcag ggacctgaga   3360
gtaagcacat gacagcgtct gcttgcgttg tgtctgtttt atgtttttat atctacatct   3420
atatatctat aattttatta aaaaaaagaa aaagaaaaaa aaaaaaaaaa aaaaaaaaaa   3480
aaaaaaaaaa aaaaaaaaaa aaaaaaaaaa aaaaaaaaaa                         3520
```

<210> SEQ ID NO 54
<211> LENGTH: 2949
<212> TYPE: DNA
<213> ORGANISM: Homo sapiens

<400> SEQUENCE: 54

```
tgaggagcgt tccatttggc cagtggtggg cggttgccac agctggttta gggccccgac     60
cactggggcc ccttgtcagg aggagacagc ctcccggccc ggggaggaca agtcgctgcc    120
acctttggct gccgacgtga ttccctggga cggtccgttt cctgccgtca gctgccggcc    180
gagttgggtc tccgtggttc aggccggctc ccccttcctg gtctcccttc tcccgctggg    240
ccggtttatc gggaggagat tgtcttccag ggctagcaat tggacttttg atgatgtttg    300
acccagcggc aggaatagca ggcaacgtga tttcaaagct gggctcagcc tctgtttctt    360
ctctcgtgta atcgcaaaac ccattttgga gcaggaattc caatcatgtc tgtgatggtg    420
gtgagaaaga aggtgacacg gaaatgggag aaactcccag gcaggaacac cttttgctgt    480
gatggccgcg tcatgatggc ccggcaaaag ggcattttct acctgaccct tttcctcatc    540
ctggggacat gtacactctt cttcgccttt gagtgccgct acctggctgt tcagctgtct    600
cctgccatcc ctgtatttgc tgccatgctc ttccttttct ccatggctac actgttgagg    660
accagcttca gtgaccctgg agtgattcct cgggcgctac cagatgaagc agctttcata    720
gaaatggaga tagaagctac caatggtgcg gtgccccagg gccagcgacc accgcctcgt    780
atcaagaatt tccagataaa caaccagatt gtgaaactga aatactgtta cacatgcaag    840
atcttccggc ctccccgggc ctcccattgc agcatctgtg acaactgtgt ggagcgcttc    900
gaccatcact gcccctgggt ggggaattgt gttggaaaga ggaactaccg ctacttctac    960
ctcttcatcc tttctctctc cctcctcaca atctatgtct tcgccttcaa catcgtctat   1020
```

-continued gtggccctca aatctttgaa aattggcttc ttggagacat tgaaagaaac tcctggaact 1080
gttctagaag tcctcatttg cttctttaca ctctggtccg tcgtgggact gactggattt 1140
catactttcc tcgtggctct caaccagaca accaatgaag acatcaaagg atcatggaca 1200
gggaagaatc gcgtccagaa tccctacagc catggcaata ttgtgaagaa ctgctgtgaa 1260
gtgctgtgtg gccccttgcc ccccagtgtg ctggatcgaa ggggtatttt gccactggag 1320
gaaagtggaa gtcgacctcc cagtactcaa gagaccagta gcagcctctt gccacagagc 1380 ccagcccccca cagaacacct gaactcaaat gagatgccgg aggacagcag cactcccgaa 1440
gagatgccac ctccagagcc cccagagcca ccacaggagg cagctgaagc tgagaagtag 1500
cctatctatg gaagagactt ttgtttgtgt ttaattaggg ctatgagaga tttcaggtga 1560
gaagttaaac ctgagacaga gagcaagtaa gctgtccctt ttaactgttt ttctttggtc 1620
tttagtcacc cagttgcaca ctggcatttt cttgctgcaa gcttttttaa atttctgaac 1680
tcaaggcagt ggcagaagat gtcagtcacc tctgataact ggaaaaatgg gtctcttggg 1740
ccctggcact ggttctccat ggcctcagcc acagggtccc cttggacccc ctctcttccc 1800
tccagatccc agccctcctg cttggggtca ctggtctcat tctggggcta aaagtttttg 1860
agactggctc aaatcctccc aagctgctgc acgtgctgag tccagaggca gtcacagaga 1920
cctctggcca ggggatccta actgggttct tggggtcttc aggactgaag aggagggaga 1980
gtggggtcag aagattctcc tggccaccaa gtgccagcat tgcccacaaa tccttttagg 2040
aatgggacag gtaccttcca cttgttgtat ttattagtgt agcttctcct ttgtctccca 2100
tccactctga cacctaagcc ccactctttt cccattagat atatgtaagt agttgtagta 2160
gagataataa ttgacatttc tcgtagacta cccagaaact tttttaatac ctgtgccatt 2220
ctcaataaga atttatgaga tgccagcggc atagcccttc acactctctg tctcatctct 2280
cctcctttct cattagcccc ttttaatttg tttttccttt tgactcctgc tcccattagg 2340
agcaggaatg gcagtaataa aagtctgcac tttggtcatt tcttttcctc agaggaagcc 2400
tgagtgctca cttaaacact atcccctcag actccctgtg tgaggcctgc agaggccctg 2460
aatgcacaaa tgggaaacca aggcacagag aggctctcct ctcctctcct ctcccccgat 2520
gtaccctcaa aaaaaaaaaa atgctaacca gttcttccat taagcctcgg ctgagtgagg 2580
gaaagcccag cactgctgcc ctctcgggta actcacccta aggcctcggc ccacctctgg 2640
ctatggtaac cacactgggg gcttcctcca agccccgctc ttccagcact tccaccggca 2700
gagtcccaga gccacttcac cctgggggtg ggctgtggcc cccagtcagc tctgctcagg 2760
acctgctcta tttcagggaa gaagatttat gtattatatg tggctatatt tcctagagca 2820
cctgtgtttt cctctttcta agccagggtc ctgtctggat gacttatgcg gtgggggagt 2880
gtaaaccaga acttttcatc tatttgaagg cgattaaact gtgtctaatg caaaaaaaaa 2940
aaaaaaaaa 2949

<210> SEQ ID NO 55
<211> LENGTH: 2618
<212> TYPE: DNA
<213> ORGANISM: Homo sapiens

<400> SEQUENCE: 55
gtgaacgggt tgtgggacct gtcgctgtgt gggggctgtc gagcactccc cagaacgtaa 60
caaatcctca ggggaactga tgggcggtcg cgcgggcact gggtcctcca caccctggag 120
agccgttttc cgttgccact cggctctggc cggggtcaca ttctgcagca tgtctgttca 180

-continued

```
ttcccctggg cggggccctg caccgactcc agcccagccc ctgctccctc tgcggggaac    240
gtggccccag gcagtgctgg gccattggct gtcagtgctg gtcctggcgg ctgcattccc    300
agtccccttg gtctctgtga cagtgggcgg ggccggccct cccaggatct gacggcgcag    360
gtcctcccct tctgtgtcct gcagatggac acccgctccg ggagccagtg ttccgtcacc    420
ccagaagcca tactcaataa tgaaaagctg gtcttgccgc cccgcatctc cagagtgaac    480
ggctggtcgt tacccctgca ctacttccag gtggtgacct gggctgtctt cgtgggcctt    540
tcctcggcca ccttcgggat cttcattccc ttcctgcctc acgcgtggaa atacattgcc    600
tacgtggtga ccggggggat cttctcgttc cacctcgtcg tccacctgat cgcgtcctgc    660
atcgacccgg ccgactccaa tgtcagactc atgaagaact attctcagcc catgcccctc    720
ttcgacagat caaaacatgc acacgtgatc cagaatcagt tctgccacct gtgcaaggtc    780
accgtgaaca agaaaaccaa acactgcatt tcctgcaata agtgtgtgtc cggcttcgac    840
caccactgca aatggatcaa caactgcgtg ggaagccgga attattggtt cttcttcagc    900
actgtggcct cggccacagc tggcatgctc tgcctgatcg ccatcctgct gtatgtcctc    960
gtccagtacc tcgtgaaccc cggggtgctc cgcacggacc ccaggtatga agatgtcaag   1020
aatatgaaca cgtggctgct gttcctcccc ctgttcccgg tgcaggtgca gaccctgata   1080
gtcgtgatca tcgggatgct cgtgctcctg ctggactttc ttggcttggt gcacctgggc   1140
cagctgctca tcttccacat ctacctgaag gccaagaaga tgaccacctt tgagtatctc   1200
attaataacc gcaaagaaga gagttcaaaa catcaagcag tgaggaaaga tccatacgtg   1260
caaatggaca aaggagttct ccagcaagga gctggcgccc tgggctcatc tgcacaggga   1320
gtcaaagcca agagctccct gctgattcac aagcacttat gtcacttctg cacttcagta   1380
aaccaggatg gggattcgac ggcacgggaa ggggatgaag acccgtgtcc atctgcactt   1440
ggagccaagg ccaggaactc ccggctgatt tgcaggcgcc tgtgtcagtt ctccactcgt   1500
gtacacccag acgggggctc gatggcacag gaagcagatg atgccccgag tatatctaca   1560
cttgggctgc aacaagaaac aacagagccc atgaaaactg acagtgctga aagtgaagac   1620
tgagattcag gagctcaggt gcccctgtga tccaggtctt ctaccctgaa accccaccct   1680
ccatcaaggt cctgcctgta gagtctacct tgcaaagcct cctgctccta cccatgctac   1740
aggccaggaa ccagagccca tcatctcaga ggcccctgga tgtccttcga aggaaccagg   1800
accctcagag cccagcatcc atctctgtca tcatcttcat cacacccaaa gaagagccag   1860
ccttgcagga gggtttacat ctccaggaag atgggctgcc agcaactgca gaggatgcag   1920
ccacctgctt aactgtgctg tccagccagc cagccagctg cagggcctct tgctgcttaa   1980
gagctgatgg gccgggcatg ttggctcaca cctgtgagca cagtactggg aaatgggagc   2040
acagtactag gaaatgggag cacagtactg ggaaatggga gcacagtact gggaaatggg   2100
ggctcacagc actgcaaaat gggagcacag tattgggaaa tgggagcaca gtactgggaa   2160
gtgggagcac agtactgaga agtgggagca cagtactgag aaatgggagt acactactga   2220
gaaatgggag cacagtactg ggaaatgggc atacagtact gagaaatggg agcacacagt   2280
actgggaaat gggagcacag tactgggaaa tgggagccca cagtactggg aaaggggagt   2340
tcacagtact cggaaatggg agcatagtac tgggaaatgg gagcacagta ctgggaaatg   2400
ggagcatagt actgggaaac cccagacctg gattctgagt tttcagcct agcccagact    2460
tcttatctta gtagacaaaa agagtcaata ccagagaacc agaggcatcc tctgtatttt   2520
```

aatgaactct gcattttaat ctgtttagta gtcatttttt aaaagataat cagttttcca 2580
aatatatcta taagttacta cgtgcaaaaa aaaaaaaa 2618

<210> SEQ ID NO 56
<211> LENGTH: 1621
<212> TYPE: DNA
<213> ORGANISM: Homo sapiens

<400> SEQUENCE: 56
atggacaccc gctccgggag ccagtgttcc gtcaccccag aagccatacg caacaatgaa 60
gagctggtct tgccgccccg catctccaga gtgaacggct ggtcgttacc cctgcactac 120
ttccgggtgg tgacttgggc tgtcttcgtt ggcctttcct tggccacctt caggatcttc 180
attcccctcc tgcctcactc gtggaaatac atcgcctatg tggtgaccgg ggggatcttc 240
tcgttccacc tcgtcgtcca cctgatcgcg tcctgcatcg acccggccga ctccaatgtc 300
agactcatga agaactattc tcagcccatg cccctcttcg acagatcaaa acatgcacac 360
gtgatccaga atcagttctg ccacctgtgc aaggtcaccg tgaacaagaa aaccaaacac 420
tgcatttcct gcaataagtg tgtgtccggc ttcgaccacc actgcaaatg gatcaacaac 480
tgcgtgggaa gccggaatta ttggttcttc ttcagcactg tggcctcggc cacagctggc 540
atgctctgcc tgatcgccat cctgctgtat gtcctcgtcc agtacctcgt gaaccccagg 600
gtgctccgca cggaccccag gtatgaagat gtcaagaata tgaacacgtg gctgctgttc 660 ctcccccctgt tcccggtgca ggtgcagact ctgatagtcg tgatcatcag gatgctcgtg 720
ctcctgctgg accttcttgg cttggtgcag ctgggccagc tgctcatctt ccacatctac 780
ctgaaggcca agaagatgac cacctttgag tatctcatta atacccgcaa agaagagagt 840
tcaaaacatc aagcagtgag gaaagatcca tacgtgcaaa tggacaaagg atttctccag 900
caaggagctg gcgccctggg ctcatctgca cagggagtca aggccaagag ctccctgctg 960
atttacaaat gcccatgtca cttctgcact tcagtaaacc aggacgggga ttcgaaggca 1020
cagggccgcc tcaccgcact tccccaggat ttcagggaac aggctcctgt gacttggaaa 1080
tgaaaatgga tcacccaacc tggaggaaca gtgaggctgg tgtccaagac ttgccccttg 1140
cctgcacttc cagcaaagat ttggagacac tcagtggaaa ccaatcgagc ccccagccca 1200
cccccgccca gactcagcca ccaaagttcc ctcactgcat gtggcacacg ggctcatggg 1260
agtttctctg cctgcgattg tccacgttga caccttctgc acaggtgcat ttgtgagtcc 1320
cctcggtgtc tctgcagcat ctatgtgtgg atgaatagtg aagccacatg aggcctggtc 1380
tgaagcagag aagatccgct cagcatcacg ttgaatccca agcccgcatc tccgtgggct 1440
ccaggacaat cctatgaaaa tgacaccgtc ggttcattgt tcacatcggg gaggagaatt 1500
ccgtctgaaa atgagcgtga cttcactgac acccaagtcc gtggcacagc cctgtgctga 1560
gctccacaga cctacagtcc atcgcctccc cttcgagtgg gcccagggct gcagacagca 1620
t 1621

<210> SEQ ID NO 57
<211> LENGTH: 1184
<212> TYPE: DNA
<213> ORGANISM: Homo sapiens

<400> SEQUENCE: 57
gggcgcttct tccgggtggg gccccgggcc gaggcgatgg cgccctgggc gctcctcagc 60
cctggggtcc tggtgcggac cgggcacacc gtgctgacct ggggaatcac gctggtgctc 120

```
ttcctgcacg ataccgagct gcggcaatgg gaggagcagg gggagctgct cctgcccctc    180
accttcctgc tcctggtgct gggctccctg ctgctctacc tcgctgtgtc actcatggac    240
cctggctacg tgaatgtgca gccccagcct caggaggagc tcaaagagga gcagacagcc    300
atggttcctc cagccatccc tcttcggcgc tgcagatact gcctggtgct gcagcccctg    360
agggctcggc actgccgtga gtgccgccgt tgcgtccgcc gctacgacca ccactgcccc    420
tggatggaga actgtgtggg agagcgcaac cacccactct ttgtggtcta cctggcgctg    480
cagctggtgg tgcttctgtg ggcctgtac ctggcatggt caggcctccg gttcttccag     540
ccctggggtc tgtggttgcg gtccagcggg ctcctgttcg ccaccttcct gctgctgtcc    600
ctcttctcgt tggtggccag cctgctcctc gtctcgcacc tctacctggt ggccagcaac    660
accaccacct gggaattcat ctcctcacac cgcatcgcct atctccgcca gcgccccagc    720
aacccccttcg accgaggcct gacccgcaac ctggcccact tcttctgtgg atggccctca   780
gggtcctggg agaccctctg ggctgaggag gaggaagagg gcagcagccc agctgtttag    840
ggttgctgga ggccgggcta ccgtcttgtg cctgaaaacc acggggcctg tccccagctg    900
gggtgagcgc tcagagggcc tggggccctc actcctgccc acgcctccca gaccccagaa    960
cggagcttca agtcagacag atccctgcct tggtgggcag ttctgccttc caaggaagaa   1020
ggggaagaaa aggacctgtg ggtggctcag gcccaagcag accccgggct ccaccccagc   1080
cccgcccagg ctgctgccag tgcacacttt tacaaattta atataaagca agtccagtct   1140
taaaaagaca aaaaaaaaaa aaaaaaaaaa aaaaaaaaaa aaaa                    1184
```

<210> SEQ ID NO 58
<211> LENGTH: 2448
<212> TYPE: DNA
<213> ORGANISM: Homo sapiens

<400> SEQUENCE: 58

```
gggcgccagc aggaagtggg agaagaggcg acccaaggcg ggctggcggg ctggcggcag     60
tcgctacttg cctagtagcc tcagccgctg tgggctcctg ggagatgga ggggccgggg    120
ctgggctcgc agtgcaggaa tcacagccat ggcccccacc ctccaggatt tggtcgatat    180
ggcatctgtg cacatgaaaa caaagaactt gccaatgcaa gagaagctct tcctcttata    240
gaggactcta gtaactgtga cattgtcaaa gctactcaat acggaatttt tgaacgatgt    300
aaagagttgg tagaagcagg atatgatgtc aggcaaccag ataaagaaaa tgtgtcgctt    360
cttcattggg ctgctattaa caacagactg gatcttgtaa agttttatat ttcaaaaggt    420
gctgttgtag atcagttggg tggagattta aattcaactc ctcttcactg ggccatccga    480
caaggacatt tacctatggt catattatta ctccagcatg gtgcagaccc cactcttatt    540
gatggagagg gattcagcag catccacctg gcagtattgt ttcaacacat gcctattata    600
gcatatctca tctcaaaggg acagagtgtg aatatgacag atgtaaatgg gcagacacct    660
ctcatgttat cagctcacaa agtaattggg ccagaaccaa ctggatttct tttaaagttt    720
aatccttctc tcaatgtggt tgataaaata caccaaaaca ctccacttca ctgggcagtt    780
gcagcaggaa atgttaatgc agttgataag cttttggaag ctggttctag cctggatatc    840
cagaatgtta agggagaaac acctcttgat atggctctac aaaacaaaaa tcagctcatt    900
attcatatgc taaaaacaga agccaaaatg agagccaacc aaaagttcag actttggagg    960
tggctgcaga aatgcgagct cttcctgctg ctgatgcttt ctgtgattac catgtgggct   1020
```

attggataca tattggactt caattcagat tcttggcttt taaaaggatg tcttctagta 1080
acactgtttt ttctgacatc tttgtttcca aggttcttgg ttgggtataa gaaccttgta 1140
tacttaccaa cagcctttct gctaagttct gttttttgga tatttatgac ttggttcatc 1200
ttattttttc ctgatttagc aggagcccct ttctatttca gtttcatttt cagcatagta 1260
gcctttctat actttttcta taagacttgg gcaactgatc caggcttcac taaggcttct 1320
gaagaagaaa agaaagtgaa tatcatcacc cttgcagaaa ctggctctct ggacttcaga 1380
acattttgta catcatgtct tataaggaag ccattaaggt cactccactg ccatgtatgc 1440
aactgctgtg tggctcgata tgatcaacac tgcctgtgga ctggacggtg cataggtttt 1500
ggcaaccatc actattacat attcttcttg tttttccttt ccatggtatg tggctggatt 1560
atatatggat ctttcatcta tttgtccagt cattgtgcca caacattcaa agaagatgga 1620
ttatggactt acctcaatca gattgtggcc tgttcccctt gggttttata tatcttgatg 1680
ctagcaactt tccatttctc atggtcaaca ttttttattat taaatcaact ctttcagatt 1740
gcctttctgg gcctgacctc ccatgagaga atcagcctgc agaagcagag caagcatatg 1800
aaacagacgt tgtccctcag gaagacacca tacaatcttg gattcatgca gaacctggca 1860
gatttctttc agtgtggctg ctttggcttg gtgaagccct gtgtggtaga ttggacatca 1920
cagtacacca tggtctttca cccagccagg gagaaggttc ttcgctcagt atgaagaaaa 1980
gcaacccaaa actctcaatc tgatttgttt ttgtttatgt cgatgccctg tagtttgaaa 2040
gtgaagtaaa gatttagaat tcacctaagt ccaaaggaaa acacgtggtt tttaaagcca 2100
ttaggtaaaa aaagttctca ataaaggcat tacaattttt taggtttaga aagatggact 2160
tttctgataa atcttggcag acatctaaaa aaaaaaccat atttttcaca agaaaatgca 2220
agttactttt tttggaaata atactcactg attatggata aaatggaata ttttcagata 2280
ctatattggc tgtttcaaaa tagtactatt ctttaaactt gtaatttttg ctaagttatt 2340
tgtctttgtt gtatctataa atatgtaaaa aatatttaaa tagatgtacc tgttttgctt 2400
tcacacttaa taaaaaattt ttttttgtag ttgaaaaaaa aaaaaaaa 2448

<210> SEQ ID NO 59
<211> LENGTH: 2821
<212> TYPE: DNA
<213> ORGANISM: Homo sapiens

<400> SEQUENCE: 59
gaaggagtgg acccaacctg gccgcgccgc agaagtggct cccgaggaag ccggcgccgg 60
ggccgccgcc tcgtgtcccc tcggggcgca gtgctcgggg gtcggcgggc cagagccgag 120
gcgcggccgg ggagccgggg gctgcggggc cgagcgggca gccgcgcgag ggggcgggcg 180
ctcggcgacc cgggggccgg ccgggctgag ccccgcgccc cgggacgcgg gctggaagcg 240
acggaggagt gctgccgcgg gctgcggacc agcgccgtcc cctcacggag cggggattct 300
gctatgacag ttgggctccc cggagggtta acctgggtgt cctcggcaaa gttgtcgccg 360
agccgggagc ccgtgtaggg gccgcggcgc cgcggctcgg ggggcggccg ggcggccggc 420
ggcggtcgtg gctcggcggg gcccgcgcgg ccgggggggct cctgggggtg tgcgccccca 480
gccggctgcc ctcgtggatg cctcccggcg gcggcgggcc catgaaagac tgcgagtaca 540
gccagatcag cacccacagc tcctccccca tggagtcgcc ccacaagaag aagaaaatcg 600
cggcccggag gaaatgggag gtgttcccgg gaagaaacaa gttcttctgt aacgggagga 660
tcatgatggc ccggcagacg ggcgtcttct acctgacgct cgtcctcatc ctggtcacta 720

-continued

```
gcggactctt cttcgccttc gactgtccgt acctggcggt gaaaatcacc cctgccatcc    780
ctgcagtcgc tggcatcctg ttcttctttg tgatggggac cctgctccgc accagcttca    840
gcgaccccgg agtcctccca cgagccacgc ctgatgaagc cgccgatctg gaaaggcaaa    900
tagatatcgc aaacggcacc agttcagggg ggtaccgccc gcctcccaga accaaagaag    960
tcatcatcaa tggccagacc gtgaaactta aatactgttt cacctgcaag attttccggc   1020
cccctcgcgc ctcccattgc agcctttgtg ataactgcgt agaacggttt gatcaccact   1080
gtccctgggt aggcaactgt gtggggaaaa gaaactacag attttttat atgtttattt    1140
tatctctgtc ttttctgaca gtctttatat ttgcattcgt tatcacccac gtcattcttc   1200
gttcacagca aacaggattc ctaaatgccc ttaaggacag tcctgcaagc gtcctggagg   1260
ctgtggtgtg cttcttctct gtctggtcca tcgttggcct ctcaggattc cacacctact   1320
tgatcagctc caaccagaca acaaatgagg acattaaagg atcctggtca aataaaagag   1380
gtaaagaaaa ttacaatccc tacagctacg gaaatatctt taccaactgc tgtgttgccc   1440
tgtgtgggcc catctcacca agcctgatcg acagaagagg gtacatccag cccgacacgc   1500
cgcagccagc agcaccctcc aatggcatca ccatgtacgg ggccacgcag tcacagagtg   1560
acatgtgcga ccaagaccag tgcattcaga gcaccaaatt cgttttgcag gctgcagcca   1620
cgcccctgct gcagagcgag cccagcctca ccagcgacga gctgcacctg cccgggaagc   1680
ctggcctggg cacgccctgc gccagcctca cactgggccc gcccacaccg cccgcctcca   1740
tgcccaacct cgccgaggcc acgctcgcgg acgtgatgcc ccggaaagat gagcacatgg   1800
gccaccagtt cctgacgccc gatgaggcgc cctcgccccc caggctactg gcggcgggca   1860
gcccccctggc gcacagccgc accatgcacg tgctgggcct ggccagccag gactccctgc   1920
atgaggactc tgtgcgcggc ctggtgaagc tcagctccgt gtgacccaca tggccccagg   1980
ccgggggaca ccagaggctc ctccatgggc agcaggagtg agcggagggg tgtgtcccac   2040
agcgactttc ccagccaatg ccacggtgga gatgacagcc ccaggtctgg ggtacagaga   2100
ccacttagga tggcacaggg tggctggccc cggatgctga gagcttggtt tcatttgaat   2160
tttcttcccc aacctgagtg ctttgacaac aatggaaata gagaagtggc tgctttcttt   2220
tggtgaccct ccaggggtgg aatcggagtg tgtctgcccg cccttgtgac agacacacgg   2280
aaggcttctg acgcttgtgg ccagactgca attgcactta tgtgttatgc tactaatatt   2340
tgaaacagac ctgccattcc atttgttaat taaaaaaaaa aaaaatccta aagggaaaaa   2400
accgaccagg tgtggatctg catgccacgc tgccgtctgt gttacagtgg tgttgctatt   2460
tccaaggaag tgctgctttc tttttctttt tttaattttg tgaattttca agtgctgttt   2520
tgttggaaga cagtgcaacg aactgagact aatggacagt gtcatcactc agcttactgg   2580
gctgaggcgt ctgtggagag gtggcaccgg ggctgcagag ggcggctggg gttccgtcgt   2640
gtcgggtgtc acttcacctt ctgtttggcc gctcgatgag gtctcgtgtt gagatattgt   2700
gtgccacaac ccccacagtc ttcacctccg tgtgtgatga aacttcccgt ggacagccaa   2760
taaaatgacg tcctctgtta ttttggaaaa aaaaaaaaaa aaaaaaaaaa aaaaaaaaaa   2820
a                                                                   2821
```

```
<210> SEQ ID NO 60
<211> LENGTH: 1782
<212> TYPE: DNA
<213> ORGANISM: Homo sapiens
```

<400> SEQUENCE: 60
gatcttcgag ccaaagatgc ggcgaggctg gaagatggct ctgtctgggg ggctgcggtg 60
ctgccgccgg gtactgtcct gggtgccagt gctcgttatt gtcctcgtcg tgctctggtc 120
ctactatgcc tacgtctttg aactctgcct ggtgactgtt ttgagcccag cagaaaaagt 180
tatttacctc atactctacc atgccatctt tgtgttcttt acctggacct actggaagtc 240
tatctttaca ctcccacagc agccaaacca gaagttccac ttgtcctaca cagacaagga 300
gcgctatgaa aatgaagaaa gacctgaggt ccagaagcag atgcttgttg atatggccaa 360
aaagctaccg gtttacacaa gaactggaag tggagctgta cgattctgtg accggtgtca 420
tctgatcaag ccagaccgct gccaccactg ctctgtctgt gctatgtgtg tgttaaaaat 480
ggatcatcac tgcccttggg ttaataactg cattggattt tccaactaca aattcttcct 540
tcaattctta gcttactctg ttctctactg cctgtacatt gctacgacag tcttcagcta 600
tttcatcaaa tactggagag gggaattacc cagtgttcgc tctaagttcc atgtcctttt 660
tcttctcttt gtggcctgca tgttttttgt cagccttgtg attctctttg gttaccattg 720
ttggcttgtc agcagaaaca aaaccacctt agaggccttc tgcactccag tgtttacaag 780
tggcccagag aaaaatgggt tcaaccttgg cttcatcaag aatatccagc aggtgtttgg 840
agataagaag aagttctggt taatacctat tggttccagc cctggtgatg gacactcctt 900
ccctatgagg tctatgaatg agtcacagaa cccactgcta gcaaatgaag aaacctggga 960
agacaacgag gatgacaacc aagattatcc agaaggctca tcatctcttg ctgtggaaac 1020
ggaaacatag cagttttcac atttcctgca tctctcagac aggactcacc atctctgcct 1080
cccatgaggc ttacagagtt caatgttgga aatcattgta atcttcaaaa taagtcaccg 1140
tgttggattg aaagcttcaa aatttgaaag aattccatca aatacttgct gtgtaaatgt 1200
ttctggactt tatgttattt aatttactga ctgaaatcca atttggaatt tggtagcagt 1260
taattcaagc caattttttt tgtttcttca tttcccctcc cccaatccat gaaagcctaa 1320
atgtaaaata tatcttttca ttcatcttat caggtaaaag gaaattcaga aaatttcctt 1380
agagtcttta attcccccac aaagattatt aatcacatat atagggcctt tttggtgttg 1440
aagggaatca aactacattt gctgcttgtg tgcgtgtgca tttgtgaaca cgtacagcat 1500
atctatacaa aattctgcta tagtgtgaaa atcagggcta aaaacctgaa gcctttgttt 1560
aattatgctt ttcctctaaa tagcaactta aatatttgct agactttgaa tcatcgctat 1620
atcaagtatc taaaatttgg gagggtgaat cagtacactg tgaccaaggt cctcaaattg 1680
gaatttgaac aacaatgtaa aacctgttct gtcacaaatg ttcctgaaag caccacagct 1740
actcaagaag atcaaattca ggacataaac tttattgaac at 1782

<210> SEQ ID NO 61
<211> LENGTH: 1816
<212> TYPE: DNA
<213> ORGANISM: Homo sapiens

<400> SEQUENCE: 61
gtgtggttga ggatgggctg gcggcgggtc cgggtccgct gcctggcgct gcgggcggcg 60
ggccatggtg gtttggattg agccgggccc ggccggggcg ccgagtcgga gggggtggca 120
gtgagcggcg gcagaggcta cggggctcgg tttggctgac tggggagtcg gcaggcggca 180
ggaaccatgc gaggccagcg gagcctgctg ctgggcccgg cccgcctctg cctccgcctc 240
cttctgctgc tgggttacag gcgccgctgt ccacctctac tccggggtct agtacagcgc 300
tggcgctacg gcaaggtctg cctgcgctcc ctgctctaca actcctttgg gggcagtgac 360
accgctgttg atgctgcctt tgagcctgtc tactggctgg tagacaacgt gatccgctgg 420
tttggagtgg tgttcgtggt cctggtgatc gtgctgacag gctccattgt agctatcgcc 480
tacctgtgtg tcctgcctct catcctccga acctactcag tgccacgact ctgctggcat 540
ttcttctata gccactggaa tctgatcctg attgtcttcc actactacca ggccatcacc 600
actccgcctg ggtacccacc ccagggcagg aatgatatcg ccaccgtctc catctgtaag 660
aagtgcattt accccaagcc agcccgaaca caccactgca gcatctgcaa caggtgtgtg 720
ctgaagatgg atcaccactg cccctggcta aacaattgtg tgggccacta taaccatcgg 780
tacttcttct ctttctgctt tttcatgact ctgggctgtg tctactgcag ctatggaagt 840
tgggaccttt tccgggaggc ttatgctgcc attgagaaaa tgaaacagct cgacaagaac 900
aaactacagg cggttgccaa ccagacttat caccagaccc caccacccac cttctccttt 960
cgagaaagga tgactcacaa gagtcttgtc tacctctggt tcctgtgcag ttctgtggca 1020
cttgccctgg gtgccctaac tgtatggcat gctgttctca tcagtcgagg tgagactagc 1080
atcgaaaggc acatcaacaa gaaggagaga cgtcggctac aggccaaggg cagagtattt 1140
aggaatcctt acaactacgg ctgcttggac aactggaagg tattcctggg tgtggataca 1200
ggaaggcact ggcttactcg ggtgctctta ccttctagtc acttgcccca tgggaatgga 1260
atgagctggg agccccctcc ctgggtgact gctcactcag cctctgtgat ggcagtgtga 1320
gctggactgt gtcagccacg actcgagcac tcattctgct ccctatgtta tttcaagggc 1380
ctccaagggc agcttttctc agaatccttg atcaaaaaga gccagtgggc ctgccttagg 1440
gtaccatgca ggacaattca aggaccagcc tttttaccac tgcagaagaa agacacaatg 1500
tggagaaatc ttaggactga catcccttta ctcaggcaaa cagaagttcc aaccccagac 1560
taggggtcag gcagctagct acctaccttg cccagtgctg acccggacct cctccaggat 1620
acagcactgg agttggccac cacctcttct acttgctgtc tgaaaaaaca cctgactagt 1680
acagctgaga tcttggcttc tcaacagggc aaagatacca ggcctgctgc tgaggtcact 1740
gccacttctc acatgctgct taagggagca caaataaagg tattcgattt ttaaagataa 1800
aaaaaaaaaa aaaaaa 1816

<210> SEQ ID NO 62
<211> LENGTH: 4771
<212> TYPE: DNA
<213> ORGANISM: Homo sapiens

<400> SEQUENCE: 62
agaaacccgc gccctccgag gggggagggg acagaggggg cgtcacgggg gcaggagaag 60
aaggaggagg aggcccgcgt cgcctccggc ggggctcgcg ctcgccccgc gctcgccctc 120
cgcctcgccc gagccccggg agggtgaaac gctttctccc agcatgcagc gggaggaggg 180
atttaacacc aagatggcgg acggcccgga tgagtacgat accgaagcgg gctgtgtgcc 240
ccttctccac ccagaggaaa tcaaacccca aagccattat aaccatggat atggtgaacc 300
tcttggacgg aaaactcata ttgatgatta cagcacatgg gacatagtca aggctacaca 360
atatggaata tatgaacgct gtcgagaatt ggtggaagca ggttatgatg tacggcaacc 420
ggacaaagaa aatgttaccc tcctccattg ggctgccatc aataacagaa tagatttagt 480
caaatactat atttcgaaag gtgctattgt ggatcaactt ggaggggacc tgaattcaac 540

-continued

```
tccattgcac tgggccacaa gacaaggcca tctatccatg gttgtgcaac taatgaaata    600
tggtgcagat ccttcattaa ttgatggaga aggatgtagc tgtattcatc tggctgctca    660
gttcggacat acctcaattg ttgcttatct catagcaaaa ggacaggatg tagatatgat    720
ggatcagaat ggaatgacgc ctttaatgtg ggcagcatat agaacacata gtgtggatcc    780
aactagattg cttttaacat tcaatgtttc agttaacctt ggtgacaagt atcacaaaaa    840
cactgctctg cattgggcag tgctagcagg gaataccaca gtcattagcc ttcttctgga    900
agctggagct aatgttgatg cccagaatat caagggcgaa tcagcgcttg atttggcaaa    960
acagagaaaa aatgtgtgga tgatcaacca cttacaagag gcaaggcaag caaaaggata   1020
tgacaatccg tccttcctta gaaagctgaa agctgataag gaatttcggc agaaagtaat   1080
gttaggaact cctttcctag ttatttggct ggttgggttt atagcagacc taaatattga   1140
ttcttggctc attaaagggc taatgtatgg tggtgtttgg gctacagtac agtttctttc   1200
aaaatccttt ttcgatcatt caatgcatag tgcattgccc cttgggatat atttggcaac   1260
caaattctgg atgtatgtga cgtggttctt ctggttttgg aatgatctca actttttatt   1320
tatccatctt ccattccttg ccaatagtgt tgcacttttc tacaattttg gaaaatcttg   1380
gaaatcagat ccagggatta ttaaagcaac agaagagcaa aagaaaaaga caatagttga   1440
acttgcagag acaggaagtc tggacctcag tatattctgc agtacctgtt tgatacgaaa   1500
accggtgagg tccaaacatt gtggtgtgtg caaccgctgt atagcaaaat ttgatcatca   1560
ttgcccatgg gtgggtaact gtgtaggtgc aggcaaccat agatatttta tgggctacct   1620
attcttcttg ctttttatga tctgctggat gatttatggt tgtatatctt actggggact   1680
ccactgtgag accacttaca ccaaggatgg attttggaca tacattactc agattgccac   1740
gtgttcacct tggatgtttt ggatgttcct gaacagtgtt ttccacttca tgtgggtggc   1800
tgtattactc atgtgtcaga tgtaccagat atcatgttta ggtattacta caaatgaaag   1860
aatgaatgcc aggagataca agcactttaa agtcacaaca acgtctattg aaagcccatt   1920
caaccatgga tgtgtaagaa atattataga cttctttgaa tttcgatgct gtggcctctt   1980
tcgtcctgtt atcgtggact ggaccaggca gtatacaata gaatatgacc aaatatcagg   2040
atctgggtac cagctggtgt agcgacatct tatcctatga agcatattgc tgagtggtgc   2100
ctgaaaattg tgtctgtccg tgtctttctc acactcgaat ccacatcctt tgaacaagag   2160
catgctatgt gtagggctaa tggtgaattt tacagtcttt ttttcaacac ttttattaac   2220
aaaagtaaac atggacagaa cacactgcca tttctgggaa gagtaaagat gataaaaaat   2280
aattttaatg gttcttaatg tggaaattca caacatactc aacttttggg ttttgttctc   2340
acagtatttt tcacaaaaaa agggtaaact tattctattg acagacatgg tgtactgatc   2400
agaaatgttc agttttaact aaaactaaat ttatgttatt tggctaaatg ttatgatgca   2460
gtctagtacg agtattgcat ctaattccag gagcattgtt ttaagttgat tgactagtta   2520
ttatgtacat ttcagaatgt acacataaat actgtgatga aaatcatgtg attgggatct   2580
actgtgatgt tgtcttcaaa ggcaggagaa aataatgttc acaataaaat gtgctaacaa   2640
tgttttgttt ctatcagctg ttgcaatgct gatatatttc tagttcagtg aaataatttg   2700
tagtaacctt actctgaggt tttacggtct gataatgaag cacttgcatg agtatagtaa   2760
gtcatgtttt tttgttcaaa tttaaaagcc ctgctaattg catgacacac cacatagaat   2820
gtatactagc agatactatc cagtgaagca taaattagaa tttaatttga tgttcaaaaa   2880
cagttccatt tttaagggtt aaggtggtat tttcaagaaa aggcagaaca aataatgcaa   2940
```

aattctcagt aatagtgata catggatata cttcctttta aattctcagc tgcaaaataa 3000
ttgtagacaa aataatggca tttaactaaa gatggagcat gatctaagta catagcacat 3060
gtgaataaaa gaaaagctga cagtatattc tggtttcaat aaaatgacct atcagaaagt 3120
agaatttcat ccccaagagt atttcagttt atccaatatt gagtaagttc tgaaacagtt 3180
ttagaaaaaa ttttcttttt gttaaatgtg atgcactgat caatttttgt cacagcattt 3240
tcataccttc atggtggact actagtcact gcttccataa atattgttta cagggtgaga 3300
tttggtttat tcatcttaag tgctgtagca aactgtggtt cgagcaacct gtgggaaatc 3360
tgtgagaggg aatggggtgg gagatgtggg ggaatggtgg tcagactgat gacagatcct 3420
agaccaatgt aaagaatgtg tatctgtata taaataattt atcaaatagt tttctctttg 3480
tgtctgtgtt agtgttttta aagctgctca tttcattttg tccaaccaaa aagaaaaggg 3540
agataactaa tgagcttcta gtgatgttca aaattgctgt taataggcat tataccctgc 3600
aagttcactg catgtctgat gcttggtaaa actagtcttc cctgtaaaat gcagattaca 3660
ggtattaaag caatctagtg gtatacccgc cccttgcctt agtaagagga gcagtgaaat 3720
gtatatagtt gatgttcagt atttccaagt accattttta tatagtagct tatttgacca 3780
taagtcacac atcaaaaaaa gattaccctt agtgtatgtg ttttaatatt agaaaattgg 3840
catatgtact ttatttttga aaagggaaga gatgggtgtg gggtggcaat agcattgtgc 3900
cattttgtca tagaatgtaa aaattggtta actttacaaa tgtcagctag ttttgactac 3960
taattggggg aaattttaga taatttttaa attcaaagtt atttataaaa tgctagaatt 4020
tgttttaatt ttttgtattt tgagccactt cacatgaaga ctcagttgca tttttatcga 4080
atacattttt atcaacagtt aaagactatg gtggtttttt cagagtttgg ctaagaatgt 4140
tgttaccatc ttctttgttt gtggtacaat attttcagtg caaaagagat gtcattcagt 4200
taaaaagaca aacctctaga tgtgtaatta catggaaaat actagcaatg tgaatgcttt 4260
tgtagtaacc atcttgtagt acctgtgaaa tctataactc agaaatggtc agatggtcag 4320
gagccagcta tgcagcagta taccatctgt ttaattattt tgtaggtcct gtgtgtggaa 4380
ccaactataa acccagttct aaagttgtgt atgatggtga acctttggga atagttctta 4440
tcaacttaat tggatacttt tagcaaatag gaacttaatt ctcagcactg aacatgaatt 4500
acttccttgg agtttttttt cattcatatt tttgttgttt ccaggaattt atttgatatt 4560
aatgggcgta aaacagcatc attgtactta agctatggat gtttttattt tatattttct 4620
ttatttataa ctgtgccaag tattattttg ctacttaccg tgttattctg tggaaagaaa 4680
aacctgtaaa gtgtttaata aattagccct ccttacataa attaaatgtc aaaattttgt 4740
aaaatattaa tcagaataaa tactgactct t 4771

<210> SEQ ID NO 63
<211> LENGTH: 3163
<212> TYPE: DNA
<213> ORGANISM: Homo sapiens

<400> SEQUENCE: 63
gcgcgcgccg ccgctgccac ctccgctgct cggcccggtc ccggagtggc ccggccggcc 60
cgcggggcgc ggagccgagg cccgcggctg gctgcatgaa ggactgcgag taccagcaga 120
tcagccccgg ggccgccccg ctgcccgcct ccccgggggc gcgccgtccc ggccccgccg 180
cgtccccgac tccgggcccc gggcccgcgc cgcccgccgc ccccgccccg ccgcgctgga 240

-continued

```
gcagcagcgg cagcggcagc ggcagcggga gcgggagcct cggccgccgc ccacggcgca    300
agtgggaggt gttcccgggt cgcaatcgct tctactgcgg cggccgcctc atgctggccg    360
gccacggcgg cgtcttcgcg ctcacgctgc tgctcatcct caccaccacc ggcctcttct    420
tcgtctttga ctgtccctac ctggctcgca agctgaccct tgccatcccc atcatcgctg    480
ccatcctctt cttcttcgtc atgagctgcc tgctgcagac aagcttcacc gaccctggga    540
tcctgccccg ggccactgtc tgtgaagcag ccgccctgga gaaacagatc gacaacacag    600
gcagttctac ataccggcca ccccctcgga cccgggaggt gctgatcaac gggcagatgg    660
tgaagctgaa gtactgcttc acctgcaaga tgttccggcc accccgaacc tcacactgca    720
gtgtctgcga caactgtgtg gaacgatttg accatcactg cccctgggtg ggcaactgtg    780
tggggagacg gaactatcgc ttcttctacg cgtttattct ctccctctca ttcctgacgg    840
ccttcatctt cgcctgtgtg gtcacccacc tgacgttgcg cgctcaggga agcaacttcc    900
tctccactct gaaggagaca ccagcaagcg tgctggagtt ggtgatctgc ttcttctcca    960
tctggtccat tctgggcctc tcagggtttc acacgtacct cgtcgcctcc aacctgacta   1020
ctaatgaaga catcaaaggc tcgtggtcca gcaagagggg cggtgaggcc tctgtcaacc   1080
cctacagcca taaaagtatt atcaccaact gctgtgctgt gctctgtggc cccctacctc   1140
ccagcctaat tgaccggagg ggatttgtgc agtccgacac cgtgttgccc tcacccatca   1200
gaagcgatga gccagcctgc agagccaagc ctgatgccag catggtagga ggccacccct   1260
gaccacggct cagtacttgc cacctgctgg cctgtctgac cctccgcact cacctgccgg   1320
gaccctccct attccatcca agggaagcag aactgccaaa gactcaagtc ttttcatatt   1380
tatttcccat cctgcgtggc tttccctgaa ctgttccgtg gctgtgccct ctgctcccca   1440
aacccaggtt cccacagcct tgggccctag gtaccccagc tgatcagtgc caggagagac   1500
cagagcctct ggaggctacc caggggacca caccaagtcc ttgcctgtgc cgggcgagcc   1560
ctgtgtgagt gaggctgtga actgagcgtg aggcctccca ggtgggggaa ctgcttgggc   1620
cttgctgagc cagggtcctc agggtgaagc aggactgagg agtggccagc tctggatagc   1680
tggctgtgga gaggaagcct ccatgggctg ctttggtctg tgggctcctt cattcccttg   1740
gtgataattt ccctttcttc tgtgggattt ttggtggggt tttcccccct tttttatgga   1800
gttggccaat aggattgagt tggggctcca gtagagaagg cagggttggt ggtgggtggg   1860
ggcagcctgt atcagacaaa ggtaaatcag ccagccaggc acccacagcc tcagctcctg   1920
tgcagttcct gggcagcaca gtggaagtgg gagcctggtc cttcccctgc ccatggagag   1980
ctctttaagg gatcccagcc tgcccctcca cttctctccc aagccaggtc ccggcatggg   2040
tgggttatgc tcatgctggc aatacttgaa acgggtttat taatgctggg tattttgcac   2100
aattttatag acctcttttc tacatagtct tttttaaatg gaaggagaaa atgtcagcca   2160
cattactgtc tgtgtagtgc caggtgaagg gttatcagaa ggctggttgg ttttaataag   2220
tttattccaa gagaccttct ggctggaatg agtgagagtg tgtgtgcatg tgtgtgtgtg   2280
ttcatgtgtg ccctgtatga atgtggctgg ctcccatatc ccctgggctg ccccctgccc   2340
catccccttt gagtatcaga agcactctga gccaagggga cagggggcac gtgcactggt   2400
cacgagaaaa ccctgggctc ccactggggc tcagcccagc ctcctatctt tccttcttct   2460
atggacttca gacagccagt gtctggggac tctgccactc tacccccagc cctacccacc   2520
agcccccagg tgaggcttcc agctgggacc tgcccagaca ggctgagcct gggcgtggtg   2580
ggtggggtga tggctctggg gagcggctgc catcctacaa gccacacccc ctcctctgag   2640
```

```
ctctgaatat gggacccagt gccaggagct ggaagacaag gtgtttctgc caaacgggga   2700
cctccatcca gagaaaagga agaaggtgca gggtgggcca agaggcaagt gaaggttggc   2760
ctgagtctgg gccggaaact cagaggatgt ttctcctctg ctgggagctg tagtttctta   2820
tcaaaataga tattgttcca ccatccccct ccttggccct tcaagtgggc tgaagccctt   2880
ggaaagtgac ataggaagtc cccagatctt gcccttctca ctccagaggc tagtggtcac   2940
agacagctgg gaatggcagc cacagagggt cccctctggg agaaacagct tcaccccagc   3000
ctcagggccc tgggccatca ctgcagtggc cctgggaggt gaggaagaag ctggctagag   3060
gagggggctc ccacctacct tttatttaag ccagtattct ttgttcctgc ttgtaataaa   3120
acttcagttt ataagaaaaa aaaaaagaaa aaaaaaaaaa aaa                     3163
```

<210> SEQ ID NO 64
<211> LENGTH: 1370
<212> TYPE: DNA
<213> ORGANISM: Homo sapiens

<400> SEQUENCE: 64

```
ctttcaccct gggctgcggc tctgaggctg ccgtggccat ggagctctgg aagctgggct     60
gggggaggaa gcctggtggc tctgacctcc cctggaggcg aaggaggccc agccatgaca    120
ctcttaacgg atgccacgcc gctggtgaag gagccccatc cctgcctctt ggtcccacgt    180
ccctggttcc tccctagcct ctttgctgcc ttcaatgtgg tgctgctggt ctttttcagt    240
ggcctcttct tcgcattccc ttgcaggtgg ctggctcaga acggggagtg ggcctttcct    300
gttatcacag gctccctctt tgtccttacc ttcttcagtc ttgtttcact caacttctca    360
gaccctggca tcttacatca aggctccgct gagcagggcc ccttgacggt gcacgtggtg    420
tgggtgaacc acggggcctt ccgcctgcaa tggtgtccaa agtgctgctt ccaccgcccg    480
ccccggactt accactgccc ctggtgcaac atctgtgtgg aggactttga ccaccactgc    540
aagtgggtca ataactgcat cggtcaccgc aacttccgct tcttcatgct gcttgtcctg    600
tccctgtgcc tctactcggg cgccatgctg gtcacctgtc tcatcttcct ggtgcgcaca    660
acccacctgc ccttctccac cgacaaggcc atcgccatcg tggtggccgt gtccgccgcg    720
ggcctcctgg tgccgctgtc cctcctgctg ctgatccagg cactgtccgt gagctcggcc    780
gaccgcacct acaagggcaa gtgcagacac cttcagggat acaacccctt cgaccagggc    840
tgtgccagca actggtattt aacaatttgt gcaccactgg gacccaagta catggctgaa    900
gctgtccagc tgcagagagt ggtggggcct gactggacat ccatgccgaa tctgcaccct    960
ccaatgtccc cctctgctct caacccccca gccccaacct ctgggtccct acaaagcagg   1020
gaagggaccc ccggggcgtg gtgaggctgc agctctccag gagttccaca cgggcccagt   1080
gctgcccctg ctgctgcagg agcccccagg cgaggttcgg ccttcctctc gcccctgtgc   1140
acccggagat gcccacagca ccagcacctg agctcacctc cgaacccgcc tcctgaaccc   1200
gcctcctgaa cctgcctcct tacctcccac ttcctgagcc ctgagtggaa gcctttctgt   1260
gccttgccct ttgcccactc ccctggtggg actgccaaga ccctcaatgc ccattaaata   1320
ctcttgcctg cctcttaaaa aaaaaaaaaa aaaaaaaaaa aaaaaaaaaa              1370
```

<210> SEQ ID NO 65
<211> LENGTH: 1514
<212> TYPE: DNA
<213> ORGANISM: Homo sapiens

<400> SEQUENCE: 65

```
cggaggcggg ggagctggac cagcagccgc ctggagcgtc cgagtcaccg tcgccggggc      60
tcccgcgctc cccagaacgg tgggacgcgg ggctcggcag ccgccagcgg aacatggcgc     120
cctggacgct gtggcgctgc tgccagcgcg tcgtgggctg ggtgccggtg ctcttcatca     180
ccttcgtggt cgtctggtcc tactacgcgt acgtggtgga gctctgcgtg tttactattt     240
ttggaaatga agaaaatgga aagaccgttg tttaccttgt ggctttccat ctgttctttg     300
ttatgtttgt atggtcctat tggatgacaa ttttcacatc tcccgcttcc ccctccaaag     360
agttctactt gtccaattct gaaaaggaac gttatgaaaa agaattcagc caagaaagac     420
aacaagaaat tttgagaaga gcagcaagag ctttacctat ctataccaca tcagcttcaa     480
aaactatcag atattgtgaa aaatgtcagc tgattaaacc tgatcgggcg catcactgct     540
cagcctgtga ctcatgtatt cttaagatgg atcatcactg tccttgggtg aataactgtg     600
tgggattttc taattacaaa ttcttcctgc tgtttttatt gtattcccta ttatattgcc     660
ttttcgtggc tgcaacagtt ttagagtact ttataaaatt ttggacgaat gaactgacag     720
atacacgtgc aaaattccac gtactttttc ttttctttgt gtctgcaatg ttcttcatca     780
gcgtcctctc acttttcagc taccactgct ggctagttgg aaaaaataga acaacaatag     840
aatcattccg cgcacccacg ttttcatacg gacctgatgg aaatggtttc tctcttggat     900
gcagtaaaaa ttggagacaa gtctttggtg atgaaaagaa atattggcta cttccaatat     960
tttcaagctt gggtgatggt tgcagttttc caactcgcct tgtggggatg gatccagaac    1020
aagcttctgt tacaaaccag aatgagtatg ccagaagtgg ctcaaatcaa ccttttccta    1080
tcaaaccact tagtgaatca aaaaaccgct tgttggacag tgaatctcag tggctggaga    1140
atggagctga agaaggcatc gtcaaatcag gtgtatgaaa acattataga ctggtatttt    1200
caattttcat ttgcaagaaa atgatcagtg gaatgaaata actgaagtat aacagaagat    1260
atatttttta aaacggaaag cctttgtaca gttcctggga ttcacagaag cactactcca    1320
gagcagaatg atgccttaat cttaagtgtc catttgtgca gcattgactt agagctacaa    1380
aagtgactta atgttattct ggaaataata cttacctgtt atgagttgct ataatatgag    1440
ctgtcatcac attttaaaaa aaaaaaaaaa aaaaaaaaaa aaaaaaaaaa aaaaaaaaaa    1500
aaaaaaaaaa aaaa                                                       1514
```

<210> SEQ ID NO 66
<211> LENGTH: 3265
<212> TYPE: DNA
<213> ORGANISM: Homo sapiens

<400> SEQUENCE: 66

```
ccgtcgcggc tcccgggagc taagcgagac ggcgacggcg gcagtcgtcc ctccccacgc      60
gggcgcgcgg gcatgcggac acccactcgg ccggtccagg ccctcaggct cccggaagcg     120
gaaggggaga gcggcccggc ctgggcggcg gcgccggagg aggcggaggt ggcgcggcag     180
gaggagggga aagagctgct ggtggtcggg agagcggcgg cagcgagagg cgagccagcg     240
gcgacgaatg aagaactttt tcacttactg caggattttc agcttcagca agcaggttct     300
catggagaac tgttattgaa gagagatcca tttggtggga tataattaaa aaaaatgaat     360
caaaagaaaa tctctaaatg cagattccag aaaaattaca gcacatctca gtgaatttgc     420
aagtggatca tccttccttg tgggttagca ggcagttata agattgcaaa atgggtctcc     480
ggattcactt tgttgttgac ccacatggtt ggtgctgcat gggtttgatt gtctttgttt     540
```

```
ggttatacaa tattgtttta attcccaaaa ttgtcctctt tcctcactat gaagaaggac    600
atattccagg catattaata ataatattct atggcatttc catattctgt ctggttgcct    660
tagtgagggc ctccataact gatccaggaa gactccctga gaaccccaag atcccacatg    720
gagaaaggga gttctgggaa ttatgtaaca agtgtaattt gatgagacca aagcgttccc    780
atcactgcag ccgctgcggc cactgtgtga ggagaatgga tcatcactgt ccatggatta    840
acaattgtgt tggtgaagat aatcattggc tctttctgca gttgtgtttc tacactgaac    900
ttcttacttg ctacgcactg atgttttctt tctgccacta ttactatttt cttccactaa    960
aaaagcgtaa tttggacctc tttgttttta gacatgaatt ggccataatg agactagcag   1020
cctttatggg cattactatg ttagttggaa taactggact cttttacact caactaattg   1080
gcatcatcac agatacaaca tctattgaaa agatgtcaaa ctgttgtgaa gatatatcga   1140
ggccccgaaa gccatggcag cagaccttct cagaagtttt tggcactcgt tggaagatcc   1200
tgtggttcat tcctttcagg cagaggcaac cactgcgagt tccctaccac tttgccaatc   1260
atgtctaaac agatggatgg tgggcacaga tgggtcctcc atgctggcaa tgcgttacag   1320
gttttatgat aatagaacta tgacagtctt caagtcaatt aaaatccacc caccaatctt   1380
aggcatcata atgtgcccca ggctttattt taatagtgat cttgatcctg ttgtgggact   1440
aatacaagat ctatatttaa gttttaaagc atgtttactt tcaaattagc tttccacagg   1500
gatttcttga aatgcttttg ttattaaact caaaaggcag tgattaggat gaaataattg   1560
tacataattt attttagtac tgacagtgtt acagattcta atttatggta aatttcagat   1620
gtttatttaa aattttcact tttaaacagt aaccaaatct aaatttaatt attcaggttt   1680
tacaaaagtt gatacacctt cttatagtat aggtaaattt tctttttcaa atccaattta   1740
aaataacctt tccttttaaa tgtgctgcaa cgtttttaaa aatgcagcag cataggagtg   1800
aacaacagca acacaaaacg ggcattggtt tcttaggagt ggcttgctta cgtttcttc    1860
tttttcttc accaaaacca acatgaaagt accactgaag taaaacacca actacctacc   1920
ttactataaa ggaaatgtta aaattttttt cacaataatt ttttcaattt tcactattac   1980
tgttgtaatt attgattgtg attaaaatat ttgctcccag gagaactcct gaccagtggg   2040
catgtattcc tattttatcc taagatttta atgagcaaaa aggggagaga atttgcaata   2100
acttcacaat taccttttct agtgcagtta tattagaatg catatgtttt taaaatgcta   2160
gtataactag atagtatata atgtacagta taaagaggaa tattgtgctt ttgaaaagag   2220
tatacttttt acttttattt atgtactagt agatgtaaaa tttcgcattg aaggtttata   2280
tatattggcc aactcatata gaaattttat ttataggaag ctactactaa aaaaagtcac   2340
taactttgtg tacctataat ccctaaatta aaattaaatt ttaattggct ggctgtaatt   2400
tgcattgaga gaccttttac tagtagctag tgttaggaag tgaacctaaa ataagaaaat   2460
ataatgatct gtgtttatca ttagccttgt acaaatgtaa attactaata gtgatgttct   2520
tttgcaaggc atagaacatt tgtatgaaaa gacatttagt atgctttgaa aaaaactcag   2580
cttttagttt ttttccatta gaatactgca aaacccatat atctttttaa aaaatttatg   2640
tactcacagt ctttcccttg aagagaagat tgaaaaagtc tactgttcat aaaccatgct   2700
aacattttcc ttttagctag ttttgaaagt aaggaacaat acctgggaaa taataaaaca   2760
gaaggttacc attgtcagcc agttggctat actgtggtta gttctttcag aaattgtaaa   2820
tatcttgtag catattctga aataatagag taagttcttc tcagagatgt taatatcatg   2880
```

-continued

```
tttttcatgt tctaattaga atactttatt acttacaaac tcagaaatac gaacagaaat   2940

acagcagacg aacatattta ttggtactga aaagagatgt agtaaattaa atagaagaaa   3000

tatatttata aagcttagtg aaacacaaaa ttagaatgtt catgtcaggc acaagggttt   3060

ggattttgtg caagctaatt tggccacatt tggcctggtg acagaactgt tcataaggaa   3120

gtaatatata gataaggtag gtagatatca gttgaatgcc ttatattgta tacattcctt   3180

tcaaataaag accttgagaa aacaaaaaaa aaaaaaaaaa aaaaaaaaaa aaaaaaaaaa   3240

aaaaaaaaac aaaaaaaaaa aaaaa                                         3265


<210> SEQ ID NO 67
<211> LENGTH: 3408
<212> TYPE: DNA
<213> ORGANISM: Homo sapiens

<400> SEQUENCE: 67

ccttactcgc tggcgcccaa gtgggaagcc agcagctgcc cgctccctcc tccccacatc     60

cccgctactt gcccagttcc cgaagcgaag cgcaggctgc gagccagccg ggccgagtcc    120

acaactttgc agcctcgggc agggcgagag ccggcgtccg gggctcctct tgtcggcgac    180

cagagctcgg aatgtaatcg aggatgctgg ccctgcggct gctcaacgtg gtggcccccg    240

cctacttctt gtgcatctcc ctggtgacct tcgtgctgca gctcttcctc ttcctgccca    300

gcatgcgcga ggaccccgcg gccgcccggc tcttctcgcc cgccctgctc cacggggcgc    360

tcttcctatt cctctcggcc aacgccctgg gcaattacgt ccttgtcatc cagaactccc    420

cagacgacct gggggcctgc caggggggcct cggccaggaa gactccatgc ccctcaccta    480

gcacccactt ctgccgagtg tgcgccagag tcaccctgag gcacgaccat cactgtttct    540

tcaccggcaa ctgcatcggc agcaggaaca tgcgcaactt cgtcctgttc tgcctctaca    600

cctccctggc ctgcctctac tccatggtgg ccggcgtggc ctacatctcc gctgtccttt    660

ccatctcctt cgcccacccc ttggccttcc tcacgctcct gcccacctcc atcagccagt    720

tcttctccgg agctgtcctg ggttctgaaa tgttcgtcat cctcatgctc tacctctggt    780

tcgccatcgg cctggcctgc gccggcttct gctgccacca gctgctgttg atcctccgcg    840

ggcagacccg ccaccaggtg cggaaggggg tggcagtgag ggcccggccc tggcgcaaga    900

acttacaaga ggtcttcgga aagaggtggc tgctgggcct gctggtcccc atgttcaatg    960

tcggaagtga gagctccaag cagcaggata agtagtagac actcccgtca tttatctctc   1020

tgtctctgtc ttgactcctc ctgagcataa aaccatggca gccttgtctc cacccatgac   1080

tcactacaac cttgtgctgg taaggtccta gcatcttccc ctcaccttcc acccatgaga   1140

acagcgtgag ctggtggatc atgacaagga ggaaaaatgt ccccccaggc atttctaggc   1200

tcctcacgag ccagccaggt ggctgctagc tgttaggctg cctctgcttt ctttccgtcc   1260

ccttgggatc cctgctttcc ccctcttcct ggctcatcca ttctccaccg tgtctcattc   1320

atcactgctg tctgctagag cccttcctct cagcccccat gttgggagag gggagtggat   1380

tcttgctgct ggtatgagac tccctgggac ctagaggctg gcaaatgttt aaaatcacca   1440

cgtgtaagag gcagccaagt cagctctgcc aactgctagg ggagttggga aagagtgggt   1500

gtgtgtccgc atcccctctg taggaaaaag aacttagtag cttgctgctc cctcaccacc   1560

ccccaccagg ttcaagaccc tttttctggg agacagcaat caatggcctg ctttttccaa   1620

atgttattcc ctgtccaccc tgccccatct ggccggccca gcccagtcca ggacctggct   1680

ggatgcttcc tgtccctgga actcttccag cctttctact tgatctccag cccccaggtc   1740
```

```
tttgccagat gatgggaagg caaggaagaa gggacaggga aagataatta ctgataaatg   1800
aaggggatat tcgactgtat aaccatatgg aagtgtgtgt gtgtgtgtgt gtgtgtgtgt   1860
gagagagaga gagagagaga tgggtggtgg tgagaagtgt tgttagaaac atataggaat   1920
aatgcctagg ggaaagggag aagtgagagg gacaattggg ttcatttatg ccctatacaa   1980
agggcattcc agcagctgaa actcttcaat gtttgaatgg ctgcctgtga aggtagtgag   2040
tgccccatca ctggaggtat tccagcagag tctaggcagt cgtctgccag gcatgctgtg   2100
gaagggattt ctgtacaggg tcattctagg tgagcttaca cattccttcc aaccccaagg   2160
ttctgatgtc ctggttgtga ttgctggacc cagaggcaag atctgcagag atgcctgtga   2220
gatatttgct ttcctagagg ggagtgtggg catgggaggg gtctgaaaat caggacccaa   2280
cccagccact gaagagagag tctctgcaga gacagggcta cctgggtggt tgaggggact   2340
gacatttgag gacagggaga tggagcagtg tcattgtcag tggcagggca tggggggcag   2400
tggtgagcta aggctgagga gtggagatga ccagaatata agggtgcaat tcccagacca   2460
tccctgcgca tctgactgac tccggtggag gcactgctgt gtgttttctg aaacctagag   2520
gaccagacct ctggggcata taagggagta gggacaacac aagtgccccc tcctgactgg   2580
gtcccaaagc caatatgaca tccatgcagg cagcagtgct gaatccatgc cctgcaatgt   2640
ccaaccgcca actgcagtga cccgctgata gctgcgcaac agcctgggtt cttgagcaga   2700
gattgggagg actttactgt ggttctgcct tcacaccccc tagagagcta atgtagtatt   2760
ggctccacct gctcacattt ctccctccca tactcattcc ttcactcatc catcctacgt   2820
atatttattg agtgccaact acgttcccag cctcttccag gcactggcaa tgcagtgatg   2880
aacaggatga caagattcat gccatcaggg gcaccttgtc actgccgtct gtgcactgat   2940
tcacactccc tgcaaaatgg tcactctgcc atcttggtgg ttggtggggc aggtcatttg   3000
gaaataaaga atgtgataga gatggctgaa gaggggaagc ctaggctgcc tcaatggagg   3060
agtcgctggg ggcattttca cccacaattc tggccatact taagcaatgg gagggagagg   3120
gaggagggga agatctgggc aattttggcc ttgactcttt cctggctcca gagctcaagc   3180
ttagaagcca gccctgctat ttccagcctc ctgaaggctc agcacggtga ggcctgacat   3240
cctggggaag ggcaacaggg agacctacag gatgttggct gcttgcagac tggtcaatgg   3300
gggatgacgg tggggaggtt gccagatgtg agacttgagt agcatttgta cacatggccc   3360
tgtattgtcc ttgaagaaca tcaataaaat atatggtttt aaattgga                3408
```

<210> SEQ ID NO 68
<211> LENGTH: 3778
<212> TYPE: DNA
<213> ORGANISM: Homo sapiens

<400> SEQUENCE: 68

```
ggggcacccg gaagcgcgcg tggacctggc gcaccgagcc gggcgggcgg aggggcggtt     60
gggacggcgc ggggaggcgg gcgcgccgcc cgggccgcgg cgggctgtgg tcacaggtgg    120
gcggctgcgg cgagggagcg gccgagcgga gcccgggtcc cggagactcc tgccgtcacg    180
cccggggctc cgcgtagcag agatcgggag acgcgtctgt gcctccgggg aagccgaccc    240
atctcccctc cgcctctttg gctgcagttg cacctccggc cagagggcag gtgcaaatca    300
tgacacagaa gggcagtatg aagcctgtga agaaaaagaa aaccgaagaa cctgaattgg    360
agcccctgtg ctgctgcgag tacatagatc ggaatgggga aaagaaccac gtggctactt    420
```

-continued

```
gtttgtgtga ttgtcaagat ctggatgaag ggtgtgatcg atggattaca tgtaaatctt    480
tacagccaga gacttgtgaa agaatcatgg atacaatttc tgatcgcctc cgaattcctt    540
ggcttagggg agccaaaaaa gtgaacatca gcatcatccc tccgcttgtc ctgctgcctg    600
tcttccttca tgtggcttcc tggcatttcc tcctgggggt ggtggttttg acctcccttc    660
ctgtgctggc actgtggtac tactacctca ctcacagaag gaaagaacag accctgtttt    720
tcctgagcct tggactgttc tctctgggct acatgtacta tgtgttcctg caggaagtgg    780
tccccaaagg gcgtgtgggt cccgttcagc tggcggttct tacctgcggg ttatttctga    840
tactcttagc cttgcacaga gccaagaaga atccaggcta cctcagcaat ccagcaagcg    900
gtgacagatc tctaagcagc agccagctgg agtgcctgag cagaaaaggg caggagaaga    960
ccaaagggtt ccctggggca gacatgtcgg gcagtctcaa caatcgcaca acaaaggatg   1020
accccaaggg ctcttccaag atgccagctg gaagccccac caaagcgaag gaggactggt   1080
gtgccaagtg ccagctggtg cgaccagccc gggcatggca ctgccggata tgtggcatct   1140
gtgtgaggag aatggatcat cattgtgtct ggataaatag ctgcgttgga gaatcaaatc   1200
atcaagcatt tatacttgcc cttttgatct tcttgctcac ctcggtgtat gggatcacac   1260
tgaccttgga caccatttgt agagacagaa gtgtcttcac agctcttttc tattgtcctg   1320
gagtttatgc aaattacagc tcggctctgt ccttcacctg cgtgtggtac tctgtgatca   1380
tcacagcagg catggcctac atcttcctga tccagctgat caacatcagc tacaatgtga   1440
ctgagcggga agtccagcag gccctccgac agaagactgg gcgccggctc ctctgcgggc   1500
tcatcgtgga cacagggtta cttggatgag ccaactccgc ttccttccca tggataggaa   1560
gggactctgt gtattattca ggtttattgg cacgaagata cttgttttaa gttccttgag   1620
aacccatgat ggacagttga cagaatgctt aaacctgtca aaagatgagt gatcttgtgt   1680
gggaaaagcc ttcccaggcg tctgtaccga aaggagcagc aaacaagggg ctaatccatg   1740
agcagtgttc tgtaggctct gtgacatctt tggtttatag gattttggag ccttttatga   1800
tctggaacta tttgaggggt ttcattatag gccttggttc tctccagggg ccagatgagt   1860
ttattgtgga atctttgaaa ggacaaggcc tctgtgaatg aatcagtccc agggaagcat   1920
ttggtggtgg cggcagtgga ggattgcccg gtgaacctat aaatcagcag tctcttgggc   1980
agaggagcaa gcccctcgaa catgatttca aacaagcagg tcctcttctc tcatctcacg   2040
tccttagtct ctgttaatga acatactgga tgtggagttt aataaattac ctactatcat   2100
ctggccactt agattattat cacaccactg tggactgttc ctgggggggag aagaacagac   2160
cgatttgaaa gattcaaggg agaaagatta aggatcagga ttgcatgaaa gaagaaaatc   2220
cttcaatatt taaaatgttt cttacaatac ccacggagca cttttatggt tccagccgag   2280
cgttcctgaa atgaactgac cattaacagc gcctctttga taggttaccc tgatgctgct   2340
aaagtaaagc cttaagtgtg tttttgggac aacgtgctgc ttattccacc tcagccacat   2400
atgtgtttgt gtttaggata ttgtaaatct ttgctaagta gtgttttcct tggtgaatga   2460
agtcattgtt gtcttcaagt gtaccatctg cctagcaaaa aattgctaca aactttctct   2520
tatgcaatag tccttggtac ttctaatatt tttagcaaga gacaattttc tgtactagaa   2580
tcttccactg ccagaaaaca cagtgccagt aaggttctac ataccactga ccatctgctt   2640
aatagacatg tatttccttt gagtaggaca ttagcttttg attataaagc tcaactagta   2700
taagcaaaaa tataacatct agaagcacag ttttagccag gatgtttaaa aattacagtt   2760
ttgtgagact taagggtctt tttaacctag gtaagtttat atgacctaac ttaattgtag   2820
```

ccatattctg gtaccttcca ttttgaaaag tagaggttgc ttaagcaagc aatggataat 2880
aagagacttt tcctgaggca cctgtttgga atctggtttt ctcagcggca gcttgacatg 2940
tgcacccttt tgtattaaac actgcaaggg tgatgcaggg gagcaggaaa gccatcctaa 3000
actcactact gagtacgatt cagtatgttc ctgtggatgt ctgctgtgac taatataaat 3060
ttcttgcaga atcagctaca cttaattatg ttgctgatag acaagcatcc acgcttcagc 3120
tggcactaag tgttttcatt gtaggatcag cagcaggtta aagactgaac ggttagtgaa 3180
gacaaatgtc ttaagaggct gcgatgtcta ggttgggctt gtgacttctt agtggcctag 3240
ccttcttgat ggcaccttga aagtgaactt ctagaaatct acatttaaaa ggcaaagctt 3300
taaaagcaga gctagtctat tctagttact gatgcaacta aaattctgta tttcttaaga 3360
tggagccact gacgagatgt cacagtatag agcctgcagt ctcaactcat tgtgatccta 3420
atggtctggg tgattggatg gtttgagttg ttagggattt tgagtttttc attttattgc 3480
atatctgggt tggatgttag actaaaggaa acccaggaat atttacctgg tgttacattt 3540
aatatttaat gtaactggtc tagcaacatt aaggggggatt tctgaagcca actccggagg 3600
ctgtgggctg cacattttgc actgttttta tatacttgta ttcatatcct cttatcacct 3660
cagactcaga cacaaggcct tttacatgga aattttacaa attacttcca tttatgtaaa 3720
ataacgtcct gtgaccaagt tgtttaaatg gaaaataaag tgctttcttt aaggaaaa 3778

<210> SEQ ID NO 69
<211> LENGTH: 1319
<212> TYPE: DNA
<213> ORGANISM: Homo sapiens

<400> SEQUENCE: 69
gattccgagc gcctccactg ctggtccgtt ggccagatca actcgccgcg tgggccggcc 60
gttccctgag agtctgagcg ctcgccgcac ccccttccga gcttctattg gccgtagcag 120
acgtccgtct gccgctatct ccgccccaat acggaagcgg cctagtcctc cggctccgac 180
agctgggtgt ccaggccatg gggcagccct gggcggctgg gagcacggac ggggcgcccg 240
cgcagctgcc tctcgtgctc accgcgctgt gggccgcggc cgtgggcctg gagctggctt 300
acgtgctggt gctcggtccc gggccgccgc cgctgggacc cctggcccgg gccttgcagc 360
tggcgctggc cgccttccag ctgctcaacc tgctgggcaa cgtggggctc ttcctgcgct 420
cggatcccag catccgtggc gtgatgctgg ccggccgcgg tctgggccag ggctgggctt 480
actgctacca atgccaaagc caggtgccgc cacgcagcgg acactgctct gcctgccgcg 540
tctgcatcct gcgtcgggac caccactgcc gcctgctggg ccgctgcgtg ggcttcggca 600
actaccggcc cttcctgtgc ctgctgcttc atgccgccgg cgtcctgctc cacgtctctg 660
tgctgctggg ccctgcactg tcggccctgc tgcgagccca cacgcccctc cacatggctg 720
ccctcctcct gcttccctgg ctcatgttgc tcacaggcag agtgtctctg gcacagtttg 780
ccttggcctt cgtgacggac acgtgcgtgg cgggtgcgct gctgtgcggg gctgggctgc 840
tcttccatgg gatgctgctg ctgcggggcc agaccacatg ggagtgggct cggggccagc 900
actcctatga cctgggtccc tgccacaacc tgcaggcagc cctggggccc cgctgggccc 960
tcgtctggct ctggcccttc ctggcctccc cattgcctgg ggatgggatc accttccaga 1020
ccacagcaga tgtgggacac acagcctcct gactccagga agagccagag ctgtgcaggg 1080
aggaaggggt gagagggggg cccccacacc tagactcagt aaggaagtcg ggttggacct 1140
taacatctgc attggacaac tccacccctt ccttggcctt gcccctgccc gcctacactc 1200
ctacgtgtcc agggcttggg ccgtgactta ggcagaggag tgcagaggag ggtctggcag 1260
gggctgctca ggccgcctag ctgccccttt gccaggttaa taaagcactg acttgttaa 1319

<210> SEQ ID NO 70
<211> LENGTH: 8481
<212> TYPE: DNA
<213> ORGANISM: Homo sapiens

<400> SEQUENCE: 70
gagagacggc agcggccccg gcctccctct ccgccgcgct tcagcctccc gctccgccgc 60
gctccagcct cgctctccgc cgcccgcacc gccgcccgcg ccctcaccag agcagccatg 120
gaggaggtgg tgattgccgg catgtccggg aagctgccag agtcggagaa cttgcaggag 180
ttctgggaca acctcatcgg cggtgtggac atggtcacgg acgatgaccg tcgctggaag 240
gcggggctct acggcctgcc ccggcggtcc ggcaagctga aggacctgtc taggtttgat 300
gcctccttct tcggagtcca ccccaagcag gcacacacga tggaccctca gctgcggctg 360
ctgctggaag tcacctatga agccatcgtg gacggaggca tcaacccaga ttcactccga 420
ggaacacaca ctggcgtctg ggtgggcgtg agcggctctg agacctcgga ggccctgagc 480
cgagaccccg agacactcgt gggctacagc atggtgggct gccagcgagc gatgatggcc 540
aaccggctct ccttcttctt cgacttcaga gggcccagca tcgcactgga cacagcctgc 600
tcctccagcc tgatggccct gcagaacgcc taccaggcca tccacagcgg gcagtgccct 660
gccgccatcg tgggggggcat caatgtcctg ctgaagccca acacctccgt gcagttcttg 720
aggctgggga tgctcagccc cgagggcacc tgcaaggcct tcgacacagc ggggaatggg 780
tactgccgct cggagggtgt ggtggccgtc ctgctgacca agaagtccct ggcccggcgg 840
gtgtacgcca ccatcctgaa cgccggcacc aatacagatg gcttcaagga gcaaggcgtg 900
accttcccct caggggatat ccaggagcag ctcatccgct cgttgtacca gtcggccgga 960
gtggcccctg agtcatttga atacatcgaa gcccacggca caggcaccaa ggtgggcgac 1020
ccccaggagc tgaatggcat cacccgagcc ctgtgcgcca cccgccagga gccgctgctc 1080
atcggctcca ccaagtccaa catggggcac ccggagccag cctcggggct ggcagccctg 1140
gccaaggtgc tgctgtccct ggagcacggg ctctgggccc ccaacctgca cttccatagc 1200
cccaaccctg agatcccagc gctgttggat gggcggctgc aggtggtgga ccagcccctg 1260
cccgtccgtg gcggcaacgt gggcatcaac tcctttggct tcgggggctc caacgtgcac 1320
atcatcctga ggcccaacac gcagccgccc cccgcacccg ccccacatgc caccctgccc 1380
cgtctgctgc gggccagcgg acgcacccct gaggccgtgc agaagctgct ggagcagggc 1440
ctccggcaca gccaggacct ggctttcctg agcatgctga acgacatcgc ggctgtcccc 1500
gccaccgcca tgcccttccg tggctacgct gtgctgggtg gtgagcgcgg tggcccagag 1560
gtgcagcagg tgcccgctgg cgagcgcccg ctctggttca tctgctctgg gatgggcaca 1620
cagtggcgcg ggatggggct gagcctcatg cgcctggacc gcttccgaga ttccatccta 1680
cgctccgatg aggctgtgaa gccattcggc ctgaaggtgt cacagctgct gctgagcaca 1740
gacgagagca cctttgatga catcgtccat tcgtttgtga gcctgactgc catccagata 1800
ggcctcatag acctgctgag ctgcatgggg ctgaggccag atggcatcgt cggccactcc 1860
ctgggggagg tggcctgtgg ctacgccgac ggctgcctgt cccaggagga ggccgtcctc 1920
gctgcctact ggaggggaca gtgcatcaaa gaagcccatc tcccgccggg cgccatggca 1980

-continued

```
gccgtgggct tgtcctggga ggagtgtaaa cagcgctgcc ccccgggcgt ggtgcccgcc   2040
tgccacaact ccaaggacac agtcaccatc tcgggacctc aggccccggt gtttgagttc   2100
gtggagcagc tgaggaagga gggtgtgttt gccaaggagg tgcggaccgg cggtatggcc   2160
ttccactcct acttcatgga ggccatcgca cccccactgc tgcaggagct caagaaggtg   2220
atccgggagc cgaagccacg ttcagcccgc tggctcagca cctctatccc cgaggcccag   2280
tggcacagca gcctggcacg cacgtcctcc gccgagtaca atgtcaacaa cctggtgagc   2340
cctgtgctgt tccaggaggc cctgtggcac gtgcctgagc acgcggtggt gctggagatc   2400
gcgccccacg ccctgctgca ggctgtcctg aagcgtggcc tgaagccgag ctgcaccatc   2460
atccccctga tgaagaagga tcacagggac aacctggagt tcttcctggc cggcatcggc   2520
aggctgcacc tctcaggcat cgacgccaac cccaatgcct tgttcccacc tgtggagttc   2580
ccagctcccc gaggaactcc cctcatctcc ccactcatca agtgggacca cagcctggcc   2640
tgggacgtgc cggccgccga ggacttcccc aacggttcag gttcccccctc agccgccatc   2700
tacaacatcg acaccagctc cgagtctcct gaccactacc tggtggacca caccctcgac   2760
ggtcgcgtcc tcttccccgc cactggctac ctgagcatag tgtggaagac gctggcccgc   2820
gccctgggcc tgggcgtcga gcagctgcct gtggtgtttg aggatgtggt gctgcaccag   2880
gccaccatcc tgcccaagac tgggacagtg tccctggagg tacggctcct ggaggcctcc   2940
cgtgccttcg aggtgtcaga gaacggcaac ctggtagtga gtgggaaggt gtaccagtgg   3000
gatgaccctg accccaggct cttcgaccac ccggaaagcc ccacccccaa ccccacggag   3060
cccctcttcc tggcccaggc tgaagtttac aaggagctgc gtctgcgtgg ctacgactac   3120
ggccctcatt tccagggcat cctggaggcc agcctggaag gtgactcggg gaggctgctg   3180
tggaaggata actgggtgag cttcatggac accatgctgc agatgtccat cctgggctcg   3240
gccaagcacg gcctgtacct gcccacccgt gtcaccgcca tccacatcga ccctgccacc   3300
cacaggcaga agctgtacac actgcaggac aaggcccaag tggctgacgt ggtggtgagc   3360
aggtggctga gggtcacagt ggccggaggc gtccacatct ccgggctcca cactgagtcg   3420
gccccgcggc ggcagcagga gcagcaggtg cccatcctgg agaagttttg cttcactccc   3480
cacacggagg aggggtgcct gtctgagcgc gctgccctgc aggaggagct gcaactgtgc   3540
aaggggctgg tgcaggcact gcagaccaag gtgacccagc aggggctgaa gatggtggtg   3600
cccggactgg atggggccca gatccccccgg gacccctcac agcaggaact gccccggctg   3660
ttgtcggctg cctgcaggct tcagctcaac gggaacctgc agctggagct ggcgcaggtg   3720
ctggcccagg agaggcccaa gctgccagag gaccctctgc tcagcggcct cctggactcc   3780
ccggcactca aggcctgcct ggacactgcc gtggagaaca tgcccagcct gaagatgaag   3840
gtggtggagg tgctggctgg ccacggtcac ctgtattccc gcatcccagg cctgctcagc   3900
ccccatcccc tgctgcagct gagctacacg gccaccgacc gccaccccca ggccctggag   3960
gctgcccagg ccgagctgca gcagcacgac gttgcccagg gccagtggga tcccgcagac   4020
cctgccccca gcgccctggg cagcgccgac ctcctggtgt gcaactgtgc tgtggctgcc   4080
ctcggggacc cggcctcagc tctcagcaac atggtggctg ccctgagaga agggggcttt   4140
ctgctcctgc acacactgct ccgggggcac cccctcgggg acatcgtggc cttcctcacc   4200
tccactgagc cgcagtatgg ccagggcatc ctgagccagg acgcgtggga gagcctcttc   4260
tccagggtgt cgctgcgcct ggtgggcctg aagaagtcct tctacggctc cacgctcttc   4320
```

-continued

```
ctgtgccgcc ggcccacccc gcaggacagc cccatcttcc tgccggtgga cgataccagc   4380
ttccgctggg tggagtctct gaagggcatc ctggctgacg aagactcttc ccggcctgtg   4440
tggctgaagg ccatcaactg tgccacctcg ggcgtggtgg gcttggtgaa ctgtctccgc   4500
cgagagcccg gcgggaaccg cctccggtgt gtgctgctct ccaacctcag cagcacctcc   4560
cacgtcccgg aggtggaccc gggctccgca gaactgcaga aggtgttgca gggagacctg   4620
gtgatgaacg tctaccgcga cggggcctgg ggggctttcc gccacttcct gctggaggag   4680
gacaagcctg aggagccgac ggcacatgcc tttgtgagca ccctcacccg ggggggacctg   4740
tcctccatcc gctgggtctg ctcctcgctg cgccatgccc agcccacctg ccctggcgcc   4800
cagctctgca cggtctacta cgcctccctc aacttccgcg acatcatgct ggccactggc   4860
aagctgtccc ctgatgccat cccagggaag tggacctccc aggacagcct gctaggtatg   4920
gagttctcgg gccgagacgc cagcggcaag cgtgtgatgg gactggtgcc tgccaagggc   4980
ctggccacct ctgtcctgct gtcaccggac ttcctctggg atgtgccttc caactggacg   5040
ctggaggagg cggcctcggt gcctgtcgtc tacagcacgg cctactacgc gctggtggtg   5100
cgtgggcggg tgcgccccgg ggagacgctg ctcatccact cgggctcggg cggcgtgggc   5160
caggccgcca tcgccatcgc cctcagtctg ggctgccgcg tcttcaccac cgtggggtcg   5220
gctgagaagc gggcgtacct ccaggccagg ttcccccagc tcgacagcac cagcttcgcc   5280
aactcccggg acacatcctt cgagcagcat gtgctgtggc acacgggcgg gaagggcgtt   5340
gacctggtct tgaactcctt ggcggaagag aagctgcagg ccagcgtgag gtgcttggct   5400
acgcacggtc gcttcctgga aattggcaaa ttcgaccttt ctcagaacca cccgctcggc   5460
atggctatct tcctgaagaa cgtgacattc cacggggtcc tactggatgc gttcttcaac   5520
gagagcagtg ctgactggcg ggaggtgtgg gcgcttgtgc aggccggcat ccgggatggg   5580
gtggtacggc ccctcaagtg cacggtgttc catggggccc aggtggagga cgccttccgc   5640
tacatggccc aagggaagca cattggcaaa gtcgtcgtgc aggtgcttgc ggaggagccg   5700
gaggcagtgc tgaagggggc caaacccaag ctgatgtcgg ccatctccaa gaccttctgc   5760
ccggcccaca agagctacat catcgctggt ggtctgggtg gcttcggcct ggagttggcg   5820
cagtggctga tacagcgtgg ggtgcagaag ctcgtgttga cttctcgctc cgggatccgg   5880
acaggctacc aggccaagca ggtccgccgg tggaggcgcc agggcgtaca ggtgcaggtg   5940
tccaccagca acatcagctc actggagggg gcccggggcc tcattgccga ggcggcgcag   6000
cttgggcccg tgggcggcgt cttcaacctg gccgtggtct tgagagatgg cttgctggag   6060
aaccagaccc cagagttctt ccaggacgtc tgcaagccca agtacagcgg caccctgaac   6120
ctggacaggg tgacccgaga ggcgtgccct gagctggact actttgtggt cttctcctct   6180
gtgagctgcg ggcgtggcaa tgcgggacag agcaactacg gctttgccaa ttccgccatg   6240
gagcgtatct gtgagaaacg ccggcacgaa ggcctcccag gcctggccgt gcagtggggc   6300
gccatcggcg acgtgggcat tttggtggag acgatgagca ccaacgacac gatcgtcagt   6360
ggcacgctgc cccagcgcat ggcgtcctgc ctggaggtgc tggacctctt cctgaaccag   6420
ccccacatgg tcctgagcag ctttgtgctg gctgagaagg ctgcggccta tagggacagg   6480
gacagccagc gggacctggt ggaggccgtg gcacacatcc tgggcatccg cgacttggct   6540
gctgtcaacc tggacagctc actggcggac ctgggcctgg actcgctcat gagcgtggag   6600
gtgcgccaga cgctggagcg tgagctcaac ctggtgctgt ccgtgcgcga ggtgcggcaa   6660
ctcacgctcc ggaaactgca ggagctgtcc tcaaaggcgg atgaggccag cgagctggca   6720
```

-continued

```
tgccccacgc ccaaggagga tggtctggcc cagcagcaga ctcagctgaa cctgcgctcc   6780
ctgctggtga acccggaggg ccccaccctg atgcggctca actccgtgca gagctcggag   6840
cggcccctgt tcctggtgca cccaatcgag ggctccacca ccgtgttcca cagcctggcc   6900
tcccggctca gcatccccac ctatggcctg cagtgcaccc gagctgcgcc ccttgacagc   6960
atccacagcc tggctgccta ctacatcgac tgcatcaggc aggtgcagcc cgagggcccc   7020
taccgcgtgg ccggctactc ctacggggcc tgcgtggcct ttgaaatgtg ctcccagctg   7080
caggcccagc agagcccagc ccccacccac aacagcctct tcctgttcga cggctcgccc   7140
acctacgtac tggcctacac ccagagctac cgggcaaagc tgaccccagg ctgtgaggct   7200
gaggctgaga cggaggccat atgcttcttc gtgcagcagt tcacggacat ggagcacaac   7260
agggtgctgg aggcgctgct gccgctgaag ggcctagagg agcgtgtggc agccgccgtg   7320
gacctgatca tcaagagcca ccagggcctg gaccgccagg agctgagctt tgcggcccgg   7380
tccttctact acaagctgcg tgccgctgag cagtacacac ccaaggccaa gtaccatggc   7440
aacgtgatgc tactgcgcgc caagacgggt ggcgcctacg gcgaggacct gggcgcggac   7500
tacaacctct cccaggtatg cgacgggaaa gtatccgtcc acgtcatcga gggtgaccac   7560
cgcacgctgc tggagggcag cggcctggag tccatcatca gcatcatcca cagctccctg   7620
gctgagccac gcgtgagcgt gcgggagggc taggcccgtg cccccgcctg ccaccggagg   7680
tcactccacc atccccaccc caccccaccc cacccccgcc atgcaacggg attgaagggt   7740
cctgccggtg ggaccctgtc cggcccagtg ccactgcccc ccgaggctgc tagatgtagg   7800
tgttaggcat gtcccaccca cccgccgcct cccacggcac ctcggggaca ccagagctgc   7860
cgacttggag actcctggtc tgtgaagagc cggtggtgcc cgtgcccgca ggaactgggc   7920
tgggcctcgt gcgcccgtgg ggtctgcgct tggtctttct gtgcttggat ttgcatattt   7980
attgcattgc tggtagagac ccccaggcct gtccaccctg ccaagactcc tcaggcagcg   8040
tgtgggtccc gcactctgcc cccatttccc cgatgtcccc tgcgggcgcg ggcagccacc   8100
caagcctgct ggctgcggcc ccctctcggc caggcattgg ctcagcccgc tgagtggggg   8160
gtcgtgggcc agtccccgag gagctgggcc cctgcacagg cacacagggc ccggccacac   8220
ccagcggccc cccgcacagc cacccgtggg gtgctgccct tatgcccggc gccgggcacc   8280
aactccatgt ttggtgtttg tctgtgtttg tttttcaaga aatgattcaa attgctgctt   8340
ggattttgaa atttactgta actgtcagtg tacacgtctg gaccccgttt catttttaca   8400
ccaatttggt aaaaatgctg ctctcagcct cccacaatta aaccgcatgt gatctccaaa   8460
aaaaaaaaaa aaaaaaaaaa a                                             8481
```